(12) United States Patent
Ono et al.

(10) Patent No.: US 11,584,737 B2
(45) Date of Patent: Feb. 21, 2023

(54) HETEROCYCLIC COMPOUND

(71) Applicant: TAKEDA PHARMACEUTICAL COMPANY LIMITED, Osaka (JP)

(72) Inventors: Koji Ono, Kanagawa (JP); Masahiro Ito, Kanagawa (JP); Toshio Tanaka, Kanagawa (JP); Moriteru Asano, Kanagawa (JP); Takaharu Hirayama, Kanagawa (JP); Jun Fujimoto, Kanagawa (JP); Nobuki Sakauchi, Kanagawa (JP); Yasuhiro Hirata, Kanagawa (JP); Akinori Toita, Kanagawa (JP); Nao Morishita, Kanagawa (JP); Hironori Kokubo, Kanagawa (JP); Yasuhiro Imaeda, Kanagawa (JP); Hironobu Maezaki, Kanagawa (JP); Douglas Robert Cary, Kanagawa (JP); Ryo Mizojiri, Kanagawa (JP); Nobuo Cho, Kanagawa (JP); Hiroshi Banno, Kanagawa (JP); Hidekazu Tokuhara, Kanagawa (JP); Yasuyoshi Arikawa, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 17/042,394

(22) PCT Filed: Mar. 28, 2019

(86) PCT No.: PCT/JP2019/013531
§ 371 (c)(1),
(2) Date: Sep. 28, 2020

(87) PCT Pub. No.: WO2019/189555
PCT Pub. Date: Oct. 3, 2019

(65) Prior Publication Data
US 2021/0363130 A1    Nov. 25, 2021

(30) Foreign Application Priority Data
Mar. 29, 2018  (JP) ............... JP2018-063740

(51) Int. Cl.
| C07D 401/14 | (2006.01) |
| C07D 403/14 | (2006.01) |
| A61P 35/00 | (2006.01) |
| C07D 213/84 | (2006.01) |
| C07D 401/12 | (2006.01) |
| C07D 403/12 | (2006.01) |
| C07D 405/12 | (2006.01) |
| C07D 405/14 | (2006.01) |
| C07D 471/10 | (2006.01) |
| C07D 487/10 | (2006.01) |
| C07D 495/10 | (2006.01) |

(52) U.S. Cl.
CPC ............ *C07D 401/14* (2013.01); *A61P 35/00* (2018.01); *C07D 213/84* (2013.01); *C07D 401/12* (2013.01); *C07D 403/12* (2013.01); *C07D 403/14* (2013.01); *C07D 405/12* (2013.01); *C07D 405/14* (2013.01); *C07D 471/10* (2013.01); *C07D 487/10* (2013.01); *C07D 495/10* (2013.01)

(58) Field of Classification Search
CPC ......................... C07D 401/14; C07D 403/14
See application file for complete search history.

(56) References Cited

U.S. PATENT DOCUMENTS

| 2005/0197350 A1 | 9/2005 | Sekiguchi et al. |
| 2009/0143302 A1 | 6/2009 | Yen et al. |

FOREIGN PATENT DOCUMENTS

| EP | 1464335 | 10/2004 |
| JP | 2007-91649 | 4/2007 |
| JP | 2016-533379 | 10/2016 |
| WO | 99/31072 | 6/1999 |
| WO | 2006/035967 | 4/2006 |
| WO | 2011/012661 | 2/2011 |
| WO | 2012/066065 | 5/2012 |
| WO | 2012/101065 | 8/2012 |
| WO | 2015/058140 | 4/2015 |
| WO | 2016/058544 | 4/2016 |
| WO | 2016/142855 | 9/2016 |

(Continued)

OTHER PUBLICATIONS

Extended European Search Report dated Oct. 22, 2021 in corresponding European Patent Application No. 19774394.1.
International Search Report dated May 21, 2019 in International (PCT) Patent Application No. PCT/JP2019/013531.

(Continued)

*Primary Examiner* — Brian E McDowell
(74) *Attorney, Agent, or Firm* — Wenderoth, Lind & Ponack, L.L.P.

(57) ABSTRACT

Provided is a compound that may have a superior CDK12 inhibitory action and is expected to be useful as a prophylactic or therapeutic drug for cancer and the like. A compound represented by the following formula (I):

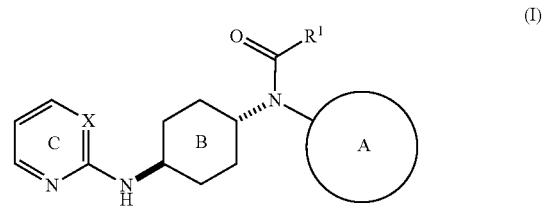

wherein each symbol is as described in the DESCRIPTION, or a salt thereof.

15 Claims, 1 Drawing Sheet

(56) References Cited

FOREIGN PATENT DOCUMENTS

WO    2016/193939    12/2016

OTHER PUBLICATIONS

File Registry on STN, RN 1026426-87-8, American Chemical Society (ACS), 2020, 2 total pages.
File Registry on STN, RN 1348645-64-6, American Chemical Society (ACS), 2020, 2 total pages.
Ito et al., "Discovery of 3-Benzyl-1-(trans-4-((5-cyanopyridin-2-yl)amino)cyclohexyl)-1-arylurea Derivatives as Novel and Selective Cyclin-Dependent Kinase 12 (CDK12) Inhibitors", Journal of Medicinal Chemistry, 2018, vol. 61, pp. 7710-7728.
Bartkowiak et al., "CDK12 is a transcription elongation-associated CTD kinase, the metazoan ortholog of yeast Ctk1", Genes & Development, 2010, vol. 24, pp. 2303-2316.
Ekumi et al., "Ovarian carcinoma CDK12 mutations misregulate expression of DNA repair genes via deficient formation and function of the Cdk12/CycK complex", Nucleic Acids Research, 2015, vol. 43, No. 5, pp. 2575-2589.
Blazek et al., "The Cyclin K/Cdk12 complex maintains genomic stability via regulation of expression of DNA damage response genes", Genes & Development, 2011, vol. 25, pp. 2158-2172.
Bajrami et al., "Genome-wide Profiling of Genetic Synthetic Lethality Identifies CDK12 as a Novel Determinant of PARP1/2 Inhibitor Sensitivity", Cancer Research, 2014, vol. 74, pp. 287-297.
File Registry on STN, RN 1026673-82-4, American Chemical Society (ACS), 2020, 2 total pages.

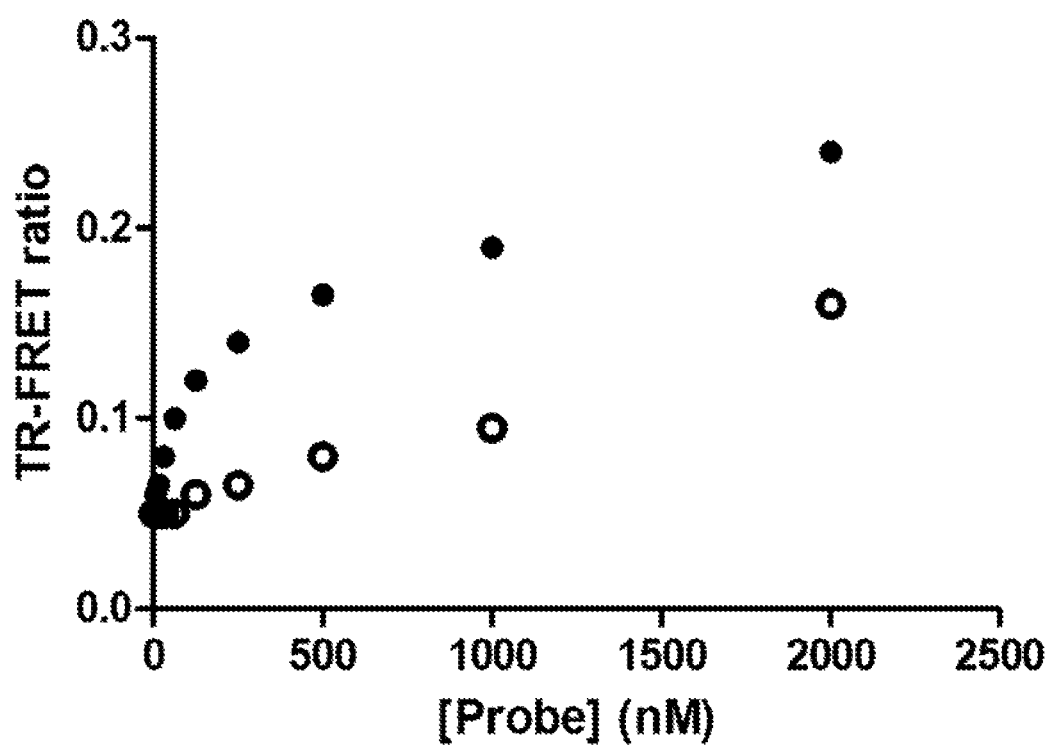

HETEROCYCLIC COMPOUND

TECHNICAL FIELD

The present invention relates to a heterocyclic compound that may have a Cyclin-dependent kinase 12 (CDK12) inhibitory action, and is expected to be useful as a prophylactic or therapeutic drug for cancer and the like.

BACKGROUND OF THE INVENTION

Cyclin-dependent kinase 12 (CDK12) is a serine/threonine kinase belonging to the CDK family. It becomes an active substance by binding to Cyclin K and transmits signals to the downstream. The process of copying the genetic information of DNA to messenger RNA (mRNA) is called "transcription". CDK12 is considered to be involved mainly in this transcription reaction and regulate the expression levels of various genes (non-patent document 1). CDK12 extends the transcription reaction of mRNA by phosphorylating the second serine (Ser2) at the C-terminal region of RNA polymerase II (non-patent document 2). In particular, CDK12 is considered to be involved in the transcription elongation reaction of genes with a long gene length, and affects the expression of BRCA1, ATM, FANCD2 genes and the like (non-patent document 3). All of these genes are a group of genes involved in DNA damage response (DDR), and are mainly involved in the maintenance of the stability of genomic DNA through the DNA repair mechanism. Inhibition of CDK12 decreases the expression of DDR-related genes, which in turn suppresses the DNA repair reaction. Therefrom it is considered that the damaged DNA of cancer cells cannot be repaired, and the growth and survival of the cancer cells can be suppressed. In particular, it has been shown that inhibition of both PARP involved in DNA repair and CDK12 completely suppresses the DNA repair reaction and induces cell death in cancer cells by a synthetic lethal action (non-patent document 4). From the foregoing, the action of inhibiting CDK12 is extremely useful for the prophylaxis and treatment of cancer.

Patent document 1 discloses the following compounds as compounds having an MCH receptor antagonistic action and useful for treating anxiety, depression, schizophrenia, obesity and the like.

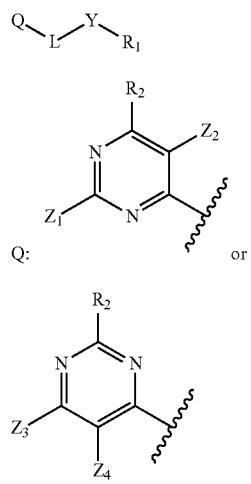

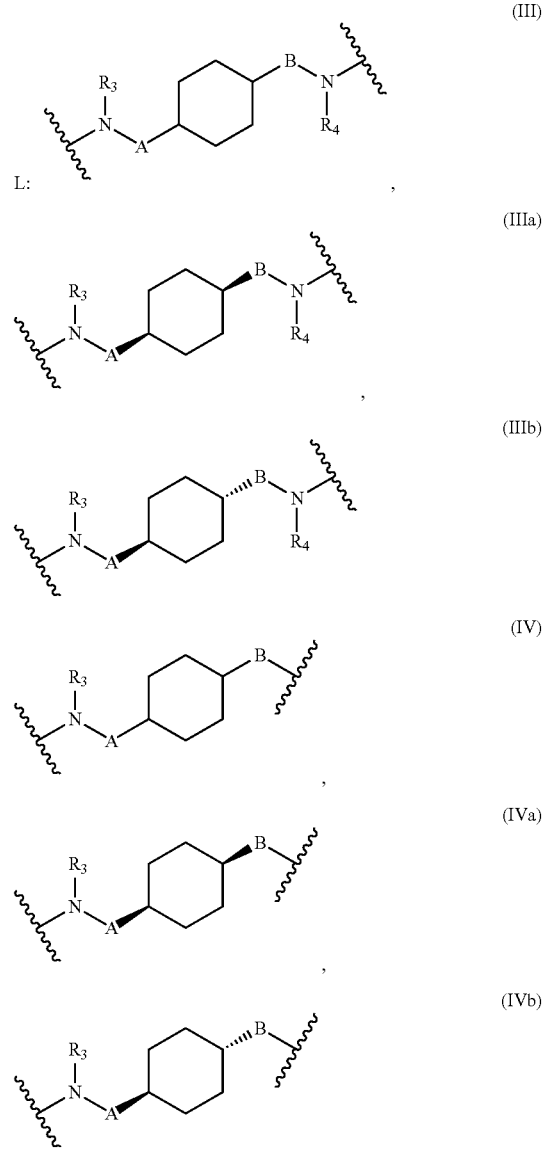

wherein each symbol is as defined in the document.

Patent document 2 discloses the following compounds as compounds useful as arthropodicide, fungicide and the like.

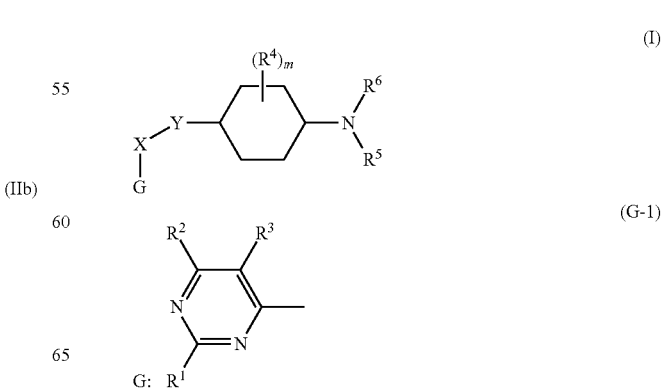

-continued

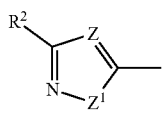
(G-2)

wherein each symbol is as defined in the document.

Non-patent document 5 discloses the following compound.

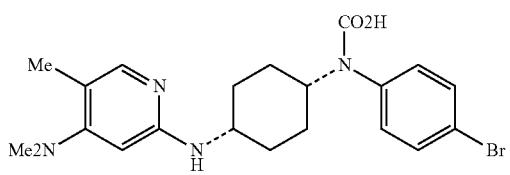

Non-patent document 6 discloses the following compound.

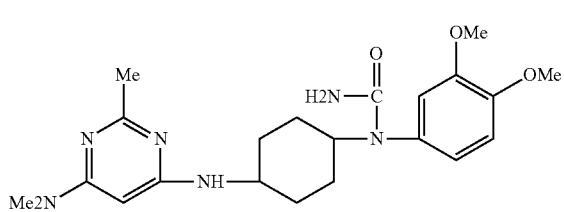 [SMILES: COc1ccc(N(C(N)=O)C2CCC(Nc3cc(N(C)C)nc(C)n3)CC2)cc1OC]

Non-patent document 7 discloses the following compound.

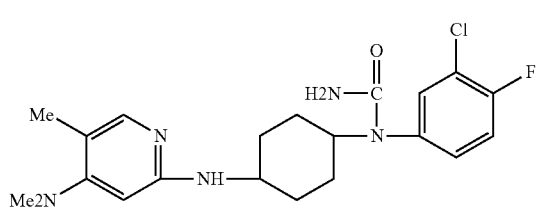 [SMILES: Cc1cnc(NC2CCC(N(C(N)=O)c3ccc(F)c(Cl)c3)CC2)cc1N(C)C]

Patent document 3 discloses the following compound as a compound having a CDK7 inhibitory action (also capable of selectively inhibiting CDK7, CDK12 and/or CDK13) and useful for treating cancer, inflammatory diseases and the like.

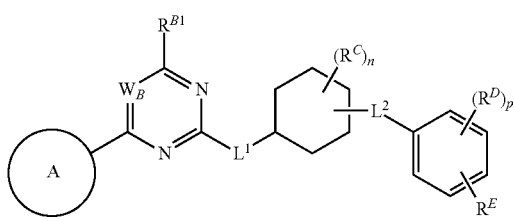
(I)

wherein each symbol is as defined in the document.

Patent document 4 discloses the following compound as a compound having a CDK7 inhibitory action (also capable of selectively inhibiting CDK7, CDK12 and/or CDK13) and useful for treating cancer, inflammatory diseases and the like.

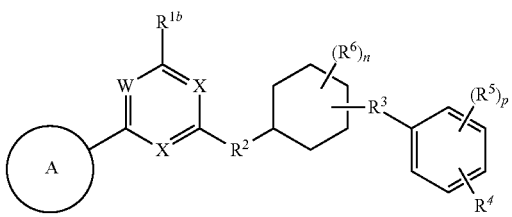
(I)

wherein each symbol is as defined in the document.

Patent document 5 discloses the following compound as a compound having a CDK9 (CDK1-9) inhibitory action and useful for treating cancer, inflammation, HIV and the like.

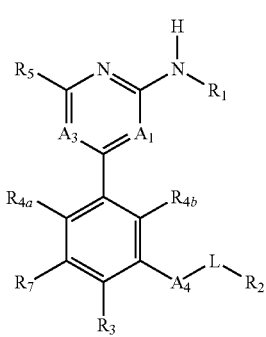

wherein each symbol is as defined in the document.

Patent document 6 discloses the following compound as a compound having a CDK9 (CDK1-9) inhibitory action and useful for treating cancer and the like.

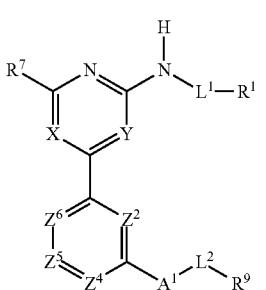
(I)

wherein each symbol is as defined in the document.

Patent document 7 discloses the following compound as a compound having a CDK9 (CDK1-9) inhibitory action and useful for treating cancer, inflammation, HIV and the like.

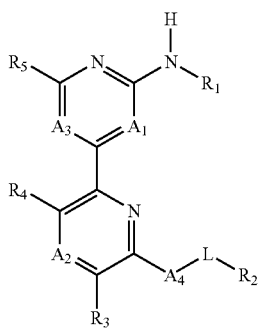

wherein each symbol is as defined in the document.

Patent document 8 discloses the following compound as a compound having a chemokine receptor CXCR3, CXCR4 inhibitory action and useful for treating cancer, inflammation and the like.

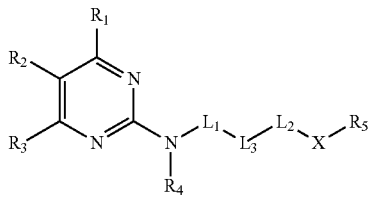

wherein each symbol is as defined in the document.

Non-patent document 8 discloses the following compounds as selective cyclin dependency kinase 12 (CDK12) inhibitors.

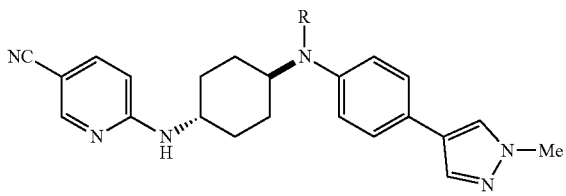

21-28
21 (R = Ao)
23 (R = phenylpropionyl)
24 (R = methoxycarbonyl)
25 (R = benzyloxycarbonyl)
26 (R = ethylamino carbonyl)
27 (R = benzylamino carbonyl)
28 (R = cyclohexylamino carbonyl)

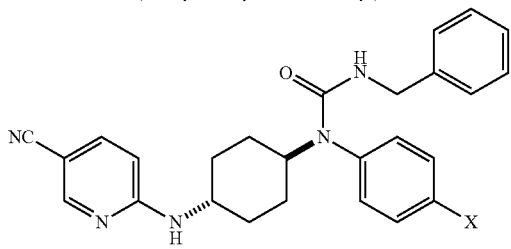

38 (X = Br)
39 (X = H)
40 (X = pyridin-3-yl)

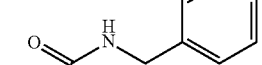

2, 44-47

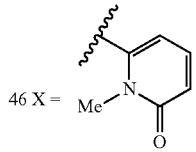

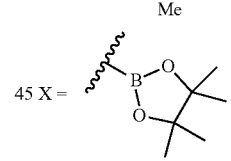

DOCUMENT LIST

Patent Documents patent document 1: JP2007091649A
patent document 2: WO 99/31072
patent document 3: WO 2015/058140A1
patent document 4: WO 2016/058544A1
patent document 5: WO 2012/066065A1
patent document 6: WO 2012/101065A2
patent document 7: WO 2011/012661A1
patent document 8: US2009/0143302A1

Non-Patent Document non-patent document 1: Bartkowiak B. et al., Genes Dev., 2010, 24, 2303-2316
non-patent document 2: Ekumi K M. et al., Nucleic Acids Res., 2015, 43, 2575-2589
non-patent document 3: Blazek D. et al., Genes Dev., 2011, 25, 2158-2172
non-patent document 4: Bajrami I. et al., Cancer Res., 2014, 74, 287-297
non-patent document 5: RN 1348645-64-6 REGISTRY
non-patent document 6: RN 1026673-82-4 REGISTRY
non-patent document 7: RN 1026426-87-8 REGISTRY
non-patent document 8: Ito M. et al., J. Med. Chem., 2018, 61, 7710-7728

SUMMARY OF INVENTION

Technical Problem

The present invention aims to provide a novel compound that may have a CDK12 inhibitory action, and is expected to be useful as a prophylactic or therapeutic drug for cancer and the like, and a medicament containing same.

Solution to Problem

The present inventors have conducted intensive studies in an attempt to solve the above-mentioned problems and found that a compound represented by the following formula (I) may have a CDK12 inhibitory action, which resulted in the completion of the present invention.

That is, the present invention is as described below.

[1] A compound represented by the formula (I):

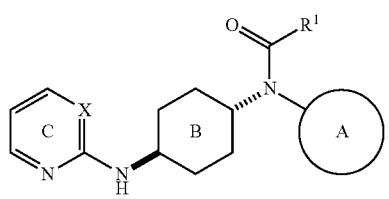

wherein
X is CH or N;
R$^1$ is an optionally substituted C$_{1-6}$ alkyl group, an optionally substituted C$_{1-6}$ alkoxy group, an optionally substituted C$_{6-14}$ aryl group, an optionally substituted heterocyclic group, or —NR$^2$R$^3$;
R$^2$ is a hydrogen atom or a substituent;
R$^3$ is a substituent;
ring A is an optionally further substituted aromatic ring;
ring B is an optionally further substituted cyclohexane ring;
ring C is an optionally further substituted 6-membered nitrogen-containing aromatic heterocycle,
or a salt thereof (sometimes to be abbreviated as "compound (I)" in the present specification).
[2] The compound of [1], wherein the ring C is an optionally further substituted pyridine ring (that is, X is CH).
[3] The compound of [1], wherein the ring C is an optionally further substituted pyrimidine ring (that is, X is N).
[4] The compound of [3], wherein the ring A is an optionally further substituted C$_{6-14}$ aromatic hydrocarbon ring.
[5] The compound of [3], wherein the ring A is an optionally further substituted 5- to 14-membered aromatic heterocycle.
[6] The compound of [1], wherein R$^1$ is (1) a C$_{1-6}$ alkyl group optionally substituted by 1 to 3 substituents selected from an optionally substituted C$_{6-14}$ aryl group, an optionally substituted C$_{6-14}$ aryloxy group and an optionally substituted 5- to 14-membered aromatic heterocyclic group, (2) a C$_{1-6}$ alkoxy group optionally substituted by 1 to 3 substituents selected from an optionally substituted C$_{6-14}$ aryl group and an optionally substituted 5- to 14-membered aromatic heterocyclic group, (3) an optionally substituted C$_{6-14}$ aryl group, (4) a 3- to 14-membered non-aromatic heterocyclic group optionally substituted by 1 to 3 substituents selected from an optionally substituted C$_{6-14}$ aryl group or (5) —NR$^2$R$^3$ [R$^2$ is a hydrogen atom or a C$_{1-6}$ alkyl group optionally substituted by 1 to 3 substituents selected from an optionally substituted C$_{6-14}$ aryl group, R$^3$ is (i) a C$_{1-6}$ alkyl group optionally substituted by 1 to 3 substituents selected from an optionally substituted C$_{3-10}$ cycloalkyl group, an optionally substituted C$_{6-14}$ aryl group, an optionally substituted 3- to 14-membered non-aromatic heterocyclic group and an optionally substituted 5- to 14-membered aromatic heterocyclic group or (ii) an optionally substituted C$_{6-14}$ aryl group;
ring A is a C$_{6-14}$ aromatic hydrocarbon ring or a 5- to 14-membered aromatic heterocycle each of which is optionally further substituted by 1-5 substituents selected from (1) a halogen atom, (2) a cyano group, (3) a hydroxy group, (4) an optionally substituted C$_{1-6}$ alkyl group, (5) an optionally substituted C$_{2-6}$ alkenyl group, (6) an optionally substituted C$_{6-14}$ aryl group, (7) an optionally substituted C$_{1-6}$ alkoxy group, (8) an optionally substituted amino group, (9) a carboxy group, (10) an optionally substituted carbamoyl group, (11) an optionally substituted 3- to 14-membered non-aromatic heterocyclic group (the 3- to 14-membered non-aromatic heterocyclic group also includes one having a spiro ring structure) and (12) an optionally substituted 5- to 14-membered aromatic heterocyclic group;
ring B is a cyclohexane ring not substituted further; and
ring C is a pyridine ring (that is, X is CH) or a pyrimidine ring (that is, X is N) each of which is optionally further substituted by 1 to 3 substituents selected from (1) a halogen atom, (2) a cyano group, (3) an optionally substituted C$_{1-6}$ alkyl group, (4) an optionally substituted C$_{6-14}$ aryl group, (5) an optionally substituted C$_{1-6}$ alkoxy group, (6) an optionally substituted C$_{6-14}$ aryloxy group, (7) an optionally substituted 3- to 14-membered non-aromatic heterocyclic-oxy group, (8) an optionally substituted amino group, (9) an optionally substituted carbamoyl group, (10) an optionally substituted 3- to 14-membered non-aromatic heterocyclic group (the 3- to 14-membered non-aromatic heterocyclic group also includes one having a bicyclo ring structure, a bridged ring structure, or a spiro ring structure) and (11) an optionally substituted 5- to 14-membered aromatic heterocyclic group.
[7] The compound of [1], wherein
R$^1$ is (1) a C$_{1-6}$ alkyl group optionally substituted by 1 to 3 substituents selected from a C$_{6-14}$ aryl group optionally substituted by 1 to 3 halogen atoms, a C$_{6-14}$ aryloxy group and a 5- to 14-membered aromatic heterocyclic group, (2) a C$_{1-6}$ alkoxy group optionally substituted by 1 to 3 substituents selected from a C$_{6-14}$ aryl group and a 5- to 14-membered aromatic heterocyclic group, (3) a C$_{6-14}$ aryl group, (4) a 3- to 14-membered non-aromatic heterocyclic group optionally substituted by 1 to 3 C$_{6-14}$ aryl groups, or (5) —NR$^2$R$^3$ [R$^2$ is a hydrogen atom or a C$_{1-6}$ alkyl group optionally substituted by 1 to 3 C$_{6-14}$ aryl groups, R$^3$ is (i) a C$_{1-6}$ alkyl group optionally substituted by 1 to 3 substituents selected from (a) a C$_{3-10}$ cycloalkyl group, (b) a C$_{6-14}$ aryl group optionally substituted by 1 to 3 substituents selected from a halogen atom, a cyano group, a C$_{1-6}$ alkoxy group, a C$_{1-6}$ alkylsulfonyl group and a C$_{1-6}$ alkylsulfonylamino group, (c) a 3- to 14-membered non-aromatic heterocyclic group, and (d) a 5- to 14-membered aromatic heterocyclic group optionally substituted by 1 to 3 substituents selected from a C$_{1-6}$ alkyl group and a C$_{1-6}$ alkoxy group, or (ii) a C$_{6-14}$ aryl group];
ring A is a C$_{6-14}$ aromatic hydrocarbon ring or a 5- to 14-membered aromatic heterocycle each of which is optionally further substituted by 1-5 substituents selected from (1) a halogen atom, (2) a cyano group, (3) a hydroxy group, (4) a C$_{1-6}$ alkyl group optionally substituted by 1 to 3 substituents selected from (a) a halogen atom, (b) a C$_{1-6}$ alkoxy group and (c) a 3- to 14-membered non-aromatic heterocyclic group optionally substituted by 1 to 3 $C_{1-6}$ alkyl groups, (5) a $C_{2-6}$ alkenyl group, (6) a $C_{6-14}$ aryl group optionally substituted by 1 to 3 substituents selected from (a) a halogen atom, (b) a cyano group, (c) a $C_{1-6}$ alkoxy group and (d) a carbamoyl group, (7) a $C_{1-6}$ alkoxy group, (8) an amino group optionally mono- or di-substituted by substituent(s) selected from (a) a $C_{1-6}$ alkyl group optionally substituted by 1 to 3 $C_{1-6}$ alkoxy groups, (b) a $C_{6-14}$ aryl group optionally substituted by 1 to 3 substituents selected from a cyano group and a $C_{1-6}$ alkoxy group, and (c) a 5- to 14-membered aromatic heterocyclic group optionally substituted by 1 to 3 $C_{1-6}$ alkyl groups, (9) a carboxy group, (10) a carbamoyl group optionally mono- or di-substituted by a $C_{1-6}$ alkyl group, (11) a 3- to 14-membered non-aromatic heterocyclic group optionally substituted by 1 to 3 substituents selected from (a) an oxo group, (b) a cyano group, (c) a $C_{1-6}$ alkyl group, (d) a $C_{1-6}$ alkoxy group, (e) a $C_{1-6}$ alkyl-carbonyl group, (f) a carbamoyl group, (g) a mono- or di-$C_{1-6}$ alkylamino group and (h) a $C_{1-6}$ alkylsulfonyl group (the 3- to 14-membered non-aromatic heterocyclic group also includes one having a spiro ring structure) and (12) a 5- to 14-membered aromatic heterocyclic group optionally substituted by 1 to 3 substituents selected from (a) an oxo group, (b) a $C_{1-6}$ alkyl group optionally substituted by 1 to 3 substituents selected from a hydroxy group, a $C_{1-6}$ alkoxy group, a carbamoyl group, a 3- to 14-membered non-aromatic heterocyclic group and a 5- to 14-membered aromatic heterocyclic group, (c) a $C_{1-6}$ alkoxy group, (d) an amino group, (e) a carboxy group, (f) a $C_{1-6}$ alkoxy-carbonyl group, (g) a carbamoyl group and (h) a 3- to 14-membered non-aromatic heterocyclic group;

ring B is a cyclohexane ring not substituted further;

ring C is a pyridine ring (that is, X is CH) or a pyrimidine ring (that is, X is N) each of which is optionally further substituted by 1 to 3 substituents selected from (1) a halogen atom, (2) a cyano group, (3) $C_{1-6}$ alkyl group optionally substituted by 1 to 3 halogen atoms, (4) a $C_{6-14}$ aryl group optionally substituted by 1 to 3 substituents selected from (a) a halogen atom, (b) a cyano group, (c) a $C_{1-6}$ alkyl group optionally substituted by 1 to 3 halogen atoms, (d) a $C_{1-6}$ alkoxy group optionally substituted by 1 to 3 halogen atoms, (e) a mono- or di-$C_{1-6}$ alkylamino group, (f) a $C_{1-6}$ alkyl-carbonylamino group, (g) a $C_{1-6}$ alkyl-carbonyl group, (h) a carbamoyl group, (i) a sulfamoyl group and (j) a 3- to 14-membered non-aromatic heterocyclic-sulfonyl group, (5) a $C_{1-6}$ alkoxy group optionally substituted by 1 to 3 substituents selected from (a) a halogen atom and (b) a 5- to 14-membered aromatic heterocyclic group optionally substituted by 1 to 3 $C_{1-6}$ alkyl groups, (6) a $C_{6-14}$ aryloxy group optionally substituted by 1 to 3 $C_{1-6}$ alkylsulfonyl groups, (7) a 3- to 14-membered non-aromatic heterocyclic-oxy group, (8) an amino group optionally mono- or di-substituted by substituent(s) selected from (a) a $C_{1-6}$ alkyl group optionally substituted by 1 to 3 substituents selected from (i) a halogen atom, (ii) a hydroxy group, (iii) a cyano group, (iv) a $C_{3-10}$ cycloalkyl group optionally substituted by 1 to 3 hydroxy groups, (v) a $C_{6-14}$ aryl group optionally substituted by 1 to 3 substituents selected from a $C_{1-6}$ alkylsulfonyl group and a sulfamoyl group, (vi) a $C_{1-6}$ alkoxy group optionally substituted by 1 to 3 halogen atoms, (vii) a mono- or di-$C_{1-6}$ alkylamino group, (viii) a $C_{1-6}$ alkyl-carbonylamino group, (ix) a carbamoyl group, (x) a $C_{1-6}$ alkylsulfonyl group, (xi) a 3- to 14-membered non-aromatic heterocyclic group optionally substituted by 1 to 3 substituents selected from an oxo group and a $C_{1-6}$ alkyl group and (xii) a $C_{1-6}$ alkyl group optionally substituted by 1 to 3 substituents selected from a 5- to 14-membered aromatic heterocyclic group optionally substituted by 1 to 3 substituents selected from a $C_{1-6}$ alkyl group, a $C_{3-10}$ cycloalkyl group and a ($C_{1-6}$ alkyl) ($C_{1-6}$ alkyl-sulfonyl)amino group, (b) a $C_{3-10}$ cycloalkyl group optionally substituted by 1 to 3 substituents selected from a halogen atom, a hydroxy group, a $C_{1-6}$ alkyl group optionally substituted by 1 to 3 hydroxy groups and a $C_{1-6}$ alkoxy group optionally substituted by 1 to 3 halogen atoms (the $C_{3-10}$ cycloalkyl group also includes one having a spiro ring structure), (c) a $C_{6-14}$ aryl group optionally substituted by 1 to 3 $C_{1-6}$ alkylsulfonyl groups, (d) a $C_{3-10}$ cycloalkyl-carbonyl group, (e) a 3- to 14-membered non-aromatic heterocyclic group optionally substituted by 1 to 3 substituents selected from an oxo group, a hydroxy group and a $C_{1-6}$ alkyl group (the 3- to 14-membered non-aromatic heterocyclic group also includes one having a bicyclo ring structure, a bridged ring structure, or a spiro ring structure) and (f) a 5- to 14-membered aromatic heterocyclic group, (9) a carbamoyl group, (10) a 3- to 14-membered non-aromatic heterocyclic group optionally substituted by 1 to 3 substituents selected from (a) an oxo group, (b) a halogen atom, (c) a hydroxy group, (d) a cyano group, (e) a $C_{1-6}$ alkyl group optionally substituted by 1 to 3 substituents selected from a halogen atom, a hydroxy group and a $C_{1-6}$ alkoxy group, (f) a $C_{3-10}$ cycloalkyl group, (g) a $C_{1-6}$ alkoxy group optionally substituted by 1 to 3 halogen atoms, (h) a $C_{1-6}$ alkyl-carbonyl group, (i) a carbamoyl group, (j) a $C_{1-6}$ alkylsulfonyl group, (k) a ($C_{1-6}$ alkyl) ($C_{1-6}$ alkyl-carbonyl)amino group, (l) a dimethyl(oxide)-$\lambda^6$-sulfanylideneamino group and (m) a methylimino group (the 3- to 14-membered non-aromatic heterocyclic group also includes one having a bicyclo ring structure, a bridged ring structure, or a spiro ring structure) and (11) a 5- to 14-membered aromatic heterocyclic group optionally substituted by 1 to 3 substituents selected from (a) an oxo group, (b) a hydroxy group, (c) a cyano group, (d) a halogen atom, (e) a $C_{1-6}$ alkyl group optionally substituted by 1 to 3 substituents selected from a hydroxy group, a halogen atom, a $C_{3-10}$ cycloalkyl group, a $C_{6-14}$ aryl group, a $C_{1-6}$ alkoxy-carbonyl group and a carbamoyl group, (f) a $C_{1-6}$ alkoxy group, (g) a $C_{1-6}$ alkoxy-carbonyl group, (h) a $C_{1-6}$ alkylsulfonyl group and (i) a 3- to 14-membered non-aromatic heterocyclic group.

[8] The compound of [1], wherein
$R^1$ is (1) a $C_{1-6}$ alkyl group optionally substituted by 1 to 3 substituents selected from a $C_{6-14}$ aryl group, a $C_{6-14}$ aryloxy group and a 5- to 14-membered aromatic heterocyclic group, (2) a $C_{1-6}$ alkoxy group optionally substituted by 1 to 3 substituents selected from a $C_{6-14}$ aryl group and a 5- to 14-membered aromatic heterocyclic group, or (3) —NR$^2$R$^3$ [R$^2$ is a hydrogen atom, and R$^3$ is a $C_{1-6}$ alkyl group optionally substituted by 1 to 3 substituents selected from (a) a $C_{6-14}$ aryl group optionally substituted by 1 to 3 halogen atoms and (b) a 5- to 14-membered aromatic heterocyclic group];

ring A is a $C_{6-14}$ aromatic hydrocarbon ring or a 5- to 14-membered aromatic heterocycle each of which is optionally further substituted by 1-5 substituents selected from (a) an oxo group, (b) a $C_{1-6}$ alkyl group and (c) a 5- to 14-membered aromatic heterocyclic group optionally substituted by 1 to 3 substituents selected from a $C_{1-6}$ alkoxy group;
ring B is a cyclohexane ring not substituted further; and
ring C is a pyrimidine ring (that is, X is N) optionally further substituted by 1 to 3 substituents selected from (1) a cyano group, (2) a $C_{1-6}$ alkyl group optionally substituted by 1 to 3 halogen atoms, (3) a 3- to 14-membered non-aromatic heterocyclic-oxy group, (4) an amino group optionally mono- or di-substituted by substituent(s) selected from (a) a $C_{1-6}$ alkyl group optionally substituted by 1 to 3 hydroxy groups and (b) a 3- to 14-membered non-aromatic heterocyclic group optionally substituted by 1 to 3 $C_{1-6}$ alkyl groups (the 3- to 14-membered non-aromatic heterocyclic group also includes one having a bicyclo ring structure, a bridged ring structure, or a spiro ring structure), (5) a 3- to 14-membered non-aromatic heterocyclic group optionally substituted by 1 to 3 substituents selected from (a) a halogen atom, (b) a hydroxy group and (c) a $C_{1-6}$ alkyl group optionally substituted by 1 to 3 hydroxy groups (the 3- to 14-membered non-aromatic heterocyclic group also includes one having a bicyclo ring structure, a bridged ring structure, or a spiro ring structure) and (6) a 5- to 14-membered aromatic heterocyclic group optionally substituted by 1 to 3 substituents selected from (a) a cyano group, (b) a halogen atom, (c) a $C_{1-6}$ alkyl group and (d) a $C_{1-6}$ alkylsulfonyl group.

[9] The compound of [1], wherein
$R^1$ is (1) a $C_{1-6}$ alkyl group optionally substituted by 1 to 3 substituents selected from a halogen atom, an optionally substituted $C_{3-10}$ cycloalkyl group, an optionally substituted $C_{1-6}$ alkoxy group, an optionally substituted $C_{6-14}$ aryl group and an optionally substituted $C_{6-14}$ aryloxy group, (2) a $C_{1-6}$ alkoxy group optionally substituted by 1 to 3 substituents selected from a halogen atom, a hydroxy group, an optionally substituted $C_{3-10}$ cycloalkyl group, an optionally substituted $C_{1-6}$ alkoxy group, an optionally substituted $C_{6-14}$ aryl group, an optionally substituted amino group, an optionally substituted 3- to 14-membered non-aromatic heterocyclic group and an optionally substituted 5- to 14-membered aromatic heterocyclic group, (3) an optionally substituted $C_{6-14}$ aryl group, (4) a 3- to 14-membered non-aromatic heterocyclic group optionally substituted by 1 to 3 substituents selected from a halogen atom, a hydroxy group, an optionally substituted $C_{1-6}$ alkyl group, an optionally substituted $C_{1-6}$ alkoxy group and an optionally substituted $C_{6-14}$ aryl group or (5) —$NR^2R^3$ [$R^2$ is a hydrogen atom or a $C_{1-6}$ alkyl group optionally substituted by 1 to 3 substituents selected from an optionally substituted $C_{6-14}$ aryl group, and $R^3$ is (i) a $C_{1-6}$ alkyl group optionally substituted by 1 to 3 substituents selected from a halogen atom, a hydroxy group, an optionally substituted $C_{3-10}$ cycloalkyl group, an optionally substituted $C_{1-6}$ alkoxy group, an optionally substituted $C_{6-14}$ aryl group, an optionally substituted amino group, an optionally substituted 3- to 14-membered non-aromatic heterocyclic group and an optionally substituted 5- to 14-membered aromatic heterocyclic group, (ii) an optionally substituted $C_{3-10}$ cycloalkyl group or (iii) an optionally substituted $C_{6-14}$ aryl group];
ring A is a $C_{6-14}$ aromatic hydrocarbon ring or a 5- to 14-membered aromatic heterocycle each of which is optionally further substituted by 1-5 substituents selected from (1) a halogen atom, (2) a cyano group, (3) a hydroxy group, (4) an optionally substituted $C_{1-6}$ alkyl group, (5) an optionally substituted $C_{2-6}$ alkenyl group, (6) an optionally substituted $C_{6-14}$ aryl group, (7) an optionally substituted $C_{1-6}$ alkoxy group, (8) an optionally substituted amino group, (9) a carboxy group, (10) an optionally substituted carbamoyl group, (11) an optionally substituted 3- to 14-membered non-aromatic heterocyclic group (the 3- to 14-membered non-aromatic heterocyclic group also includes one having a spiro ring structure) and (12) an optionally substituted 5- to 14-membered aromatic heterocyclic group;
ring B is a cyclohexane ring not substituted further; and
ring C is a pyridine ring (that is, X is CH) or a pyrimidine ring (that is, X is N) each of which is optionally further substituted by 1 to 3 substituents selected from (1) a halogen atom, (2) a cyano group, (3) an optionally substituted $C_{1-6}$ alkyl group, (4) an optionally substituted $C_{6-14}$ aryl group, (5) an optionally substituted $C_{1-6}$ alkoxy group, (6) an optionally substituted $C_{6-14}$ aryloxy group, (7) an optionally substituted 3- to 14-membered non-aromatic heterocyclic-oxy group, (8) an optionally substituted amino group, (9) an optionally substituted carbamoyl group, (10) an optionally substituted 3- to 14-membered non-aromatic heterocyclic group (the 3- to 14-membered non-aromatic heterocyclic group also includes one having a bicyclo ring structure, a bridged ring structure, or a spiro ring structure) and (11) an optionally substituted 5- to 14-membered aromatic heterocyclic group.

[10] The compound of [1], wherein
$R^1$ is (1) a $C_{1-6}$ alkyl group optionally substituted by 1 to 3 substituents selected from a halogen atom, a $C_{3-10}$ cycloalkyl group, a $C_{1-6}$ alkoxy group, and a $C_{6-14}$ aryloxy group, (2) a $C_{1-6}$ alkoxy group optionally substituted by 1 to 3 substituents selected from (a) a halogen atom, (b) a hydroxy group, (c) a $C_{3-10}$ cycloalkyl group optionally substituted by 1 to 3 substituents selected from a halogen atom and an amino group, (d) a $C_{6-14}$ aryl group, (e) a $C_{1-6}$ alkoxy group, (f) an amino group optionally mono- or di-substituted by a $C_{1-6}$ alkyl group, (g) a 3- to 14-membered non-aromatic heterocyclic group optionally substituted by 1 to 3 halogen atoms and (h) a 5- to 14-membered aromatic heterocyclic group, (3) a 3- to 14-membered non-aromatic heterocyclic group optionally substituted by 1 to 3 substituents selected from a halogen atom, a hydroxy group, a $C_{1-6}$ alkyl group, a $C_{1-6}$ alkoxy group and a $C_{6-14}$ aryl group or (4) —$NR^2R^3$ [$R^2$ is a hydrogen atom or a $C_{1-6}$ alkyl group, and $R^3$ is (i) a $C_{1-6}$ alkyl group optionally substituted by 1 to substituents selected from (a) a halogen atom, (b) a hydroxy group, (c) a $C_{3-10}$ cycloalkyl group optionally substituted by 1 to 3 substituents selected from a halogen atom and an amino group, (d) a $C_{1-6}$ alkoxy group, (e) a $C_{6-14}$ aryl group optionally substituted by 1 to 3 halogen atoms, (f) an amino group optionally mono- or di-substituted by a $C_{1-6}$ alkyl group, (g) a 3- to 14-membered non-aromatic heterocyclic group and (h) a 5-to 14-membered aromatic heterocyclic group, or (ii) a $C_{3-10}$ cycloalkyl group optionally substituted by 1 to 3 halogen atoms];
ring A is a $C_{6-14}$ aromatic hydrocarbon ring or a 5- to 14-membered aromatic heterocycle each of which is optionally further substituted by 1-5 substituents selected from (1) a halogen atom, (2) a $C_{1-6}$ alkyl group optionally substituted by 1 to 3 substituents selected from (a) a halogen atom and (b) a $C_{3-10}$ cycloalkyl group, (3) a $C_{1-6}$ alkoxy group optionally substituted by 1 to 3 substituents selected from (a) a halogen atom, (b) a $C_{1-6}$ alkoxy group and (c) a carbamoyl group optionally mono- or di-substituted by a $C_{1-6}$ alkyl group, (4) a carbamoyl group optionally mono- or di-substituted by a C$_{1-6}$ alkyl group optionally substituted by a C$_{1-6}$ alkoxy group, (5) a 3- to 14-membered non-aromatic heterocyclic group (the 3- to 14-membered non-aromatic heterocyclic group also includes one having a spiro ring structure) and (6) a 5- to 14-membered aromatic heterocyclic group optionally substituted by 1 to 3 substituents selected from (a) an oxo group, (b) a C$_{1-6}$ alkyl group optionally substituted by 1 to 3 substituents selected from a halogen atom, a C$_{3-10}$ cycloalkyl group and a 3- to 14-membered non-aromatic heterocyclic group, (c) a C$_{3-10}$ cycloalkyl group, (d) a C$_{1-6}$ alkoxy group, (e) an amino group, (f) a carboxy group, (g) a C$_{1-6}$ alkoxy-carbonyl group and (h) a 3- to 14-membered non-aromatic heterocyclic group;

ring B is a cyclohexane ring not substituted further;

ring C is a pyrimidine ring (that is, X is N) optionally further substituted by 1 to 3 substituents selected from (1) a halogen atom, (2) a cyano group, (3) C$_{1-6}$ alkyl group optionally substituted by 1 to 3 halogen atoms, (4) a C$_{6-14}$ aryl group optionally substituted by 1 to 3 substituents selected from (a) a halogen atom, (b) a cyano group, (c) a C$_{1-6}$ alkyl group optionally substituted by 1 to 3 halogen atoms, (d) a C$_{1-6}$ alkoxy group optionally substituted by 1 to 3 halogen atoms, (e) a mono- or di-C$_{1-6}$ alkylamino group, (f) a C$_{1-6}$ alkyl-carbonylamino group, (g) a C$_{1-6}$ alkyl-carbonyl group, (h) a carbamoyl group, (i) a sulfamoyl group and (j) a 3- to 14-membered non-aromatic heterocyclic-sulfonyl group, (5) a C$_{1-6}$ alkoxy group optionally substituted by 1 to 3 substituents selected from (a) a halogen atom, (b) a 3- to 14-membered non-aromatic heterocyclic group and (c) a 5- to 14-membered aromatic heterocyclic group optionally substituted by 1 to 3 C$_{1-6}$ alkyl groups, (6) a C$_{6-14}$ aryloxy group optionally substituted by 1 to 3 C$_{1-6}$ alkylsulfonyl groups, (7) a 3- to 14-membered non-aromatic heterocyclic-oxy group optionally substituted by 1 to 3 C$_{1-6}$ alkyl groups, (8) an amino group optionally mono- or di-substituted by substituent(s) selected from (a) a C$_{1-6}$ alkyl group optionally substituted by 1 to 3 substituents selected from (i) a halogen atom, (ii) a hydroxy group, (iii) a cyano group, (iv) a C$_{3-10}$ cycloalkyl group optionally substituted by 1 to 3 hydroxy groups, (v) a C$_{6-14}$ aryl group optionally substituted by 1 to 3 substituents selected from a C$_{1-6}$ alkylsulfonyl group and a sulfamoyl group, (vi) a C$_{1-6}$ alkoxy group optionally substituted by 1 to 3 halogen atoms, (vii) a mono- or di-C$_{1-6}$ alkylamino group, (viii) a C$_{1-6}$ alkyl-carbonylamino group, (ix) a carbamoyl group, (x) a C$_{1-6}$ alkylsulfonyl group, (xi) a 3- to 14-membered non-aromatic heterocyclic group optionally substituted by 1 to 3 substituents selected from an oxo group and a C$_{1-6}$ alkyl group and (xii) a 5- to 14-membered aromatic heterocyclic group optionally substituted by 1 to 3 substituents selected from a C$_{1-6}$ alkyl group, a C$_{3-10}$ cycloalkyl group and a (C$_{1-6}$ alkyl) (C$_{1-6}$ alkyl-sulfonyl)amino group, (b) a C$_{3-10}$ cycloalkyl group optionally substituted by 1 to 3 substituents selected from a halogen atom, a hydroxy group, a C$_{1-6}$ alkyl group optionally substituted by 1 to 3 hydroxy groups and a C$_{1-6}$ alkoxy group optionally substituted by 1 to 3 halogen atoms (the C$_{3-10}$ cycloalkyl group also includes one having a spiro ring structure), (c) a C$_{6-14}$ aryl group optionally substituted by 1 to 3 C$_{1-6}$ alkylsulfonyl groups, (d) a C$_{3-10}$ cycloalkyl-carbonyl group, (e) a 3- to 14-membered non-aromatic heterocyclic group optionally substituted by 1 to 3 substituents selected from an oxo group, a hydroxy group and a C$_{1-6}$ alkyl group (the 3- to 14-membered non-aromatic heterocyclic group also includes one having a bicyclo ring structure, a bridged ring structure, or a spiro ring structure) and (f) a 5- to 14-membered aromatic heterocyclic group, (9) a carbamoyl group, (10) a 3- to 14-membered non-aromatic heterocyclic group optionally substituted by 1 to 3 substituents selected from (a) an oxo group, (b) a halogen atom, (c) a hydroxy group, (d) a cyano group, (e) a C$_{1-6}$ alkyl group optionally substituted by 1 to 3 substituents selected from a halogen atom, a hydroxy group and a C$_{1-6}$ alkoxy group, (f) a C$_{3-10}$ cycloalkyl group, (g) a C$_{1-6}$ alkoxy group optionally substituted by 1 to 3 halogen atoms, (h) a C$_{1-6}$ alkyl-carbonyl group, (i) a carbamoyl group, (j) a C$_{1-6}$ alkylsulfonyl group, (k) a (C$_{1-6}$ alkyl) (C$_{1-6}$ alkyl-carbonyl)amino group, (l) a dimethyl(oxide)-$\lambda^6$-sulfanylideneamino group and (m) a methylimino group (the 3- to 14-membered non-aromatic heterocyclic group also includes one having a bicyclo ring structure, a bridged ring structure, or a spiro ring structure) and (11) a 5- to 14-membered aromatic heterocyclic group optionally substituted by 1 to 3 substituents selected from (a) an oxo group, (b) a hydroxy group, (c) a cyano group, (d) a halogen atom, (e) a C$_{1-6}$ alkyl group optionally substituted by 1 to 3 substituents selected from a hydroxy group, a halogen atom, a C$_{3-10}$ cycloalkyl group, a C$_{6-14}$ aryl group, a C$_{1-6}$ alkoxy-carbonyl group and a carbamoyl group, (f) a C$_{3-10}$ cycloalkyl group, (g) a C$_{1-6}$ alkoxy group, (h) a C$_{1-6}$ alkoxy-carbonyl group, (i) a C$_{1-6}$ alkylsulfonyl group and (j) a 3- to 14-membered non-aromatic heterocyclic group.

[11] The compound of [1], wherein

R$^1$ is (1) a C$_{1-6}$ alkyl group optionally substituted by 1 to 3 substituents selected from a halogen atom, a C$_{1-6}$ alkoxy group and a C$_{6-14}$ aryloxy group, (2) a C$_{1-6}$ alkoxy group optionally substituted by 1 to 3 substituents selected from (a) a halogen atom, (b) a hydroxy group, (c) a C$_{6-14}$ aryl group, (d) an amino group optionally mono- or di-substituted by a C$_{1-6}$ alkyl group and (e) a 5- to 14-membered aromatic heterocyclic group or (3) —NR$^2$R$^3$ [R$^2$ is a hydrogen atom, and R$^3$ is a C$_{1-6}$ alkyl group optionally substituted by 1 to 3 substituents selected from (a) a halogen atom, (b) a hydroxy group, (c) a C$_{3-10}$ cycloalkyl group optionally substituted by 1 to 3 halogen atoms, (d) a C$_{6-14}$ aryl group optionally substituted by 1 to 3 halogen atoms and (e) a 5- to 14-membered aromatic heterocyclic group];

ring A is a C$_{6-14}$ aromatic hydrocarbon ring or a 5- to 14-membered aromatic heterocycle each of which is optionally further substituted by 1-5 substituents selected from a 5- to 14-membered aromatic heterocyclic group optionally substituted by 1 to 3 substituents selected from (a) an oxo group, (b) a C$_{1-6}$ alkyl group and (c) a C$_{1-6}$ alkoxy group;

ring B is a cyclohexane ring not substituted further; and ring C is a pyrimidine ring (that is, X is N) optionally further substituted by 1 to 3 substituents selected from (1) a cyano group, (2) a C$_{1-6}$ alkyl group optionally substituted by 1 to 3 halogen atoms, (3) a 3- to 14-membered non-aromatic heterocyclic-oxy group, (4) an amino group optionally mono- or di-substituted by substituent(s) selected from (a) a C$_{1-6}$ alkyl group optionally substituted by 1 to 3 hydroxy groups and (b) a 3- to 14-membered non-aromatic heterocyclic group optionally substituted by 1 to 3 C$_{1-6}$ alkyl groups (the 3- to 14-membered non-aromatic heterocyclic group also includes one having a bicyclo ring structure, a bridged ring structure, or a spiro ring structure), (5) a 3- to 14-membered non-aromatic heterocyclic group optionally substituted by 1 to 3 substituents selected from (a) a halogen atom, (b) a hydroxy group and (c) a $C_{1-6}$ alkyl group optionally substituted by 1 to hydroxy groups (the 3- to 14-membered non-aromatic heterocyclic group also includes one having a bicyclo ring structure, a bridged ring structure, or a spiro ring structure) and (6) a 5- to 14-membered aromatic heterocyclic group optionally substituted by 1 to 3 substituents selected from (a) a cyano group, (b) a halogen atom, (c) a $C_{1-6}$ alkyl group optionally substituted by 1 to 3 halogen atoms and (d) a $C_{1-6}$ alkylsulfonyl group.

[12] A medicament comprising the compound of [1] or a salt thereof.

[13] The medicament of [12], wherein the medicament is a CDK12 inhibitor.

[14] The medicament of [12], wherein the medicament is a prophylactic or therapeutic drug for cancer.

Advantageous Effects of Invention

The compound of the present invention may have a CDK12 inhibitory action, and may be useful as a medicament such as a prophylactic or therapeutic drug for cancer and the like.

BRIEF DESCRIPTION OF DRAWINGS

FIG. 1 shows the binding of BODIPY-FL-labeled AT-7519 to CDK12/CycK protein by TR-FRET. Black and white circles show TR-FRET signals in the absence and presence of 2 μM AT-7519, respectively.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "$C_{1-12}$ alkyl group" include heptyl, octyl, nonyl, decyl, undecyl, and dodecyl in addition to the above-mentioned "$C_{1-6}$ alkyl group".

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-4}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-4}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),

(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group and (62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5-to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacridinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituent selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$ alkyl)amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl)amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl)amino group (e.g., N-acetyl-N-methylamino) and a ($C_{1-6}$ alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 selected from substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5-to 14-membered aromatic heterocyclyl-carbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho [2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

In the present specification, examples of the "aromatic ring" of the "optionally further substituted aromatic ring" include the above-mentioned "$C_{6-14}$ aromatic hydrocarbon ring" and "aromatic heterocycle". As the substituent thereof, the above-mentioned "substituent" can be mentioned.

In the present specification, examples of the "6-membered nitrogen-containing aromatic heterocycle" of the "optionally further substituted 6-membered nitrogen-containing aromatic heterocycle" include the above-mentioned "aromatic heterocycle" that is 6-membered and contains at least one nitrogen atom as the constituting atom. As the substituent thereof, the above-mentioned "substituent" can be mentioned.

The definition of each symbol in the formula (I) is explained below.

$R^1$ is an optionally substituted $C_{1-6}$ alkyl group, an optionally substituted $C_{1-6}$ alkoxy group, an optionally substituted $C_{6-14}$ aryl group, an optionally substituted heterocyclic group, or —$NR^2R^3$; $R^2$ is a hydrogen atom or a substituent; and $R^3$ is a substituent.

Examples of the "substituent" of the "optionally substituted $C_{1-6}$ alkyl group" for $R^1$ include an optionally substituted $C_{6-14}$ aryl group (e.g., phenyl), an optionally substituted $C_{6-14}$ aryloxy group (e.g., phenoxy), and an optionally substituted 5- to 14-membered aromatic heterocyclic group (e.g., pyridyl).

Examples of the "substituent" of the "optionally substituted $C_{1-6}$ alkoxy group" for $R^1$ include an optionally substituted $C_{6-14}$ aryl group (e.g., phenyl), and an optionally substituted 5- to 14-membered aromatic heterocyclic group (e.g., pyridyl).

Examples of the "heterocyclic group" of the "optionally substituted heterocyclic group" for $R^1$ include a 3- to 14-membered non-aromatic heterocyclic group (e.g., azetidinyl, tetrahydropyranyl). As the "substituent" thereof, an optionally substituted $C_{6-14}$ aryl group (e.g., phenyl) can be mentioned.

Examples of the "substituent" for $R^2$ include an optionally substituted $C_{1-6}$ alkyl group (e.g., methyl, ethyl).

Examples of the "substituent" for $R^3$ include an optionally substituted $C_{1-6}$ alkyl group (e.g., methyl, ethyl, neopentyl), and an optionally substituted $C_{6-14}$ aryl group (e.g., phenyl).

$R^1$ is preferably
(1) a $C_{1-6}$ alkyl group (e.g., methyl, ethyl, isopropyl) optionally substituted by 1 to 3 substituents selected from an optionally substituted $C_{6-14}$ aryl group (e.g., phenyl), an optionally substituted $C_{6-14}$ aryloxy group (e.g., phenoxy) and an optionally substituted 5- to 14-membered aromatic heterocyclic group (e.g., pyridyl), (2) a $C_{1-6}$ alkoxy group (e.g., methoxy) optionally substituted by 1 to 3 substituents selected from an optionally substituted $C_{6-14}$ aryl group (e.g., phenyl) and an optionally substituted 5- to 14-membered aromatic heterocyclic group (e.g., pyridyl), (3) an optionally substituted $C_{6-14}$ aryl group (e.g., phenyl), (4) a 3- to 14-membered non-aromatic heterocyclic group (e.g., azetidinyl, tetrahydropyranyl) optionally substituted by 1 to 3 substituents selected from an optionally substituted $C_{6-14}$ aryl group (e.g., phenyl) or (5) —$NR^2R^3$[$R^2$ is a hydrogen atom or a $C_{1-6}$ alkyl group (e.g., methyl, ethyl) optionally substituted by 1 to 3 substituents selected from an optionally substituted $C_{6-14}$ aryl group (e.g., phenyl), $R^3$ is (i) a $C_{1-6}$ alkyl group (e.g., methyl, ethyl, neopentyl) optionally substituted by 1 to 3 substituents selected from an optionally substituted $C_{3-10}$ cycloalkyl group (e.g., cyclopropyl, cyclohexyl), an optionally substituted $C_{6-14}$ aryl group (e.g., phenyl), an optionally substituted 3- to 14-membered non-aromatic heterocyclic group (e.g., tetrahydropyranyl) and an optionally substituted 5- to 14-membered aromatic heterocyclic group (e.g., furyl, thienyl, thiazolyl, pyridyl, pyrimidinyl) or (ii) an optionally substituted $C_{6-14}$ aryl group (e.g., phenyl).

$R^1$ is more preferably,
(1) a $C_{1-6}$ alkyl group (e.g., methyl, ethyl, isopropyl) optionally substituted by 1 to 3 substituents selected from a $C_{6-14}$ aryl group (e.g., phenyl) optionally substituted by 1 to 3 halogen atoms (e.g., chlorine atom), a $C_{6-14}$ aryloxy group (e.g., phenoxy) and a 5- to 14-membered aromatic heterocyclic group (e.g., pyridyl), (2) a $C_{1-6}$ alkoxy group (e.g., methoxy) optionally substituted by 1 to 3 substituents selected from a $C_{6-14}$ aryl group (e.g., phenyl) and a 5- to 14-membered aromatic heterocyclic group (e.g., pyridyl), (3) a $C_{6-14}$ aryl group (e.g., phenyl), (4) a 3- to 14-membered non-aromatic heterocyclic group (e.g., azetidinyl, tetrahydropyranyl) optionally substituted by 1 to 3 $C_{6-14}$ aryl groups (e.g., phenyl) or (5) —$NR^2R^3$ [$R^2$ is a hydrogen atom or a $C_{1-6}$ alkyl group (e.g., methyl, ethyl) optionally substituted by 1 to 3 $C_{6-14}$ aryl groups (e.g., phenyl), $R^3$ is (i) a $C_{1-6}$ alkyl group (e.g., methyl, ethyl, neopentyl) optionally substituted by 1 to 3 substituents selected from (a) a $C_{3-10}$ cycloalkyl group (e.g., cyclopropyl, cyclohexyl), (b) a $C_{6-14}$ aryl group (e.g., phenyl) optionally substituted by 1 to 3 substituents selected from a halogen atom (e.g., fluorine atom), a cyano group, a $C_{1-6}$ alkoxy group (e.g., methoxy), a $C_{1-6}$ alkylsulfonyl group (e.g., methylsulfonyl) and a $C_{1-6}$ alkylsulfonylamino group (e.g., methylsulfonylamino), (c) a 3- to 14-membered non-aromatic heterocyclic group (e.g., tetrahydropyranyl) and (d) a 5- to 14-membered aromatic heterocyclic group (e.g., furyl, thienyl, thiazolyl, pyridyl, pyrimidinyl) optionally substituted by 1 to 3 substituents selected from a $C_{1-6}$ alkyl group (e.g., methyl) and a $C_{1-6}$ alkoxy group (e.g., methoxy) or (ii) a $C_{6-14}$ aryl group (e.g., phenyl)].

$R^1$ is further preferably,
(1) a $C_{1-6}$ alkyl group (e.g., methyl, ethyl) optionally substituted by 1 to 3 substituents selected from a $C_{6-14}$ aryl group (e.g., phenyl), a $C_{6-14}$ aryloxy group (e.g., phenoxy) and a 5- to 14-membered aromatic heterocyclic group (e.g., pyridyl), (2) a $C_{1-6}$ alkoxy group (e.g., methoxy) optionally substituted by 1 to 3 substituents selected from a $C_{6-14}$ aryl group (e.g., phenyl) and a 5- to 14-membered aromatic heterocyclic group (e.g., pyridyl) or (3) —$NR^2R^3$ [$R^2$ is a hydrogen atom, and $R^3$ is a $C_{1-6}$ alkyl group (e.g., methyl) optionally substituted by 1 to substituents selected from (a) a $C_{6-14}$ aryl group (e.g., phenyl) optionally substituted by 1 to 3 halogen atoms (e.g., fluorine atom) and (b) a 5- to 14-membered aromatic heterocyclic group (e.g., pyridyl)].

Ring A is an optionally further substituted aromatic ring.

Examples of the "aromatic ring" of the "optionally further substituted aromatic ring" for ring A include a $C_{6-14}$ aromatic hydrocarbon ring (e.g., benzene ring), and a 5- to 14-membered aromatic heterocycle (e.g., pyridine ring, pyrimidine ring, pyridazine ring, pyrazine ring, indazole ring, pyrazolopyridine ring).

The "aromatic ring" of the "optionally further substituted aromatic ring" for ring A is optionally further substituted by 1-5 (preferably 1-3, more preferably 1-2) substituents at substitutable position(s). Examples of such substituent include the above-mentioned "substituent".

In one embodiment of the present invention, the "aromatic ring" of the "optionally further substituted aromatic ring" for ring A is preferably further substituted by a substituent at the 3-position or the 4-position with the position bonded to the nitrogen atom substituted by $R^1CO$ as the 1-position.

The substituent of the "aromatic ring" of the "optionally further substituted aromatic ring" for ring A is preferably
(1) a halogen atom (e.g., fluorine atom, chlorine atom, bromine atom), (2) a cyano group, (3) a hydroxy group, (4) an optionally substituted $C_{1-6}$ alkyl group (e.g., methyl, ethyl), (5) an optionally substituted $C_{2-6}$ alkenyl group (e.g., ethenyl, 2-propenyl), (6) an optionally substituted $C_{6-14}$ aryl group (e.g., phenyl), (7) an optionally substituted $C_{1-6}$ alkoxy group (e.g., methoxy), (8) an optionally substituted amino group, (9) a carboxy group, (10) an optionally substituted carbamoyl group, (11) an optionally substituted 3- to 14-membered non-aromatic heterocyclic group (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5]nonyl) or (12) an optionally substituted 5- to 14-membered aromatic heterocyclic group (e.g., thienyl, pyrazolyl, imidazolyl, thiazolyl, furyl, oxazolyl, pyridyl, pyrimidinyl, pyrazinyl).

The substituent of the "aromatic ring" of the "optionally further substituted aromatic ring" for ring A is more preferably,
(1) a halogen atom (e.g., fluorine atom, chlorine atom, bromine atom), (2) a cyano group, (3) a hydroxy group, (4) a $C_{1-6}$ alkyl group (e.g., methyl, ethyl) optionally substituted by 1 to 3 substituents selected from (a) a halogen atom (e.g., fluorine atom), (b) a $C_{1-6}$ alkoxy group (e.g., methoxy) and (c) a 3- to 14-membered non-aromatic heterocyclic group (e.g., piperazinyl, piperidinyl, morpholinyl) optionally substituted 1 to 3 $C_{1-6}$ alkyl groups (e.g., methyl), (5) a $C_{2-6}$ alkenyl group (e.g., ethenyl, 2-propenyl), (6) a $C_{6-14}$ aryl group (e.g., phenyl) optionally substituted by 1 to 3 substituents selected from (a) a halogen atom (e.g., fluorine atom), (b) a cyano group, (c) a $C_{1-6}$ alkoxy group (e.g., methoxy) and (d) a carbamoyl group, (7) a $C_{1-6}$ alkoxy group (e.g., methoxy), (8) an amino group optionally mono- or di-substituted by substituent(s) selected from (a) a $C_{1-6}$ alkyl group (e.g., ethyl) optionally substituted by 1 to 3 $C_{1-6}$ alkoxy groups (e.g., methoxy), (b) a $C_{6-14}$ aryl group (e.g., phenyl) optionally substituted by 1 to 3 substituents selected from a cyano group and a $C_{1-6}$ alkoxy group (e.g., methoxy) and (c) a 5- to 14-membered aromatic heterocyclic group (e.g., pyrazolyl, pyridyl) optionally substituted by 1 to 3 $C_{1-6}$ alkyl groups (e.g., methyl), (9) a carboxy group, (10) a carbamoyl group optionally mono- or di-substituted by a $C_{1-6}$ alkyl group (e.g., methyl), (11) a 3- to 14-membered non-aromatic heterocyclic group optionally substituted by 1 to 3 substituents selected from (a) an oxo group, (b) a cyano group, (c) a $C_{1-6}$ alkyl group (e.g., methyl), (d) a $C_{1-6}$ alkoxy group (e.g., methoxy), (e) a $C_{1-6}$ alkyl-carbonyl (e.g., methylcarbonyl), (f) a carbamoyl group, (g) a mono- or di-$C_{1-6}$ alkylamino group (e.g., dimethylamino) and (h) a $C_{1-6}$ alkylsulfonyl group (e.g., methylsulfonyl) (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5]nonyl) or (12) a 5- to 14-membered aromatic heterocyclic group (e.g., thienyl, pyrazolyl, imidazolyl, thiazolyl, furyl, oxazolyl, pyridyl, pyrimidinyl, pyrazinyl) optionally substituted by 1 to 3 substituents selected from (a) an oxo group, (b) a $C_{1-6}$ alkyl group (e.g., methyl, ethyl, isopropyl, isobutyl) optionally substituted by 1 to 3 substituents selected from a hydroxy group, a $C_{1-6}$ alkoxy group (e.g., methoxy), a carbamoyl group, a 3- to 14-membered non-aromatic heterocyclic group (e.g., morpholinyl) and a 5- to 14-membered aromatic heterocyclic group (e.g., pyridyl), (c) a $C_{1-6}$ alkoxy group (e.g., methoxy), (d) an amino group, (e) a carboxy group, (f) a $C_{1-6}$ alkoxy-carbonyl group (e.g., methoxycarbonyl, ethoxycarbonyl), (g) a carbamoyl group and (h) a 3- to 14-membered non-aromatic heterocyclic group (e.g., tetrahydropyranyl).

The substituent of the "aromatic ring" of the "optionally further substituted aromatic ring" for ring A is further preferably,
a 5- to 14-membered aromatic heterocyclic group (e.g., pyrazolyl, pyridyl, pyrimidinyl) optionally substituted by 1 to substituents selected from (a) an oxo group, (b) a $C_{1-6}$ alkyl group (e.g., methyl) and (c) a $C_{1-6}$ alkoxy group (e.g., methoxy)

Ring A is preferably a $C_{6-14}$ aromatic hydrocarbon ring (e.g., benzene ring) or a 5- to 14-membered aromatic heterocycle (e.g., pyridine ring, pyrimidine ring, pyridazine ring, pyrazine ring, indazole ring, pyrazolopyridine ring), each of which is optionally further substituted by 1-5 (preferably 1-3, more preferably 1-2) substituents selected from (1) a halogen atom (e.g., fluorine atom, chlorine atom, bromine atom), (2) a cyano group, (3) a hydroxy group, (4) an optionally substituted $C_{1-6}$ alkyl group (e.g., methyl, ethyl), (5) an optionally substituted $C_{2-6}$ alkenyl group (e.g., ethenyl, 2-propenyl), (6) an optionally substituted $C_{6-14}$ aryl group (e.g., phenyl), (7) an optionally substituted $C_{1-6}$ alkoxy group (e.g., methoxy), (8) an optionally substituted amino group, (9) a carboxy group, (10) an optionally substituted carbamoyl group, (11) an optionally substituted 3- to 14-membered non-aromatic heterocyclic group (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5]nonyl) and (12) an optionally substituted 5- to 14-membered aromatic heterocyclic group (e.g., thienyl, pyrazolyl, imidazolyl, thiazolyl, furyl, oxazolyl, pyridyl, pyrimidinyl, pyrazinyl).

Ring A is more preferably, a $C_{6-14}$ aromatic hydrocarbon ring (e.g., benzene ring) or a 5- to 14-membered aromatic heterocycle (e.g., pyridine ring, pyrimidine ring, pyridazine ring, pyrazine ring, indazole ring, pyrazolopyridine ring), each of which is optionally further substituted by 1-5 (preferably 1-3, more preferably 1-2) substituents selected from (1) a halogen atom (e.g., fluorine atom, chlorine atom, bromine atom), (2) a cyano group, (3) a hydroxy group, (4) a $C_{1-6}$ alkyl group (e.g., methyl, ethyl) optionally substituted by 1 to 3 substituents selected from (a) a halogen atom (e.g., fluorine atom), (b) a $C_{1-6}$ alkoxy group (e.g., methoxy) and (c) a 3- to 14-membered non-aromatic heterocyclic group (e.g., piperazinyl, piperidinyl, morpholinyl) optionally substituted by 1 to 3 $C_{1-6}$ alkyl groups (e.g., methyl), (5) a $C_{2-6}$ alkenyl group (e.g., ethenyl, 2-propenyl), (6) a $C_{6-14}$ aryl group (e.g., phenyl) optionally substituted by 1 to 3 substituents selected from (a) a halogen atom (e.g., fluorine atom), (b) a cyano group, (c) a $C_{1-6}$ alkoxy group (e.g., methoxy) and (d) a carbamoyl group, (7) a $C_{1-6}$ alkoxy group (e.g., methoxy), (8) an amino group optionally mono- or di-substituted by substituent(s) selected from (a) a $C_{1-6}$ alkyl group (e.g., ethyl) optionally substituted by 1 to 3 $C_{1-6}$ alkoxy groups (e.g., methoxy), (b) a $C_{6-14}$ aryl group (e.g., phenyl) optionally substituted by 1 to 3 substituents selected from a cyano group and a $C_{1-6}$ alkoxy group (e.g., methoxy) and (c) a 5- to 14-membered aromatic heterocyclic group (e.g., pyrazolyl, pyridyl) optionally substituted by 1 to 3 $C_{1-6}$ alkyl groups (e.g., methyl), (9) a carboxy group, (10) a carbamoyl group optionally mono- or di-substituted by a $C_{1-6}$ alkyl group (e.g., methyl), (11) a 3- to 14-membered non-aromatic heterocyclic group optionally substituted by 1 to 3 substituents selected from (a) an oxo group, (b) a cyano group, (c) a $C_{1-6}$ alkyl group (e.g., methyl), (d) a $C_{1-6}$ alkoxy group (e.g., methoxy), (e) a $C_{1-6}$ alkyl-carbonyl group (e.g., methylcarbonyl), (f) a carbamoyl group, (g) a mono- or di-$C_{1-6}$ alkylamino group (e.g., dimethylamino) and (h) a $C_{1-6}$ alkylsulfonyl group (e.g., methylsulfonyl) (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5]nonyl) and (12) a 5- to 14-membered aromatic heterocyclic group (e.g., thienyl, pyrazolyl, imidazolyl, thiazolyl, furyl, oxazolyl, pyridyl, pyrimidinyl, pyrazinyl) optionally substituted by 1 to 3 substituents selected from (a) an oxo group, (b) a $C_{1-6}$ alkyl group (e.g., methyl, ethyl, isopropyl, isobutyl) optionally substituted by 1 to 3 substituents selected from a hydroxy group, a $C_{1-6}$ alkoxy group (e.g., methoxy), a carbamoyl group, a 3- to 14-membered non-aromatic heterocyclic group (e.g., morpholinyl) and a 5- to 14-membered aromatic heterocyclic group (e.g., pyridyl), (c) a $C_{1-6}$ alkoxy group (e.g., methoxy), (d) an amino group, (e) a carboxy group, (f) a $C_{1-6}$ alkoxy-carbonyl group (e.g., methoxycarbonyl, ethoxycarbonyl), (g) a carbamoyl group and (h) a 3- to 14-membered non-aromatic heterocyclic group (e.g., tetrahydropyranyl).

Ring A is further preferably, a $C_{6-14}$ aromatic hydrocarbon ring (e.g., benzene ring) or a 5- to 14-membered aromatic heterocycle (e.g., a pyridine ring, a pyrimidine ring, a pyridazine ring, a pyrazine ring), each of which is optionally further substituted by 1-5 (preferably 1-3, more preferably 1-2) substituents selected from (a) an oxo group, (b) a $C_{1-6}$ alkyl group (e.g., methyl) and (c) a 5- to 14-membered aromatic heterocyclic group (e.g., pyrazolyl, pyridyl, pyrimidinyl) optionally substituted by 1 to 3 substituents selected from a $C_{1-6}$ alkoxy group (e.g., methoxy).

Ring B is an optionally further substituted cyclohexane ring.

The "cyclohexane ring" of the "optionally further substituted cyclohexane ring" for ring B is optionally further substituted by 1-5 (preferably 1-3, more preferably 1-2) substituents at substitutable position(s). Examples of such substituent include the above-mentioned "substituent".

Ring B is preferably a cyclohexane ring not substituted further.

X is CH or N, and ring C is an optionally further substituted 6-membered nitrogen-containing aromatic heterocycle.

The "6-membered nitrogen-containing aromatic heterocycle" of the "optionally further substituted 6-membered nitrogen-containing aromatic heterocycle" for ring C is a pyridine ring (that is, X is CH), or a pyrimidine ring (that is, X is N).

The "6-membered nitrogen-containing aromatic heterocycle" of the "optionally further substituted 6-membered nitrogen-containing aromatic heterocycle" for ring C is optionally further substituted by 1-3 (preferably 1-2) substituents at substitutable position(s) (when X is CH, the CH is unsubstituted). Examples of such substituent include the above-mentioned "substituent".

In one embodiment of the present invention, the "6-membered nitrogen-containing aromatic heterocycle" of the "optionally further substituted 6-membered nitrogen-containing aromatic heterocycle" for ring C is preferably further substituted by substituent(s) at the 4-position and/or the 5-position, further preferably at both the 4-position and the 5-position.

The substituent of the "6-membered nitrogen-containing aromatic heterocycle" of the "optionally further substituted 6-membered nitrogen-containing aromatic heterocycle" for ring C is preferably (1) a halogen atom (e.g., fluorine atom, chlorine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) an optionally substituted $C_{6-14}$ aryloxy group (e.g., phenoxy), (7) an optionally substituted 3-to 14-membered non-aromatic heterocyclic-oxy group (e.g., oxetanyloxy), (8) an optionally substituted amino group, (9) an optionally substituted carbamoyl group, (10) an optionally substituted 3- to 14-membered non-aromatic heterocyclic group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) or (11) an optionally substituted 5- to 14-membered aromatic heterocyclic group (e.g., thienyl, pyrazolyl, imidazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl).

The substituent of the "6-membered nitrogen-containing aromatic heterocycle" of the "optionally further substituted 6-membered nitrogen-containing aromatic heterocycle" for ring C is more preferably (1) a halogen atom (e.g., fluorine atom, chlorine atom), (2) a cyano group, (3) a $C_{1-6}$ alkyl group (e.g., methyl) optionally substituted by 1 to 3 halogen atoms (e.g., fluorine atom), (4) a $C_{6-14}$ aryl group (e.g., phenyl) optionally substituted by 1 to 3 substituents selected from (a) a halogen atom (e.g., fluorine atom, chlorine atom), (b) a cyano group, (c) a $C_{1-6}$ alkyl group (e.g., methyl) optionally substituted by to 3 halogen atoms (e.g., fluorine atom), (d) a $C_{1-6}$ alkoxy group (e.g., methoxy) optionally substituted by 1 to 3 halogen atoms (e.g., fluorine atom), (e) a mono- or di-$C_{1-6}$ alkylamino group (e.g., dimethylamino), (f) a $C_{1-6}$ alkyl-carbonylamino group (e.g., acetylamino), (g) a $C_{1-6}$ alkyl-carbonyl group (e.g., methylcarbonyl), (h) a carbamoyl group, (i) a sulfamoyl group and (j) a 3- to 14-membered non-aromatic heterocyclic-sulfonyl group (e.g., morpholinylsulfonyl), (5) a $C_{1-6}$ alkoxy group (e.g., methoxy) optionally substituted by 1 to 3 substituents selected from (a) a halogen atom (e.g., fluorine atom) and (b) a 5- to 14-membered aromatic heterocyclic group (e.g., oxazolyl) optionally substituted by 1 to 3 $C_{1-6}$ alkyl groups (e.g., tert-butyl), (6) a $C_{6-14}$ aryloxy group (e.g., phenoxy) optionally substituted by 1 to 3 $C_{1-6}$ alkylsulfonyl groups (e.g., methylsulfonyl, isopropylsulfonyl), (7) a 3- to 14-membered non-aromatic heterocyclic-oxy group (e.g., oxetanyloxy), (8) an amino group optionally mono- or di-substituted by substituent(s) selected from (a) a $C_{1-6}$ alkyl group (e.g., methyl, ethyl, n-propyl, isopropyl, n-butyl, isobutyl, tert-butyl, neopentyl, 1,2-dimethylpropyl) optionally substituted by 1 to 3 substituents selected from (i) a halogen atom (e.g., fluorine atom), (ii) a hydroxy group, (iii) a cyano group, (iv) a $C_{3-10}$ cycloalkyl group (e.g., cyclopropyl, cyclobutyl, cyclopentyl, cyclohexyl) optionally substituted by 1 to 3 hydroxy groups, (v) a $C_{6-14}$ aryl group (e.g., phenyl) optionally substituted by 1 to 3 substituents selected from a $C_{1-6}$ alkylsulfonyl group (e.g., methylsulfonyl) and a sulfamoyl group, (vi) a $C_{1-6}$ alkoxy group (e.g., methoxy, ethoxy) optionally substituted by 1 to 3 halogen atoms (e.g., fluorine atom), (vii) a mono- or di-$C_{1-6}$ alkylamino group (e.g., dimethylamino), (viii) a $C_{1-6}$ alkyl-carbonylamino group (e.g., acetylamino), (ix) a carbamoyl group, (x) a $C_{1-6}$ alkylsulfonyl group (e.g., methylsulfonyl), (xi) a 3- to 14-membered non-aromatic heterocyclic group (e.g., oxetanyl, thietanyl, morpholinyl, pyrrolidinyl, tetrahydrofuryl, tetrahydropyranyl) optionally substituted by 1 to 3 substituents selected from an oxo group and a $C_{1-6}$ alkyl group (e.g., methyl) and (xii) a 5-to 14-membered aromatic heterocyclic group (e.g., thienyl, furyl, pyrazolyl, imidazolyl, thiazolyl, oxazolyl, tetrazolyl, pyridyl, pyrimidinyl, pyridazinyl, pyrazinyl, oxadiazolyl) optionally substituted by 1 to 3 substituents selected from a $C_{1-6}$ alkyl group (e.g., methyl, tert-butyl), a $C_{3-10}$ cycloalkyl group (e.g., cyclopropyl) and a ($C_{1-6}$ alkyl) ($C_{1-6}$ alkylsulfonyl)amino group (e.g., N-methylsulfonyl-N-methylamino), (b) a $C_{3-10}$ cycloalkyl group optionally substituted by 1 to 3 substituents selected from a halogen atom (e.g., fluorine atom), a hydroxy group, a $C_{1-6}$ alkyl group optionally substituted by 1 to 3 hydroxy groups (e.g., methyl) and a $C_{1-6}$ alkoxy group (e.g., methoxy) optionally substituted by 1 to 3 halogen atoms (e.g., fluorine atom) (the $C_{3-10}$ cycloalkyl group also includes one having a spiro ring structure; for example, cyclopropyl, cyclobutyl, cyclopentyl, cyclohexyl, adamantyl, spiro [2.2]pentyl), (c) a $C_{6-14}$ aryl group (e.g., phenyl) optionally substituted by 1 to 3 $C_{1-6}$ alkylsulfonyl groups (e.g., methylsulfonyl, isopropylsulfonyl), (d) a $C_{3-10}$ cycloalkyl-carbonyl group (e.g., cyclopropylcarbonyl), (e) a 3- to 14-membered non-aromatic heterocyclic group optionally substituted by 1 to 3 substituents selected from an oxo group, a hydroxy group and $C_{1-6}$ alkyl group (e.g., methyl) (the 3- to 14-membered non-aromatic heterocyclic group also includes one having a bicyclo ring structure, a bridged ring structure, or a spiro ring structure; for example, oxetanyl, thietanyl, pyrrolidinyl, tetrahydrothienyl, tetrahydrothiopyranyl, tetrahydrofuryl, dihydroindolyl, tetrahydropyranyl, oxabicyclo[2.2.1]heptyl, azaspiro[2.4]heptyl, oxabicyclo[4.2.0]octyl) and (f) a 5- to 14-membered aromatic heterocyclic group (e.g., pyrazolyl), (9) a carbamoyl group, (10) a 3- to 14-membered non-aromatic heterocyclic group optionally substituted by 1 to 3 substituents selected from (a) an oxo group, (b) a halogen atom (e.g., fluorine atom), (c) a hydroxy group, (d) a cyano group, (e) a $C_{1-6}$ alkyl group (e.g., methyl, ethyl, isopropyl) optionally substituted by 1 to 3 substituents selected from a halogen atom (e.g., fluorine atom), a hydroxy group and a $C_{1-6}$ alkoxy group (e.g., methoxy), (f) a $C_{3-10}$ cycloalkyl group (e.g., cyclopropyl), (g) a $C_{1-6}$ alkoxy group (e.g., methoxy) optionally substituted by 1 to 3 halogen atoms (e.g., fluorine atom), (h) a $C_{1-6}$ alkyl-carbonyl group (e.g., methylcarbonyl), (i) a carbamoyl group, (j) a $C_{1-6}$ alkylsulfonyl group (e.g., methylsulfonyl, ethylsulfonyl), (k) a ($C_{1-6}$ alkyl) ($C_{1-6}$ alkyl-carbonyl)amino group (e.g., N-acetyl-N-ethylamino), (l) a dimethyl (oxide)-$\lambda^6$-sulfanylideneamino group and (m) a methylimino group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) or (11) a 5- to 14-membered aromatic heterocyclic group (e.g., thienyl, pyrazolyl, imidazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl) optionally substituted by 1 to 3 substituents selected from (a) an oxo group, (b) a hydroxy group, (c) a cyano group, (d) a halogen atom (e.g., chlorine atom), (e) a $C_{1-6}$ alkyl group (e.g., methyl, ethyl) optionally substituted by 1 to 3 substituents selected from a hydroxy group, a halogen atom (e.g., fluorine atom), a $C_{3-10}$ cycloalkyl group (e.g., cyclopropyl), a $C_{6-14}$ aryl group (e.g., phenyl), a $C_{1-6}$ alkoxy-carbonyl group (e.g., ethoxycarbonyl) and a carbamoyl group, (f) a $C_{1-6}$ alkoxy group (e.g., methoxy), (g) a $C_{1-6}$ alkoxy-carbonyl group (e.g., methoxycarbonyl), (h) a $C_{1-6}$ alkylsulfonyl group (e.g., methylsulfonyl) and (i) a 3- to 14-membered non-aromatic heterocyclic group (e.g., tetrahydropyranyl).

The substituent of the "6-membered nitrogen-containing aromatic heterocycle" of the "optionally further substituted 6-membered nitrogen-containing aromatic heterocycle" for ring C is further preferably, (1) a cyano group, (2) a $C_{1-6}$ alkyl group (e.g., methyl) optionally substituted by 1 to 3 halogen atoms (e.g., fluorine atom), (3) a 3- to 14-membered non-aromatic heterocyclic-oxy group (e.g., oxetanyloxy), (4) an amino group optionally mono- or di-substituted by substituent(s) selected from (a) a $C_{1-6}$ alkyl group (e.g., n-propyl) optionally substituted by 1 to 3 hydroxy groups and (b) a 3- to 14-membered non-aromatic heterocyclic group optionally substituted by 1 to 3 $C_{1-6}$ alkyl groups (e.g., methyl) (the 3- to 14-membered non-aromatic heterocyclic group also includes one having a bicyclo ring structure, a bridged ring structure, or a spiro ring structure; for example, oxetanyl), (5) a 3- to 14-membered non-aromatic heterocyclic group optionally substituted by 1 to 3 substituents selected from (a) a halogen atom (e.g., fluorine atom), (b) a hydroxy group and (c) a $C_{1-6}$ alkyl group (e.g., methyl) optionally substituted by 1 to 3 hydroxy groups (the 3- to 14-membered non-aromatic heterocyclic group also includes one having a bicyclo ring structure, a bridged ring structure, or a spiro ring structure; for example, azetidinyl, azepanyl, oxazaspiro[3.4]octyl) or (6) a 5- to 14-membered aromatic heterocyclic group (e.g., thienyl, pyrazolyl, pyridyl) optionally substituted by 1 to 3 substituents selected from (a) a cyano group, (b) a halogen atom (e.g., chlorine atom), (c) a $C_{1-6}$ alkyl group (e.g., methyl) and (d) a $C_{1-6}$ alkylsulfonyl group (e.g., methylsulfonyl).

Ring C is preferably a pyridine ring (that is, X is CH) or a pyrimidine ring (that is, X is N), each of which is optionally further substituted by 1-3 (preferably 1-2) substituents selected from (1) a halogen atom (e.g., fluorine atom, chlorine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) an optionally substituted $C_{6-14}$ aryloxy group (e.g., phenoxy), (7) an optionally substituted 3- to 14-membered non-aromatic heterocyclic-oxy group (e.g., oxetanyloxy), (8) an optionally substituted amino group, (9) an optionally substituted carbamoyl group, (10) an optionally substituted 3- to 14-membered non-aromatic heterocyclic group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) and (11) an optionally substituted 5- to 14-membered aromatic heterocyclic group (e.g., thienyl, pyrazolyl, imidazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl).

Ring C is more preferably, a pyridine ring (that is, X is CH) or a pyrimidine ring (that is, X is N), each of which is optionally further substituted by 1-3 (preferably 1-2) substituents selected from (1) a halogen atom (e.g., fluorine atom, chlorine atom), (2) a cyano group, (3) a $C_{1-6}$ alkyl group (e.g., methyl) optionally substituted by 1 to 3 halogen atoms (e.g., fluorine atom), (4) a $C_{6-14}$ aryl group (e.g., phenyl) optionally substituted by 1 to 3 substituents selected from (a) a halogen atom (e.g., fluorine atom, chlorine atom), (b) a cyano group, (c) a $C_{1-6}$ alkyl group (e.g., methyl) optionally substituted by 1 to 3 halogen atoms (e.g., fluorine atom), (d) a $C_{1-6}$ alkoxy group (e.g., methoxy) optionally substituted by 1 to 3 halogen atoms (e.g., fluorine atom), (e) a mono- or di-$C_{1-6}$ alkylamino group (e.g., dimethylamino), (f) a $C_{1-6}$ alkyl-carbonylamino group (e.g., acetylamino), (g) a $C_{1-6}$ alkyl-carbonyl group (e.g., methylcarbonyl), (h) a carbamoyl group, (i) a sulfamoyl group and (j) a 3- to 14-membered non-aromatic heterocyclic-sulfonyl group (e.g., morpholinylsulfonyl), (5) a $C_{1-6}$ alkoxy group (e.g., methoxy) optionally substituted by 1 to 3 substituents selected from (a) a halogen atom (e.g., fluorine atom) and (b) a 5- to 14-membered aromatic heterocyclic group (e.g., oxazolyl) optionally substituted by 1 to 3 $C_{1-6}$ alkyl groups (e.g., tert-butyl), (6) a $C_{6-14}$ aryloxy group (e.g., phenoxy) optionally substituted by 1 to 3 $C_{1-6}$ alkylsulfonyl groups (e.g., methylsulfonyl, isopropylsulfonyl), (7) a 3- to 14-membered non-aromatic heterocyclic-oxy group (e.g., oxetanyloxy), (8) an amino group optionally mono- or di-substituted by substituent(s) selected from (a) a $C_{1-6}$ alkyl group (e.g., methyl, ethyl, n-propyl, isopropyl, n-butyl, isobutyl, tert-butyl, neopentyl, 1,2-dimethylpropyl) optionally substituted by 1 to 3 substituents selected from (i) a halogen atom (e.g., fluorine atom), (ii) a hydroxy group, (iii) a cyano group, (iv) a $C_{3-10}$ cycloalkyl group (e.g., cyclopropyl, cyclobutyl, cyclopentyl, cyclohexyl) optionally substituted by 1 to 3 hydroxy groups, (v) a $C_{6-14}$ aryl group (e.g., phenyl) optionally substituted by 1 to 3 substituents selected from a $C_{1-6}$ alkylsulfonyl group (e.g., methylsulfonyl) and a sulfamoyl group, (vi) a $C_{1-6}$ alkoxy group (e.g., methoxy, ethoxy) optionally substituted by 1 to 3 halogen atoms (e.g., fluorine atom), (vii) a mono- or di-$C_{1-6}$ alkylamino group (e.g., dimethylamino), (viii) a $C_{1-6}$ alkyl-carbonylamino group (e.g., acetylamino), (ix) a carbamoyl group, (x) a $C_{1-6}$ alkylsulfonyl group (e.g., methylsulfonyl), (xi) a 3- to 14-membered non-aromatic heterocyclic group (e.g., oxetanyl, thietanyl, morpholinyl, pyrrolidinyl, tetrahydrofuryl, tetrahydropyranyl) optionally substituted by 1 to 3 substituents selected from an oxo group and a $C_{1-6}$ alkyl group (e.g., methyl) and (xii) a 5-to 14-membered aromatic heterocyclic group (e.g., thienyl, furyl, pyrazolyl, imidazolyl, thiazolyl, oxazolyl, tetrazolyl, pyridyl, pyrimidinyl, pyridazinyl, pyrazinyl, oxadiazolyl) optionally substituted by 1 to 3 substituents selected from a $C_{1-6}$ alkyl group (e.g., methyl, tert-butyl), a $C_{3-10}$ cycloalkyl group (e.g., cyclopropyl) and a ($C_{1-6}$ alkyl) ($C_{1-6}$ alkyl-sulfonyl)amino group (e.g., N-methylsulfonyl-N-methylamino) (b) a $C_{3-10}$ cycloalkyl group optionally substituted by 1 to 3 substituents selected from a halogen atom (e.g., fluorine atom), a hydroxy group, a $C_{1-6}$ alkyl group (e.g., methyl) optionally substituted by 1 to 3 hydroxy groups and a $C_{1-6}$ alkoxy group (e.g., methoxy) optionally substituted by 1 to 3 halogen atoms (e.g., fluorine atom) (the $C_{3-10}$ cycloalkyl group also includes one having a spiro ring structure; for example, cyclopropyl, cyclobutyl, cyclopentyl, cyclohexyl, adamantyl, spiro [2.2]pentyl), (c) a $C_{6-14}$ aryl group (e.g., phenyl) optionally substituted by 1 to 3 $C_{1-6}$ alkylsulfonyl groups (e.g., methylsulfonyl, isopropylsulfonyl), (d) a $C_{3-10}$ cycloalkyl-carbonyl group (e.g., cyclopropylcarbonyl), (e) a 3- to 14-membered non-aromatic heterocyclic group optionally substituted by 1 to 3 substituents selected from an oxo group, a hydroxy group and a $C_{1-6}$ alkyl group (e.g., methyl) (the 3- to 14-membered non-aromatic heterocyclic group also includes one having a bicyclo ring structure, a bridged ring structure, or a spiro ring structure; for example, oxetanyl, thietanyl, pyrrolidinyl, tetrahydrothienyl, tetrahydrothiopyranyl, tetrahydrofuryl, dihydroindolyl, tetrahydropyranyl, oxabicyclo[2.2.1]heptyl, azaspiro[2.4]heptyl, oxabicyclo[4.2.0]octyl) and (f) a 5- to 14-membered aromatic heterocyclic group (e.g., pyrazolyl), (9) a carbamoyl group, (10) a 3- to 14-membered non-aromatic heterocyclic group optionally substituted by 1 to 3 substituents selected from (a) an oxo group, (b) a halogen atom (e.g., fluorine atom), (c) a hydroxy group, (d) a cyano group, (e) a $C_{1-6}$ alkyl group (e.g., methyl, ethyl, isopropyl) optionally substituted by 1 to 3 substituents selected from a halogen atom (e.g., fluorine atom), a hydroxy group and a $C_{1-6}$ alkoxy group (e.g., methoxy), (f) a $C_{3-10}$ cycloalkyl group (e.g., cyclopropyl), (g) a $C_{1-6}$ alkoxy group (e.g., methoxy) optionally substituted by 1 to 3 halogen atoms (e.g., fluorine atom), (h) a $C_{1-6}$ alkyl-carbonyl group (e.g., methylcarbonyl), (i) a carbamoyl group, (j) a $C_{1-6}$ alkylsulfonyl group (e.g., methylsulfonyl, ethylsulfonyl), (k) a ($C_{1-6}$ alkyl) ($C_{1-6}$ alkyl-carbonyl)amino group (e.g., N-acetyl-N-ethylamino), (1) a dimethyl(oxide)-$\lambda^6$-sulfanylideneamino group and (m) a methylimino group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) and (11) a 5- to 14-membered aromatic heterocyclic group (e.g., thienyl, pyrazolyl, imidazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl) optionally substituted by 1 to 3 substituents selected from (a) an oxo group, (b) a hydroxy group, (c) a cyano group, (d) a halogen atom (e.g., chlorine atom), (e) a $C_{1-6}$ alkyl group (e.g., methyl, ethyl) optionally substituted by 1 to 3 substituents selected from a hydroxy group, a halogen atom (e.g., fluorine atom), a $C_{3-10}$ cycloalkyl group (e.g., cyclopropyl), a $C_{6-14}$ aryl group (e.g., phenyl), a $C_{1-6}$ alkoxy-carbonyl group (e.g., ethoxycarbonyl) and a carbamoyl group, (f) a $C_{1-6}$ alkoxy group (e.g., methoxy), (g) a $C_{1-6}$ alkoxy-carbonyl group (e.g., methoxycarbonyl), (h) a $C_{1-6}$ alkylsulfonyl group (e.g., methylsulfonyl) and (i) a 3- to 14-membered non-aromatic heterocyclic group (e.g., tetrahydropyranyl).

Ring C is further preferably, a pyrimidine ring (that is, X is N) optionally further substituted by 1-3 (preferably 1-2) substituents selected from (1) a cyano group, (2) a $C_{1-6}$ alkyl group (e.g., methyl) optionally substituted by 1 to 3 halogen atoms (e.g., fluorine atom), (3) a 3- to 14-membered non-aromatic heterocyclic-oxy group (e.g., oxetanyloxy), (4) an amino group optionally mono- or di-substituted by substituent(s) selected from (a) a $C_{1-6}$ alkyl group (e.g., n-propyl) optionally substituted by 1 to 3 hydroxy groups and (b) a 3- to 14-membered non-aromatic heterocyclic group optionally substituted by 1 to 3 $C_{1-6}$ alkyl groups (e.g., methyl) (the 3- to 14-membered non-aromatic heterocyclic group also includes one having a bicyclo ring structure, a bridged ring structure, or a spiro ring structure; for example, oxetanyl), (5) a 3- to 14-membered non-aromatic heterocyclic group optionally substituted by 1 to 3 substituents selected from (a) a halogen atom (e.g., fluorine atom), (b) a hydroxy group and (c) a $C_{1-6}$ alkyl group (e.g., methyl) optionally substituted by 1 to 3 hydroxy groups (the 3-to 14-membered non-aromatic heterocyclic group also includes one having a bicyclo ring structure, a bridged ring structure, or a spiro ring structure; for example, azetidinyl, azepanyl, oxazaspiro[3.4]octyl) and (6) a 5- to 14-membered aromatic heterocyclic group (e.g., thienyl, pyrazolyl, pyridyl) optionally substituted by 1 to 3 substituents selected from (a) a cyano group, (b) a halogen atom (e.g., chlorine atom), (c) a $C_{1-6}$ alkyl group (e.g., methyl) and (d) a $C_{1-6}$ alkylsulfonyl group (e.g., methylsulfonyl).

In one preferred embodiment of the present invention, ring C has a substituent other than halogen atom at least at a para-position relative to the bonding position of group: —NH-ring B—N(C(=O)R$^1$)-ring A. As such substituent, preferable substituents (excluding halogen atom) of ring C mentioned above can be recited.

Preferable examples of compound (I) include the following compounds.

[Compound I-1]

Compound (I) wherein $R^1$ is (1) a $C_{1-6}$ alkyl group (e.g., methyl, ethyl, isopropyl) optionally substituted by 1 to 3 substituents selected from an optionally substituted $C_{6-14}$ aryl group (e.g., phenyl), an optionally substituted $C_{6-14}$ aryloxy group (e.g., phenoxy) and an optionally substituted 5- to 14-membered aromatic heterocyclic group (e.g., pyridyl), (2) a $C_{1-6}$ alkoxy group (e.g., methoxy) optionally substituted by 1 to 3 substituents selected from an optionally substituted $C_{6-14}$ aryl group (e.g., phenyl) and an optionally substituted 5- to 14-membered aromatic heterocyclic group (e.g., pyridyl), (3) an optionally substituted $C_{6-14}$ aryl group (e.g., phenyl), (4) a 3-to 14-membered non-aromatic heterocyclic group (e.g., azetidinyl, tetrahydropyranyl) optionally substituted by 1 to 3 substituents selected from an optionally substituted $C_{6-14}$ aryl group (e.g., phenyl) or (5) —NR$^2$R$^3$ [R$^2$ is a hydrogen atom or a $C_{1-6}$ alkyl group (e.g., methyl, ethyl) optionally substituted by 1 to 3 substituents selected from an optionally substituted $C_{6-14}$ aryl group (e.g., phenyl), R$^3$ is (i) a $C_{1-6}$ alkyl group (e.g., methyl, ethyl, neopentyl) optionally substituted by 1 to 3 substituents selected from an optionally substituted $C_{3-10}$ cycloalkyl group (e.g., cyclopropyl, cyclohexyl), an optionally substituted $C_{6-14}$ aryl group (e.g., phenyl), an optionally substituted 3- to 14-membered non-aromatic heterocyclic group (e.g., tetrahydropyranyl) and an optionally substituted 5- to 14-membered aromatic heterocyclic group (e.g., furyl, thienyl, thiazolyl, pyridyl, pyrimidinyl) or (ii) an optionally substituted $C_{6-14}$ aryl group (e.g., phenyl);

ring A is a $C_{6-14}$ aromatic hydrocarbon ring (e.g., benzene ring) or a 5- to 14-membered aromatic heterocycle (e.g., pyridine ring, pyrimidine ring, pyridazine ring, pyrazine ring, indazole ring, pyrazolopyridine ring), each of which is optionally further substituted by 1-5 (preferably 1-3, more preferably 1-2) substituents selected from (1) a halogen atom (e.g., fluorine atom, chlorine atom, bromine atom), (2) a cyano group, (3) a hydroxy group, (4) an optionally substituted $C_{1-6}$ alkyl group (e.g., methyl, ethyl), (5) an optionally substituted $C_{2-6}$ alkenyl group (e.g., ethenyl, 2-propenyl), (6) an optionally substituted $C_{6-14}$ aryl group (e.g., phenyl), (7) an optionally substituted $C_{1-6}$ alkoxy group (e.g., methoxy), (8) an optionally substituted amino group, (9) a carboxy group, (10) an optionally substituted carbamoyl group, (11) an optionally substituted 3- to 14-membered non-aromatic heterocyclic group (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5]nonyl) and (12) an optionally substituted 5- to 14-membered aromatic heterocyclic group (e.g., thienyl, pyrazolyl, imidazolyl, thiazolyl, furyl, oxazolyl, pyridyl, pyrimidinyl, pyrazinyl);

ring B is a cyclohexane ring not substituted further; and ring C is a pyridine ring (that is, X is CH) or a pyrimidine ring (that is, X is N), each of which is optionally further substituted by 1-3 (preferably 1-2) substituents selected from (1) a halogen atom (e.g., fluorine atom, chlorine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) an optionally substituted $C_{6-14}$ aryloxy group (e.g., phenoxy), (7) an optionally substituted 3- to 14-membered non-aromatic heterocyclic-oxy group (e.g., oxetanyloxy), (8) an optionally substituted amino group, (9) an optionally substituted carbamoyl group, (10) an optionally substituted 3- to 14-membered non-aromatic heterocyclic group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) and (11) an optionally substituted 5- to 14-membered aromatic heterocyclic group (e.g., thienyl, pyrazolyl, imidazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl).

[Compound I-2]

Compound (I) wherein $R^1$ is (1) a $C_{1-6}$ alkyl group (e.g., methyl, ethyl, isopropyl) optionally substituted by 1 to 3 substituents selected from a $C_{6-14}$ aryl group (e.g., phenyl) optionally substituted by 1 to 3 halogen atoms (e.g., chlorine atom), a $C_{6-14}$ aryloxy group (e.g., phenoxy) and a 5- to 14-membered aromatic heterocyclic group (e.g., pyridyl), (2) a $C_{1-6}$ alkoxy group (e.g., methoxy) optionally substituted by 1 to 3 substituents selected from a $C_{6-14}$ aryl group (e.g., phenyl) and a 5- to 14-membered aromatic heterocyclic group (e.g., pyridyl), (3) a $C_{6-14}$ aryl group (e.g., phenyl), (4) a 3- to 14-membered non-aromatic heterocyclic group (e.g., azetidinyl, tetrahydropyranyl) optionally substituted by 1 to 3 $C_{6-14}$ aryl groups (e.g., phenyl) or (5) —NR$^2$R$^3$[R$^2$ is a hydrogen atom or a $C_{1-6}$ alkyl group (e.g., methyl, ethyl) optionally substituted by 1 to 3 $C_{6-14}$ aryl groups (e.g., phenyl), R$^3$ is (i) a $C_{1-6}$ alkyl group (e.g., methyl, ethyl, neopentyl) optionally substituted by 1 to 3 substituents selected from (a) a $C_{3-10}$ cycloalkyl group (e.g., cyclopropyl, cyclohexyl), (b) a $C_{6-14}$ aryl group (e.g., phenyl) optionally substituted by 1 to 3 substituents selected from a halogen atom (e.g., fluorine atom), a cyano group, a $C_{1-6}$ alkoxy group (e.g., methoxy), a $C_{1-6}$ alkylsulfonyl group (e.g., methylsulfonyl) and a $C_{1-6}$ alkylsulfonylamino group (e.g., methylsulfonylamino), (c) a 3- to 14-membered non-aromatic heterocyclic group (e.g., tetrahydropyranyl) and (d) a 5- to 14-membered aromatic heterocyclic group (e.g., furyl, thienyl, thiazolyl, pyridyl, pyrimidinyl) optionally substituted by 1 to 3 substituents selected from a $C_{1-6}$ alkyl group (e.g., methyl) and a $C_{1-6}$ alkoxy group (e.g., methoxy) or (ii) a $C_{6-14}$ aryl group (e.g., phenyl)];

ring A is a $C_{6-14}$ aromatic hydrocarbon ring (e.g., benzene ring) or a 5- to 14-membered aromatic heterocycle (e.g., pyridine ring, pyrimidine ring, pyridazine ring, pyrazine ring, indazole ring, pyrazolopyridine ring), each of which is optionally further substituted by 1-5 (preferably 1-3, more preferably 1-2) substituents selected from (1) a halogen atom (e.g., fluorine atom, chlorine atom, bromine atom), (2) a cyano group, (3) a hydroxy group, (4) a $C_{1-6}$ alkyl group (e.g., methyl, ethyl) optionally substituted by 1 to 3 substituents selected from (a) a halogen atom (e.g., fluorine atom), (b) a $C_{1-6}$ alkoxy group (e.g., methoxy) and (c) a 3- to 14-membered non-aromatic heterocyclic group (e.g., piperazinyl, piperidinyl, morpholinyl) optionally substituted by 1 to 3 $C_{1-6}$ alkyl groups (e.g., methyl), (5) a $C_{2-6}$ alkenyl group (e.g., ethenyl, 2-propenyl), (6) a $C_{6-14}$ aryl group (e.g., phenyl) optionally substituted by 1 to 3 substituents selected from (a) a halogen atom (e.g., fluorine atom), (b) a cyano group, (c) a $C_{1-6}$ alkoxy group (e.g., methoxy) and (d) a carbamoyl group, (7) a $C_{1-6}$ alkoxy group (e.g., methoxy), (8) an amino group optionally mono- or di-substituted by substituent(s) selected from (a) a $C_{1-6}$ alkyl group (e.g., ethyl) optionally substituted by 1 to 3 $C_{1-6}$ alkoxy groups (e.g., methoxy), (b) a $C_{6-14}$ aryl group (e.g., phenyl) optionally substituted by 1 to 3 substituents selected from a cyano group and a $C_{1-6}$ alkoxy group (e.g., methoxy) and (c) a 5- to 14-membered aromatic heterocyclic group (e.g., pyrazolyl, pyridyl) optionally substituted by 1 to 3 $C_{1-6}$ alkyl groups (e.g., methyl), (9) a carboxy group, (10) a carbamoyl group optionally mono- or di-substituted by a $C_{1-6}$ alkyl group (e.g., methyl), (11) a 3- to 14-membered non-aromatic heterocyclic group optionally substituted by 1 to 3 substituents selected from (a) an oxo group, (b) a cyano group, (c) a $C_{1-6}$ alkyl group (e.g., methyl), (d) a $C_{1-6}$ alkoxy group (e.g., methoxy), (e) a $C_{1-6}$ alkyl-carbonyl group (e.g., methylcarbonyl), (f) a carbamoyl group, (g) a mono- or di-$C_{1-6}$ alkylamino group (e.g., dimethylamino) and (h) a $C_{1-6}$ alkylsulfonyl group (e.g., methylsulfonyl) (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5]nonyl) and (12) a 5- to 14-membered aromatic heterocyclic group (e.g., thienyl, pyrazolyl, imidazolyl, thiazolyl, furyl, oxazolyl, pyridyl, pyrimidinyl, pyrazinyl) optionally substituted by 1 to 3 substituents selected from (a) an oxo group, (b) a $C_{1-6}$ alkyl group (e.g., methyl, ethyl, isopropyl, isobutyl) optionally substituted by 1 to 3 substituents selected from a hydroxy group, a $C_{1-6}$ alkoxy group (e.g., methoxy), a carbamoyl group, a 3- to 14-membered non-aromatic heterocyclic group (e.g., morpholinyl) and a 5- to 14-membered aromatic heterocyclic group (e.g., pyridyl), (c) a $C_{1-6}$ alkoxy group (e.g., methoxy), (d) an amino group, (e) a carboxy group, (f) a $C_{1-6}$ alkoxy-carbonyl group (e.g., methoxycarbonyl, ethoxycarbonyl), (g) a carbamoyl group and (h) a 3- to 14-membered non-aromatic heterocyclic group (e.g., tetrahydropyranyl);

ring B is a cyclohexane ring not substituted further; and ring C is a pyridine ring (that is, X is CH) or a pyrimidine ring (that is, X is N), each of which is optionally further substituted by 1-3 (preferably 1-2) substituents selected from (1) a halogen atom (e.g., fluorine atom, chlorine atom), (2) a cyano group, (3) a $C_{1-6}$ alkyl group (e.g., methyl) optionally substituted by 1 to 3 halogen atoms (e.g., fluorine atom), (4) a $C_{6-14}$ aryl group (e.g., phenyl) optionally substituted by 1 to 3 substituents selected from (a) a halogen atom (e.g., fluorine atom, chlorine atom), (b) a cyano group, (c) a $C_{1-6}$ alkyl group (e.g., methyl) optionally substituted by 1 to 3 halogen atoms (e.g., fluorine atom), (d) a $C_{1-6}$ alkoxy group (e.g., methoxy) optionally substituted by 1 to 3 halogen atoms (e.g., fluorine atom), (e) a mono- or di-$C_{1-6}$ alkylamino group (e.g., dimethylamino), (f) a $C_{1-6}$ alkyl-carbonylamino group (e.g., acetylamino), (g) a $C_{1-6}$ alkyl-carbonyl group (e.g., methylcarbonyl), (h) a carbamoyl group, (i) a sulfamoyl group and (j) a 3- to 14-membered non-aromatic heterocyclic-sulfonyl group (e.g., morpholinylsulfonyl), (5) a $C_{1-6}$ alkoxy group (e.g., methoxy) optionally substituted by 1 to 3 substituents selected from (a) a halogen atom (e.g., fluorine atom) and (b) a 5- to 14-membered aromatic heterocyclic group (e.g., oxazolyl) optionally substituted by 1 to 3 $C_{1-6}$ alkyl groups (e.g., tert-butyl), (6) a $C_{6-14}$ aryloxy group (e.g., phenoxy) optionally substituted by 1 to 3 $C_{1-6}$ alkylsulfonyl groups (e.g., methylsulfonyl, isopropylsulfonyl), (7) a 3- to 14-membered non-aromatic heterocyclic-oxy group (e.g., oxetanyloxy), (8) an amino group optionally mono- or di-substituted by substituent(s) selected from (a) a $C_{1-6}$ alkyl group (e.g., methyl, ethyl, n-propyl, isopropyl, n-butyl, isobutyl, tert-butyl, neopentyl, 1,2-dimethylpropyl) optionally substituted by 1 to 3 substituents selected from (i) a halogen atom (e.g., fluorine atom), (ii) a hydroxy group, (iii) a cyano group, (iv) a $C_{3-10}$ cycloalkyl group (e.g., cyclopropyl, cyclobutyl, cyclopentyl, cyclohexyl) optionally substituted by 1 to 3 hydroxy groups, (v) a $C_{6-14}$ aryl group (e.g., phenyl) optionally substituted by 1 to 3 substituents selected from a $C_{1-6}$ alkylsulfonyl group (e.g., methylsulfonyl) and a sulfamoyl group, (vi) a $C_{1-6}$ alkoxy group (e.g., methoxy, ethoxy) optionally substituted by 1 to 3 halogen atoms (e.g., fluorine atom), (vii) a mono- or di-$C_{1-6}$ alkylamino group (e.g., dimethylamino), (viii) a $C_{1-6}$ alkyl-carbonylamino group (e.g., acetylamino), (ix) a carbamoyl group, (x) a $C_{1-6}$ alkylsulfonyl group (e.g., methylsulfonyl), (xi) a 3- to 14-membered non-aromatic heterocyclic group (e.g., oxetanyl, thietanyl, morpholinyl, pyrrolidinyl, tetrahydrofuryl, tetrahydropyranyl) optionally substituted by 1 to 3 substituents selected from an oxo group and a $C_{1-6}$ alkyl group (e.g., methyl) and (xii) a 5-to 14-membered aromatic heterocyclic group (e.g., thienyl, furyl, pyrazolyl, imidazolyl, thiazolyl, oxazolyl, tetrazolyl, pyridyl, pyrimidinyl, pyridazinyl, pyrazinyl, oxadiazolyl) optionally substituted by 1 to 3 substituents selected from a $C_{1-6}$ alkyl group (e.g., methyl, tert-butyl), a $C_{3-10}$ cycloalkyl group (e.g., cyclopropyl) and a ($C_{1-6}$ alkyl) ($C_{1-6}$ alkylsulfonyl)amino group (e.g., N-methylsulfonyl-N-methylamino), (b) a $C_{3-10}$ cycloalkyl group optionally substituted by 1 to 3 substituents selected from a halogen atom (e.g., fluorine atom), a hydroxy group, a $C_{1-6}$ alkyl group (e.g., methyl) optionally substituted by 1 to 3 hydroxy groups and a $C_{1-6}$ alkoxy group (e.g., methoxy) optionally substituted by 1 to 3 halogen atoms (e.g., fluorine atom) (the $C_{3-10}$ cycloalkyl group also includes one having a spiro ring structure; for example, cyclopropyl, cyclobutyl, cyclopentyl, cyclohexyl, adamantyl, spiro-[2.2]pentyl), (c) a $C_{6-14}$ aryl group (e.g., phenyl) optionally substituted by 1 to 3 $C_{1-6}$ alkylsulfonyl groups (e.g., methylsulfonyl, isopropylsulfonyl), (d) a $C_{3-10}$ cycloalkyl-carbonyl group (e.g., cyclopropylcarbonyl), (e) a 3- to 14-membered non-aromatic heterocyclic group optionally substituted by 1 to 3 substituents selected from an oxo group, a hydroxy group and a $C_{1-6}$ alkyl group (e.g., methyl) (the 3- to 14-membered non-aromatic heterocyclic group also includes one having a bicyclo ring structure, a bridged ring structure, or a spiro ring structure; for example, oxetanyl, thietanyl, pyrrolidinyl, tetrahydrothienyl, tetrahydrothiopyranyl, tetrahydrofuryl, dihydroindolyl, tetrahydropyranyl, oxabicyclo[2.2.1]heptyl, azaspiro[2.4]heptyl, oxabicyclo[4.2.0]octyl) and (f) a 5- to 14-membered aromatic heterocyclic group (e.g., pyrazolyl), (9) a carbamoyl group, (10) a 3- to 14-membered non-aromatic heterocyclic group optionally substituted by 1 to 3 substituents selected from (a) an oxo group, (b) a halogen atom (e.g., fluorine atom), (c) a hydroxy group, (d) a cyano group, (e) a $C_{1-6}$ alkyl group (e.g., methyl, ethyl, isopropyl) optionally substituted by 1 to 3 substituents selected from a halogen atom (e.g., fluorine atom), a hydroxy group and a $C_{1-6}$ alkoxy group (e.g., methoxy), (f) a $C_{3-10}$ cycloalkyl group (e.g., cyclopropyl), (g) a $C_{1-6}$ alkoxy group (e.g., methoxy) optionally substituted by 1 to 3 halogen atoms (e.g., fluorine atom), (h) a $C_{1-6}$ alkyl-carbonyl group (e.g., methylcarbonyl), (i) a carbamoyl group, (j) a $C_{1-6}$ alkylsulfonyl group (e.g., methylsulfonyl, ethylsulfonyl), (k) a ($C_{1-6}$ alkyl) ($C_{1-6}$ alkyl-carbonyl)amino group (e.g., N-acetyl-N-ethylamino), (l) a dimethyl(oxide)-$\lambda^6$-sulfanylideneamino group and (m) a methylimino group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) and (11) a 5- to 14-membered aromatic heterocyclic group (e.g., thienyl, pyrazolyl, imidazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl) optionally substituted by 1 to 3 substituents selected from (a) an oxo group, (b) a hydroxy group, (c) a cyano group, (d) a halogen atom (e.g., chlorine atom), (e) a $C_{1-6}$ alkyl group (e.g., methyl, ethyl) optionally substituted by 1 to 3 substituents selected from a hydroxy group, a halogen atom (e.g., fluorine atom), a $C_{3-10}$ cycloalkyl group (e.g., cyclopropyl), a $C_{6-14}$ aryl group (e.g., phenyl), a $C_{1-6}$ alkoxy-carbonyl group (e.g., ethoxycarbonyl) and a carbamoyl group, (f) a $C_{1-6}$ alkoxy group (e.g., methoxy), (g) a $C_{1-6}$ alkoxy-carbonyl group (e.g., methoxycarbonyl), (h) a $C_{1-6}$ alkylsulfonyl group (e.g., methylsulfonyl) and (i) a 3- to 14-membered non-aromatic heterocyclic group (e.g., tetrahydropyranyl).

[Compound I-3]

Compound (I) wherein $R^1$ is (1) a $C_{1-6}$ alkyl group (e.g., methyl, ethyl) optionally substituted by 1 to 3 substituents selected from a $C_{6-14}$ aryl group (e.g., phenyl), a $C_{6-14}$ aryloxy group (e.g., phenoxy) and a 5- to 14-membered aromatic heterocyclic group (e.g., pyridyl), (2) a $C_{1-6}$ alkoxy group (e.g., methoxy) optionally substituted by 1 to 3 substituents selected from a $C_{6-14}$ aryl group (e.g., phenyl) and a 5- to 14-membered aromatic heterocyclic group (e.g., pyridyl), or (3) —$NR^2R^3$ [$R^2$ is a hydrogen atom, $R^3$ is a $C_{1-6}$ alkyl group (e.g., methyl) optionally substituted by 1 to 3 substituents selected from (a) a $C_{6-14}$ aryl group (e.g., phenyl) optionally substituted by 1 to 3 halogen atoms (e.g., fluorine atom) and (b) a 5- to 14-membered aromatic heterocyclic group (e.g., pyridyl);

ring A is a $C_{6-14}$ aromatic hydrocarbon ring (e.g., benzene ring) or a 5- to 14-membered aromatic heterocycle (e.g., a pyridine ring, a pyrimidine ring, a pyridazine ring, a pyrazine ring), each of which is optionally further substituted by 1-5 (preferably 1-3, more preferably 1-2) substituents selected from (a) an oxo group, (b) a $C_{1-6}$ alkyl group (e.g., methyl) and (c) a 5- to 14-membered aromatic heterocyclic group (e.g., pyrazolyl, pyridyl, pyrimidinyl) optionally substituted by 1 to substituents selected from a $C_{1-6}$ alkoxy group (e.g., methoxy);

ring B is a cyclohexane ring not substituted further; and ring C is a pyrimidine ring (that is, X is N) optionally further substituted by 1-3 (preferably 1-2) substituents selected from (1) a cyano group, (2) a $C_{1-6}$ alkyl group (e.g., methyl) optionally substituted by 1 to 3 halogen atoms (e.g., fluorine atom), (3) a 3- to 14-membered non-aromatic heterocyclic-oxy group (e.g., oxetanyloxy), (4) an amino group optionally mono- or di-substituted by substituent(s) selected from (a) a $C_{1-6}$ alkyl group (e.g., n-propyl) optionally substituted by 1 to 3 hydroxy groups and (b) a 3- to 14-membered non-aromatic heterocyclic group optionally substituted by 1 to 3 $C_{1-6}$ alkyl groups (e.g., methyl) (the 3- to 14-membered non-aromatic heterocyclic group also includes one having a bicyclo ring structure, a bridged ring structure, or a spiro ring structure; for example, oxetanyl), (5) a 3- to 14-membered non-aromatic heterocyclic group optionally substituted by 1 to 3 substituents selected from (a) a halogen atom (e.g., fluorine atom), (b) a hydroxy group and (c) a $C_{1-6}$ alkyl group (e.g., methyl) optionally substituted by 1 to 3 hydroxy groups (the 3- to 14-membered non-aromatic heterocyclic group also includes one having a bicyclo ring structure, a bridged ring structure, or a spiro ring structure; for example, azetidinyl, azepanyl, oxazaspiro[3.4]octyl) and (6) a 5- to 14-membered aromatic heterocyclic group (e.g., thienyl, pyrazolyl, pyridyl) optionally substituted by 1 to 3 substituents selected from (a) a cyano group, (b) a halogen atom (e.g., chlorine atom), (c) a $C_{1-6}$ alkyl group (e.g., methyl) and (d) a $C_{1-6}$ alkylsulfonyl group (e.g., methylsulfonyl).

[Compound I-4]

Compound (I) wherein $R^1$ is (1) a $C_{1-6}$ alkyl group (e.g., methyl, ethyl, propyl, isopropyl, butyl, isobutyl) optionally substituted by 1 to 3 substituents selected from a halogen atom (e.g., fluorine atom), optionally substituted $C_{3-10}$ cycloalkyl group (e.g., cyclopropyl), optionally substituted $C_{1-6}$ alkoxy group (e.g., methoxy, ethoxy), optionally substituted $C_{6-14}$ aryl group (e.g., phenyl) and optionally substituted $C_{6-14}$ aryloxy group (e.g., phenoxy), (2) a $C_{1-6}$ alkoxy group (e.g., methoxy, ethoxy, propoxy, isopropoxy, isobutoxy) optionally substituted by 1 to 3 substituents selected from a halogen atom (e.g., fluorine atom), a hydroxy group, optionally substituted $C_{3-10}$ cycloalkyl group (e.g., cyclopropyl), optionally substituted $C_{6-14}$ aryl group (e.g., phenyl), optionally substituted $C_{1-6}$ alkoxy group (e.g., methoxy), optionally substituted amino group, optionally substituted 3- to 14-membered non-aromatic heterocyclic group (e.g., azetidinyl, morpholinyl) and optionally substituted 5- to 14-membered aromatic heterocyclic group (e.g., pyridyl), (3) an optionally substituted $C_{6-14}$ aryl group (e.g., phenyl), (4) 3- to 14-membered non-aromatic heterocyclic group (e.g., azetidinyl, pyrrolidinyl, tetrahydropyranyl) optionally substituted by 1 to 3 substituents selected from a halogen atom (e.g., fluorine atom), a hydroxy group, optionally substituted $C_{1-6}$ alkyl group (e.g., methyl), optionally substituted $C_{1-6}$ alkoxy group (e.g., methoxy) and optionally substituted $C_{6-14}$ aryl group (e.g., phenyl) or (5)-$NR^2R^3$[$R^2$ is a hydrogen atom or a $C_{1-6}$ alkyl group (e.g., methyl, ethyl) optionally substituted by 1 to 3 substituents selected from optionally substituted $C_{6-14}$ aryl group (e.g., phenyl), $R^3$, (i) a $C_{1-6}$ alkyl group (e.g., methyl, ethyl, propyl, isopropyl, isobutyl, neopentyl) optionally substituted by 1 to 3 substituents selected from a halogen atom (e.g., fluorine atom), a hydroxy group, optionally substituted $C_{3-10}$ cycloalkyl group (e.g., cyclopropyl, cyclohexyl), optionally substituted $C_{1-6}$ alkoxy group (e.g., methoxy), optionally substituted $C_{6-14}$ aryl group (e.g., phenyl), optionally substituted amino group, optionally substituted 3-to 14-membered non-aromatic heterocyclic group (e.g., oxetanyl, tetrahydropyranyl) and optionally substituted 5- to 14-membered aromatic heterocyclic group (e.g., furyl, thienyl, thiazolyl, pyridyl, pyrimidinyl), (ii) optionally substituted $C_{3-10}$ cycloalkyl group (e.g., cyclopropyl, cyclobutyl) or (iii) an optionally substituted $C_{6-14}$ aryl group (e.g., phenyl)];

ring A is a $C_{6-14}$ aromatic hydrocarbon ring (e.g., benzene ring) or a 5- to 14-membered aromatic heterocycle (e.g., pyrazole ring, pyridine ring, pyrimidine ring, pyridazine ring, pyrazine ring, indazole ring, pyrazolopyridine ring), each of which is optionally further substituted by 1-5 (preferably 1-3, more preferably 1-2) substituents selected from (1) a halogen atom (e.g., fluorine atom, chlorine atom, bromine atom), (2) a cyano group, (3) a hydroxy group, (4) an optionally substituted $C_{1-6}$ alkyl group (e.g., methyl, ethyl), (5) an optionally substituted $C_{2-6}$ alkenyl group (e.g., ethenyl, 2-propenyl), (6) an optionally substituted $C_{6-14}$ aryl group (e.g., phenyl), (7) an optionally substituted $C_{1-6}$ alkoxy group (e.g., methoxy, ethoxy), (8) an optionally substituted amino group, (9) a carboxy group, (10) an optionally substituted carbamoyl group, (11) an optionally substituted 3- to 14-membered non-aromatic heterocyclic group (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5]nonyl) and (12) an optionally substituted 5- to 14-membered aromatic heterocyclic group (e.g., thienyl, pyrazolyl, imidazolyl, thiazolyl, furyl, oxazolyl, pyridyl, pyrimidinyl, pyrazinyl);

ring B is a cyclohexane ring not substituted further; and ring C is a pyridine ring (that is, X is CH) or a pyrimidine ring (that is, X is N), each of which is optionally further substituted by 1-3 (preferably 1-2) substituents selected from (1) a halogen atom (e.g., fluorine atom, chlorine atom), (2) a cyano group, (3) an optionally substituted $C_{1-6}$ alkyl group (e.g., methyl), (4) an optionally substituted $C_{6-14}$ aryl group (e.g., phenyl), (5) an optionally substituted $C_{1-6}$ alkoxy group (e.g., methoxy), (6) an optionally substituted $C_{6-14}$ aryloxy group (e.g., phenoxy), (7) an optionally substituted 3- to 14-membered non-aromatic heterocyclic-oxy group (e.g., oxetanyloxy), (8) an optionally substituted amino group, (9) an optionally substituted carbamoyl group, (10) an optionally substituted 3- to 14-membered non-aromatic heterocyclic group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydropyranyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, tetrahydronaphthyridinyl, tetrahydroimidazopyrazinyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) and (11) an optionally substituted 5- to 14-membered aromatic heterocyclic group (e.g., thienyl, pyrazolyl, imidazolyl, triazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl).

[Compound I-5]

Compound (I) wherein $R^1$ is (1) a $C_{1-6}$ alkyl group (e.g., methyl, ethyl, propyl, isopropyl, butyl, isobutyl) optionally substituted by 1 to 3 substituents selected from a halogen atom (e.g., fluorine atom), a $C_{3-10}$ cycloalkyl group (e.g., cyclopropyl), a $C_{1-6}$ alkoxy group (e.g., methoxy, ethoxy) and a $C_{6-14}$ aryloxy group (e.g., phenoxy), (2) a $C_{1-6}$ alkoxy group (e.g., methoxy, ethoxy, propoxy, isopropoxy, isobutoxy) optionally substituted by 1 to 3 substituents selected from (a) a halogen atom (e.g., fluorine atom), (b) a hydroxy group, (c) a $C_{3-10}$ cycloalkyl group (e.g., cyclopropyl) optionally substituted by 1 to 3 substituents selected from a halogen atom (e.g., fluorine atom) and an amino group, (d) a $C_{6-14}$ aryl group (e.g., phenyl), (e) a $C_{1-6}$ alkoxy group (e.g., methoxy), (f) an amino group optionally mono- or di-substituted by a $C_{1-6}$ alkyl group (e.g., methyl), (g) a 3- to 14-membered non-aromatic heterocyclic group (e.g., azetidinyl, morpholinyl) optionally substituted by 1 to 3 halogen atoms (e.g., fluorine atom) and (h) a 5- to 14-membered aromatic heterocyclic group (e.g., pyridyl), (3) a 3- to 14-membered non-aromatic heterocyclic group (e.g., azetidinyl, pyrrolidinyl, tetrahydropyranyl) optionally substituted by 1 to 3 substituents selected from a halogen atom (e.g., fluorine atom), a hydroxy group, a $C_{1-6}$ alkyl group (e.g., methyl), a $C_{1-6}$ alkoxy group (e.g., methoxy) and a $C_{6-14}$ aryl group (e.g., phenyl) or (4) —$NR^2R^3$[$R^2$ is a hydrogen atom or a $C_{1-6}$ alkyl group (e.g., methyl, ethyl), and $R^3$ is (i) a $C_{1-6}$ alkyl group (e.g., methyl, ethyl, propyl, isopropyl, isobutyl, neopentyl) optionally substituted by 1 to substituents selected from (a) a halogen atom (e.g., fluorine atom), (b) a hydroxy group, (c) a $C_{3-10}$ cycloalkyl group (e.g., cyclopropyl, cyclohexyl) optionally substituted by 1 to 3 substituents selected from a halogen atom (e.g., fluorine atom) and an amino group, (d) a $C_{1-6}$ alkoxy group (e.g., methoxy), (e) a $C_{6-14}$ aryl group (e.g., phenyl) optionally substituted by 1 to halogen atoms (e.g., fluorine atom), (f) an amino group optionally mono- or di-substituted by a $C_{1-6}$ alkyl group (e.g., methyl), (g) a 3- to 14-membered non-aromatic heterocyclic group (e.g., oxetanyl, tetrahydropyranyl) and (h) a 5- to 14-membered aromatic heterocyclic group (e.g., furyl, thienyl, thiazolyl, pyridyl, pyrimidinyl) or (ii) a $C_{3-10}$ cycloalkyl group (e.g., cyclopropyl, cyclobutyl) optionally substituted by 1 to 3 halogen atoms (e.g., fluorine atom)];

ring A is a $C_{6-14}$ aromatic hydrocarbon ring (e.g., benzene ring) or a 5- to 14-membered aromatic heterocycle (e.g., pyrazole ring, pyridine ring, pyrimidine ring, pyridazine ring, pyrazine ring, indazole ring, pyrazolopyridine ring), each of which is optionally further substituted by 1-5 (preferably 1-3, more preferably 1-2) substituents selected from (1) a halogen atom (e.g., fluorine atom, chlorine atom, bromine atom), (2) a $C_{1-6}$ alkyl group (e.g., methyl, ethyl) optionally substituted by 1 to 3 substituents selected from (a) a halogen atom (e.g., fluorine atom) and (b) a $C_{3-10}$ cycloalkyl group (e.g., cyclopropyl), (3) a $C_{1-6}$ alkoxy group (e.g., methoxy, ethoxy) optionally substituted by 1 to 3 substituents selected from (a) a halogen atom (e.g., fluorine atom), (b) a $C_{1-6}$ alkoxy group (e.g., methoxy) and (c) a carbamoyl group optionally mono- or di-substituted by a $C_{1-6}$ alkyl group (e.g., methyl), (4) a carbamoyl group optionally mono- or di-substituted by a $C_{1-6}$ alkyl group (e.g., methyl, ethyl) optionally substituted by a $C_{1-6}$ alkoxy group (e.g., methoxy), (5) a 3- to 14-membered non-aromatic heterocyclic group (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5]nonyl) and (6) a 5- to 14-membered aromatic heterocyclic group (e.g., thienyl, pyrazolyl, imidazolyl, thiazolyl, furyl, oxazolyl, pyridyl, pyrimidinyl, pyrazinyl) optionally substituted by 1 to 3 substituents selected from (a) an oxo group, (b) a $C_{1-6}$ alkyl group (e.g., methyl, ethyl, isopropyl, isobutyl) optionally substituted by 1 to 3 substituents selected from a halogen atom (e.g., fluorine atom), a $C_{3-10}$ cycloalkyl group (e.g., cyclopropyl) and a 3- to 14-membered non-aromatic heterocyclic group (e.g., morpholinyl), (c) a $C_{3-10}$ cycloalkyl group (e.g., cyclopropyl), (d) a $C_{1-6}$ alkoxy group (e.g., methoxy), (e) an amino group, (f) a carboxy group, (g) a $C_{1-6}$ alkoxy-carbonyl group (e.g., methoxycarbonyl, ethoxycarbonyl) and (h) a 3- to 14-membered non-aromatic heterocyclic group (e.g., tetrahydropyranyl);

ring B is a cyclohexane ring not substituted further; and ring C is a pyrimidine ring (that is, X is N) optionally further substituted by 1-3 (preferably 1-2) substituents selected from (1) a halogen atom (e.g., fluorine atom, chlorine atom), (2) a cyano group, (3) a $C_{1-6}$ alkyl group (e.g., methyl) optionally substituted by 1 to 3 halogen atoms (e.g., fluorine atom), (4) a $C_{6-14}$ aryl group (e.g., phenyl) optionally substituted by 1 to 3 substituents selected from (a) a halogen atom (e.g., fluorine atom, chlorine atom), (b) a cyano group, (c) a $C_{1-6}$ alkyl group (e.g., methyl) optionally substituted by 1 to 3 halogen atoms (e.g., fluorine atom), (d) a $C_{1-6}$ alkoxy group (e.g., methoxy) optionally substituted by 1 to 3 halogen atoms (e.g., fluorine atom), (e) a mono- or di-$C_{1-6}$ alkylamino group (e.g., dimethylamino), (f) a $C_{1-6}$ alkyl-carbonylamino group (e.g., acetylamino), (g) a $C_{1-6}$ alkyl-carbonyl group (e.g., methylcarbonyl), (h) a carbamoyl group, (i) a sulfamoyl group and (j) a 3- to 14-membered non-aromatic heterocyclic-sulfonyl group (e.g., morpholinylsulfonyl), (5) a $C_{1-6}$ alkoxy group (e.g., methoxy) optionally substituted by 1 to 3 substituents selected from (a) a halogen atom (e.g., fluorine atom), (b) a 3- to 14-membered non-aromatic heterocyclic group (e.g., oxetanyl) and (c) a 5- to 14-membered aromatic heterocyclic group (e.g., oxazolyl) optionally substituted by 1 to 3 $C_{1-6}$ alkyl groups (e.g., tert-butyl), (6) a $C_{6-14}$ aryloxy group (e.g., phenoxy) optionally substituted by 1 to 3 $C_{1-6}$ alkylsulfonyl groups (e.g., methylsulfonyl, isopropylsulfonyl), (7) a 3- to 14-membered non-aromatic heterocyclic-oxy group (e.g., oxetanyloxy) optionally substituted by 1 to 3 $C_{1-6}$ alkyl groups (e.g., methyl), (8) an amino group optionally mono- or di-substituted by substituent(s) selected from (a) a $C_{1-6}$ alkyl group (e.g., methyl, ethyl, n-propyl, isopropyl, n-butyl, isobutyl, tert-butyl, neopentyl, 1,2-dimethylpropyl) optionally substituted by 1 to 3 substituents selected from (i) a halogen atom (e.g., fluorine atom), (ii) a hydroxy group, (iii) a cyano group, (iv) a $C_{3-10}$ cycloalkyl group (e.g., cyclopropyl, cyclobutyl, cyclopentyl, cyclohexyl) optionally substituted by 1 to 3 hydroxy groups, (v) a $C_{6-14}$ aryl group (e.g., phenyl) optionally substituted by 1 to 3 substituents selected from a $C_{1-6}$ alkylsulfonyl group (e.g., methylsulfonyl) and a sulfamoyl group, (vi) a $C_{1-6}$ alkoxy group (e.g., methoxy, ethoxy) optionally substituted by 1 to 3 halogen atoms (e.g., fluorine atom), (vii) a mono- or di-$C_{1-6}$ alkylamino group (e.g., dimethylamino), (viii) a $C_{1-6}$ alkyl-carbonylamino group (e.g., acetylamino), (ix) a carbamoyl group, (x) a $C_{1-6}$ alkylsulfonyl group (e.g., methylsulfonyl), (xi) a 3- to 14-membered non-aromatic heterocyclic group (e.g., oxetanyl, thietanyl, morpholinyl, pyrrolidinyl, tetrahydrofuryl, tetrahydropyranyl) optionally substituted by 1 to 3 substituents selected from an oxo group and a $C_{1-6}$ alkyl group (e.g., methyl) and (xii) a 5-to 14-membered aromatic heterocyclic group (e.g., thienyl, furyl, pyrazolyl, imidazolyl, thiazolyl, oxazolyl, tetrazolyl, pyridyl, pyrimidinyl, pyridazinyl, pyrazinyl, oxadiazolyl) optionally substituted by 1 to 3 substituents selected from a $C_{1-6}$ alkyl group (e.g., methyl, tert-butyl), a $C_{3-10}$ cycloalkyl group (e.g., cyclopropyl) and a ($C_{1-6}$ alkyl) ($C_{1-6}$ alkyl-sulfonyl)amino group (e.g., N-methylsulfonyl-N-methylamino), (b) a $C_{3-10}$ cycloalkyl group optionally substituted by 1 to 3 substituents selected from a halogen atom (e.g., fluorine atom), a hydroxy group, a $C_{1-6}$ alkyl group optionally substituted by 1 to 3 hydroxy groups (e.g., methyl) and a $C_{1-6}$ alkoxy group (e.g., methoxy) optionally substituted by 1 to 3 halogen atoms (e.g., fluorine atom) (the $C_{3-10}$ cycloalkyl group also includes one having a spiro ring structure; for example, cyclopropyl, cyclobutyl, cyclopentyl, cyclohexyl, adamantyl, spiro [2.2]pentyl), (c) a $C_{6-14}$ aryl group (e.g., phenyl) optionally substituted by 1 to 3 $C_{1-6}$ alkylsulfonyl groups (e.g., methylsulfonyl, isopropylsulfonyl), (d) a $C_{3-10}$ cycloalkyl-carbonyl group (e.g., cyclopropylcarbonyl), (e) a 3- to 14-membered non-aromatic heterocyclic group optionally substituted by 1 to 3 substituents selected from an oxo group, a hydroxy group and $C_{1-6}$ alkyl group (e.g., methyl) (the 3- to 14-membered non-aromatic heterocyclic group also includes one having a bicyclo ring structure, a bridged ring structure, or a spiro ring structure; for example, oxetanyl, thietanyl, pyrrolidinyl, tetrahydrothienyl, tetrahydrothiopyranyl, tetrahydrofuryl, dihydroindolyl, tetrahydropyranyl, oxabicyclo[2.2.1]heptyl, azaspiro[2.4]heptyl, oxabicyclo[4.2.0]octyl) and (f) a 5- to 14-membered aromatic heterocyclic group (e.g., pyrazolyl), (9) a carbamoyl group, (10) a 3- to 14-membered non-aromatic heterocyclic group optionally substituted by 1 to 3 substituents selected from (a) an oxo group, (b) a halogen atom (e.g., fluorine atom), (c) a hydroxy group, (d) a cyano group, (e) a $C_{1-6}$ alkyl group (e.g., methyl, ethyl, isopropyl) optionally substituted by 1 to 3 substituents selected from a halogen atom (e.g., fluorine atom), a hydroxy group and a $C_{1-6}$ alkoxy group (e.g., methoxy), (f) a $C_{3-10}$ cycloalkyl group (e.g., cyclopropyl), (g) a $C_{1-6}$ alkoxy group (e.g., methoxy) optionally substituted by 1 to 3 halogen atoms (e.g., fluorine atom), (h) a $C_{1-6}$ alkyl-carbonyl group (e.g., methylcarbonyl), (i) a carbamoyl group, (j) a $C_{1-6}$ alkylsulfonyl group (e.g., methylsulfonyl, ethylsulfonyl), (k) a ($C_{1-6}$ alkyl) ($C_{1-6}$ alkyl-carbonyl)amino group (e.g., N-acetyl-N-ethyl-amino), (l) a dimethyl(oxide)-$\lambda^6$-sulfanylideneamino group and (m) a methylimino group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydropyranyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, tetrahydronaphthyridinyl, tetrahydroimidazopyrazinyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) and (11) a 5- to 14-membered aromatic heterocyclic group (e.g., thienyl, pyrazolyl, imidazolyl, triazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl) optionally substituted by 1 to 3 substituents selected from (a) an oxo group, (b) a hydroxy group, (c) a cyano group, (d) a halogen atom (e.g., fluorine atom, chlorine atom, bromine atom), (e) a $C_{1-6}$ alkyl group (e.g., methyl, ethyl) optionally substituted by 1 to 3 substituents selected from a hydroxy group, a halogen atom (e.g., fluorine atom), a $C_{3-10}$ cycloalkyl group (e.g., cyclopropyl), a $C_{6-14}$ aryl group (e.g., phenyl), a $C_{1-6}$ alkoxy-carbonyl group (e.g., ethoxycarbonyl) and a carbamoyl group, (f) a $C_{3-10}$ cycloalkyl group (e.g., cyclopropyl), (g) a $C_{1-6}$ alkoxy group (e.g., methoxy), (h) a $C_{1-6}$ alkoxy-carbonyl group (e.g., methoxycarbonyl), (i) a $C_{1-6}$ alkylsulfonyl group (e.g., methylsulfonyl) and (j) a 3- to 14-membered non-aromatic heterocyclic group (e.g., tetrahydropyranyl).

[Compound I-6]

Compound (I) wherein $R^1$ is (1) a $C_{1-6}$ alkyl group (e.g., methyl, ethyl, propyl) optionally substituted by 1 to 3 substituents selected from a halogen atom (e.g., fluorine atom), a $C_{1-6}$ alkoxy group (e.g., ethoxy) and a $C_{6-14}$ aryloxy group (e.g., phenoxy), (2) a $C_{1-6}$ alkoxy group (e.g., methoxy, ethoxy, isobutoxy) optionally substituted by 1 to 3 substituents selected from (a) a halogen atom (e.g., fluorine atom), (b) a hydroxy group, (c) a $C_{6-14}$ aryl group (e.g., phenyl), (d) an amino group optionally mono- or di-substituted by a $C_{1-6}$ alkyl group (e.g., methyl) and (e) a 5- to 14-membered aromatic heterocyclic group (e.g., pyridyl) or (3) —$NR^2R^3$ [$R^2$ is a hydrogen atom, and $R^3$ is a $C_{1-6}$ alkyl group (e.g., methyl, ethyl, propyl, isobutyl) optionally substituted by 1 to 3 substituents selected from (a) a halogen atom (e.g., fluorine atom), (b) a hydroxy group, (c) a $C_{3-10}$ cycloalkyl group (e.g., cyclopropyl) optionally substituted by 1 to 3 halogen atoms (e.g., fluorine atom), (d) a $C_{6-14}$ aryl group (e.g., phenyl) optionally substituted by 1 to 3 halogen atoms (e.g., fluorine atom) and (e) a 5- to 14-membered aromatic heterocyclic group (e.g., pyridyl)];

ring A is a $C_{6-14}$ aromatic hydrocarbon ring (e.g., benzene ring) or a 5- to 14-membered aromatic heterocycle (e.g., a pyridine ring, a pyrimidine ring, a pyridazine ring, a pyrazine ring), each of which is optionally further substituted by 1-5 (preferably 1-3, more preferably 1-2) substituents selected from (a) an oxo group, (b) a $C_{1-6}$ alkyl group (e.g., methyl) and (c) a 5- to 14-membered aromatic heterocyclic group (e.g., pyrazolyl, pyridyl, pyrimidinyl) optionally substituted by 1 to substituents selected from a $C_{1-6}$ alkoxy group (e.g., methoxy);

ring B is a cyclohexane ring not substituted further; and ring C is a pyrimidine ring (that is, X is N) optionally further substituted by 1-3 (preferably 1-2) substituents selected from (1) a cyano group, (2) a $C_{1-6}$ alkyl group (e.g., methyl) optionally substituted by 1 to 3 halogen atoms (e.g., fluorine atom), (3) a 3- to 14-membered non-aromatic heterocyclic-oxy group (e.g., oxetanyloxy), (4) an amino group optionally mono- or di-substituted by substituent(s) selected from (a) a $C_{1-6}$ alkyl group (e.g., n-propyl) optionally substituted by 1 to 3 hydroxy groups and (b) a 3- to 14-membered non-aromatic heterocyclic group optionally substituted by 1 to 3 $C_{1-6}$ alkyl groups (e.g., methyl) (the 3- to 14-membered non-aromatic heterocyclic group also includes one having a bicyclo ring structure, a bridged ring structure, or a spiro ring structure; for example, oxetanyl), (5) a 3- to 14-membered non-aromatic heterocyclic group optionally substituted by 1 to 3 substituents selected from (a) a halogen atom (e.g., fluorine atom), (b) a hydroxy group and (c) a $C_{1-6}$ alkyl group (e.g., methyl) optionally substituted by 1 to 3 hydroxy groups (the 3- to 14-membered non-aromatic heterocyclic group also includes one having a bicyclo ring structure, a bridged ring structure, or a spiro ring structure; for example, azetidinyl, azepanyl, oxazaspiro [3.4]octyl) and (6) a 5- to 14-membered aromatic heterocyclic group (e.g., thienyl, pyrazolyl, pyridyl) optionally substituted by 1 to 3 substituents selected from (a) a cyano group, (b) a halogen atom (e.g., chlorine atom), (c) a $C_{1-6}$ alkyl group (e.g., methyl) optionally substituted by 1 to 3 halogen atoms (e.g., fluorine atom) and (d) a $C_{1-6}$ alkylsulfonyl group (e.g., methylsulfonyl).

Specific examples of compound (I) include, for example, the compounds of Examples 1-19, 21-187, 191-483, 485- and 634-858.

The present invention also encompasses the following compounds.

A compound represented by the formula (I'):

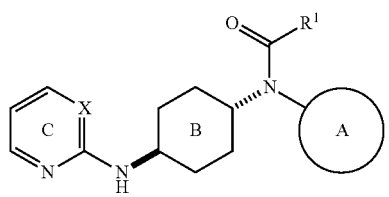

(I')

wherein
X is N;
$R^1$ is an optionally substituted $C_{1-6}$ alkyl group, an optionally substituted $C_{3-10}$ cycloalkyl group, an optionally substituted $C_{1-6}$ alkoxy group, an optionally substituted $C_{3-10}$ cycloalkyloxy group, an optionally substituted $C_{6-14}$ aryl group, an optionally substituted heterocyclic group, or $—NR^2R^3$;
$R^2$ is a hydrogen atom or a substituent;
$R^3$ is a hydrogen atom or a substituent;
ring A is an optionally further substituted aromatic ring;
ring B is an optionally further substituted cyclohexane ring; and
ring C is an optionally further substituted 6-membered nitrogen-containing aromatic heterocycle, or a salt thereof (sometimes to be abbreviated as "compound (I')" in the present specification).

Preferable examples of compound (I') include the following compounds.

[Compound I'-1]

Compound (I') wherein X is N;
$R^1$ is (1) a $C_{1-6}$ alkyl group (e.g., methyl, ethyl, propyl, isopropyl, butyl, isobutyl) optionally substituted by 1 to 3 substituents selected from a halogen atom (e.g., fluorine atom), a $C_{3-10}$ cycloalkyl group (e.g., cyclopropyl), a $C_{1-6}$ alkoxy group (e.g., methoxy, ethoxy) and a $C_{6-14}$ aryloxy group (e.g., phenoxy), (2) a $C_{3-10}$ cycloalkyl group (e.g., cyclopropyl), (3) a $C_{1-6}$ alkoxy group (e.g., methoxy, ethoxy, propoxy, isopropoxy, isobutoxy) optionally substituted by 1 to 3 substituents selected from (a) a halogen atom (e.g., fluorine atom), (b) a hydroxy group, (c) a $C_{3-10}$ cycloalkyl group (e.g., cyclopropyl) optionally substituted by 1 to 3 substituents selected from a halogen atom (e.g., fluorine atom) and an amino group, (d) a $C_{6-14}$ aryl group (e.g., phenyl), (e) a $C_{1-6}$ alkoxy group (e.g., methoxy), (f) an amino group optionally mono- or di-substituted by a $C_{1-6}$ alkyl group (e.g., methyl), (g) a 3- to 14-membered non-aromatic heterocyclic group (e.g., azetidinyl, morpholinyl) optionally substituted by 1 to 3 halogen atoms (e.g., fluorine atom) and (h) a 5- to 14-membered aromatic heterocyclic group (e.g., pyridyl), (4) a $C_{3-10}$ cycloalkyloxy group (e.g., cyclopropyloxy, cyclobutyloxy) optionally substituted by 1 to 3 halogen atoms (e.g., fluorine atom), (5) a 3- to 14-membered non-aromatic heterocyclic group (e.g., azetidinyl, pyrrolidinyl, tetrahydropyranyl) optionally substituted by 1 to 3 substituents selected from a halogen atom (e.g., fluorine atom), a hydroxy group, a $C_{1-6}$ alkyl group (e.g., methyl), a $C_{1-6}$ alkoxy group (e.g., methoxy) and a $C_{6-14}$ aryl group (e.g., phenyl) or (6) $—NR^2R^3$[$R^2$ is a hydrogen atom or a $C_{1-6}$ alkyl group (e.g., methyl, ethyl), and $R^3$ is (i) a hydrogen atom, (ii) a $C_{1-6}$ alkyl group (e.g., methyl, ethyl, propyl, isopropyl, isobutyl, neopentyl) optionally substituted by 1 to 3 substituents selected from (a) a halogen atom (e.g., fluorine atom), (b) a hydroxy group, (c) a $C_{3-10}$ cycloalkyl group (e.g., cyclopropyl, cyclohexyl) optionally substituted by 1 to 3 substituents selected from a halogen atom (e.g., fluorine atom) and an amino group, (d) a $C_{1-6}$ alkoxy group (e.g., methoxy), (e) a $C_{6-14}$ aryl group (e.g., phenyl) optionally substituted by 1 to 3 halogen atoms (e.g., fluorine atom), (f) an amino group optionally mono- or di-substituted by a $C_{1-6}$ alkyl group (e.g., methyl), (g) a 3- to 14-membered non-aromatic heterocyclic group (e.g., oxetanyl, tetrahydropyranyl) and (h) a 5- to 14-membered aromatic heterocyclic group (e.g., furyl, thienyl, thiazolyl, pyridyl, pyrimidinyl) or (iii) a $C_{3-10}$ cycloalkyl group (e.g., cyclopropyl, cyclobutyl) optionally substituted by 1 to 3 halogen atoms (e.g., fluorine atom)];

ring A is a $C_{6-14}$ aromatic hydrocarbon ring (e.g., benzene ring) or a 5- to 14-membered aromatic heterocycle (e.g., pyrazole ring, pyridine ring, pyrimidine ring, pyridazine ring, pyrazine ring, indazole ring, pyrazolopyridine ring), each of which is optionally further substituted by 1-5 (preferably 1-3, more preferably 1-2) substituents selected from (1) a halogen atom (e.g., fluorine atom, chlorine atom, bromine atom), (2) a $C_{1-6}$ alkyl group (e.g., methyl, ethyl) optionally substituted by 1 to 3 substituents selected from (a) a halogen atom (e.g., fluorine atom) and (b) a $C_{3-10}$ cycloalkyl group (e.g., cyclopropyl), (3) a $C_{1-6}$ alkoxy group (e.g., methoxy, ethoxy) optionally substituted by 1 to 3 substituents selected from (a) a halogen atom (e.g., fluorine atom), (b) a $C_{1-6}$ alkoxy group (e.g., methoxy) and (c) a carbamoyl group optionally mono- or di-substituted by a $C_{1-6}$ alkyl group (e.g., methyl), (4) a carbamoyl group optionally mono- or di-substituted by a $C_{1-6}$ alkyl group (e.g., methyl, ethyl) optionally substituted by a $C_{1-6}$ alkoxy group (e.g., methoxy), (5) a 3- to 14-membered non-aromatic heterocyclic group (the 3- to 14-membered non-aromatic heterocyclic group also includes one having a spiro ring structure; for example, piperazinyl, piperidinyl, morpholinyl, dihydropyranyl, tetrahydropyridyl, pyrrolidinyl, thiomorpholinyl, tetrahydropyrazolopyridyl, oxazaspiro[3.5] nonyl) and (6) a 5- to 14-membered aromatic heterocyclic group (e.g., thienyl, pyrazolyl, imidazolyl, thiazolyl, furyl, oxazolyl, pyridyl, pyrimidinyl, pyrazinyl) optionally substituted by 1 to 3 substituents selected from (a) an oxo group, (b) a $C_{1-6}$ alkyl group (e.g., methyl, ethyl, isopropyl, isobutyl) optionally substituted by 1 to 3 substituents selected from a halogen atom (e.g., fluorine atom), a $C_{3-10}$ cycloalkyl group (e.g., cyclopropyl) and a 3- to 14-membered non-aromatic heterocyclic group (e.g., morpholinyl), (c) a $C_{3-10}$ cycloalkyl group (e.g., cyclopropyl), (d) a $C_{1-6}$ alkoxy group (e.g., methoxy), (e) an amino group, (f) a carboxy group, (g) a $C_{1-6}$ alkoxy-carbonyl group (e.g., methoxycarbonyl, ethoxycarbonyl) and (h) a 3- to 14-membered non-aromatic heterocyclic group (e.g., tetrahydropyranyl);

ring B is a cyclohexane ring not substituted further; and
ring C is a pyrimidine ring optionally further substituted by 1-3 (preferably 1-2) substituents selected from (1) a halogen atom (e.g., fluorine atom, chlorine atom), (2) a cyano group, (3) a $C_{1-6}$ alkyl group (e.g., methyl) optionally substituted by 1 to 3 halogen atoms (e.g., fluorine atom), (4) a $C_{6-14}$ aryl group (e.g., phenyl) optionally substituted by 1 to 3 substituents selected from (a) a halogen atom (e.g., fluorine atom, chlorine atom), (b) a cyano group, (c) a $C_{1-6}$ alkyl group (e.g., methyl) optionally substituted by 1 to 3 halogen atoms (e.g., fluorine atom), (d) a $C_{1-6}$ alkoxy group (e.g., methoxy) optionally substituted by 1 to 3 halogen atoms (e.g., fluorine atom), (e) a mono- or di-$C_{1-6}$ alkylamino group (e.g., dimethylamino), (f) a $C_{1-6}$ alkyl-carbonylamino group (e.g., acetylamino), (g) a $C_{1-6}$ alkyl-carbonyl group (e.g., methylcarbonyl), (h) a carbamoyl group, (i) a sulfamoyl group and (j) a 3- to 14-membered non-aromatic heterocyclic-sulfonyl group (e.g., morpholinylsulfonyl), (5) a $C_{1-6}$ alkoxy group (e.g., methoxy) optionally substituted by 1 to 3 substituents selected from (a) a halogen atom (e.g., fluorine atom), (b) a 3- to 14-membered non-aromatic heterocyclic group (e.g., oxetanyl) and (c) a 5- to 14-membered aromatic heterocyclic group (e.g., oxazolyl) optionally substituted by 1 to 3 $C_{1-6}$ alkyl groups (e.g., tert-butyl), (6) a $C_{6-14}$ aryloxy group (e.g., phenoxy) optionally substituted by 1 to 3 $C_{1-6}$ alkylsulfonyl groups (e.g., methylsulfonyl, isopropylsulfonyl), (7) a 3- to 14-membered non-aromatic heterocyclic-oxy group (e.g., oxetanyloxy) optionally substituted by 1 to 3 $C_{1-6}$ alkyl groups (e.g., methyl), (8) an amino group optionally mono- or di-substituted by substituent(s) selected from (a) a $C_{1-6}$ alkyl group (e.g., methyl, ethyl, n-propyl, isopropyl, n-butyl, isobutyl, tert-butyl, neopentyl, 1,2-dimethylpropyl) optionally substituted by 1 to 3 substituents selected from (i) a halogen atom (e.g., fluorine atom), (ii) a hydroxy group, (iii) a cyano group, (iv) a $C_{3-10}$ cycloalkyl group (e.g., cyclopropyl, cyclobutyl, cyclopentyl, cyclohexyl) optionally substituted by 1 to 3 hydroxy groups, (v) a $C_{6-14}$ aryl group (e.g., phenyl) optionally substituted by 1 to 3 substituents selected from a $C_{1-6}$ alkylsulfonyl group (e.g., methylsulfonyl) and a sulfamoyl group, (vi) a $C_{1-6}$ alkoxy group (e.g., methoxy, ethoxy) optionally substituted by 1 to 3 halogen atoms (e.g., fluorine atom), (vii) a mono- or di-$C_{1-6}$ alkylamino group (e.g., dimethylamino), (viii) a $C_{1-6}$ alkyl-carbonylamino group (e.g., acetylamino), (ix) a carbamoyl group, (x) a $C_{1-6}$ alkylsulfonyl group (e.g., methylsulfonyl), (xi) a 3- to 14-membered non-aromatic heterocyclic group (e.g., oxetanyl, thietanyl, morpholinyl, pyrrolidinyl, tetrahydrofuryl, tetrahydropyranyl) optionally substituted by 1 to 3 substituents selected from an oxo group and a $C_{1-6}$ alkyl group (e.g., methyl) and (xii) a 5-to 14-membered aromatic heterocyclic group (e.g., thienyl, furyl, pyrazolyl, imidazolyl, thiazolyl, oxazolyl, tetrazolyl, pyridyl, pyrimidinyl, pyridazinyl, pyrazinyl, oxadiazolyl) optionally substituted by 1 to 3 substituents selected from a $C_{1-6}$ alkyl group (e.g., methyl, tert-butyl), a $C_{3-10}$ cycloalkyl group (e.g., cyclopropyl) and a ($C_{1-6}$ alkyl) ($C_{1-6}$ alkyl-sulfonyl)amino group (e.g., N-methylsulfonyl-N-methylamino), (b) a $C_{3-10}$ cycloalkyl group optionally substituted by 1 to 3 substituents selected from a halogen atom (e.g., fluorine atom), a hydroxy group, a $C_{1-6}$ alkyl group optionally substituted by 1 to 3 hydroxy groups (e.g., methyl) and a $C_{1-6}$ alkoxy group (e.g., methoxy) optionally substituted by 1 to 3 halogen atoms (e.g., fluorine atom) (the $C_{3-10}$ cycloalkyl group also includes one having a spiro ring structure; for example, cyclopropyl, cyclobutyl, cyclopentyl, cyclohexyl, adamantyl, spiro-[2.2]pentyl), (c) a $C_{6-14}$ aryl group (e.g., phenyl) optionally substituted by 1 to 3 $C_{1-6}$ alkylsulfonyl groups (e.g., methylsulfonyl, isopropylsulfonyl), (d) a $C_{3-10}$ cycloalkylcarbonyl group (e.g., cyclopropylcarbonyl), (e) a 3- to 14-membered non-aromatic heterocyclic group optionally substituted by 1 to 3 substituents selected from an oxo group, a hydroxy group and $C_{1-6}$ alkyl group (e.g., methyl) (the 3- to 14-membered non-aromatic heterocyclic group also includes one having a bicyclo ring structure, a bridged ring structure, or a spiro ring structure; for example, oxetanyl, thietanyl, pyrrolidinyl, tetrahydrothienyl, tetrahydrothiopyranyl, tetrahydrofuryl, dihydroindolyl, tetrahydropyranyl, oxabicyclo[2.2.1]heptyl, azaspiro[2.4]heptyl, oxabicyclo[4.2.0]octyl) and (f) a 5- to 14-membered aromatic heterocyclic group (e.g., pyrazolyl), (9) a carbamoyl group, (10) a 3- to 14-membered non-aromatic heterocyclic group optionally substituted by 1 to 3 substituents selected from (a) an oxo group, (b) a halogen atom (e.g., fluorine atom), (c) a hydroxy group, (d) a cyano group, (e) a $C_{1-6}$ alkyl group (e.g., methyl, ethyl, isopropyl) optionally substituted by 1 to 3 substituents selected from a halogen atom (e.g., fluorine atom), a hydroxy group and a $C_{1-6}$ alkoxy group (e.g., methoxy), (f) a $C_{3-10}$ cycloalkyl group (e.g., cyclopropyl), (g) a $C_{1-6}$ alkoxy group (e.g., methoxy) optionally substituted by 1 to 3 halogen atoms (e.g., fluorine atom), (h) a $C_{1-6}$ alkyl-carbonyl group (e.g., methylcarbonyl), (i) a carbamoyl group, (j) a $C_{1-6}$ alkylsulfonyl group (e.g., methylsulfonyl, ethylsulfonyl), (k) a ($C_{1-6}$ alkyl) ($C_{1-6}$ alkyl-carbonyl)amino group (e.g., N-acetyl-N-ethylamino), (l) a dimethyl(oxide)-$\lambda^6$-sulfanylideneamino group and (m) a methylimino group (the 3- to 14-membered non-aromatic heterocyclic group also includes one having a bicyclo ring structure, a bridged ring structure, or a spiro ring structure; for example, azetidinyl, piperazinyl, piperidinyl, morpholinyl, azepanyl, thiazepanyl, pyrrolidinyl, oxazepanyl, diazepanyl, thiomorpholinyl, imidazolidinyl, dihydropyranyl, dihydroimidazopyrazinyl, dihydrothiazolopyridyl, dihydrotriazolopyrazinyl, dihydrobenzimidazolyl, dihydronaphthyridyl, dihydroquinazolyl, dihydropyridoxazinyl, dihydroindolyl, dihydrotriazolopyrazinyl, oxazolidinyl, dihydropyrrolopyridyl, thiadianyl, tetrahydronaphthyridinyl, tetrahydroimidazopyrazinyl, hexahydropyrrolopyrrolyl, octahydropyrrolopyridyl, azabicyclo[3.2.1]octyl, azabicyclo[3.1.0]hexyl, oxazaspiro[3.5]nonyl, diazaspiro[4.5]decyl, diazaspiro[3.5]nonyl, oxazaspiro[5.5]undecyl, oxazaspiro[4.5]decyl, diazaspiro[4.4]nonyl, diazaspiro[3.4]octyl, azaspiro[2.4]heptyl, oxazaspiro[3.4]octyl, thiazaspiro[4.5]decyl, oxazaspiro[4.4]nonyl, oxazaspiro[3.3]heptyl, dioxazaspiro[3.5]nonyl, oxadiazaspiro[4.5]decenyl, oxadiazaspiro[4.6]undecenyl, oxadiazaspiro[3.4]octyl, oxadiazaspiro[4.4]nonenyl, oxadiazaspiro[3.4]octenyl) and (11) a 5- to 14-membered aromatic heterocyclic group (e.g., thienyl, pyrazolyl, imidazolyl, triazolyl, thiazolyl, oxazolyl, pyridyl, pyrimidinyl, pyridazinyl, indazolyl, indolyl, pyrazolopyridyl, benzoxazolyl, benzothiazolyl, benzimidazolyl, imidazopyridyl, benzoxadiazolyl) optionally substituted by 1 to 3 substituents selected from (a) an oxo group, (b) a hydroxy group, (c) a cyano group, (d) a halogen atom (e.g., chlorine atom, bromine atom), (e) a $C_{1-6}$ alkyl group (e.g., methyl, ethyl) optionally substituted by 1 to 3 substituents selected from a hydroxy group, a halogen atom (e.g., fluorine atom), a $C_{3-10}$ cycloalkyl group (e.g., cyclopropyl), a $C_{6-14}$ aryl group (e.g., phenyl), a $C_{1-6}$ alkoxy-carbonyl group (e.g., ethoxycarbonyl) and a carbamoyl group, (f) a $C_{3-10}$ cycloalkyl group (e.g., cyclopropyl), (g) a $C_{1-6}$ alkoxy group (e.g., methoxy), (h) a $C_{1-6}$ alkoxy-carbonyl group (e.g., methoxycarbonyl), (i) a $C_{1-6}$ alkylsulfonyl group (e.g., methylsulfonyl) and (j) a 3- to 14-membered non-aromatic heterocyclic group (e.g., tetrahydropyranyl).

As a salt of a compound represented by the formula (I), a pharmacologically acceptable salt is preferable, and examples of such salt include a salt with inorganic base, a salt with organic base, a salt with inorganic acid, a salt with organic acid, and a salt with basic or acidic amino acid.

Preferable examples of the salt with inorganic base include alkali metal salts such as sodium salt, potassium salt and the like, alkaline earth metal salts such as calcium salt, magnesium salt and the like, aluminum salt, and ammonium salt.

Preferable examples of the salt with organic base include salts with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine, and N,N-dibenzylethylenediamine.

Preferable examples of the salt with inorganic acid include salts with hydrogen chloride, hydrogen bromide, nitric acid, sulfuric acid, and phosphoric acid.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

Preferable examples of the salt with basic amino acid include salts with arginine, lysine, and ornithine.

Preferable examples of the salt with acidic amino acid include salts with aspartic acid, and glutamic acid.

The production method of the compound of the present invention is explained in the following.

The starting materials and reagents used in each step in the following production method, and the obtained compounds each may form a salt. Examples of the salt include those similar to the aforementioned salts of the compound of the present invention and the like.

When the compound obtained in each step is a free compound, it can be converted to a desired salt by a method known per se. Conversely, when the compound obtained in each step is a salt, it can be converted to a free form or a desired other kind of salt by a method known per se.

The compound obtained in each step can also be used for the next reaction as a reaction mixture thereof or after obtaining a crude product thereof. Alternatively, the compound obtained in each step can be isolated and/or purified from the reaction mixture by a separation means such as concentration, crystallization, recrystallization, distillation, solvent extraction, fractionation, chromatography and the like according to a conventional method.

When the starting materials and reagent compounds of each step are commercially available, the commercially available products can be used as they are.

In the reaction of each step, while the reaction time varies depending on the reagents and solvents to be used, unless otherwise specified, it is generally 1 min-48 hr, preferably 10 min-8 hr.

In the reaction of each step, while the reaction temperature varies depending on the reagents and solvents to be used, unless otherwise specified, it is generally −78° C. to 300° C., preferably −78° C. to 150° C.

In the reaction of each step, while the pressure varies depending on the reagents and solvents to be used, unless otherwise specified, it is generally 1 atm-20 atm, preferably atm-3 atm.

In the reaction of each step, for example, microwave synthesizers such as Initiator manufactured by Biotage and the like are sometimes used. While the reaction temperature varies depending on the reagents and solvents to be used, unless otherwise specified, it is generally room temperature-300° C., preferably 50° C.-250° C. While the reaction time varies depending on the reagents and solvents to be used, unless otherwise specified, it is generally 1 min-48 hr, preferably 1 min-8 hr.

In the reaction of each step, unless otherwise specified, a reagent is used in 0.5 equivalent-20 equivalents, preferably 0.8 equivalent-5 equivalents, relative to the substrate. When a reagent is used as a catalyst, the reagent is used in 0.001 equivalent-1 equivalent, preferably 0.01 equivalent-0.2 equivalent, relative to the substrate. When the reagent is also a reaction solvent, the reagent is used in a solvent amount.

In the reaction of each step, unless otherwise specified, it is performed without solvent or by dissolving or suspending in a suitable solvent. Specific examples of the solvent include those described in Examples and the following.
alcohols: methanol, ethanol, tert-butyl alcohol, 2-methoxyethanol and the like;
ethers: diethyl ether, diphenyl ether, diisopropyl ether, tetrahydrofuran, 1,4-dioxane, 1,2-dimethoxyethane and the like; aromatic hydrocarbons: chlorobenzene, toluene, xylene and the like;
saturated hydrocarbons: cyclohexane, hexane and the like;
amides: N,N-dimethylformamide, N,N-dimethylacetamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
acid anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; and
water.

Two or more kinds of the above-mentioned solvents may be used by mixing at an appropriate ratio.

When a base is used in the reaction of each step, for example, bases shown below or those described in Examples are used.
inorganic bases: sodium hydroxide, magnesium hydroxide, sodium carbonate, calcium carbonate, sodium hydrogen carbonate and the like;

organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;

metal alkoxides: sodium ethoxide, potassium tert-butoxide and the like;

alkali metal hydrides: sodium hydride and the like; metal amides: sodium amide, lithium diisopropyl amide, lithium hexamethyl disilazide and the like; and organic lithiums: n-butyllithium and the like.

When an acid or acidic catalyst is used in the reaction of each step, for example, acids and acidic catalysts shown below or those described in Examples are used.

inorganic acids: hydrochloric acid, sulfuric acid, nitric acid, hydrobromic acid, phosphoric acid and the like; organic acids: acetic acid, trifluoroacetic acid, citric acid, p-toluenesulfonic acid, 10-camphorsulfonic acid and the like; and Lewis acids: boron trifluoride diethyl ether complex, zinc iodide, anhydrous aluminum chloride, anhydrous zinc chloride, anhydrous iron chloride and the like.

Unless otherwise specified, the reaction of each step is performed according to a method known per se, for example, the methods described in Jikken Kagaku Kouza 5th edition, vol. 13-vol. 19 (The Chemical Society of Japan ed.); Shinjikken Kagaku Kouza (Courses in Experimental Chemistry), vol. 14-vol. 15 (The Chemical Society of Japan ed.); Fine Organic Chemistry rev. 2nd edition (L. F. Tietze, Th. Eicher, NANKODO); rev. Organic Name Reactions, Their Mechanism and Essence (Hideo Togo, Kodansha); ORGANIC SYNTHESES Collective Volume I-VII (John Wiley & Sons Inc); Modern Organic Synthesis in the Laboratory, A Collection of Standard Experimental Procedures (Jie Jack Li, OXFORD UNIVERSITY); Comprehensive Heterocyclic Chemistry III, Vol. 1-Vol. 14 (Elsevier Japan KK); Strategic Applications of Named Reactions in Organic Synthesis (translation supervisor Kiyoshi Tomioka, KAGAKUDOJIN); Comprehensive Organic Transformations (VCH Publishers Inc.), 1989 and the like, or the methods described in the Examples.

In each step, protection or deprotection reaction of a functional group is performed by the method known per se, for example, the methods described in "Protective Groups in Organic Synthesis, 4th Ed." (Theodora W. Greene, Peter G. M. Wuts) Wiley-Interscience, 2007; "Protecting Groups 3rd Ed." (P. J. Kocienski) Thieme, 2004 and the like, or the methods described in the Examples.

Examples of the protecting group of the hydroxyl group of alcohol and the like and a phenolic hydroxyl group include ether protecting groups such as methoxymethyl ether, benzyl ether, tert-butyldimethylsilyl ether, tetrahydropyranyl ether and the like; carboxylate ester protecting groups such as acetate ester and the like; sulfonate ester protecting groups such as methanesulfonate ester and the like; carbonate ester protecting groups such as tert-butylcarbonate and the like, and the like.

Examples of the protecting group of the carbonyl group of aldehyde include acetal protecting groups such as dimethyl acetal and the like; cyclic acetal protecting groups such as 1,3-dioxane and the like, and the like.

Examples of the protecting group of the carbonyl group of ketone include ketal protecting groups such as dimethyl ketal and the like; cyclic ketal protecting groups such as 1,3-dioxane and the like; oxime protecting groups such as O-methyloxime and the like; hydrazone protecting groups such as N,N-dimethylhydrazone and the like, and the like.

Examples of the carboxyl protecting group include ester protecting groups such as methyl ester and the like; amide protecting groups such as N,N-dimethylamide and the like, and the like.

Examples of the thiol protecting group include ether protecting groups such as benzyl thioether and the like; ester protecting groups such as thioacetate ester, thiocarbonate, thiocarbamate and the like, and the like.

Examples of the protecting group of an amino group and an aromatic heterocycle such as imidazole, pyrrole, indole and the like include carbamate protecting groups such as benzyl carbamate and the like; amide protecting groups such as acetamide and the like; alkylamine protecting groups such as N-triphenylmethylamine and the like, sulfonamide protecting groups such as methanesulfonamide and the like, and the like.

The protecting group can be removed by a method known per se, for example, a method using acid, base, ultraviolet light, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide), a reduction method and the like.

When a reduction reaction is performed in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane, and the like. When a carbon-carbon double bond or triple bond is reduced, a method using a catalyst such as palladium-carbon, Lindlar catalyst and the like is used.

When an oxidation reaction is performed in each step, examples of an oxidant to be used include peracids such as m-chloroperbenzoic acid (mCPBA), hydrogen peroxide, tert-butyl hydroperoxide and the like; perchlorates such as tetrabutylammonium perchlorate and the like; chlorates such as sodium chlorate and the like; chlorites such as sodium chlorite and the like; periodic acids such as sodium periodate and the like; high valent iodine reagents such as iodosylbenzene and the like; reagents containing manganese such as manganese dioxide, potassium permanganate and the like; leads such as lead tetraacetate and the like; reagents containing chrome such as pyridinium chlorochromate (PCC), pyridinium dichromate (PDC), Jones reagent and the like; halogen compounds such as N-bromosuccinimide (NBS) and the like; oxygen; ozone; sulfur trioxide pyridine complex; osmium tetraoxide; selenium dioxide; 2,3-dichloro-5, 6-dicyano-1,4-benzoquinone (DDQ) and the like.

When a radical cyclization reaction is performed in each step, examples of the radical initiator to be used include azo compounds such as azobisisobutyronitrile (AIBN) and the like; water-soluble radical initiators such as 4,4'-azobis-4-cyanopentanoic acid (ACPA) and the like; triethylboron in the presence of air or oxygen; benzoyl peroxide and the like. In addition, examples of the radical reaction agent to be used include tributylstannane, tristrimethylsilylsilane, 1,1,2,2-tetraphenyldisilane, diphenylsilane, samarium iodide and the like.

When the Wittig reaction is performed in each step, examples of the Wittig reagent to be used include alkylidenephosphoranes and the like. Alkylidenephosphoranes can be prepared by a method known per se, for example, by reacting a phosphonium salt with a strong base.

When the Horner-Emmons reaction is performed in each step, examples of the reagent to be used include phosphonoacetic acid esters such as methyl dimethylphosphonoacetate, ethyl diethylphosphonoacetate and the like; and bases such as alkali metal hydrides, organic lithiums and the like.

When the Friedel-Crafts reaction is performed in each step, examples of the reagent to be used include a combination of Lewis acid and acid chloride, and a combination of Lewis acid and alkylating agent (e.g., alkyl halides, alcohol, olefins and the like). Alternatively, an organic acid and an inorganic acid can also be used instead of the Lewis acid, and acid anhydride such as acetic anhydride and the like can also be used instead of acid chloride.

When an aromatic nucleophilic substitution reaction is performed in each step, a nucleophilic agent (e.g., amines, imidazole and the like) and a base (e.g., organic bases and the like) are used as the reagent.

When a nucleophilic addition reaction with carbanion, a nucleophilic 1,4-addition reaction with carbanion (Michael addition reaction) or a nucleophilic substitution reaction with carbanion is performed in each step, examples of the base to be used for developing carbanion include organic lithiums, metal alkoxides, inorganic bases, organic bases and the like.

When the Grignard reaction is performed in each step, examples of the Grignard reagent include aryl magnesium halides such as phenyl magnesium bromide and the like; and alkyl magnesium halides such as methyl magnesium bromide and the like. The Grignard reagent can be prepared by a method known per se, for example, by reacting alkyl halide or aryl halide with metal magnesium in ether or tetrahydrofuran as a solvent.

When the Knoevenagel condensation reaction is performed in each step, an active methylene compound held between two electron-withdrawing groups (e.g., malonic acid, diethyl malonate, malononitrile and the like) and a base (e.g., organic bases, metal alkoxides, inorganic bases) are used as the reagents.

When the Vilsmeier-Haack reaction is performed in each step, phosphoryl chloride and an amide derivative (e.g., N,N-dimethylformamide and the like) are used as the reagents.

When an azidation reaction of alcohols, alkyl halides or sulfonate esters is performed in each step, examples of the azidation agent to be used include diphenylphosphoryl azide (DPPA), trimethylsilyl azide, sodium azide and the like. For example, when alcohols are azidated, a method using diphenylphosphoryl azide and 1,8-diazabicyclo[5,4,0]undec-7-ene (DBU), a method using trimethylsilyl azide and the Lewis acid and the like can be employed.

When a reductive amination reaction is performed in each step, examples of the reducing agent to be used include sodium triacetoxyborohydride, sodium cyanoborohydride, hydrogen, formic acid and the like. When the substrate is an amine compound, examples of the carbonyl compound to be used besides para-formaldehyde include aldehydes such as acetaldehyde and the like, ketones such as cyclohexanone and the like. When the substrate is a carbonyl compound, examples of the amines to be used include primary amines such as ammonia, methylamine and the like; secondary amines such as dimethylamine and the like, and the like.

When the Mitsunobu reaction is performed in each step, azodicarboxylate esters (e.g., diethyl azodicarboxylate (DEAD), diisopropyl azodicarboxylate (DIAD) and the like) and triphenylphosphine are used as the reagents.

When an esterification reaction, amidation reaction or ureation reaction is performed in each step, examples of the reagent to be used include halogenated acyl forms such as acid chloride, acid bromide and the like; and activated carboxylic acids such as acid anhydride, active ester form, sulfuric acid ester form and isocyanates. Examples of the carboxylic acid activator include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methylpyridinium iodide (Mukaiyama reagent); thionyl chloride; lower alkyl haloformates such as ethyl chloroformate and the like; 0-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocene palladium(II) chloride, palladium(II) acetate and the like; nickel compounds such as tetrakis(triphenylphosphine)nickel(0) and the like; rhodium compounds such as tris(triphenylphosphine)rhodium(III) chloride and the like; a cobalt compound; copper compounds such as copper oxide, copper(I) iodide and the like; a platinum compound and the like. A base may be further added to the reaction and examples of such base include inorganic bases, and the like.

When a thiocarbonylation reaction is performed in each step, diphosphorus pentasulfide is representatively used as a thiocarbonylating agent. Besides diphosphorus pentasulfide, a reagent having a 1,3,2,4-dithiadiphosphetane-2,4-disulfide structure such as 2,4-bis(4-methoxyphenyl-1,3,2,4-dithiadiphosphetane-2,4-disulfide (Lawesson reagent) and the like may also be used.

When the Wohl-Ziegler reaction is performed in each step, examples of the halogenating agent to be used include N-iodosuccinimide, N-bromosuccinimide (NBS), N-chlorosuccinimide (NCS), bromine, sulfuryl chloride and the like. Furthermore, the reaction can be accelerated by adding heat, light, radical initiators such as benzoyl peroxide, azobisisobutyronitrile and the like to the reaction.

When a halogenating reaction of a hydroxy group is performed in each step, examples of the halogenating agent to be used include acid halide of hydrohalic acid and inorganic acid; specifically, hydrochloric acid, thionyl chloride, phosphorus oxychloride and the like for chlorination, and 48% hydrobromic acid and the like for bromination. In addition, a method of obtaining a alkyl halide form from alcohol by reacting with triphenylphosphine and carbon tetrachloride or carbon tetrabromide, and the like may be used. Alternatively, a method of synthesizing a alkyl halide form via a two-step reaction including conversion of alcohol to sulfonic acid ester, and reacting same with lithium bromide, lithium chloride or sodium iodide may also be used.

When the Arbuzov reaction is performed in each step, examples of the reagent to be used include alkyl halides such as ethyl bromoacetate and the like; and phosphites such as triethyl phosphite, tri(isopropyl) phosphite and the like.

When a sulfonate esterification reaction is performed in each step, examples of the sulfonylation agent to be used include methanesulfonyl chloride, p-toluenesulfonyl chloride, methanesulfonic anhydride, p-toluenesulfonic anhydride and the like.

When a hydrolysis reaction is performed in each step, an acid or a base is used as the reagent. In addition, when an acid hydrolysis reaction of tert-butyl ester is performed, formic acid, triethylsilane and the like are sometimes added to reductively trap the by-produced tert-butyl cation.

When a dehydration reaction is performed in each step, examples of the dehydrating agent to be used include sulfuric acid, phosphorus pentaoxide, phosphorus oxychloride, N,N'-dicyclohexylcarbodiimide, alumina, polyphosphoric acid and the like.

When an acylation reaction is performed in each step, examples of the reagent to be used include halogenated acyl forms such as acid chloride, acid bromide and the like; and activated carboxylic acids such as active ester form, ester form, sulfuric acid ester form and the like. Examples of the carboxylic acid activator include acid anhydride (e.g., acetic anhydride), carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride-n-hydrate (DMT-MM) and the like; carbonate ester condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; 0-(7-azabenzotriazol-1-yl)-N,N,N',N'-tetramethyluronium hexafluorophosphate (HATU); sulfuric acid; a combination thereof and the like. When a carbodiimide condensing agent is used, additives such as 1-hydroxybenzotriazole (HOBt), N-hydroxysuccinimide (HOSu), dimethylaminopyridine (DMAP) and the like can be further added to the reaction.

When a coupling reaction is performed in each step, a ligand may be added in the reaction system. Examples of the ligand include phosphine ligands [e.g., triphenylphosphine, 2,2'-bis(diphenylphosphino)-1,1'-binaphthyl, 2-dicyclohexylphosphino-2',6'-diisopropoxy-1,1'-biphenyl, 2-(dicyclohexylphosphino)-3,6-dimethoxy-2',4',6'-triisopropyl-1,1'-biphenyl, 2-di-tert-butylphosphino-3,4,5,6-tetramethyl-2',4',6'-triisopropyl-1,1'-biphenyl, 2-(di-tert-butylphosphino) biphenyl, 2-(dicyclohexylphosphino)biphenyl, 2-dicyclohexylphosphino-2',6'-dimethoxy-1,1'-biphenyl, 2-dicyclohexylphosphino-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, 4,5-bis(diphenylphosphino)-9,9-dimethylxanthene], amine ligands (N,N'-dimethylethylenediamine, trans-1,2-diaminocyclohexane, trans-N,N'-dimethyl-1,2-cyclohexanediamine, 1,10-phenanthrolin, 4,7-dimethoxy-1,10-phenanthrolin, 3,4,7,8-tetramethyl-1,10-phenanthrolin etc.), diketone ligands (2-acetylcyclohexanone, 2-isobutyrylhexanone, 2,2,6,6-tetramethyl-3,5-heptanedione etc.), salicylaldoxime, and proline.

Examples of the leaving group to be used in each step include a halogen atom (e.g., fluorine atom, chlorine atom, bromine atom, iodine atom), a $C_{1-6}$ alkoxy group (e.g., methoxy, etc.), a $C_{6-14}$ aryloxy group (e.g., phenoxy, etc.), an optionally substituted acyloxy group (e.g., acetyloxy, benzoyloxy, etc.), an optionally substituted $C_{1-6}$ alkoxysulfonyloxy group (e.g., methoxysulfonyloxy, etc.), an optionally halogenated $C_{1-6}$ alkylsulfonyloxy group [e.g., methanesulfonyloxy, ethanesulfonyloxy, trichloromethanesulfonyloxy, trifluoromethanesulfonyloxy(triflate), etc.], an optionally substituted $C_{6-14}$ arylsulfonyloxy group [e.g., $C_{6-14}$ arylsulfonyloxy group optionally having 1 to 3 substituents selected from $C_{1-6}$ alkyl group (e.g., methyl, ethyl, propyl, isopropyl, butyl, isobutyl, sec-butyl, tert-butyl, pentyl, hexyl etc.), $C_{1-6}$ alkoxy group (e.g., methoxy, ethoxy, propoxy, isopropoxy, butoxy, isobutoxy, sec-butoxy, pentyloxy, hexyloxy, etc.) and nitro group, and the like. Specific examples include benzenesulfonyloxy, m-nitrobenzenesulfonyloxy, p-toluenesulfonyloxy, naphthylsulfonyloxy, etc.] and the like.

When an aromatic nucleophilic substitution reaction is performed in each step, alcohols, thiols and salts thereof can also be used as a nucleophilic agent.

In the following, the production method of compound (I) is explained.

Unless otherwise specified, each symbol in the following reaction schemes is as defined above.

Unless otherwise specified, the starting compounds used in the following various production methods can be produced by methods known per se.

[Production method A-1]

Compound (I) can be produced from compound (2) by the following method or a method analogous thereto.

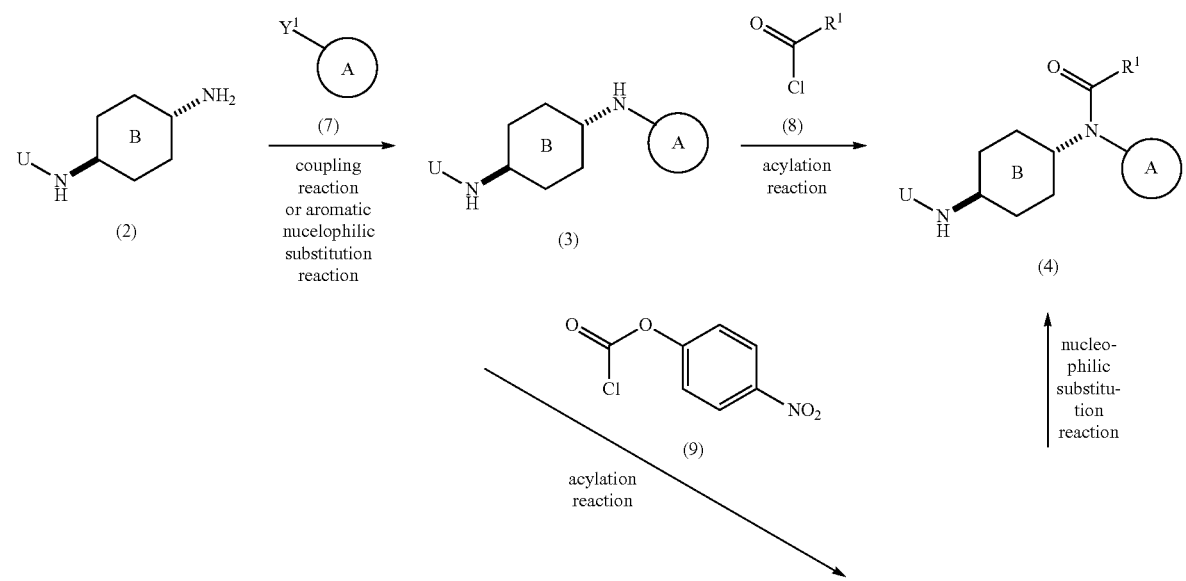

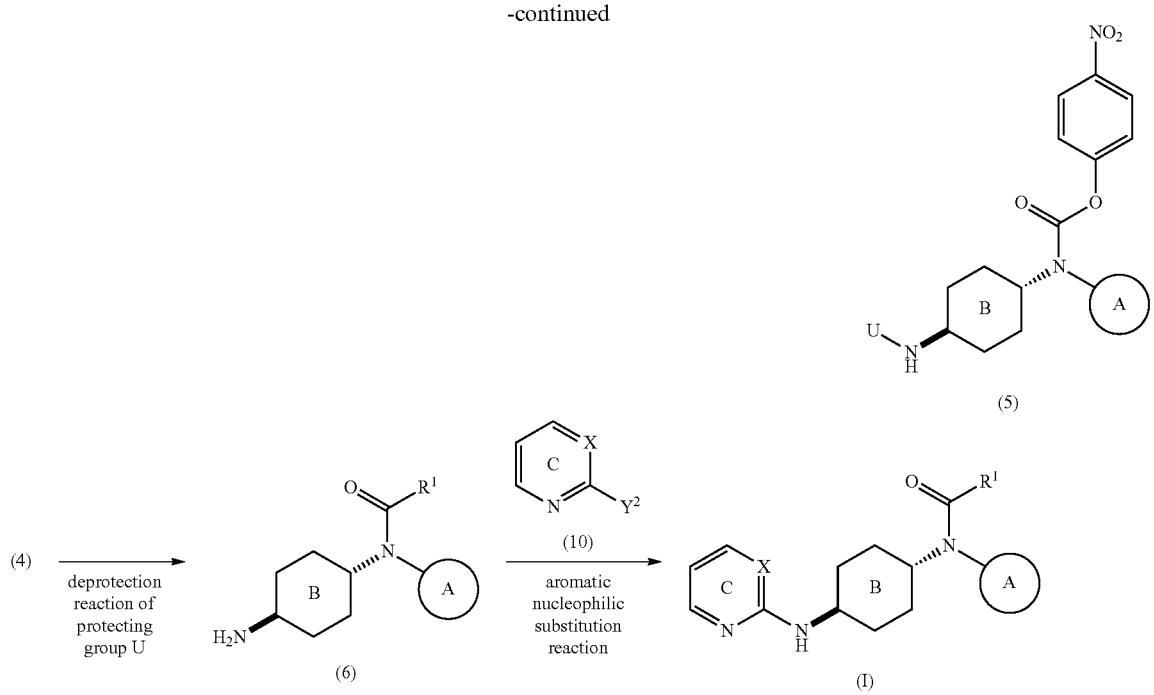

(4) →(deprotection reaction of protecting group U)→ (6) →(aromatic nucleophilic substitution reaction with (10))→ (I)

wherein $Y^1$ and $Y^2$ are the same or different and each is a leaving group, U is an amino-protecting group, and other symbols are as defined above.

[Production method A-2]

Compound (Ia) included in compound (I) can be produced from compound (2) by the method shown in the following reaction scheme or a method analogous thereto.

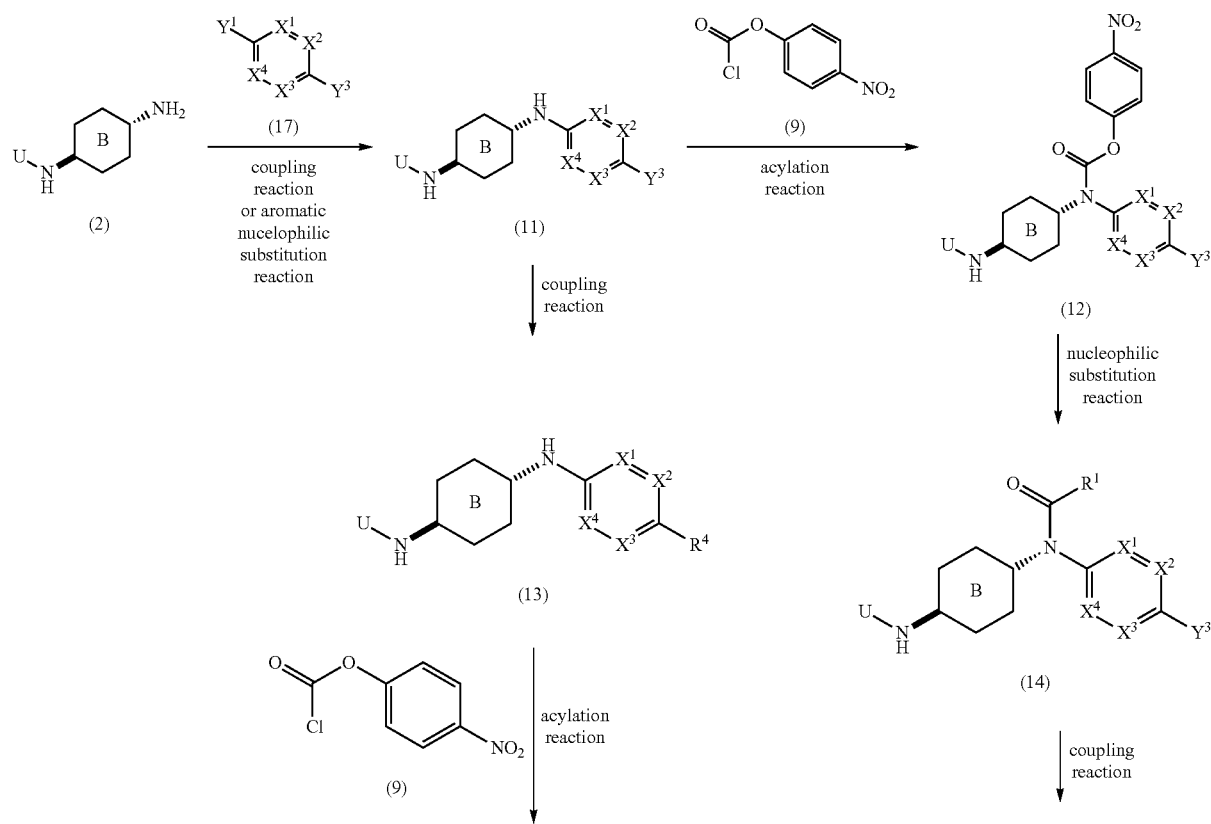

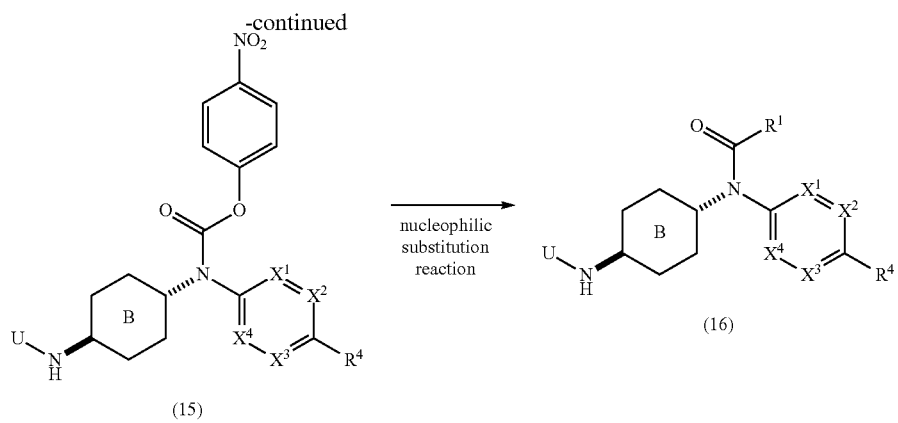

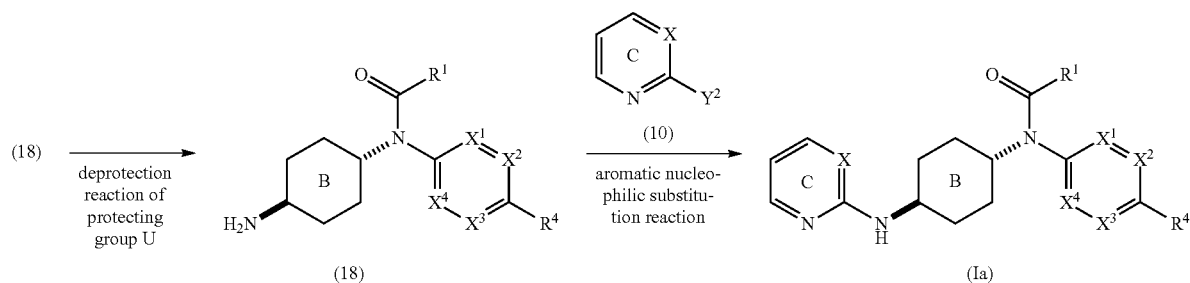

wherein $R^4$ is an optionally substituted aromatic ring group, $X^1, X^2, X^3$ and $X^4$ are the same or different $CR^5$ or a nitrogen atom, $R^5$ is a hydrogen atom, a halogen atom, or an optionally substituted $C_{1-6}$ alkyl group, $Y^3$ is a leaving group, and other symbols are as defined above.

[Production method A-3]

Compound (Ib) included in compound (I) can be produced from compound (6) by the method shown in the following reaction scheme or a method analogous thereto.

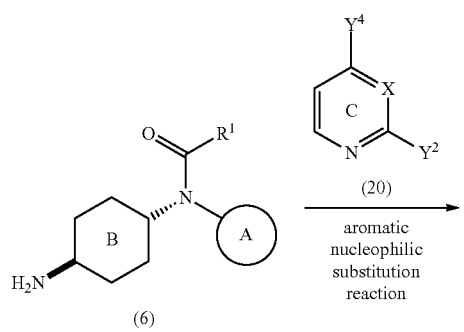

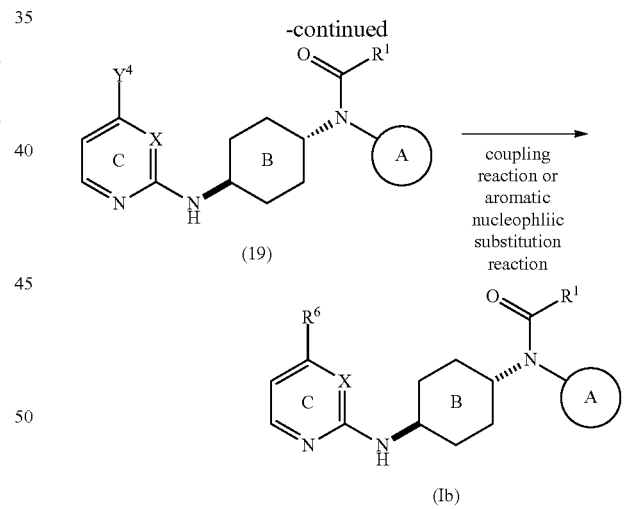

wherein $R^6$ is an optionally substituted aromatic ring group, $NR^7R^8$, an optionally substituted $C_{1-6}$ alkoxy group (e.g., methoxy etc.), an optionally substituted $C_{3-7}$ cycloalkoxy group, or an optionally substituted $C_{6-14}$ aryloxy group (e.g., phenoxy etc.), $R^7$ is a hydrogen atom or a substituent, and $R^8$ is a substituent. $R^7$ and $R^8$ may form a ring. $Y^4$ is a leaving group, and other symbols are as defined above.

[Production method A-4]

Compound (Ic) included in compound (I) can be produced from compound (2) by the method shown in the following reaction scheme or a method analogous thereto.

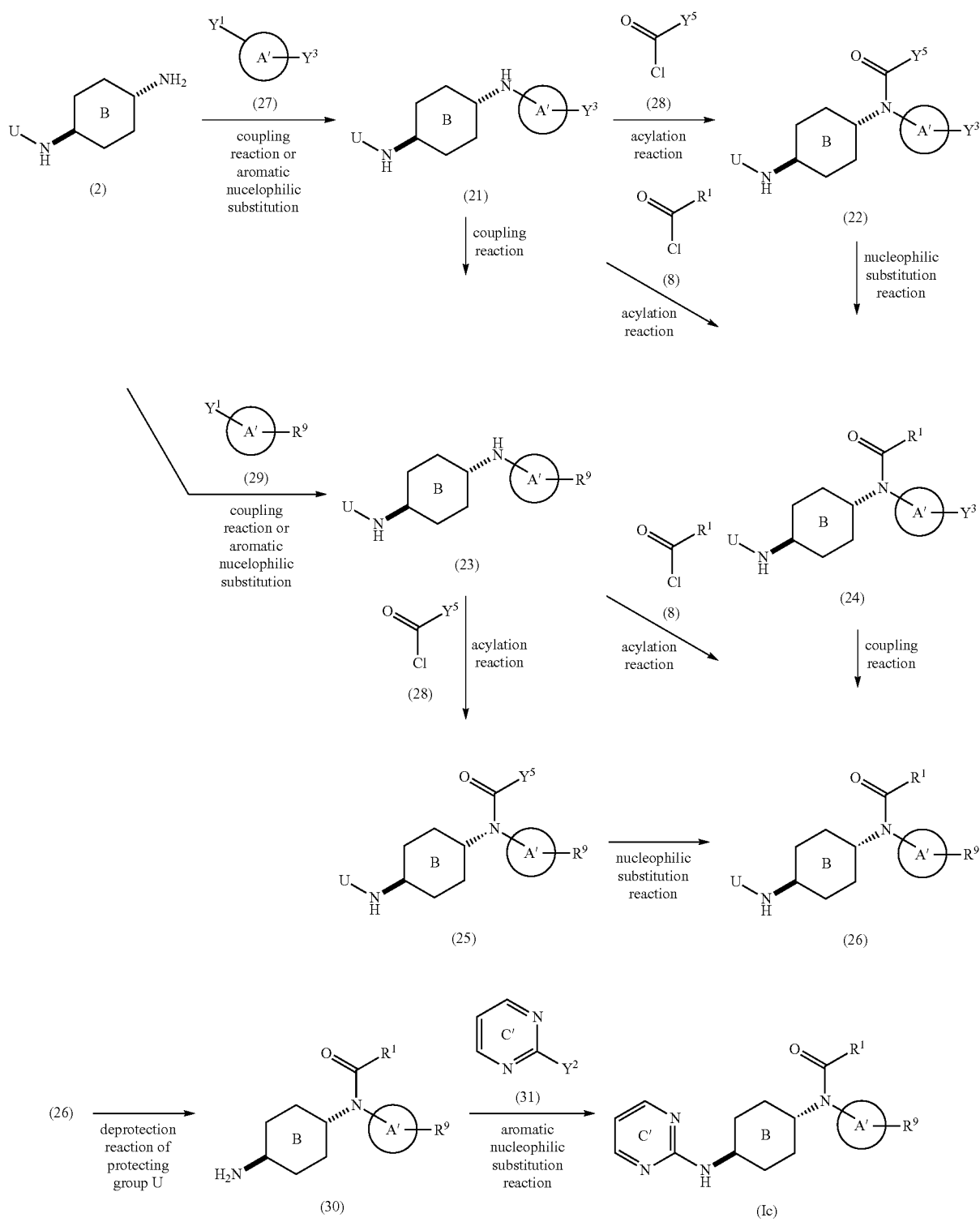

wherein A' is an optionally substituted pyridine ring, a pyrimidine ring, a pyrazine ring, a pyridazine ring, or a pyrazole ring, $R^9$ is an optionally substituted aromatic ring group, an alkyl group, an alkoxy group, an alkylaminocarbonyl group or a heterocyclic group, $Y^5$ is a leaving group, C' is an optionally substituted pyrimidine ring, and other symbols are as defined above.

[Production method A-5]

Compounds (32) and (35) included in compound (10) and compound (31) included in the previous reaction can be produced from compound (20) by the method shown in the following reaction scheme or a method analogous thereto.

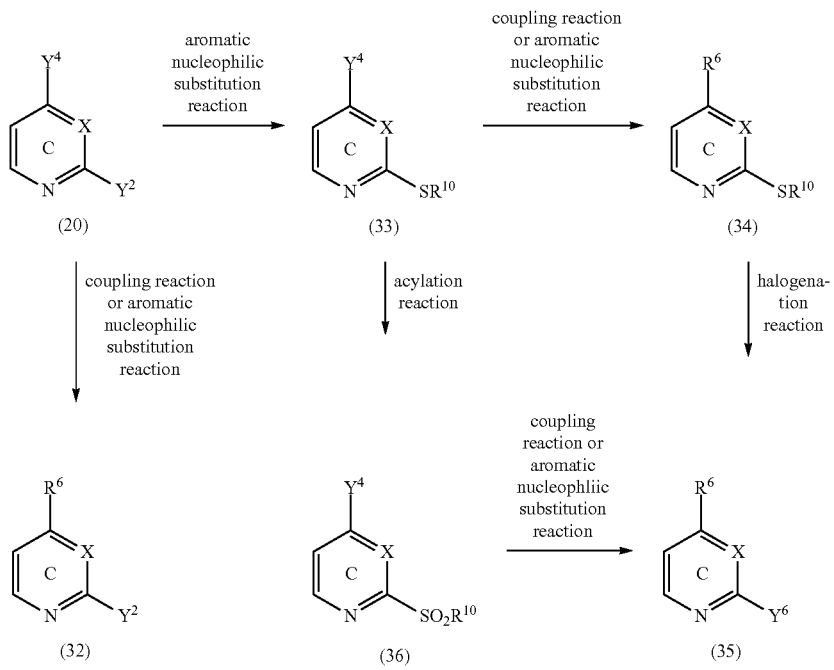

wherein $R^{10}$ is an alkyl group, $Y^6$ is a leaving group, and other symbols are as defined above.

The substituent of the thus-obtained compound (I) is converted (that is, introduction of a substituent or conversion of a functional group) by applying means known per se to produce another compound or a salt thereof encompassed in compound (I).

As a method for introduction of substituent or conversion of functional group, a known general method is used. For example, conversion of halogen atom (e.g., fluorine, chlorine, bromine, iodine), optionally halogenated $C_{1-6}$ alkylsulfonyloxy group [e.g., methanesulfonyloxy, ethanesulfonyloxy, trichloromethanesulfonyloxy, trifluoromethanesulfonyloxy (triflate)] to methyl group, cyclopropyl group, vinyl group, a cyano group, formyl group, carbonyl group, carboxyl group, hydroxyl group, amino group, boryl group and the like, conversion of formyl group to ethynyl group by Seyferth-Gilbert homologation reaction, conversion of ester to carboxy group by hydrolysis, conversion of carboxy group to carbamoyl group by amidation, conversion of carboxy group to hydroxymethyl group by reduction, conversion of carbonyl group to alcohol form by reduction or alkylation, reductive amination of carbonyl group, oximation of carbonyl group, acylation of amino group, ureation of amino group, sulfonylation of amino group, alkylation of amino group, substitution or amination of active halogen by amine, alkylation of hydroxy group, substitution or amination of hydroxy group can be mentioned.

In the introduction of substituent and conversion of functional group, when a reactive site possibly causing a reaction other than the desired reaction is present, a protecting group is introduced as necessary into the reactive site in advance by means known per se, the object reaction is performed, and then the protecting group is also removed by means known per se, whereby a compound within the scope of the present invention can also be produced.

When the starting compound and intermediate have an amino group, a carboxy group or a hydroxy group as a substituent, these groups may be protected by a protecting group generally used in the peptide chemistry and the like. In this case, the object compound can be obtained by eliminating the protecting group as necessary after the reaction.

Compound (I) obtained by the above-mentioned production method can be isolated and purified by a known means, such as solvent extraction, pH change of solution, phase transfer, crystallization, recrystallization, chromatography and the like.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se.

Compound (I) may be a crystal.

A crystal of compound (I) (hereinafter sometimes to be abbreviated as the crystal of the present invention) can be produced by crystallization, by applying a crystallization method known per se.

The crystal of the present invention is superior in the physicochemical properties (e.g., melting point, solubility, stability) and biological properties (e.g., pharmacokinetics (absorbability, distribution, metabolism, excretion), efficacy), and is expected to be useful as a medicament.

compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization methods known per se.

Compound (I) may be a hydrate, non-hydrate, non-solvate or solvate.

Furthermore, compound (I) also encompasses a deuterium conversion form wherein 1H is converted to $^2$H(D).

Compound (I) may be labeled with an isotope (e.g., $^3$H, $^{13}$C, $^{14}$C, $^{18}$F, $^{35}$S, $^{125}$I) and the like. Compound (I) labeled or substituted with an isotope may be used as, for example, a tracer (PET tracer) used for Positron Emission Tomography (PET), and may be useful in the fields of medical diagnosis and the like.

Compound (I) may be used as a prodrug.

The prodrug of compound (I) means a compound which is converted to compound (I) with a reaction due to an enzyme, gastric acid and the like under the physiological condition in the living body, that is, a compound which is converted to compound (I) by enzymatic oxidation, reduction, hydrolysis and the like; a compound which is converted to compound (I) by hydrolysis and the like due to gastric acid, and the like.

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, tert-butylation); a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. The se compounds may be produced from compound (I) according to a method known per se.

The prodrug of compound (I) may also be one which is converted to compound (I) under physiological conditions as described in "IYAKUHIN no KAIHATSU (Development of Pharmaceuticals)", Vol. 7, Design of Molecules, p. 163-198, Published by HIROKAWA SHOTEN (1990).

In the present specification, the prodrug may form a salt. Examples of such salt include those exemplified as the salt of the aforementioned compound represented by the formula (I).

Compound (I) or a prodrug thereof (hereinafter sometimes to be simply abbreviated as the compound of the present invention) may have a superior CDK12 inhibitory activity in living organisms, and may be useful as a prophylactic or therapeutic drug for cancer, a cancer proliferation inhibitor, or a cancer metastasis inhibitor.

The compound of the present invention exhibits CDK12 inhibitory activity, and the compound of the present invention may be expected to be also superior in efficacy expression, pharmacokinetics (e.g., absorbability, distribution, metabolism, excretion), solubility (e.g., water solubility), and interaction with other pharmaceutical products (e.g., drug-metabolizing enzyme inhibitory action), stability (e.g., chemical stability, stability against enzyme), and thus the compound may be useful as a medicine.

The compound of the present invention may be expected to have low toxicity (e.g., acute toxicity, chronic toxicity, genetic toxicity, reproductive toxicity, heart toxicity, carcinogenicity, central nervous system toxicity), and may be used administered to mammals (e.g., mouse, rat, hamster, rabbit, cat, dog, bovine, sheep, monkey, human).

The compound of the present invention may be useful as a prophylactic or therapeutic agent for pathology or disease caused by CDK12. In addition, the compound of the present invention may be superior in the selectivity for inhibiting CDK12 in the CDK subfamily and is expected to have low toxicity.

The compound of the present invention is expected to be useful for the prophylaxis or treatment of, for example, cancer [e.g., colorectal cancer (e.g., colon cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophageal cancer, stomach cancer (e.g., papillary adenocarcinoma, mucinous adenocarcinoma, adenosquamous carcinoma), duodenal cancer, small intestinal cancer, breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testicular cancer, prostate cancer (e.g., hormone-dependent prostate cancer, non-hormone dependent prostate cancer, castration-resistant prostate cancer), liver cancer (e.g., hepatoma, primary liver cancer, extrahepatic bile duct cancer), thyroid cancer (e.g., medullary thyroid carcinoma), kidney cancer (e.g., renal cell carcinoma (e.g., clear cell type renal cell carcinoma), transitional cell carcinoma in renal pelvis and ureter), uterine cancer (e.g., cervix cancer, uterine body cancer, uterine sarcoma), gestational choriocarcinoma, brain tumor (e.g., medulloblastoma, glioma, pineal astrocytoma, pilocytic astrocytoma, diffuse astrocytoma, anaplastic astrocytoma, pituitary adenoma), neuroblastoma, retina blastoma, skin cancer (e.g., basalioma, malignant melanoma (melanoma)), sarcoma (e.g., rhabdomyosarcoma, leiomyosarcoma, soft tissue sarcoma, spindle cell sarcoma, osteosarcoma), malignant bone tumor, bladder cancer, hematologic cancer (e.g., multiple myeloma, leukemia (e.g., acute myeloid leukemia, acute lymphocytic leukemia), malignant lymphoma, Hodgkin's disease, chronic myeloproliferative disease), cancer of unknown primary], inhibiting proliferation of cancer, suppression of metastasis, promotion of apoptosis, or prophylaxis or treatment of precancerous lesion (e.g., myelodysplastic syndrome). In addition, the compound of the present invention is expected to be useful for the prophylaxis or treatment of scleroderma, cirrhosis, idiopathic pulmonary fibrosis, inflammatory bowel disease or muscular dystrophy.

The compound of the present invention may be administered orally or parenterally to a mammal (preferably, human) as it is or as a medicament mixed with a pharmacologically acceptable carrier.

A medicament containing the compound of the present invention (sometimes to be abbreviated as "the medicament of the present invention") is described in detail below. Examples of the dosage form of the medicament of the present invention include oral preparations such as tablet (e.g., sugar-coated tablet, film-coated tablet, sublingual tablet, buccal, orally quick-integrating tablet), pill, granule, powder, capsule (e.g., soft capsule, microcapsule), syrup, emulsion, suspension, film (e.g., orally disintegrable film, mouth cavity mucosa patch film) and the like. Also, examples of the dosage form of the medicament of the present invention include parenteral agents such as injection, drip transfusion, transdermal agent (e.g., Iontophoresis transdermal preparation), suppository, ointment, nasal preparation, pulmonary preparation, eye drop and the like. The medicament of the present invention may be a controlled-release preparation such as immediate-release preparation, sustained-release preparation (e.g., sustained-release microcapsule) and the like.

The medicament of the present invention may be produced by a known production method (e.g., the method described in the Japanese Pharmacopoeia) generally used in the technical field of preparation formulations. The medicament of the present invention can contain, where necessary, an appropriate amount of an additive generally used in the pharmaceutical field such as excipient, binder, disintegrant, lubricant, sweetening agent, surfactant, suspending agent, emulsifier, colorant, preservative, aromatic, corrigent, stabilizer, thickening agent and the like.

These additives can be recited as the aforementioned pharmacologically acceptable carrier.

For example, tablet may be produced using excipient, binder, disintegrant, lubricant and the like, and pill and granule may be produced using excipient, binder, disintegrant. In addition, powder and capsule may be produced using excipient and the like, syrup may be produced using sweetening agent and the like, and emulsion and suspension may be produced using suspending agent, surfactant, emulsifier and the like.

Examples of the excipient include lactose, sucrose, glucose, starch, sucrose, microcrystalline cellulose, powdered *glycyrrhiza*, mannitol, sodium hydrogen carbonate, calcium phosphate, and calcium sulfate.

Examples of the binder include 5-10 wt % starch liquid paste, 10-20 wt % gum arabic solution or gelatin solution, 1-5 wt % tragacanth solution, carboxymethyl cellulose solution, sodium alginate solution, and glycerin.

Examples of the disintegrant include starch, and calcium carbonate.

Examples of the lubricant include magnesium stearate, stearic acid, calcium stearate, and purified talc.

Examples of the sweetener include glucose, fructose, invert sugar, sorbitol, xylitol, glycerin, and simple syrup.

Examples of the surfactant include sodium lauryl sulfate, polysorbate 80, sorbitan monofatty acid ester, and polyoxyl 40 stearate.

Examples of the suspending agent include gum arabic, sodium alginate, sodium carboxymethyl cellulose, methyl cellulose, and bentonite.

Examples of the emulsifier include gum arabic, tragacanth, gelatin, and polysorbate 80.

For example, when the medicament of the present invention is a tablet, the tablet may be produced according to a method known per se by adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose) or lubricant (e.g., talc, magnesium stearate, polyethylene glycol 6000) to the compound of the present invention, compression molding the mixture and, where necessary, applying a coating for the purpose of taste masking, enteric property or sustainability by a coating method known per se. As the coating agent used for the coating, hydroxypropylmethylcellulose, ethylcellulose, hydroxymethylcellulose, hydroxypropylcellulose, polyoxyethyleneglycol, Tween 80, pluronic F68, cellulose acetate phthalate, hydroxypropylmethylcellulose phthalate, hydroxymethylcellulose acetate succinate, Eudragit (manufactured by Rohm, Germany, methacrylic acid-acrylic acid copolymer) and dye (e.g., red iron oxide, titanium dioxide) may be used.

The aforementioned injection includes intravenous injection, subcutaneous injection, intradermal injection, muscular injection, intraperitoneal injection, drip injection and the like.

Such injection may be prepared by a method known per se, that is, by dissolving, suspending or emulsifying the compound of the present invention in an aseptic aqueous solution or oily solution. Examples of the aqueous solution include saline, isotonic solution (e.g., D-sorbitol, D-mannitol, sodium chloride) containing glucose and other auxiliary agents and the like. The aqueous solution may contain suitable solubilizing agents, for example, alcohol (e.g., ethanol), polyalcohol (e.g., propylene glycol, polyethylene glycol), non-ionic surfactant (e.g., polysorbate 80, HCO-50). Examples of the oily solution include sesame oil, soybean oil and the like. The oily solution may contain a suitable solubilizing agent. Examples of the solubilizing agent include benzyl benzoate, benzyl alcohol and the like. The injection may contain buffering agent (e.g., phosphate buffer, sodium acetate buffer), soothing agent (e.g., benzalkonium chloride, procaine hydrochloride), stabilizer (e.g., human serum albumin, polyethylene glycol), preservative (e.g., benzyl alcohol, phenol) and the like. An injection thus prepared may be generally filled in an ampoule.

While the content of the compound of the present invention in the medicament of the present invention varies depending on the preparation form, it is generally about 0.01-about 100 wt %, preferably about 2-about 85 wt %, further preferably about 5-about 70 wt %, relative to the whole preparation.

While the content of the additive in the medicament of the present invention varies depending on the preparation form, it is generally about 1 to about 99.9 wt %, preferably about 10 to about 90 wt %, relative to the whole preparation.

The compound of the present invention is stable and low toxic, and may be used safely. While the daily dose of the compound of the present invention varies depending on the condition and body weight of patients, the kind of compound, administration route and the like, in the case of, for example, oral administration to patients for the treatment of cancer, the daily dose to an adult (body weight about 60 kg) is about 1 to about 1000 mg, preferably about 3 to about 300 mg, more preferably about 10 to 200 mg, as the compound of the present invention, which may be given in a single administration or administered in 2 or 3 portions a day.

When the compound of the present invention is administered parenterally, it is generally administered in the form of a liquid (e.g., injection). While the dose of the compound of the present invention varies depending on the subject of administration, target organ, symptom, administration method and the like, it is, for example, about 0.01 mg-about 100 mg, preferably about 0.01-about 50 mg, more preferably about 0.01-about 20 mg, of the compound of the present invention relative to 1 kg of body weight, which is preferably given by intravenous injection.

The compound of the present invention may be used concurrently with other drugs. To be specific, the compound of the present invention may be used together with medicaments such as hormonal therapeutic agents, chemotherapeutic agents, immunotherapeutic agents, medicaments inhibiting the action of cell growth factors or cell growth factor receptors and the like. In the following, the drugs that can be used in combination with the compound of the present invention are abbreviated as concomitant drugs.

As the "hormonal therapeutic agent", for example, fosfestrol, diethylstylbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), pill preparation, mepitiostane, testrolactone, aminoglutethimide, LH-RH agonist (e.g., goserelin acetate, buserelin, leuprorelin acetate), droloxifene, epitiostanol, ethinylestradiol sulfonate, aromatase inhibitor (e.g., fadrozole hydrochloride, anastrozole, retrozole, exemestane, vorozole, formestane), anti-androgen (e.g., flutamide, bicartamide, nilutamide, enzalutamido), 5α-reductase inhibitor (e.g., finasteride, epristeride, dutasteride), adrenocortical hormone drug (e.g., dexamethasone, predonisolone, betamethasone, triamcinolone), androgen synthesis inhibitor (e.g., abiraterone), retinoid and drugs that retard retinoid metabolism (e.g., liarozole), thyroid gland hormone, and DDS (Drug Delivery System) preparation thereof are used.

As the "chemotherapeutic agents", alkylating agents, antimetabolites, anticancer antibiotics, and plant-derived anticancer agents may be used.

As the "alkylating agent", for example, nitrogen mustard, nitrogen mustard-N-oxide hydrochloride, chlorambutyl, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trophosphamide, zinostatin stimalamer, adozelesin, cystemustine, bizelesin, and DDS preparations thereof may be used.

As the "antimetabolite", for example, mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterin, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, tiazofurin, ambamustine, bendamustine, and DDS preparations thereof may be used.

As the "antitumor antibiotic", for example, actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorubicin hydrochloride, mitoxantrone hydrochloride, idarubicin hydrochloride, and DDS preparations thereof (e.g., Doxorubicin encapsulated PEG ribosome) may be used.

As the "plant-derived antitumor drug", for example, etoposide, etoposide phosphate, vinblastine sulfate, vincristine sulfate, vindesine sulfate, teniposide, paclitaxel, docetaxel, cabazitaxel, vinorelbine, and DDS preparations thereof may be used.

As the "immunotherapeutic agent", for example, picibanil, krestin, schizophyllan, lentinan, ubenimex, interferon, interleukin, macrophage colony stimulating factor, granulocyte colony stimulating factor, erythropoietin, lymphotoxin, BCG vaccine, *Corynebacterium parvum*, levamisole, polysaccharide K, procodazole, anti-CTLA4 antibody (e.g., ipilimumab, tremelimumab), anti-PD-1 antibody (e.g., nivolumab, pembrolizumab), anti-PD-L1 antibody may be used.

The "cell growth factors" in the "medicament inhibiting actions of cell growth factor and receptor thereof" may be any substance that promotes cell proliferation, which is normally peptide having not more than 20,000 molecular weight, and capable of exhibiting the activity at low concentrations by binding to a receptor, and specifically
  (1) EGF (epidermal growth factor) or substances possessing substantially the same activity as EGF (e.g., TGFα);
  (2) insulin or substances possessing substantially the same activity as insulin (e.g., insulin, IGF (insulin-like growth factor)-1, IGF-2),
  (3) FGF (fibroblast growth factor) or substances possessing substantially the same activity as FGF (e.g., acidic FGF, basic FGF, KGF (keratinocyte growth factor), FGF-10), and
  (4) other cell growth factors (e.g., CSF (colony stimulating factor), EPO (erythropoietin), IL-2 (interleukin-2), NGF (nerve growth factor), PDGF (platelet-derived growth factor), TGFβ (transforming growth factor β), HGF (hepatocyte growth factor), VEGF (vascular endothelial growth factor), heregulin, angiopoietin); may be used.

The "cell growth factor receptor" may be any receptor capable of binding to the aforementioned cell growth factors, and specifically, EGF receptor, heregulin receptor (e.g., HER3), insulin receptor, IGF receptor-1, IGF receptor-2, FGF receptor- or FGF receptor-2, VEGF receptor, angiopoietin receptor (e.g., Tie2), PDGF receptor, and the like may be used.

As the "medicament inhibiting actions of cell growth factor and receptor thereof", for example, EGF inhibitor, TGFα inhibitor, heregulin inhibitor, insulin inhibitor, IGF inhibitor, FGF inhibitor, KGF inhibitor, CSF inhibitor, EPO inhibitor, IL-2 inhibitor, NGF inhibitor, PDGF inhibitor, TGFβ inhibitor, HGF inhibitor, VEGF inhibitor, angiopoietin inhibitor, EGF receptor inhibitor, HER2 inhibitor, HER4 inhibitor, insulin receptor inhibitor, IGF-1 receptor inhibitor, IGF-2 receptor inhibitor, FGF receptor-1 inhibitor, FGF receptor-2 inhibitor, FGF receptor-3 inhibitor, FGF receptor-4 inhibitor, VEGF receptor inhibitor, Tie-2 inhibitor, PDGF receptor inhibitor, Abl inhibitor, Raf inhibitor, FLT3 inhibitor, c-Kit inhibitor, Src inhibitor, PKC inhibitor, Smo inhibitor, ALK inhibitor, ROR1 inhibitor, Trk inhibitor, Ret inhibitor, mTOR inhibitor, Aurora inhibitor, PLK inhibitor, MEK (MEK1/2) inhibitor, MET inhibitor, CDK inhibitor, Akt inhibitor, ERK inhibitor, PI3K inhibitor, and the like may be used. More specifically, anti-VEGF antibody (e.g., Bevacizumab, Ramucurumab), anti-HER2 antibody (e.g., Trastuzumab, Pertuzumab), anti-EGFR antibody (e.g., Cetuximab, Panitumumab, Matuzumab, Nimotuzumab), anti-HGF antibody, Imatinib, Erlotinib, Gefitinib, Sorafenib, Sunitinib, Dasatinib, Lapatinib, Vatalanib, Ibrutinib, Bosutinib, Cabozantinib, Crizotinib, Alectinib, Vismodegib, Axitinib, Motesanib, Nilotinib, 6-[4-(4-ethylpiperazin-1-ylmethyl)phenyl]-N-[1(R)-phenylethyl]-7H-pyrrolo[2,3-d]pyrimidin-4-amine (AEE-788), Vandetanib, Temsirolimus, Everolimus, Enzastaurin, Tozasertib, 2-[N-[3-[4-[5-[N-(3-fluorophenyl)carbamoylmethyl]-1H-pyrazol-3-ylamino]quinazolin-7-yloxy]propyl]-N-ethylamino]ethyl phosphate (AZD-1152), 4-[9-chloro-7-(2,6-difluorophenyl)-5H-pyrimido[5,4-d][2]benzazepin-2-ylamino]benzoic acid, N-[2-methoxy-5-[(E)-2-(2,4,6-trimethoxyphenyl)vinylsulfonylmethyl]phenyl]glycine sodium salt (ON-1910Na), Volasertib, Selumetinib, Trametinib, N-[2(R),3-dihydroxypropoxy]-3,4-difluoro-2-(2-fluoro-4-iodophenylamino)benzamide (PD-0325901), Bosutinib, Regorafenib, Afatinib, Idelalisib, Ceritinib, Dabrafenib, and the like may be used.

Besides the above-mentioned drugs, asparaginase, aceglatone, procarbazine hydrochloride, protoporphyrin-cobalt complex salt, mercuric hematoporphyrin-sodium, topoisomerase I inhibitor (e.g., irinotecan, topotecan, indotecan, Indimitecan), topoisomerase II inhibitor (e.g., sobuzoxane), differentiation-inducing factor (e.g., retinoid, vitamin D), other angiogenesis inhibitor (e.g., fumagillin, shark extract, COX-2 inhibitor), α-blocker (e.g., tamsulosin hydrochloride), bisphosphonic acid (e.g., pamidronate, zoledronate), thalidomide, lenalidomide, pomalidomide, 5-azacytidine, decitabine, proteasome inhibitor (e.g., bortezomib, carfilzomib, ixazomib), NEDD8 inhibitor (e.g., Pevonedistat), UAE inhibitor, PARP inhibitor (e.g., Olaparib, Niraparib, Veliparib, Rucaparib), antitumor antibodies such as anti-CD20 antibody (e.g., Rituximab, Obinutuzumab), anti-CCR4 antibody (e.g., Mogamulizumab) and the like, antibody drug complex (e.g., trastuzumab emtansine, brenximab vedotin), and the like may also be used as a concomitant drug.

By combining the compound of the present invention and a concomitant drug, superior effects such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer, (4) a sustained treatment effect can be designed, (5) a synergistic effect can be afforded by a combined use of the compound of the present invention and a concomitant drug, and the like, can be achieved.

In the following, the compound of the present invention and a concomitant drug used in combination are referred to as the "combination agent of the present invention".

When the combination agent of the present invention is administered, the administration period is not limited and the compound of the present invention and the concomitant drug may be administered simultaneously, or may be administered at a time interval to an administration subject. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (e.g., the compound of the present invention and the concomitant drug are administered in this order, or in the reverse order), and the like.

The dose of the concomitant drug may be appropriately determined based on the dose employed in clinical situations. The mixing ratio of the compound of the present invention and a concomitant drug may be appropriately determined depending on the administration subject, administration route, target disease, symptom, combination and the like. For example, when the subject of administration is a human, 0.01 to 100 parts by weight of a concomitant drug may be used per 1 part by weight of the compound of the present invention.

Furthermore, the compound of the present invention or the combination agent of the present invention may be used in combination with a non-drug therapy. Specifically, the compound of the present invention or the combination agent of the present invention may be combined with a non-drug therapy such as (1) surgery, (2) pressurized chemotherapy using angiotensin II and the like, (3) gene therapy, (4) hyperthermic therapy, (5) cryotherapy, (6) laser cautery method, (7) radiation therapy.

For example, using the compound of the present invention or the combination agent of the present invention before or after the aforementioned surgery or the like, or before or after a treatment combining two or three kinds of these, effects such as prevention of resistance expression, elongation of disease-free period (Disease-Free Survival), suppression of cancer metastasis or recurrence, life-prolongation and the like may be achieved.

In addition, a treatment by the compound of the present invention or the combination agent of the present invention and a supporting therapy [(i) administration of various antibiotics (e.g., β-lactams such as pansporin and the like, macrolides such as clarithromycin and the like) for combination of infectious diseases, (ii) administration of intravenous hyperalimentation, amino acid preparation, general vitamin preparation for improvement of malnutrition, (iii) administration of morphine for relieving pain, (iv) administration of medicaments that improve side effects such as nausea, vomiting, anorexia, diarrhea, leucopenia, thrombocytopenia, hemoglobin concentration reduction, hair loss, hepatopathy, renopathy, DIC, fever and the like and (v) administration of medicaments that suppress resistance of cancer to multiple drugs] may also be combined.

EXAMPLE

The present invention is further explained in detail by referring to the following Examples, Experimental Examples and Formulation Examples which do not limit the present invention and may be changed without departing from the scope of the present invention.

The "room temperature" in the following Examples indicates the range of generally from about 10° C. to about 35° C.

The ratio for a mixed solvent is, unless otherwise specified, a volume mixing ratio and % means wt % unless otherwise specified.

Unless particularly indicated, the elution in column chromatography in the Examples was performed under observation by TLC (Thin Layer Chromatography). For TLC observation, 60F$_{254}$ manufactured by Merck was used as a TLC plate, and the solvent used as an elution solvent for column chromatography was used as developing solvent. For detection, moreover, a UV detector was adopted. In silica gel column chromatography, the indication of NH means use of aminopropylsilane-bonded silica gel. In preparative HPLC (high performance liquid chromatography), the indication of C$_{18}$ means use of octadecyl-bonded silica gel. The ratio shown for elution solvents is, unless otherwise specified, a volume mixing ratio.

For the analysis of $^1$H NMR, ACD/SpecManager (trade name) software and the like were used. Very mild peaks for protons of a hydroxy group, an amino group and the like are sometimes not described.

MS was measured by LC/MS. As ionization method, ESI method, or APCI method was used. The data indicates those found. Generally, molecular ion peaks are observed; however, they may be observed as a fragment ion. In the case of a salt, generally, a molecular ion peak or a fragment ion peak of a free form is observed.

In the following Examples, the following abbreviations are used.
mp: melting point
MS: mass spectrum
M: mol concentration
N: normality
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: electrospray ionization
APCI: atmospheric pressure chemical ionization
Pd$_2$(dba)$_3$: tris(dibenzylideneacetone)dipalladium (0)
XANTPHOS: (9,9-dimethyl-9H-xanthene-4,5-diyl)bis(diphenylphosphine)
TFA: trifluoroacetic acid
DIPEA: N,N-diisopropylethylamine
PdCl$_2$(dppf): dichloro[1,1'-bis(diphenylphosphino)ferrocene]palladium(II)
PdCl$_2$(Amnphos)$_2$: dichlorobis(di-tert-butyl(4-dimethylaminophenyl)phosphine)palladium(II)
Pd(PPh$_3$)$_4$: tetrakis triphenylphosphinepalladium (0)
DMA: N,N-dimethylacetamide
DMF: N,N-dimethylformamide
THF: tetrahydrofuran
DME: 1,2-dimethoxyethane
MeOH: methanol
DMSO: dimethyl sulfoxide
AcOH: acetic acid
NMP: N-methylpyrrolidone
TEA: triethylamine
DMAP: 4-dimethylaminopyridine Example 199

3-benzyl-1-(trans-4-((5-cyano-4-((3-hydroxypropyl) amino)pyrimidin-2-yl)amino)cyclohexyl)-1-(4-(1-methyl-1H-pyrazol-4-yl)phenyl)urea A) tert-butyl (trans-4-((4-bromophenyl)amino)cyclohexyl)carbamate A mixture of tert-butyl (trans-4-aminocyclohexyl)carbamate (1.5 g), 1-bromo-4-iodobenzene (1.98 g), XANTPHOS (0.486 g), sodium 2-methylpropane-2-olate (1.01 g) and toluene (30 mL) was deaerated and substituted with argon. To the mixture was added Pd$_2$(dba)$_3$ (0.385 g) at room temperature, and the mixture was stirred under an argon atmosphere at 80° C. overnight. The reaction mixture was added to water at room temperature, and the mixture was extracted with ethyl acetate. The organic layer was separated, washed with water and saturated brine, and dried over anhydrous magnesium sulfate, and the solvent was evaporated under reduced pressure. The residue was purified by silica gel column chromatography (silica gel, ethyl acetate/ hexane and NH, ethyl acetate/hexane) to give the title compound (1.16 g).
MS: [M+H]$^+$ 369.1, 371.1.

B) tert-butyl (trans-4-((4-(1-methyl-1H-pyrazol-4-yl)phenyl)amino)cyclohexyl)carbamate A mixture of tert-butyl (trans-4-((4-bromophenyl)amino) cyclohexyl)carbamate (1.67 g), 1-methyl-4-(4,4,5,5-tetramethyl-1,3,2-dioxaborolan-2-yl)-1H-pyrazole (1.411 g), cesium carbonate (2.95 g), DMF (30 mL) and water (3 mL) was deaerated, and substituted with argon. To the mixture was added PdCl$_2$(Amphos)$_2$ (0.304 g) at room temperature, and the mixture was stirred under an argon atmosphere at 100° C. overnight. The reaction mixture was added to water at room temperature, and the mixture was extracted with ethyl acetate. The organic layer was separated, washed with water and saturated brine, dried over anhydrous magnesium sulfate, and concentrated under reduced pressure. The residue was purified by silica gel column chromatography (ethyl acetate/hexane) to give the title compound (1.41 g).
MS: [M+H]$^+$ 371.2.

C) tert-butyl (trans-4-((benzylcarbamoyl) (4-(1-methyl-1H-pyrazol-4-yl)phenyl)amino)cyclohexyl) carbamate To a mixture of tert-butyl (trans-4-((4-(1-methyl-1H-pyrazol-4-yl)phenyl)amino)cyclohexyl)carbamate (500 mg), TEA (0.563 mL) and THF (12 mL) was added benzylisocyanate (0.500 mL) at room temperature, and the mixture was stirred overnight. The reaction mixture was added to water at room temperature, and the precipitate was collected by filtration. The obtained solid was purified by silica gel column chromatography (NH, ethyl acetate/ hexane) to give the title compound (610 mg).
MS: [M+H]$^+$ 504.3.

D) 1-(trans-4-aminocyclohexyl)-3-benzyl-1-(4-(1-methyl-1H-pyrazol-4-yl)phenyl)urea hydrochloride To a mixture of tert-butyl (trans-4-((benzylcarbamoyl) (4-(1-methyl-1H-pyrazol-4-yl)phenyl)amino)cyclohexyl) carbamate (610 mg) and THF (15 mL) was added 4 M hydrochloric acid ethyl acetate solution (30.3 mL) at room temperature, and the mixture was stirred at room temperature for 3 hr. The mixture was concentrated under reduced pressure to give the title compound (533 mg).
MS: [M+H]$^+$ 404.2.

E) 3-benzyl-1-(trans-4-((5-cyano-4-((3-hydroxypropyl)amino)-pyrimidin-2-yl)amino)cyclohexyl)-1-(4-(1-methyl-1H-pyrazol-4-yl)phenyl)urea A mixture of 1-(trans-4-aminocyclohexyl)-3-benzyl-1-(4-(1-methyl-1H-pyrazol-4-yl)phenyl)urea hydrochloride (207 mg), DIPEA (0.334 mL), 2-chloro-4-((3-hydroxypropyl)amino)pyrimidine-5-carbonitrile (100 mg) and DMF (5 mL) was stirred at room temperature overnight. To the reaction mixture was added water at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (ethyl acetate/hexane), and the obtained solid was washed with ethyl acetate/heptane and crystallized to give the title compound (34.4 mg). $^1$H NMR (300 MHz, DMSO-d$_6$) δ 0.99-1.20 (2H, m), 1.37 (2H, d, J=12.7 Hz), 1.55-1.72 (2H, m), 1.72-1.98 (4H, m), 3.25-3.51 (5H, m), 3.87 (3H, s), 4.15 (2H, d, J=5.8 Hz), 4.18-4.31 (1H, m), 4.38-4.52 (1H, m), 5.70-5.91 (1H, m), 7.11-7.52 (9H, m), 7.62 (2H, dd, J=8.3, 2.7 Hz), 7.89 (1H, s), 8.06-8.12 (1H, m), 8.17 (1H, s).

Example 319

3-benzyl-1-(trans-4-((5-cyano-4-(oxetan-3-ylamino)pyrimidin-2-yl)amino)cyclohexyl)-1-(5-(1-methyl-1H-pyrazol-4-yl)pyridin-2-yl)urea A) tert-butyl (trans-4-((5-bromopyridin-2-yl)amino)cyclohexyl)carbamate A mixture of tert-butyl (trans-4-aminocyclohexyl)carbamate (14.53 mL), 5-bromo-2-fluoropyridine (22.8 g), DIPEA (30.5 g) and NMP (250 mL) was stirred at 180° C. for 4 hr. To the reaction mixture was added water at 0° C., and the mixture was stirred at room temperature for 1 hr. The obtained solid was collected by filtration and crystallized from ethyl acetate/heptane to give the title compound (11.62 g) MS: [M+H]$^+$ 370.1.

B) 4-nitrophenyl (5-bromopyridin-2-yl) (trans-4-((tert-butoxycarbonyl)amino)cyclohexyl)carbamate A mixture of tert-butyl (trans-4-((5-bromopyridin-2-yl)amino)cyclohexyl)carbamate (50.96 g), DIPEA (73.3 g), 4-nitrophenyl carbonochloridate (56.6 g) and THF (600 mL) was stirred at room temperature for 4 hr. To the reaction mixture was added saturated ammonium chloride aqueous solution at room temperature, and the mixture was extracted with ethyl acetate. The organic layer was separated, washed with saturated aqueous sodium hydrogen carbonate solution and saturated brine, and dried over anhydrous magnesium sulfate. The solvent was evaporated under reduced pressure. The residue was crystallized from ethyl acetate/hexane to give the title compound (62.26 g).
MS: [M+H-Boc]+435.1.

C) tert-butyl (trans-4-((benzylcarbamoyl) (5-bromopyridin-2-yl)amino)cyclohexyl)carbamate A mixture of 4-nitrophenyl (5-bromopyridin-2-yl) (trans-4-((tert-butoxycarbonyl)amino)cyclohexyl)carbamate (66.54 g), 1-phenylmethanamine (40.4 g) and NMP (500 mL) was stirred at 70° C. overnight. To the reaction mixture was added saturated ammonium chloride aqueous solution at room temperature, and the mixture was stirred at room temperature for 1 hr. The obtained precipitate was collected by filtration, washed with water and crystallized from ethyl acetate/hexane to give the title compound (50.19 g).
MS: [M+H]$^+$ 503.2.

D) tert-butyl (trans-4-((benzylcarbamoyl) (5-(1-methyl-1H-pyrazol-4-yl)pyridin-2-yl)amino)cyclohexyl)carbamate A mixture of tert-butyl (trans-4-((benzylcarbamoyl) (5-bromopyridin-2-yl)amino)cyclohexyl)carbamate (50.19 g), 1-methyl-4-(4,4,5,5-tetramethyl-1,3,2-dioxaborolan-2-yl)-1H-pyrazole (27.8 g), PdCl$_2$(dppf) dichloromethane adduct (4.15 g), 2 M cesium carbonate aqueous solution (100 mL) and DMF (500 mL) was stirred under an argon atmosphere at 100° C. for 3 hr. To the reaction mixture was added water at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (NH, ethyl acetate/hexane), and the obtained solid was crystallized from ethyl acetate/hexane to give the title compound (42.37 g).
MS: [M+H]$^+$ 505.3.

E) 1-(trans-4-aminocyclohexyl)-3-benzyl-1-(5-(1-methyl-1H-pyrazol-4-yl)pyridin-2-yl)urea hydrochloride To a mixture of tert-butyl (trans-4-((benzylcarbamoyl) (5-(1-methyl-1H-pyrazol-4-yl)pyridin-2-yl)amino)cyclohexyl)carbamate (42.37 g) and THF (700 mL) was added 4 M hydrochloric acid ethyl acetate solution (70 mL) at room temperature. The reaction mixture was stirred under a nitrogen atmosphere at room temperature for 9 hr. The precipitate was collected by filtration to give the title compound (40.23 g).
MS: [M+H]$^+$ 405.2.

F) 3-benzyl-1-(trans-4-((4-chloro-5-cyanopyrimidin-2-yl)amino)cyclohexyl)-1-(5-(1-methyl-1H-pyrazol-4-yl)pyridin-2-yl) urea A mixture of 1-(trans-4-aminocyclohexyl)-3-benzyl-1-(5-(1-methyl-1H-pyrazol-4-yl)pyridin-2-yl)urea hydrochloride (10.01 g), 2,4-dichloropyrimidine-5-carbonitrile (4.34 g), DIPEA (8.8 g) and DMA (250 mL) was stirred at room temperature for 3 hr. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/methanol) to give the title compound (3.59 g).
MS: [M+H]$^+$ 542.2.

G) 3-benzyl-1-(trans-4-((5-cyano-4-(oxetan-3-ylamino)pyrimidin-2-yl)amino)cyclohexyl)-1-(5-(1-methyl-1H-pyrazol-4-yl)pyridin-2-yl)urea To a mixture of 3-benzyl-1-(trans-4-((4-chloro-5-cyanopyrimidin-2-yl)amino)cyclohexyl)-1-(5-(1-methyl-1H- pyrazol-4-yl)pyridin-2-yl)urea (150 mg) and NMP (3 mL) were added oxetan-3-amine (40.5 mg) and DIPEA (0.147 mL) at room temperature. The reaction mixture was stirred under a nitrogen atmosphere at 60° C. for 3 hr. To the reaction mixture was added saturated ammonium chloride aqueous solution at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (NH, methanol/ethyl acetate) and crystallized from ethyl acetate/heptane to give the title compound (113 mg). $^1$H NMR (300 MHz, DMSO-d$_6$) δ 1.21-1.57 (4H, m), 1.67-1.94 (4H, m), 3.34-3.64 (1H, m), 3.89 (3H, s), 4.09-4.27 (3H, m), 4.53-4.72 (4H, m), 4.74-5.03 (1H, m), 6.45-6.54 (1H, m), 7.15-7.33 (6H, m), 7.36-7.64 (1H, m), 7.93-8.08 (3H, m), 8.13-8.21 (1H, m), 8.23-8.31 (1H, m), 8.73-8.81 (1H, m).

Example 440

3-benzyl-1-(trans-4-((5-cyano-4-(5-(methylsulfonyl) pyridin-3-yl)pyrimidin-2-yl)amino)cyclohexyl)-1-(5-(1-methyl-1H-pyrazol-4-yl) pyridin-2-yl) urea A mixture of 3-benzyl-1-(trans-4-((4-chloro-5-cyanopyrimidin-2-yl)amino)cyclohexyl)-1-(5-(1-methyl-1H-pyrazol-4-yl)pyridin-2-yl)urea (100 mg), (5-(methylsulfonyl) pyridin-3-yl)boronic acid (55.6 mg), PdCl$_2$(Amphos)$_2$ (12.41 mg), 2 M cesium carbonate aqueous solution (0.184 mL) and NMP (3 mL) was stirred under microwave irradiation at 100° C. for 1 hr. The reaction mixture was diluted with ethyl acetate (30 mL) and water (20 mL), and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (NH, ethyl acetate). The residue was purified by HPLC (L-Column 2 ODS, mobile phase: water/acetonitrile (5 mM ammonium acetate-based)). To the obtained fraction was added saturated aqueous sodium hydrogen carbonate solution, and the mixture was extracted with ethyl acetate. The organic layer was separated, dried over anhydrous magnesium sulfate, concentrated under reduced pressure, crystallized from DMSO and water to give the title compound (30.3 mg).
$^1$H NMR (300 MHz, DMSO-d$_6$) δ 1.36-1.57 (4H, m), 1.75-2.06 (4H, m), 3.34-3.41 (3H, m), 3.59-3.77 (1H, m), 3.84-3.94 (3H, m), 4.09-4.32 (3H, m), 6.44-6.59 (1H, m), 7.14-7.35 (6H, m), 7.94-8.03 (2H, m), 8.22-8.29 (1H, m), 8.49-8.67 (1H, m), 8.70-8.78 (2H, m), 8.78-8.87 (1H, m), 9.22-9.27 (1H, m), 9.29-9.37 (1H, mi).

Example 469

3-benzyl-1-(trans-4-((5-cyano-4-(3-methyl-1H-pyrazol-5-yl)pyrimidin-2-yl)amino)cyclohexyl)-1-(5-(1-methyl-1H-pyrazol-4-yl) pyridin-2-yl) urea A) 3-benzyl-1-(trans-4-((5-cyano-4-(3-methyl-1-(tetrahydro-2H-pyran-2-yl)-1H-pyrazol-5-yl)pyrimidin-2-yl)amino)cyclohexyl)-1-(5-(1-methyl-1H-pyrazol-4-yl)pyridin-2-yl)urea A mixture of 3-benzyl-1-(trans-4-((4-chloro-5-cyanopyrimidin-2-yl)amino)cyclohexyl)-1-(5-(1-methyl-1H-pyrazol-4-yl)pyridin-2-yl)urea (168.7 mg), 3-methyl-1-(tetrahydro-2H-pyran-2-yl)-5-(4,4,5,5-tetramethyl-1,3,2-dioxaborolan-2-yl)-1H-pyrazole (100 mg), PdCl$_2$(Amphos)$_2$ (22.04 mg), 2 M sodium carbonate aqueous solution (0.311 mL), DME (1.2 mL) and DMF (0.6 mL) was stirred under microwave irradiation at 100° C. for 1 hr. Insoluble material was filtered off, and the filtrate was concentrated under reduced pressure. The residue was purified by silica gel column chromatography (ethyl acetate/methanol) to give the title compound (210 mg).
MS: [M+H]$^+$ 672.5.

B) 3-benzyl-1-(trans-4-((5-cyano-4-(3-methyl-1H-pyrazol-5-yl)pyrimidin-2-yl)amino)cyclohexyl)-1-(5-(1-methyl-1H-pyrazol-4-yl) pyridin-2-yl) urea A mixture of 3-benzyl-1-(trans-4-((5-cyano-4-(3-methyl-1-(tetrahydro-2H-pyran-2-yl)-1H-pyrazol-5-yl)pyrimidin-2-yl)amino)cyclohexyl)-1-(5-(1-methyl-1H-pyrazol-4-yl) pyridin-2-yl)urea (210 mg), 2 M hydrochloric acid methanol solution (0.469 mL) and methanol (3 mL) was stirred at room temperature overnight. To the reaction mixture was added saturated aqueous sodium hydrogen carbonate solution, and the solvent was evaporated under reduced pressure. The residue was purified by silica gel column chromatography (ethyl acetate/methanol) to give the title compound (43.2 mg).
$^1$H NMR (300 MHz, DMSO-d$_6$) δ 1.32-1.59 (4H, m), 1.75-2.03 (4H, m), 2.29 (3H, d, J=4.1 Hz), 3.55-3.73 (1H, m), 3.89 (3H, s), 4.20 (3H, d, J=5.7 Hz), 6.49-6.60 (2H, m), 7.15-7.34 (6H, m), 7.94-8.16 (3H, m), 8.24-8.31 (1H, m), 8.59 (1H, d, J=13.0 Hz), 8.73-8.82 (1H, m), 13.11-13.22 (1H, m).

Example 482

3-benzyl-1-(trans-4-((5-cyano-4-(3-hydroxy-3-methylazetidin-1-yl)pyrimidin-2-yl)amino)cyclohexyl)-1-(5-(1-methyl-1H-pyrazol-4-yl) pyridin-2-yl) urea A mixture of 3-methylazetidin-3-ol hydrochloride (22.91 mg), DIPEA (0.097 mL), 3-benzyl-1-(trans-4-((4-chloro-5-cyanopyrimidin-2-yl)amino)cyclohexyl)-1-(5-(1-methyl-1H-pyrazol-4-yl)pyridin-2-yl)urea (75 mg) and DMF (5 mL) was stirred at room temperature. The reaction mixture was purified by silica gel column chromatography (ethyl acetate/hexane/methanol) to give the title compound (48 mg).
$^1$H NMR (300 MHz, DMSO-d$_6$) δ 1.39 (7H, s), 1.79 (3H, brs), 1.92 (1H, brs), 3.36-3.73 (1H, m), 3.89 (3H, s), 4.19 (7H, d, J=5.95 Hz), 5.66 (1H, d, J=13.79 Hz), 6.45-6.55 (1H, m), 7.16-7.31 (6H, m), 7.51 (1H, dd, J=18.32, 7.84 Hz), 7.95-8.02 (2H, m), 8.16 (1H, d, J=16.63 Hz), 8.26 (1H, d, J=3.31 Hz), 8.76 (1H, dd, J=3.76 Hz).

Example 483

3-benzyl-1-(trans-4-((5-cyano-4-(oxetan-3-ylamino) pyrimidin-2-yl)amino)cyclohexyl)-1-(4-(1-methyl-6-oxo-1,6-dihydropyridin-3-yl)phenyl)urea A) tert-butyl (trans-4-((benzylcarbamoyl) (4-(1-methyl-6-oxo-1,6-dihydropyridin-3-yl)phenyl) amino)cyclohexyl)carbamate A mixture of tert-butyl (trans-4-((benzylcarbamoyl) (4-bromophenyl)amino)cyclohexyl)carbamate (2.5 g), 1-methyl-5-(4,4,5,5-tetramethyl-1,3,2-dioxaborolan-2-yl)

pyridin-2(1H)-one (1.755 g), PdCl$_2$(dppf) methylene chloride adduct (0.406 g), cesium carbonate (3.24 g), water (5 mL) and DMF (50 mL) was stirred under an argon atmosphere at 90° C. for 2 hr. To the reaction mixture was added saturated brine, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (2.09 g).
MS: [M+H]$^+$ 531.3.

B) 1-(trans-4-aminocyclohexyl)-3-benzyl-1-(4-(1-methyl-6-oxo-1,6-dihydropyridin-3-yl)phenyl)urea hydrochloride A mixture of tert-butyl (trans-4-((benzylcarbamoyl) (4-(1-methyl-6-oxo-1,6-dihydropyridin-3-yl)phenyl)amino)cyclohexyl)carbamate (2.09 g), 4 M hydrochloric acid ethyl acetate solution (50 mL) and MeOH (90 mL) was stirred at room temperature for 18 hr. The solvent was evaporated under reduced pressure, and the precipitate was suspended in ethyl acetate and diisopropyl ether and collected by filtration to give the title compound (1.67 g).
MS: [M+H]$^+$ 431.2.

C) 3-benzyl-1-(trans-4-((5-cyano-4-(oxetan-3-ylamino)pyrimidin-2-yl)amino)cyclohexyl)-1-(4-(1-methyl-6-oxo-1,6-dihydropyridin-3-yl)phenyl)urea A mixture of 1-(trans-4-aminocyclohexyl)-3-benzyl-1-(4-(1-methyl-6-oxo-1,6-dihydropyridin-3-yl)phenyl)urea hydrochloride (107.1 mg), 2-chloro-4-(oxetan-3-ylamino)pyrimidine-5-carbonitrile (58.4 mg), DIPEA (148 mg) and NMP (2 mL) was stirred at room temperature for 16 hr. To the reaction mixture was added water at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (NH, ethyl acetate/methanol) and crystallized from ethanol and hexane to give the title compound (17.1 mg). $^1$H NMR (300 MHz, DMSO-d$_6$) δ 0.99-1.21 (2H, m), 1.26-1.49 (2H, m), 1.73-1.96 (4H, m), 3.37-3.48 (1H, m), 3.52 (3H, s), 4.16 (2H, d, J=5.7 Hz), 4.19-4.37 (1H, m), 4.49-4.70 (4H, m), 4.71-5.05 (1H, m), 5.72-5.94 (1H, m), 6.41-6.58 (1H, m), 7.12-7.43 (7H, m), 7.53-7.92 (4H, m), 7.93-8.09 (1H, m), 8.10-8.31 (2H, m).

Example 485

3-benzyl-1-(trans-4-((5-cyano-4-(oxetan-3-yloxy)pyrimidin-2-yl)amino)cyclohexyl)-1-(5-(1-methyl-1H-pyrazol-4-yl)pyridin-2-yl)urea A) 2-chloro-4-(oxetan-3-yloxy)pyrimidine-5-carbonitrile To a mixture of sodium hydride (60% oil dispersion, 25.3 mg) and THF (8 mL) was added oxetan-3-ol (46.8 mg) and the mixture was stirred at 0° C. for 10 min. To the mixture was added 2,4-dichloropyrimidine-5-carbonitrile (100 mg) at 0° C. and the mixture was stirred for 1 hr. To the reaction mixture were added saturated ammonium chloride aqueous solution and ethyl acetate, and the mixture was extracted with ethyl acetate. The organic layer was separated and dried over anhydrous magnesium sulfate. The solvent was evaporated under reduced pressure. The residue was purified by silica gel column chromatography (ethyl acetate/hexane) to give the title compound (58 mg).
MS: [M+H]$^+$ 212.0.

B) 3-benzyl-1-(trans-4-((5-cyano-4-(oxetan-3-yloxy)pyrimidin-2-yl)amino)cyclohexyl)-1-(5-(1-methyl-1H-pyrazol-4-yl)pyridin-2-yl)urea A mixture of 1-(trans-4-aminocyclohexyl)-3-benzyl-1-(5-(1-methyl-1H-pyrazol-4-yl)pyridin-2-yl)urea hydrochloride (101 mg), 2-chloro-4-(oxetan-3-yloxy)pyrimidine-5-carbonitrile (58 mg), DIPEA (0.14 mL) and DMF (5 mL) was stirred at room temperature for 2 hr. The reaction mixture was purified by silica gel column chromatography (ethyl acetate/hexane) to give the title compound (59 mg). $^1$H NMR (300 MHz, DMSO-d$_6$) δ 1.30-1.56 (4H, m), 1.73-1.91 (4H, m), 3.60 (1H, dt, J=12.18, 6.09 Hz), 3.34-3.49 (1H, m), 3.89 (3H, s), 4.13-4.23 (3H, m), 4.56-4.64 (2H, m), 4.72-4.78 (1H, m), 4.80-4.91 (1H, m), 5.53-5.62 (1H, m), 6.45-6.52 (1H, m), 7.16-7.32 (6H, m), 7.97-8.07 (2H, m), 8.21-8.32 (1H, m), 8.47-8.51 (1H, m), 8.76 (1H, dd, J=4.18 Hz).

Example 495

3-benzyl-1-(trans-4-((5-cyano-4-(5-cyano-2-thienyl)pyrimidin-2-yl)amino)cyclohexyl)-1-(5-(1-methyl-1H-pyrazol-4-yl)pyrazin-2-yl)urea A) tert-butyl (trans-4-((5-bromopyrazin-2-yl)amino)cyclohexyl)carbamate To a mixture of tert-butyl (trans-4-aminocyclohexyl)carbamate (20 g) and 1-butanol (100 mL) were added 2,5-dibromopyrazine (26.6 g) and DIPEA (24.1 g), and the mixture was stirred under reflux overnight. To the reaction mixture was added water, and the mixture was extracted with ethyl acetate. The organic layer was dried over anhydrous sodium sulfate, and the solvent was evaporated under reduced pressure. The residue was purified by silica gel column chromatography (ethyl acetate/petroleum ether) to give the title compound (22.8 g).
MS: [M+H-tBu]+315.1.

B) tert-butyl (trans-4-((5-(1-methyl-1H-pyrazol-4-yl)pyrazin-2-yl)amino)cyclohexyl)carbamate A mixture of tert-butyl (trans-4-((5-bromopyrazin-2-yl)amino)cyclohexyl)carbamate (1.1 g), 1-methyl-4-(4,4,5,5-tetramethyl-1,3,2-dioxaborolan-2-yl)-1H-pyrazole (936 mg), PdCl$_2$(dppf) (220 mg), cesium carbonate (2 g), water and dioxane (1:10) (10 mL) was stirred under a nitrogen atmosphere at 110° C. overnight. To the reaction mixture was added water, and the mixture was extracted with ethyl acetate. The organic layer was separated and dried over anhydrous sodium sulfate, and the solvent was evaporated under reduced pressure. The residue was purified by silica gel column chromatography (ethyl acetate/petroleum ether) to give the title compound (810 mg).
MS: [M+H]$^+$ 373.3.

C) 4-nitrophenyl (trans-4-((tert-butoxycarbonyl)amino)-cyclohexyl) (5-(1-methyl-1H-pyrazol-4-yl)pyrazin-2-yl)carbamate To a solution of tert-butyl (trans-4-((5-(1-methyl-1H-pyrazol-4-yl)pyrazin-2-yl)amino)cyclohexyl)carbamate (9 g) in THF (80 mL) were added 4-nitrophenyl carbonochloridate (7.3 g) and DIPEA (6.2 g), and the mixture was stirred at room temperature overnight. The solvent was evaporated under reduced pressure, and the residue was purified by silica gel column chromatography (ethyl acetate/petroleum ether) to give the title compound (10.2 g).

MS: [M+H-tBu] 482.2.

D) tert-butyl (trans-4-((benzylcarbamoyl) (5-(1-methyl-1H-pyrazol-4-yl)pyrazin-2-yl)amino)cyclohexyl)carbamate A mixture of 4-nitrophenyl (trans-4-((tert-butoxycarbonyl)amino)cyclohexyl) (5-(1-methyl-1H-pyrazol-4-yl)pyrazin-2-yl)carbamate (10 g), 1-phenylmethanamine (12 g) and DMF (20 mL) was stirred at 70° C. overnight. To the reaction mixture was added water, and the mixture was extracted with ethyl acetate. The organic layer was separated and dried over anhydrous magnesium sulfate. The solvent was evaporated under reduced pressure. The residue was purified by silica gel column chromatography (ethyl acetate/petroleum ether) to give the title compound (3.7 g).

MS: [M+H]$^+$ 506.3.

E) 1-(trans-4-aminocyclohexyl)-3-benzyl-1-(5-(1-methyl-1H-pyrazol-4-yl)pyrazin-2-yl)urea trifluoroacetate A mixture of tert-butyl (trans-4-((benzylcarbamoyl) (5-(1-methyl-1H-pyrazol-4-yl)pyrazin-2-yl)amino)cyclohexyl) carbamate (3.70 g), TFA (5 mL) and dichloromethane (10 mL) was stirred at room temperature for 2 hr. The reaction mixture was evaporated under reduced pressure to give the title compound (3.7 g).

MS: [M+H]$^+$ 406.4.

F) 3-benzyl-1-(trans-4-((5-cyano-4-(5-cyano-2-thienyl)pyrimidin-2-yl)amino)cyclohexyl)-1-(5-(1-methyl-1H-pyrazol-4-yl)pyrazin-2-yl)urea A mixture of 2-chloro-4-(5-cyano-2-thienyl)pyrimidine-5-carbonitrile (45.6 mg), 1-(trans-4-aminocyclohexyl)-3-benzyl-1-(5-(1-methyl-1H-pyrazol-4-yl)pyrazin-2-yl)urea trifluoroacetate (80 mg), DIPEA (0.134 mL) and DMF (3 mL) was stirred at room temperature for 2 hr. The reaction mixture was purified by silica gel column chromatography (ethyl acetate/hexane/methanol) to give the title compound (25 mg). $^1$H NMR (300 MHz, DMSO-d$_6$) δ 1.36-1.55 (4H, m), 1.80-1.93 (3H, m), 1.93-2.04 (1H, m), 3.52-3.78 (1H, m), 3.92 (3H, s), 4.16-4.30 (3H, m), 6.79-6.87 (1H, m), 7.18-7.33 (5H, m), 8.07-8.18 (3H, m), 8.39-8.53 (3H, m), 8.78 (1H, d, J=10.20 Hz), 8.91 (1H, dd, J=11.38, 1.37 Hz).

Example 527

3-benzyl-1-(trans-4-((5-cyano-4-(oxetan-3-ylamino) pyrimidin-2-yl)amino)cyclohexyl)-1-(4-(1-methyl-1H-pyrazol-4-yl)phenyl)urea

A) 2-chloro-4-(oxetan-3-ylamino)pyrimidine-5-carbonitrile

To a mixture of 2,4-dichloropyrimidine-5-carbonitrile (2.36 g) and THF (50 mL) was added oxetan-3-amine (0.991 g) at 0° C. The reaction mixture was stirred under a nitrogen atmosphere at 0° C. for 1 hr. To the reaction mixture was added water at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (ethyl acetate/hexane) to give the title compound (753.2 mg).

MS: [M+H]$^+$ 211.0.

B) 3-benzyl-1-(trans-4-((5-cyano-4-(oxetan-3-ylamino)pyrimidin-2-yl)amino)cyclohexyl)-1-(4-(1-methyl-1H-pyrazol-4-yl) phenyl) urea To a mixture of 2-chloro-4-(oxetan-3-ylamino)pyrimidine-5-carbonitrile (54.8 mg), 1-(trans-4-aminocyclohexyl)-3-benzyl-1-(4-(1-methyl-1H-pyrazol-4-yl)phenyl)urea hydrochloride (104.3 mg) and NMP (2 mL) was added DIPEA (153 mg) at room temperature. The reaction mixture was stirred at room temperature for 16 hr. To the reaction mixture was added at room temperature water was added, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (ethyl acetate/hexane) and crystallized from ethanol and hexane to give the title compound (37 mg). $^1$H NMR (300 MHz, DMSO-d$_6$) δ 1.06-1.20 (2H, m), 1.28-1.49 (2H, m), 1.69-1.97 (4H, m), 3.44 (1H, qd, J=7.0, 5.1 Hz), 3.87 (3H, s), 4.15 (2H, d, J=5.8 Hz), 4.24 (1H, t, J=11.6 Hz), 4.32-4.70 (4H, m), 4.72-5.04 (1H, m), 5.70-5.89 (1H, m), 7.09-7.21 (5H, m), 7.23-7.32 (2H, m), 7.33-7.69 (3H, m), 7.84-7.92 (1H, m), 7.93-8.06 (1H, m), 8.11-8.22 (2H, m).

Example 530

3-benzyl-1-(trans-4-((5-cyano-4-(oxetan-3-ylamino) pyrimidin-2-yl)amino)cyclohexyl)-1-(4-(1-methyl-2-oxo-1,2-dihydropyridin-4-yl) phenyl) urea

A) tert-butyl (trans-4-((benzylcarbamoyl) (4-(1-methyl-2-oxo-1,2-dihydropyridin-4-yl)phenyl) amino)cyclohexyl)carbamate A mixture of tert-butyl (trans-4-((benzylcarbamoyl) (4-bromophenyl)amino)cyclohexyl)carbamate (6.2 g), 1-methyl-4-(4,4,5,5-tetramethyl-1,3,2-dioxaborolan-2-yl) pyridin-2(1H)-one (2.8 g), Pd(PPh$_3$)$_4$(0.72 g), potassium carbonate (2.6 g), dioxane (40 mL) and water (10 mL) was stirred under a nitrogen atmosphere at 100° C. for 2 hr. The solvent was evaporated under reduced pressure and the residue was purified by silica gel column chromatography (dichloromethane/methanol) to give the title compound (4.2 g).

MS: [M+H]$^+$ 531.1.

B) 1-(trans-4-aminocyclohexyl)-3-benzyl-1-(4-(1-methyl-2-oxo-1,2-dihydropyridin-4-yl)phenyl)urea hydrochloride A mixture of tert-butyl (trans-4-((benzylcarbamoyl) (4-(1-methyl-2-oxo-1,2-dihydropyridin-4-yl)phenyl)amino)cyclohexyl)carbamate (4.2 g) and 4 M hydrochloric acid dioxane solution (30 mL) was stirred at room temperature for 4 hr. The solvent was evaporated under reduced pressure to give the title compound (3.1 g).

MS: [M+H]$^+$ 431.3.

C) 3-benzyl-1-(trans-4-((5-cyano-4-(oxetan-3-ylamino)pyrimidin-2-yl)amino)cyclohexyl)-1-(4-(1-methyl-2-oxo-1,2-dihydropyridin-4-yl)phenyl)urea To a mixture of 2-chloro-4-(oxetan-3-ylamino)pyrimidine-5-carbonitrile (53.6 mg), 1-(trans-4-aminocyclohexyl)-3-benzyl-1-(4-(1-methyl-2-oxo-1,2-dihydropyridin-4-yl)phenyl)urea hydrochloride (111.2 mg) and NMP (2 mL) was added DIPEA (0.207 mL) at room temperature. The reaction mixture was stirred at room temperature for 16 hr. To the reaction mixture was added water at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (ethyl acetate/methanol) and crystallized from ethyl acetate and hexane. The obtained crude crystal was purified by silica gel column chromatography (NH, ethyl acetate/methanol) and crystallized from ethanol and hexane to give the title compound (29.1 mg).

$^1$H NMR (300 MHz, DMSO-$d_6$) δ 1.06-1.23 (2H, m), 1.26-1.48 (2H, m), 1.73-1.96 (4H, m), 3.28-3.40 (1H, m), 3.46 (3H, s), 4.15 (2H, d, J=5.9 Hz), 4.20-4.31 (1H, m), 4.47-4.61 (3H, m), 4.68 (1H, t, J=6.8 Hz), 4.73-5.03 (1H, m), 5.88-6.03 (1H, m), 6.56-6.67 (1H, m), 6.69-6.80 (1H, m), 7.10-7.66 (8H, m), 7.74-7.89 (3H, m), 7.92-8.07 (1H, m), 8.13-8.21 (1H, m).

Example 532

3-benzyl-1-(trans-4-((5-cyano-4-(oxetan-3-ylamino)pyrimidin-2-yl)amino)cyclohexyl)-1-(6-(1-methyl-1H-pyrazol-4-yl)pyridazin-3-yl)urea A) tert-butyl (trans-4-((6-bromopyridazin-3-yl)amino)cyclohexyl)carbamate A mixture of tert-butyl (trans-4-aminocyclohexyl)carbamate (20 g), 3,6-dibromopyridazine (26.6 g), DIPEA (24.1 g) and 1-butanol (100 mL) was stirred with heating under reflux overnight. To the reaction mixture was added water at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (ethyl acetate/petroleum ether) to give the title compound (26.4 g).

MS: [M+H]$^+$ 371.1.

B) 4-nitrophenyl (6-bromopyridazin-3-yl) (trans-4-((tert-butoxycarbonyl)amino)cyclohexyl)carbamate To a mixture of tert-butyl (trans-4-((6-bromopyridazin-3-yl)amino)cyclohexyl)carbamate (20 g) and THF (100 mL) were added 4-nitrophenyl carbonochloridate (13 g) and DIPEA (13.9 g) at room temperature. The reaction mixture was stirred at room temperature overnight. The solvent was evaporated under reduced pressure to give the title compound (28.9 g).

MS: [M+H-tBu]+480.1.

C) tert-butyl (trans-4-((benzylcarbamoyl) (6-bromopyridazin-3-yl)amino)cyclohexyl)carbamate A mixture of 4-nitrophenyl (6-bromopyridazin-3-yl) (trans-4-((tert-butoxycarbonyl)amino)cyclohexyl)carbamate (28.9 g), 1-phenylmethanamine (6.9 g) and THF (100 mL) was stirred at 50° C. overnight. To the reaction mixture was added water, and the mixture was extracted with ethyl acetate. The organic layer was separated and dried over anhydrous magnesium sulfate. The solvent was evaporated under reduced pressure. The residue was purified by silica gel column chromatography (ethyl acetate/petroleum ether) to give the title compound (7.2 g).

MS: [M+H]$^+$ 504.3.

D) tert-butyl (trans-4-((benzylcarbamoyl) (6-(1-methyl-1H-pyrazol-4-yl)pyridazin-3-yl)amino)cyclohexyl)carbamate A mixture of tert-butyl (trans-4-((benzylcarbamoyl) (6-bromopyridazin-3-yl)amino)cyclohexyl)carbamate (343 mg), PdCl$_2$(dppf) (50 mg), 1-methyl-4-(4,4,5,5-tetramethyl-1,3,2-dioxaborolan-2-yl)-1H-pyrazole (211 mg), cesium carbonate (443 mg), dioxane and water (10:1) (10 mL) was stirred under a nitrogen atmosphere at 110° C. overnight. The solvent was evaporated under reduced pressure, and the residue was purified by silica gel column chromatography (ethyl acetate/petroleum ether) to give the title compound (220 mg).

MS: [M+H]$^+$ 506.4.

E) 1-(trans-4-aminocyclohexyl)-3-benzyl-1-(6-(1-methyl-1H-pyrazol-4-yl)pyridazin-3-yl)urea hydrochloride A mixture of tert-butyl (trans-4-((benzylcarbamoyl) (6-(1-methyl-1H-pyrazol-4-yl)pyridazin-3-yl)amino)cyclohexyl)carbamate (2.8 g) and 4 M hydrochloric acid dioxane solution (10 mL) was stirred at room temperature for 2 hr. The solvent was evaporated under reduced pressure to give the title compound (2.3 g).

MS: [M+H-tBu]+406.3.

F) 3-benzyl-1-(trans-4-((5-cyano-4-(oxetan-3-ylamino)pyrimidin-2-yl)amino)cyclohexyl)-1-(6-(1-methyl-1H-pyrazol-4-yl)pyridazin-3-yl)urea To a mixture of 2-chloro-4-(oxetan-3-ylamino)pyrimidine-5-carbonitrile (49.6 mg), 1-(trans-4-aminocyclohexyl)-3-benzyl-1-(6-(1-methyl-1H-pyrazol-4-yl)pyridazin-3-yl)urea hydrochloride (99 mg) and NMP (2 mL) was added DIPEA (0.195 mL) at room temperature. The reaction mixture was stirred at room temperature for 16 hr. To the reaction mixture was added water at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (ethyl acetate/methanol) and crystallized from ethanol and hexane to give the title compound (40.6 mg).

$^1$H NMR (300 MHz, DMSO-$d_6$) δ 1.25-1.59 (4H, m), 1.85 (4H, d, J=12.9 Hz), 3.37-3.69 (1H, m), 3.93 (3H, s), 4.14-4.36 (3H, m), 4.49-4.72 (4H, m), 4.76-5.07 (1H, m), 6.87 (1H, t, J=5.8 Hz), 7.11-7.36 (5H, m), 7.38-7.69 (2H, m), 7.88-8.11 (2H, m), 8.11-8.24 (2H, m), 8.40-8.57 (1H, m).

Example 536

3-benzyl-1-(trans-4-((4-(4-chloro-1H-pyrazol-5-yl)-5-cyanopyrimidin-2-yl)amino)cyclohexyl)-1-(5-(1-methyl-1H-pyrazol-4-yl)pyridin-2-yl)urea

A) 2-(methylsulfanyl)-4-(1-(tetrahydro-2H-pyran-2-yl)-1H-pyrazol-5-yl)pyrimidine-5-carbonitrile A mixture of 4-chloro-2-(methylsulfanyl)pyrimidine-5-carbonitrile (0.98 g), 1-(tetrahydro-2H-pyran-2-yl)-5-(4,4,5,5-tetramethyl-1,3,2-dioxaborolan-2-yl)-1H-pyrazole (1.615 g), PdCl$_2$(Amphos)$_2$ (0.374 g), 2 M sodium carbonate aqueous solution (5.28 mL) and DME (13 mL) was stirred under microwave irradiation at 100° C. for 1 hr. Insoluble material was filtered off, and the solvent was evaporated under reduced pressure. The residue was purified by silica gel column chromatography (ethyl acetate/hexane) to give the title compound (0.9 g).

$^1$H NMR (300 MHz, DMSO-d$_6$) δ 1.43-1.57 (3H, m), 1.92-2.05 (2H, m), 2.22-2.39 (1H, m), 2.64 (3H, s), 3.43-3.55 (1H, m), 3.74-3.85 (1H, m), 6.02 (1H, dd, J=9.3, 2.0 Hz), 7.11 (1H, d, J=2.0 Hz), 7.76 (1H, d, J=2.0 Hz), 9.18 (1H, s).

B) 2-(methylsulfanyl)-4-(1H-pyrazol-5-yl)pyrimidine-5-carbonitrile

A mixture of 2-(methylsulfanyl)-4-(1-(tetrahydro-2H-pyran-2-yl)-1H-pyrazol-5-yl)pyrimidine-5-carbonitrile (0.8 g), 6 M aqueous hydrochloric acid solution (1.327 mL) and MeOH (10 mL) was stirred at room temperature overnight. To the reaction mixture was added saturated aqueous sodium hydrogen carbonate solution, and the solvent was evaporated under reduced pressure. The residue was purified by silica gel column chromatography (ethyl acetate/hexane) to give the title compound (0.33 g).

MS: [M+H]$^+$ 218.1.

C) 2-chloro-4-(4-chloro-1H-pyrazol-5-yl)pyrimidine-5-carbonitrile

To a mixture of 2-(methylsulfanyl)-4-(1H-pyrazol-5-yl)pyrimidine-5-carbonitrile (49 mg) and acetonitrile (5 mL) was added sulfuryl dichloride (152 mg) at 0° C. The reaction mixture was stirred at room temperature overnight. To the reaction mixture was added saturated aqueous sodium hydrogen carbonate solution, and the mixture was extracted with ethyl acetate. The organic layer was separated, washed with saturated brine, and dried over anhydrous magnesium sulfate. The solvent was evaporated under reduced pressure. The residue was crystallized from ethyl acetate and diisopropyl ether to give the title compound (22.6 mg).

MS: [M+H]$^+$ 240.0.

D) 3-benzyl-1-(trans-4-((4-(4-chloro-1H-pyrazol-5-yl)-5-cyanopyrimidin-2-yl)amino)cyclohexyl)-1-(5-(1-methyl-1H-pyrazol-4-yl)pyridin-2-yl)urea A mixture of 2-chloro-4-(4-chloro-1H-pyrazol-5-yl)pyrimidine-5-carbonitrile (22.6 mg), 1-(trans-4-aminocyclohexyl)-3-benzyl-1-(5-(1-methyl-1H-pyrazol-4-yl)pyridin-2-yl)urea (41.4 mg), potassium carbonate (26 mg) and DMF (1 mL) was stirred at 60° C. for 3 hr was stirred. The reaction mixture was cooled to room temperature, water was added, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/methanol) to give the title compound (13 mg).

$^1$H NMR (300 MHz, DMSO-d$_6$) δ 1.35-1.53 (4H, m), 1.75-2.03 (4H, m), 3.58-3.77 (1H, m), 3.89 (3H, s), 4.15-4.30 (3H, m), 6.47-6.57 (1H, m), 7.15-7.36 (6H, m), 7.96-8.03 (2H, m), 8.14-8.19 (1H, m), 8.23-8.31 (2H, m), 8.62-8.79 (2H, m), 13.72-13.84 (1H, m).

Example 538

3-benzyl-1-(trans-4-((5-cyano-4-(5-cyano-2-thienyl)pyrimidin-2-yl)amino)cyclohexyl)-1-(6-(1-methyl-1H-pyrazol-4-yl)pyridazin-3-yl)urea A mixture of 1-(trans-4-aminocyclohexyl)-3-benzyl-1-(6-(1-methyl-1H-pyrazol-4-yl)pyridazin-3-yl)urea hydrochloride (40.7 mg), 2-chloro-4-(5-cyano-2-thienyl)pyrimidine-5-carbonitrile (25 mg), DIPEA (0.08 mL) and DMF (3 mL) was stirred at room temperature for 2 hr. The reaction mixture was purified by silica gel column chromatography (ethyl acetate/hexane/methanol) to give the title compound (23.8 mg).

$^1$H NMR (300 MHz, DMSO-d$_6$) δ 1.39-1.60 (4H, m), 1.81-2.22 (4H, m), 3.55-3.75 (1H, m), 3.93 (3H, s), 4.19-4.34 (3H, m), 6.90 (1H, d, J=4.89 Hz), 7.18-7.33 (5H, m), 7.53 (1H, t, J=8.56 Hz), 7.97 (1H, t, J=8.64 Hz), 8.09 (1H, t, J=4.20 Hz), 8.16 (2H, t, J=4.67 Hz), 8.45-8.54 (2H, m), 8.78 (1H, d, J=8.31 Hz).

Example 539

3-benzyl-1-(trans-4-((5-cyano-4-(oxetan-3-ylamino)pyrimidin-2-yl)amino)cyclohexyl)-1-(5-(1-methyl-1H-pyrazol-4-yl)pyrazin-2-yl)urea To a mixture of 2-chloro-4-(oxetan-3-ylamino)pyrimidine-5-carbonitrile (30.5 mg), 1-(trans-4-aminocyclohexyl)-3-benzyl-1-(5-(1-methyl-1H-pyrazol-4-yl)pyrazin-2-yl)urea trifluoroacetate (72.1 mg) and NMP (1.5 mL) was added DIPEA (0.121 mL) at room temperature. The reaction mixture was stirred at room temperature for 3 days. The reaction mixture was purified by silica gel column chromatography (ethyl acetate/methanol) to give the title compound (21.9 mg).

$^1$H NMR (300 MHz, DMSO-d$_6$) δ 1.26-1.46 (4H, m), 1.73-1.93 (4H, m), 3.36-3.64 (1H, m), 3.92 (3H, s), 4.20 (3H, d, J=5.9 Hz), 4.52-5.06 (5H, m), 6.73-6.87 (1H, m), 7.11-7.65 (6H, m), 7.91-8.22 (3H, m), 8.35-8.46 (2H, m), 8.82-8.95 (1H, m).

Example 542

3-benzyl-1-(trans-4-((5-cyano-4-(3-methyl-1H-pyrazol-5-yl)pyrimidin-2-yl)amino)cyclohexyl)-1-(6-(1-methyl-1H-pyrazol-4-yl)pyridazin-3-yl)urea

A) 3-benzyl-1-(trans-4-((4-chloro-5-cyanopyrimidin-2-yl)amino)cyclohexyl)-1-(6-(1-methyl-1H-pyrazol-4-yl)pyridazin-3-yl)urea A mixture of 2,4-dichloropyrimidine-5-carbonitrile (0.368 g), 1-(trans-4-aminocyclohexyl)-3-benzyl-1-(6-(1-methyl-1H-pyrazol-4-yl)pyridazin-3-yl)urea hydrochloride (0.85 g), DIPEA (1.243 g) and DMA (15 mL) was stirred at room temperature for 3 hr. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/methanol) to give the title compound (223.8 mg).

MS: [M+H]$^+$ 543.2.

B) 3-benzyl-1-(trans-4-((5-cyano-4-(3-methyl-1-(tetrahydro-2H-pyran-2-yl)-1H-pyrazol-5-yl)pyrimidin-2-yl)amino)cyclohexyl)-1-(6-(1-methyl-1H-pyrazol-4-yl)pyridazin-3-yl)urea A mixture of 3-benzyl-1-(trans-4-((4-chloro-5-cyanopyrimidin-2-yl)amino)cyclohexyl)-1-(6-(1-methyl-1H-pyrazol-4-yl)pyridazin-3-yl)urea (78 mg), 3-methyl-1-(tetrahydro-2H-pyran-2-yl)-5-(4,4,5,5-tetramethyl-1,3,2-dioxaborolan-2-yl)-1H-pyrazole (46.2 mg), PdCl$_2$(Amphos)$_2$ (10.17 mg), 2 M sodium carbonate aqueous solution (0.144 mL), DME (1 mL) and DMF (0.5 mL) was stirred under microwave irradiation at 100° C. for 1 hr. Insoluble material was filtered off and the filtrate was concentrated under reduced pressure. The residue was purified by silica gel column chromatography (ethyl acetate/methanol) to give the title compound (86 mg).

MS: [M+H]$^+$ 673.3.

C) 3-benzyl-1-(trans-4-((5-cyano-4-(3-methyl-1H-pyrazol-5-yl)pyrimidin-2-yl)amino)cyclohexyl)-1-(6-(1-methyl-1H-pyrazol-4-yl)pyridazin-3-yl)urea A mixture of 3-benzyl-1-(trans-4-((5-cyano-4-(3-methyl-1-(tetrahydro-2H-pyran-2-yl)-1H-pyrazol-5-yl)pyrimidin-2-yl)amino)cyclohexyl)-1-(6-(1-methyl-1H-pyrazol-4-yl)pyridazin-3-yl)urea (86 mg) and TFA (1 mL) was stirred at room temperature overnight. To the reaction mixture was added saturated aqueous sodium hydrogen carbonate solution, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/methanol) to give the title compound (27.8 mg).

$^1$H NMR (300 MHz, DMSO-d$_6$) δ 1.35-1.62 (4H, m), 1.78-2.04 (4H, m), 2.23-2.32 (3H, m), 3.60-3.75 (1H, m), 3.93 (3H, s), 4.17-4.35 (3H, m), 6.54-6.61 (1H, m), 6.84-6.94 (1H, m), 7.16-7.36 (5H, m), 7.52 (1H, dd, J=9.0, 4.7 Hz), 7.92-8.02 (1H, m), 8.05-8.22 (2H, m), 8.47 (1H, d, J=1.4 Hz), 8.59 (1H, d, J=10.8 Hz), 13.11-13.23 (1H, m).

Example 552

3-benzyl-1-(trans-4-((5-cyano-4-(3-methyl-1H-pyrazol-5-yl)pyrimidin-2-yl)amino)cyclohexyl)-1-(5-(1-methyl-1H-pyrazol-4-yl) pyrazin-2-yl) urea A) 3-benzyl-1-(trans-4-((4-chloro-5-cyanopyrimidin-2-yl)amino)cyclohexyl)-1-(5-(1-methyl-1H-pyrazol-4-yl)pyrazin-2-yl)urea A mixture of 2,4-dichloropyrimidine-5-carbonitrile (236 mg), 1-(trans-4-aminocyclohexyl)-3-benzyl-1-(5-(1-methyl-1H-pyrazol-4-yl)pyrazin-2-yl)urea trifluoroacetate (641.2 mg), DIPEA (1.078 mL) and DMA (10 mL) was stirred at room temperature for 3 hr. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/methanol) to give the title compound (192.9 mg).

MS: [M+H]$^+$ 543.2.

B) 3-benzyl-1-(trans-4-((5-cyano-4-(3-methyl-1-(tetrahydro-2H-pyran-2-yl)-1H-pyrazol-5-yl)pyrimidin-2-yl)amino)cyclohexyl)-1-(5-(1-methyl-1H-pyrazol-4-yl)pyrazin-2-yl)urea A mixture of 3-benzyl-1-(trans-4-((4-chloro-5-cyanopyrimidin-2-yl)amino)cyclohexyl)-1-(5-(1-methyl-1H-pyrazol-4-yl)pyrazin-2-yl)urea (64.9 mg), 3-methyl-1-(tetrahydro-2H-pyran-2-yl)-5-(4,4,5,5-tetramethyl-1,3,2-dioxaborolan-2-yl)-1H-pyrazole (38.4 mg), PdCl$_2$(Amphos)$_2$ (8.46 mg), 2 M sodium carbonate aqueous solution (0.12 mL), THF (0.5 mL) and DMF (0.25 mL) was stirred under microwave irradiation at 100° C. for 1 hr. Insoluble material was filtered off and the filtrate was concentrated under reduced pressure. The residue was purified by silica gel column chromatography (ethyl acetate/methanol) to give the title compound (61.1 mg).

MS: [M−H]$^-$ 671.3.

C) 3-benzyl-1-(trans-4-((5-cyano-4-(3-methyl-1H-pyrazol-5-yl)pyrimidin-2-yl)amino)cyclohexyl)-1-(5-(1-methyl-1H-pyrazol-4-yl)pyrazin-2-yl)urea A mixture of 3-benzyl-1-(trans-4-((5-cyano-4-(3-methyl-1-(tetrahydro-2H-pyran-2-yl)-1H-pyrazol-5-yl)pyrimidin-2-yl)amino)cyclohexyl)-1-(5-(1-methyl-1H-pyrazol-4-yl)pyrazin-2-yl)urea (61.1 mg) and TFA (1 mL) was stirred at room temperature overnight. To the reaction mixture was added saturated aqueous sodium hydrogen carbonate solution, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/methanol) to give the title compound (9.4 mg).

$^1$H NMR (300 MHz, DMSO-d$_6$) δ 1.34-1.55 (4H, m), 1.80-2.01 (4H, m), 2.24-2.32 (3H, m), 3.58-3.76 (1H, m), 3.92 (3H, s), 4.16-4.32 (3H, m), 6.58 (1H, d, J=4.3 Hz), 6.76-6.87 (1H, m), 7.15-7.35 (5H, m), 8.04-8.16 (2H, m), 8.39-8.45 (2H, m), 8.59 (1H, d, J=13.0 Hz), 8.87-8.94 (1H, m), 13.11-13.21 (1H, m).

Example 553

3-benzyl-1-(trans-4-((5-cyano-4-(oxetan-3-ylamino) pyrimidin-2-yl)amino)cyclohexyl)-1-(5-(2-methoxypyrimidin-5-yl)pyridin-2-yl)urea A) tert-butyl (trans-4-((benzylcarbamoyl) (5-(2-methoxypyrimidin-5-yl)pyridin-2-yl)amino)cyclohexyl)carbamate A mixture of (2-methoxypyrimidin-5-yl)boronic acid (1.376 g), tert-butyl (trans-4-((benzylcarbamoyl) (5-bromopyridin-2-yl)amino)cyclohexyl)carbamate (3 g), PdCl$_2$(Amphos)$_2$ (0.401 g), 2 M cesium carbonate aqueous solution (5.96 mL) and DMF (60 mL) was stirred at 80° C. overnight. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate and diisopropyl ether to give the title compound (2.62 g).
MS: [M+H]$^+$ 533.3.

B) 1-(trans-4-aminocyclohexyl)-3-benzyl-1-(5-(2-methoxypyrimidin-5-yl)pyridin-2-yl)urea A mixture of tert-butyl (trans-4-((benzylcarbamoyl) (5-(2-methoxypyrimidin-5-yl)pyridin-2-yl)amino)cyclohexyl) carbamate (2.12 g) and TFA (50 mL) was stirred at room temperature for 1 hr. The solvent of the reaction mixture was evaporated under reduced pressure, and the residue was purified by silica gel column chromatography (NH, ethyl acetate/methanol) to give the title compound (1.722 g).
MS: [M+H]$^+$ 433.3.

C) 3-benzyl-1-(trans-4-((5-cyano-4-(oxetan-3-ylamino) pyrimidin-2-yl)amino)cyclohexyl)-1-(5-(2-methoxy-pyrimidin-5-yl)pyridin-2-yl)urea A mixture of 2-chloro-4-(oxetan-3-ylamino)pyrimidine-5-carbonitrile (35 mg), 1-(trans-4-aminocyclohexyl)-3-benzyl-1-(5-(2-methoxypyrimidin-5-yl)pyridin-2-yl)urea (41.4 mg), DIPEA (0.067 mL) and NMP (3 mL) was stirred at room temperature overnight. The reaction mixture was purified by silica gel column chromatography (NH, ethyl acetate/hexane) and HPLC (L-Column 2 ODS, mobile phase: water/acetonitrile (5 mM ammonium bicarbonate-based)). The obtained fraction was concentrated under reduced pressure, and the obtained solid was treated with ethyl acetate and diisopropyl ether to give the title compound (18.2 mg).
$^1$H NMR (300 MHz, DMSO-d$_6$) δ 1.28-1.46 (2H, m), 1.46-1.66 (2H, m), 1.75-1.93 (4H, m), 3.38-3.65 (1H, m), 3.98 (3H, s), 4.15-4.29 (3H, m), 4.55-5.06 (5H, m), 6.75-6.88 (1H, m), 7.18-7.41 (6H, m), 7.63 (1H, d, J=7.13 Hz), 7.95-8.09 (1H, m), 8.15-8.24 (2H, m), 8.88-8.92 (1H, m), 9.04 (2H, s).

Example 566

3-benzyl-1-(5-(1-methyl-1H-pyrazol-4-yl)pyridin-2-yl)-1-(trans-4-((4-(2-oxa-6-azaspiro[3.4]octa-6-yl)-5-(trifluoromethyl)pyrimidin-2-yl)amino)cyclo-hexyl)urea A) 3-benzyl-1-(trans-4-((4-chloro-5-(trifluorom-ethyl)pyrimidin-2-yl)amino)cyclohexyl)-1-(5-(1-methyl-1H-pyrazol-4-yl)pyridin-2-yl)urea To a mixture of 2,4-dichloro-5-(trifluoromethyl)pyrimi-dine (1.48 g), dichloroethane and tert-butanol (1:1) (15 mL) was added 1 M zinc chloride tetrahydrofuran solution (13.6 mL) under a nitrogen atmosphere 0° C. The mixture was stirred for 1 hr, and 1-(trans-4-aminocyclohexyl)-3-benzyl-1-(5-(1-methyl-1H-pyrazol-4-yl)pyridin-2-yl)urea hydrochloride (600 mg) and TEA (275 mg) were added at the same temperature. The reaction mixture was stirred at room temperature overnight. To the reaction mixture was added water, and the mixture was extracted with dichloromethane. The organic layer was separated, washed with water and saturated brine, and dried over anhydrous sodium sulfate. The solvent was evaporated under reduced pressure. The residue was purified by HPLC (L-Column 2 ODS, mobile phase: water/acetonitrile (0.1% trifluoroacetic acid-based)) to give the title compound (140 mg).
MS: [M+H]$^+$ 585.2.

B) 3-benzyl-1-(5-(1-methyl-1H-pyrazol-4-yl)pyri-din-2-yl)-1-(trans-4-((4-(2-oxa-6-azaspiro[3.4]octa-6-yl)-5-(trifluoromethyl)pyrimidin-2-yl)amino)cy-clohexyl)urea A mixture of 3-benzyl-1-(trans-4-((4-chloro-5-(trifluo-romethyl)pyrimidin-2-yl)amino)cyclohexyl)-1-(5-(1-methyl-1H-pyrazol-4-yl)pyridin-2-yl)urea (60 mg), 2-oxa-6-azaspiro[3.4]octane (12.8 mg), DIPEA (40.1 mg) and DMF (2 mL) was stirred at 60° C. for 3 hr. The reaction mixture was purified by HPLC (L-Column 2 ODS, mobile phase: water/acetonitrile (0.1% trifluoroacetic acid-based)) to give the title compound (25.2 mg).
$^1$H NMR (400 MHz, DMSO-d$_6$) δ 1.31-1.43 (4H, m), 1.79-1.81 (3H, m), 1.94-1.97 (1H, m), 2.13-2.15 (2H, m), 3.49 (3H, t, J=6.4 Hz), 3.70 (2H, s), 3.89 (3H, s), 4.18-4.20 (3H, m), 4.48-4.51 (4H, m), 6.49-6.51 (1H, m), 7.17-7.23 (5H, m), 7.27-7.31 (2H, m), 7.99-8.02 (2H, m), 8.10-8.15 (1H, m), 8.27 (1H, s), 8.76-8.78 (1H, m).

Example 574

3-benzyl-1-(5-(1-methyl-1H-pyrazol-4-yl)pyridin-2-yl)-1-(trans-4-((4-(oxetan-3-ylamino)-5-(trifluorom-ethyl)pyrimidin-2-yl)amino)cyclohexyl)urea A mixture of 3-benzyl-1-(trans-4-((4-chloro-5-(trifluo-romethyl)pyrimidin-2-yl)amino)cyclohexyl)-1-(5-(1-methyl-1H-pyrazol-4-yl)pyridin-2-yl)urea (55.0 mg), oxetan-3-amine (7.56 mg) and DMF (2 mL) was stirred at 60° C. for 4 hr. The reaction mixture was purified by HPLC (L-Column 2 ODS, mobile phase: water/acetonitrile (0.1% trifluoroacetic acid-based)) to give the title compound (21.6 mg).
$^1$H NMR (400 MHz, DMSO-d$_6$) δ 1.31-1.41 (4H, m), 1.79-1.90 (4H, m), 3.31-3.53 (1H, m), 3.89 (3H, s), 4.14-4.20 (3H, m), 4.56-4.71 (4H, m), 4.76-4.97 (1H, m), 6.49-6.54 (1H, m), 7.06-7.37 (8H, m), 7.98-8.06 (3H, m), 8.26-8.28 (1H, m), 8.76-8.78 (1H, m).

Example 575

3-benzyl-1-(trans-4-((5-cyano-4-(oxetan-3-ylamino) pyrimidin-2-yl)amino)cyclohexyl)-1-(5-(1-methyl-1H-pyrazol-4-yl)pyridin-2-yl)urea A) tert-butyl (trans-4-((5-bromopyrimidin-2-yl) amino)cyclohexyl)carbamate A mixture of tert-butyl (trans-4-aminocyclohexyl)car-bamate (28.3 g), 5-bromo-2-chloropyrimidine (25 g), DIPEA (56 mL) and 1-butanol (150 mL) was stirred at 110° C. for 16 hr. The solvent was evaporated under reduced pressure. To the residue were added ethanol (100 mL) and water (100 mL) at room temperature, and the mixture was stirred for 30 min. The obtained solid was collected by filtration, and washed with water and 2-propanol to give the title compound (41.5 g).
MS: [M+H-tBu]+315.0.

B) 4-nitrophenyl (5-bromopyrimidin-2-yl) (trans-4-((tert-butoxycarbonyl)amino)cyclohexyl)carbamate To a mixture of tert-butyl (trans-4-((5-bromopyrimidin-2-yl)amino)cyclohexyl)carbamate (9.17 g), DIPEA (17.25 mL) and THF (120 mL) was added 4-nitrophenyl carbonochloridate (15.96 g) at room temperature. The reaction mixture was stirred at room temperature for 16 hr. Insoluble material was filtered off, and the solvent was evaporated under reduced pressure. The residue was purified by silica gel column chromatography (ethyl acetate/hexane) to give the title compound (13.02 g).

MS: [M+H-tBu]+480.0.

C) tert-butyl (trans-4-((benzylcarbamoyl) (5-bromopyrimidin-2-yl)amino)cyclohexyl)carbamate To a mixture of 4-nitrophenyl (5-bromopyrimidin-2-yl)(trans-4-((tert-butoxycarbonyl)amino)cyclohexyl)carbamate (13.02 g) and NMP (150 mL) was added 1-phenylmethanamine (7.8 g) at room temperature. The reaction mixture was stirred under a nitrogen atmosphere at 70° C. for 2 hr. To the reaction mixture was added water, and the resulting solid was collected by filtration and washed with water and diisopropyl ether to give the title compound (8.1 g).

MS: [M+H]$^+$ 504.1.

D) tert-butyl (trans-4-((benzylcarbamoyl) (5-(1-methyl-1H-pyrazol-4-yl)pyrimidin-2-yl)amino)cyclohexyl)carbamate A mixture of tert-butyl (trans-4-((benzylcarbamoyl) (5-bromopyrimidin-2-yl)amino)cyclohexyl)carbamate (1.7 g), PdCl$_2$(dppf) (310 mg), 1-methyl-4-(4,4,5,5-tetramethyl-1,3,2-dioxaborolan-2-yl)-1H-pyrazole (1.7 g), 2 M sodium carbonate aqueous solution (3.37 mL) and DME (50 mL) was stirred under a nitrogen atmosphere at 80° C. for 6 hr. The solvent was evaporated under reduced pressure, and the residue was purified by silica gel column chromatography (ethyl acetate/hexane) and silica gel column chromatography (NH, ethyl acetate/hexane) to give the title compound (1.435 g).

MS: [M+H]$^+$ 506.3.

E) 1-(trans-4-aminocyclohexyl)-3-benzyl-1-(5-(1-methyl-1H-pyrazol-4-yl)pyrimidin-2-yl)urea hydrochloride To a mixture of tert-butyl (trans-4-((benzylcarbamoyl) (5-(1-methyl-1H-pyrazol-4-yl)pyrimidin-2-yl)amino)cyclohexyl)carbamate (112.5 mg) and THF (1 mL) was added 4 M hydrochloric acid ethyl acetate solution (3 mL) at room temperature. The reaction mixture was stirred at room temperature for 16 hr, and the solvent was evaporated under reduced pressure to give the title compound (92.3 mg).

MS: [M+H]$^+$ 406.1.

F) 3-benzyl-1-(trans-4-((5-cyano-4-(oxetan-3-ylamino)pyrimidin-2-yl)amino)cyclohexyl)-1-(5-(1-methyl-1H-pyrazol-4-yl)pyrimidin-2-yl)urea To a mixture of 2-chloro-4-(oxetan-3-ylamino)pyrimidine-5-carbonitrile (36.1 mg), 1-(trans-4-aminocyclohexyl)-3-benzyl-1-(5-(1-methyl-1H-pyrazol-4-yl)pyrimidin-2-yl)urea hydrochloride (46.1 mg) and NMP (2 mL) was added DIPEA (0.091 mL) at room temperature. The reaction mixture was stirred at room temperature for 16 hr, and 2-chloro-4-(oxetan-3-ylamino)pyrimidine-5-carbonitrile (17.1 mg) was added. The reaction mixture was stirred at 70° C. for 2 hr. To the reaction mixture was added water at room temperature, and the mixture was extracted with ethyl acetate. The organic layer was separated, washed with water and saturated brine, and dried over anhydrous magnesium sulfate. The solvent was evaporated under reduced pressure. The residue was washed with ethyl acetate and ethanol to give the title compound (31.7 mg).

$^1$H NMR (300 MHz, DMSO-d$_6$) δ 1.27-1.49 (2H, m), 1.62-2.01 (4H, m), 2.07-2.28 (2H, m), 3.51-3.83 (1H, m), 3.88 (3H, s), 4.32-4.74 (7H, m), 4.76-5.06 (1H, m), 7.16-7.38 (5H, m), 7.40-7.73 (1H, m), 7.95 (1H, s), 7.97-8.14 (1H, m), 8.15-8.32 (2H, m), 8.78-8.91 (2H, m), 9.03 (1H, t, J=5.7 Hz).

Example 577

3-benzyl-1-(trans-4-((5-cyano-4-(5-methyl-1H-pyrazol-4-yl)pyrimidin-2-yl)amino)cyclohexyl)-1-(5-(2-methoxypyrimidin-5-yl)pyridin-2-yl)urea A) 4-(3-methyl-1H-pyrazol-4-yl)-2-(methylsulfanyl)pyrimidine-5-carbonitrile A mixture of 4-chloro-2-(methylsulfanyl)pyrimidine-5-carbonitrile (966 mg), tert-butyl 3-methyl-4-(4,4,5,5-tetramethyl-1,3,2-dioxaborolan-2-yl)-1H-pyrazole-1-carboxylate (3.22 g), PdCl$_2$(Amphos)$_2$ (193.8 mg), 2 M sodium carbonate aqueous solution (5.2 mL) and DME (30 mL) was stirred under a nitrogen atmosphere at 80° C. for 16 hr. Insoluble material was filtered off, 1 M aqueous hydrochloric acid solution was added to the filtrate, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (ethyl acetate/hexane) and treated with diisopropyl ether to give the title compound (629.9 mg).

$^1$H NMR (300 MHz, DMSO-d$_6$) δ 2.57 (3H, s), 2.60 (3H, s), 8.37 (1H, brs), 8.95 (1H, s), 13.36 (1H, brs).

B) 2-chloro-4-(5-methyl-1H-pyrazol-4-yl)pyrimidine-5-carbonitrile

To a mixture of 4-(3-methyl-1H-pyrazol-4-yl)-2-(methylsulfanyl)pyrimidine-5-carbonitrile (164.5 mg) and acetic acid (10 mL) was added sulfuryl dichloride (0.288 mL) at room temperature. The reaction mixture was stirred at room temperature for 5 min. The solvent was evaporated under reduced pressure. The residue was washed with diisopropyl ether to give the title compound (103.9 mg).

MS: [M+H]$^+$ 220.1.

C) 3-benzyl-1-(trans-4-((5-cyano-4-(5-methyl-1H-pyrazol-4-yl)pyrimidin-2-yl)amino)cyclohexyl)-1-(5-(2-methoxypyrimidin-5-yl)pyridin-2-yl)urea A mixture of DIPEA (0.12 mL), 1-(trans-4-aminocyclohexyl)-3-benzyl-1-(5-(2-methoxypyrimidin-5-yl)pyridin-2-yl)urea (74 mg), 2-chloro-4-(5-methyl-1H-pyrazol-4-yl)pyrimidine-5-carbonitrile (37.6 mg) and DMF (2 mL) was stirred at room temperature for 18 hr. The reaction mixture was purified by silica gel column chromatography (NH, ethyl acetate/hexane/methanol) to give the title compound (12.8 mg).

$^1$H NMR (300 MHz, DMSO-d$_6$) δ 1.36-1.68 (4H, m), 1.77-2.06 (4H, m), 2.16-2.80 (3H, m), 3.54-3.74 (1H, m), 3.99 (3H, s), 4.17-4.31 (3H, m), 6.70-6.93 (1H, m), 7.18-

7.36 (6H, m), 7.87-8.48 (3H, m), 8.54-8.61 (1H, m), 8.90 (1H, t, J=3.36 Hz), 9.02-9.07 (2H, m), 12.94-13.23 (1H, m).

Example 581 benzyl (trans-4-((5-cyano-4-(oxetan-3-ylamino)pyrimidin-2-yl)amino)cyclohexyl) (5-(2-methoxypyrimidin-5-yl)pyridin-2-yl)carbamate A) benzyl (5-bromopyridin-2-yl) (trans-4-((tert-butoxycarbonyl)amino)cyclohexyl)carbamate To a mixture of tert-butyl (trans-4-((5-bromopyridin-2-yl)amino)cyclohexyl)carbamate (5.08 g), and THF (70 mL) were added DIPEA (7.31 mL) and benzyl carbonochloridate (3.09 mL) at room temperature. The reaction mixture was stirred under a nitrogen atmosphere at room temperature overnight. DIPEA (7.31 mL) and benzyl carbonochloridate (3.09 mL) were further added, and the reaction mixture was stirred under a nitrogen atmosphere at room temperature for 6 hr. To the reaction mixture was added saturated aqueous sodium hydrogen carbonate solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (5.2 g).
MS: [M+H]$^+$ 504.2.

B) benzyl (trans-4-((tert-butoxycarbonyl)amino) cyclohexyl) (5-(2-methoxypyrimidin-5-yl)pyridin-2-yl)carbamate A mixture of benzyl (5-bromopyridin-2-yl) (trans-4-((tert-butoxycarbonyl)amino)cyclohexyl)carbamate (5 g), (2-methoxypyrimidin-5-yl)boronic acid (2.289 g), PdCl$_2$ (dppf) (0.725 g), cesium carbonate (6.46 g) and DMF (100 mL) was stirred at 110° C. for 3 hr. To the reaction mixture was added saturated ammonium chloride aqueous solution, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (3.83 g).
MS: [M+H]$^+$ 534.2.

C) benzyl (trans-4-aminocyclohexyl) (5-(2-methoxypyrimidin-5-yl)pyridin-2-yl)carbamate A mixture of benzyl (trans-4-((tert-butoxycarbonyl)amino)cyclohexyl) (5-(2-methoxypyrimidin-5-yl)pyridin-2-yl)carbamate (200 mg) and TFA (4 mL) was stirred at room temperature for 2 hr, and the solvent was evaporated under reduced pressure. The residue was purified by silica gel column chromatography (NH, ethyl acetate/methanol) to give the title compound (34 mg).
MS: [M+H]$^+$ 434.2.

D) benzyl (trans-4-((5-cyano-4-(oxetan-3-ylamino) pyrimidin-2-yl)amino)cyclohexyl) (5-(2-methoxypyrimidin-5-yl)pyridin-2-yl)carbamate A mixture of DIPEA (0.055 mL), benzyl (trans-4-aminocyclohexyl) (5-(2-methoxypyrimidin-5-yl)pyridin-2-yl)carbamate (34 mg), 2-chloro-4-(oxetan-3-ylamino)pyrimidine-5-carbonitrile (18.17 mg) and DMF (2 mL) was stirred at room temperature for 18 hr. The reaction mixture was purified by silica gel column chromatography (NH, ethyl acetate/hexane) to give the title compound (7.2 mg).
$^1$H NMR (300 MHz, DMSO-d$_6$) δ 1.28-1.44 (2H, m), 1.48-1.73 (2H, m), 1.80-1.99 (4H, m), 3.35-3.67 (1H, m), 3.98 (3H, s), 4.08 (1H, brs), 4.55-4.98 (5H, m), 5.12 (2H, s), 7.17-7.65 (7H, m), 7.90-8.26 (3H, m), 8.84-8.92 (1H, m), 9.04 (2H, s).

Example 582

1-(trans-4-((5-cyano-4-(oxetan-3-ylamino)pyrimidin-2-yl) amino) cyclohexyl)-3-(2-fluorobenzyl)-1-(5-(2-methoxypyrimidin-5-yl)pyridin-2-yl)urea A) tert-butyl (trans-4-((5-(2-methoxypyrimidin-5-yl)pyridin-2-yl)amino)cyclohexyl)carbamate A mixture of benzyl (trans-4-((tert-butoxycarbonyl) amino)cyclohexyl)-(5-(2-methoxypyrimidin-5-yl)pyridin-2-yl)carbamate (3.48 g), 10% palladium carbon (1.5 g) and MeOH (400 mL) was stirred under a hydrogen atmosphere at normal pressure at room temperature for 1 hr. The catalyst was filtered off, and the filtrate was concentrated under reduced pressure to give the title compound (2.599 g).
MS: [M+H]$^+$ 400.3.

B) 4-nitrophenyl (trans-4-((tert-butoxycarbonyl) amino)cyclohexyl) (5-(2-methoxypyrimidin-5-yl) pyridin-2-yl)carbamate To a mixture of tert-butyl (trans-4-((5-(2-methoxypyrimidin-5-yl)pyridin-2-yl)amino)cyclohexyl)carbamate (1.05 g), DIPEA (2 mL) and THF (25 mL) was added 4-nitrophenyl carbonochloridate (1.59 g) at 0° C. The reaction mixture was stirred under a nitrogen atmosphere at room temperature overnight. Insoluble material was filtered off and the filtrate was evaporated under reduced pressure. The residue was purified by silica gel column chromatography (ethyl acetate/hexane) to give the title compound (1.44 g).
MS: [M+H]$^+$ 565.3.

C) tert-butyl (trans-4-(((2-fluorobenzyl)carbamoyl) (5-(2-methoxypyrimidin-5-yl)pyridin-2-yl)amino) cyclohexyl)carbamate A mixture of 4-nitrophenyl (trans-4-((tert-butoxycarbonyl)amino)-cyclohexyl) (5-(2-methoxypyrimidin-5-yl)pyridin-2-yl)carbamate (185 mg), 1-(2-fluoro-phenyl)methanamine (123 mg) and NMP (10 mL) was stirred at 70° C. overnight. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (180 mg).
MS: [M+H]$^+$ 551.1.

D) 1-(trans-4-aminocyclohexyl)-3-(2-fluorobenzyl)-1-(5-(2-methoxypyrimidin-5-yl)pyridin-2-yl)urea A mixture of tert-butyl (trans-4-(((2-fluorobenzyl)carbamoyl) (5-(2-methoxypyrimidin-5-yl)pyridin-2-yl)amino) cyclohexyl)carbamate (180 mg) and TFA (4 mL) was stirred at room temperature for 3 hr. The solvent was evaporated under reduced pressure, and the residue was purified by silica gel column chromatography (NH, ethyl acetate/methanol) to give the title compound (60 mg).
MS: [M+H]+ 451.3.

E) 1-(trans-4-((5-cyano-4-(oxetan-3-ylamino)pyrimidin-2-yl) amino) cyclohexyl)-3-(2-fluorobenzyl)-1-(5-(2-methoxypyrimidin-5-yl)pyridin-2-yl) urea A mixture of DIPEA (0.093 mL), 1-(trans-4-aminocyclohexyl)-3-(2-fluorobenzyl)-1-(5-(2-methoxypyrimidin-5-yl)pyridin-2-yl)urea (60 mg), 2-chloro-4-(oxetan-3-ylamino)pyrimidine-5-carbonitrile (30.9 mg) and DMF (2 mL) was stirred at room temperature for 18 hr. The reaction mixture was purified by silica gel column chromatography (NH, ethyl acetate/hexane) to give the title compound (20.8 mg).
$^1$H NMR (300 MHz, DMSO-$d_6$) δ 1.28-1.44 (2H, m), 1.44-1.65 (2H, m), 1.75-1.93 (4H, m), 3.36-3.64 (1H, m), 3.98 (3H, s), 4.13-4.30 (3H, m), 4.54-4.72 (4H, m), 4.74-5.01 (1H, m), 6.72-6.84 (1H, m), 7.01-7.72 (6H, m), 7.84-8.09 (1H, m), 8.15-8.26 (2H, m), 8.89-8.94 (1H, m), 9.05 (2H, s).

Example 587

N-(trans-4-((5-cyano-4-(oxetan-3-ylamino)pyrimidin-2-yl)amino)cyclohexyl)-N-(5-(2-methoxypyrimidin-5-yl)pyridin-2-yl)-2-phenoxyacetamide A) tert-butyl (trans-4-((5-(2-methoxypyrimidin-5-yl) pyridin-2-yl) (phenoxyacetyl)amino)cyclohexyl) carbamate To a mixture of tert-butyl (trans-4-((5-(2-methoxypyrimidin-5-yl)pyridin-2-yl)amino)cyclohexyl)carbamate (500 mg), DIPEA (0.7 mL) and THF (10 mL) was added phenoxyacetyl chloride (0.35 mL) at room temperature. The reaction mixture was stirred at room temperature for 1 hr. To the reaction mixture was added saturated aqueous sodium hydrogen carbonate solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (660 mg).
MS: [M+H]+ 534.3.

B) N-(trans-4-aminocyclohexyl)-N-(5-(2-methoxypyrimidin-5-yl)pyridin-2-yl)-2-phenoxyacetamide To a mixture of tert-butyl (trans-4-((5-(2-methoxypyrimidin-5-yl)pyridin-2-yl) (phenoxyacetyl)amino)cyclohexyl) carbamate (655 mg) and acetonitrile (3 mL) was added TFA (1.5 mL) at room temperature. The reaction mixture was stirred at room temperature for 1 hr, and the solvent was evaporated under reduced pressure. The residue was purified by silica gel column chromatography (NH, ethyl acetate/ hexane) to give the title compound (520 mg).
MS: [M+H]+ 434.2.

C) N-(trans-4-((5-cyano-4-(oxetan-3-ylamino)pyrimidin-2-yl)amino)cyclohexyl)-N-(5-(2-methoxypyrimidin-5-yl)pyridin-2-yl)-2-phenoxyacetamide A mixture of DIPEA (0.063 mL), N-(trans-4-aminocyclohexyl)-N-(5-(2-methoxypyrimidin-5-yl)pyridin-2-yl)-2-phenoxyacetamide (39 mg), 2-chloro-4-(oxetan-3-ylamino) pyrimidine-5-carbonitrile (20.84 mg) and DMF (2 mL) was stirred at room temperature for 18 hr. The reaction mixture was purified by silica gel column chromatography (NH, ethyl acetate/hexane/methanol) to give the title compound (14.7 mg).
$^1$H NMR (300 MHz, DMSO-$d_6$) δ 1.29-1.55 (4H, m), 1.79-2.01 (4H, m), 3.38-3.65 (1H, m), 3.99 (3H, s), 4.24-4.46 (3H, m), 4.54-4.72 (4H, m), 4.74-5.03 (1H, m), 6.75 (2H, d, J=7.84 Hz), 6.91 (1H, t, J=7.25 Hz), 7.24 (2H, t, J=7.32 Hz), 7.35-7.72 (2H, m), 7.91-8.09 (1H, m), 8.13-8.21 (1H, m), 8.30-8.39 (1H, m), 8.94-9.03 (1H, m), 9.04-9.13 (2H, m).

Example 588

3-benzyl-1-(5-(2-methoxypyrimidin-5-yl)pyridin-2-yl)-1-(trans-4-((4-(oxetan-3-yloxy)-5-(trifluoromethyl)pyrimidin-2-yl)amino)cyclohexyl)urea A) 2-chloro-4-(oxetan-3-yloxy)-5-(trifluoromethyl) pyrimidine To a mixture of oxetan-3-ol (1.88 g) and THF (100 mL) was added sodium hydride (60% oil dispersion, 1.133 g) at 0° C. The mixture was stirred under a nitrogen atmosphere at 0° C. for 30 min and was added to a mixture of 2,4-dichloro-5-(trifluoromethyl)pyrimidine (5.23 g) and THF (10 mL) at 0° C. The reaction mixture was stirred under a nitrogen atmosphere at room temperature overnight. To the reaction mixture was added saturated ammonium chloride aqueous solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (782.7 mg).
MS: [M+H]+ 255.0.

B) 3-benzyl-1-(5-(2-methoxypyrimidin-5-yl)pyridin-2-yl)-1-(trans-4-((4-(oxetan-3-yloxy)-5-(trifluoromethyl)pyrimidin-2-yl)amino)cyclohexyl)urea A mixture of DIPEA (0.081 mL), 1-(trans-4-aminocyclohexyl)-3-benzyl-1-(5-(2-methoxypyrimidin-5-yl)pyridin-2-yl)urea (50 mg), 2-chloro-4-(oxetan-3-yloxy)-5-(trifluoromethyl)pyrimidine (32.4 mg) and DMF (2 mL) was stirred at room temperature for 18 hr. The reaction mixture was purified by silica gel column chromatography (NH, ethyl acetate/hexane/methanol) to give the title compound (7.1 mg).
$^1$H NMR (300 MHz, DMSO-$d_6$) δ 1.32-1.49 (2H, m), 1.49-1.72 (2H, m), 1.76-1.95 (4H, m), 3.30 (1H, s), 3.98 (3H, s), 4.14-4.28 (3H, m), 4.50-4.64 (2H, m), 4.74-4.93 (2H, m), 5.51-5.65 (1H, m), 6.50-6.95 (1H, m), 7.11-7.44 (6H, m), 7.71-8.03 (1H, m), 8.15-8.27 (1H, m), 8.28-8.37 (1H, m), 8.88-8.95 (1H, m), 9.05 (2H, d, J=2.08 Hz).

Example 589

3-benzyl-1-(5-(2-methoxypyrimidin-5-yl)pyridin-2-yl)-1-(trans-4-((4-(oxetan-3-ylamino)-5-(trifluoromethyl)pyrimidin-2-yl) amino) cyclohexyl) urea A) 2-chloro-N-(oxetan-3-yl)-5-(trifluoromethyl) pyrimidine-4-amine To a mixture of 2,4-dichloro-5-(trifluoromethyl)pyrimidine (4.8 g), DIPEA (7.7 mL) and THF (100 mL) was added oxetan-3-amine (1.552 mL) at 0° C. The reaction mixture was stirred under a nitrogen atmosphere at room temperature for 7 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (2.3 g).

MS: [M+H]$^+$ 254.0.

B) 3-benzyl-1-(5-(2-methoxypyrimidin-5-yl)pyridin-2-yl)-1-(trans-4-((4-(oxetan-3-ylamino)-5-(trifluoromethyl)pyrimidin-2-yl)amino)cyclohexyl)urea A mixture of DIPEA (0.162 mL), 1-(trans-4-aminocyclohexyl)-3-benzyl-1-(5-(2-methoxypyrimidin-5-yl)pyridin-2-yl)urea (100 mg), 2-chloro-N-(oxetan-3-yl)-5-(trifluoromethyl)pyrimidine-4-amine (64.5 mg) and DMF (2 mL) was stirred at room temperature for 18 hr. The reaction mixture was purified by silica gel column chromatography (NH, ethyl acetate/hexane/methanol) to give the title compound (16.6 mg).

$^1$H NMR (300 MHz, DMSO-d$_6$) δ 1.24-1.42 (2H, m), 1.42-1.69 (2H, m), 1.76-1.94 (4H, m), 3.37-3.68 (1H, m), 3.98 (3H, s), 4.15-4.27 (3H, m), 4.54-4.72 (4H, m), 4.75-5.00 (1H, m), 6.64-6.89 (1H, m), 7.08-7.37 (8H, m), 8.00-8.05 (1H, m), 8.22 (1H, dd, J=8.31, 2.64 Hz), 8.90 (1H, s), 9.04 (2H, s).

Example 592

3-benzyl-1-(trans-4-((4-(4-hydroxyazepan-1-yl)-5-(trifluoromethyl)pyrimidin-2-yl)amino)cyclohexyl)-1-(5-(2-methoxypyrimidin-5-yl)pyridin-2-yl)urea A) 1-(2-chloro-5-(trifluoromethyl)pyrimidin-4-yl)azepan-4-ol To a mixture of azepan-4-ol hydrochloride (680 mg), DIPEA (2.39 mL) and THF (30 mL) was added a mixture of 2,4-dichloro-5-(trifluoromethyl)pyrimidine (993 mg) and THF (10 mL) at room temperature. The reaction mixture was stirred under a nitrogen atmosphere at room temperature for 2 days. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (201.5 mg).

MS: [M+H]$^+$ 296.2.

B) 3-benzyl-1-(trans-4-((4-(4-hydroxyazepan-1-yl)-5-(trifluoromethyl)pyrimidin-2-yl) amino) cyclohexyl)-1-(5-(2-methoxypyrimidin-5-yl)pyridin-2-yl)urea A mixture of DIPEA (0.081 mL), 1-(trans-4-aminocyclohexyl)-3-benzyl-1-(5-(2-methoxypyrimidin-5-yl)pyridin-2-yl)urea (50 mg), 1-(2-chloro-5-(trifluoromethyl)pyrimidin-4-yl)azepan-4-ol (37.6 mg) and DMF (2 mL) was stirred at room temperature for 18 hr. The reaction mixture was purified by silica gel column chromatography (NH, ethyl acetate/hexane/methanol) and HPLC (L-Column 2 ODS, mobile phase: water/acetonitrile (5 mM ammonium bicarbonate-based)) to give the title compound (6 mg).

$^1$H NMR (300 MHz, DMSO-d$_6$) δ 1.27-2.04 (14H, m), 3.38-3.73 (6H, m), 3.98 (3H, s), 4.15-4.28 (3H, m), 4.51 (1H, d, J=3.97 Hz), 6.65-7.09 (1H, m), 7.18-7.34 (7H, m), 8.11-8.23 (2H, m), 8.89 (1H, d, J=1.89 Hz), 9.04 (2H, s).

Example 595

3-benzyl-1-(trans-4-((5-cyano-4-(4-hydroxyazepan-1-yl)pyrimidin-2-yl)amino)cyclohexyl)-1-(5-(2-methoxypyrimidin-5-yl)pyridin-2-yl)urea A mixture of DIPEA (0.07 mL), 1-(trans-4-aminocyclohexyl)-3-benzyl-1-(5-(2-methoxypyrimidin-5-yl)pyridin-2-yl)urea (50 mg), 2-chloro-4-(4-hydroxyazepan-1-yl)pyrimidine-5-carbonitrile (35 mg) and DMF (1 mL) was stirred at room temperature overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate and diisopropyl ether to give the title compound (34.8 mg).

$^1$H NMR (300 MHz, DMSO-d$_6$) δ 1.31-1.72 (8H, m), 1.74-2.01 (6H, m), 3.40-3.82 (6H, m), 3.98 (3H, s), 4.22 (3H, d, J=5.8 Hz), 4.57 (1H, d, J=3.8 Hz), 6.73-7.59 (8H, m), 8.12-8.25 (2H, m), 8.89 (1H, d, J=2.3 Hz), 9.04 (2H, s).

Example 596

3-benzyl-1-(trans-4-((5-cyano-4-(4-hydroxyazepan-1-yl)pyrimidin-2-yl)amino)cyclohexyl)-1-(2'-methoxy-5,5'-bipyrimidin-2-yl)urea A) tert-butyl (trans-4-((benzylcarbamoyl) (2'-methoxy-5,5'-bipyrimidin-2-yl)amino)cyclohexyl) carbamate A mixture of tert-butyl (trans-4-((benzylcarbamoyl) (5-bromopyrimidin-2-yl)amino)cyclohexyl)carbamate (2 g), (2-methoxypyrimidin-5-yl)boronic acid (1.221 g), PdCl$_2$ (dppf) (0.29 g), 2 M sodium carbonate aqueous solution (3.96 mL) and DME (20 mL) was stirred under a nitrogen atmosphere at 80° C. for 2 hr. The solvent of the reaction mixture was evaporated under reduced pressure, water was added at room temperature, and the mixture was extracted with ethyl acetate. The organic layer was separated, washed with water and saturated brine, and dried over anhydrous magnesium sulfate. The solvent was evaporated under reduced pressure. The residue was purified by silica gel column chromatography (NH, ethyl acetate/hexane) to give the title compound (1.86 g).

MS: [M+H]$^+$ 534.3.

B) 1-(trans-4-aminocyclohexyl)-3-benzyl-1-(2'-methoxy-5,5'-bipyrimidin-2-yl)urea A mixture of tert-butyl (trans-4-((benzylcarbamoyl) (2'-methoxy-5,5'-bipyrimidin-2-yl)amino)cyclohexyl)carbamate (1.86 g) and TFA (10 mL) was stirred at room temperature for 20 min. The solvent of the reaction mixture was evaporated under reduced pressure, and the residue was purified by silica gel column chromatography (NH, ethyl acetate/hexane) to give the title compound (1.26 g).

MS: [M+H]$^+$ 434.2.

C) 2-chloro-4-(4-hydroxyazepan-1-yl)pyrimidine-5-carbonitrile

To a mixture of 2,4-dichloropyrimidine-5-carbonitrile (2.22 g), DIPEA (6.7 mL) and THF (30 mL) was added a mixture of azepan-4-ol hydrochloride (1.93 g) and DMF (10 mL) at 0° C. The reaction mixture was stirred at 0° C. for 40 min, water was added, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) and crystallized from ethyl acetate and diisopropyl ether, and the crystal was filtered off. The obtained filtrate was concentrated, and the residue was purified by HPLC (L-Column 2 ODS, mobile phase: water/acetonitrile (5 mM ammonium acetate-based)). The obtained fraction was concentrated under reduced pressure, water was added to the residue, and the mixture was extracted with ethyl acetate. The organic layer was separated, washed with saturated brine, dried over anhydrous magnesium sulfate, and concentrated under reduced pressure to give the title compound (971 mg).

MS: $[M+H]^+$ 253.1.

D) 3-benzyl-1-(trans-4-((5-cyano-4-(4-hydroxyazepan-1-yl)pyrimidin-2-yl)amino)cyclohexyl)-1-(2'-methoxy-5,5'-bipyrimidin-2-yl)urea A mixture of DIPEA (0.07 mL), 1-(trans-4-aminocyclohexyl)-3-benzyl-1-(2'-methoxy-5,5'-bipyrimidin-2-yl)urea (50 mg), 2-chloro-4-(4-hydroxyazepan-1-yl)pyrimidine-5-carbonitrile (35 mg) and DMF (1 mL) was stirred at room temperature overnight. To the reaction mixture was added water at room temperature, and the mixture was extracted with ethyl acetate. The organic layer was separated, washed with saturated brine and dried over anhydrous magnesium sulfate. The solvent was evaporated under reduced pressure. The residue was purified by silica gel column chromatography (NH, ethyl acetate/hexane) and crystallized from ethyl acetate to give the title compound (71 mg).

$^1$H NMR (300 MHz, DMSO-$d_6$) δ 1.31-2.17 (14H, m), 3.53-3.85 (6H, m), 3.97 (3H, s), 4.40 (2H, d, J=5.9 Hz), 4.47-4.64 (2H, m), 7.19-7.63 (6H, m), 8.13-8.30 (1H, m), 8.93-9.03 (4H, m), 9.05-9.17 (1H, m).

Example 599 benzyl (trans-4-((5-cyano-4-(4-hydroxyazepan-1-yl)pyrimidin-2-yl)amino)cyclohexyl) (5-(2-methoxypyrimidin-5-yl)pyridin-2-yl)carbamate A mixture of DIPEA (0.081 mL), benzyl (trans-4-aminocyclohexyl) (5-(2-methoxypyrimidin-5-yl)pyridin-2-yl)carbamate (50 mg), 2-chloro-4-(4-hydroxyazepan-1-yl)pyrimidine-5-carbonitrile (32.1 mg) and DMF (2 mL) was stirred at room temperature for 18 hr. The reaction mixture was purified by silica gel column chromatography (NH, ethyl acetate/hexane/methanol) to give the title compound (29.1 mg).

$^1$H NMR (300 MHz, DMSO-$d_6$) δ 1.30-1.48 (2H, m), 1.48-1.70 (6H, m), 1.80-2.00 (6H, m), 3.38-3.79 (6H, m), 3.98 (3H, s), 4.01-4.20 (1H, m), 4.57 (1H, d, J=3.87 Hz), 5.12 (2H, s), 7.25-7.61 (7H, m), 8.14-8.25 (2H, m), 8.88 (1H, d, J=3.59 Hz), 9.04 (2H, s).

Example 600 benzyl (trans-4-((4-(3-fluoro-3-(hydroxymethyl)azetidin-1-yl)-5-(trifluoromethyl)pyrimidin-2-yl)amino)cyclohexyl) (5-(2-methoxypyrimidin-5-yl)pyridin-2-yl)carbamate

A) (1-(2-chloro-5-(trifluoromethyl)pyrimidin-4-yl)-3-fluoroazetidin-3-yl)methanol To a mixture of (3-fluoroazetidin-3-yl)methanol (500 mg), DIPEA (1.69 mL) and THF (30 mL) was added a mixture of 2,4-dichloro-5-(trifluoromethyl)pyrimidine (1.053 g) and acetonitrile (30 mL) at room temperature. The reaction mixture was stirred under a nitrogen atmosphere at room temperature overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (371 mg).

MS: $[M+H]^+$ 286.0.

B) benzyl (trans-4-((4-(3-fluoro-3-(hydroxymethyl)azetidin-1-yl)-5-(trifluoromethyl)pyrimidin-2-yl)amino)cyclohexyl) (5-(2-methoxypyrimidin-5-yl)pyridin-2-yl)carbamate A mixture of DIPEA (0.09 mL), benzyl (trans-4-aminocyclohexyl) (5-(2-methoxypyrimidin-5-yl)pyridin-2-yl)carbamate (55.6 mg), (1-(2-chloro-5-(trifluoromethyl)pyrimidin-4-yl)-3-fluoroazetidin-3-yl)methanol (36.6 mg) and DMF (2 mL) was stirred at room temperature for 18 hr. The reaction mixture was purified by silica gel column chromatography (NH, ethyl acetate/hexane/methanol) to give the title compound (18 mg).

$^1$H NMR (300 MHz, DMSO-$d_6$) δ 1.27-1.47 (2H, m), 1.49-1.67 (2H, m), 1.80-2.04 (4H, m), 3.46-3.75 (3H, m), 3.98 (3H, s), 4.00-4.13 (3H, m), 4.24 (2H, dd, J=19.17, 10.76 Hz), 5.12 (2H, s), 5.30-5.37 (1H, m), 7.22-7.48 (7H, m), 8.06-8.16 (1H, m), 8.23 (1H, d, J=5.67 Hz) 8.86-8.91 (1H, m), 9.05 (2H, s).

Example 603 benzyl (trans-4-((5-cyano-4-(3-fluoro-3-(hydroxymethyl)-azetidin-1-yl)pyrimidin-2-yl)amino)cyclohexyl) (5-(2-methoxypyrimidin-5-yl)pyridin-2-yl) carbamate

A) 2-chloro-4-(3-fluoro-3-(hydroxymethyl)azetidin-1-yl)pyrimidine-5-carbonitrile To a mixture of (3-fluoroazetidin-3-yl)methanol (500 mg), DIPEA (1.69 mL) and THF (10 mL) was added a mixture of 2,4-dichloropyrimidine-5-carbonitrile (845 mg) and acetonitrile (30 mL) at room temperature. The reaction mixture was stirred under a nitrogen atmosphere at room temperature overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (187 mg).

$^1$H NMR (300 MHz, DMSO-d$_6$) δ 3.75 (2H, dd, J=21.1, 6.0 Hz), 4.12-4.88 (4H, m), 5.39 (1H, t, J=6.0 Hz), 8.63 (1H, s).

B) benzyl (trans-4-((5-cyano-4-(3-fluoro-3-(hydroxymethyl)-azetidine-1-yl)pyrimidin-2-yl)amino) cyclohexyl) (5-(2-methoxypyrimidin-5-yl)pyridin-2-yl)carbamate A mixture of DIPEA (0.084 mL), benzyl (trans-4-aminocyclohexyl) (5-(2-methoxypyrimidin-5-yl)pyridin-2-yl)carbamate (52 mg), 2-chloro-4-(3-fluoro-3-(hydroxymethyl) azetidin-1-yl)pyrimidine-5-carbonitrile (29.1 mg) and DMF (2 mL) was stirred at room temperature for 18 hr. The reaction mixture was purified by silica gel column chromatography (NH, ethyl acetate/hexane/methanol) to give the title compound (24.5 mg).

$^1$H NMR (300 MHz, DMSO-d$_6$) δ 1.22-1.45 (2H, m), 1.45-1.69 (2H, m), 1.78-2.00 (4H, m), 3.44-3.77 (3H, m), 3.98 (3H, s), 4.03-4.40 (5H, m), 5.11 (2H, s), 5.31-5.37 (1H, m), 7.25-7.38 (5H, m), 7.45 (1H, dd, J=8.26, 6.09 Hz), 7.62 (1H, dd, J=17.99, 7.70 Hz), 8.18-8.26 (2H, m), 8.88 (1H, dd, J=6.99, 2.45 Hz), 9.04 (2H, d, J=3.21 Hz).

Example 605

3-benzyl-1-(trans-4-((5-cyano-4-((3-methyloxetan-3-yl)amino)-pyrimidin-2-yl)amino)cyclohexyl)-1-(5-(1-methyl-1H-pyrazol-4-yl)pyridin-2-yl)urea A mixture of DIPEA (0.071 mL), 3-benzyl-1-(trans-4-((4-chloro-5-cyanopyrimidin-2-yl)amino)cyclohexyl)-1-(5-(1-methyl-1H-pyrazol-4-yl)pyridin-2-yl)urea (73.1 mg), 3-methyloxetan-3-amine (14.1 mg) and DMF (1 mL) was stirred at room temperature overnight, and at 60° C. for 3 hr. To the reaction mixture was added water, and the mixture was extracted with ethyl acetate. The organic layer was separated, washed with saturated brine, and dried over anhydrous magnesium sulfate. The solvent was evaporated under reduced pressure. The reaction mixture was purified by silica gel column chromatography (ethyl acetate/methanol) to give the title compound (62.1 mg).

$^1$H NMR (300 MHz, DMSO-d$_6$) δ 1.22-1.50 (4H, m), 1.52-1.60 (3H, m), 1.74-1.91 (4H, m), 3.21-3.42 (1H, m), 3.88 (3H, s), 4.10-4.33 (5H, m), 4.58-4.72 (2H, m), 6.43-6.58 (1H, m), 7.14-7.63 (7H, m), 7.69-7.90 (1H, m), 7.96-8.04 (2H, m), 8.12-8.19 (1H, m), 8.27 (1H, s), 8.76 (1H, d, J=2.0 Hz).

Example 606

3-benzyl-1-(2'-methoxy-5,5'-bipyrimidin-2-yl)-1-(trans-4-((4-(oxetan-3-yloxy)-5-(trifluoromethyl) pyrimidin-2-yl)amino)cyclohexyl)urea A) 2-chloro-4-(oxetan-3-yloxy)-5-(trifluoromethyl) pyrimidine To a mixture of oxetan-3-ol (1.88 g) and THF (100 mL) was added sodium hydride (60% oil dispersion, 1.133 g) at 0° C. The mixture was stirred under a nitrogen atmosphere at 0° C. for 30 min, and added to a mixture of 2,4-dichloro-5-(trifluoromethyl)pyrimidine (5.23 g) and THF (10 mL) at 0° C. The reaction mixture was stirred under a nitrogen atmosphere at room temperature overnight. To the reaction mixture was added saturated ammonium chloride aqueous solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (782.7 mg).

MS: [M+H]$^+$ 255.0.

B) 3-benzyl-1-(2'-methoxy-5,5'-bipyrimidin-2-yl)-1-(trans-4-((4-(oxetan-3-yloxy)-5-(trifluoromethyl) pyrimidin-2-yl)amino)cyclohexyl)urea A mixture of DIPEA (0.161 mL), 1-(trans-4-aminocyclohexyl)-3-benzyl-1-(2'-methoxy-5,5'-bipyrimidin-2-yl)urea (100 mg), 2-chloro-4-(oxetan-3-yloxy)-5-(trifluoromethyl) pyrimidine (58.7 mg) and DMF (2 mL) was stirred at room temperature for 18 hr. The reaction mixture was purified by silica gel column chromatography (NH, ethyl acetate/ hexane/methanol) to give the title compound (45.8 mg).

$^1$H NMR (300 MHz, DMSO-d$_6$) δ 1.30-1.50 (2H, m), 1.77-2.01 (4H, m), 2.04-2.20 (2H, m), 3.43-3.88 (1H, m), 3.97 (3H, s), 4.41 (2H, d, J=5.85 Hz), 4.50-4.67 (3H, m) 4.82-4.91 (2H, m), 5.64 (1H, dt, J=18.55, 5.83 Hz), 7.15-7.43 (5H, m), 7.72-8.09 (1H, m), 8.34-8.47 (1H, m), 8.95-9.05 (4H, m), 9.06-9.17 (1H, m).

Example 608 benzyl (trans-4-((5-cyano-4-(oxetan-3-ylamino)pyrimidin-2-yl)amino)cyclohexyl) (2'-methoxy-5,5'-bipyrimidin-2-yl)carbamate A) benzyl (5-bromopyrimidin-2-yl) (trans-4-((tert-butoxycarbonyl)amino)cyclohexyl)carbamate A mixture of 4-nitrophenyl (5-bromopyrimidin-2-yl) (trans-4-((tert-butoxycarbonyl)amino)cyclohexyl)carbamate (22.7 g), phenylmethanol (18.3 g), potassium carbonate (20.4 g) and DMF (80 mL) was stirred under a nitrogen atmosphere at 90° C. for 7 hr. Insoluble material was filtered off, water was added to the filtrate, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane), and treated with diisopropyl ether to give the title compound (16.2 g)

MS: [M+H]$^+$ 505.1.

B) benzyl (trans-4-((tert-butoxycarbonyl)amino) cyclohexyl) (2'-methoxy-5,5'-bipyrimidin-2-yl)carbamate A mixture of benzyl (5-bromopyrimidin-2-yl) (trans-4-((tert-butoxycarbonyl)amino)cyclohexyl)carbamate (8 g), (2-methoxypyrimidin-5-yl)boronic acid (4.87 g), PdCl$_2$ (dppf) (1.15 g), 2 M sodium carbonate aqueous solution (30 mL) and DME (100 mL) was stirred under a nitrogen atmosphere at 90° C. for 2 hr. The reaction mixture was concentrated under reduced pressure, water was added and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane), and treated with ethyl acetate and diisopropyl ether to give the title compound (5.47 g).

MS: [M+H]$^+$ 535.1.

C) benzyl (trans-4-aminocyclohexyl) (2'-methoxy-5,5'-bipyrimidin-2-yl)carbamate

To a mixture of benzyl (trans-4-((tert-butoxycarbonyl)amino)cyclohexyl) (2'-methoxy-5,5'-bipyrimidin-2-yl)carbamate (5.2 g) and acetonitrile (10 mL) was added dropwise TFA (10 mL) at 0° C. The reaction mixture was stirred at room temperature for 1 hr, and the solvent was evaporated under reduced pressure. To the residue was added saturated aqueous sodium hydrogen carbonate solution, and the mixture was extracted with ethyl acetate and THF. The organic layer was separated, washed with saturated brine, and dried over anhydrous magnesium sulfate. The solvent was evaporated under reduced pressure. The residue was purified by silica gel column chromatography (NH, ethyl acetate/methanol) to give the title compound (1.51 g).

MS: [M+H]$^+$ 435.3.

D) benzyl (trans-4-((5-cyano-4-(oxetan-3-ylamino)pyrimidin-2-yl)amino)cyclohexyl) (2'-methoxy-5,5'-bipyrimidin-2-yl)carbamate A mixture of DIPEA (0.07 mL), benzyl (trans-4-aminocyclohexyl) (2'-methoxy-5,5'-bipyrimidin-2-yl)carbamate (50 mg), 2-chloro-4-(oxetan-3-ylamino)pyrimidine-5-carbonitrile (35 mg) and DMF (1 mL) was stirred at room temperature overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate to give the title compound (59.1 mg).

$^1$H NMR (300 MHz, DMSO-d$_6$) δ 1.28-1.48 (2H, m), 1.56-1.78 (2H, m), 1.81-1.97 (4H, m), 3.41-3.73 (1H, m), 3.99 (3H, s), 4.08-4.20 (1H, m), 4.55-4.72 (4H, m), 4.77-5.02 (1H, m), 5.15 (2H, s), 7.24-7.68 (6H, m), 7.96-8.12 (1H, m), 8.14-8.26 (1H, m), 9.08-9.14 (2H, m), 9.20-9.29 (2H, m).

Example 609

3-benzyl-1-(trans-4-((5-cyano-4-(oxetan-3-yloxy)pyrimidin-2-yl)amino)cyclohexyl)-1-(5-(2-methoxypyrimidin-5-yl)pyridin-2-yl)urea A mixture of DIPEA (0.162 mL), benzyl (trans-4-aminocyclohexyl) (2'-methoxy-5,5'-bipyrimidin-2-yl)carbamate (100 mg), 2-chloro-4-(oxetan-3-yloxy)pyrimidine-5-carbonitrile (48.9 mg) and DMF (2 mL) was stirred at room temperature for 18 hr. The reaction mixture was purified by silica gel column chromatography (NH, ethyl acetate/hexane/methanol) to give the title compound (21.2 mg).

$^1$H NMR (300 MHz, DMSO-d$_6$) δ 1.34-1.50 (2H, m), 1.50-1.67 (2H, m), 1.76-1.93 (4H, m), 3.39-3.71 (1H, m), 3.98 (3H, s), 4.15-4.29 (3H, m), 4.55-4.66 (2H, m), 4.72-4.89 (2H, m), 5.53-5.63 (1H, m), 6.81 (1H, dt, J=18.81, 5.98 Hz), 7.18-7.36 (6H, m), 8.00-8.37 (2H, m), 8.48-8.53 (1H, m), 8.90 (1H, dd, J=3.60 Hz), 9.04 (2H, d, J=2.74 Hz).

Example 610

1-(5-(2-methoxypyrimidin-5-yl)pyridin-2-yl)-1-(trans-4-((4-(oxetan-3-yloxy)-5-(trifluoromethyl)pyrimidin-2-yl)amino)cyclohexyl)-3-(pyridin-2-ylmethyl)urea A) tert-butyl (trans-4-((5-(2-methoxypyrimidin-5-yl)pyridin-2-yl) ((pyridin-2-ylmethyl)carbamoyl)amino)cyclohexyl)carbamate A mixture of 4-nitrophenyl (trans-4-((tert-butoxycarbonyl)amino)cyclohexyl) (5-(2-methoxypyrimidin-5-yl)pyridin-2-yl)carbamate (720 mg), 1-(pyridin-2-yl)methanamine (414 mg) and NMP (15 mL) was stirred at 70° C. overnight. To the reaction mixture was added saturated brine, and the mixture was extracted with ethyl acetate. The organic layer was separated, washed with water, and the solvent was evaporated under reduced pressure. The residue was purified by silica gel column chromatography (NH, hexane/ethyl acetate/methanol) to give the title compound (681 mg).

MS: [M+H]$^+$ 534.3.

B) 1-(trans-4-aminocyclohexyl)-1-(5-(2-methoxypyrimidin-5-yl)pyridin-2-yl)-3-(pyridin-2-ylmethyl)urea A mixture of tert-butyl (trans-4-((5-(2-methoxypyrimidin-5-yl)pyridin-2-yl) ((pyridin-2-ylmethyl)carbamoyl)amino)cyclohexyl)carbamate (681 mg) and TFA (10 mL) was stirred at room temperature for 2 hr. The solvent of the reaction mixture was evaporated under reduced pressure, and the residue was purified by silica gel column chromatography (NH, hexane/ethyl acetate/methanol) to give the title compound (486 mg).

MS: [M+H]$^+$ 434.2.

C) 1-(5-(2-methoxypyrimidin-5-yl)pyridin-2-yl)-1-(trans-4-((4-(oxetan-3-yloxy)-5-(trifluoromethyl)pyrimidin-2-yl)amino)cyclohexyl)-3-(pyridin-2-ylmethyl)urea A mixture of DIPEA (0.135 mL), 1-(trans-4-aminocyclohexyl)-1-(5-(2-methoxypyrimidin-5-yl)pyridin-2-yl)-3-(pyridin-2-ylmethyl)urea (84 mg), 2-chloro-4-(oxetan-3-yloxy)-5-(trifluoromethyl)pyrimidine (52.4 mg) and DMF (2 mL) was stirred at room temperature for 18 hr. The reaction mixture was purified by silica gel column chromatography (NH, ethyl acetate/hexane/methanol) to give the title compound (75.4 mg).

$^1$H NMR (300 MHz, DMSO-d$_6$) δ 1.30-1.70 (4H, m), 1.80-1.95 (4H, m), 3.40-3.75 (1H, m), 3.99 (3H, s), 4.16-4.36 (3H, m), 4.51-4.61 (2H, m), 4.75-4.89 (2H, m), 5.54-5.64 (1H, m), 6.82-6.92 (1H, m), 7.22 (1H, t, J=6.23 Hz), 7.30 (1H, d, J=7.93 Hz), 7.44 (1H, dd, J=8.31, 5.67 Hz), 7.73-8.08 (2H, m), 8.25 (1H, td, J=7.60, 2.55 Hz), 8.33 (1H, d, J=4.91 Hz), 8.46 (1H, d, J=4.91 Hz), 8.93 (1H, dd, J=5.29, 2.55 Hz), 9.06 (2H, d, J=2.36 Hz).

Example 611 benzyl (trans-4-((5-cyano-4-(4-hydroxyazepan-1-yl)pyrimidin-2-yl)amino)cyclohexyl) (2'-methoxy-5,5'-bipyrimidin-2-yl)carbamate A mixture of DIPEA (0.07 mL), benzyl (trans-4-aminocyclohexyl) (2'-methoxy-5,5'-bipyrimidin-2-yl)carbamate (50 mg), 2-chloro-4-(4-hydroxyazepan-1-yl)pyrimidine-5-carbonitrile (32 mg) and DMF (1 mL) was stirred at room temperature overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate and diisopropyl ether to give the title compound (29.2 mg).

$^1$H NMR (300 MHz, DMSO-$d_6$) δ 1.40 (2H, brs), 1.64 (5H, brs), 1.80-1.99 (6H, m), 3.44-3.84 (7H, m), 3.99 (3H, s), 4.13 (1H, brs), 4.58 (1H, brs), 5.15 (2H, brs), 7.25-7.58 (6H, m), 8.11-8.25 (1H, m), 9.11 (2H, s), 9.24 (2H, brs).

Example 612

3-benzyl-1-(5-(2-methoxypyrimidin-5-yl)pyrazin-2-yl)-1-(trans-4-((4-(oxetan-3-yloxy)-5-(trifluoromethyl)pyrimidin-2-yl)amino)cyclohexyl)urea A) tert-butyl (trans-4-((5-(2-methoxypyrimidin-5-yl)pyrazin-2-yl)amino)cyclohexyl)carbamate A mixture of tert-butyl (trans-4-((5-bromopyrazin-2-yl)amino)cyclohexyl)carbamate (1.5 g), (2-methoxypyrimidin-5-yl)boronic acid (0.933 g), PdCl$_2$(dppf) (0.302 g), 2 M cesium carbonate aqueous solution (5.05 mL) and DME (20 mL) was stirred under a nitrogen atmosphere at 90° C. for 2 hr. To the reaction mixture was added water at room temperature, and the mixture was extracted with ethyl acetate and THF. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (1.41 g).

MS: [M+H]$^+$ 401.2.

B) 4-nitrophenyl (trans-4-((tert-butoxycarbonyl)amino)cyclohexyl) (5-(2-methoxypyrimidin-5-yl)pyrazin-2-yl)carbamate A mixture of tert-butyl (trans-4-((5-(2-methoxypyrimidin-5-yl)pyrazin-2-yl)amino)cyclohexyl)carbamate (500 mg), 4-nitrophenyl carbonochloridate (755 mg), DIPEA (1.308 mL) and THF (50 mL) was stirred at 70° C. for 5 hr. To the reaction mixture was added water, and the mixture was extracted with ethyl acetate. The organic layer was separated and dried over anhydrous magnesium sulfate. The solvent was evaporated under reduced pressure. The residue was purified by silica gel column chromatography (ethyl acetate/hexane) to give the title compound (412 mg).

MS: [M+H]$^+$ 566.2.

C) tert-butyl (trans-4-((benzylcarbamoyl) (5-(2-methoxypyrimidin-5-yl)pyrazin-2-yl)amino)cyclohexyl)carbamate A mixture of 4-nitrophenyl (trans-4-((tert-butoxycarbonyl)amino)cyclohexyl) (5-(2-methoxypyrimidin-5-yl)pyrazin-2-yl)carbamate (420 mg), 1-phenylmethanamine (0.244 mL) and NMP (10 mL) was stirred at 70° C. overnight. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (340 mg).

MS: [M+H]$^+$ 534.3.

D) 1-(trans-4-aminocyclohexyl)-3-benzyl-1-(5-(2-methoxypyrimidin-5-yl)pyrazin-2-yl)urea A mixture of tert-butyl (trans-4-((benzylcarbamoyl) (5-(2-methoxypyrimidin-5-yl)pyrazin-2-yl)amino)cyclohexyl) carbamate (340 mg) and TFA (10 mL) was stirred at room temperature for 3 hr, and the solvent was evaporated under reduced pressure. The residue was purified by silica gel column chromatography (NH, ethyl acetate/methanol) to give the title compound (220 mg).

MS: [M+H]$^+$ 434.2.

E) 3-benzyl-1-(5-(2-methoxypyrimidin-5-yl)pyrazin-2-yl)-1-(trans-4-((4-(oxetan-3-yloxy)-5-(trifluoromethyl)pyrimidin-2-yl) amino) cyclohexyl) urea A mixture of DIPEA (0.101 mL), 1-(trans-4-aminocyclohexyl)-3-benzyl-1-(5-(2-methoxypyrimidin-5-yl)pyrazin-2-yl)urea (50 mg), 2-chloro-4-(oxetan-3-yloxy)-5-(trifluoromethyl)pyrimidine (32.3 mg) and DMF (2 mL) was stirred at 70° C. for 2 hr. The reaction mixture was purified by silica gel column chromatography (NH, ethyl acetate/hexane/methanol) to give the title compound (10 mg).

$^1$H NMR (300 MHz, DMSO-$d_6$) 51.32-1.47 (2H, m), 1.47-1.66 (2H, m), 1.78-1.98 (4H, m), 3.22-3.70 (1H, m), 4.01 (3H, s), 4.20-4.33 (3H, m), 4.51-4.62 (2H, m), 4.76-4.90 (2H, m), 5.54-5.64 (1H, m), 7.11-7.35 (6H, m), 7.70-8.06 (1H, m), 8.33 (1H, d, J=5.10 Hz), 8.58 (1H, dd, J=7.18, 1.32 Hz), 9.22 (1H, d, J=6.83 Hz), 9.32 (2H, d, J=5.29 Hz).

Example 614

3-benzyl-1-(trans-4-((5-cyano-4-(3-hydroxy-3-methylazetidin-1-yl)pyrimidin-2-yl)amino)cyclohexyl)-1-(2'-methoxy-5,5'-bipyrimidin-2-yl)urea A) 2-chloro-4-(3-hydroxy-3-methylazetidin-1-yl)pyrimidine-5-carbonitrile A mixture of 2,4-dichloropyrimidine-5-carbonitrile (0.54 g), 3-methylazetidin-3-ol hydrochloride (0.422 g), DIPEA (1.084 mL) and THF (10 mL) was stirred at room temperature overnight. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (0.32 g).

MS: [M+H]$^+$ 225.1.

B) 3-benzyl-1-(trans-4-((5-cyano-4-(3-hydroxy-3-methylazetidin-1-yl)pyrimidin-2-yl) amino) cyclohexyl)-1-(2'-methoxy-5,5'-bipyrimidin-2-yl)urea A mixture of 1-(trans-4-aminocyclohexyl)-3-benzyl-1-(2'-methoxy-5,5'-bipyrimidin-2-yl)urea (64.4 mg), 2-chloro-4-(3-hydroxy-3-methylazetidin-1-yl)pyrimidine-5-carbonitrile (36.7 mg), DIPEA (0.13 mL) and DMF (1 mL) was stirred at 60° C. overnight. The reaction mixture was cooled to room temperature, water was added, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (41.1 mg).

$^1$H NMR (300 MHz, DMSO-d$_6$) δ 1.29-1.50 (5H, m), 1.71-2.24 (6H, m), 3.55-3.88 (1H, m), 3.93-4.18 (7H, m), 4.40 (2H, d, J=5.9 Hz), 4.46-4.61 (1H, m), 5.71 (1H, d, J=2.0 Hz), 7.20-7.45 (5H, m), 7.49-7.65 (1H, m), 8.13-8.30 (1H, m), 8.95-9.01 (4H, m), 9.05-9.18 (1H, m).

Example 617

3-benzyl-1-(trans-4-((4-(3-hydroxy-3-methylazetidin-1-yl)-5-(trifluoromethyl)pyrimidin-2-yl) amino) cyclohexyl)-1-(5-(2-methoxypyrimidin-5-yl)pyrazin-2-yl)urea A) 1-(2-chloro-5-(trifluoromethyl)pyrimidin-4-yl)-3-methylazetidin-3-ol To a mixture of 2,4-dichloro-5-(trifluoromethyl)pyrimidine (843 mg), DIPEA (2.5 mL), DMF (5 mL) and THF (5 mL) was added 3-methylazetidin-3-ol hydrochloride (480 mg) at room temperature. The reaction mixture was stirred at room temperature for 2 hr, water was added, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (722 mg).
MS: [M+H]$^+$ 268.1.

B) 3-benzyl-1-(trans-4-((4-(3-hydroxy-3-methylazetidin-1-yl)-5-(trifluoromethyl)pyrimidin-2-yl)amino) cyclohexyl)-1-(5-(2-methoxypyrimidin-5-yl)pyrazin-2-yl)urea A mixture of 1-(trans-4-aminocyclohexyl)-3-benzyl-1-(5-(2-methoxypyrimidin-5-yl)pyrazin-2-yl)urea (48.4 mg), 1-(2-chloro-5-(trifluoromethyl)pyrimidin-4-yl)-3-methylazetidin-3-ol (32.9 mg), DIPEA (0.097 mL) and DMF (1 mL) was stirred at 60° C. overnight. The reaction mixture was cooled to room temperature, water was added, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (14.8 mg).

$^1$H NMR (300 MHz, DMSO-d$_6$) δ 1.28-1.65 (7H, m), 1.75-2.04 (4H, m), 3.40-3.70 (1H, m), 3.93 (4H, s), 4.01 (3H, s), 4.19-4.34 (3H, m), 5.58-5.66 (1H, m), 7.10-7.38 (7H, m), 8.01-8.11 (1H, m), 8.57 (1H, s), 9.18-9.26 (1H, m), 9.32 (2H, s).

Example 618

3-benzyl-1-(5-(1-methyl-1H-pyrazol-4-yl)pyrazin-2-yl)-1-(trans-4-((4-(oxetan-3-yloxy)-5-(trifluoromethyl)pyrimidin-2-yl) amino) cyclohexyl) urea A mixture of 1-(trans-4-aminocyclohexyl)-3-benzyl-1-(5-(1-methyl-1H-pyrazol-4-yl)pyrazin-2-yl)urea trifluoroacetate (60.5 mg), 2-chloro-4-(oxetan-3-yloxy)-5-(trifluoromethyl)pyrimidine (32.6 mg), DIPEA (0.102 mL) and DMF (1 mL) was stirred at 60° C. overnight. The reaction mixture was cooled to room temperature, water was added, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (18.1 mg).

$^1$H NMR (300 MHz, DMSO-d$_6$) δ 1.32-1.47 (4H, m), 1.76-1.97 (4H, m), 3.34-3.69 (1H, m), 3.92 (3H, s), 4.15-4.29 (3H, m), 4.50-4.63 (2H, m), 4.71-4.91 (2H, m), 5.52-5.64 (1H, m), 6.76-6.85 (1H, m), 7.16-7.35 (5H, m), 7.69-8.03 (1H, m), 8.08-8.15 (1H, m), 8.31 (1H, s), 8.38-8.45 (2H, m), 8.85-8.94 (1H, m).

Example 619 benzyl (trans-4-((5-cyano-4-(3-hydroxy-3-methylazetidin-1-yl)pyrimidin-2-yl)amino)cyclohexyl) (2'-methoxy-5,5'-bipyrimidin-2-yl)carbamate A mixture of benzyl (trans-4-aminocyclohexyl) (2'-methoxy-5,5'-bipyrimidin-2-yl)carbamate (80 mg), 2-chloro-4-(3-hydroxy-3-methylazetidin-1-yl)pyrimidine-5-carbonitrile (50 mg), DIPEA (0.15 mL) and DMF (1.5 mL) was stirred at room temperature overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate to give the title compound (96 mg).

$^1$H NMR (300 MHz, DMSO-d$_6$) δ 1.31-1.46 (5H, m), 1.67 (2H, brs), 1.79-1.99 (4H, m), 3.45-3.73 (1H, m), 3.89-4.20 (8H, m), 5.15 (2H, s), 5.69 (1H, d, J=4.2 Hz), 7.26-7.39 (5H, m), 7.47-7.62 (1H, m), 8.11-8.26 (1H, m), 9.11 (2H, d, J=3.1 Hz), 9.24 (2H, d, J=6.0 Hz).

Example 620

3-benzyl-1-(trans-4-((5-cyano-4-(3-hydroxy-3-methylazetidin-1-yl)pyrimidin-2-yl)amino)cyclohexyl)-1-(5-(2-methoxypyrimidin-5-yl)pyrazin-2-yl)urea A mixture of 1-(trans-4-aminocyclohexyl)-3-benzyl-1-(5-(2-methoxypyrimidin-5-yl)pyrazin-2-yl)urea (66.3 mg), 2-chloro-4-(3-hydroxy-3-methylazetidin-1-yl)pyrimidine-5-carbonitrile (37.8 mg), DIPEA (0.134 mL) and DMF (1 mL) was stirred at 60° C. overnight. The reaction mixture was cooled to room temperature, water was added and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (65.5 mg).

$^1$H NMR (300 MHz, DMSO-d$_6$) δ 1.28-1.64 (7H, m), 1.72-2.00 (4H, m), 3.41-3.72 (1H, m), 3.88-4.15 (7H, m), 4.18-4.33 (3H, m), 5.68 (1H, d, J=8.6 Hz), 7.08-7.36 (6H, m), 7.56 (1H, dd, J=19.0, 7.9 Hz), 8.17 (1H, d, J=19.9 Hz), 8.57 (1H, dd, J=3.9, 1.4 Hz), 9.21 (1H, dd, J=7.1, 1.3 Hz), 9.31 (2H, d, J=4.6 Hz).

Example 623

N-(trans-4-((4-(3-hydroxy-3-methylazetidin-1-yl)-5-(trifluoromethyl)pyrimidin-2-yl)amino)cyclohexyl)-N-(5-(2-methoxypyrimidin-5-yl)pyridin-2-yl)-2-phenoxyacetamide A mixture of N-(trans-4-aminocyclohexyl)-N-(5-(2-methoxypyrimidin-5-yl)pyridin-2-yl)-2-phenoxyacetamide (50 mg), 1-(2-chloro-5-(trifluoromethyl)pyrimidin-4-yl)-3-methylazetidin-3-ol (37 mg), DIPEA (0.1 mL) and DMF (1 mL) was stirred at 70° C. for 4 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate and diisopropyl ether to give the title compound (21.1 mg).
$^1$H NMR (300 MHz, DMSO-$d_6$) δ 1.29-1.48 (7H, m), 1.79-2.03 (4H, m), 3.41-3.64 (1H, m), 3.92 (4H, brs), 3.99 (3H, s), 4.26-4.51 (3H, m), 5.61 (1H, d, J=7.6 Hz), 6.75 (2H, d, J=8.1 Hz), 6.91 (1H, t, J=7.2 Hz), 7.09-7.31 (3H, m), 7.57-7.70 (1H, m), 8.06 (1H, d, J=7.5 Hz), 8.28-8.40 (1H, m), 8.94-9.03 (1H, m), 9.08 (2H, brs).

Example 625

3-benzyl-1-(trans-4-((4-(3-hydroxy-3-methylazetidin-1-yl)-5-(trifluoromethyl)pyrimidin-2-yl)amino)cyclohexyl)-1-(5-(2-methoxypyrimidin-5-yl)pyridin-2-yl)urea A mixture of 1-(trans-4-aminocyclohexyl)-3-benzyl-1-(5-(2-methoxypyrimidin-5-yl)pyridin-2-yl)urea (60 mg), 1-(2-chloro-5-(trifluoromethyl)pyrimidin-4-yl)-3-methylazetidin-3-ol (37.1 mg), DIPEA (71.7 mg) and DMF (2 mL) was stirred at room temperature for 18 hr. The reaction mixture was purified by silica gel column chromatography (NH, ethyl acetate/hexane) and HPLC (L-Column 2 ODS, mobile phase: water/acetonitrile (5 mM ammonium bicarbonate-based)) to give the title compound (11.5 mg).
$^1$H NMR (300 MHz, DMSO-$d_6$) δ 1.32-1.44 (5H, m), 1.45-1.61 (2H, m), 1.75-1.89 (3H, m), 1.91-2.00 (1H, m), 3.42-3.66 (1H, m), 3.90-3.93 (4H, m), 3.98 (3H, s), 4.17-4.26 (3H, m), 5.62 (1H, d, J=5.38 Hz), 6.80 (1H, s), 7.13-7.35 (7H, m), 8.07 (1H, d, J=13.88 Hz), 8.20 (1H, brs), 8.90 (1H, brs), 9.05 (2H, s).

Example 626

3-benzyl-1-(trans-4-((5-cyano-4-(3-hydroxy-3-methylazetidin-1-yl)pyrimidin-2-yl)amino)cyclohexyl)-1-(5-(2-methoxypyrimidin-5-yl)pyridin-2-yl)urea A mixture of 1-(trans-4-aminocyclohexyl)-3-benzyl-1-(5-(2-methoxypyrimidin-5-yl)pyridin-2-yl)urea (60 mg), 2-chloro-4-(3-hydroxy-3-methylazetidin-1-yl)pyrimidine-5-carbonitrile (31.2 mg), DIPEA (71.7 mg) and DMF (2 mL) was stirred at room temperature for 18 hr. The reaction mixture was purified by silica gel column chromatography (NH, ethyl acetate/hexane) to give the title compound (13.53 mg).
$^1$H NMR (300 MHz, DMSO-$d_6$) δ 1.23-1.61 (7H, m), 1.72-1.86 (3H, m), 1.86-1.98 (1H, m), 3.37-3.67 (1H, m), 3.91-4.27 (10H, m), 5.68 (1H, d, J=8.69 Hz), 6.75-6.83 (1H, m), 7.17-7.34 (6H, m), 7.54 (1H, dd, J=18.65, 7.98 Hz), 8.13-8.24 (2H, m), 8.89 (1H, dd, J=6.80, 2.27 Hz), 9.04 (2H, d, J=3.87 Hz).

Example 627

N-(5-(2-methoxypyrimidin-5-yl)pyridin-2-yl)-N-(trans-4-((4-(oxetan-3-yloxy)-5-(trifluoromethyl)pyrimidin-2-yl)amino)cyclohexyl)-2-phenoxyacetamide A mixture of N-(trans-4-aminocyclohexyl)-N-(5-(2-methoxypyrimidin-5-yl)pyridin-2-yl)-2-phenoxyacetamide (100 mg), 2-chloro-4-(oxetan-3-yloxy)-5-(trifluoromethyl)pyrimidine (70.5 mg), DIPEA (0.2 mL) and DMF (2 mL) was stirred at 70° C. for 4 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate and diisopropyl ether to give the title compound (84.9 mg).
$^1$H NMR (300 MHz, DMSO-$d_6$) δ 1.29-1.56 (4H, m), 1.77-1.98 (4H, m), 3.36-3.68 (1H, m), 3.99 (3H, s), 4.26-4.48 (3H, m), 4.49-4.63 (2H, m), 4.72-4.91 (2H, m), 5.52-5.64 (1H, m), 6.75 (2H, d, J=8.1 Hz), 6.91 (1H, t, J=7.3 Hz), 7.24 (2H, t, J=7.9 Hz), 7.57-7.69 (1H, m), 7.72-8.04 (1H, m), 8.28-8.42 (2H, m), 8.99 (1H, dd, J=10.5, 2.2 Hz), 9.06-9.11 (2H, m).

Example 628 pyridin-2-ylmethyl (trans-4-((4-(3-hydroxy-3-methylazetidin-1-yl)-5-(trifluoromethyl)pyrimidin-2-yl)amino)cyclohexyl) (5-(2-methoxypyrimidin-5-yl)pyridin-2-yl)carbamate A) pyridin-2-ylmethyl (trans-4-aminocyclohexyl) (5-(2-methoxypyrimidin-5-yl)pyridin-2-yl)carbamate To a mixture of pyridin-2-ylmethyl (trans-4-((tert-butoxycarbonyl)amino)cyclohexyl) (5-(2-methoxypyrimidin-5-yl)pyridin-2-yl)carbamate (655 mg) and acetonitrile (3 mL) was added TFA (1.5 mL) at room temperature, and the mixture was stirred at room temperature for 1 hr. The solvent was evaporated under reduced pressure, and the residue was purified by silica gel column chromatography (NH, ethyl acetate/methanol) and crystallized from ethyl acetate and diisopropyl ether to give the title compound (487 mg).
MS: [M+H]$^+$ 435.2.

B) pyridin-2-ylmethyl (trans-4-((4-(3-hydroxy-3-methylazetidin-1-yl)-5-(trifluoromethyl)pyrimidin-2-yl) amino) cyclohexyl) (5-(2-methoxypyrimidin-5-yl)pyridin-2-yl)carbamate A mixture of pyridin-2-ylmethyl (trans-4-aminocyclohexyl) (5-(2-methoxypyrimidin-5-yl)pyridin-2-yl)carbamate (100 mg), 1-(2-chloro-5-(trifluoromethyl)pyrimidin-4-yl)-3-methylazetidin-3-ol (73.9 mg), DIPEA (0.2 mL) and DMF (2 mL) was stirred 70° C. for 4 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate and diisopropyl ether to give the title compound (86.6 mg).

¹H NMR (300 MHz, DMSO-$d_6$) δ 1.28-1.47 (5H, m), 1.50-1.72 (2H, m), 1.80-2.06 (4H, m), 3.42-3.70 (1H, m), 3.93 (4H, s), 3.97-4.14 (4H, m), 5.17 (2H, s), 5.62 (1H, brs), 7.08-7.36 (3H, m), 7.48-7.60 (1H, m), 7.80 (1H, t, J=6.9 Hz), 8.07 (1H, d, J=15.0 Hz), 8.19-8.30 (1H, m), 8.53 (1H, d, J=4.2 Hz), 8.85-8.96 (1H, m), 9.06 (2H, s).

Example 629 pyridin-2-ylmethyl (5-(2-methoxypyrimidin-5-yl) pyridin-2-yl) (trans-4-((4-(oxetan-3-yloxy)-5-(trifluoromethyl)pyrimidin-2-yl)amino)cyclohexyl)carbamate A mixture of pyridin-2-ylmethyl (trans-4-aminocyclohexyl) (5-(2-methoxypyrimidin-5-yl)pyridin-2-yl)carbamate (100 mg), 2-chloro-4-(oxetan-3-yloxy)-5-(trifluoromethyl)pyrimidine (70.3 mg), DIPEA (0.2 mL) and DMF (2 mL) was stirred at 70° C. for 4 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) and crystallized from ethyl acetate and diisopropyl ether to give the title compound (122 mg).

¹H NMR (300 MHz, DMSO-$d_6$) δ 1.28-1.50 (2H, m), 1.51-1.77 (2H, m), 1.85-2.02 (4H, m), 3.38-3.70 (1H, m), 3.98 (3H, s), 4.04-4.22 (1H, m), 4.49-4.64 (2H, m), 4.73-4.92 (2H, m), 5.17 (2H, s), 5.52-5.65 (1H, m), 7.22-7.36 (2H, m), 7.50-7.61 (1H, m), 7.72-8.04 (2H, m), 8.25 (1H, td, J=8.1, 2.5 Hz), 8.34 (1H, d, J=6.4 Hz), 8.53 (1H, d, J=4.5 Hz), 8.91 (1H, dd, J=8.1, 2.5 Hz), 9.01-9.10 (2H, m).

Example 630

1-(trans-4-((4-(3-hydroxy-3-methylazetidin-1-yl)-5-(trifluoromethyl)pyrimidin-2-yl) amino) cyclohexyl)-1-(5-(2-methoxypyrimidin-5-yl)pyridin-2-yl)-3-(pyridin-2-ylmethyl)urea A mixture of 1-(trans-4-aminocyclohexyl)-1-(5-(2-methoxypyrimidin-5-yl)pyridin-2-yl)-3-(pyridin-2-ylmethyl)urea (114 mg), 1-(2-chloro-5-(trifluoromethyl)pyrimidin-4-yl)-3-methylazetidin-3-ol (84.2 mg), DIPEA (0.183 mL) and DMF (2 mL) was stirred at 70° C. overnight. The reaction mixture was purified by silica gel column chromatography (NH, ethyl acetate/hexane/methanol) to give the title compound (77 mg).

¹H NMR (300 MHz, DMSO-$d_6$) δ 1.33-1.44 (5H, m), 1.46-1.63 (2H, m), 1.84 (3H, brs), 1.89-2.02 (1H, m), 3.40-3.67 (1H, m), 3.93 (4H, s), 3.99 (3H, s), 4.23 (1H, brs), 4.31 (2H, d, J=5.38 Hz), 5.62 (1H, d, J=4.15 Hz), 6.85 (1H, t, J=5.74 Hz), 7.03-7.31 (3H, m), 7.43 (1H, d, J=4.36 Hz), 7.76 (1H, t, J=7.78 Hz), 8.07 (1H, d, J=14.35 Hz), 8.24 (1H, brs), 8.45 (1H, d, J=4.76 Hz), 8.93 (1H, brs), 9.06 (2H, s).

Example 631

1-(trans-4-((4-(3-hydroxy-3-methylazetidin-1-yl)-5-(trifluoromethyl)pyrimidin-2-yl) amino) cyclohexyl)-1-(5-(2-methoxypyrimidin-5-yl)pyridin-2-yl)-3-((1R)-1-phenylethyl)urea A) tert-butyl (trans-4-((5-(2-methoxypyrimidin-5-yl) pyridin-2-yl) (((1R)-1-phenylethyl)carbamoyl) amino)cyclohexyl)carbamate A mixture of (1R)-1-phenylethaneamine (455 mg), 4-nitrophenyl (trans-4-((tert-butoxycarbonyl)amino)cyclohexyl) (5-(2-methoxypyrimidin-5-yl)pyridin-2-yl)carbamate (706 mg) and NMP (25 mL) was stirred at 70° C. for 18 hr and at 100° C. overnight. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (617 mg).

MS: [M+H]⁺ 547.3.

B) 1-(trans-4-aminocyclohexyl)-1-(5-(2-methoxypyrimidin-5-yl)pyridin-2-yl)-3-((1R)-1-phenylethyl) urea A mixture of TFA (5 mL) and tert-butyl (trans-4-((5-(2-methoxypyrimidin-5-yl)pyridin-2-yl) (((1R)-1-phenylethyl)carbamoyl)amino)cyclohexyl)carbamate (617 mg) was stirred at room temperature for 2 hr. The solvent was evaporated under reduced pressure, and the residue was purified by silica gel column chromatography (NH, ethyl acetate/methanol) to give the title compound (480 mg).

MS: [M+H]⁺ 447.2.

C) 1-(trans-4-((4-(3-hydroxy-3-methylazetidin-1-yl)-5-(trifluoromethyl)pyrimidin-2-yl) amino) cyclohexyl)-1-(5-(2-methoxypyrimidin-5-yl)pyridin-2-yl)-3-((1R)-1-phenylethyl)urea A mixture of 1-(trans-4-aminocyclohexyl)-1-(5-(2-methoxypyrimidin-5-yl)pyridin-2-yl)-3-((1R)-1-phenylethyl)urea (116 mg), 1-(2-chloro-5-(trifluoromethyl)pyrimidin-4-yl)-3-methylazetidin-3-ol (76 mg), DIPEA (0.181 mL) and DMF (2 mL) was stirred at 70° C. for 18 hr. The reaction mixture was purified by silica gel column chromatography (NH, ethyl acetate/hexane) and HPLC (water/acetonitrile (5 mM ammonium bicarbonate-based)) to give the title compound (60.3 mg).

¹H NMR (300 MHz, DMSO-$d_6$) δ 1.27-1.44 (8H, m), 1.49-1.71 (2H, m), 1.71-2.00 (4H, m), 3.40-3.69 (1H, m), 3.93 (4H, s), 3.98 (3H, s), 4.22 (1H, brs), 4.91 (1H, t, J=7.55 Hz), 5.62 (1H, brs) 6.87-7.04 (1H, m), 7.08-7.33 (7H, m), 8.03-8.20 (2H, m), 8.86 (1H, d, J=2.36 Hz), 9.04 (2H, s).

Example 633

1-(trans-4-((4-(3-hydroxy-3-methylazetidin-1-yl)-5-(trifluoromethyl)pyrimidin-2-yl)amino)cyclohexyl)-1-(5-(2-methoxypyrimidin-5-yl)pyridin-2-yl)-3-((1S)-1-phenylethyl)urea A) tert-butyl (trans-4-((5-(2-methoxypyrimidin-5-yl) pyridin-2-yl) (((1S)-1-phenylethyl)carbamoyl) amino)cyclohexyl)carbamate A mixture of (1S)-1-phenylethaneamine (455 mg), 4-nitrophenyl (trans-4-((tert-butoxycarbonyl)amino)cyclohexyl)

(5-(2-methoxypyrimidin-5-yl)pyridin-2-yl)carbamate (706 mg) and NMP (25 mL) was stirred at 70° C. for 18 hr and at 100° C. overnight. To the reaction mixture was added water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (617 mg).

MS: [M+H]$^+$ 547.3.

B) 1-(trans-4-aminocyclohexyl)-1-(5-(2-methoxypyrimidin-5-yl)pyridin-2-yl)-3-((1S)-1-phenylethyl) urea A mixture of TFA (5 mL) and tert-butyl (trans-4-((5-(2-methoxypyrimidin-5-yl)pyridin-2-yl) (((1S)-1-phenylethyl)carbamoyl)amino)cyclohexyl)carbamate (617 mg) was stirred at room temperature for 2 hr. The solvent was evaporated under reduced pressure, and the residue was purified by silica gel column chromatography (NH, ethyl acetate/methanol) to give the title compound (484 mg).

MS: [M+H]$^+$ 447.2.

C) 1-(trans-4-((4-(3-hydroxy-3-methylazetidin-1-yl)-5-(trifluoromethyl)pyrimidin-2-yl)amino)cyclohexyl)-1-(5-(2-methoxypyrimidin-5-yl)pyridin-2-yl)-3-((1S)-1-phenylethyl)urea A mixture of 1-(trans-4-aminocyclohexyl)-1-(5-(2-methoxypyrimidin-5-yl)pyridin-2-yl)-3-((1S)-1-phenylethyl)urea (118 mg), 1-(2-chloro-5-(trifluoromethyl)pyrimidin-4-yl)-3-methylazetidin-3-ol (78 mg), DIPEA (0.185 mL) and DMF (2 mL) was stirred at room temperature for 18 hr. The reaction mixture was purified by silica gel column chromatography (NH, ethyl acetate/hexane) and HPLC (L-Column 2 ODS, mobile phase: water/acetonitrile (5 mM ammonium bicarbonate-based)) to give the title compound (50.3 mg).

$^1$H NMR (300 MHz, DMSO-d$_6$) δ 1.28-1.43 (8H, m), 1.51-2.02 (6H, m), 3.41-3.66 (1H, m), 3.93 (4H, s), 3.98 (3H, s), 4.23 (1H, brs), 4.86-4.96 (1H, m), 5.62 (1H, brs), 6.87-7.02 (1H, m), 7.11-7.34 (7H, m), 8.07 (1H, d, J=16.24 Hz), 8.17 (1H, d, J=4.38 Hz), 8.86 (1H, s), 9.04 (2H, s).

Example 693

1-(trans-4-((4-(4-chloro-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyridin-2-yl)urea A) tert-butyl (trans-4-((5-(2-methoxypyrimidin-5-yl)pyridin-2-yl)amino)cyclohexyl)carbamate A mixture of tert-butyl (trans-4-((5-bromopyridin-2-yl)amino)cyclohexyl)carbamate (5.0 g), (2-methoxypyrimidin-5-yl)boronic acid (2.5 g), PdCl$_2$(dppf) (0.494 g), 2 M sodium carbonate aqueous solution (13.5 mL) and DME (52 mL) was stirred with heating under reflux under a nitrogen atmosphere for 2.5 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by isopropanol/ethyl acetate to give the title compound (3.23 g).

MS: [M+H]$^+$ 400.2.

B) tert-butyl (trans-4-(3-(2,2-difluoroethyl)-1-(5-(2-methoxypyrimidin-5-yl)pyridin-2-yl)ureido)cyclohexyl)carbamate A mixture of tert-butyl (trans-4-((5-(2-methoxypyrimidin-5-yl)pyridin-2-yl)amino)cyclohexyl)carbamate (1.36 g), triphosgene (505 mg), DIPEA (1.3 g) and THF (25 mL) was stirred at 70° C. for 30 min. 2,2-difluoroethane-1-amine (1.4 g) was added to the reaction mixture, and the mixture was stirred at 70° C. for 2 hr. The reaction mixture was added to water, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/hexane) to give the title compound (1.42 g).

MS: [M+H]$^+$ 507.3.

C) 1-(trans-4-aminocyclohexyl)-3-(2,2-difluoroethyl)-1-(5-(2-methoxypyrimidin-5-yl)pyridin-2-yl) urea A mixture of tert-butyl (trans-4-(3-(2,2-difluoroethyl)-1-(5-(2-methoxypyrimidin-5-yl)pyridin-2-yl)ureido)cyclohexyl)carbamate (1.429 g) and TFA (4.3 mL) was stirred at room temperature for 1 hr. The reaction mixture was concentrated under reduced pressure, and the residue was purified by silica gel column chromatography (NH, ethyl acetate/hexane/methanol) to give the title compound (1.07 g).

MS: [M+H]$^+$ 407.3.

D) 4-chloro-2-(methylthio)-5-(trifluoromethyl)pyrimidine

To a solution of 2,4-dichloro-5-(trifluoromethyl)pyrimidine (7.52 g) in THF (110 mL) was added dropwise 2 M zinc chloride•2-methyltetrahydrofuran solution (20.8 mL) at 0° C., and the mixture was stirred while allowing to return to room temperature for 2 hr. To the reaction mixture was added sodium methanethiolate (2.7 g), and the mixture was stirred at room temperature for 16 hr. To the reaction mixture was added 2M hydrochloric acid at 0° C., and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (5.25 g).

MS: [M+H]$^+$ 229.0.

E) 2-(methylthio)-4-(1-(tetrahydro-2H-pyran-2-yl)-1H-pyrazol-5-yl)-5-(trifluoromethyl)pyrimidine A mixture of 4-chloro-2-(methylthio)-5-(trifluoromethyl)-pyrimidine (7.44 g), 1-(tetrahydro-2H-pyran-2-yl)-5-(4,4,5,5-tetramethyl-1,3,2-dioxaborolan-2-yl)-1H-pyrazole (10.9 g), PdCl$_2$(Amphos)$_2$ (1.6 g), 3 M sodium carbonate (21 mL) and DME (84 mL) was stirred under a nitrogen atmosphere at 100° C. for 1.5 hr. The mixture was added to water at room temperature, and the mixture was extracted with ethyl acetate. The organic layer was separated, washed with saturated brine, and dried over anhydrous magnesium sulfate. The solvent was evaporated under reduced pressure.

The residue was purified by silica gel column chromatography (ethyl acetate/hexane) to give the title compound (8.6 g).

$^1$H NMR (300 MHz, DMSO-d$_6$) 51.40-1.52 (2H, m), 1.54-1.66 (1H, m), 1.86-2.00 (2H, m), 2.21-2.35 (1H, m), 2.60 (3H, s), 3.33-3.41 (1H, m), 3.62 (1H, dt, J=11.1, 3.7 Hz), 5.67 (1H, dd, J=8.3, 2.7 Hz), 6.65 (1H, dd, J=2.0, 1.0 Hz), 7.67 (1H, d, J=2.0 Hz), 9.12 (1H, s).

F) 2-(methylthio)-4-(1H-pyrazol-3-yl)-5-(trifluoromethyl)pyrimidine

A mixture of 2-(methylthio)-4-(1-(tetrahydro-2H-pyran-2-yl)-1H-pyrazol-5-yl)-5-(trifluoromethyl)pyrimidine (7.03 g), 6 M aqueous hydrochloric acid solution (10 mL) and MeOH (70 mL) was stirred at room temperature for 1 hr. The reaction mixture was stirred at 0° C. for 30 min, and the precipitated solid was collected by filtration and washed with cold methanol to give the title compound (4.55 g).
MS: [M+H]$^+$ 261.1.

G) 2-chloro-4-(4-chloro-1H-pyrazol-3-yl)-5-(trifluoromethyl)pyrimidine

To a solution of 2-(methylthio)-4-(1H-pyrazol-3-yl)-5-(trifluoromethyl)pyrimidine (5.24 g) in acetonitrile (150 mL) was added sulfuryl chloride (8.1 mL) at 0° C., and the mixture was stirred at room temperature for 1.5 hr. The reaction mixture was added to saturated aqueous sodium hydrogen carbonate solution at room temperature, and the mixture was extracted with ethyl acetate. The organic layer was separated, washed with saturated aqueous sodium hydrogen carbonate solution and saturated brine, and dried over anhydrous magnesium sulfate. The solvent was evaporated under reduced pressure. The residue was purified by silica gel column chromatography (ethyl acetate/hexane) to give the title compound (4.3 g).
MS: [M+H]$^+$ 283.0.

H) 2-chloro-4-(4-chloro-1-(tetrahydro-2H-pyran-2-yl)-1H-pyrazol-3-yl)-5-(trifluoromethyl)pyrimidine A mixture of 2-chloro-4-(4-chloro-1H-pyrazol-3-yl)-5-(trifluoromethyl)pyrimidine (1.00 g), 3,4-dihydro-2H-pyran (0.48 mL), TFA (0.27 mL) and toluene (20 mL) was stirred at 80° C. for 30 min. The reaction mixture was concentrated under reduced pressure, and the residue was purified by silica gel column chromatography (ethyl acetate/hexane) to give the title compound (1.295 g).
MS: [M+H]$^+$ 367.0.

I) 1-(trans-4-((4-(4-chloro-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyridin-2-yl)urea A mixture of 1-(trans-4-aminocyclohexyl)-3-(2,2-difluoroethyl)-1-(5-(2-methoxypyrimidin-5-yl)pyridin-2-yl)urea (70 mg), 2-chloro-4-(4-chloro-1-(tetrahydro-2H-pyran-2-yl)-1H-pyrazol-3-yl)-5-(trifluoromethyl)pyrimidine (97 mg), DIPEA (0.15 mL) and acetonitrile (2 mL) was stirred at 80° C. for 4 hr. The reaction mixture was concentrated under reduced pressure. The residue was dissolved in MeOH (2 mL), and 6 M aqueous hydrochloric acid solution (0.20 mL) was added at room temperature. The mixture was stirred at 60° C. for 2 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/hexane), and treated with ethyl acetate and hexane to give the title compound (59 mg).

$^1$H NMR (300 MHz, DMSO-d$_6$) δ 1.30-1.68 (4H, m), 1.73-2.08 (4H, m), 3.25-3.50 (2H, m), 3.51-3.79 (1H, m), 3.92-4.05 (3H, m), 4.12-4.33 (1H, m), 5.71-6.24 (1H, m), 6.46-6.69 (1H, m), 7.23-7.43 (1H, m), 8.00-8.18 (2H, m), 8.18-8.28 (1H, m), 8.58-8.69 (1H, m), 8.86-8.94 (1H, m), 9.01-9.10 (2H, m), 13.33-13.66 (1H, m).

Example 729

1-(trans-4-((4-(4-chloro-1H-pyrazol-3-yl)-5-(trifluoromethyl)pyrimidin-2-yl) amino) cyclohexyl)-1-(5-(2-methoxypyrimidin-5-yl)pyridin-2-yl)-3-(2,2,2-trifluoroethyl)urea A) tert-butyl (trans-4-((chlorocarbonyl) (5-(2-methoxypyrimidin-5-yl)pyridin-2-yl)amino)cyclohexyl)carbamate To a mixture of tert-butyl (trans-4-((5-(2-methoxypyrimidin-5-yl)pyridin-2-yl)amino)cyclohexyl)carbamate (1.6 g) and DIPEA (2.1 mL) in THF (50 mL) was added triphosgene (594 mg) at room temperature. The reaction mixture was stirred at 60° C. for 3 hr. To the reaction mixture was added saturated aqueous sodium hydrogen carbonate solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (1.75 g).
MS: [M+H-tBu]+406.1.

B) tert-butyl (trans-4-(1-(5-(2-methoxypyrimidin-5-yl)pyridin-2-yl)-3-(2,2,2-trifluoroethyl)ureido)cyclohexyl)carbamate A mixture of tert-butyl (trans-4-((chlorocarbonyl) (5-(2-methoxypyrimidin-5-yl)pyridin-2-yl)amino)cyclohexyl)carbamate (100 mg), 2,2,2-trifluoroethane-1-amine (64 mg), TEA (0.091 mL) and THF (2 mL) was stirred under microwave irradiation at 70° C. for 2 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/hexane) to give the title compound (112 mg).
MS: [M+H]$^+$ 525.3.

C) 1-(trans-4-((4-(4-chloro-1H-pyrazol-3-yl)-5-(trifluoromethyl)pyrimidin-2-yl) amino) cyclohexyl)-1-(5-(2-methoxypyrimidin-5-yl)pyridin-2-yl)-3-(2,2,2-trifluoroethyl)urea tert-Butyl (trans-4-(1-(5-(2-methoxypyrimidin-5-yl)pyridin-2-yl)-3-(2,2,2-trifluoroethyl)ureido)cyclohexyl)carbamate (100 mg) was dissolved in TFA (1 mL) at room temperature. After stirring at room temperature for 30 min, the reaction mixture was concentrated under reduced pressure. The residue was dissolved in acetonitrile (3 mL), and 2-chloro-4-(4-chloro-1-(tetrahydro-2H-pyran-2-yl)-1H-pyrazol-3-yl)-5-(trifluoromethyl)pyrimidine (108 mg) and DIPEA (0.33 mL) were added at room temperature. The mixture was stirred at 80° C. for 4 hr. The reaction mixture was concentrated under reduced pressure. The residue was dissolved in MeOH (2 mL), and 6 M aqueous hydrochloric acid solution (0.20 mL) was added at room temperature. The mixture was stirred at 60° C. for 2 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/hexane), and treated with ethyl acetate and hexane to give the title compound (55 mg).

$^1$H NMR (300 MHz, DMSO-d$_6$) δ 1.31-1.65 (4H, m), 1.71-2.07 (4H, m), 3.52-3.89 (3H, m), 3.92-4.05 (3H, m), 4.14-4.33 (1H, m), 6.68-6.85 (1H, m), 7.24-7.38 (1H, m), 8.01-8.18 (2H, m), 8.19-8.31 (1H, m), 8.57-8.69 (1H, m), 8.86-8.98 (1H, m), 9.00-9.12 (2H, m), 13.35-13.63 (1H, m).

Example 740

1-(trans-4-((4-(4-chloro-1H-pyrazol-3-yl)-5-(trifluoromethyl)pyrimidin-2-yl)amino)cyclohexyl)-3-(2,2-difluoropropyl)-1-(5-(2-methoxypyrimidin-5-yl)pyrazin-2-yl)urea A) tert-butyl (trans-4-((chlorocarbonyl) (5-(2-methoxypyrimidin-5-yl)pyrazin-2-yl)amino)cyclohexyl)carbamate To a mixture of tert-butyl (trans-4-((5-(2-methoxypyrimidin-5-yl)pyrazin-2-yl)amino)cyclohexyl)carbamate (3.0 g) and DIPEA (2.9 g) in THF (50 mL) was added triphosgene (1.1 g) at room temperature. The reaction mixture was stirred at 60° C. for 1 hr. To the reaction mixture were added DIPEA (2.9 g) and triphosgene (778 mg), and the mixture was stirred at 75° C. for 1 hr. The reaction mixture was added to ice water, saturated aqueous sodium hydrogen carbonate solution was added, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (3.1 g).

MS: [M+H-tBu]+407.2.

B) tert-butyl (trans-4-(3-(2,2-difluoropropyl)-1-(5-(2-methoxypyrimidin-5-yl)pyrazin-2-yl)ureido)cyclohexyl)carbamate To a mixture of tert-butyl (trans-4-((chlorocarbonyl) (5-(2-methoxypyrimidin-5-yl)pyrazin-2-yl)amino)cyclohexyl) carbamate (400 mg) and 2,2-difluoropropane-1-amine hydrochloride (182 mg) in THF (5 mL) was added DIPEA (391 mg) at room temperature. The reaction mixture was stirred at 75° C. for 1 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure, and the obtained solid was washed with diisopropyl ether to give the title compound (370 mg).

MS: [M+H]$^+$ 522.3.

C) 1-(trans-4-aminocyclohexyl)-3-(2,2-difluoropropyl)-1-(5-(2-methoxypyrimidin-5-yl)pyrazin-2-yl)urea A mixture of tert-butyl (trans-4-(3-(2,2-difluoropropyl)-1-(5-(2-methoxypyrimidin-5-yl)pyrazin-2-yl)ureido)cyclohexyl)carbamate (388 mg) and TFA (5 mL) was stirred at room temperature overnight. The solvent of the reaction mixture was evaporated under reduced pressure, and the residue was purified by silica gel column chromatography (NH, ethyl acetate/hexane/methanol) to give the title compound (300 mg).

MS: [M+H]$^+$ 422.3.

D) 1-(trans-4-((4-(4-chloro-1H-pyrazol-3-yl)-5-(trifluoromethyl)pyrimidin-2-yl)amino)cyclohexyl)-3-(2, 2-difluoropropyl)-1-(5-(2-methoxypyrimidin-5-yl) pyrazin-2-yl)urea To a solution of 1-(trans-4-aminocyclohexyl)-3-(2,2-difluoropropyl)-1-(5-(2-methoxypyrimidin-5-yl)pyrazin-2-yl) urea (50 mg) and 2-chloro-4-(4-chloro-1H-pyrazol-3-yl)-5-(trifluoromethyl)pyrimidine (50 mg) in DMF (2.0 mL) was added DIPEA (0.06 mL) at room temperature. The reaction mixture was stirred at 70° C. overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by HPLC (YMCTriartC18, mobile phase: water/acetonitrile (10 mM ammonium bicarbonate-based)) to give the title compound (22 mg).

$^1$H NMR (300 MHz, DMSO-d$_6$) δ 1.33-1.68 (7H, m), 1.74-1.88 (2H, m), 1.90-2.04 (2H, m), 3.38-3.57 (2H, m), 3.57-3.81 (1H, m), 4.01 (3H, d, J=2.3 Hz), 4.21-4.37 (1H, m), 6.98-7.11 (1H, m), 7.97-8.26 (2H, m), 8.49-8.58 (1H, m), 8.59-8.70 (1H, m), 9.21 (1H, dd, J=4.9, 1.1 Hz), 9.32 (2H, d, J=6.0 Hz), 13.48 (1H, br d, J=4.2 Hz).

Example 742

1-(trans-4-((4-(4-chloro-1H-pyrazol-3-yl)-5-(trifluoromethyl)pyrimidin-2-yl)amino)cyclohexyl)-3-((1-fluorocyclopropyl)methyl)-1-(5-(2-methoxypyrimidin-5-yl)pyrazin-2-yl)urea A) tert-butyl (trans-4-(3-((1-fluorocyclopropyl) methyl)-1-(5-(2-methoxypyrimidin-5-yl)pyrazin-2-yl) ureido) cyclohexyl) carbamate To a mixture of tert-butyl (trans-4-((chlorocarbonyl) (5-(2-methoxypyrimidin-5-yl)pyrazin-2-yl)amino)cyclohexyl) carbamate (50 mg) and (1-fluorocyclopropyl)methanamine hydrochloride (16 mg) in THF (2.0 mL) was added DIPEA (0.056 mL) at room temperature, and the reaction mixture was stirred at room temperature for 2 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (48 mg).
MS: [M+H]$^+$ 516.3.

B) 1-(trans-4-((4-(4-chloro-1H-pyrazol-3-yl)-5-(trifluoromethyl)pyrimidin-2-yl)amino)cyclohexyl)-3-((1-fluorocyclopropyl)methyl)-1-(5-(2-methoxypyrimidin-5-yl)pyrazin-2-yl)urea tert-Butyl (trans-4-(3-((1-fluorocyclopropyl)methyl)-1-(5-(2-methoxypyrimidin-5-yl)pyrazin-2-yl)ureido)cyclohexyl)carbamate (48 mg) was dissolved in TFA (3.0 mL) at room temperature, and the mixture was stirred at room temperature for 1 hr. The solvent of the reaction mixture was evaporated under reduced pressure, and the residue was dissolved in DMF (3.0 mL), and 2-chloro-4-(4-chloro-1H-pyrazol-3-yl)-5-(trifluoromethyl)pyrimidine (40 mg) and DIPEA (0.32 mL) were added at room temperature. The reaction mixture was stirred at 70° C. overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane/methanol) and HPLC (YMCTriartC18, mobile phase: water/acetonitrile (10 mM ammonium bicarbonate-based)) to give the title compound (12 mg).
$^1$H NMR (300 MHz, DMSO-d$_6$) δ 0.62-0.80 (2H, m), 0.85-1.04 (2H, m), 1.33-1.72 (4H, m), 1.72-1.87 (2H, m), 1.89-2.05 (2H, m), 3.41-3.56 (2H, m), 3.58-3.80 (1H, m), 4.01 (3H, d, J=2.3 Hz), 4.20-4.39 (1H, m), 6.98-7.15 (1H, m), 7.98-8.23 (2H, m), 8.48-8.56 (1H, m), 8.59-8.71 (1H, m), 9.13-9.23 (1H, m), 9.30 (2H, d, J=6.0 Hz), 13.48 (1H, br s).

Example 743

1-(trans-4-((4-(4-chloro-1H-pyrazol-3-yl)-5-(trifluoromethyl)pyrimidin-2-yl)amino)cyclohexyl)-1-(5-(2-methoxypyrimidin-5-yl)pyrazin-2-yl)-3-(2,2,2-trifluoroethyl)urea A) tert-butyl (trans-4-(1-(5-(2-methoxypyrimidin-5-yl)pyrazin-2-yl)-3-(2,2,2-trifluoroethyl)ureido)cyclohexyl)carbamate To a mixture of tert-butyl (trans-4-((chlorocarbonyl) (5-(2-methoxypyrimidin-5-yl)pyrazin-2-yl)amino)cyclohexyl) carbamate (394 mg) and DIPEA (385 mg) in THF (5.0 mL) was added 2,2,2-trifluoroethane-1-amine hydrochloride (184 mg) at room temperature, and the reaction mixture was stirred at 70° C. for 1 hr. The reaction mixture was added to ice water, and the mixture was extracted with ethyl acetate. The organic layer was separated, washed with water and saturated brine, and dried over anhydrous sodium sulfate. The solvent was evaporated under reduced pressure. The precipitated solid was collected by filtration, and the obtained solid was washed with diisopropyl ether to give the title compound (395 mg).
MS: [M+H]$^+$ 526.4.

B) 1-(trans-4-aminocyclohexyl)-1-(5-(2-methoxypyrimidin-5-yl)pyrazin-2-yl)-3-(2,2,2-trifluoroethyl) urea A mixture of tert-butyl (trans-4-(1-(5-(2-methoxypyrimidin-5-yl)pyrazin-2-yl)-3-(2,2,2-trifluoroethyl)ureido)cyclohexyl)carbamate (388 mg) and TFA (4.0 mL) was stirred at room temperature overnight. The solvent of the reaction mixture was evaporated under reduced pressure, and the residue was purified by silica gel column chromatography (NH, ethyl acetate/hexane/methanol) to give the title compound (320 mg).
MS: [M+H]$^+$ 426.2.

C) 1-(trans-4-((4-(4-chloro-1H-pyrazol-3-yl)-5-(trifluoromethyl)pyrimidin-2-yl)amino)cyclohexyl)-1-(5-(2-methoxypyrimidin-5-yl)pyrazin-2-yl)-3-(2,2,2-trifluoroethyl)urea A mixture of 1-(trans-4-aminocyclohexyl)-1-(5-(2-methoxypyrimidin-5-yl)pyrazin-2-yl)-3-(2,2,2-trifluoroethyl)urea (40 mg), 2-chloro-4-(4-chloro-1H-pyrazol-3-yl)-5-(trifluoromethyl)pyrimidine (40 mg), DIPEA (0.03 mL) and DMF (1 mL) was stirred at 70° C. for 3 hr. The reaction mixture was concentrated under reduced pressure, and the residue was purified by silica gel column chromatography (ethyl acetate/hexane) to give the title compound (12 mg).
$^1$H NMR (300 MHz, DMSO-d$_6$) δ 1.35-1.63 (4H, m), 1.77-2.06 (4H, m), 3.65 (1H, br s), 3.73-3.91 (2H, m), 4.02 (3H, d, J=2.3 Hz), 4.18-4.35 (1H, m), 7.07-7.19 (1H, m), 8.03-8.20 (2H, m), 8.55 (1H, dd, J=5.7, 1.1 Hz), 8.59-8.70 (1H, m), 9.25 (1H, dd, J=5.1, 1.3 Hz), 9.33 (2H, d, J=6.0 Hz), 13.48 (1H, br s).

Example 744

1-(trans-4-((4-(4-chloro-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl) pyrazin-2-yl)urea A) tert-butyl (trans-4-(3-(2,2-difluoroethyl)-1-(5-(2-methoxypyrimidin-5-yl)pyrazin-2-yl)ureido)cyclohexyl)carbamate To a mixture of tert-butyl (trans-4-((chlorocarbonyl) (5-(2-methoxypyrimidin-5-yl)pyrazin-2-yl)amino)cyclohexyl) carbamate (400 mg) and 2,2-difluoroethane-1-amine (112 mg) in THF (5.0 mL) was added DIPEA (0.223 mg) at room temperature, and the reaction mixture was stirred at 75° C. for 1 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The precipitated solid was collected by filtration to give the title compound (392 mg).

B) 1-(trans-4-aminocyclohexyl)-3-(2,2-difluoroethyl)-1-(5-(2-methoxypyrimidin-5-yl)pyrazin-2-yl) urea A mixture of tert-butyl (trans-4-(3-(2,2-difluoroethyl)-1-(5-(2-methoxypyrimidin-5-yl)pyrazin-2-yl)ureido)cyclohexyl)carbamate (388 mg) and TFA (4.7 mL) was stirred at room temperature overnight. The solvent of the reaction mixture was evaporated under reduced pressure, and the residue was purified by silica gel column chromatography (NH, ethyl acetate/hexane/methanol) to give the title compound (311 mg).
MS: [M+H]$^+$ 408.2.

C) 1-(trans-4-((4-(4-chloro-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyrazin-2-yl)urea To a solution of 1-(trans-4-aminocyclohexyl)-3-(2,2-difluoroethyl)-1-(5-(2-methoxypyrimidin-5-yl)pyrazin-2-yl)urea (100 mg) and 2-chloro-4-(4-chloro-1H-pyrazol-3-yl)-5-(trifluoromethyl)pyrimidine (139 mg) in DMF (2.0 mL) was added DIPEA (0.13 mL) at room temperature. The reaction mixture was purified by HPLC (YMCTriartC18, mobile phase: water/acetonitrile (10 mM ammonium bicarbonate-based)) to give the title compound (33 mg).
$^1$H NMR (300 MHz, DMSO-d$_6$) δ 1.30-1.63 (4H, m), 1.73-2.06 (4H, m), 3.35-3.50 (2H, m), 3.56-3.80 (1H, m), 4.02 (3H, d, J=2.6 Hz), 4.17-4.36 (1H, m), 5.78-6.25 (1H, m), 6.89-7.05 (1H, m), 7.99-8.26 (2H, m), 8.57 (1H, dd, J=5.5, 1.3 Hz), 8.64 (1H, d, J=9.4 Hz), 9.23 (1H, dd, J=4.9, 1.1 Hz), 9.32 (2H, d, J=6.0 Hz), 13.49 (1H, br s).

Example 764

1-(trans-4-((4-(1-(difluoromethyl)-1H-pyrazol-3-yl)-5-(trifluoromethyl)pyrimidin-2-yl)amino)cyclohexyl)-3-ethyl-1-(5-(1-methyl-1H-pyrazol-4-yl)pyrazin-2-yl)urea

A) tert-butyl (trans-4-((chlorocarbonyl) (5-(1-methyl-1H-pyrazol-4-yl)pyrazin-2-yl)amino)cyclohexyl)carbamate To a mixture of tert-butyl (trans-4-((5-(1-methyl-1H-pyrazol-4-yl)pyrazin-2-yl)amino)cyclohexyl)carbamate (1.8 g) and DIPEA (1.9 g) in THF (40 mL) was added triphosgene (717 mg) at room temperature. The reaction mixture was stirred at 70° C. for 1 hr. The reaction mixture was added to ice water, saturated aqueous sodium hydrogen carbonate solution was added, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (1.82 g).
MS: [M+H-tBu]+379.2.

B) tert-butyl (trans-4-(3-ethyl-1-(5-(1-methyl-1H-pyrazol-4-yl)pyrazin-2-yl)ureido)cyclohexyl)carbamate To a mixture of tert-butyl (trans-4-((chlorocarbonyl) (5-(1-methyl-1H-pyrazol-4-yl)pyrazin-2-yl)amino)cyclohexyl) carbamate (300 mg) and DIPEA (356 mg) in THF (5.0 mL) was added ethaneamine hydrochloride (79 mg) at room temperature, and the reaction mixture was stirred at 70° C. for 3 hr. To the reaction mixture was added water and ethyl acetate at room temperature, and the precipitated solid was collected by filtration to give the title compound (250 mg).
MS: [M+H]$^+$ 444.3.

C) 1-(trans-4-aminocyclohexyl)-3-ethyl-1-(5-(1-methyl-1H-pyrazol-4-yl)pyrazin-2-yl)urea A mixture of tert-butyl (trans-4-(3-ethyl-1-(5-(1-methyl-1H-pyrazol-4-yl)pyrazin-2-yl)ureido)cyclohexyl)carbamate (294 mg) and TFA (4.0 mL) was stirred at room temperature for 3 hr. The solvent of the reaction mixture was evaporated under reduced pressure, and the residue was purified by silica gel column chromatography (NH, ethyl acetate/hexane/methanol) to give the title compound (214 mg).
MS: [M+H]$^+$ 344.2.

D) 1-(difluoromethyl)-3-(4,4,5,5-tetramethyl-1,3,2-dioxaborolan-2-yl)-1H-pyrazole A mixture of 3-(4,4,5,5-tetramethyl-1,3,2-dioxaborolan-2-yl)-1H-pyrazole (5 g), sodium 2-chloro-2,2-difluoroacetate (4.71 g), 18-crown-6 (1.36 g) and acetonitrile (120 mL) was stirred at 80° C. overnight. The reaction mixture was concentrated under reduced pressure, and the residue was added to water at room temperature, and the mixture was extracted with ethyl acetate. The organic layer was separated, washed with water and saturated brine, and dried over anhydrous sodium sulfate. The solvent was evaporated under reduced pressure. The residue was washed with diisopropyl ether/hexane to give the title compound (2.2 g).
$^1$H NMR (300 MHz, DMSO-d$_6$) δ 1.29 (12H, s), 6.73 (1H, d, J=2.6 Hz), 7.87 (1H, t, J=59.1 Hz), 8.28 (1H, d, J=2.6 Hz).

E) 4-(1-(difluoromethyl)-1H-pyrazol-3-yl)-2-(methylthio)-5-(trifluoromethyl)pyrimidine A mixture of 4-chloro-2-(methylthio)-5-(trifluoromethyl)pyrimidine (1.5 g), 1-(difluoromethyl)-3-(4,4,5,5-tetramethyl-1,3,2-dioxaborolan-2-yl)-1H-pyrazole (1.76 g), PdCl$_2$ (Amphos)$_2$ (465 mg), 2M sodium carbonate aqueous solution (6.6 mL) and DME (30 mL) was stirred under an argon atmosphere at 100° C. for 4 hr. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (ethyl acetate/hexane) to give the title compound (1.51 g).
MS: [M+H]$^+$ 311.0.

F) 4-(1-(difluoromethyl)-1H-pyrazol-3-yl)-2-(methylsulfonyl)-5-(trifluoromethyl)pyrimidine A mixture of 4-(1-(difluoromethyl)-1H-pyrazol-3-yl)-2-(methylthio)-5-(trifluoromethyl)pyrimidine (1 g), m-chloroperbenzoic acid (1.99 g) and ethyl acetate (30 mL) was stirred at room temperature overnight. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (ethyl acetate/hexane) to give the title compound (825 mg).
MS: [M+H]$^+$ 343.0.

G) 1-(trans-4-((4-(1-(difluoromethyl)-1H-pyrazol-3-yl)-5-(trifluoromethyl)pyrimidin-2-yl)amino)cyclohexyl)-3-ethyl-1-(5-(1-methyl-1H-pyrazol-4-yl)pyrazin-2-yl)urea A mixture of 1-(trans-4-aminocyclohexyl)-3-ethyl-1-(5-(1-methyl-1H-pyrazol-4-yl)pyrazin-2-yl)urea (141 mg), 4-(1-(difluoromethyl)-1H-pyrazol-3-yl)-2-(methylsulfonyl)-5-(trifluoromethyl)pyrimidine (155 mg), DIPEA (0.21 mL) and DMF (2 mL) was stirred at 70° C. for 3 hr. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (silica gel, ethyl acetate/hexane and NH, ethyl acetate/hexane) to give the title compound (80 mg).

$^1$H NMR (300 MHz, DMSO-d$_6$) δ 0.97 (3H, t, J=7.0 Hz), 1.33-1.54 (4H, m), 1.73-1.98 (4H, m), 2.96-3.11 (2H, m), 3.64 (1H, br s), 3.92 (3H, s), 4.21 (1H, br s), 6.25-6.37 (1H, m), 6.87 (1H, dd, J=10.0, 2.8 Hz), 7.64-8.07 (1H, m), 8.02-8.18 (2H, m), 8.30-8.36 (2H, m), 8.39 (1H, s), 8.63 (1H, d, J=7.2 Hz), 8.85 (1H, d, J=1.1 Hz).

Example 766

2,2-difluoroethyl (trans-4-((4-(5-(methanesulfonyl) pyridin-3-yl)-5-(trifluoromethyl)pyrimidin-2-yl) amino)cyclohexyl) (5-(2-methoxypyrimidin-5-yl) pyrazin-2-yl)carbamate A) 2,2-difluoroethyl (trans-4-aminocyclohexyl) (5-(2-methoxypyrimidin-5-yl)pyrazin-2-yl)carbamate To a mixture of tert-butyl (trans-4-((chlorocarbonyl) (5-(2-methoxypyrimidin-5-yl)pyrazin-2-yl)amino)cyclohexyl) carbamate (300 mg), 2,2-difluoroethan-1-ol (160 mg) and DIPEA (0.34 mL) in THF (4.0 mL) was added DMAP (95 mg) at room temperature, and the mixture was stirred at 60° C. overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give 2,2-difluoroethyl (trans-4-((tert-butoxycarbonyl)amino)cyclohexyl) (5-(2-methoxypyrimidin-5-yl)pyrazin-2-yl)carbamate (308 mg). 2,2-Difluoroethyl (trans-4-((tert-butoxycarbonyl) amino) cyclohexyl) (5-(2-methoxypyrimidin-5-yl)pyrazin-2-yl)carbamate (308 mg) was dissolved in TFA (3.0 mL), and the mixture was stirred at room temperature for 30 min. The solvent of the reaction mixture was evaporated under reduced pressure. The residue was purified by silica gel column chromatography (NH, ethyl acetate/methanol) to give the title compound (212 mg).

MS: [M+H]$^+$ 409.2.

B) 4-(5-(methylsulfonyl)pyridin-3-yl)-2-(methylthio)-5-(trifluoromethyl)pyrimidine A mixture of 4-chloro-2-(methylthio)-5-(trifluoromethyl) pyrimidine (1.0 g), 3-(methylsulfonyl)-5-(4,4,5,5-tetramethyl-1,3,2-dioxaborolan-2-yl)pyridine (1.3 g), PdCl$_2$(Amphos)$_2$ (310 mg), 2 M sodium carbonate aqueous solution (4.4 mL) and DME (10 mL) was stirred under microwave irradiation at 100° C. for 1 hr. A similar reaction was repeated times, to the combined reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (7.1 g).

MS: [M+H]$^+$ 350.0.

C) 2-(methylsulfonyl)-4-(5-(methylsulfonyl)pyridin-3-yl)-5-(trifluoromethyl)pyrimidine To a solution of 4-(5-(methylsulfonyl)pyridin-3-yl)-2-(methylthio)-5-(trifluoromethyl)pyrimidine (7.1 g) in ethyl acetate (200 mL) was added m-chloroperbenzoic acid (11.0 g) at 0° C. After stirring at room temperature for 5 hr, the reaction solvent was evaporated under reduced pressure. The residue was purified by silica gel column chromatography (ethyl acetate/hexane) to give the title compound (5.7 g).

MS: [M+H]$^+$ 382.0.

D) 2,2-difluoroethyl (trans-4-((4-(5-(methanesulfonyl)pyridin-3-yl)-5-(trifluoromethyl)pyrimidin-2-yl) amino) cyclohexyl) (5-(2-methoxypyrimidin-5-yl) pyrazin-2-yl)carbamate To a solution of 2,2-difluoroethyl (trans-4-aminocyclohexyl) (5-(2-methoxypyrimidin-5-yl)pyrazin-2-yl)carbamate (81 mg) and 2-(methylsulfonyl)-4-(5-(methylsulfonyl) pyridin-3-yl)-5-(trifluoromethyl)pyrimidine (76 mg) in DMF (1.0 mL) was added DIPEA (0.1 mL) at room temperature, and the reaction mixture was stirred at 70° C. for 3 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane and silica gel, ethyl acetate/hexane) to give the title compound (64 mg).

$^1$H NMR (300 MHz, DMSO-d$_6$) δ 1.34-1.80 (4H, m), 1.85-2.09 (4H, m), 3.34-3.43 (3H, m), 3.56-3.86 (1H, m), 3.96-4.05 (3H, m), 4.08-4.23 (1H, m), 4.27-4.53 (2H, m), 5.93-6.51 (1H, m), 8.23 (1H, br d, J=3.4 Hz), 8.38-8.50 (1H, m), 8.67-8.78 (2H, m), 9.01 (1H, s), 9.17-9.26 (2H, m), 9.27-9.34 (2H, m).

Example 767

2-(dimethylamino)ethyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate A) 2-(dimethylamino)ethyl (trans-4-((tert-butoxycarbonyl)amino)cyclohexyl) (5-(2-methoxypyrimidin-5-yl)pyrazin-2-yl)carbamate A mixture of tert-butyl (trans-4-((chlorocarbonyl) (5-(2-methoxypyrimidin-5-yl)pyrazin-2-yl)amino)cyclohexyl) carbamate (200 mg), 2-(dimethylamino)ethanol (0.22 mL), DMAP (63.3 mg), TEA (0.18 mL) and THF (5 mL) was stirred at 70° C. for 8 hr. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (NH, ethyl acetate/hexane) to give the title compound (142 mg).

MS: [M+H]$^+$ 516.4.

B) 2-(dimethylamino)ethyl (trans-4-aminocyclohexyl) (5-(2-methoxypyrimidin-5-yl)pyrazin-2-yl) carbamate A mixture of 2-(dimethylamino)ethyl (trans-4-((tert-butoxycarbonyl)amino)cyclohexyl) (5-(2-methoxypyrimidin-5-yl)pyrazin-2-yl)carbamate (142 mg) and TFA (2 mL) was stirred at room temperature for 1 hr. The reaction mixture was concentrated under reduced pressure, and the residue was purified by silica gel column chromatography (NH, methanol/ethyl acetate) to give the title compound (105 mg). MS: [M+H]+ 416.2.

C) 2-(dimethylamino)ethyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate To a solution of 2-(dimethylamino)ethyl (trans-4-aminocyclohexyl) (5-(2-methoxypyrimidin-5-yl)pyrazin-2-yl)carbamate (41 mg) and 2-(methylsulfonyl)-4-(5-(methylsulfonyl)pyridin-3-yl)-5-(trifluoromethyl)pyrimidine (38 mg) in DMF (2.0 mL) was added DIPEA (0.05 mL) at room temperature, and the mixture was stirred at 70° C. overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by was purified by silica gel column chromatography (ethyl acetate/hexane/methanol) to give the title compound (26 mg).
$^1$H NMR (300 MHz, DMSO-$d_6$) δ 1.34-1.52 (2H, m), 1.56-1.82 (2H, m), 1.83-2.03 (4H, m), 2.07-2.13 (6H, m), 2.37-2.46 (2H, m), 3.35-3.43 (3H, m), 3.60-3.85 (1H, m), 3.96-4.04 (3H, m), 4.09-4.21 (3H, m), 8.21-8.36 (1H, m), 8.39-8.51 (1H, m), 8.65-8.76 (2H, m), 8.98-9.04 (1H, m), 9.14-9.22 (2H, m), 9.26-9.33 (2H, m).

Example 798

N-(trans-4-((4-(5-(methanesulfonyl)pyridin-3-yl)-5-(trifluoromethyl)pyrimidin-2-yl) amino) cyclohexyl)-N-(5-(2-methoxypyrimidin-5-yl)pyrazin-2-yl) butanamide A) tert-butyl (trans-4-(1-(5-(2-methoxypyrimidin-5-yl)pyrazin-2-yl)butylamido)cyclohexyl)carbamate To a mixture of tert-butyl (trans-4-((5-(2-methoxypyrimidin-5-yl)pyrazin-2-yl)amino)cyclohexyl)carbamate (1 g), DMAP (275 mg) and DMA (30 mL) was slowly added butyryl chloride (1.3 mL) at room temperature. The mixture was stirred at 70° C. for 4 hr, and at 100° C. for 2 hr. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (ethyl acetate/hexane) to give the title compound (214 mg). MS: [M+H]+ 471.3.

B) N-(trans-4-aminocyclohexyl)-N-(5-(2-methoxypyrimidin-5-yl)pyrazin-2-yl)butylamide A mixture of tert-butyl (trans-4-(1-(5-(2-methoxypyrimidin-5-yl)pyrazin-2-yl)butylamido)cyclohexyl)carbamate (214 mg) and TFA (2 mL) was stirred at room temperature for 1 hr. The reaction mixture was concentrated under reduced pressure, and the residue was purified by silica gel column chromatography (NH, methanol/ethyl acetate) to give the title compound (144 mg).

C) N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl) butanamide A mixture of N-(trans-4-aminocyclohexyl)-N-(5-(2-methoxypyrimidin-5-yl)pyrazin-2-yl)butylamide (144 mg), 2-(methylsulfonyl)-4-(5-(methylsulfonyl)pyridin-3-yl)-5-(trifluoromethyl)pyrimidine (163 mg), DIPEA (0.2 mL) and DMF (2 mL) was stirred at 70° C. for 3 hr. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (ethyl acetate/hexane and NH, ethyl acetate/hexane) to give the title compound (66 mg).
$^1$H NMR (300 MHz, DMSO-$d_6$) δ 0.73-0.82 (3H, m), 1.20-1.57 (6H, m), 1.79-2.02 (6H, m), 3.32-3.42 (3H, m), 3.66 (1H, br s), 3.98-4.07 (3H, m), 4.43 (1H, br s), 8.19-8.48 (2H, m), 8.68-8.78 (2H, m), 8.96-9.02 (1H, m), 9.15-9.22 (1H, m), 9.25-9.39 (3H, m).

Example 799

3-ethyl-1-(trans-4-((4-(5-(methanesulfonyl)pyridin-3-yl)-5-(trifluoromethyl)pyrimidin-2-yl)amino)cyclohexyl)-1-(5-(2-methoxypyrimidin-5-yl)pyrazin-2-yl)urea A) tert-butyl (trans-4-(3-ethyl-1-(5-(2-methoxypyrimidin-5-yl)pyrazin-2-yl)ureido)cyclohexyl)carbamate A mixture of tert-butyl (trans-4-((chlorocarbonyl) (5-(2-methoxypyrimidin-5-yl)pyrazin-2-yl)amino)cyclohexyl) carbamate (300 mg) and 2 M ethylamine THF solution (2.6 mL) was stirred at 70° C. for 2 hr. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was washed with ethyl acetate/hexane to give the title compound (237 mg).
MS: [M+H]+ 472.3.

B) 1-(trans-4-aminocyclohexyl)-3-ethyl-1-(5-(2-methoxypyrimidin-5-yl)pyrazin-2-yl)urea A mixture of tert-butyl (trans-4-(3-ethyl-1-(5-(2-methoxypyrimidin-5-yl)pyrazin-2-yl)ureido)cyclohexyl) carbamate (237 mg) and TFA (2 mL) was stirred at room temperature for 1 hr. The reaction mixture was concentrated under reduced pressure, and the residue was purified by silica gel column chromatography (NH, methanol/ethyl acetate) to give the title compound (158 mg).
MS: [M+H]+ 372.2.

C) 3-ethyl-1-(trans-4-((4-(5-(methanesulfonyl)pyridin-3-yl)-5-(trifluoromethyl)pyrimidin-2-yl)amino)cyclohexyl)-1-(5-(2-methoxypyrimidin-5-yl)pyrazin-2-yl)urea To a solution of 1-(trans-4-aminocyclohexyl)-3-ethyl-1-(5-(2-methoxypyrimidin-5-yl)pyrazin-2-yl)urea (44 mg) and 2-(methylsulfonyl)-4-(5-(methylsulfonyl)pyridin-3-yl)-5-(trifluoromethyl)pyrimidine (50 mg) in DMF (1.0 mL) was added DIPEA (0.04 mL) at room temperature. The reaction mixture was stirred at 70° C. for 3 hr. To the reaction mixture was added saturated aqueous sodium hydrogen carbonate solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (29 mg).
$^1$H NMR (300 MHz, DMSO-$d_6$) δ 1.00 (3H, q, J=6.9 Hz), 1.34-1.73 (4H, m), 1.74-2.03 (4H, m), 2.98-3.14 (2H, m), 3.35-3.42 (3H, m), 3.55-3.82 (1H, m), 3.97-4.05 (3H, m), 4.16-4.36 (1H, m), 6.64-6.81 (1H, m), 8.25-8.39 (1H, m), 8.39-8.53 (2H, m), 8.68-8.77 (1H, m), 9.01 (1H, s), 9.09-9.22 (2H, m), 9.24-9.34 (2H, m).

Example 804

1-(trans-4-((4-(1-(difluoromethyl)-1H-pyrazol-3-yl)-5-(trifluoromethyl)pyrimidin-2-yl)amino)cyclohexyl)-3-(2-hydroxy-2-methylpropyl)-1-(5-(2-methoxypyrimidin-5-yl)pyrazin-2-yl)urea A) tert-butyl (trans-4-(3-(2-hydroxy-2-methylpropyl)-1-(5-(2-methoxypyrimidin-5-yl)pyrazin-2-yl)ureido)cyclohexyl)carbamate To a mixture of tert-butyl (trans-4-((chlorocarbonyl) (5-(2-methoxypyrimidin-5-yl)pyrazin-2-yl)amino)cyclohexyl)carbamate (200 mg) and 1-amino-2-methylpropan-2-ol (46 mg) in THF (5.0 mL) was added DIPEA (0.23 mL) at room temperature, and the mixture was stirred at room temperature for 3 hr. To the reaction mixture was added saturated aqueous sodium hydrogen carbonate solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (221 mg).
MS: [M+H]$^+$ 516.3.

B) 1-(trans-4-aminocyclohexyl)-3-(2-hydroxy-2-methylpropyl)-1-(5-(2-methoxypyrimidin-5-yl)pyrazin-2-yl)urea A mixture of tert-butyl (trans-4-(3-(2-hydroxy-2-methylpropyl)-1-(5-(2-methoxypyrimidin-5-yl)pyrazin-2-yl)ureido)cyclohexyl)carbamate (221 mg) and TFA (3 mL) was stirred at room temperature for 1 hr. The solvent of the reaction mixture was evaporated under reduced pressure, and azeotropically distilled with toluene. The residue was purified by silica gel column chromatography (NH, ethyl acetate/methanol) to give the title compound (171 mg).
MS: [M+H]$^+$ 416.3.

C) 1-(trans-4-((4-(1-(difluoromethyl)-1H-pyrazol-3-yl)-5-(trifluoromethyl)pyrimidin-2-yl)amino)cyclohexyl)-3-(2-hydroxy-2-methylpropyl)-1-(5-(2-methoxypyrimidin-5-yl)pyrazin-2-yl)urea To a solution of 1-(trans-4-aminocyclohexyl)-3-(2-hydroxy-2-methylpropyl)-1-(5-(2-methoxypyrimidin-5-yl)pyrazin-2-yl)urea (85 mg) and 4-(1-(difluoromethyl)-1H-pyrazol-3-yl)-2-(methylsulfonyl)-5-(trifluoromethyl)pyrimidine (70 mg) in DMF (1.0 mL) was added DIPEA (0.11 mL) at room temperature. The reaction mixture was stirred at 70° C. overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (66 mg).
$^1$H NMR (300 MHz, DMSO-$d_6$) δ 1.05 (6H, s), 1.35-1.54 (2H, m), 1.59-2.05 (6H, m), 3.06 (2H, br d, J=5.7 Hz), 3.59-3.82 (1H, m), 4.01 (3H, s), 4.22 (1H, s), 4.41-4.47 (1H, m), 6.60-6.74 (1H, m), 6.87 (1H, dd, J=11.7, 2.6 Hz), 7.65-8.07 (1H, m), 8.07-8.21 (1H, m), 8.33-8.38 (1H, m), 8.58 (1H, d, J=1.1 Hz), 8.65 (1H, d, J=12.5 Hz), 9.17 (1H, d, J=1.5 Hz), 9.30 (2H, s).

Example 820

2,2-difluoroethyl (trans-4-((4-(5-(methanesulfonyl)pyridin-3-yl)-5-(trifluoromethyl)pyrimidin-2-yl)amino)cyclohexyl) (5-(1-methyl-1H-pyrazol-4-yl)pyrazin-2-yl)carbamate A) 2,2-difluoroethyl (trans-4-((tert-butoxycarbonyl)amino)cyclohexyl) (5-(1-methyl-1H-pyrazol-4-yl)pyrazin-2-yl)carbamate A mixture of tert-butyl (trans-4-((chlorocarbonyl) (5-(1-methyl-1H-pyrazol-4-yl)pyrazin-2-yl)amino)cyclohexyl)carbamate (300 mg), DMAP (93 mg), DIPEA (268 mg) and 2,2-difluoroethan-1-(1.5 mL) was stirred at 70° C. for 2 hr. The reaction mixture was added to water, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/hexane) to give the title compound (320 mg).
MS: [M+H-tBu+H]$^+$ 425.2.

B) 2,2-difluoroethyl (trans-4-aminocyclohexyl) (5-(1-methyl-1H-pyrazol-4-yl)pyrazin-2-yl)carbamate A mixture of 2,2-difluoroethyl (trans-4-((tert-butoxycarbonyl)amino)cyclohexyl) (5-(1-methyl-1H-pyrazol-4-yl)pyrazin-2-yl)carbamate (320 mg) and TFA (4.08 mL) was stirred at room temperature for 1 hr. The reaction mixture was concentrated under reduced pressure, and the residue was purified by silica gel column chromatography (NH, ethyl acetate/hexane/methanol) to give the title compound (244 mg).
MS: [M+H]$^+$ 381.2.

C) 2,2-difluoroethyl (trans-4-((4-(5-(methanesulfonyl)pyridin-3-yl)-5-(trifluoromethyl)pyrimidin-2-yl)amino) cyclohexyl) (5-(1-methyl-1H-pyrazol-4-yl)pyrazin-2-yl)carbamate A mixture of 2,2-difluoroethyl (trans-4-aminocyclohexyl) (5-(1-methyl-1H-pyrazol-4-yl)pyrazin-2-yl)carbamate (30 mg), 2-(methylsulfonyl)-4-(5-(methylsulfonyl)pyridin-3-yl)-5-(trifluoromethyl)pyrimidine (30 mg), DIPEA (0.69 mL) and acetonitrile (2 mL) was stirred at room temperature overnight. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/hexane/methanol), and treated with ethyl acetate and hexane to give the title compound (23 mg).

$^1$H NMR (300 MHz, DMSO-d$_6$) δ 1.31-1.72 (4H, m), 1.82-2.07 (4H, m), 3.34-3.41 (3H, m), 3.57-3.81 (1H, m), 3.86-3.98 (3H, m), 4.00-4.18 (1H, m), 4.24-4.45 (2H, m), 5.96-6.43 (1H, m), 8.04-8.16 (1H, m), 8.21-8.56 (4H, m), 8.67-8.78 (1H, m), 8.81-8.93 (1H, m), 8.97-9.05 (1H, m), 9.17-9.24 (1H, m).

Example 826

4,4-difluoro-N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)butanamide A) tert-butyl (trans-4-(4,4-difluoro-N-(5-(2-methoxypyrimidin-5-yl)pyrazin-2-yl)butaneamido)cyclohexyl)carbamate A mixture of 4,4-difluorobutanoic acid (1.35 g), oxalyl chloride (1.4 mL), DMF (0.01 mL) and diethyl ether (20 mL) was stirred at room temperature for 2 hr. The solvent was evaporated under reduced pressure to give, 4,4-difluorobutanoyl chloride (1.43 g). A mixture of tert-butyl (trans-4-((5-(2-methoxypyrimidin-5-yl)pyrazin-2-yl)amino)cyclohexyl)carbamate (400 mg), 4,4-difluorobutanoyl chloride (712 mg), DMAP (122 mg) and DMA (10 mL) was stirred at 70° C. for 6 hr. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (ethyl acetate/hexane) to give the title compound (80 mg).

MS: [M+Na]+529.3.

B) 4,4-difluoro-N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)butanamide A mixture of tert-butyl (trans-4-(4,4-difluoro-N-(5-(2-methoxypyrimidin-5-yl)pyrazin-2-yl)butanamido)cyclohexyl)carbamate (80 mg) and TFA (1 mL) was stirred at room temperature for 1 hr. The solvent was evaporated under reduced pressure. A mixture of the residue, 2-(methylsulfonyl)-4-(5-(methylsulfonyl)pyridin-3-yl)-5-(trifluoromethyl)pyrimidine (78 mg), DIPEA (0.08 mL) and DMF (1 mL) was stirred at 70° C. for 4 hr. The reaction mixture was concentrated under reduced pressure, and the residue was purified by silica gel column chromatography (ethyl acetate/hexane) to give the title compound (3.8 mg).

$^1$H NMR (300 MHz, DMSO-d$_6$) δ 1.21-1.57 (4H, m), 1.80-2.22 (8H, m), 3.33-3.40 (3H, m), 3.52-3.78 (1H, m), 4.02 (3H, d, J=4.2 Hz), 4.42 (1H, br s), 5.81-6.26 (1H, m), 8.21-8.36 (1H, m), 8.36-8.48 (1H, m), 8.70 (1H, s), 8.73-8.82 (1H, m), 8.96-9.01 (1H, m), 9.16-9.22 (1H, m), 9.27-9.38 (3H, m).

Example 827

2-ethoxy-N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)acetamide A) tert-butyl (trans-4-(2-ethoxy-N-(5-(2-methoxypyrimidin-5-yl)pyrazin-2-yl)acetamido)cyclohexyl)carbamate To a mixture of 2-ethoxyacetic acid (1.82 mL), DMF (0.01 mL) and diethyl ether (20 mL) was slowly added oxalyl chloride (2.5 mL), and the mixture was stirred at room temperature for 2 hr. The solvent was evaporated under reduced pressure to give 2-ethoxyacetyl chloride (2.4 g). To a mixture of tert-butyl (trans-4-((5-(2-methoxypyrimidin-5-yl)pyrazin-2-yl)amino)cyclohexyl)carbamate (600 mg), DMAP (183 mg) and DMA (15 mL) was added 2-ethoxyacetyl chloride (918 mg) at room temperature, and the mixture was stirred at 70° C. overnight. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (ethyl acetate/hexane) to give the title compound (99 mg).

MS: [M+Na]+509.3.

B) 2-ethoxy-N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)acetamide A mixture of tert-butyl (trans-4-(2-ethoxy-N-(5-(2-methoxypyrimidin-5-yl)pyrazin-2-yl)acetamido)cyclohexyl)carbamate (99 mg), 2-(methylsulfonyl)-4-(5-(methylsulfonyl)pyridin-3-yl)-5-(trifluoromethyl)pyrimidine (101 mg), DIPEA (0.11 mL) and DMF (1 mL) was stirred at 70° C. for 3 hr. The reaction mixture was concentrated under reduced pressure, and the residue was purified by silica gel column chromatography (ethyl acetate/hexane) to give the title compound (6 mg).

$^1$H NMR (300 MHz, DMSO-d$_6$) δ 0.91 (3H, td, J=7.0, 4.2 Hz), 1.32-1.55 (4H, m), 1.91 (4H, br d, J=22.3 Hz), 3.22-3.29 (2H, m), 3.33-3.40 (3H, m), 3.62-3.77 (1H, m), 3.85-

3.94 (2H, m), 3.99-4.05 (3H, m), 4.39 (1H, br s), 8.23-8.36 (1H, m), 8.37-8.48 (1H, m), 8.70 (1H, d, J=2.3 Hz), 8.76 (1H, d, J=12.1 Hz), 9.00 (1H, s), 9.17-9.22 (1H, m), 9.22-9.29 (1H, m), 9.30-9.37 (2H, m).

Example 831

2-ethoxy-N-(trans-4-((4-(5-(methanesulfonyl)pyridin-3-yl)-5-(trifluoromethyl)pyrimidin-2-yl)amino)cyclohexyl)-N-(5-(1-methyl-1H-pyrazol-4-yl)pyrazin-2-yl)acetamide A) tert-butyl (trans-4-(2-ethoxy-N-(5-(1-methyl-1H-pyrazol-4-yl)pyrazin-2-yl)acetamido)cyclohexyl) carbamate A mixture of 2-ethoxyacetic acid (0.30 mL), triphosgene (319 mg), DMF (0.01 mL) and THF (3 mL) was stirred at room temperature for 2 hr. The reaction mixture was concentrated to not more than half the volume under reduced pressure and added to a solution of tert-butyl (trans-4-((5-(1-methyl-1H-pyrazol-4-yl)pyrazin-2-yl)amino)cyclohexyl) carbamate (300 mg) in pyridine (3 mL). The mixture was stirred at 60° C. for 4 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/hexane) and silica gel column chromatography (NH, ethyl acetate/hexane) to give the title compound (117 mg).
MS: [M+H]$^+$ 459.3.

B) 2-ethoxy-N-(trans-4-((4-(5-(methanesulfonyl)pyridin-3-yl)-5-(trifluoromethyl)pyrimidin-2-yl)amino)cyclohexyl)-N-(5-(1-methyl-1H-pyrazol-4-yl)pyrazin-2-yl)acetamide tert-Butyl (trans-4-(2-ethoxy-N-(5-(1-methyl-1H-pyrazol-4-yl)pyrazin-2-yl)acetamido)cyclohexyl)carbamate (50 mg) was dissolved in TFA (1 mL) at room temperature. After stirring at room temperature for 30 min, the reaction mixture was concentrated under reduced pressure. The residue was dissolved in THF (2 mL), 2-(methylsulfonyl)-4-(5-(methylsulfonyl)pyridin-3-yl)-5-(trifluoromethyl)pyrimidine (50 mg) and DIPEA (0.19 mL) were added at room temperature. The mixture was stirred at 60° C. for 1 hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue was purified by silica gel column chromatography (ethyl acetate/methanol), and treated with ethyl acetate and hexane to give the title compound (43 mg).
$^1$H NMR (300 MHz, DMSO-d$_6$) δ 0.87-0.98 (3H, m), 1.21-1.56 (4H, m), 1.76-2.06 (4H, m), 3.21-3.43 (5H, m), 3.53-3.77 (1H, m), 3.78-3.88 (2H, m), 3.88-3.97 (3H, m), 4.27-4.44 (1H, m), 8.06-8.17 (1H, m), 8.20-8.36 (1H, m), 8.36-8.49 (2H, m), 8.50-8.61 (1H, m), 8.66-8.74 (1H, m), 8.84-8.96 (1H, m), 8.96-9.03 (1H, m), 9.16-9.23 (1H, m).

Example 836

2-hydroxy-2-methylpropyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate A) 2-hydroxy-2-methylpropyl (trans-4-((tert-butoxycarbonyl)amino)cyclohexyl) (5-(2-methoxypyrimidin-5-yl)pyrazin-2-yl)carbamate To a mixture of tert-butyl (trans-4-((chlorocarbonyl) (5-(2-methoxypyrimidin-5-yl)pyrazin-2-yl)amino)cyclohexyl) carbamate (100 mg), DIPEA (0.08 mL) and 2-methylpropane-1,2-diol (97 mg) in THF (2 mL) was added DMAP (26 mg) at room temperature. The reaction mixture was stirred at 70° C. overnight. To the reaction mixture was added saturated aqueous sodium hydrogen carbonate solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (91 mg).
MS: [M+H]$^+$ 517.3.

B) 2-hydroxy-2-methylpropyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate A mixture of 2-hydroxy-2-methylpropyl (trans-4-((tert-butoxycarbonyl)amino)cyclohexyl) (5-(2-methoxypyrimidin-5-yl)pyrazin-2-yl)carbamate (91 mg) and TFA (3.0 mL) was stirred at room temperature for 30 min. The solvent of the reaction mixture was evaporated under reduced pressure, and the residue was azeotropically distilled with toluene. The residue was dissolved in DMF (1.0 mL), and 2-(methylsulfonyl)-4-(5-(methylsulfonyl)pyridin-3-yl)-5-(trifluoromethyl)pyrimidine (67 mg) and DIPEA (0.31 mL) were added at room temperature. The reaction mixture was stirred at 70° C. overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane/methanol) to give the title compound (53 mg).
$^1$H NMR (300 MHz, DMSO-d$_6$) δ 0.94-1.05 (6H, m), 1.33-1.53 (2H, m), 1.56-1.82 (2H, m), 1.84-2.08 (4H, m), 3.33-3.40 (3H, m), 3.57-3.79 (1H, m), 3.80-3.90 (2H, m), 3.98-4.04 (3H, m), 4.10-4.26 (2H, m), 4.49-4.61 (1H, m), 8.23-8.36 (1H, m), 8.37-8.50 (1H, m), 8.68-8.78 (2H, m), 8.98-9.07 (1H, m), 9.16-9.23 (2H, m), 9.25-9.35 (2H, m).

Example 838

2-hydroxy-2-methylpropyl (trans-4-((4-(5-(methanesulfonyl)pyridin-3-yl)-5-(trifluoromethyl)pyrimidin-2-yl)amino)cyclohexyl) (5-(1-methyl-1H-pyrazol-4-yl)pyrazin-2-yl)carbamate A) 2-hydroxy-2-methylpropyl (trans-4-((tert-butoxycarbonyl)amino)cyclohexyl) (5-(1-methyl-1H-pyrazol-4-yl)pyrazin-2-yl)carbamate To a mixture of tert-butyl (trans-4-((chlorocarbonyl) (5-(1-methyl-1H-pyrazol-4-yl)pyrazin-2-yl)amino)cyclohexyl) carbamate (150 mg), DIPEA (0.12 mL) and 2-methylpropane-1,2-diol (93 mg) in THF (2 mL) was added DMAP (42 mg) at room temperature. The reaction mixture was stirred at 70° C. for 2 days. To the reaction mixture was added saturated aqueous sodium hydrogen carbonate solution at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/methanol) to give the title compound (157 mg).

MS: [M+H]+ 489.3.

B) 2-hydroxy-2-methylpropyl (trans-4-((4-(5-(methanesulfonyl)pyridin-3-yl)-5-(trifluoromethyl)pyrimidin-2-yl)amino)cyclohexyl) (5-(1-methyl-1H-pyrazol-4-yl)pyrazin-2-yl)carbamate A mixture of 2-hydroxy-2-methylpropyl (trans-4-((tert-butoxycarbonyl)amino)cyclohexyl) (5-(1-methyl-1H-pyrazol-4-yl)pyrazin-2-yl)carbamate (82 mg) and TFA (3.0 mL) was stirred at room temperature for 30 min. The solvent of the reaction mixture was evaporated under reduced pressure, and the residue was azeotropically distilled with toluene. The residue was dissolved in DMF (1.0 mL), 2-(methylsulfonyl)-4-(5-(methylsulfonyl)pyridin-3-yl)-5-(trifluoromethyl)pyrimidine (64 mg) and DIPEA (0.29 mL) were added at room temperature. The reaction mixture was stirred at 70° C. overnight. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (ethyl acetate/hexane) to give the title compound (42 mg).

$^1$H NMR (300 MHz, DMSO-$d_6$) δ 0.89-1.03 (6H, m), 1.34-1.70 (4H, m), 1.81-2.02 (4H, m), 3.35-3.41 (3H, m), 3.56-3.77 (1H, m), 3.78-3.83 (2H, m), 3.89-3.96 (3H, m), 4.03-4.21 (1H, m), 4.45-4.58 (1H, m), 8.03-8.13 (1H, m), 8.21-8.35 (1H, m), 8.36-8.53 (3H, m), 8.72 (1H, d, J=9.1 Hz), 8.81-8.91 (1H, m), 8.98-9.06 (1H, m), 9.11-9.29 (1H, m).

Example 841

2-hydroxy-2-methylpropyl (trans-4-((4-(4-chloro-1H-pyrazol-3-yl)-5-(trifluoromethyl)pyrimidin-2-yl)amino)cyclohexyl) (5-(2-methoxypyrimidin-5-yl)pyrazin-2-yl)carbamate 2-Hydroxy-2-methylpropyl (trans-4-((tert-butoxycarbonyl)amino)cyclohexyl) (5-(2-methoxypyrimidin-5-yl)pyrazin-2-yl)carbamate (91 mg) was dissolved in TFA (3.0 mL) at room temperature, and the mixture was stirred at room temperature for 30 min. The solvent of the reaction mixture was evaporated under reduced pressure, and the residue was azeotropically distilled with toluene. The residue was dissolved in DMF (1.0 mL), and 2-chloro-4-(4-chloro-1H-pyrazol-3-yl)-5-(trifluoromethyl)pyrimidine (100 mg) and DIPEA (0.31 mL) were added at room temperature. The reaction mixture was stirred at 70° C. overnight. The reaction mixture was purified by HPLC (YMCTriartC18, mobile phase: water/acetonitrile (10 mM ammonium bicarbonate-based)) to give the title compound (17 mg) $^1$H NMR (300 MHz, DMSO-$d_6$) δ 1.01 (6H, s), 1.33-1.54 (2H, m), 1.55-1.78 (2H, m), 1.85 (4H, br d, J=3.8 Hz), 3.56-3.77 (1H, m), 3.86 (2H, d, J=3.0 Hz), 4.01 (3H, d, J=2.3 Hz), 4.09-4.26 (1H, m), 4.56 (1H, d, J=3.0 Hz), 7.98-8.20 (2H, m), 8.58-8.68 (1H, m), 8.71-8.76 (1H, m), 9.15-9.26 (1H, m), 9.31 (2H, d, J=5.7 Hz), 13.35-13.66 (1H, m).

Example 848

2-(dimethylamino)ethyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyridin-2-yl)carbamate A) 2-(dimethylamino)ethyl (trans-4-((tert-butoxycarbonyl)amino)cyclohexyl) (5-(2-methoxypyrimidin-5-yl)pyridin-2-yl)carbamate To a mixture of tert-butyl (trans-4-((chlorocarbonyl) (5-(2-methoxypyrimidin-5-yl)pyridin-2-yl)amino)cyclohexyl) carbamate (100 mg), DIPEA (0.08 mL), 2-(dimethylamino)ethan-1-ol (96 mg) and THF (3 mL) was added DMAP (26 mg) at room temperature. The mixture was stirred at 70° C. overnight. The reaction mixture was added to water, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (61 mg).

MS: [M+H]+ 515.4.

B) 2-(dimethylamino)ethyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyridin-2-yl)carbamate 2-(Dimethylamino)ethyl (trans-4-((tert-butoxycarbonyl)amino)cyclohexyl) (5-(2-methoxypyrimidin-5-yl)pyridin-2-yl)carbamate (60 mg) was dissolved in TFA (1 mL) at room temperature. After stirring at room temperature for 30 min, the reaction mixture was concentrated under reduced pressure. The residue was dissolved in THF (2 mL), and 2-(methylsulfonyl)-4-(5-(methylsulfonyl)pyridin-3-yl)-5-(trifluoromethyl)pyrimidine (53 mg) and DIPEA (0.20 mL) were added at room temperature. The mixture was stirred at 60° C. for hr. The reaction mixture was added to saturated aqueous sodium hydrogen carbonate solution, and the mixture was extracted with ethyl acetate. The organic layer was washed with saturated brine, and dried over anhydrous magnesium sulfate. The solvent was evaporated under reduced pressure. The residue was purified by silica gel column chromatography (NH, ethyl acetate/hexane/methanol), and treated with ethyl acetate and diisopropyl ether to give the title compound (35 mg).

$^1$H NMR (300 MHz, DMSO-$d_6$) δ 1.30-1.80 (4H, m), 1.81-2.04 (4H, m), 2.05-2.16 (6H, m), 2.34-2.46 (2H, m), 3.34-3.42 (3H, m), 3.54-3.83 (1H, m), 3.94-4.03 (3H, m), 4.03-4.19 (3H, m), 7.35-7.49 (1H, m), 8.13-8.36 (2H, m), 8.38-8.50 (1H, m), 8.67-8.77 (1H, m), 8.78-8.90 (1H, m), 8.98-9.08 (3H, m), 9.20 (1H, d, J=1.9 Hz).

Example 849

1-(trans-4-((4-(1-(difluoromethyl)-1H-pyrazol-3-yl)-5-(trifluoromethyl)pyrimidin-2-yl)amino)cyclohexyl)-3-(2-hydroxy-2-methylpropyl)-1-(5-(2-methoxypyrimidin-5-yl)pyridin-2-yl)urea To a mixture of tert-butyl (trans-4-((chlorocarbonyl) (5-(2-methoxypyrimidin-5-yl)pyridin-2-yl)amino)cyclohexyl) carbamate (100 mg) and 1-amino-2-methylpropan-2-ol (23 mg) in THF (3.0 mL) was added DIPEA (0.075 mL) at room temperature, and the mixture was stirred at room temperature overnight. To the reaction mixture was added saturated aqueous sodium hydrogen carbonate solution at room temperature, and the mixture was extracted with ethyl acetate. The organic layer was separated, washed with saturated brine, and dried over anhydrous magnesium sulfate. The solvent was evaporated under reduced pressure. The residue was dissolved in TFA (3.0 mL), and the mixture was stirred at room temperature for 30 min. The solvent of the reaction mixture was evaporated under reduced pressure, and the residue was azeotropically distilled with toluene. The residue was dissolved in DMF (1.0 mL), and 4-(1-(difluoromethyl)-1H-pyrazol-3-yl)-2-(methylsulfonyl)-5-(trifluoromethyl)pyrimidine (74 mg) and DIPEA (0.38 mL) were added at room temperature. The reaction mixture was stirred at 70° C. for 3 hr. To the reaction mixture was added water at room temperature, and the mixture was extracted with ethyl acetate. The organic layer was separated, washed with saturated brine, and dried over anhydrous magnesium sulfate. The solvent was evaporated under reduced pressure. The residue was purified by silica gel column chromatography (NH, ethyl acetate/hexane) to give the title compound (51 mg).

$^1$H NMR (300 MHz, DMSO-$d_6$) δ 1.02 (6H, s), 1.35-1.53 (2H, m), 1.55-1.75 (2H, m), 1.75-1.88 (2H, m), 1.88-2.05 (2H, m), 3.03 (2H, br d, J=5.3 Hz), 3.60-3.78 (1H, m), 3.99 (3H, s), 4.15-4.34 (1H, m), 4.41-4.49 (1H, m), 6.08-6.24 (1H, m), 6.87 (1H, dd, J=8.5, 2.5 Hz), 7.36 (1H, d, J=8.3 Hz), 7.63-8.07 (1H, m), 8.06-8.18 (1H, m), 8.22 (1H, dd, J=8.7, 2.6 Hz), 8.29-8.42 (1H, m), 8.65 (1H, d, J=11.0 Hz), 8.88 (1H, d, J=2.3 Hz), 8.98-9.10 (2H, m).

Example 858

N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyridin-2-yl)butanamide A) tert-butyl (trans-4-(N-(5-(2-methoxypyrimidin-5-yl)pyridin-2-yl)butylamido)cyclohexyl)carbamate A mixture of tert-butyl (trans-4-((5-(2-methoxypyrimidin-5-yl)pyridin-2-yl)amino)cyclohexyl)carbamate (1 g), DMAP (306 mg), butyryl chloride (1.25 mL) and DMA (15 mL) was stirred at 70° C. overnight. The reaction mixture was added to water at room temperature, and the mixture was extracted with ethyl acetate. The organic layer was separated, washed with water and saturated brine, and dried over anhydrous sodium sulfate. The solvent was evaporated under reduced pressure. The residue was purified by silica gel column chromatography (ethyl acetate/hexane) to give the title compound (400 mg).

MS: [M+H]$^+$ 470.3.

B) N-(trans-4-aminocyclohexyl)-N-(5-(2-methoxypyrimidin-5-yl)pyridin-2-yl)butylamide A mixture of tert-butyl (trans-4-(N-(5-(2-methoxypyrimidin-5-yl)pyridin-2-yl)butylamido)cyclohexyl)carbamate (149 mg) and TFA (2 mL) was stirred at room temperature for 1 hr. The reaction mixture was concentrated under reduced pressure, and the residue was purified by silica gel column chromatography (NH, methanol/ethyl acetate) to give the title compound (111 mg).

MS: [M+H]$^+$ 370.2.

C) N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyridin-2-yl) butanamide A mixture of N-(trans-4-aminocyclohexyl)-N-(5-(2-methoxypyrimidin-5-yl)pyridin-2-yl)butylamide (111 mg), 2-(methylsulfonyl)-4-(5-(methylsulfonyl)pyridin-3-yl)-5-(trifluoromethyl)pyrimidine (172 mg), DIPEA (0.16 mL) and DMF (2 mL) was stirred at 70° C. for 3 hr. 2-(Methylsulfonyl)-4-(5-(methylsulfonyl)pyridin-3-yl)-5-(trifluoromethyl)pyrimidine (92 mg) and DIPEA (0.16 mL) were added, and the mixture was stirred at 70° C. for 2 hr. The reaction mixture was added to water at room temperature, and the mixture was extracted with ethyl acetate. The organic layer was separated, washed with water and saturated brine, and dried over anhydrous sodium sulfate. The solvent was evaporated under reduced pressure, and the residue was purified by silica gel column chromatography (ethyl acetate/hexane and NH, ethyl acetate/hexane) to give the title compound (47.6 mg).

$^1$H NMR (300 MHz, DMSO-$d_6$) δ 0.70-0.81 (3H, m), 1.21-1.56 (6H, m), 1.78-2.02 (6H, m), 3.34-3.40 (3H, m), 3.63 (1H, br d, J=2.6 Hz), 3.96-4.01 (3H, m), 4.41 (1H, br d, J=3.4 Hz), 7.42-7.54 (1H, m), 8.21-8.36 (2H, m), 8.36-8.48 (1H, m), 8.70 (1H, d, J=2.6 Hz), 8.89-9.02 (2H, m), 9.03-9.11 (2H, m), 9.16-9.23 (1H, m).

The Example compounds are shown in the following Tables. In the Tables, MS shows the measured values. The compounds of Examples 1-19, 21-187, 191-198, 200-318, 320-439, 441-468, 470-481, 486-494, 496-526, 528, 529, 531, 533-535, 537, 540, 541, 543-551, 554-565, 567-573, 576, 578-580, 583-586, 590, 591, 593, 594, 597, 598, 601, 602, 604, 607, 613, 615, 616, 621, 622, 624, 632, 634-692, 694-728, 730-739, 741, 745-763, 765, 768-797, 800-803, 805-819, 821-825, 828-830, 832-835, 837, 839, 840, 842-847, 850-857 and Reference Examples 1-10 in the following Tables were produced according to the methods shown in the above-mentioned Examples or a method analogous thereto.

TABLE 1-1

| Ex. No. | IUPAC name | structural formula | salt | MS |
|---|---|---|---|---|
| 1 | N-(trans-4-((5-cyanopyridin-2-yl)amino)cyclohexyl)-N-(4-(1-methyl-1H-pyrazol-4-yl)phenyl)acetamide | | | 413.1 |
| 2 | N-(4-(1-methyl-1H-pyrazol-4-yl)phenyl)-N-(trans-4-((5-(trifluoromethyl)pyridin-2-yl)amino)cyclohexyl)acetamide | | | 458.2 |
| 3 | N-(trans-4-((5-cyanopyridin-2-yl)amino)cyclohexyl)-N-(2-methyl-4-(1-methyl-1H-pyrazol-4-yl)phenyl)acetamide | | | 429.3 |
| 4 | N-(trans-4-((5-cyanopyridin-2-yl)amino)cyclohexyl)-N-(2-fluoro-4-(1-methyl-1H-pyrazol-4-yl)phenyl)acetamide | | | 433.1 |

TABLE 1-1-continued

| Ex. No. | IUPAC name | structural formula | salt | MS |
|---|---|---|---|---|
| 5 | N-(2-cyano-4-(1-methyl-1H-pyrazol-4-yl)phenyl)-N-(trans-4-((5-cyanopyridin-2-yl)amino)cyclohexyl)acetamide | | | 440.2 |

TABLE 1-2

| Ex. No. | IUPAC name | structural formula | salt | MS |
|---|---|---|---|---|
| 6 | N-(3-cyano-4-(1-methyl-1H-pyrazol-4-yl)phenyl)-N-(trans-4-((5-cyanopyridin-2-yl)amino)cyclohexyl)acetamide | | | 440.2 |
| 7 | N-(2-chloro-4-(1-methyl-1H-pyrazol-4-yl)phenyl)-N-(trans-4-((5-cyanopyridin-2-yl)amino)cyclohexyl)acetamide | | | 449.1 |
| 8 | N-(trans-4-((5-cyanopyridin-2-yl)amino)cyclohexyl)-N-(4-(1-methyl-1H-pyrazol-4-yl)phenyl)propanamide | | | 429.2 |

TABLE 1-2-continued

| Ex. No. | IUPAC name | structural formula | salt | MS |
|---|---|---|---|---|
| 9 | N-(3-chloro-4-(1-methyl-1H-pyrazol-4-yl)phenyl)-N-(trans-4-((5-cyanopyridin-2-yl)amino)cyclohexyl)acetamide | | | 449.1 |
| 10 | N-(trans-4-((5-cyanopyridin-2-yl)amino)cyclohexyl)-2-methyl-N-(4-(1-methyl-1H-pyrazol-4-yl)phenyl)propanamide | | | 443.3 |

TABLE 1-3

| Ex. No. | IUPAC name | structural formula | salt | MS |
|---|---|---|---|---|
| 11 | N-(trans-4-((5-cyanopyridin-2-yl)amino)cyclohexyl)-N-(3-methyl-4-(1-methyl-1H-pyrazol-4-yl)phenyl)acetamide | | | 429.2 |
| 12 | N-(trans-4-((5-cyanopyridin-2-yl)amino)cyclohexyl)-N-(3-fluoro-4-(1-methyl-1H-pyrazol-4-yl)phenyl)acetamide | | | 433.1 |

TABLE 1-3-continued

| Ex. No. | IUPAC name | structural formula | salt | MS |
|---|---|---|---|---|
| 13 | N-(trans-4-((5-cyanopyridin-2-yl)amino)cyclohexyl)-N-(4-(1-methyl-1H-pyrazol-4-yl)phenyl)benzamide | | | 477.3 |
| 14 | N-(trans-4-((5-cyanopyridin-2-yl)amino)cyclohexyl)-N-(2-methoxy-4-(1-methyl-1H-pyrazol-4-yl)phenyl)acetamide | | | 445.2 |
| 15 | benzyl (trans-4-((5-cyanopyridin-2-yl)amino)cyclohexyl)(4-(1-methyl-1H-pyrazol-4-yl)phenyl)carbamate | | | 507.3 |

TABLE 1-4

| Ex. No. | IUPAC name | structural formula | salt | MS |
|---|---|---|---|---|
| 16 | N-(trans-4-((5-cyanopyridin-2-yl)amino)cyclohexyl)-N-(4-(1-methyl-1H-pyrazol-4-yl)phenyl)tetrahydro-2H-pyrane-4-carboxamide | | | 485.3 |

TABLE 1-4-continued

| Ex. No. | IUPAC name | structural formula | salt | MS |
|---|---|---|---|---|
| 17 | 3-benzyl-1-(trans-4-((5-cyanopyridin-2-yl)amino)cyclohexyl)-1-(4-(1-methyl-1H-pyrazol-4-yl)phenyl)urea | | | 506.2 |
| 18 | methyl (trans-4-((5-cyanopyridin-2-yl)amino)cyclohexyl)(4-(1-methyl-1H-pyrazol-4-yl)phenyl)carbamate | | | 431.1 |
| 19 | 1-(trans-4-((5-cyanopyridin-2-yl)amino)cyclohexyl)-3-ethyl-1-(4-(1-methyl-1H-pyrazol-4-yl)phenyl)urea | | | 444.3 |
| 21 | 3-benzyl-1-(trans-4-((5-cyanopyridin-2-yl)amino)cyclohexyl)-1-(4-(3-furyl)phenyl)urea | | | 492.3 |

TABLE 1-5

| Ex. No. | IUPAC name | structural formula | salt | MS |
|---|---|---|---|---|
| 22 | N-(trans-4-((5-cyanopyridin-2-yl)amino)cyclohexyl)-N-(4-(1-methyl-1H-pyrazol-4-yl)-2-(trifluoromethyl)phenyl)acetamide | | | 483.2 |
| 23 | N-(trans-4-((5-cyanopyridin-2-yl)amino)cyclohexyl)-N-(3-methoxy-4-(1-methyl-1H-pyrazol-4-yl)phenyl)acetamide | | | 445.2 |
| 24 | N-(trans-4-((5-cyanopyridin-2-yl)amino)cyclohexyl)-N-(3-fluoro-4-(1-methyl-1H-pyrazol-4-yl)phenyl)propanamide | | | 447.1 |
| 25 | N-(trans-4-((5-cyanopyridin-2-yl)amino)cyclohexyl)-N-(3-methoxy-4-(1-methyl-1H-pyrazol-4-yl)phenyl)propanamide | | | 457.1 | ns
TABLE 1-5-continued

| Ex. No. | IUPAC name | structural formula | salt | MS |
|---|---|---|---|---|
| 26 | N-(trans-4-((5-cyanopyridin-2-yl)amino)cyclohexyl)-N-(2,6-dichloro-4-(1-methyl-1H-pyrazol-4-yl)phenyl)acetamide | | | 483.1 |

TABLE 1-6

| Ex. No. | IUPAC name | structural formula | salt | MS |
|---|---|---|---|---|
| 27 | N-(3-chloro-4-(1-methyl-1H-pyrazol-4-yl)phenyl)-N-(trans-4-((5-cyanopyridin-2-yl)amino)cyclohexyl)propanamide | | | 461.2 |
| 28 | 1-(trans-4-((5-cyanopyridin-2-yl)amino)cyclohexyl)-3-(cyclohexylmethyl)-1-(4-(1-methyl-1H-pyrazol-4-yl)phenyl)urea | | | 512.2 |
| 29 | 1-(trans-4-((5-cyanopyridin-2-yl)amino)cyclohexyl)-3-(3-methoxybenzyl)-1-(4-(1-methyl-1H-pyrazol-4-yl)phenyl)urea | | | 536.3 |

TABLE 1-6-continued

| Ex. No. | IUPAC name | structural formula | salt | MS |
|---|---|---|---|---|
| 30 | 1-(trans-4-((5-cyanopyridin-2-yl)amino)cyclohexyl)-3-(4-methoxybenzyl)-1-(4-(1-methyl-1H-pyrazol-4-yl)phenyl)urea | | | 536.3 |
| 31 | 1-(trans-4-((5-cyanopyridin-2-yl)amino)cyclohexyl)-3-(4-fluorobenzyl)-1-(4-(1-methyl-1H-pyrazol-4-yl)phenyl)urea | | | 524.3 |

TABLE 1-7

| Ex. No. | IUPAC name | structural formula | salt | MS |
|---|---|---|---|---|
| 32 | 1-(trans-4-((5-cyanopyridin-2-yl)amino)cyclohexyl)-3-(3-fluorobenzyl)-1-(4-(1-methyl 1H-pyrazol-4-yl)phenyl)urea | | | 524.3 |

TABLE 1-7-continued

| Ex. No. | IUPAC name | structural formula | salt | MS |
|---|---|---|---|---|
| 33 | 1-(trans-4-((5-cyanopyridin-2-yl)amino)cyclohexyl)-3-(2-methoxybenzyl)-1-(4-(1-methyl-1H-pyrazol-4-yl)phenyl)urea | | | 536.3 |
| 34 | 1-(trans-4-((5-cyanopyridin-2-yl)amino)cyclohexyl)-1-(4-(1-methyl-1H-pyrazol-4-yl)phenyl)-3-(pyridin-2-ylmethyl)urea | | | 507.3 |
| 35 | 1-(trans-4-((5-cyanopyridin-2-yl)amino)cyclohexyl)-3-(2-fluorobenzyl)-1-(4-(1-methyl-1H-pyrazol-4-yl)phenyl)urea | | | 524.3 |
| 36 | 3-benzyl-1-(4-bromo-phenyl)-1-(trans-4-((5-cyanopyridin-2-yl)amino)cyclohexyl)urea | | | 504.1 |

TABLE 1-8

| Ex. No. | IUPAC name | structural formula | salt | MS |
|---|---|---|---|---|
| 37 | N-(trans-4-((5-cyanopyridin-2-yl)amino)cyclohexyl)-N-(4-(1-methyl-1H-pyrazol-4-yl)phenyl)-2-phenoxyacetamide | | | 507.3 |
| 38 | 3-benzyl-1-(trans-4-((5-cyanopyridin-2-yl)amino)cyclohexyl)-1-(6-(1-methyl-1H-pyrazol-4-yl)pyridin-3-yl)urea | | | 507.3 |
| 39 | 1-(trans-4-((5-cyanopyridin-2-yl)amino)cyclohexyl)-1-(4-(1-methyl-1H-pyrazol-4-yl)phenyl)-3-(pyridin-3-ylmethyl)urea | | | 507.3 |
| 40 | 1-(trans-4-((5-cyanopyridin-2-yl)amino)cyclohexyl)-3-(2-furylmethyl)-1-(4-(1-methyl-1H-pyrazol-4-yl)phenyl)urea | | | 496.2 |

TABLE 1-8-continued

| Ex. No. | IUPAC name | structural formula | salt | MS |
|---|---|---|---|---|
| 41 | 1-(trans-4-((5-cyanopyridin-2-yl)amino)cyclohexyl)-1-(4-(1-methyl-1H-pyrazol-4-yl)phenyl)-3-(pyridin-4-ylmethyl)urea | | | 507.3 |

TABLE 1-9

| Ex. No. | IUPAC name | structural formula | salt | MS |
|---|---|---|---|---|
| 42 | N-(trans-4-((5-cyanopyridin-2-yl)amino)cyclohexyl)-N-(4-(1-methyl-1H-pyrazol-4-yl)phenyl)-2-phenylacetamide | | | 491.3 |
| 43 | 2-(4-bromophenyl)-N-(trans-4-((5-cyanopyridin-2-yl)amino)cyclohexyl)-N-(4-(1-methyl-1H-pyrazol-4-yl)phenyl)acetamide | | | 569.2 |

TABLE 1-9-continued

| Ex. No. | IUPAC name | structural formula | salt | MS |
|---|---|---|---|---|
| 44 | 3-benzyl-1-(trans-4-((5-cyanopyridin-2-yl)amino)cyclohexyl)-1-(4-(3,5-dimethyl-1,2-oxazol-4-yl)phenyl)urea | | | 521.2 |
| 45 | 3-benzyl-1-(trans-4-((5-cyanopyridin-2-yl)amino)cyclohexyl)-1-(4-(2-cyanopyrimidin-5-yl)phenyl)urea | | | 529.3 |
| 46 | 3-benzyl-1-(trans-4-((5-cyanopyridin-2-yl)amino)cyclohexyl)-1-(4-(2-furyl)phenyl)urea | | | 492.3 |

TABLE 1-10

| Ex. No. | IUPAC name | structural formula | salt | MS |
|---|---|---|---|---|
| 47 | 1-(4-(6-aminopyridin-3-yl)phenyl)-3-benzyl-1-(trans-4-((5-cyanopyridin-2-yl)amino)cyclohexyl)urea | | | 518.3 |
| 48 | 1-(4-(2-aminopyridin-3-yl)phenyl)-3-benzyl-1-(trans-4-((5-cyanopyridin-2-yl)amino)cyclohexyl)urea | | | 518.3 |
| 49 | 1-(4-(2-aminopyridin-4-yl)phenyl)-3-benzyl-1-(trans-4-((5-cyanopyridin-2-yl)amino)cyclohexyl)urea | | | 518.3 |

TABLE 1-10-continued

| Ex. No. | IUPAC name | structural formula | salt | MS |
|---|---|---|---|---|
| 50 | 3-benzyl-1-(trans-4-((5-cyanopyridin-2-yl)amino)-cyclohexyl)-1-(4-(morpholin-4-ylmethyl)phenyl)urea | | | 525.4 |
| 51 | 3-benzyl-1-(trans-4-((5-cyanopyridin-2-yl)amino)-cyclohexyl)-1-(4-methylphenyl)urea | | | 440.2 |

TABLE 1-11

| Ex. No. | IUPAC name | structural formula | salt | MS |
|---|---|---|---|---|
| 52 | 3-benzyl-1-biphenyl-4-yl-1-(trans-4-((5-cyanopyridin-2-yl)amino)cyclohexyl)urea | | | 502.3 |
| 53 | 3-benzyl-1-(trans-4-((5-cyanopyridin-2-yl)amino)cyclohexyl)-1-(3'-methoxybiphenyl-4-yl)urea | | | 532.2 |

TABLE 1-11-continued

| Ex. No. | IUPAC name | structural formula | salt | MS |
|---|---|---|---|---|
| 54 | 3-benzyl-1-(2'-cyanobiphenyl-4-yl)-1-(trans-4-((5-cyanopyridin-2-yl)amino)cyclohexyl)urea | | | 527.2 |
| 55 | 3-benzyl-1-(4'-cyanobiphenyl-4-yl)-1-(trans-4-((5-cyanopyridin-2-yl)amino)cyclohexyl)urea | | | 527.2 |
| 56 | 3-benzyl-1-(3'-cyanobiphenyl-4-yl)-1-(trans-4-((5-cyanopyridin-2-yl)amino)cyclohexyl)urea | | | 527.3 |

TABLE 1-12

| Ex. No. | IUPAC name | structural formula | salt | MS |
|---|---|---|---|---|
| 57 | 3-benzyl-1-(trans-4-((5-cyanopyridin-2-yl)amino)-cyclohexyl)-1-(4-(2-methoxyethyl)phenyl)urea | | | 484.3 |

TABLE 1-12-continued

| Ex. No. | IUPAC name | structural formula | salt | MS |
|---|---|---|---|---|
| 58 | 3-benzyl-1-(trans-4-((5-cyanopyridin-2-yl)amino)-cyclohexyl)-1-(4-(piperidin-1-ylmethyl)phenyl)urea | | | 523.4 |
| 59 | 3-benzyl-1-(trans-4-((5-cyanopyridin-2-yl)amino)-cyclohexyl)-1-(4-(1-methyl-6-oxo-1,6-dihydropyridin-3-yl)phenyl)urea | | | 533.3 |
| 60 | 3-benzyl-1-(trans-4-((5-cyanopyridin-2-yl)amino)-cyclohexyl)-1-(4-(6-methoxypyridin-2-yl)phenyl)urea | | | 533.3 |
| 61 | 3-benzyl-1-(trans-4-((5-cyanopyridin-2-yl)amino)cyclohexyl)-1-(4-(6-methoxypyridin-3-yl)phenyl)urea | | | 533.3 |

TABLE 1-13

| Ex. No. | IUPAC name | structural formula | salt | MS |
|---|---|---|---|---|
| 62 | 2-(4-(4-((benzylcarbamoyl)(trans-4-((5-cyanopyridin-2-yl)amino)cyclohexyl)amino)phenyl)-1H-pyrazol-1-yl)acetamide | | | 549.3 |
| 63 | 3-benzyl-1-(trans-4-((5-cyanopyridin-2-yl)amino)cyclohexyl)-1-(4-(1-(2-hydroxy-2-methylpropyl)-1H-pyrazol-4-yl)phenyl)urea | | | 564.3 |
| 64 | 3-benzyl-1-(trans-4-((5-cyanopyridin-2-yl)amino)cyclohexyl)-1-(4-(1-(2-(morpholin-4-yl)ethyl)-1H-pyrazol-4-yl)phenyl)urea | | | 605.4 |
| 65 | 3-benzyl-1-(trans-4-((5-cyanopyridin-2-yl)amino)cyclohexyl)-1-(4-(1-ethyl-1H-pyrazol-4-yl)phenyl)urea | | | 520.3 |

TABLE 1-13-continued

| Ex. No. | IUPAC name | structural formula | salt | MS |
|---|---|---|---|---|
| 66 | 3-benzyl-1-(trans-4-((5-cyanopyridin-2-yl)amino)cyclohexyl)-1-(4-(1-isopropyl-1H-pyrazol-4-yl)phenyl)urea | | | 534.3 |

TABLE 1-14

| Ex. No. | IUPAC name | structural formula | salt | MS |
|---|---|---|---|---|
| 67 | 3-benzyl-1-(trans-4-((5-cyanopyridin-2-yl)amino)cyclohexyl)-1-(4-(2-methoxypyridin-3-yl)phenyl)urea | | | 533.3 |
| 68 | 3-benzyl-1-(trans-4-((5-cyanopyridin-2-yl)amino)cyclohexyl)-1-(4-(methoxymethyl)phenyl)urea | | | 470.3 |
| 69 | 3-benzyl-1-(trans-4-((5-cyanopyridin-2-yl)amino)cyclohexyl)-1-(4-(3,6-dihydro-2H-pyran-4-yl)phenyl)urea | | | 508.3 |

TABLE 1-14-continued

| Ex. No. | IUPAC name | structural formula | salt | MS |
|---|---|---|---|---|
| 70 | 3-benzyl-1-(trans-4-((5-cyanopyridin-2-yl)amino)cyclohexyl)-1-(4-(1-methyl-1,2,3,6-tetrahydropyridin-4-yl)phenyl)urea | 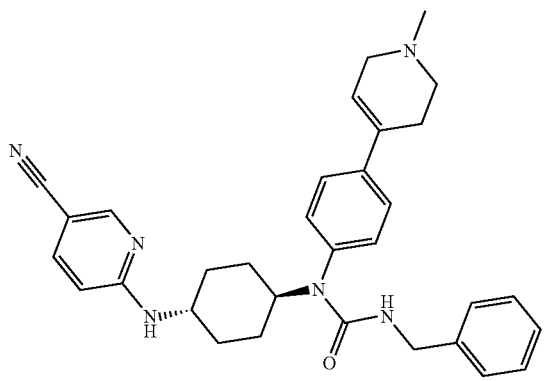 [SMILES: CN1CC=C(c2ccc(N(C(=O)NCc3ccccc3)[C@H]3CC[C@H](Nc4ccc(C#N)cn4)CC3)cc2)CC1] | | 521.3 |
| 71 | 3-benzyl-1-(trans-4-((5-cyanopyridin-2-yl)amino)cyclohexyl)-1-(4-vinylphenyl)urea | 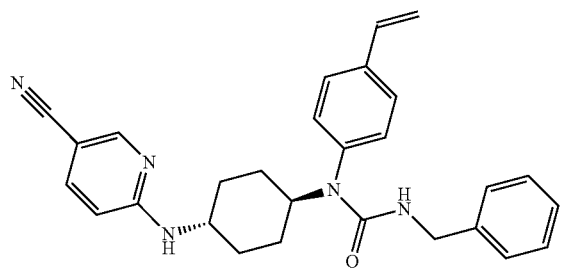 [SMILES: C=Cc1ccc(N(C(=O)NCc2ccccc2)[C@H]2CC[C@H](Nc3ccc(C#N)cn3)CC2)cc1] | | 452.2 |

TABLE 1-15

| Ex. No. | IUPAC name | structural formula | salt | MS |
|---|---|---|---|---|
| 72 | 3-benzyl-1-(trans-4-((5-cyanopyridin-2-yl)amino)cyclohexyl)-1-(4-(prop-1-en-2-yl)phenyl)urea | 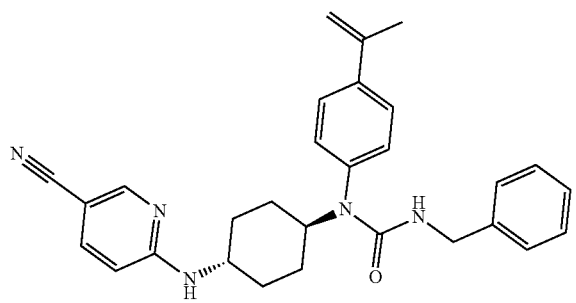 [SMILES: C=C(C)c1ccc(N(C(=O)NCc2ccccc2)[C@H]2CC[C@H](Nc3ccc(C#N)cn3)CC2)cc1] | | 466.2 |
| 73 | 3-benzyl-1-(trans-4-((5-cyanopyridin-2-yl)amino)cyclohexyl)-1-(4-(1-(pyridin-2-ylmethyl)-1H-pyrazol-4-yl)phenyl)urea | 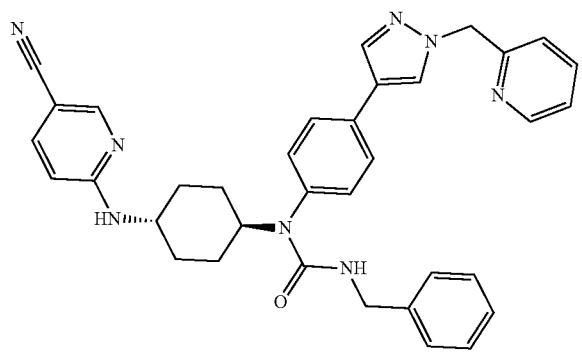 [SMILES: N#Cc1ccc(N[C@H]2CC[C@H](N(C(=O)NCc3ccccc3)c3ccc(-c4cnn(Cc5ccccn5)c4)cc3)CC2)nc1] | | 583.3 |

TABLE 1-15-continued

| Ex. No. | IUPAC name | structural formula | salt | MS |
|---|---|---|---|---|
| 74 | 3-benzyl-1-(trans-4-((5-cyanopyridin-2-yl)amino)cyclohexyl)-1-(4-(1-(pyridin-3-ylmethyl)-1H-pyrazol-4-yl)phenyl)urea | | | 583.3 |
| 75 | 3-benzyl-1-(trans-4-((5-cyanopyridin-2-yl)amino)cyclohexyl)-1-(4-(4,5,6,7-tetrahydropyrazolo[1,5-a]pyridin-3-yl)phenyl)urea | | | 546.3 |
| 76 | 3-(4-(4-((benzylcarbamoyl)(trans-4-((5-cyanopyridin-2-yl)amino)cyclohexyl)amino)phenyl)-1H-pyrazol-1-yl)propanamide | | | 563.3 |

TABLE 1-16
| Ex. No. | IUPAC name | structural formula | salt | MS |
|---|---|---|---|---|
| 77 | 3-benzyl-1-(trans-4-((5-cyanopyridin-2-yl)amino)cyclohexyl)-1-(4-(2-thienyl)phenyl)urea | 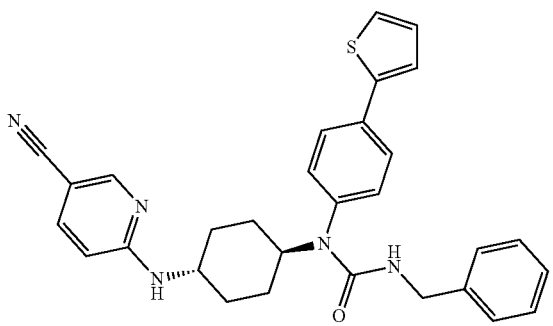 [SMILES: N#Cc1ccc(N[C@H]2CC[C@H](N(C(=O)NCc3ccccc3)c3ccc(-c4cccs4)cc3)CC2)nc1] | | 508.3 |
| 78 | 3-benzyl-1-(6-(1-methyl-1H-pyrazol-4-yl)pyridin-3-yl)-1-(trans-4-((5-(trifluoromethyl)pyridin-2-yl)amino)cyclohexyl)urea | 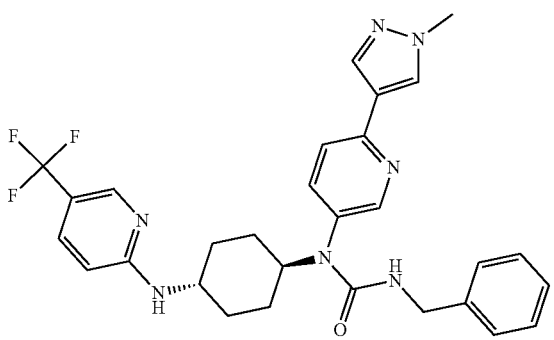 [SMILES: Cn1cc(-c2ccc(N(C(=O)NCc3ccccc3)[C@H]3CC[C@H](Nc4ccc(C(F)(F)F)cn4)CC3)cn2)cn1] | | 550.2 |
| 79 | 3-benzyl-1-(trans-4-((5-cyanopyridin-2-yl)amino)cyclohexyl)-1-(4-(pyridin-3-yl)phenyl)urea | 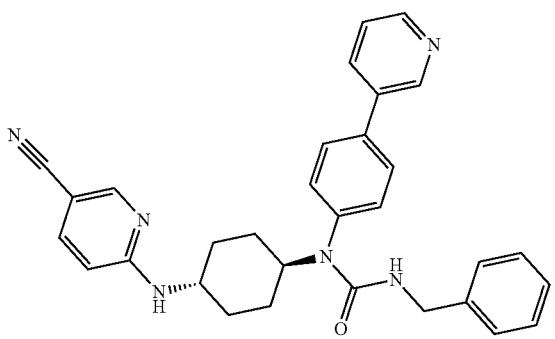 [SMILES: N#Cc1ccc(N[C@H]2CC[C@H](N(C(=O)NCc3ccccc3)c3ccc(-c4cccnc4)cc3)CC2)nc1] | | 503.3 |
| 80 | 3-benzyl-1-(trans-4-((5-cyanopyridin-2-yl)amino)cyclohexyl)-1-(4-(morpholin-4-yl)phenyl)urea | 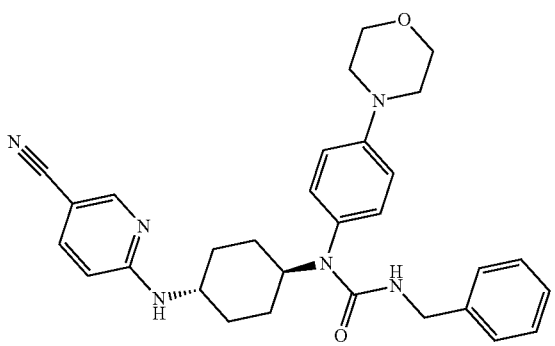 [SMILES: N#Cc1ccc(N[C@H]2CC[C@H](N(C(=O)NCc3ccccc3)c3ccc(N4CCOCC4)cc3)CC2)nc1] | | 511.2 |

TABLE 1-16-continued

| Ex. No. | IUPAC name | structural formula | salt | MS |
|---|---|---|---|---|
| 81 | 3-benzyl-1-(trans-4-((5-cyanopyridin-2-yl)amino)cyclohexyl)-1-(4-(pyrimidin-5-yl)phenyl)urea | | | 504.2 |

TABLE 1-17

| Ex. No. | IUPAC name | structural formula | salt | MS |
|---|---|---|---|---|
| 82 | 1-(4-(4-acetylpiperazin-1-yl)phenyl)-3-benzyl-1-(trans-4-((5-cyanopyridin-2-yl)amino)cyclohexyl)urea | | | 552.4 |
| 83 | 1-(4-anilinophenyl)-3-benzyl-1-(trans-4-((5-cyanopyridin-2-yl)amino)cyclohexyl)urea | | | 517.2 |

TABLE 1-17-continued

| Ex. No. | IUPAC name | structural formula | salt | MS |
|---|---|---|---|---|
| 84 | 3-benzyl-1-(trans-4-((5-cyanopyridin-2-yl)amino)cyclohexyl)-1-(4-(1-methyl-1H-pyrazol-3-yl)phenyl)urea | | | 506.2 |
| 85 | 3-benzyl-1-(trans-4-((5-cyanopyridin-2-yl)amino)cyclohexyl)-1-(4-(1H-pyrazol-4-yl)phenyl)urea | | | 492.3 |
| 86 | 3-benzyl-1-(trans-4-((5-cyanopyridin-2-yl)amino)cyclohexyl)-1-(4-(pyridin-4-yl)phenyl)urea | | | 503.2 |

TABLE 1-18

| Ex. No. | IUPAC name | structural formula | salt | MS |
|---|---|---|---|---|
| 87 | 3-benzyl-1-(trans-4-((5-cyanopyridin-2-yl)amino)cyclohexyl)-1-(4-(1-methyl-1H-pyrazol-5-yl)phenyl)urea | | | 506.3 |

TABLE 1-18-continued

| Ex. No. | IUPAC name | structural formula | salt | MS |
|---|---|---|---|---|
| 88 | 3-benzyl-1-(trans-4-((5-cyanopyridin-2-yl)amino)cyclohexyl)-1-(4-(pyridin-2-yl)phenyl)urea | | | 503.2 |
| 89 | 3-benzyl-1-(trans-4-((5-cyanopyridin-2-yl)amino)cyclohexyl)-1-phenylurea | | | 426.2 |
| 90 | 1-benzyl-3-(trans-4-((5-cyanopyridin-2 yl)amino)cyclohexyl)-1-methyl-3-(4-(1-methyl-1H-pyrazol-4-yl)phenyl)urea | | | 520.3 |
| 91 | 1-(trans-4-((5-cyanopyridin-2-yl)amino)cyclohexyl)-1-(4-(1-methyl-1H-pyrazol-4-yl)phenyl)-3-((1R)-1-phenylethyl)urea | | | 520.3 |

TABLE 1-19

| Ex. No. | IUPAC name | structural formula | salt | MS |
|---|---|---|---|---|
| 92 | 1-(trans-4-((5-cyanopyridin-2-yl)amino)cyclohexyl)-1-(4-(1-methyl-1H-pyrazol-4-yl)phenyl)-3-((1S)-1-phenylethyl)urea | | | 520.3 |
| 93 | 1-(trans-4-((5-cyanopyridin-2-yl)amino)cyclohexyl)-3-((2-methoxypyridin-4-yl)methyl)-1-(4-(1-methyl-1H-pyrazol-4-yl)phenyl)urea | | | 537.2 |
| 94 | 1-(trans-4-((5-cyanopyridin-2-yl)amino)cyclohexyl)-1-(4-(1-methyl-1H-pyrazol-4-yl)phenyl)-3-(3-(methylsulfonyl)benzyl)urea | | | 584.2 |
| 95 | 3-benzyl-1-(trans-4-((5-cyanopyridin-2-yl)amino)cyclohexyl)-1-(6-(1-methyl-1H-pyrazol-4-yl)pyridazin-3-yl)urea | | | 508.4 |

TABLE 1-19-continued

| Ex. No. | IUPAC name | structural formula | salt | MS |
|---|---|---|---|---|
| 96 | 3-benzyl-1-(trans-4-((5-cyanopyridin-2-yl)amino)cyclohexyl)-1-(5-(1-methyl-1H-pyrazol-4-yl)pyridin-2-yl)urea | | | 507.3 |

TABLE 1-20

| Ex. No. | IUPAC name | structural formula | salt | MS |
|---|---|---|---|---|
| 97 | 3-benzyl-1-(trans-4-((5-cyanopyridin-2-yl)amino)cyclohexyl)-1-(4-(4-methoxypiperidin-1-yl)phenyl)urea | | | 539.3 |
| 98 | 3-benzyl-1-(trans-4-((5-cyanopyridin-2-yl)amino)cyclohexyl)-1-(4-((2-methoxyethyl)amino)-phenyl)urea | | | 499.3 |

TABLE 1-20-continued

| Ex. No. | IUPAC name | structural formula | salt | MS |
|---|---|---|---|---|
| 99 | 3-benzyl-1-(4-(4-cyanopiperidin-1-yl)phenyl)-1-(trans-4-((5-cyanopyridin-2-yl)amino)cyclohexyl)urea | | | 534.3 |
| 100 | 1-(4-((benzylcarbamoyl)(trans-4-((5-cyanopyridin-2-yl)amino)cyclohexyl)amino)-phenyl)piperidine-4-carboxamide | | | 552.3 |
| 101 | 3-benzyl-1-(trans-4-((5-cyanopyridin-2-yl)amino)cyclohexyl)-1-(4-(4-(dimethylamino)piperidin-1-yl)phenyl)urea | | | 552.4 |

TABLE 1-21
| Ex. No. | IUPAC name | structural formula | salt | MS |
|---|---|---|---|---|
| 102 | 3-benzyl-1-(trans-4-((5-cyanopyridin-2-yl)amino)cyclohexyl)-1-(4-(2-oxa-7-azaspiro[3.5]nonan-7-yl)phenyl)urea | 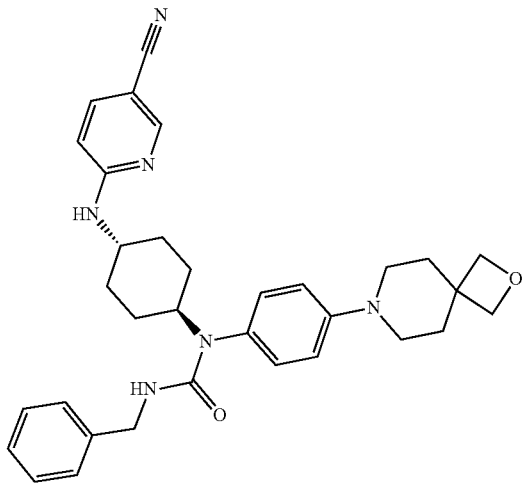 [SMILES: N#Cc1ccc(N[C@H]2CC[C@H](N(C(=O)NCc3ccccc3)c3ccc(N4CCC5(CC4)COC5)cc3)CC2)nc1] | | 551.3 |
| 103 | 3-benzyl-1-(trans-4-((5-cyanopyridin-2-yl)amino)cyclohexyl)-1-(4-(2-oxa-6-azaspiro[3.5]nonan-6-yl)phenyl)urea | 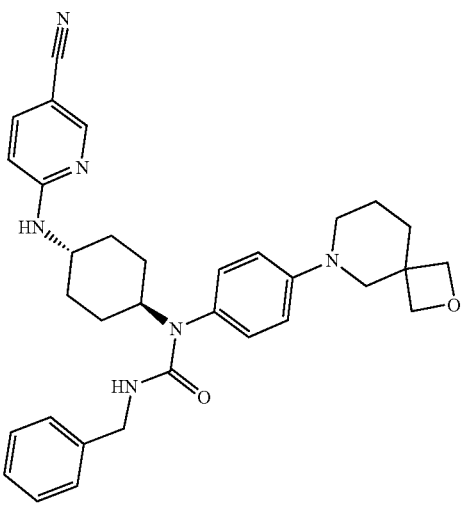 [SMILES: N#Cc1ccc(N[C@H]2CC[C@H](N(C(=O)NCc3ccccc3)c3ccc(N4CCCC5(COC5)C4)cc3)CC2)nc1] | | 551.4 |
| 104 | 3-benzyl-1-(trans-4-((5-cyanopyridin-2-yl)amino)cyclohexyl)-1-(4-(1,1-dioxide-thiomorpholin-4-yl)phenyl)urea | 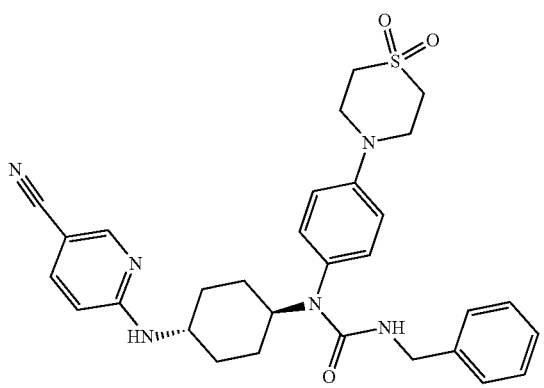 [SMILES: N#Cc1ccc(N[C@H]2CC[C@H](N(C(=O)NCc3ccccc3)c3ccc(N4CCS(=O)(=O)CC4)cc3)CC2)nc1] | | 559.3 |

TABLE 1-21-continued

| Ex. No. | IUPAC name | structural formula | salt | MS |
|---|---|---|---|---|
| 105 | 3-benzyl-1-(trans-4-((5-cyanopyridin-2-yl)amino)cyclohexyl)-1-(4-(4-methylpiperazin-1-yl)phenyl)urea | | | 524.3 |
| 106 | 3-benzyl-1-(trans-4-((5-cyanopyridin-2-yl)amino)cyclohexyl)-1-(4-(4-(methylsulfonyl)piperazin-1-yl)phenyl)urea | | | 588.3 |

TABLE 1-22

| Ex. No. | IUPAC name | structural formula | salt | MS |
|---|---|---|---|---|
| 107 | 3-benzyl-1-(trans-4-((5-cyanopyridin-2-yl)amino)cyclohexyl)-1-(4-((3S)-3-methoxypyrrolidin-1-yl)phenyl)urea | | | 525.4 |

TABLE 1-22-continued

| Ex. No. | IUPAC name | structural formula | salt | MS |
|---|---|---|---|---|
| 108 | 3-benzyl-1-(4-((4-cyanophenyl)amino)phenyl)-1-(trans-4-((5-cyanopyridin-2-yl)amino)cyclohexyl)urea | | | 542.3 |
| 109 | 3-benzyl-1-(4-((3-cyanophenyl)amino)phenyl)-1-(trans-4-((5-cyanopyridin-2-yl)amino)cyclohexyl)urea | | | 542.3 |
| 110 | 3-benzyl-1-(4-((2-cyanophenyl)amino)phenyl)-1-(trans-4-((5-cyanopyridin-2-yl)amino)cyclohexyl)urea | | | 542.3 |
| 111 | 3-benzyl-1-(trans-4-((5-cyanopyridin-2-yl)amino)cyclohexyl)-1-(4-((4-methoxyphenyl)amino)phenyl)urea | | | 547.3 |

TABLE 1-23

| Ex. No. | IUPAC name | structural formula | salt | MS |
|---|---|---|---|---|
| 112 | 3-benzyl-1-(trans-4-((5-cyanopyridin-2-yl)amino)cyclohexyl)-1-(4-((3-methoxyphenyl)amino)phenyl)urea | | | 547.3 |
| 113 | 3-benzyl-1-(trans-4-((5-cyanopyridin-2-yl)amino)cyclohexyl)-1-(4-((2-methoxyphenyl)amino)phenyl)urea | | | 547.3 |
| 114 | 3-benzyl-1-(trans-4-((5-cyanopyridin-2-yl)amino)cyclohexyl)-1-(4-((1-methyl-1H-pyrazol-5-yl)amino)phenyl)urea | | | 521.3 |
| 115 | 3-benzyl-1-(trans-4-((5-cyanopyridin-2-yl)amino)cyclohexyl)-1-(4-((1-methyl-1H-pyrazol-4-yl)amino)phenyl)urea | | | 521.3 |
| 116 | 3-benzyl-1-(trans-4-((5-cyanopyridin-2-yl)amino)cyclohexyl)-1-(4-((1-methyl-1H-pyrazol-3-yl)amino)phenyl)urea | | | 521.3 |

TABLE 1-24

| Ex. No. | IUPAC name | structural formula | salt | MS |
|---|---|---|---|---|
| 117 | 4-((benzylcarbamoyl)(trans-4-((5-cyanopyridin-2-yl)amino)cyclohexyl)amino)-N,N-dimethylbenzamido | | | 497.3 |
| 118 | 3-benzyl-1-(trans-4-((5-cyanopyridin-2-yl)amino)cyclohexyl)-1-(5-(1-methyl-1H-pyrazol-4-yl)pyrazin-2-yl)urea | | | 508.3 |
| 119 | 3-benzyl-1-(trans-4-((5-cyanopyridin-2-yl)amino)cyclohexyl)-1-(4-(2-oxopyrrolidin-1-yl)phenyl)urea | | | 509.3 |
| 120 | 4'-((benzylcarbamoyl)(trans-4-((5-cyanopyridin-2-yl)amino)cyclohexyl)amino)biphenyl-3-carboxamide | | | 545.3 |

TABLE 1-24-continued

| Ex. No. | IUPAC name | structural formula | salt | MS |
|---|---|---|---|---|
| 121 | 4-((benzylcarbamoyl)(trans-4-((5-cyanopyridin-2-yl)amino)cyclohexyl)amino)benzoic acid | | | 470.2 |

TABLE 1-25

| Ex. No. | IUPAC name | structural formula | salt | MS |
|---|---|---|---|---|
| 122 | 4-((benzylcarbamoyl)(trans-4-((5-cyanopyridin-2-yl)amino)cyclohexyl)amino)benzamide | | | 469.3 |
| 123 | 3-benzyl-1-(trans-4-((5-cyanopyridin-2-yl)amino)cyclohexyl)-1-(4-(pyrazin-2-yl)phenyl)urea | | | 504.2 |
| 124 | 3-benzyl-1-(trans-4-((5-cyanopyridin-2-yl)amino)cyclohexyl)-1-(4-(1H-pyrazol-1-yl)phenyl)urea | | | 492.3 |

TABLE 1-25-continued

| Ex. No. | IUPAC name | structural formula | salt | MS |
|---|---|---|---|---|
| 125 | ethyl 1-(4-((benzylcarbamoyl)(trans-4-((5-cyanopyridin-2-yl)amino)cyclohexyl)amino)phenyl)-1H-pyrazole-4-carboxylate | | | 564.3 |
| 126 | methyl 5-(4-((benzylcarbamoyl)(trans-4-((5-cyanopyridin-2-yl)amino)cyclohexyl)amino)phenyl)-2-furoate | | | 550.2 |

TABLE 1-26

| Ex. No. | IUPAC name | structural formula | salt | MS |
|---|---|---|---|---|
| 127 | 3-benzyl-1-(trans-4-((5-cyanopyridin-2-yl)amino)cyclohexyl)-1-(4-(1H-imidazol-1-yl)phenyl)urea | | | 492.3 |
| 128 | 3-benzyl-1-(trans-4-((5-cyanopyridin-2-yl)amino)cyclohexyl)-1-(4-hydroxyphenyl)urea | | | 442.2 |

TABLE 1-26-continued

| Ex. No. | IUPAC name | structural formula | salt | MS |
|---|---|---|---|---|
| 129 | 1-(4-((benzylcarbamoyl)(trans-4-((5-cyanopyridin-2-yl)amino)cyclohexyl)amino)phenyl)-1H-pyrazole-4-carboxylic acid | | | 536.3 |
| 130 | 5-(4-((benzylcarbamoyl)(trans-4-((5-cyanopyridin-2-yl)amino)cyclohexyl)amino)phenyl)-2-furamide | | | 535.2 |
| 131 | 1-(4-((benzylcarbamoyl)(trans-4-((5-cyanopyridin-2-yl)amino)cyclohexyl)amino)phenyl)-1H-pyrazole-4-carboxamide | | | 535.3 |

TABLE 1-27

| Ex. No. | IUPAC name | structural formula | salt | MS |
|---|---|---|---|---|
| 132 | 2-(4-((benzylcarbamoyl)(trans-4-((5-cyanopyridin-2-yl)amino)cyclohexyl)amino)phenyl)-1,3-thiazole-5-carboxamide | | | 552.2 |
| 133 | 1-(trans-4-((5-cyanopyridin-2-yl)amino)cyclohexyl)-1-(4-(1-methyl-1H-pyrazol-4-yl)phenyl)-3-((6-methylpyridin-2-yl)methyl)urea | | | 521.3 |
| 134 | 1-(trans-4-((5-cyanopyridin-2-yl)amino)cyclohexyl)-1-(4-(1-methyl-1H-pyrazol-4-yl)phenyl)-3-((1-methyl-1H-pyrrol-2-yl)methyl)urea | | | 509.3 |
| 135 | 1-(trans-4-((5-cyanopyridin-2-yl)amino)cyclohexyl)-1-(4-(1-methyl-1H-pyrazol-4-yl)phenyl)-3-(pyrimidin-5-ylmethyl)urea | | | 508.3 |

TABLE 1-27-continued

| Ex. No. | IUPAC name | structural formula | salt | MS |
|---|---|---|---|---|
| 136 | 1-(trans-4-((5-cyanopyridin-2-yl)amino)cyclohexyl)-3-((6-methoxypyridin-2-yl)methyl)-1-(4-(1-methyl-1H-pyrazol-4-yl)phenyl)urea | | | 537.3 |

TABLE 1-28

| Ex. No. | IUPAC name | structural formula | salt | MS |
|---|---|---|---|---|
| 137 | 1-(trans-4-((5-cyanopyridin-2-yl)amino)cyclohexyl)-1-(4-(1-methyl-1H-pyrazol-4-yl)phenyl)-3-(1,3-thiazol-2-ylmethyl)urea | | | 513.2 |
| 138 | 1-(trans-4-((5-cyanopyridin-2-yl)amino)cyclohexyl)-3-((5-methoxypyridin-3-yl)methyl)-1-(4-(1-methyl-1H-pyrazol-4-yl)phenyl)urea | | | 537.3 |

TABLE 1-28-continued

| Ex. No. | IUPAC name | structural formula | salt | MS |
|---|---|---|---|---|
| 139 | N-(3-(((((trans-4-((5-cyanopyridin-2-yl)amino)cyclohexyl)(4-(1-methyl-1H-pyrazol-4-yl)phenyl)carbamoyl)amino)methyl)phenyl)-methanesulfonamide | | | 599.3 |
| 140 | 3-(3-cyanobenzyl)-1-(trans-4-((5-cyanopyridin-2-yl)amino)cyclohexyl)-1-(4-(1-methyl-1H-pyrazol-4-yl)phenyl)urea | | | 531.3 |
| 141 | 1-(trans-4-((5-cyanopyridin-2-yl)amino)cyclohexyl)-1-(4-(1-methyl-1H-pyrazol-4-yl)phenyl)-3-(pyrimidin-2-ylmethyl)urea | | | 508.3 |

TABLE 1-29

| Ex. No. | IUPAC name | structural formula | salt | MS |
|---|---|---|---|---|
| 142 | 4'-((benzylcarbamoyl)(trans-4-((5-cyanopyridin-2-yl)amino)cyclohexyl)amino)biphenyl-4-carboxamide | | | 545.3 |
| 143 | 3-benzyl-1-(3,3'-bipyridin-6-yl)-1-(trans-4-((5-cyanopyridin-2-yl)amino)cyclohexyl)urea | | | 504.2 |
| 144 | 3-benzyl-1-(5-(1-methyl-1H-pyrazol-4-yl)pyrazin-2-yl)-1-(trans-4-((5-(trifluoromethyl)pyridin-2-yl)amino)cyclohexyl)urea | | | 551.3 |
| 145 | 3-benzyl-1-(2,3'-bipyridin-5-yl)-1-(trans-4-((5-cyanopyridin-2-yl)amino)cyclohexyl)urea | | | 504.2 |

TABLE 1-29-continued

| Ex. No. | IUPAC name | structural formula | salt | MS |
|---|---|---|---|---|
| 146 | 1-(trans-4-((5-cyanopyridin-2-yl)amino)cyclohexyl)-3-(3-methoxybenzyl)-1-(6-(1-methyl-1H-pyrazol-4-yl)pyridin-3-yl)urea | | | 537.2 |

TABLE 1-30

| Ex. No. | IUPAC name | structural formula | salt | MS |
|---|---|---|---|---|
| 147 | 3-benzyl-1-(trans-4-((5-cyanopyridin-2-yl)amino)cyclohexyl)-1-(4-(pyridin-3-yl)phenyl)urea hydrochloride | | HCl | 503.3 |
| 148 | 3-benzyl-1-(5-(1-methyl-1H-pyrazol-4-yl)pyridin-2-yl)-1-(trans-4-((5-(trifluoromethyl)pyridin-2-yl)amino)cyclohexyl)urea | | | 550.3 |
| 149 | 3-benzyl-1-(trans-4-((5-cyanopyridin-2-yl)amino)cyclohexyl)-1-(6'-oxo-1',6'-dihydro-2,3'-bipyridin-5-yl)urea | | | 520.2 |

TABLE 1-30-continued

| Ex. No. | IUPAC name | structural formula | salt | MS |
|---|---|---|---|---|
| 150 | 3-benzyl-1-(trans-4-((5-cyanopyridin-2-yl)amino)cyclohexyl)-1-(6'-oxo-1',6'-dihydro-3,3'-bipyridin-6-yl)urea | | | 520.2 |
| 151 | 3-benzyl-1-(trans-4-((5-cyanopyridin-2-yl)amino)cyclohexyl)-1-(6-(6-oxo-1,6-dihydropyridin-3-yl)-pyridazin-3-yl)urea | | | 521.3 |

TABLE 1-31

| Ex. No. | IUPAC name | structural formula | salt | MS |
|---|---|---|---|---|
| 152 | 3-benzyl-1-(trans-4-((5-cyanopyridin-2-yl)amino)cyclohexyl)-1-(5-(1-methyl-1H-pyrazol-4-yl)pyrimidin-2-yl)urea | | | 508.4 |

TABLE 1-31-continued

| Ex. No. | IUPAC name | structural formula | salt | MS |
|---|---|---|---|---|
| 153 | 1-(trans-4-((5-cyanopyridin-2-yl)amino)cyclohexyl)-3-(2,2-dimethylpropyl)-1-(4-(1-methyl-1H-pyrazol-4-yl)phenyl)urea | | | 486.3 |
| 154 | 1-(trans-4-((5-cyanopyridin-2-yl)amino)cyclohexyl)-1-(4-(1-methyl-1H-pyrazol-4-yl)phenyl)-3-(tetrahydro-2H-pyran-4-ylmethyl)urea | | | 514.3 |
| 155 | 1-(trans-4-((5-cyanopyridin-2-yl)amino)cyclohexyl)-3-(cyclopropylmethyl)-1-(4-(1-methyl-1H-pyrazol-4-yl)phenyl)urea | | | 470.3 |
| 156 | 3-benzyl-1-(trans-4-((5-cyanopyridin-2-yl)amino)cyclohexyl)-1-(3-fluoro-4-(1-methyl-1H-pyrazol-4-yl)phenyl)urea | | | 524.3 |

TABLE 1-32

| Ex. No. | IUPAC name | structural formula | salt | MS |
|---|---|---|---|---|
| 157 | 3-benzyl-1-(trans-4-((5-cyanopyridin-2-yl)amino)cyclohexyl)-1-(4-((4-methylpiperazin-1-yl)methyl)phenyl)urea | | | 538.4 |
| 158 | 3-benzyl-1-(trans-4-((5-cyanopyridin-2-yl)amino)cyclohexyl)-1-(2'-fluorobiphenyl-4-yl)urea | | | 520.3 |
| 159 | 3-benzyl-1-(trans-4-((5-cyanopyridin-2-yl)amino)cyclohexyl)-1-(3'-fluorobiphenyl-4-yl)urea | | | 520.2 |
| 160 | 3-benzyl-1-(trans-4-((5-cyanopyridin-2-yl)amino)cyclohexyl)-1-(4'-methoxybiphenyl-4-yl)urea | | | 532.2 |

TABLE 1-32-continued

| Ex. No. | IUPAC name | structural formula | salt | MS |
|---|---|---|---|---|
| 161 | 3-benzyl-1-(4-(1-methyl-1H-pyrazol-4-yl)phenyl)-1-(trans-4-((5-(trifluoromethyl)pyridin-2-yl)amino)cyclohexyl)urea | | | 549.3 |

TABLE 1-33

| Ex. No. | IUPAC name | structural formula | salt | MS |
|---|---|---|---|---|
| 162 | 3-benzyl-1-(trans-4-((5-cyanopyridin-2-yl)amino)cyclohexyl)-1-(4-(pyridin-2-ylamino)phenyl)urea | | | 518.3 |
| 163 | 3-benzyl-1-(trans-4-((5-cyanopyridin-2-yl)amino)cyclohexyl)-1-(4-(pyridin-3-ylamino)phenyl)urea | | | 518.3 |
| 164 | 3-benzyl-1-(trans-4-((5-cyanopyridin-2-yl)amino)cyclohexyl)-1-(4-(pyridin-4-ylamino)phenyl)urea | | | 518.3 |

TABLE 1-33-continued

| Ex. No. | IUPAC name | structural formula | salt | MS |
|---|---|---|---|---|
| 165 | 2-(4-((benzylcarbamoyl)(trans-4-((5-cyanopyridin-2-yl)amino)cyclohexyl)amino)phenyl)-1,3-thiazole-4-carboxamide | 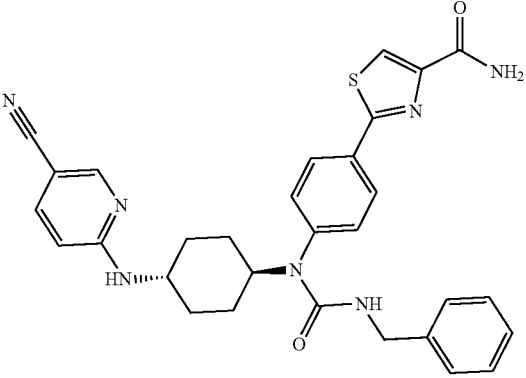 [SMILES: N#Cc1ccc(N[C@H]2CC[C@H](N(C(=O)NCc3ccccc3)c3ccc(-c4nc(C(N)=O)cs4)cc3)CC2)nc1] | | 552.3 |
| 166 | 3-benzyl-1-(trans-4-((5-cyanopyridin-2-yl)amino)cyclohexyl)-1-(4-(6-oxo-1,6-dihydropyridin-2-yl)phenyl)urea | 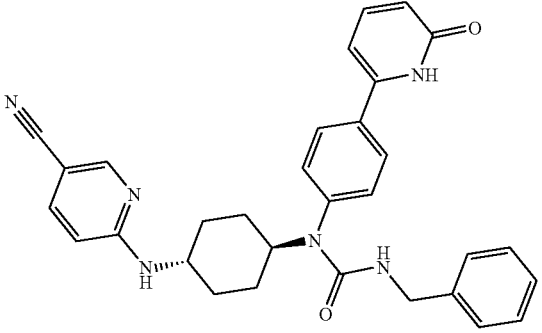 [SMILES: N#Cc1ccc(N[C@H]2CC[C@H](N(C(=O)NCc3ccccc3)c3ccc(-c4cccc(=O)[nH]4)cc3)CC2)nc1] | | 519.2 |

TABLE 1-34

| Ex. No. | IUPAC name | structural formula | salt | MS |
|---|---|---|---|---|
| 167 | 3-benzyl-1-(trans-4-((5-cyanopyridin-2-yl)amino)cyclohexyl)-1-(4-(6-oxo-1,6-dihydropyridin-3-yl)phenyl)urea | 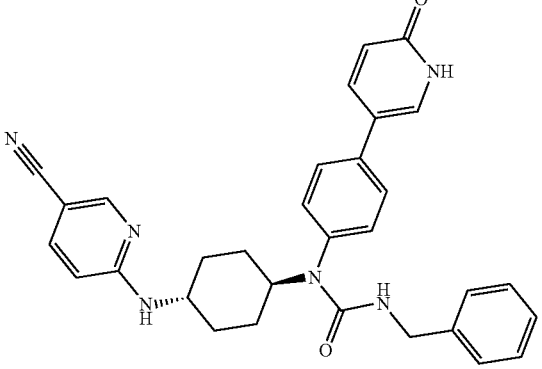 | | 519.3 |

TABLE 1-34-continued

| Ex. No. | IUPAC name | structural formula | salt | MS |
|---|---|---|---|---|
| 168 | 3-benzyl-1-(trans-4-((5-cyanopyridin-2-yl)amino)cyclohexyl)-1-(4-(2-oxo-1,2-dihydropyridin-4-yl)phenyl)urea | | | 519.2 |
| 169 | 3-benzyl-1-(trans-4-((5-cyanopyridin-2-yl)amino)cyclohexyl)-1-(4-(2-oxo-1,2-dihydropyridin-3-yl)phenyl)urea | | | 519.2 |
| 170 | 3-benzyl-1-(trans-4-((5-cyanopyridin-2-yl)amino)cyclohexyl)-1-(5-(pyridin-3-yl)-pyrazin-2-yl)urea | | | 505.3 |
| 171 | 3-benzyl-1-(trans-4-((5-cyanopyrimidin-2-yl)amino)cyclohexyl)-1-(4-(1-methyl-1H-pyrazol-4-yl)phenyl)urea | | | 507.3 |

TABLE 1-35

| Ex. No. | IUPAC name | structural formula | salt | MS |
|---|---|---|---|---|
| 172 | 3-benzyl-1-(5-(1-methyl-1H-pyrazol-4-yl)pyrimidin-2-yl)-1-(trans-4-((5-(trifluoromethyl)pyridin-2-yl)amino)cyclohexyl)urea | 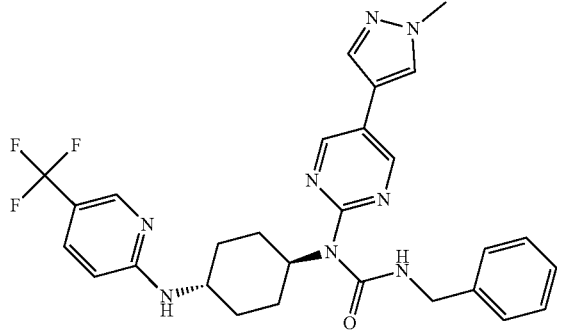 [SMILES: Cn1cc(-c2cnc(N(C(=O)NCc3ccccc3)[C@H]3CC[C@H](Nc4ccc(C(F)(F)F)cn4)CC3)nc2)cn1] | | 551.3 |
| 173 | 3-benzyl-1-(trans-4-((5-cyanopyridin-2-yl)amino)cyclohexyl)-1-(4-(pyridin-3-yl)phenyl)urea methanesulfonate | 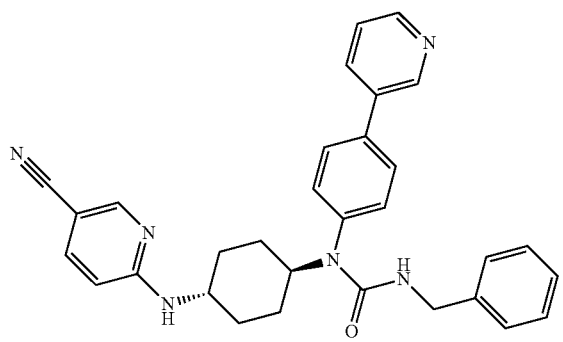 [SMILES: N#Cc1ccc(N[C@H]2CC[C@H](N(C(=O)NCc3ccccc3)c3ccc(-c4cccnc4)cc3)CC2)nc1] | MsOH | 503.3 |
| 174 | 1-(trans-4-((5-cyanopyridin-2-yl)amino)cyclohexyl)-1-(4-(1-methyl-1H-pyrazol-4-yl)phenyl)-3-(2-thienylmethyl)urea | 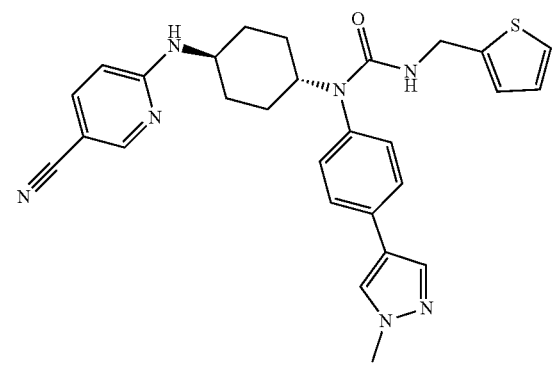 [SMILES: Cn1cc(-c2ccc(N(C(=O)NCc3cccs3)[C@H]3CC[C@H](Nc4ccc(C#N)cn4)CC3)cc2)cn1] | | 512.3 |
| 175 | N-(trans-4-((5-cyanopyridin-2-yl)amino)cyclohexyl)-N-(4-(1-methyl-1H-pyrazol-4-yl)phenyl)-3-phenylpropaneamide | 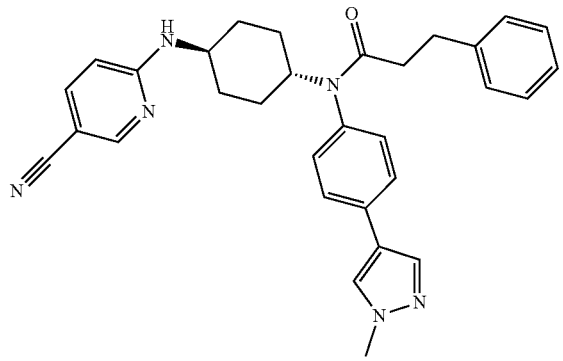 [SMILES: Cn1cc(-c2ccc(N(C(=O)CCc3ccccc3)[C@H]3CC[C@H](Nc4ccc(C#N)cn4)CC3)cc2)cn1] | | 505.3 |

TABLE 1-35-continued

| Ex. No. | IUPAC name | structural formula | salt | MS |
|---|---|---|---|---|
| 176 | 1-(trans-4-((5-cyanopyridin-2-yl)amino)cyclohexyl)-1-(4-(1-methyl-1H-pyrazol-4-yl)phenyl)-3-(2-phenylethyl)urea | | | 520.2 |

TABLE 1-36

| Ex. No. | IUPAC name | structural formula | salt | MS |
|---|---|---|---|---|
| 177 | 1-(trans-4-((5-cyanopyridin-2-yl)amino)cyclohexyl)-1-(4-(1-methyl-1H-pyrazol-4-yl)phenyl)-3-phenylurea | | | 492.3 |
| 178 | 3-benzyl-1-(trans-4-((5-cyanopyridin-2-yl)amino)cyclohexyl)-1-(3-methoxy-4-(1-methyl-1H-pyrazol-4-yl)phenyl)urea | | | 536.3 |

TABLE 1-36-continued

| Ex. No. | IUPAC name | structural formula | salt | MS |
|---|---|---|---|---|
| 179 | 3-benzyl-1-(trans-4-((5-cyanopyridin-2-yl)amino)cyclohexyl)-1-(4-(1-methyl-2-oxo-1,2-dihydropyridin-3-yl)phenyl)urea | | | 533.3 |
| 180 | 3-benzyl-1-(trans-4-((5-cyanopyridin-2-yl)amino)cyclohexyl)-1-(4-(1-methyl-2-oxo-1,2-dihydropyridin-4-yl)phenyl)urea | | | 533.3 |
| 181 | 3-benzyl-1-(trans-4-((5-cyanopyridin-2-yl)amino)cyclohexyl)-1-(4-(1-methyl-6-oxo-1,6-dihydropyridin-2-yl)phenyl)urea | | | 533.3 |

TABLE 1-37

| Ex. No. | IUPAC name | structural formula | salt | MS |
|---|---|---|---|---|
| 182 | 3-benzyl-1-(trans-4-((5-cyanopyridin-2-yl)amino)cyclohexyl)-1-(1'-methyl-6'-oxo-1',6'-dihydro-2,3'-bipyridin-5-yl)urea | | | 534.3 |
| 183 | 3-benzyl-1-phenyl-1-(trans-4-((5-(trifluoromethyl)pyridin-2-yl)amino)cyclohexyl)urea | | | 469.2 |
| 184 | 3-benzyl-1-(4-(1-methyl-1H-pyrazol-4-yl)phenyl)-1-(trans-4-(pyridin-2-ylamino)cyclohexyl)urea | | | 481.3 |
| 185 | 3-benzyl-1-(4-(1-methyl-1H-pyrazol-4-yl)phenyl)-1-(trans-4-(pyrimidin-2-ylamino)cyclohexyl)urea | | | 482.3 |

TABLE 1-37-continued

| Ex. No. | IUPAC name | structural formula | salt | MS |
|---|---|---|---|---|
| 186 | 2-((trans-4-((benzylcarbamoyl)(4-(1-methyl-1H-pyrazol-4-yl)phenyl)amino)cyclohexyl)amino)pyrimidine-5-carboxamide | | | 525.3 |

TABLE 1-38

| Ex. No. | IUPAC name | structural formula | salt | MS |
|---|---|---|---|---|
| 187 | 3-benzyl-1-(trans-4-((5-cyanopyridin-2-yl)amino)cyclohexyl)-1-(4-(2-oxopyridin-1(2H)-yl)phenyl)urea | | | 519.3 |
| 191 | 3-benzyl-1-(trans-4-((5-fluoropyrimidin-2-yl)amino)cyclohexyl)-1-(4-(1-methyl-1H-pyrazol-4-yl)phenyl)urea | | | 500.3 |
| 192 | 3-benzyl-1-(4-(1-methyl-1H-pyrazol-4-yl)phenyl)-1-(trans-4-((5-(trifluoromethyl)pyrimidin-2-yl)amino)cyclohexyl)urea | | | 550.3 |

TABLE 1-38-continued

| Ex. No. | IUPAC name | structural formula | salt | MS |
|---|---|---|---|---|
| 193 | 3-benzyl-1-(4-(1-methyl-1H-pyrazol-4-yl)phenyl)-1-(trans-4-((4-(pyridin-3-yl)pyrimidin-2-yl)amino)cyclohexyl)urea | | | 559.4 |
| 194 | 3-benzyl-1-(trans-4-((5-(difluoromethoxy)pyrimidin-2-yl)amino)cyclohexyl)-1-(4-(1-methyl-1H-pyrazol-4-yl)phenyl)urea | | | 548.3 |

TABLE 1-39

| Ex. No. | IUPAC name | structural formula | salt | MS |
|---|---|---|---|---|
| 195 | 3-benzyl-1-(trans-4-((4-(difluoromethoxy)pyrimidin-2-yl)amino)cyclohexyl)-1-(4-(1-methyl-1H-pyrazol-4-yl)phenyl)urea | | | 548.3 |
| 196 | 3-benzyl-1-(trans-4-((4-(4-methoxy-1H-pyrazol-1-yl)pyrimidin-2-yl)amino)cyclohexyl)-1-(4-(1-methyl-1H-pyrazol-4-yl)phenyl)urea | | | 578.3 |

TABLE 1-39-continued

| Ex. No. | IUPAC name | structural formula | salt | MS |
|---|---|---|---|---|
| 197 | 3-benzyl-1-(trans-4-((5-cyano-4-(1H-pyrazol-1-yl)pyrimidin-2-yl)amino)cyclohexyl)-1-(4-(1-methyl-1H-pyrazol-4-yl)phenyl)urea | | | 571.3 |
| 198 | N-(2-((trans-4-((benzylcarbamoyl)(4-(1-methyl-1H-pyrazol-4-yl)phenyl)amino)cyclohexyl)amino)pyrimidin-4-yl)-cyclopropanecarboxamide | | | 565.4 |
| 199 | 3-benzyl-1-(trans-4-((5-cyano-4-((3-hydroxypropyl)amino)pyrimidin-2-yl)amino)cyclohexyl)-1-(4-(1-methyl-1H-pyrazol-4-yl)phenyl)urea | | | 580.4 |

TABLE 1-40

| Ex. No. | IUPAC name | structural formula | salt | MS |
|---|---|---|---|---|
| 200 | 3-benzyl-1-(trans-4-((5-cyano-4-((2-oxo-2,3-dihydro-1H-indol-5-yl)amino)pyrimidin-2-yl)amino)cyclohexyl)-1-(4-(1-methyl-1H-pyrazol-4-yl)phenyl)urea | | | 651.3 |

TABLE 1-40-continued

| Ex. No. | IUPAC name | structural formula | salt | MS |
|---|---|---|---|---|
| 201 | 3-benzyl-1-(trans-4-((5-cyano-4-(1H-imidazol-5-yl)pyrimidin-2-yl)amino)cyclohexyl)-1-(4-(1-methyl-1H-pyrazol-4-yl)phenyl)urea hydrochloride | | HCl | 573.5 |
| 202 | 3-benzyl-1-(trans-4-((5-cyano-4-(1-methyl-1H-imidazol-5-yl)pyrimidin-2-yl)amino)cyclohexyl)-1-(4-(1-methyl-1H-pyrazol-4-yl)phenyl)urea | | | 587.4 |
| 203 | 3-benzyl-1-(trans-4-((5-chloro-4-(morpholin-4-yl)pyrimidin-2-yl)amino)cyclohexyl)-1-(4-(1-methyl-1H-pyrazol-4-yl)phenyl)urea | | | 601.4 |
| 204 | 3-benzyl-1-(trans-4-((5-chloro-4-(2-(methylsulfonyl)phenoxy)pyrimidin-2-yl)amino)cyclohexyl)-1-(4-(1-methyl-1H-pyrazol-4-yl)phenyl)urea | | | 686.4 |

TABLE 1-41

| Ex. No. | IUPAC name | structural formula | salt | MS |
|---|---|---|---|---|
| 205 | 3-benzyl-1-(trans-4-((5-cyano-4-(1-methyl-1H-benzimidazol-5-yl)pyrimidin-2-yl)amino)cyclohexyl)-1-(4-(1-methyl-1H-pyrazol-4-yl)phenyl)urea | | | 637.6 |
| 206 | 3-benzyl-1-(trans-4-((5-chloro-4-((2-(methyslulfonyl)phenyl)-amino)pyrimidin-2-yl)amino)cyclohexyl)-1-(4-(1-methyl-1H-pyrazol-4-yl)phenyl)urea | | | 685.4 |
| 207 | 3-benzyl-1-(trans-4-((5-cyano-4-(1-methyl-2-oxo-2,3-dihydro-1H-benzimidazol-5-yl)pyrimidin-2-yl)amino)cyclohexyl)-1-(4-(1-methyl-1H-pyrazol-4-yl)phenyl)urea | | | |
| 208 | 3-benzyl-1-(trans-4-((5-cyano-4-(1H-pyrazol-4-yl)pyrimidin-2-yl)amino)cyclohexyl)-1-(5-(1-methyl-1H-pyrazol-4-yl)pyridin-2-yl)urea | | | 574.5 |

TABLE 1-41-continued

| Ex. No. | IUPAC name | structural formula | salt | MS |
|---|---|---|---|---|
| 209 | 3-benzyl-1-(trans-4-((5-cyano-4-(1H-pyrazol-1-yl)pyrimidin-2-yl)amino)cyclohexyl)-1-(5-(1-methyl-1H-pyrazol-4-yl)pyridin-2-yl)urea | | | 574.5 |

TABLE 1-42

| Ex. No. | IUPAC name | structural formula | salt | MS |
|---|---|---|---|---|
| 210 | 3-benzyl-1-(trans-4-((5-cyano-4-(1-methyl-1H-pyrazol-4-yl)pyrimidin-2-yl)amino)cyclohexyl)-1-(5-(1-methyl-1H-pyrazol-4-yl)pyridin-2-yl)urea | | | 588.5 |
| 211 | 3-benzyl-1-(trans-4-((5-cyano-4-(1-methyl-1H-pyrazol-5-yl)pyrimidin-2-yl)amino)cyclohexyl)-1-(5-(1-methyl-1H-pyrazol-4-yl)pyridin-2-yl)urea | | | 588.5 |
| 212 | $N^3$-(2-((trans-4-((benzylcarbamoyl)(5-(1-methyl-1H-pyrazol-4-yl)pyridin-2-yl)amino)cyclohexyl)amino)-5-cyanopyrimidin-4-yl)-beta-alanineamide | | | 594.4 |

TABLE 1-42-continued

| Ex. No. | IUPAC name | structural formula | salt | MS |
|---|---|---|---|---|
| 213 | 3-benzyl-1-(trans-4-((5-cyano-4-((2,3-dihydroxypropyl)-amino)pyrimidin-2-yl)amino)cyclohexyl)-1-(5-(1-methyl-1H-pyrazol-4-yl)pyridin-2-yl)urea | | | 597.4 |
| 214 | 3-benzyl-1-(trans-4-((5-cyano-4-((2-cyanoethyl)amino)pyrimidin-2-yl)amino)cyclohexyl)-1-(5-(1-methyl-1H-pyrazol-4-yl)pyridin-2-yl)urea | | | 574.3 |

TABLE 1-43

| Ex. No. | IUPAC name | structural formula | salt | MS |
|---|---|---|---|---|
| 215 | 3-benzyl-1-(trans-4-((5-cyano-4-((2,2-difluoro-3-hydroxypropyl)amino)pyrimidin-2-yl)amino)cyclohexyl)-1-(5-(1-methyl-1H-pyrazol-4-yl)pyridin-2-yl)urea | | | 617.4 |
| 216 | 3-benzyl-1-(trans-4-((5-cyano-4-(2-(hydroxymethyl)piperidin-1-yl)pyrimidin-2-yl)amino)cyclohexyl)-1-(5-(1-methyl-1H-pyrazol-4-yl)pyridin-2-yl)urea | | | 621.5 |

TABLE 1-43-continued

| Ex. No. | IUPAC name | structural formula | salt | MS |
|---|---|---|---|---|
| 217 | 3-benzyl-1-(trans-4-((5-cyano-4-(3-oxo-2,8-diazaspiro[4.5]deca-8-yl)pyrimidin-2-yl)amino)cyclohexyl)-1-(5-(1-methyl-1H-pyrazol-4-yl)pyridin-2-yl)urea | | | 660.5 |
| 218 | 3-benzyl-1-(trans-4-((5-cyano-4-(2-oxo-1-oxa-3,8-diazaspiro[4.5]deca-8-yl)pyrimidin-2-yl)amino)-cyclohexyl)-1-(5-(1-methyl-1H-pyrazol-4-yl)pyridin-2-yl)urea | | | 662.5 |
| 219 | 3-benzyl-1-(trans-4-((5-cyano-4-(1-oxo-2,8-diazaspiro[4.5]deca-8-yl)pyrimidin-2-yl)amino)-cyclohexyl)-1-(5-(1-methyl-1H-pyrazol-4-yl)pyridin-2-yl)urea | | | 660.5 |

TABLE 1-44

| Ex. No. | IUPAC name | structural formula | salt | MS |
|---|---|---|---|---|
| 220 | 3-benzyl-1-(trans-4-((5-cyano-4-(1,3-dioxo-2,8-diazaspiro[4.5]deca-8-yl)pyrimidin-2-yl)amino)-cyclohexyl)-1-(5-(1-methyl-1H-pyrazol-4-yl)pyridin-2-yl)urea | | | 674.5 |
| 221 | 3-benzyl-1-(trans-4-((5-cyano-4-(2-oxo-1,8-diazaspiro[4.5]deca-8-yl)pyrimidin-2-yl)amino)-cyclohexyl)-1-(5-(1-methyl-1H-pyrazol-4-yl)pyridin-2-yl)urea | | | 660.5 |
| 222 | 3-benzyl-1-(trans-4-((5-cyano-4-(2-oxo-1,7-diazaspiro[3.5]nona-7-yl)pyrimidin-2-yl)amino)-cyclohexyl)-1-(5-(1-methyl-1H-pyrazol-4-yl)pyridin-2-yl)urea | | | 646.5 |
| 223 | 3-benzyl-1-(trans-4-((5-cyano-4-(2-oxo-1,7-diazaspiro[4.4]nona-7-yl)pyrimidin-2-yl)amino)-cyclohexyl)-1-(5-(1-methyl-1H-pyrazol-4-yl)pyridin-2-yl)urea | | | 646.5 |

TABLE 1-44-continued

| Ex. No. | IUPAC name | structural formula | salt | MS |
|---|---|---|---|---|
| 224 | 3-benzyl-1-(trans-4-((5-cyano-4-((1H-imidazol-2-ylmethyl)amino)-pyrimidin-2-yl)amino)-cyclohexyl)-1-(5-(1-methyl-1H-pyrazol-4-yl)pyridin-2-yl)urea | | | 603.5 |

TABLE 1-45

| Ex. No. | IUPAC name | structural formula | salt | MS |
|---|---|---|---|---|
| 225 | 3-benzyl-1-(trans-4-((5-cyano-4-(((1-methyl-1H-imidazol-2-yl)methyl)amino)pyrimidin-2-yl)amino)cyclohexyl)-1-(5-(1-methyl-1H-pyrazol-4-yl)pyridin-2 -yl)urea | | | 617.4 |
| 226 | 3-benzyl-1-(trans-4-((4-(benzylamino)-5-cyanopyrimdiin-2-yl)amino)cyclohexyl)-1-(5-(1-methyl-1H-pyrazol-4-yl)pyridin-2-yl)urea | | | 613.5 |
| 227 | 3-benzyl-1-(trans-4-((5-cyano-4-((pyridin-2-ylmethyl)amino)pyrimidin-2-yl)amino)cyclohehxyl)-1-(5-(1-methyl-1H-pyrazol-4-yl)pyridin-2-yl)urea | | | 614.5 |

TABLE 1-45-continued

| Ex. No. | IUPAC name | structural formula | salt | MS |
|---|---|---|---|---|
| 228 | 3-benzyl-1-(trans-4-((5-cyano-4-((pyridin-3-ylmethyl)amino)pyrimidin-2-yl)amino)cyclohexyl)-1-(5-(1-methyl-1H-pyrazol-4-yl)pyridin-2-yl)urea | | | 614.4 |
| 229 | 3-benzyl-1-(trans-4-((5-cyano-4-((pyridin-4-ylmethyl)amino)pyrimidin-2-yl)amino)cyclohexyl)-1-(5-(1-methyl-1H-pyrazol-4-yl)pyridin-2-yl)urea | | | 614.5 |

TABLE 1-46

| Ex. No. | IUPAC name | structural formula | salt | MS |
|---|---|---|---|---|
| 230 | N-(3-(((2-((trans-4-((benzylcarbamoyl)(5-(1-methyl-1H-pyrazol-4-yl)pyridin-2-yl)amino)cyclohexyl)amino)-5-cyanopyrimidin-4-yl)amino)methyl)pyridin-2-yl)-N-methylmethanesulfonamide | | | 719.4 |
| 231 | 3-benzyl-1-(trans-4-((5-cyano-4-((pyrazin-2-ylmethyl)amino)-pyrimidin-2-yl)amino)-cyclohexyl)-1-(5-(1-methyl-1H-pyrazol-4-yl)pyridin-2-yl)urea | | | 615.4 |

TABLE 1-46-continued

| Ex. No. | IUPAC name | structural formula | salt | MS |
|---|---|---|---|---|
| 232 | 3-benzyl-1-(trans-4-((5-cyano-4-(((5-oxopyrrolidin-2-yl)methyl)-amino)pyrimidin-2-yl)amino)-cyclohexyl)-1-(5-(1-methyl-1H-pyrazol-4-yl)pyridin-2-yl)urea | | | 620.5 |
| 233 | 3-benzyl-1-(trans-4-((5-cyano-4-((tetrahydrofuran-2-ylmethyl)-amino)pyrimidin-2-yl)amino)-cyclohexyl)-1-(5-(1-methyl-1H-pyrazol-4-yl)pyridin-2-yl)urea | | | 607.5 |
| 234 | 3-benzyl-1-(trans-4-((5-cyano-4-((tetrahydrofuran-3-ylmethyl)-amino)pyrimidin-2-yl)amino)-cyclohexyl)-1-(5-(1-methyl-1H-pyrazol-4-yl)pyridin-2-yl)urea | | | 607.5 |

TABLE 1-47

| Ex. No. | IUPAC name | structural formula | salt | MS |
|---|---|---|---|---|
| 235 | 3-benzyl-1-(trans-4-((5-cyano-(((1-methylpyrrolidin-2-yl)methyl)-amino)pyrimidin-2-yl)amino)-cyclohexyl)-1-(5-(1-methyl-1H-pyrazol-4-yl)-pyridin 2-yl)urea | | | 620.6 |

TABLE 1-47-continued

| Ex. No. | IUPAC name | structural formula | salt | MS |
|---|---|---|---|---|
| 236 | 3-benzyl-1-(trans-4-((5-cyano-4-((2-(2-oxopyrrolidin-1-yl)ethyl)amino)-pyrimidin-2-yl)-amino)cyclohexyl)-1-(5-(1-methyl-1H-pyrazol-4-yl)-pyridin-2-yl)urea | 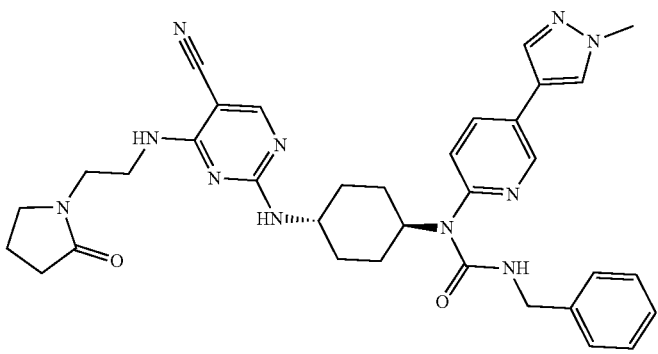 [SMILES: Cn1cc(-c2ccc(N(C(=O)NCc3ccccc3)[C@H]3CC[C@H](Nc4ncc(C#N)c(NCCN5CCCC5=O)n4)CC3)nc2)cn1] | | 634.5 |
| 237 | 3-benzyl-1-(trans-4-((5-cyano-(tetra-hydrofuran-3-yl-amino)pyrimidin-2-yl)amino)cyclo-hexyl)-1-(5-(1-methyl-1H-pyrazol-4-yl)-pyridin-2-yl)urea | 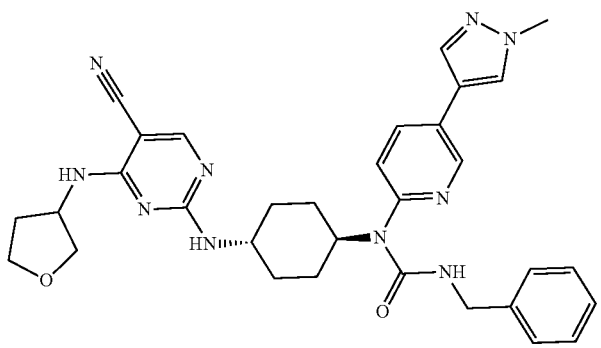 [SMILES: Cn1cc(-c2ccc(N(C(=O)NCc3ccccc3)[C@H]3CC[C@H](Nc4ncc(C#N)c(NC5CCOC5)n4)CC3)nc2)cn1] | | 593.4 |
| 238 | 3-benzyl-1-(trans-4-((5-cyano-4-((3,3,3-trifluoro-2-hydroxypropyl)-amino)pyrimidin-2-yl)amino)cyclo-hexyl)-1-(5-(1-methyl-1H-pyrazol-4-yl)-pyridin-2-yl)urea | 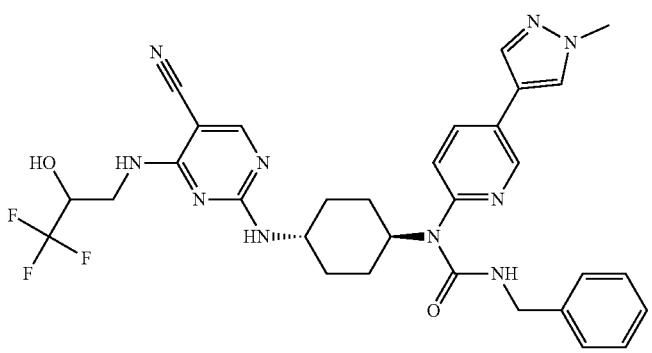 [SMILES: Cn1cc(-c2ccc(N(C(=O)NCc3ccccc3)[C@H]3CC[C@H](Nc4ncc(C#N)c(NCC(O)C(F)(F)F)n4)CC3)nc2)cn1] | | 635.5 |
| 239 | 3-benzyl-1-(trans-4-((5-cyano-((1-hydroxypropan-2-yl)amino)-pyrimidin-2-yl)-amino)cyclohexyl)-1-(5-(1-methyl-1H-pyrazol-4-yl)-pyridin-2-yl)urea | 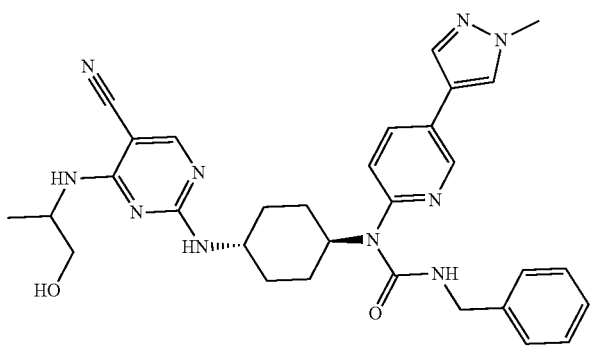 [SMILES: CC(CO)Nc1nc(N[C@H]2CC[C@H](N(C(=O)NCc3ccccc3)c3ccc(-c4cnn(C)c4)cn3)CC2)ncc1C#N] | | 581.4 |

TABLE 1-48

| Ex. No. | IUPAC name | structural formula | salt | MS |
|---|---|---|---|---|
| 240 | 3-benzyl-1-(trans-4-((5-cyano-4-((1-(hydroxymethyl)cyclopropyl)amino)-pyrimidin-2-yl)-amino)cyclohexyl)-1-(5-(1-methyl-1H-pyrazol-4-yl)-pyridin-2-yl)urea | | | 593.4 |
| 241 | 3-benzyl-1-(trans-4-((5-cyano-4-((2-hydroxycyclohexyl)amino)-pyrimidin-2-yl)-amino)cyclohexyl)-1-(5-(1-methyl-1H-pyrazol-4-yl)-pyridin-2-yl)urea | | | 621.5 |
| 242 | 3-benzyl-1-(trans-4-((5-cyano-4-((2-furylmethyl)amino)-pyrimidin-2-yl)-amino)cyclohexyl)-1-(5-(1-methyl-1H-pyrazol-4-yl)-pyridin-2-yl)urea | | | 603.4 |
| 243 | 3-benzyl-1-(trans-4-((5-cyano-4-((2-(dimethylamino)-ethyl)amino)-pyrimidin-2-yl)-amino)cyclohexyl)-1-(5-(1-methyl-1H-pyrazol-4-yl)-pyridin-2-yl)urea | | | 594.4 |

TABLE 1-48-continued

| Ex. No. | IUPAC name | structural formula | salt | MS |
|---|---|---|---|---|
| 244 | 3-benzyl-1-(trans-4-((5-cyano-4-((2-(morpholin-4-yl)-ethyl)amino)-pyrimidin-2-yl)-amino)cyclohexyl)-1-(5-(1-methyl-1H-pyrazol-4-yl)-pyridin-2-yl)urea | | | 636.6 |

TABLE 1-49

| Ex. No. | IUPAC name | structural formula | salt | MS |
|---|---|---|---|---|
| 245 | 3-benzyl-1-(trans-4-((5-cyano-4-((pyrimidin-2-yl-methyl)amino)-pyrimidin-2-yl)-amino)cyclohexyl)-1-(5-(1-methyl-1H-pyrazol-4-yl)-pyridin-2-yl)urea | | | 615.4 |
| 246 | 3-benzyl-1-(trans-4-((5-cyano-4-((pyridazin-3-yl-methyl)amino)-pyrimidin-2-yl)-amino)cyclohexyl)-1-(5-(1-methyl-1H-pyrazol-4-yl)-pyridin-2-yl)urea | | | 615.4 |
| 247 | 3-benzyl-1-(trans-4-((5-cyano-4-((pyrimidin-4-yl-methyl)amino)-pyrimidin-2-yl)-amino)cyclohexyl)-1-(5-(1-methyl-1H-pyrazol-4-yl)-pyridin-2-yl)urea | | | 615.4 |

TABLE 1-49-continued

| Ex. No. | IUPAC name | structural formula | salt | MS |
|---|---|---|---|---|
| 248 | 3-benzyl-1-(trans-4-((5-cyano-(4-hydroxy-4-(tri-fluoromethyl)-piperidin-1-yl)-pyrimidin-2-yl)-amino)cyclohexyl)-1-(5-(1-methyl-1H-pyrazol-4-yl)-pyridin-2-yl)urea | | | 675.4 |
| 249 | 3-benzyl-1-(trans-4-((5-cyano-(4-fluoro-4-(hydroxy-methyl)piperidin-1-yl)pyrimidin-2-yl)amino)cyclo-hexyl)-1-(5-(1-methyl-1H-pyrazol-4-yl)-pyridin-2-yl)urea | | | 639.5 |

TABLE 1-50

| Ex. No. | IUPAC name | structural formula | salt | MS |
|---|---|---|---|---|
| 250 | 3-benzyl-1-(trans-4-((5-cyano-4-((2-(trifluoromethoxy)-ethyl)amino)-pyrimidin-2-yl)-amino)cyclohexyl)-1-(5-(1-methyl-1H-pyrazol-4-yl)-pyridin-2-yl)urea | | | 635.5 |
| 251 | 3-benzyl-1-(trans-4-((5-cyano-4-(3-(methylsulfonyl)-azetidin-1-yl)-pyrimidin-2-yl)-amino)cyclohexyl)-1-(5-(1-methyl-1H-pyrazol-4-yl)-pyridin-2-yl)urea | | | 641.4 |

TABLE 1-50-continued

| Ex. No. | IUPAC name | structural formula | salt | MS |
|---|---|---|---|---|
| 252 | 3-benzyl-1-(trans-4-((5-cyano-4-(1-oxa-6-azaspiro-[3.5]nona-6-yl)-pyrimidin-2-yl)-amino)cyclohexyl)-1-(5-(1-methyl-1H-pyrazol-4-yl)-pyridin-2-yl)urea | | | 633.5 |
| 253 | 3-benzyl-1-(trans-4-((5-cyano-4-(4,4-difluoro-piperidin-1-yl)-pyrimidin-2-yl)-amino)cyclohexyl)-1-(5-(1-methyl-1H-pyrazol-4-yl)-pyridin-2-yl)urea | | | 627.4 |
| 254 | 3-benzyl-1-(trans-4-((5-cyano-4-(5,6-dihydro[1,2,4]-triazolo[1,5-a]-pyrazine-7(8H)-yl)pyrimidin-2-yl)amino)cyclo-hexyl)-1-(5-(1-methyl-1H-pyrazol-4-yl)-pyridin-2-yl)urea | | | 630.4 |

TABLE 1-51

| Ex. No. | IUPAC name | structural formula | salt | MS |
|---|---|---|---|---|
| 255 | 3-benzyl-1-(trans-4-((5-cyano-4-(2,2-difluoro-morpholin-4-yl)-pyrimidin-2-yl)-amino)cyclohexyl)-1-(5-(1-methyl-1H-pyrazol-4-yl)-pyridin-2-yl)urea | | | 629.4 |
| 256 | 3-benzyl-1-(trans-4-((5-cyano-4-(6,7-dihydro-[1,3]thiazolo[5,4-c]pyridine-5(4H)-yl)pyrimidin-2-yl)amino)cyclo-hexyl)-1-(5-(1-methyl-1H-pyrazol-4-yl)-pyridin-2-yl)urea | | | 646.4 |
| 257 | 3-benzyl-1-(trans-4-((5-cyano-4-((3-hydroxypropyl)-(methyl)amino)-pyrimidin-2-yl)-amino)cyclohexyl)-1-(5-(1-methyl-1H-pyrazol-4-yl)-pyridin-2-yl)urea | | | 595.4 |
| 258 | 3-benzyl-1-(trans-4-((5-cyano-(6,6-difluoro-3-aza-bicyclo[3.1.0]-hexa-3-yl)-pyrimidin-2-yl)-amino)cyclohexyl)-1-(5-(1-methyl-1H-pyrazol-4-yl)-pyridin-2-yl)urea | | | 625.5 |

TABLE 1-51-continued

| Ex. No. | IUPAC name | structural formula | salt | MS |
|---|---|---|---|---|
| 259 | 3-benzyl-1-(trans-4-((5-cyano-4-(((5-cyclopropyl-1,3,4-oxadiazol-2-yl)methyl)amino)pyrimidin-2-yl)amino)cyclohexyl)-1-(5-1-methyl-1H-pyrazol-4-yl)-pyridin-2-yl)urea | | | 645.5 |

TABLE 1-52

| Ex. No. | IUPAC name | structural formula | salt | MS |
|---|---|---|---|---|
| 260 | 3-benzyl-1-(trans-4-((4-(((3-tert-butyl-1H-pyrazol-5-yl)-methyl)amino)-5-cyanopyrimidin-2-yl)amino)cyclohexyl)-1-(5-(1-methyl-1H-pyrazol-4-yl)-pyridin-2-yl)urea | | | 659.5 |
| 261 | 3-benzyl-1-(trans-4-((5-cyano-4-((3-(methylsulfonyl)benzyl)amino)-pyrimidin-2-yl)-amino)cyclohexyl)-1-(5-(1-methyl-1H-pyrazol-4-yl)pyridin-2-yl)urea | | | 691.4 |
| 262 | 3-benzyl-1-(trans-4-((5-cyano-4-((3-(methylsulfonyl)-propyl)amino)-pyrimidin-2-yl)-amino)cyclohexyl)-1-(5-(1-methyl-1H-pyrazol-4-yl)-pyridin-2-yl)urea | | | 643.4 |

TABLE 1-52-continued

| Ex. No. | IUPAC name | structural formula | salt | MS |
|---|---|---|---|---|
| 263 | 3-benzyl-1-(trans-4-((4-(butylamino)-5-cyanopyrimidin-2-yl)amino)cyclohexyl)-1-(5-(1-methyl-1H-pyrazol-4-yl)pyridin-2-yl)urea | | | 579.5 |
| 264 | 3-benzyl-1-(trans-4-((5-cyano-4-((pyrrolidin-3-ylmethyl)amino)-pyrimidin-2-yl)-amino)cyclohexyl)-1-(5-(1-methyl-1H-pyrazol-4-yl)-pyridin-2-yl)urea trifluoroacetate | | CF$_3$COOH | 606.5 |

TABLE 1-53

| Ex. No. | IUPAC name | structural formula | salt | MS |
|---|---|---|---|---|
| 265 | 3-benzyl-1-(trans-4-((5-cyano-4-(pyrrolidin-3-ylamino)pyrimidin-2-yl)amino)cyclohexyl)-1-(5-(1-methyl-1H-pyrazol-4-yl)-pyridin-2-yl)urea trifluoroacetate | | CF$_3$COOH | 592.5 |
| 266 | 3-benzyl-1-(trans-4-((5-cyano-4-(3-hydroxy-8-azabicyclo[3.2.1]octa-8-yl)pyrimidin-2-yl)amino)cyclohexyl)-1-(5-(1-methyl-1H-pyrazol-4-yl)-pyridin-2-yl)urea | | | 633.5 |

TABLE 1-53-continued

| Ex. No. | IUPAC name | structural formula | salt | MS |
|---|---|---|---|---|
| 267 | 3-benzyl-1-(trans-4-((5-cyano-(9-oxa-2-azaspiro[5.5]undeca-2-yl)-pyrimidin-2-yl)-amino)cyclohexyl)-1-(5-(1-methyl-1H-pyrazol-4-yl)-pyridin-2-yl)urea | | | 661.6 |
| 268 | 3-benzyl-1-(trans-4-((5-cyano-4-(8-oxa-2-azaspiro[4.5]deca-2-yl)-pyrimidin-2-yl)-amino)cyclohexyl)-1-(5-(1-methyl-1H-pyrazol-4-yl)-pyridin-2-yl)urea | | | 647.6 |
| 269 | 3-benzyl-1-(trans-4-((5-cyano-(3-oxo-2,7-diazaspiro[4.5]deca-7-yl)-pyrimidin-2-yl)-amino)cyclohexyl)-1-(5-(1-methyl-1H-pyrazol-4-yl)-pyridin-2-yl)urea | | | 660.5 |

TABLE 1-54

| Ex. No. | IUPAC name | structural formula | salt | MS |
|---|---|---|---|---|
| 270 | 3-benzyl-1-(trans-4-((5-cyano-4-((dicyclopropyl-methyl)amino)-pyrimidin-2-yl)-amino)cyclohexyl)-1-(5-(1-methyl-1H-pyrazol-4-yl)-pyridin-2-yl)urea | | | 617.4 |
| 271 | 3-benzyl-1-(trans-4-((5-cyano-4-(3-(difluoromethyl)-azetidin-1-yl)-pyrimidin-2-yl)-amino)cyclohexyl)-1-(5-(1-methyl-1H-pyrazol-4-yl)-pyridin-2-yl)urea | | | 613.4 |
| 272 | 3-benzyl-1-(trans-4-((5-cyano-4-(3-(difluoromethoxy)-pyrrolidin-1-yl)-pyrimidin-2-yl)-amino)cyclohexyl)-1-(5-(1-methyl-1H-pyrazol-4-yl)-pyridin-2-yl)urea | | | 643.5 |
| 273 | 3-benzyl-1-(trans-4-((5-cyano-4-((4-(difluoromethoxy)-cyclohexyl)amino)-pyrimidin-2-yl)-amino)cyclohexyl)-1-(5-(1-methyl-1H-pyrazol-4-yl)-pyridin-2-yl)urea | | | 671.5 |

TABLE 1-54-continued

| Ex. No. | IUPAC name | structural formula | salt | MS |
|---|---|---|---|---|
| 274 | 3-benzyl-1-(trans-4-((5-cyano-4,5'-bipyrimidin-2-yl)amino)cyclohexyl)-1-(5-(1-methyl-1H-pyrazol-4-yl)pyridin-2-yl)urea | | | 586.3 |

TABLE 1-55

| Ex. No. | IUPAC name | structural formula | salt | MS |
|---|---|---|---|---|
| 275 | 3-benzyl-1-(trans-4-((5-cyano-4-((3-hydroxybutan-2-yl)amino)pyrimidin-2-yl)amino)cyclohexyl)-1-(5-(1-methyl-1H-pyrazol-4-yl)pyridin-2-yl)urea | | | 595.4 |
| 276 | 3-benzyl-1-(trans-4-((5-cyano-4-(4-(trifluoromethyl)phenyl)pyrimidin-2-yl)amino)cyclohexyl)-1-(5-(1-methyl-1H-pyrazol-4-yl)pyridin-2-yl)urea | | | 652.5 |
| 277 | 3-benzyl-1-(trans-4-((5-cyano-(3-methyl-3H-imidazo[4,5-b]pyridin-6-yl)pyrimidin-2-yl)amino)cyclohexyl)-1-(5-(1-methyl-1H-pyrazol-4-yl)pyridin-2-yl)urea | | | 639.4 |

TABLE 1-55-continued

| Ex. No. | IUPAC name | structural formula | salt | MS |
|---|---|---|---|---|
| 278 | 3-benzyl-1-(trans-4-((5-cyano-(1-methyl-1H-pyrazol-3-yl)pyrimidin-2-yl)-amino)cyclohexyl)-1-(4-(1-methyl-1H-pyrazol-4-yl)phenyl)-urea | | | 587.4 |
| 279 | 3-benzyl-1-(trans-4-((5-cyano-4-(1-methyl-1H-pyrazol-4-yl)pyrimidin-2-yl)-amino)cyclohexyl)-1-(4-(1-methyl-1H-pyrazol-4-yl)phenyl)-urea | | | 587.4 |

TABLE 1-56

| Ex. No. | IUPAC name | structural formula | salt | MS |
|---|---|---|---|---|
| 280 | 3-benzyl-1-(trans-4-((5-cyano-(1H-pyrazol-3-yl)-pyrimidin-2-yl)-amino)cyclohexyl)-1-(4-(1-methyl-1H-pyrazol-4-yl)-phenyl)urea | | | 573.4 |
| 281 | 3-benzyl-1-(trans-4-((5-cyano-4-((3-methoxypropyl)-amino)pyrimidin-2-yl)amino)cyclo-hexyl)-1-(4-(1-methyl-1H-pyrazol-4-yl)-phenyl)urea | | | 594.4 |

TABLE 1-56-continued

| Ex. No. | IUPAC name | structural formula | salt | MS |
|---|---|---|---|---|
| 282 | 3-benzyl-1-(trans-4-((5-cyano-4-((2-hydroxyethyl)-amino)pyrimidin-2-yl)amino)-cyclohexyl)-1-(4-(1-methyl-1H-pyrazol-4-yl)-phenyl)urea | | | 566.4 |
| 283 | 3-benzyl-1-(trans-4-((5-cyano-4-((3-hydroxy-propyl)amino)-pyrimidin-2-yl)-amino)cyclo-hexyl)-1-(5-(1-methyl-1H-pyrazol-4-yl)-pyridin-2-yl)urea | | | 581.5 |
| 284 | 3-benzyl-1-(trans-4-((5-cyano-(1H-pyrazol-4-yl)-pyrimidin-2-yl)-amino)cyclohexyl)-1-(4-(1-methyl-1H-pyrazol-4-yl)-phenyl)urea | | | 573.5 |

TABLE 1-57

| Ex. No. | IUPAC name | structural formula | salt | MS |
|---|---|---|---|---|
| 285 | 3-benzyl-1-trans-4-((5-cyano-4-(1-methyl-1H-pyrazol-5-yl)-pyrimidin-2-yl)-amino)cyclohexyl)-1-(4-(1-methyl-1H-pyrazol-4-yl)-phenyl)urea formate | | formic acid | 585.2 |

TABLE 1-57-continued

| Ex. No. | IUPAC name | structural formula | salt | MS |
|---|---|---|---|---|
| 286 | 3-benzyl-1-(trans-4-((5-chloro-4-(dimethylamino)-pyrimidin-2-yl)-amino)cyclohexyl)-1-(4-(1-methyl-1H-pyrazol-4-yl)phenyl)urea | | | 559.4 |
| 287 | 3-benzyl-1-(trans-4-((5-chloro-4-(1,1-dioxidethio-morpholin-4-yl)-pyrimidin-2-yl)-amino)cyclohexyl)-1-(4-(1-methyl-1H-pyrazol-4-yl)-phenyl)urea | | | 649.3 |
| 288 | 3-benzyl-1-(trans-4-((5-chloro-4-(2-(isopropyl-sulfonyl)phenoxy)-pyrimidin-2-yl)-amino)cyclohexyl)-1-(4-(1-methyl-1H-pyrazol-4-yl)-phenyl)urea | | | 714.4 |
| 289 | 3-benzyl-1-(trans-4-((5-chloro-4-(methyl (2-(methyl-sulfonyl)phenyl)-amino)pyrimidin-2-yl)amino)cyclo-hexyl)-1-(4-1-methyl-1H-pyrazol-4-yl)phenyl)urea | | | 699.5 |

TABLE 1-58

| Ex. No. | IUPAC name | structural formula | salt | MS |
|---|---|---|---|---|
| 290 | 3-benzyl-1-(trans-4-((5-cyano-(1-methyl-1H-benzimidazol-6-yl)pyrimidin-2-yl)amino)cyclohexyl)-1-(4-(1-methyl-1H-pyrazol-4-yl)phenyl)urea | | | 637.5 |
| 291 | 3-benzyl-1-(trans-4-((5-cyano-(1H-indazol-5-yl)-pyrimidin-2-yl)amino)cyclohexyl)-1-(4-(1-methyl-1H-pyrazol-4-yl)phenyl)urea | | | 623.5 |
| 292 | 3-benzyl-1-(trans-4-((5-cyano-4-(4-hydroxyazepan-1-yl)pyrimidin-2-yl)amino)cyclohexyl)-1-(5-(1-methyl-1H-pyrazol-4-yl)pyridin-2-yl)urea | | | 621.51 |
| 293 | 3-benzyl-1-(trans-4-((5-cyano-4-(((1-hydroxycyclopropyl)methyl)amino)pyrimidin-2-yl)amino)cyclohexyl)-1-(5-(1-methyl-1H-pyrazol-4-yl)pyridin-2-yl)urea | | | 593.4 |

TABLE 1-58-continued

| Ex. No. | IUPAC name | structural formula | salt | MS |
|---|---|---|---|---|
| 294 | 3-benzyl-1-(trans-4-((5-cyano-4-(3-hydroxy-azetidin-1-yl)-pyrimidin-2-yl)-amino)cyclohexyl)-1-(5-(1-methyl-1H-pyrazol-4-yl)-pyridin-2-yl)urea | | | 579.4 |

TABLE 1-59

| Ex. No. | IUPAC name | structural formula | salt | MS |
|---|---|---|---|---|
| 295 | 3-benzyl-1-(trans-4-((5-cyano-4-(3-cyano-3-methyl-pyrrolidin-1-yl)pyrimidin-2-yl)amino)cyclohexyl)-1-(5-(1-methyl-1H-pyrazol-4-yl)-pyridin-2-yl)urea | | | 616.4 |
| 296 | 3-benzyl-1-(trans-4-((5-cyano-(3-hydroxypyrrolidin-1-yl)pyrimidin-2-yl)amino)cyclohexyl)-1-(5-(1-methyl-1H-pyrazol-4-yl)pyridin-2-yl)-urea | | | 593.4 |
| 297 | 3-benzyl-1-(trans-4-((5-cyano-4-(3-(hydroxymethyl)-pyrrolidin-1-yl)pyrimidin-2-yl)amino)cyclohexyl)-1-(5-(1-methyl-1H-pyrazol-4-yl)pyridin-2-yl)-urea | | | 607.5 |

TABLE 1-59-continued

| Ex. No. | IUPAC name | structural formula | salt | MS |
|---|---|---|---|---|
| 298 | 3-benzyl-1-(trans-4-((5-cyano-4-(2-(2-hydroxyethyl)-pyrrolidin-1-yl)-pyrimidin-2-yl)-amino)cyclohexyl)-1-(5-(1-methyl-1H-pyrazol-4-yl)-pyridin-2-yl)urea | | | 621.5 |
| 299 | 3-benzyl-1-(trans-4-((5-cyano-4-(2-hydroxymethyl)-pyrrolidin-1-yl)-pyrimidin-2-yl)-amino)cyclohexyl)-1-(5-(1-methyl-1H-pyrazol-4-yl)-pyridin-2-yl)urea | | | 607.4 |

TABLE 1-60

| Ex. No. | IUPAC name | structural formula | salt | MS |
|---|---|---|---|---|
| 300 | 3-benzyl-1-(trans-4-((5-cyano-4-(3-oxopiperazin-1-yl)pyrimidin-2-yl)amino)cyclohexyl)-1-(5-(1-methyl-1H-pyrazol-4-yl)-pyridin-2-yl)urea | | | 606.5 |

TABLE 1-60-continued

| Ex. No. | IUPAC name | structural formula | salt | MS |
|---|---|---|---|---|
| 301 | 3-benzyl-1-(trans-4-((5-cyano-4-(1,1-dioxidethio-morpholin-4-yl)-pyrimidin-2-yl)-amino)cyclohexyl)-1-(5-(1-methyl-1H-pyrazol-4-yl)-pyridin-2-yl)urea | | | 641.4 |
| 302 | 1-(trans-4-((4-(4-acetylpiperazin-1-yl)-5-cyano-pyrimidin-2-yl)-amino)cyclohexyl)-3-benzyl-1-(5-(1-methyl-1H-pyrazol-4-yl)-pyridin-2-yl)urea | | | 634.5 |
| 303 | 3-benzyl-1-(trans-4-((5-cyano-(4-hydroxypiperidin-1-yl)pyrimidin-2-yl)amino)cyclo-hexyl)-1-(5-(1-methyl-1H-pyrazol-4-yl)-pyridin-2-yl)urea | | | 607.4 |
| 304 | 3-benzyl-1-(trans-4-((5-cyano-4-(3-hydroxy-piperidin-1-yl)-pyrimidin-2-yl)-amino)cyclohexyl)-1-(5-(1-methyl-1H-pyrazol-4-yl)-pyridin-2-yl)urea | | | 607.4 |

TABLE 1-61

| Ex. No. | IUPAC name | structural formula | salt | MS |
|---|---|---|---|---|
| 305 | 3-benzyl-1-(trans-4-((5-cyano-4-(3-(hydroxymethyl)-piperidin-1-yl)-pyrimidin-2-yl)-amino)cyclohexyl)-1-(5-(1-methyl-1H-pyrazol-4-yl)-pyridin-2-yl)urea | | | 621.5 |
| 306 | 3-benzyl-1-(trans-4-((5-cyano-(2-(2-hydroxyethyl)-piperidin-1-yl)-pyrimidin-2-yl)-amino)cyclohexyl)-1-(5-(1-methyl-1H-pyrazol-4-yl)-pyridin-2-yl)urea | | | 635.5 |
| 307 | 3-benzyl-1-(trans-4-((5-cyano-4-(6-oxo-2,7-diazaspiro-[4.4]nona-2-yl)-pyrimidin-2-yl)-amino)cyclohexyl)-1-(5-(1-methyl-1H-pyrazol-4-yl)-pyridin-2-yl)urea | | | 646.5 |
| 308 | 3-benzyl-1-(trans-4-((5-cyano-(6-oxo-2,5-diazaspiro-[3.4]octa-2-yl)-pyrimidin-2-yl)-amino)cyclohexyl)-1-(5-(1-methyl-1H-pyrazol-4-yl)-pyridin-2-yl)urea | | | 632.5 |

TABLE 1-61-continued

| Ex. No. | IUPAC name | structural formula | salt | MS |
|---|---|---|---|---|
| 309 | 3-benzyl-1-(trans-4-((5-cyano-4-(6-oxo-7-oxa-2,5-diazaspiro-[3.4]octa-2-yl)-pyrimidin-2-yl)-amino)cyclohexyl)-1-(5-(1-methyl-1H-pyrazol-4-yl)-pyridin-2-yl)urea | | | 634.5 |

TABLE 1-62

| Ex. No. | IUPAC name | structural formula | salt | MS |
|---|---|---|---|---|
| 310 | 3-benzyl-1-(trans-4-((5-cyano-4-(2-oxa-7-azaspiro[3.5]nona-7-yl)pyrimidin-2-yl)amino)cyclohexyl)-1-(5-(1-methyl-1H-pyrazol-4-yl)pyridin-2-yl)urea | | | 633.5 |
| 311 | 3-benzyl-1-(trans-4-((5-cyano-4-(1-oxa-7-azaspiro[3.5]nona-7-yl)pyrimidin-2-yl)amino)-cyclohexyl)-1-(5-(1-methyl-1H-pyrazol-4-yl)pyridin-2-yl)urea | | | 633.5 |

TABLE 1-62-continued

| Ex. No. | IUPAC name | structural formula | salt | MS |
|---|---|---|---|---|
| 312 | 3-benzyl-1-(trans-4-((5-cyano-4-(2-oxa-8-azaspiro[4.5]deca-8-yl)pyrimidin-2-yl)amino)-cyclohexyl)-1-(5-(1-methyl-1H-pyrazol-4-yl)pyridin-2-yl)urea | | | 647.5 |
| 313 | 3-benzyl-1-(trans-4-((5-cyano-4-(1-oxa-8-azaspiro[4.5]deca-8-yl)pyrimidin-2-yl)amino)-cyclohexyl)-1-(5-(1-methyl-1H-pyrazol-4-yl)pyridin-2-urea | | | 647.5 |
| 314 | 3-benzyl-1-(trans-4-((5-cyano-4-(3-fluoro-1-oxa-8-azaspiro-[4.5]deca-8-yl)pyrimidin-2-yl)amino)cyclohexyl)-1-(5-(1-methyl-1H-pyrazol-4-yl)pyridin-2-yl)urea | | | 665.5 |

TABLE 1-63

| Ex. No. | IUPAC name | structural formula | salt | MS |
|---|---|---|---|---|
| 315 | 3-benzyl-1-(trans-4-((5-cyano-4-(3,3-difluoro-1-oxa-8-azaspiro[4.5]deca-8-yl)pyrimidin-2-yl)amino)cyclohexyl)-1-(5-(1-methyl-1H-pyrazol-4-yl)pyridin-2-yl)urea | | | 683.5 |
| 316 | 3-benzyl-1-(trans-4-((5-cyano-4-(5,6-dihydroimidazo[1,5-a]pyrazine-7(8H)-yl)pyrimidin-2-yl)amino)cyclohexyl)-1-(5-(1-methyl-1H-pyrazol-4-yl)pyridin-2-yl)urea | | | 629.4 |
| 317 | 3-benzyl-1-(trans-4-((5-cyano-4-(5,6-dihydroimidazo[1,2-a]pyrazine-7(8H)-yl)pyrimidin-2-yl)amino)cyclohexyl)-1-(5-(1-methyl-1H-pyrazol-4-yl)pyridin-2-yl)urea | | | 629.5 |
| 318 | 3-benzyl-1-(trans-4-((5-cyano-4-((1-methylpyrrolidin-3-yl)amino)pyrimidin-2-yl)amino)cyclohexyl)-1-(5-(1-methyl-1H-pyrazol-4-yl)pyridin-2-yl)urea | | | 606.5 |

TABLE 1-63-continued

| Ex. No. | IUPAC name | structural formula | salt | MS |
|---|---|---|---|---|
| 319 | 3-benzyl-1-(trans-4-((5-cyano-4-(oxetan-3-ylamino)pyrimidin-2-yl)amino)cyclohexyl)-1-(5-(1-methyl-1H-pyrazol-4-yl)pyridin-2-yl)urea | | | 579.4 |

TABLE 1-64

| Ex. No. | IUPAC name | structural formula | salt | MS |
|---|---|---|---|---|
| 320 | 3-benzyl-1-(trans-4-((5-cyano-4-((1,1-dioxide-thietan-3-yl)amino)pyrimidin-2-yl)amino)cyclohexyl)-1-(5-(1-methyl-1H-pyrazol-4-yl)pyridin-2-yl)urea | | | 625.2 |
| 321 | 3-benzyl-1-(trans-4-((4-((5-tert-butyl-1,3-oxazol-2-yl)methoxy)-5-cyanopyrimidin-2-yl)amino)cyclohexyl)-1-(5-(1-methyl-1H-pyrazol-4-yl)pyridin-2-yl)urea | | | 661.5 |
| 322 | 3-benzyl-1-(trans-4-((5-cyano-4-(1H-pyrazol-3-yl)pyrimidin-2-yl)amino)cyclohexyl)-1-(5-(1-methyl-1H-pyrazol-4-yl)pyridin-2-yl)urea | | | 574.3 |

TABLE 1-64-continued

| Ex. No. | IUPAC name | structural formula | salt | MS |
|---|---|---|---|---|
| 323 | 3-benzyl-1-(trans-4-((5-cyano-4-(1H-pyrazol-3-ylamino)pyrimidin-2-yl)amino)cyclohexyl)-1-(5-(1-methyl-1H-pyrazol-4-yl)pyridin-2-yl)urea | | | 589.5 |
| 324 | 3-benzyl-1-(trans-4-((5-cyano-4-((3-hydroxybutyl)amino)pyrimidin-2-yl)amino)cyclohexyl)-1-(5-(1-methyl-1H-pyrazol-4-yl)pyridin-2-yl)urea | | | 595.4 |

TABLE 1-65

| Ex. No. | IUPAC name | structural formula | salt | MS |
|---|---|---|---|---|
| 325 | 3-benzyl-1-(trans-4-((5-cyano-4-((3-hydroxycyclohexyl)amino)pyrimidin-2-yl)amino)cyclohexyl)-1-(5-(1-methyl-1H-pyrazol-4-yl)pyridin-2-yl)urea | | | 621.5 |
| 326 | 3-benzyl-1-(trans-4-((5-cyano-4-((3-hydroxy-2,2-dimethylpropyl)amino)pyrimidin-2-yl)amino)cyclohexyl)-1-(5-(1-methyl-1H-pyrazol-4-yl)pyridin-2-yl)urea | | | 609.5 |

TABLE 1-65-continued

| Ex. No. | IUPAC name | structural formula | salt | MS |
|---|---|---|---|---|
| 327 | 3-benzyl-1-(trans-4-((5-cyano-4-((1-(hydroxymethyl)cyclopentyl)-amino)pyrimidin-2-yl)amino)cyclohexyl)-1-(5-(1-methyl-1H-pyrazol-4-yl)pyridin-2-yl)urea | | | 621.5 |
| 328 | 3-benzyl-1-(trans-4-((5-cyano-4-((2-hydroxybutyl)amino)pyrimidin-2-yl)amino)cyclohexyl)-1-(5-(1-methyl-1H-pyrazol-4-yl)pyridin-2-yl)urea | | | 595.4 |
| 329 | 3-benzyl-1-(trans-4-((5-cyano-4-((1-hydroxy-2-methylpropan-2-yl)amino)pyrimidin-2-yl)amino)-cyclohexyl)-1-(5-(1-methyl-1H-pyrazol-4-yl)pyridin-2-yl)urea | | | 595.4 |

TABLE 1-66

| Ex. No. | IUPAC name | structural formula | salt | MS |
|---|---|---|---|---|
| 330 | 3-benzyl-1-(trans-4-((5-cyano-4-(((1-hydroxycyclopentyl)methyl)-amino)pyrimidin-2-yl)amino)cyclohexyl)-1-(5-(1-methyl-1H-pyrazol-4-yl)pyridin-2-yl)urea | | | 621.5 |

TABLE 1-66-continued

| Ex. No. | IUPAC name | structural formula | salt | MS |
|---|---|---|---|---|
| 331 | 3-benzyl-1-(trans-4-((5-cyano-4-((2-hydroxycyclopentyl)amino)-pyrimidin-2-yl)amino)cyclohexyl)-1-(5-(1-methyl-1H-pyrazol-4-yl)pyridin-2-yl)urea | | | 607.4 |
| 332 | 3-benzyl-1-(trans-4-((5-cyano-4-((2-hydroxy-2-methylpropyl)amino)pyrimidin-2-yl)amino)cyclohexyl)-1-(5-(1-methyl-1H-pyrazol-4-yl)pyridin-2-yl)urea | | | 595.4 |
| 333 | 1,5-anhydro-3-((2-((trans-4-((benzylcarbamoyl)(5-(1-methyl-1H-pyrazol-4-yl)pyridin-2-yl)amino)cyclohexyl)amino)-5-cyanopyrimidin-4-yl)amino)-2,3-dideoxypentitol | | | 623.5 |
| 334 | 3-benzyl-1-(trans-4-((5-cyano-4-(((1-hydroxycyclohexyl)methyl)-amino)pyrimidin-2-yl)amino)cyclohexyl)-1-(5-(1-methyl-1H-pyrazol-4-yl)pyridin-2-yl)urea | | | 635.5 |

TABLE 1-67

| Ex. No. | IUPAC name | structural formula | salt | MS |
|---|---|---|---|---|
| 335 | 3-benzyl-1-(trans-4-((5-cyano-4-(((1-hydroxycyclobutyl)methyl)-amino)pyrimidin-2-yl)amino)-cyclohexyl)-1-(5-(1-methyl-1H-pyrazol-4-yl)pyridin-2-yl)urea | | | 607.4 |
| 336 | 3-benzyl-1-(trans-4-((5-cyano-4-((2-hydroxypropyl)amino)pyrimidin-2-yl)amino)cyclohexyl)-1-(5-(1-methyl-1H-pyrazol-4-yl)pyridin-2-yl)urea | | | 581.4 |
| 337 | 3-benzyl-1-(trans-4-((5-cyano-4-((3-hydroxy-3-methylbutan-2-yl)amino)pyrimidin-2-yl)amino)cyclohexyl)-1-(5-(1-methyl-1H-pyrazol-4-yl)pyridin-2-yl)urea | | | 609.5 |
| 338 | 1,5-anhydro-2-((2-((trans-4-((benzylcarbamoyl)(5-(1-methyl-1H-pyrazol-4-yl)pyridin-2-yl)amino)cyclohexyl)amino)-5-cyanopyrimidin-4-yl)amino)-2,4-dideoxypentitol | | | 623.5 |

TABLE 1-67-continued

| Ex. No. | IUPAC name | structural formula | salt | MS |
|---|---|---|---|---|
| 339 | 3-benzyl-1-(trans-4-((5-cyano-4-((2-methoxyethyl)amino)pyrimidin-2-yl)amino)cyclohexyl)-1-(5-(1-methyl-1H-pyrazol-4-yl)pyridin-2-yl)urea | | | 581.5 |

TABLE 1-68

| Ex. No. | IUPAC name | structural formula | salt | MS |
|---|---|---|---|---|
| 340 | 3-benzyl-1-(trans-4-((5-cyano-4-((3-(1H-imidazol-1-yl)propyl)amino)pyrimidin-2-yl)amino)cyclohexyl)-1-(5-(1-methyl-1H-pyrazol-4-yl)pyridin-2-yl)urea | | | 631.5 |
| 341 | 1-(2-((trans-4-((benzylcarbamoyl)(5-(1-methyl-1H-pyrazol-4-yl)pyridin-2-yl)amino)cyclohexyl)amino)-5-cyanopyrimidin-4-yl)piperidine-3-carboxamide | | | 634.5 |
| 342 | N-(2-((2-((trans-4-((benzylcarbamoyl)(5-(1-methyl-1H-pyrazol-4-yl)pyridin-2-yl)amino)cyclohexyl)amino)-5-cyanopyrimidin-4-yl)amino)ethyl)acetamide | | | |

TABLE 1-68-continued

| Ex. No. | IUPAC name | structural formula | salt | MS |
|---|---|---|---|---|
| 343 | 3-benzyl-1-(trans-4-((5-cyano-4-((3-(2-oxopyrrolidin-1-yl)-propyl)amino)pyrimidin-2-yl)amino)cyclohexyl)-1-(5-(1-methyl-1H-pyrazol-4-yl)pyridin-2-yl)urea | | | 648.5 |
| 344 | 3-benzyl-1-(trans-4-((5-cyano-4-(4-(ethylsulfonyl)-piperazin-1-yl)pyrimidin-2-yl)amino)cyclohexyl)-1-(5-(1-methyl-1H-pyrazol-4-yl)pyridin-2-yl)urea | | | |

TABLE 1-69

| Ex. No. | IUPAC name | structural formula | salt | MS |
|---|---|---|---|---|
| 345 | 3-benzyl-1-(trans-4-((5-cyano-4-((2-methoxyethyl)(methyl)-amino)pyrimidin-2-yl)amino)-cyclohexyl)-1-(5-(1-methyl-1H-pyrazol-4-yl)pyridin-2-yl)urea | | | 595.4 |
| 346 | 3-benzyl-1-(trans-4-((5-cyano-4-((2-(pyrrolidin-1-yl)-ethyl)amino)pyrimidin-2-yl)amino)cyclohexyl)-1-(5-(1-methyl-1H-pyrazol-4-yl)pyridin-2-yl)urea | | | 620.6 |

TABLE 1-69-continued

| Ex. No. | IUPAC name | structural formula | salt | MS |
|---|---|---|---|---|
| 347 | 4-(((2-((trans-4-((benzylcarbamoyl)(5-(1-methyl-1H-pyrazol-4-yl)pyridin-2-yl)amino)cyclohexyl)amino)-5-cyanopyrimidin-4-yl)amino)methyl)benzenesulfonamide | | | 692.4 |
| 348 | 3-benzyl-1-(trans-4-((5-cyano-4-((2R,6S)-2,6-dimethylmorpholin-4-yl)pyrimidin-2-yl)amino)cyclohexyl)-1-(5-(1-methyl-1H-pyrazol-4-yl)pyridin-2-yl)urea | | | 621.5 |
| 349 | 3-benzyl-1-(trans-4-((5-cyano-4-((2-thienylmethyl)amino)pyrimidin-2-yl)amino)cyclohexyl)-1-(5-(1-methyl-1H-pyrazol-4-yl)pyridin-2-yl)urea | | | 619.4 |

TABLE 1-70

| Ex. No. | IUPAC name | structural formula | salt | MS |
|---|---|---|---|---|
| 350 | 3-benzyl-1-(trans-4-((5-cyano-4-(5-oxo-1,4-diazepan-1-yl)pyrimidin-2-yl)amino)cyclohexyl)-1-(5-(1-methyl-1H-pyrazol-4-yl)pyridin-2-yl)urea | | | 620.5 |

TABLE 1-70-continued

| Ex. No. | IUPAC name | structural formula | salt | MS |
|---|---|---|---|---|
| 351 | 3-benzyl-1-(trans-4-((5-cyano-4-(3-(methylsulfonyl)pyrrolidin-1-yl)pyrimidin-2-yl)amino)-cyclohexyl)-1-(5-(1-methyl-1H-pyrazol-4-yl)pyridin-2-yl)urea | | | 655.5 |
| 352 | 3-benzyl-1-(trans-4-((5-cyano-4-((2-(methylsulfonyl)ethyl)-amino)pyrimidin-2-yl)amino)-cyclohexyl)-1-(5-(1-methyl-1H-pyrazol-4-yl)pyridin-2-yl)urea | | | 629.4 |
| 353 | 3-benzyl-1-(trans-4-((5-cyano-4-((2-(1H-1,2,4-triazol-1-yl)ethyl)amino)pyrimidin-2-yl)amino)cyclohexyl)-1-(5-(1-methyl-1H-pyrazol-4-yl)pyridin-2-yl)urea | | | 618.4 |
| 354 | 3-benzyl-1-(trans-4-((5-cyano-4-(((1,5-dimethyl-1H-pyrazol-3-yl)-methyl)amino)pyrimidin-2-yl)amino)cyclohexyl)-1-(5-(1-methyl-1H-pyrazol-4-yl)pyridin-2-yl)urea | | | 631.5 |

TABLE 1-71

| Ex. No. | IUPAC name | structural formula | salt | MS |
|---|---|---|---|---|
| 355 | 3-benzyl-1-(trans-4-((5-cyano-4-(((2,5-dimethyl-3-furyl)methyl)-amino)pyrimidin-2-yl)amino)-cyclohexyl)-1-(5-(1-methyl-1H-pyrazol-4-yl)pyridin-2-yl)urea | | | 631.5 |
| 356 | 1,5-anhydro-2-((2-((trans-4-((benzylcarbamoyl)(5-(1-methyl-1H-pyrazol-4-yl)pyridin-2-yl)amino)cyclohexyl)amino)-5-cyanopyrimidin-4-yl)amino)-2,4-dideoxy-D-threo-pentitol | | | 623.5 |
| 357 | 3-benzyl-1-(trans-4-((5-cyano-4-((3-fluoro-propyl)amino)-pyrimidin-2-yl)amino)-cyclohexyl)-1-(5-(1-methyl-1H-pyrazol-4-yl)pyridin-2-yl)urea | | | 583.4 |
| 358 | 3-benzyl-1-(trans-4-((5-cyano-4-(3-fluoro-3-(hydroxymethyl)-azetidin-1-yl)pyrimidin-2-yl)amino)cyclohexyl)-1-(5-(1-methyl-1H-pyrazol-4-yl)pyridin-2-yl)urea | | | 611.4 |

TABLE 1-71-continued

| Ex. No. | IUPAC name | structural formula | salt | MS |
|---|---|---|---|---|
| 359 | 3-benzyl-1-(trans-4-((5-cyano-4-(3-fluoro-3-(hydroxymethyl)-pyrrolidin-1-yl)pyrimidin-2-yl)amino)cyclohexyl)-1-(5-(1-methyl-1H-pyrazol-4-yl)pyridin-2-yl)urea | | | 625.5 |

TABLE 1-72

| Ex. No. | IUPAC name | structural formula | salt | MS |
|---|---|---|---|---|
| 360 | 3-benzyl-1-(trans-4-((5-cyano-4-(3-((dimethyl(oxide)-lambda$^6$-sulfanylidene)amino)pyrrolidin-1-yl)pyrimidin-2-yl)amino)-cyclohexyl)-1-(5-(1-methyl-1H-pyrazol-4-yl)pyridin-2-yl)urea | | | 668.5 |
| 361 | 3-benzyl-1-(trans-4-((5-cyano-4-((5-oxopyrrolidin-3-yl)amino)pyrimidin-2-yl)amino)-cyclohexyl)-1-(5-(1-methyl-1H-pyrazol-4-yl)pyridin-2-yl)urea | | | 606.5 |
| 362 | 3-benzyl-1-(trans-4-((5-cyano-4-(1-(methylimino)-1-oxide-llambda$^4$,4-thiazinan-4-yl)pyrimidin-2-yl)amino)-cyclohexyl)-1-(5-(1-methyl-1H-pyrazol-4-yl)pyridin-2-yl)urea | | | 654.5 |

TABLE 1-72-continued

| Ex. No. | IUPAC name | structural formula | salt | MS |
|---|---|---|---|---|
| 363 | 3-benzyl-1-(trans-4-((5-cyano-4-((4-oxo-5-azaspiro[2.4]hepta-7-yl)amino)pyrimidin-2-yl)amino)cyclohexyl)-1-(5-(1-methyl-1H-pyrazol-4-yl)pyridin-2-yl)urea | 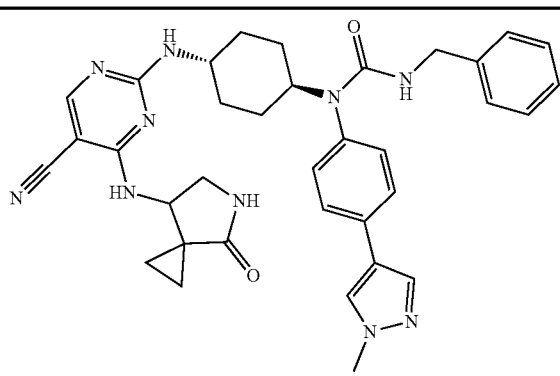 | | 632.5 |
| 364 | 3-benzyl-1-(trans-4-((5-cyano-4-(3-((dimethyl(oxide)-lambda⁶-sulfanylidene)amino)azetidin-1-yl)pyrimidin-2-yl)amino)-cyclohexyl)-1-(5-(1-methyl-1H-pyrazol-4-yl)pyridin-2-yl)urea | 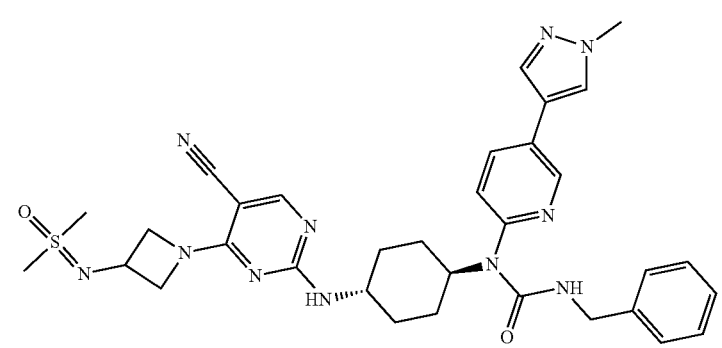 [SMILES: Cn1cc(-c2ccc(N(C(=O)NCc3ccccc3)[C@H]3CC[C@H](Nc4ncc(C#N)c(N5CC(N=S(C)(C)=O)C5)n4)CC3)nc2)cn1] | | 654.5 |

TABLE 1-73

| Ex. No. | IUPAC name | structural formula | salt | MS |
|---|---|---|---|---|
| 365 | 3-benzyl-1-(trans-4-((5-cyano-4-(4-((dimethyl(oxide)-lambda⁶-sulfanylidene)amino)piperidin-1-yl)pyrimidin-2-yl)amino)-cyclohexyl)-1-(5-(1-methyl-1H-pyrazol-4-yl)pyridin-2-yl)urea | 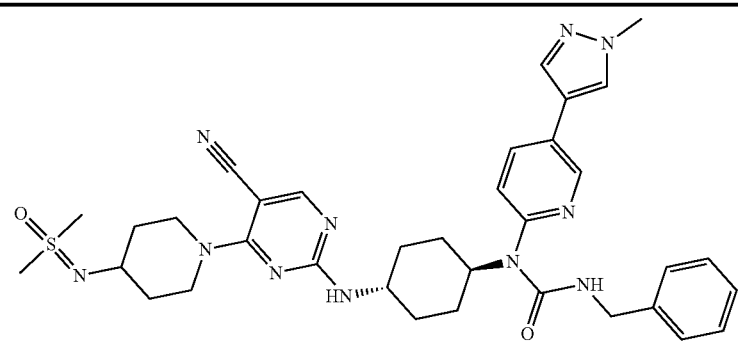 | | 682.5 |
| 366 | 3-benzyl-1-(trans-4-((5-cyano-4-(1-methylhexahydropyrrolo-[3,4-b]pyrrole-5(1H)-yl)pyrimidin-2-yl)amino)cyclohexyl)-1-(5-(1-methyl-1H-pyrazol-4-yl)pyridin-2-yl)urea | 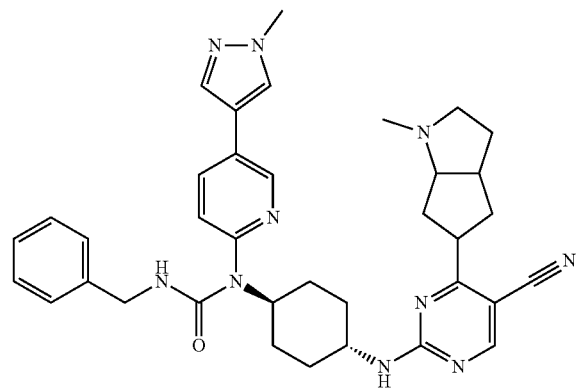 [SMILES: CN1CCC2CC(c3nc(N[C@H]4CC[C@H](N(C(=O)NCc5ccccc5)c5ccc(-c6cnn(C)c6)cn5)CC4)ncc3C#N)CC21] | | 632.6 |

TABLE 1-73-continued

| Ex. No. | IUPAC name | structural formula | salt | MS |
|---|---|---|---|---|
| 367 | 3-benzyl-1-(trans-4-((5-cyano-4-((1,1-dioxidetetrahydrothiophen-3-yl)amino)pyrimidin-2-yl)amino)-cyclohexyl)-1-(5-(1-methyl-1H-pyrazol-4-yl)pyridin-2-yl)urea | | | 641.4 |
| 368 | 3-benzyl-1-(trans-4-((5-cyano-4-(5-methylhexahydropyrrolo-[3,4-b]pyrrole-1(2H)-yl)pyrimidin-2-yl)amino)cyclohexyl)-1-(5-(1-methyl-1H-pyrazol-4-yl)pyridin-2-yl)urea | | | 632.5 |
| 369 | 3-benzyl-1-(trans-4-((5-cyano-4-((1,1-dioxidetetrahydro-2H-thiopyran-4-yl)amino)pyrimidin-2-yl)amino)cyclohexyl)-1-(5-(1-methyl-1H-pyrazol-4-yl)pyridin-yl)urea | | | 653.4 |

TABLE 1-74

| Ex. No. | IUPAC name | structural formula | salt | MS |
|---|---|---|---|---|
| 370 | 3-benzyl-1-(trans-4-((5-cyano-4-(1,1-dioxide-1,4-thiazepan-4-yl)pyrimidin-2-yl)amino)cyclohexyl)-1-(5-(1-methyl-1H-pyrazol-4-yl)pyridin-2-yl)urea | | | 655.5 |

TABLE 1-74-continued

| Ex. No. | IUPAC name | structural formula | salt | MS |
|---|---|---|---|---|
| 371 | 3-benzyl-1-(trans-4-((5-cyano-4-(2-oxabicyclo-[4.2.0]octa-7-ylamino)pyrimidin-2-yl)amino)cyclohexyl)-1-(5-(1-methyl-1H-pyrazol-4-yl)pyridin-2-yl)urea | | | 633.5 |
| 372 | 3-benzyl-1-(trans-4-((5-cyano-4-(4-fluoropiperidin-1-yl)pyrimidin-2-yl)amino)cyclohexyl)-1-(5-(1-methyl-1H-pyrazol-4-yl)pyridin-2-yl)urea | | | 609.4 |
| 373 | 3-benzyl-1-(trans-4-((5-cyano-4-(6-oxo-1,7-diazaspiro[4.4]nona-1-yl)pyrimidin-2-yl)amino)cyclohexyl)-1-(5-(1-methyl-1H-pyrazol-4-yl)pyridin-2-yl)urea | | | 646.5 |
| 374 | 3-benzyl-1-(trans-4-((5-cyano-4-((oxetan-3-ylmethyl)amino)-pyrimidin-2-yl)amino)cyclohexyl)-1-(5-(1-methyl-1H-pyrazol-4-yl)pyridin-2-yl)urea | | | 593.4 |

TABLE 1-75

| Ex. No. | IUPAC name | structural formula | salt | MS |
|---|---|---|---|---|
| 375 | 3-benzyl-1-(trans-4-((5-cyano-4-(4-(trifluoromethyl)-piperidin-1-yl)pyrimidin-2-yl)amino)cyclohexyl)-1-(5-(1-methyl-1H-pyrazol-4-yl)pyridin-2-yl)urea | | | 659.5 |
| 376 | 3-benzyl-1-(trans-4-((5-cyano-4-((3,3-difluorocyclobutyl)-amino)pyrimidin-2-yl)amino)cyclohexyl)-1-(5-(1-methyl-1H-pyrazol-4-yl)pyridin-2-yl)urea | | | 611.2 |
| 377 | 3-benzyl-1-(trans-4-((5-cyano-4-(1-oxidethiomorpholin-4-yl)pyrimidin-2-yl)amino)-cyclohexyl)-1-(5-(1-methyl-1H-pyrazol-4-yl)pyridin-2-yl)urea | | | 625.4 |
| 378 | 3-benzyl-1-(trans-4-((5-cyano-4-(1,1-difluoro-5-azaspiro[2.4]hept-5-yl)pyrimidin-2-yl)amino)-cyclohexyl)-1-(5-(1-methyl-1H-pyrazol-4-yl)pyridin-2-yl)urea | | | 639.5 |

TABLE 1-75-continued

| Ex. No. | IUPAC name | structural formula | salt | MS |
|---|---|---|---|---|
| 379 | 3-benzyl-1-(trans-4-((5-cyano-4-(3,4-dihydro-2,7-naphthyridine-2(1H)-yl)pyrimidin-2-yl)amino)-cyclohexyl)-1-(5-(1-methyl-1H-pyrazol-4-yl)pyridin-2-yl)urea | | | 640.5 |

TABLE 1-76

| Ex. No. | IUPAC name | structural formula | salt | MS |
|---|---|---|---|---|
| 380 | 3-benzyl-1-(trans-4-((5-cyano-4-(3,4-dihydro-2,6-naphthyridine-2(1H)-yl)pyrimidin-2-yl)amino)-cyclohexyl)-1-(5-(1-methyl-1H-pyrazol-4-yl)pyridin-2-yl)urea | | | 640.4 |
| 381 | 3-benzyl-1-(trans-4-((5-cyano-4-(3-methoxypyrrolidin-1-yl)pyrimidin-2-yl)amino)-cyclohexyl)-1-(5-(1-methyl-1H-pyrazol-4-yl)pyridin-2-yl)urea | | | 607.5 |

TABLE 1-76-continued

| Ex. No. | IUPAC name | structural formula | salt | MS |
|---|---|---|---|---|
| 382 | 3-benzyl-1-(trans-4-((5-cyano-4-(3-cyanopyrrolidin-1-yl)pyrimidin-2-yl)amino)-cyclohexyl)-1-(5-(1-methyl-1H-pyrazol-4-yl)pyridin-2-yl)urea | | | 602.4 |
| 383 | 3-benzyl-1-(trans-4-((5-cyano-4-((3aR,7aR)-3-oxooctahydro-5H-pyrrolo[3,4-c]pyridin-5-yl)pyrimidin-2-yl)amino)-cyclohexyl)-1-(5-(1-methyl-1H-pyrazol-4-yl)pyridin-2-yl)urea | | | 646.5 |
| 384 | 3-benzyl-1-(trans-4-((5-cyano-4-((tetrahydro-2H-pyran-3-ylmethyl)amino)pyrimidin-2-yl)amino)cyclohexyl)-1-(5-(1-methyl-1H-pyrazol-4-yl)pyridin-2-yl)urea | | | 621.5 |

TABLE 1-77

| Ex. No. | IUPAC name | structural formula | salt | MS |
|---|---|---|---|---|
| 385 | 3-benzyl-1-(trans-4-((5-cyano-4-((tetrahydro-2H-pyran-2-ylmethyl)amino)pyrimidin-2-yl)amino)cyclohexyl)-1-(5-(1-methyl-1H-pyrazol-4-yl)pyridin-2-yl)urea | | | 621.6 |

TABLE 1-77-continued

| Ex. No. | IUPAC name | structural formula | salt | MS |
|---|---|---|---|---|
| 386 | 3-benzyl-1-(trans-4-((5-cyano-4-((tetrahydro-2H-pyran-4-ylmethyl)amino)pyrimidin-2-yl)amino)cyclohexyl)-1-(5-(1-methyl-1H-pyrazol-4-yl)pyridin-2-yl)urea | 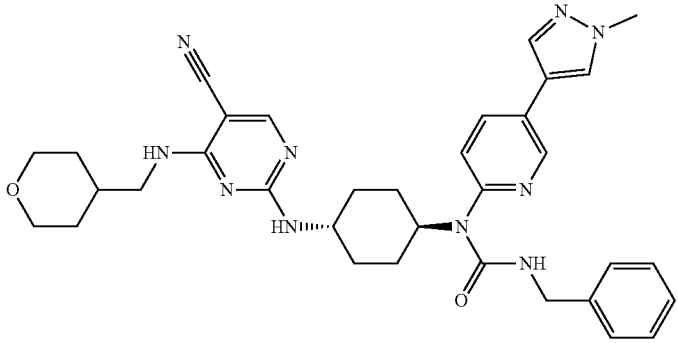 [SMILES: Cn1cc(-c2ccc(N(C(=O)NCc3ccccc3)[C@H]3CC[C@H](Nc4ncc(C#N)c(NCC5CCOCC5)n4)CC3)nc2)cn1] | | 621.5 |
| 387 | 3-benzyl-1-(trans-4-((5-cyano-4-(thiomorpholin-4-yl)pyrimidin-2-yl)amino)cyclohexyl)-1-(5-(1-methyl-1H-pyrazol-4-yl)pyridin-2-yl)urea | 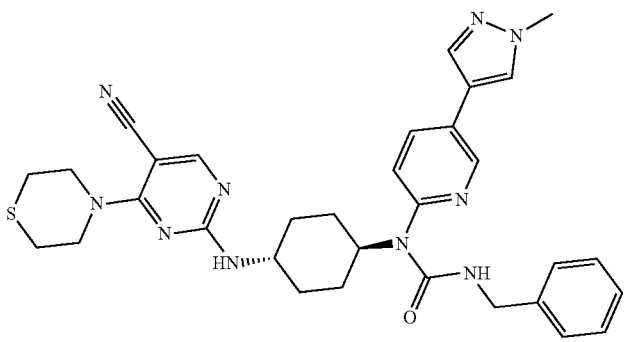 [SMILES: Cn1cc(-c2ccc(N(C(=O)NCc3ccccc3)[C@H]3CC[C@H](Nc4ncc(C#N)c(N5CCSCC5)n4)CC3)nc2)cn1] | | 609.4 |
| 388 | 3-benzyl-1-(trans-4-((5-cyano-4-(3-hydroxy-3-methylpyrrolidin-1-yl)pyrimidin-2-yl)amino)-cyclohexyl)-1-(5-(1-methyl-1H-pyrazol-4-yl)pyridin-2-yl)urea | 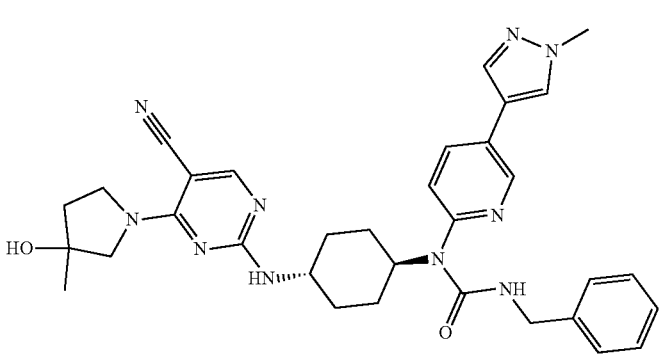 [SMILES: Cn1cc(-c2ccc(N(C(=O)NCc3ccccc3)[C@H]3CC[C@H](Nc4ncc(C#N)c(N5CCC(C)(O)C5)n4)CC3)nc2)cn1] | | 607.5 |
| 389 | 3-benzyl-1-(trans-4-((5-cyano-4-((2S)-2-(methoxymethyl)-pyrrolidin-1-yl)pyrimidin-2-yl)amino)cyclohexyl)-1-(5-(1-methyl-1H-pyrazol-4-yl)pyridin-2-yl)urea | 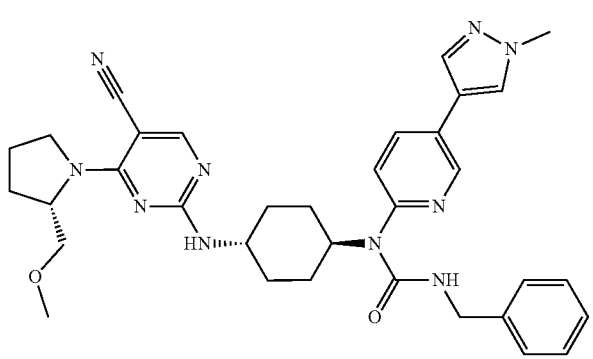 [SMILES: COC[C@@H]1CCCN1c1nc(N[C@H]2CC[C@H](N(C(=O)NCc3ccccc3)c3ccc(-c4cnn(C)c4)cn3)CC2)ncc1C#N] | | 621.5 |

TABLE 1-78

| Ex. No. | IUPAC name | structural formula | salt | MS |
|---|---|---|---|---|
| 390 | 3-benzyl-1-(trans-4-((5-cyano-4-((2R)-2-(methoxymethyl)-pyrrolidin-1-yl)pyrimidin-2-yl)amino)cyclohexyl)-1-(5-(1-methyl-1H-pyrazol-4-yl)pyridin-2-yl)urea | | | 621.5 |
| 391 | N-(1-(2-((trans-4-((benzylcarbamoyl)(5-(1-methyl-1H-pyrazol-4-yl)pyridin-2-yl)amino)cyclohexyl)amino)-5-cyanopyrimidin-4-yl)pyrrolidin-3-yl)-N-ethylacetamide | | | 662.6 |
| 392 | 3-benzyl-1-(trans-4-((5-cyano-4-(4-methyl-1,4-diazepan-1-yl)pyrimidin-2-yl)amino)-cyclohexyl)-1-(5-(1-methyl-1H-pyrazol-4-yl)pyridin-2-yl)urea | | | 620.6 |
| 393 | 3-benzyl-1-(trans-4-((5-cyano-4-((3-ethoxypropyl)amino)-pyrimidin-2-yl)amino)-cyclohexyl)-1-(5-(1-methyl-1H-pyrazol-4-yl)pyridin-2-yl)urea | | | 609.5 |

TABLE 1-78-continued

| Ex. No. | IUPAC name | structural formula | salt | MS |
|---|---|---|---|---|
| 394 | 3-benzyl-1-(trans-4-((5-cyano-4-((thietan-3-ylmethyl)amino)-pyrimidin-2-yl)amino)-cyclohexyl)-1-(5-(1-methyl-1H-pyrazol-4-yl)pyridin-2-yl)urea | | | 609.4 |

TABLE 1-79

| Ex. No. | IUPAC name | structural formula | salt | MS |
|---|---|---|---|---|
| 395 | 3-benzyl-1-(trans-4-((5-cyano-((2-hydroxy-2-methylpropyl)-(methyl)amino)pyrimidin-2-yl)amino)cyclohexyl)-1-(5-(1-methyl-1H-pyrazol-4-yl)pyridin-2-yl)urea | | | 609.5 |
| 396 | 3-benzyl-1-(trans-4-((5-cyano-4-((3-methoxypropyl)-(methyl)amino)pyrimidin-2-yl)amino)cyclohexyl)-1-(5-(1-methyl-1H-pyrazol-4-yl)pyridin-2-yl)urea | | | 609.5 |
| 397 | 3-benzyl-1-(trans-4-((5-cyano-4-((2S,3S)-3-(2-hydroxypropan-2-yl)-2-methylpyrrolidin-1-yl)pyrimidin-2-yl)amino)-cyclohexyl)-1-(5-(1-methyl-1H-pyrazol-4-yl)pyridin-2-yl)urea | | | 649.6 |

TABLE 1-79-continued

| Ex. No. | IUPAC name | structural formula | salt | MS |
|---|---|---|---|---|
| 398 | 3-benzyl-1-(trans-4-((5-cyano-4-((2R,3R)-3-(2-hydroxypropan-2-yl)-2-methylpyrrolidin-1-yl)pyrimidin-2-yl)amino)-cyclohexyl)-1-(5-(1-methyl-1H-pyrazol-4-yl)pyridin-2-yl)urea | | | 649.6 |
| 399 | 3-benzyl-1-(trans-4-((5-cyano-4-((2S,3S)-3-hydroxy-2-methyl-3-(trifluoromethyl)pyrrolidin-1-yl)pyrimidin-2-yl)amino)-cyclohexyl)-1-(5-(1-methyl-1H-pyrazol-4-yl)pyridin-2-yl)urea | | | 675.4 |

TABLE 1-80

| Ex. No. | IUPAC name | structural formula | salt | MS |
|---|---|---|---|---|
| 400 | 3-benzyl-1-(trans-4-((5-cyano-4-((2S,3R)-3-cyclopropyl-3-hydroxy-2-methylpyrrolidin-1-yl)pyrimidin-2-yl)amino)-cyclohexyl)-1-(5-(1-methyl-1H-pyrazol-4-yl)pyridin-2-yl)urea | | | 647.6 |
| 401 | 3-benzyl-1-(trans-4-((5-cyano-4-((pyrrolidin-2-ylmethyl)amino)-pyrimidin-2-yl)amino)-cyclohexyl)-1-(5-(1-methyl-1H-pyrazol-4-yl)pyridin-2-yl)urea trifluoroacetate | | CF$_3$COOH | 606.5 |

TABLE 1-80-continued

| Ex. No. | IUPAC name | structural formula | salt | MS |
|---|---|---|---|---|
| 402 | 3-benzyl-1-(trans-4-((5-cyano-4-(1-methyl-1,8-diazaspiro-[4.5]deca-8-yl)pyrimidin-2-yl)amino)cyclohexyl)-1-(5-(1-methyl-1H-pyrazol-4-yl)pyridin-2-yl)urea | | | 660.5 |
| 403 | 3-benzyl-1-(trans-4-((5-cyano-4-(3-oxa-9-azaspiro[5.5]undeca-9-yl)pyrimidin-2-yl)amino)-cyclohexyl)-1-(5-(1-methyl-1H-pyrazol-4-yl)pyridin-2-yl)urea | | | 661.5 |
| 404 | 3-benzyl-1-(trans-4-((5-cyano-4-(7-oxa-2-azaspiro[3.5]nona-2-yl)pyrimidin-2-yl)amino)-cyclohexyl)-1-(5-(1-methyl-1H-pyrazol-4-yl)pyridin-2-yl)urea | | | 633.5 |

TABLE 1-81

| Ex. No. | IUPAC name | structural formula | salt | MS |
|---|---|---|---|---|
| 405 | 3-benzyl-1-(trans-4-((5-cyano-4-(7-oxa-1-azaspiro[3.5]nona-1-yl)pyrimidin-2-yl)amino)cyclohexyl)-1-(5-(1-methyl-1H-pyrazol-4-yl)pyridin-2-yl)urea | | | 633.5 |
| 406 | 3-benzyl-1-(trans-4-((5-cyano-(8-oxo-2,7-diazaspiro[4.4]nona-2-yl)pyrimidin-2-yl)amino)cyclohexyl)-1-(5-(1-methyl-1H-pyrazol-4-yl)pyridin-2-yl)urea | | | 646.5 |
| 407 | 3-benzyl-1-(trans-4-((5-cyano-4-(6-oxa-1-azaspiro[3.4]octa-1-yl)pyrimidin-2-yl)amino)cyclohexyl)-1-(5-(1-methyl-1H-pyrazol-4-yl)pyridin-2-yl)urea | | | 619.4 |
| 408 | 3-benzyl-1-(trans-4-((5-cyano-4-(6-oxa-1-azaspiro[3.5]nona-1-yl)pyrimidin-2-yl)amino)cyclohexyl)-1-(5-(1-methyl-1H-pyrazol-4-yl)pyridin-2-yl)urea | | | 633.5 |

TABLE 1-81-continued

| Ex. No. | IUPAC name | structural formula | salt | MS |
|---|---|---|---|---|
| 409 | 3-benzyl-1-(trans-4-((5-cyano-4-(2,2-dioxide-2-thia-7-azaspiro[4.5]deca-7-yl)pyrimidin-2-yl)amino)cyclohexyl)-1-(5-(1-methyl-1H-pyrazol-4-yl)pyridin-2-yl)urea | | | 695.5 |

TABLE 1-82

| Ex. No. | IUPAC name | structural formula | salt | MS |
|---|---|---|---|---|
| 410 | 3-benzyl-1-(trans-4-((5-cyano-4-(2-oxa-6-azaspiro[3.5]nona-6-yl)pyrimidin-2-yl)amino)cyclohexyl)-1-(5-(1-methyl-1H-pyrazol-4-yl)pyridin-2-yl)urea | | | 633.5 |
| 411 | 3-benzyl-1-(trans-4-((5-cyano-4-(2-oxa-6-azaspiro[3.4]octa-6-yl)pyrimidin-2-yl)amino)cyclohexyl)-1-(5-(1-methyl-1H-pyrazol-4-yl)pyridin-2-yl)urea | | | 619.5 |

TABLE 1-82-continued

| Ex. No. | IUPAC name | structural formula | salt | MS |
|---|---|---|---|---|
| 412 | 3-benzyl-1-(trans-4-((5-cyano-4-(1-oxa-7-azaspiro[4.5]deca-7-yl)pyrimidin-2-yl)amino)cyclohexyl)-1-(5-(1-methyl-1H-pyrazol-4-yl)pyridin-2-yl)urea | | | 647.6 |
| 413 | 3-benzyl-1-(trans-4-((5-cyano-4-(2-oxa-7-azaspiro[4.5]deca-7-yl)pyrimidin-2-yl)amino)cyclohexyl)-1-(5-(1-methyl-1H-pyrazol-4-yl)pyridin-2-yl)urea | | | 647.5 |
| 414 | 3-benzyl-1-(trans-4-((5-cyano-4-(2-oxa-7-azaspiro[4.4]nona-7-yl)pyrimidin-2-yl)amino)cyclohexyl)-1-(5-(1-methyl-1H-pyrazol-4-yl)pyridin-2-yl)urea | | | 633.5 |

TABLE 1-83

| Ex. No. | IUPAC name | structural formula | salt | MS |
|---|---|---|---|---|
| 415 | 3-benzyl-1-(trans-4-((5-cyano-4-(2-oxa-6-azaspiro[3.3]hepta-6-yl)pyrimidin-2-yl)amino)cyclohexyl)-1-(5-(1-methyl-1H-pyrazol-4-yl)pyridin-2-yl)urea | | | 605.5 |
| 416 | 3-benzyl-1-(trans-4-((5-cyano-4-(2,5-dioxa-8-azaspiro[3.5]nona-8-yl)pyrimidin-2-yl)amino)cyclohexyl)-1-(5-(1-methyl-1H-pyrazol-4-yl)pyridin-2-yl)urea | | | 635.5 |
| 417 | 3-benzyl-1-(trans-4-((5-cyano-4-(6-oxa-1-azaspiro[3.3]hepta-1-yl)pyrimidin-2-yl)amino)cyclohexyl)-1-(5-(1-methyl-1H-pyrazol-4-yl)pyridin-2-yl)urea | | | 605.5 |
| 418 | 3-benzyl-1-(trans-4-((5-cyano-4-(4-fluoro-2-methoxyphenyl)pyrimidin-2-yl)amino)cyclohexyl)-1-(5-(1-methyl-1H-pyrazol-4-yl)pyridin-2-yl)urea | | | 632.5 |

TABLE 1-83-continued

| Ex. No. | IUPAC name | structural formula | salt | MS |
|---|---|---|---|---|
| 419 | 3-benzyl-1-(trans-4-((5-cyano-4-(6-hydroxypyridin-3-yl)pyrimidin-2-yl)amino)cyclohexyl)-1-(5-(1-methyl-1H-pyrazol-4-yl)pyridin-2-yl)urea | | | 601.4 |

TABLE 1-84

| Ex. No | IUPAC name | structural formula | salt | MS |
|---|---|---|---|---|
| 420 | 3-benzyl-1-(trans-4-((5-cyano-4-(2-hydroxypyridin-3-yl)pyrimidin-2-yl)amino)cyclohexyl)-1-(5-(1-methyl-1H-pyrazol-4-yl)pyridin-2-yl)urea | | | 601.4 |
| 421 | 3-benzyl-1-(trans-4-((5-cyano-4-(3-methyl-2-oxo-2,3-dihydro-1H-benzimidazol-5-yl)pyrimidin-2-yl)amino)cyclohexyl)-1-(5-(1-methyl-1H-pyrazol-4-yl)pyridin-2-yl)urea | | | 654.5 |

TABLE 1-84-continued

| Ex. No | IUPAC name | structural formula | salt | MS |
|---|---|---|---|---|
| 422 | 3-benzyl-1-(trans-4-((5-cyano-4-(imidazo[1,2-a]pyridin-6-yl)pyrimidin-2-yl)amino)cyclohexyl)-1-(5-(1-methyl-1H-pyrazol-4-yl)pyridin-2-yl)urea | | | 624.4 |
| 423 | 1-(trans-4-((4-(1,2-benzothiazol-5-yl)-5-cyanopyrimidin-2-yl)amino)cyclohexyl)-3-benzyl-1-(5-(1-methyl-1H-pyrazol-4-yl)pyridin-2-yl)urea | | | 641.4 |
| 424 | 1-(trans-4-((4-(1,2-benzothiazol-6-yl)-5-cyanopyrimidin-2-yl)amino)cyclohexyl)-3-benzyl-1-(5-(1-methyl-1H-pyrazol-4-yl)pyridin-2-yl)urea | | | 641.4 |

TABLE 1-85

| Ex. No. | IUPAC name | structural formula | salt | MS |
|---|---|---|---|---|
| 425 | 3-benzyl-1-(trans-4-((5-cyano-4-(4-oxo-3,4-dihydroquinazolin-6-yl)pyrimidin-2-yl)amino)cyclohexyl)-1-(5-(1-methyl-1H-pyrazol-4-yl)pyridin-2-yl)urea | | | 650.3 |
| 426 | 3-benzyl-1-(trans-4-((5-cyano-4-phenylpyrimidin-2-yl)amino)cyclohexyl)-1-(5-(1-methyl-1H-pyrazol-4-yl)pyridin-2-yl)urea | | | 584.4 |
| 427 | 3-benzyl-1-(trans-4-((5-cyano-4-(4-fluorophenyl)pyrimidin-2-yl)amino)cyclohexyl)-1-(5-(1-methyl-1H-pyrazol-4-yl)pyridin-2-yl)urea | | | 602.4 |
| 428 | 3-benzyl-1-(trans-4-((5-cyano-4-(4-cyanophenyl)-pyrimidin-2-yl)amino)cyclohexyl)-1-(5-(1-methyl-1H-pyrazol-4-yl)pyridin-2-yl)urea | | | 609.4 |

TABLE 1-85-continued

| Ex. No. | IUPAC name | structural formula | salt | MS |
|---|---|---|---|---|
| 429 | 3-benzyl-1-(trans-4-((5-cyano-4-(4-(trifluoromethoxy)-phenyl)pyrimidin-2-yl)amino)cyclohexyl)-1-(5-(1-methyl-1H-pyrazol-4-yl)pyridin-2-yl)urea | | | 668.4 |

TABLE 1-86

| Ex. No. | IUPAC name | structural formula | salt | MS |
|---|---|---|---|---|
| 430 | N-(3-(2-((trans-4-((benzylcarbamoyl)(5-(1-methyl-1H-pyrazol-4-yl)pyridin-2-yl)amino)-cyclohexyl)amino)-5-cyanopyrimidin-4-yl)phenyl)acetamide | | | 641.4 |
| 431 | 4-(2-((trans-4-((benzylcarbamoyl)(5-(1-methyl-1H-pyrazol-4-yl)pyridin-2-yl)amino)cyclohexyl)-amino)-5-cyanopyrimidin-4-yl)benzamide | | | 627.4 |
| 432 | 3-benzyl-1-(trans-4-((5-cyano-4-(dimethylamino)-phenyl)-pyrimidin-2-yl)amino)-cyclohexyl)-1-(5-(1-methyl-1H-pyrazol-4-yl)pyridin-2-yl)urea | | | 627.4 |

TABLE 1-86-continued

| Ex. No. | IUPAC name | structural formula | salt | MS |
|---|---|---|---|---|
| 433 | 3-benzyl-1-(trans-4-((5-cyano-4-(pyridin-4-yl)pyrimidin-2-yl)amino)cyclohexyl)-1-(5-(1-methyl-1H-pyrazol-4-yl)pyridin-2-yl)urea | | | 585.4 |
| 434 | 3-benzyl-1-(trans-4-((4-(4-chlorophenyl)-5-cyanopyrimidin-2-yl)amino)cyclohexyl)-1-(5-(1-methyl-1H-pyrazol-4-yl)pyridin-2-yl)urea | | | 618.4 |

TABLE 1-87

| Ex. No. | IUPAC name | structural formula | salt | MS |
|---|---|---|---|---|
| 435 | 1-(trans-4-((4-(4-acetylphenyl)-5-cyanopyrimidin-2-yl)amino)cyclohexyl)-3-benzyl-1-(5-(1-methyl-1H-pyrazol-4-yl)pyridin-2-yl)urea | | | 626.4 |
| 436 | 3-benzyl-1-(trans-4-((5-cyano-4-(2-methoxypyridin-3-yl)pyrimidin-2-yl)amino)cyclohexyl)-1-(5-(1-methyl-1H-pyrazol-4-yl)pyridin-2-yl)urea | | | 615.4 |

TABLE 1-87-continued

| Ex. No. | IUPAC name | structural formula | salt | MS |
|---|---|---|---|---|
| 437 | 3-benzyl-1-(trans-4-((5-cyano-4-(3-fluoro-phenyl)pyrimidin-2-yl)amino)cyclohexyl)-1-(5-(1-methyl-1H-pyrazol-4-yl)pyridin-2-yl)urea | | | 602.4 |
| 438 | 3-benzyl-1-(trans-4-((5-cyano-4-(2-fluoro-phenyl)pyrimidin-2-yl)amino)cyclohexyl)-1-(5-(1-methyl-1H-pyrazol-4-yl)pyridin-2-yl)urea | | | 602.4 |
| 439 | 3-benzyl-1-(trans-4-((5-cyano-4-(3-cyanophenyl)pyrimidin-2-yl)amino)cyclohexyl)-1-(5-(1-methyl-1H-pyrazol-4-yl)pyridin-2-yl)urea | | | 609.4 |

TABLE 1-88

| Ex. No. | IUPAC name | structural formula | salt | MS |
|---|---|---|---|---|
| 440 | 3-benzyl-1-(trans-4-((5-cyano-4-(5-(methylsulfonyl)-pyridin-3-yl)pyrimidin-2-yl)amino)-cyclohexyl)-1-(5-(1-methyl-1H-pyrazol-4-yl)pyridin-2-yl)urea | | | 663.3 |

TABLE 1-88-continued

| Ex. No. | IUPAC name | structural formula | salt | MS |
|---|---|---|---|---|
| 441 | 3-benzyl-1-(trans-4-((5-cyano-4-(6-(hydroxymethyl)-pyridin-3-yl)pyrimidin-2-yl)amino)-cyclohexyl)-1-(5-(1-methyl-1H-pyrazol-4-yl)pyridin-2-yl)urea | | | 615.4 |
| 442 | 3-(2-((trans-4-((benzylcarbamoyl)(5-(1-methyl-1H-pyrazol-4-yl)pyridin-2-yl)amino)cyclohexyl)amino)-5-cyanopyrimidin-4-yl)benzenesulfonamide | | | 663.4 |
| 443 | 4-(2-((trans-4-((benzylcarbamoyl)(5-(1-methyl-1H-pyrazol-4-yl)pyridin-2-yl)amino)cyclohexyl)amino)-5-cyanopyrimidin-4-yl)benzenesulfonamide | | | 661.3 |
| 444 | 1-(trans-4-((4-(2,1,3-benz-oxadiazol-5-yl)-5-cyanopyrimidin-2-yl)amino)cyclohexyl)-3-benzyl-1-(5-(1-methyl-1H-pyrazol-4-yl)pyridin-2-yl)urea | | | 626.4 |

TABLE 1-89

| Ex. No. | IUPAC name | structural formula | salt | MS |
|---|---|---|---|---|
| 445 | 3-benzyl-1-(trans-4-((5-cyano-4-(4-methyl-3,4-dihydro-2H-pyrido-[3,2-b][1,4]oxazin-7-yl)pyrimidin-2-yl)amino)-cyclohexyl)-1-(5-(1-methyl-1H-pyrazol-4-yl)pyridin-2-yl)urea | | | 656.4 |
| 446 | 3-benzyl-1-(trans-4-((5-cyano-4-(5-(hydroxymethyl)pyridin-3-yl)pyrimidin-2-yl)amino)-cyclohexyl)-1-(5-(1-methyl-1H-pyrazol-4-yl)pyridin-2-yl)urea | | | 615.4 |
| 447 | 3-benzyl-1-(trans-4-((5-cyano-4-(3-(trifluoromethyl)-1H-pyrazol-4-yl)pyrimidin-2-yl)amino)cyclohexyl)-1-(5-(1-methyl-1H-pyrazol-4-yl)pyridin-2-yl)urea | | | 640.4 |
| 448 | 3-benzyl-1-(trans-4-((5-cyano-4-(1,3-dimethyl-1H-pyrazol-5-yl)pyrimidin-2-yl)amino)-cyclohexyl)-1-(5-(1-methyl-1H-pyrazol-4-yl)pyridin-2-yl)urea | | | 602.4 |

TABLE 1-89-continued

| Ex. No. | IUPAC name | structural formula | salt | MS |
|---|---|---|---|---|
| 449 | 3-benzyl-1-(trans-4-((5-cyano-4-(1-(cyclopropylmethyl)-1H-pyrazol-4-yl)pyrimidin-2-yl)amino)cyclohexyl)-1-(5-(1-methyl-1H-pyrazol-4-yl)pyridin-2-yl)urea | | | 628.4 |

TABLE 1-90

| Ex. No. | IUPAC name | structural formula | salt | MS |
|---|---|---|---|---|
| 450 | 3-benzyl-1-(trans-4-((5-cyano-(1-methyl-3-(trifluoromethyl)-1H-pyrazol-5-yl)pyrimidin-2-yl)amino)cyclohexyl)-1-(5-(1-methyl-1H-pyrazol-4-yl)pyridin-2-yl)urea | | | 656.4 |
| 451 | 3-benzyl-1-(trans-4-((5-cyano-4-(1,3-dimethyl-1H-pyrazol-4-yl)pyrimidin-2-yl)amino)-cyclohexyl)-1-(5-(1-methyl-1H-pyrazol-4-yl)pyridin-2-yl)urea | | | 602.4 |
| 452 | 3-benzyl-1-(trans-4-((5-cyano-4-(1,3,5-trimethyl-1H-pyrazol-4-yl)pyrimidin-2-yl)amino)-cyclohexyl)-1-(5-(1-methyl-1H-pyrazol-4-yl)pyridin-2-yl)urea | | | 616.4 |

TABLE 1-90-continued

| Ex. No. | IUPAC name | structural formula | salt | MS |
|---|---|---|---|---|
| 453 | 3-benzyl-1-(trans-4-((5-cyano-4-(2,4-dimethyl-1,3-thiazol-5-yl)pyrimidin-2-yl)amino)-cyclohexyl)-1-(5-(1-methyl-1H-pyrazol-4-yl)pyridin-2-yl)urea | | | 619.4 |
| 454 | 3-benzyl-1-(trans-4-((5-cyano-4-(2-methyl-1,3-benzoxazol-5-yl)pyrimidin-2-yl)amino)-cyclohexyl)-1-(5-(1-methyl-1H-pyrazol-4-yl)pyridin-2-yl)urea | | | 639.4 |

TABLE 1-91

| Ex. No. | IUPAC name | structural formula | salt | MS |
|---|---|---|---|---|
| 455 | 3-benzyl-1-(trans-4-((5-cyano-4-(3,3-dimethyl-2-oxo-2,3-dihydro-1H-indol-6-yl)pyrimidin-2-yl)amino)cyclohexyl)-1-(5-(1-methyl-1H-pyrazol-4-yl)pyridin-2-yl)urea | | | 667.5 |

TABLE 1-91-continued

| Ex. No. | IUPAC name | structural formula | salt | MS |
|---|---|---|---|---|
| 456 | 3-benzyl-1-(trans-4-((5-cyano-4-(1-methyl-6-oxo-1,6-dihydropyridin-3-yl)pyrimidin-2-yl)amino)cyclohexyl)-1-(5-(1-methyl-1H-pyrazol-4-yl)pyridin-2-yl)urea | | | 615.4 |
| 457 | 3-benzyl-1-(trans-4-((5-cyano-4-(3,5-dimethyl-1,2-oxazol-4-yl)pyrimidin-2-yl)amino)-cyclohexyl)-1-(5-(1-methyl-1H-pyrazol-4-yl)pyridin-2-yl)urea | | | 603.4 |
| 458 | 3-benzyl-1-(trans-4-((5-cyano-4-(2-methoxypyridin-4-yl)pyrimidin-2-yl)amino)-cyclohexyl)-1-(5-(1-methyl-1H-pyrazol-4-yl)pyridin-2-yl)urea | | | 615.4 |
| 459 | 3-benzyl-1-(trans-4-((5-cyano-4-(1,5-dimethyl-1H-pyrazol-4-yl)pyrimidin-2-yl)amino)-cyclohexyl)-1-(5-(1-methyl-1H-pyrazol-4-yl)pyridin-2-yl)urea | | | 602.4 |

TABLE 1-92

| Ex. No. | IUPAC name | structural formula | salt | MS |
|---|---|---|---|---|
| 460 | ethyl(4-(2-((trans-4-((benzylcarbamoyl)(5-(1-methyl-1H-pyrazol-4-yl)pyridin-2-yl)amino)cyclohexyl)amino)-5-cyanopyrimidin-4-yl)-1H-pyrazol-1-yl)acetate | | | 660.4 |
| 461 | 3-(4-(2-((trans-4-((benzylcarbamoyl)(5-(1-methyl-1H-pyrazol-4-yl)pyridin-2-yl)amino)cyclohexyl)amino)-5-cyanopyrimidin-4-yl)-1H-pyrazol-1-yl)propanamide | | | 645.5 |
| 462 | 3-benzyl-1-(trans-4-((5-cyano-4-(1-(difluoromethyl)-1H-pyrazol-4-yl)pyrimidin-2-yl)amino)cyclohexyl)-1-(5-(1-methyl-1H-pyrazol-4-yl)pyridin-2-yl)urea | | | 624.4 |
| 463 | 3-benzyl-1-(trans-4-((4-(1-benzyl-1H-pyrazol-4-yl)-5-cyanopyrimidin-2-yl)amino)cyclohexyl)-1-(5-(1-methyl-1H-pyrazol-4-yl)pyridin-2-yl)urea | | | 664.5 |

TABLE 1-92-continued

| Ex. No. | IUPAC name | structural formula | salt | MS |
|---|---|---|---|---|
| 464 | 2-(4-(2-((trans-4-((benzylcarbamoyl)(5-(1-methyl-1H-pyrazol-4-yl)pyridin-2-yl)amino)cyclohexyl)amino)-5-cyanopyrimidin-4-yl)-1H-pyrazol-1-yl)acetamide | | | 631.4 |

TABLE 1-93

| Ex. No. | IUPAC name | structural formula | salt | MS |
|---|---|---|---|---|
| 465 | 3-benzyl-1-(trans-4-((5-cyano-4-(1-(tetrahydro-2H-pyran-4-yl)-1H-pyrazol-4-yl)pyrimidin-2-yl)amino)cyclohexyl)-1-(5-(1-methyl-1H-pyrazol-4-yl)pyridin-2-yl)urea | | | 658.5 |
| 466 | 3-benzyl-1-(trans-4-((5-cyano-4-(pyrazolo[1,5-a]pyridin-3-yl)pyrimidin-2-yl)amino)cyclohexyl)-1-(5-(1-methyl-1H-pyrazol-4-yl)pyridin-2-yl)urea | | | 624.4 |

TABLE 1-93-continued

| Ex. No. | IUPAC name | structural formula | salt | MS |
|---|---|---|---|---|
| 467 | methyl 2-(2-((trans-4-((benzylcarbamoyl)(5-(1-methyl-1H-pyrazol-4-yl)pyridin-2-yl)amino)cyclohexyl)amino)-5-cyanopyrimidin-4-yl)-1H-indole-6-carboxylate | | | 681.4 |
| 468 | 3-benzyl-1-(trans-4-((5-cyano-4-(1,5-dimethyl-1H-pyrazol-3-yl)pyrimidin-2-yl)amino)-cyclohexyl)-1-(5-(1-methyl-1H-pyrazol-4-yl)pyridin-2-yl)urea | | | 602.4 |
| 469 | 3-benzyl-1-(trans-4-((5-cyano-4-(3-methyl-1H-pyrazol-5-yl)pyrimidin-2-yl)amino)-cyclohexyl)-1-(5-(1-methyl-1H-pyrazol-4-yl)pyridin-2-yl)urea | | | 588.4 |

TABLE 1-94

| Ex. No. | IUPAC name | structural formula | salt | MS |
|---|---|---|---|---|
| 470 | 3-benzyl-1-(trans-4-((5-cyano-4-(3-(trifluoromethyl)-1H-pyrazol-5-yl)pyrimidin-2-yl)amino)-cyclohexyl)-1-(5-(1-methyl-1H-pyrazol-4-yl)pyridin-2-yl)urea | | | 640.4 |

TABLE 1-94-continued

| Ex. No. | IUPAC name | structural formula | salt | MS |
|---|---|---|---|---|
| 471 | 3-benzyl-1-(trans-4-((5-cyano-4-(1-methyl-1H-indazol-3-yl)pyrimidin-2-yl)amino)-cyclohexyl)-1-(5-(1-methyl-1H-pyrazol-4-yl)pyridin-2-yl)urea | | | 638.5 |
| 472 | 3-benzyl-1-(trans-4-((5-cyano-4-(1-methyl-1H-pyrazol-3-yl)pyrimidin-2-yl)amino)-cyclohexyl)-1-(5-(1-methyl-1H-pyrazol-4-yl)pyridin-2-yl)urea | | | 588.5 |
| 473 | 3-benzyl-1-(4-((5-cyano-4-(1H-imidazol-2-yl)pyrimidin-2-yl)amino)cyclohexyl)-1-(5-(1-methyl-1H-pyrazol-4-yl)pyridin-yl)urea | | | 574.4 |
| 474 | 3-benzyl-1-(trans-4-((5-cyano-4-(pyridin-2-yl)pyrimidin-2-yl)amino)cyclohexyl)-1-(5-(1-methyl-1H-pyrazol-4-yl)pyridin-2-yl)urea | | | 585.4 |

TABLE 1-95

| Ex. No. | IUPAC name | structural formula | salt | MS |
|---|---|---|---|---|
| 475 | 3-benzyl-1-(trans-4-((5-cyano-4-(pyridin-3-yl)pyrimidin-2-yl)amino)cyclohexyl)-1-(5-(1-methyl-1H-pyrazol-4-yl)pyridin-yl)urea | | | 585.4 |
| 476 | 3-benzyl-1-(trans-4-((5-cyano-4-(6-methylpyridazin-4-yl)pyrimidin-2-yl)amino)-cyclohexyl)-1-(5-(1-methyl-1H-pyrazol-4-yl)pyridin-2-yl)urea | | | 600.4 |
| 477 | 3-benzyl-1-(trans-4-((5-cyano-4-(1-(2,2,2-trifluoroethyl)-1H-pyrazol-4-yl)pyrimidin-2-yl)amino)cyclohexyl)-1-(5-(1-methyl-1H-pyrazol-4-yl)pyridin-2-yl)urea | | | 656.4 |
| 478 | 3-benzyl-1-(trans-4-((5-cyano-4-((3S)-3-cyano-3-cyclopropyl-2-oxopyrrolidin-1-yl)pyrimidin-2-yl)amino)cyclohexyl)-1-(5-(1-methyl-1H-pyrazol-4-yl)pyridin-yl)urea | | | 656.5 |

TABLE 1-95-continued

| Ex. No. | IUPAC name | structural formula | salt | MS |
|---|---|---|---|---|
| 479 | 3-benzyl-1-(trans-4-((5-cyano-4-(1-(tetrahydro-2H-pyran-2-yl)-1H-pyrazol-5-yl)pyrimidin-2-yl)amino)cyclohexyl)-1-(5-(1-methyl-1H-pyrazol-4-yl)pyridin-yl)urea | | | 658.4 |

TABLE 1-96

| Ex. No. | IUPAC name | structural formula | salt | MS |
|---|---|---|---|---|
| 480 | 3-benzyl-1-(trans-4-((5-cyano-4-(3-methoxyazetidin-1-yl)pyrimidin-2-yl)amino)-cyclohexyl)-1-(5-(1-methyl-1H-pyrazol-4-yl)pyridin-2-yl)urea | | | 593.4 |
| 481 | 3-benzyl-1-(trans-4-((5-cyano-4-(3-(hydroxymethyl)azetidin-1-yl)pyrimidin-2-yl)amino)-cyclohexyl)-1-(5-(1-methyl-1H-pyrazol-4-yl)pyridin-2-yl)urea | | | 593.4 |
| 482 | 3-benzyl-1-(trans-4-((5-cyano-4-(3-hydroxy-3-methylazetidin-1-yl)pyrimidin-2-yl)amino)-cyclohexyl)-1-(5-(1-methyl-1H-pyrazol-4-yl)pyridin-2-yl)urea | | | 593.4 |

TABLE 1-96-continued

| Ex. No. | IUPAC name | structural formula | salt | MS |
|---|---|---|---|---|
| 483 | 3-benzyl-1-(trans-4-((5-cyano-4-(oxetan-3-ylamino)pyrimidin-2-yl)amino)cyclohexyl)-1-(4-(1-methyl-6-oxo-1,6-dihydropyridin-3-yl)phenyl)urea | | | 603.2 |
| 484 | 3-benzyl-1-(trans-4-((5-cyano-2-(oxetan-3-yloxy)pyrimidin-4-yl)amino)cyclohexyl)-1-(5-(1-methyl-1H-pyrazol-4-yl)pyridin-2-yl)urea | | | 580.4 |

TABLE 1-97

| Ex. No. | IUPAC name | structural formula | salt | MS |
|---|---|---|---|---|
| 485 | 3-benzyl-1-(trans-4-((5-cyano-4-(oxetan-3-yloxy)pyrimidin-2-yl)amino)cyclohexyl)-1-(5-(1-methyl-1H-pyrazol-4-yl)pyridin-2-yl)urea | | | 580.4 |

TABLE 1-97-continued

| Ex. No. | IUPAC name | structural formula | salt | MS |
|---|---|---|---|---|
| 486 | 3-benzyl-1-(trans-4-((5-cyano-4-(2-oxa-6-azaspiro+8 3.4+9 octa-6-yl)pyrimidin-2-yl)amino)-cyclohexyl)-1-(4-(1-methyl-6-oxo-1,6-dihydropyridin-3-yl)phenyl)urea | | | 645.4 |
| 487 | 3-benzyl-1-(trans-4-((5-cyano-4-(2-oxa-6-azaspiro+8 3.4+9 octa-6-yl)pyrimidin-2-yl)amino)-cyclohexyl)-1-(4-(1-methyl-1H-pyrazol-4-yl)phenyl)urea | | | 618.4 |
| 488 | 3-benzyl-1-(trans-4-((5-cyano-4-(2-oxa-6-azaspiro+8 3.4+9 octa-6-yl)pyrimidin-2-yl)amino)cyclohexyl)-1-(6-(1-methyl-1H-pyrazol-4-yl)pyridazin-3-yl)urea | | | 620.5 |
| 489 | 3-benzyl-1-(trans-4-((5-cyano-4-(5,6-dihydro+8 1,2,4+9 triazolo[1,5-a]pyrazine-7(8H)-yl)pyrimidin-2-yl)amino)cyclohexyl)-1-(4-(1-methyl-1H-pyrazol-4-yl)phenyl)urea | | | 629.4 |

TABLE 1-98

| Ex. No. | IUPAC name | structural formula | salt | MS |
|---|---|---|---|---|
| 490 | 3-benzyl-1-(trans-4-((5-cyano-4-(2-oxa-6-azaspiro[3.4]octa-6-yl)pyrimidin-2-yl)amino)-cyclohexyl)-1-(4-(1-methyl-2-oxo-1,2-dihydropyridin-4-yl)phenyl)urea | | | 645.4 |
| 491 | 3-benzyl-1-(trans-4-((5-cyano-4-(2-oxa-6-azaspiro[3.4]octa-6-yl)pyrimidin-2-yl)amino)cyclohexyl)-1-(1'-methyl-2'-oxo-1',2'-dihydro-2,4'-bipyridin-5-yl)urea | | | 646.4 |
| 492 | 3-benzyl-1-(trans-4-((5-cyano-4-(5-cyano-2-thienyl)pyrimidin-2-yl)amino)cyclohexyl)-1-(1'-methyl-2'-oxo-1',2'-dihydro-2,4'-bipyridin-5-yl)urea | | | 642.3 |
| 493 | 3-benzyl-1-(trans-4-((5-cyano-4-(5-cyano-2-thienyl)pyrimidin-2-yl)amino)cyclohexyl)-1-(4-(1-methyl-6-oxo-1,6-dihydropyridin-3-yl)phenyl)urea | | | 639.4 |

TABLE 1-98-continued

| Ex. No. | IUPAC name | structural formula | salt | MS |
|---|---|---|---|---|
| 494 | 3-benzyl-1-(trans-4-((5-cyano-4-(5-cyano-2-thienyl)pyrimidin-2-yl)amino)cyclohexyl)-1-(4-(1-methyl-1H-pyrazol-4-yl)phenyl)urea | | | 614.3 |

TABLE 1-99

| Ex. No. | IUPAC name | structural formula | salt | MS |
|---|---|---|---|---|
| 495 | 3-benzyl-1-(trans-4-((5-cyano-4-(5-cyano-2-thienyl)pyrimidin-2-yl)amino)cyclohexyl)-1-(5-(1-methyl-1H-pyrazol-4-yl)pyrazin-2-yl)urea | | | 616.3 |
| 496 | 3-benzyl-1-(trans-4-((5-cyano-4-(5-cyano-2-thienyl)pyrimidin-2-yl)amino)cyclohexyl)-1-(4-(1-methyl-2-oxo-1,2-dihydropyridin-4-yl)phenyl)urea | | | 641.3 |
| 497 | 3-benzyl-1-(trans-4-((5-chloro-4-((2-(isopropylsulfonyl)-phenyl)amino)pyrimidin-2-yl)amino)cyclohexyl)-1-(4-(1-methyl-1H-pyrazol-4-yl)phenyl)urea | | | 713.4 |

TABLE 1-99-continued

| Ex. No. | IUPAC name | structural formula | salt | MS |
|---|---|---|---|---|
| 498 | 1-(trans-4-((4-(1,3-benzothiazol-5-yl)-5-cyanopyrimidin-2-yl)amino)cyclohexyl)-3-benzyl-1-(4-(1-methyl-1H-pyrazol-4-yl)phenyl)urea | | | 640.4 |
| 499 | 1-(trans-4-((4-(1,3-benzothiazol-6-yl)-5-cyanopyrimidin-2-yl)amino)cyclohexyl)-3-benzyl-1-(4-(1-methyl-1H-pyrazol-4-yl)phenyl)urea | | | 640.4 |

TABLE 1-100

| Ex. No. | IUPAC name | structural formula | salt | MS |
|---|---|---|---|---|
| 500 | 3-benzyl-1-(trans-4-((5-chloro-4-(methylamino)pyrimidin-2-yl)amino)cyclohexyl)-1-(4-(1-methyl-1H-pyrazol-4-yl)phenyl)urea | | | 545.4 |

TABLE 1-100-continued

| Ex. No. | IUPAC name | structural formula | salt | MS |
|---|---|---|---|---|
| 501 | 3-benzyl-1-(trans-4-((5-cyano-4-((2-(isopropylsulfonyl)-phenyl)amino)pyrimidin-2-yl)amino)cyclohexyl)-1-(4-(1-methyl-1H-pyrazol-4-yl)phenyl)urea | | | 702.4 |
| 502 | 3-benzyl-1-(trans-4-((4-chloro-5-cyanopyrimidin-2-yl)amino)cyclohexyl)-1-(4-(1-methyl-1H-pyrazol-4-yl)phenyl)urea | | | 541.4 |
| 503 | 3-benzyl-1-(trans-4-((5-cyano-4-(morpholin-4-yl)pyrimidin-2-yl)amino)cyclohexyl)-1-(5-(1-methyl-1H-pyrazol-4-yl)pyridin-2-yl)urea | | | 593.4 |
| 504 | 3-benzyl-1-(trans-4-((5-cyanopyridin-2-yl)amino)cyclohexyl)-1-(2-methoxy-4-(1-methyl-1H-pyrazol-4-yl)phenyl)urea | | | 536.3 |

TABLE 1-101

| Ex. No. | IUPAC name | structural formula | salt | MS |
|---|---|---|---|---|
| 505 | 3-benzyl-1-(trans-4-((5-cyanopyridin-2-yl)amino)-cyclohexyl)-1-(2-fluoro-4-(1-methyl-1H-pyrazol-4-yl)phenyl)urea | | | 524.3 |
| 506 | 3-benzyl-1-(trans-4-((5-cyano-4-(5,6-dihydro[1,2,4]triazolo-[4,3-a]pyrazine-7(8H)-yl)pyrimidin-2-yl)amino)-cyclohexyl)-1-(5-(1-methyl-1H-pyrazol-4-yl)pyridin-2-yl)urea | | | 630.5 |
| 507 | 3-benzyl-1-(trans-4-((5-cyano-4-(3-(trifluoromethyl)-5,6-dihydro[1,2,4]triazolo[4,3-a]pyrazine-7(8H)-yl)pyrimidin-2-yl)amino)cyclohexyl)-1-(5-(1-methyl-1H-pyrazol-4-yl)pyridin-2-yl)urea | | | 698.5 |
| 508 | 3-benzyl-1-(trans-4-((5-cyano-4-(5,7-dihydro-6H-pyrrolo-[3,4-b]pyridin-6-yl)pyrimidin-2-yl)amino)cyclohexyl)-1-(5-(1-methyl-1H-pyrazol-4-yl)pyridin-2-yl)urea | | | 626.4 |

TABLE 1-101-continued

| Ex. No. | IUPAC name | structural formula | salt | MS |
|---|---|---|---|---|
| 509 | 3-benzyl-1-(trans-4-((4-(((5-tert-butyl-1,3-oxazol-2-yl)methyl)amino)-5-cyanopyrimidin-2-yl)amino)cyclohexyl)-1-(5-(1-methyl-1H-pyrazol-4-yl)pyridin-2-yl)urea | | | 660.5 |

TABLE 1-102

| Ex. No. | IUPAC name | structural formula | salt | MS |
|---|---|---|---|---|
| 510 | 3-benzyl-1-(trans-4-((5-cyano-4-((1H-pyrazol-5-ylmethyl)-amino)pyrimidin-2-yl)amino)-cyclohexyl)-1-(5-(1-methyl-1H-pyrazol-4-yl)pyridin-2-yl)urea | | | 603.5 |
| 511 | 3-benzyl-1-(trans-4-((5-cyano-4-(((1-methyl-1H-pyrazol-3-yl)methyl)amino)pyrimidin-2-yl)amino)cyclohexyl)-1-(5-(1-methyl-1H-pyrazol-4-yl)pyridin-2-yl)urea | | | 617.4 |
| 512 | 3-benzyl-1-(trans-4-((5-cyano-4-((1,3-thiazol-2-ylmethyl)-amino)pyrimidin-2-yl)amino)-cyclohexyl)-1-(5-(1-methyl-1H-pyrazol-4-yl)pyridin-2-yl)urea | | | 620.5 |

TABLE 1-102-continued

| Ex. No. | IUPAC name | structural formula | salt | MS |
|---|---|---|---|---|
| 513 | 3-benzyl-1-(trans-4-((5-cyano-4-(7-oxabicyclo-[2.2.1]hepta-2-ylamino)pyrimidin-2-yl)amino)-cyclohexyl)-1-(5-(1-methyl-1H-pyrazol-4-yl)pyridin-2-yl)urea | 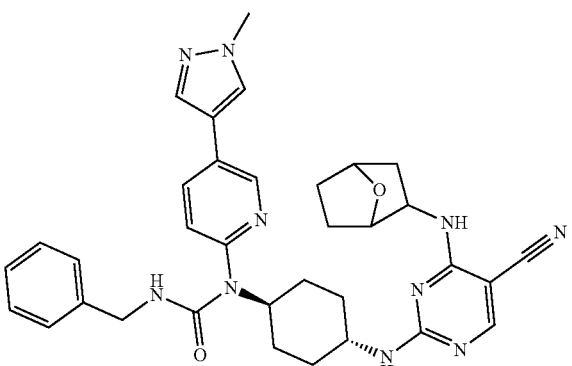 | | 619.4 |
| 514 | 3-benzyl-1-(trans-4-((5-cyano-4-(3-methyl-4-oxo-imidazolidin-1-yl)pyrimidin-2-yl)amino)-cyclohexyl)-1-(5-(1-methyl-1H-pyrazol-4-yl)pyridin-2-yl)urea | 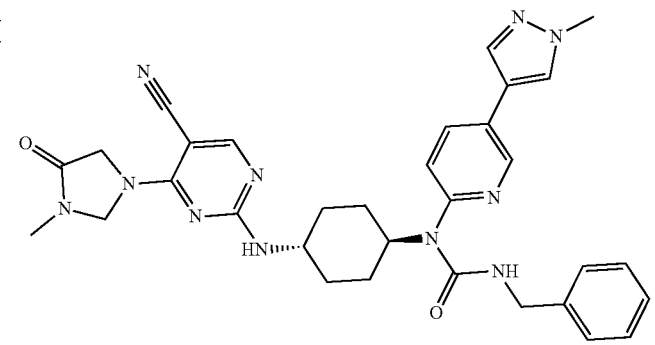 | | 606.5 |

TABLE 1-103

| Ex. No. | IUPAC name | structural formula | salt | MS |
|---|---|---|---|---|
| 515 | 3-benzyl-1-(trans-4-((5-cyano-4-(1,3-oxazolidin-3-yl)pyrimidin-2-yl)amino)cyclohexyl)-1-(5-(1-methyl-1H-pyrazol-4-yl)pyridin-2-yl)urea | 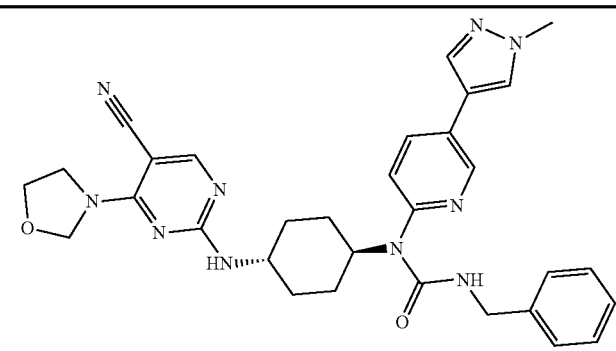 | | 579.4 |
| 516 | 3-benzyl-1-(trans-4-((5-cyano-4-(((3,3-difluorocyclobutyl)-methyl)amino)pyrimidin-2-yl)amino)cyclohexyl)-1-(5-(1-methyl-1H-pyrazol-4-yl)pyridin-2-yl)urea | 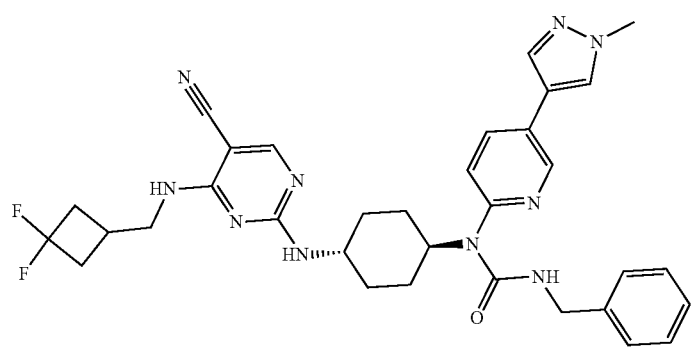 [SMILES: Cn1cc(-c2ccc(N(C(=O)NCc3ccccc3)[C@H]3CC[C@H](Nc4ncc(C#N)c(NCC5CC(F)(F)C5)n4)CC3)nc2)cn1] | | 627.4 |

TABLE 1-103-continued

| Ex. No. | IUPAC name | structural formula | salt | MS |
|---|---|---|---|---|
| 517 | 3-benzyl-1-(trans-4-((5-cyano-4-(spiro-[2.2]penta-1-ylamino)pyrimidin-2-yl)amino)cyclohexyl)-1-(5-(1-methyl-1H-pyrazol-4-yl)pyridin-2-yl)urea | | | 589.5 |
| 518 | 1-(trans-4-((4-(adamantan-1-ylamino)-5-cyanopyrimidin-2-yl)amino)cyclohexyl)-3-benzyl-1-(5-(1-methyl-1H-pyrazol-4-yl)pyridin-2-yl)urea | | | 657.5 |
| 519 | 3-benzyl-1-(trans-4-((5-cyano-4-(methylamino)pyrimidin-2-yl)amino)cyclohexyl)-1-(5-(1-methyl-1H-pyrazol-4-yl)pyridin-2-yl)urea | | | 537.4 |

TABLE 1-104

| Ex. No. | IUPAC name | structural formula | salt | MS |
|---|---|---|---|---|
| 520 | 3-benzyl-1-(trans-4-((5-cyano-4-(5-cyano-2-thienyl)pyrimidin-2-yl)amino)cyclohexyl)-1-(5-(1-methyl-1H-pyrazol-4-yl)pyridin-2-yl)urea | | | 615.3 |

TABLE 1-104-continued

| Ex. No. | IUPAC name | structural formula | salt | MS |
|---|---|---|---|---|
| 521 | 3-benzyl-1-(trans-4-((5-cyano-4-(1H-pyrazolo[3,4-b]pyridin-5-yl)pyrimidin-2-yl)amino)cyclohexyl)-1-(5-(1-methyl-1H-pyrazol-4-yl)pyridin-2-yl)urea | | | 625.4 |
| 522 | 3-benzyl-1-(trans-4-((5-cyano-4-(2-methyl-2H-indazol-6-yl)pyrimidin-2-yl)amino)cyclohexyl)-1-(5-(1-methyl-1H-pyrazol-4-yl)pyridin-2-yl)urea | | | 638.5 |
| 523 | 3-benzyl-1-(trans-4-((5-cyano-4-(3-(morpholin-4-yl-sulfonyl)phenyl)pyrimidin-2-yl)amino)cyclohexyl)-1-(5-(1-methyl-1H-pyrazol-4-yl)pyridin-2-yl)urea | | | 733.5 |
| 524 | 3-benzyl-1-(trans-4-((5-cyano-4-(3,5-dimethyl-1H-pyrazol-4-yl)pyrimidin-2-yl)amino)cyclohexyl)-1-(5-(1-methyl-1H-pyrazol-4-yl)pyridin-2-yl)urea | | | 602.4 |

TABLE 1-105

| Ex. No. | IUPAC name | structural formula | salt | MS |
|---|---|---|---|---|
| 525 | 3-benzyl-1-(trans-4-((5-cyano-4-(2-oxo-2,3-dihydro-1H-benzimidazol-5-yl)pyrimidin-2-yl)amino)cyclohexyl)-1-(5-(1-methyl-1H-pyrazol-4-yl)pyridin-2-yl)urea | | | 640.4 |
| 526 | 3-benzyl-1-(trans-4-((5-cyano-4-(3-methyl-1H-pyrazol-4-yl)pyrimidin-2-yl)amino)-cyclohexyl)-1-(5-(1-methyl-1H-pyrazol-4-yl)pyridin-2-yl)urea | | | 588.4 |
| 527 | 3-benzyl-1-(trans-4-((5-cyano-4-(oxetan-3-ylamino)pyrimidin-2-yl)amino)cyclohexyl)-1-(4-(1-methyl-1H-pyrazol-4-yl)phenyl)urea | | | 576.1 |
| 528 | 3-benzyl-1-(trans-4-((5-cyano-4,5'-bipyrimidin-2-yl)amino)cyclohexyl)-1-(4-(1-methyl-6-oxo-1,6-dihydropyridin-3-yl)phenyl)urea | | | 610.3 |

TABLE 1-105-continued

| Ex. No. | IUPAC name | structural formula | salt | MS |
|---|---|---|---|---|
| 529 | 3-benzyl-1-(trans-4-((5-cyano-4-(piperidin-1-yl)pyrimidin-2-yl)amino)cyclohexyl)-1-(5-(1-methyl-1H-pyrazol-4-yl)pyridin-2-yl)urea | | | 591.5 |

TABLE 1-106

| Ex. No. | IUPAC name | structural formula | salt | MS |
|---|---|---|---|---|
| 530 | 3-benzyl-1-(trans-4-((5-cyano-4-(oxetan-3-ylamino)pyrimidin-2-yl)amino)cyclohexyl)-1-(4-(1-methyl-2-oxo-1,2-dihydropyridin-4-yl)phenyl)urea | | | 605.4 |
| 531 | 3-benzyl-1-(trans-4-((5-cyano-4-(2-oxopyrrolidin-1-yl)pyrimidin-2-yl)amino)-cyclohexyl)-1-(5-(1-methyl-1H-pyrazol-4-yl)pyridin-2-yl)urea | | | 591.4 |
| 532 | 3-benzyl-1-(trans-4-((5-cyano-4-(oxetan-3-ylamino)pyrimidin-2-yl)amino)cyclohexyl)-1-(6-(1-methyl-1H-pyrazol-4-yl)pyridazin-3-yl)urea | | | 580.4 |

TABLE 1-106-continued

| Ex. No. | IUPAC name | structural formula | salt | MS |
|---|---|---|---|---|
| 533 | 3-benzyl-1-(trans-4-((5-cyano-4-(1-methyl-2-oxo-1,8-diazaspiro[4.5]deca-8-yl)pyrimidin-2-yl)amino)-cyclohexyl)-1-(5-(1-methyl-1H-pyrazol-4-yl)pyridin-2-yl)urea | | | 674.4 |
| 534 | 3-benzyl-1-(trans-4-((5-cyano-4,5'-bipyrimidin-2-yl)amino)cyclohexyl)-1-(6-(1-methyl-1H-pyrazol-4-yl)pyridazin-3-yl)urea | | | 587.3 |

TABLE 1-107

| Ex. No. | IUPAC name | structural formula | salt | MS |
|---|---|---|---|---|
| 535 | 3-benzyl-1-(trans-4-((5-cyano-4,5'-bipyrimidin-2-yl)amino)cyclohexyl)-1-(4-(1-methyl-1H-pyrazol-4-yl)phenyl)urea | | | 585.3 |
| 536 | 3-benzyl-1-(trans-4-((4-(4-chloro-1H-pyrazol-5-yl)-5-cyanopyrimidin-2-yl)amino)cyclohexyl)-1-(5-(1-methyl-1H-pyrazol-4-yl)pyridin-2-yl)urea | | | 608.2 |

TABLE 1-107-continued

| Ex. No. | IUPAC name | structural formula | salt | MS |
|---|---|---|---|---|
| 537 | 3-benzyl-1-(trans-4-((5-cyano-4-(1,1-dioxide-thiomorpholin-4-yl)pyrimidin-2-yl)amino)cyclohexyl)-1-(4-(1-methyl-1H-pyrazol-4-yl)phenyl)urea | | | 640.4 |
| 538 | 3-benzyl-1-(trans-4-((5-cyano-4-(5-cyano-2-thienyl)pyrimidin-2-yl)amino)cyclohexyl)-1-(6-(1-methyl-1H-pyrazol-4-yl)pyridazin-3-yl)urea | | | 616.3 |
| 539 | 3-benzyl-1-(trans-4-((5-cyano-4-(oxetan-3-ylamino)pyrimidin-2-yl)amino)cyclohexyl)-1-(5-(1-methyl-1H-pyrazol-4-yl)pyrazin-2-yl)urea | | | 578.3 |

TABLE 1-108

| Ex. No. | IUPAC name | structural formula | salt | MS |
|---|---|---|---|---|
| 540 | 3-benzyl-1-(trans-4-((5-cyano-4-(3-methyl-1H-pyrazol-5-yl)pyrimidin-2-yl)amino)cyclohexyl)-1-(4-(1-methyl-1H-pyrazol-4-yl)phenyl)urea | | | 587.4 |

TABLE 1-108-continued

| Ex. No. | IUPAC name | structural formula | salt | MS |
|---|---|---|---|---|
| 541 | 3-benzyl-1-(trans-4-((5-cyano-4-(2-oxa-6-azaspiro[3.4]octa-6-yl)pyrimidin-2-yl)amino)-cyclohexyl)-1-(5-(1-methyl-1H-pyrazol-4-yl)pyrazin-2-yl)urea | | | 620.4 |
| 542 | 3-benzyl-1-(trans-4-((5-cyano-4-(3-methyl-1H-pyrazol-5-yl)pyrimidin-2-yl)amino)-cyclohexyl)-1-(6-(1-methyl-1H-pyrazol-4-yl)pyridazin-3-yl)urea | | | 589.4 |
| 543 | 3-benzyl-1-(trans-4-((5-cyano-4-(oxetan-3-ylamino)pyrimidin-2-yl)amino)cyclohexyl)-1-(1'-methyl-2'-oxo-1',2'-dihydro-2,4'-bipyridin-5-yl)urea | | | 606.3 |
| 544 | 3-benzyl-1-(trans-4-((5-cyano-4-(1H-pyrazol-5-yl)pyrimidin-2-yl)amino)cyclohexyl)-1-(6-(1-methyl-1H-pyrazol-4-yl)pyridazin-3-yl)urea | | | 575.3 |

TABLE 1-109

| Ex. No. | IUPAC name | structural formula | salt | MS |
|---|---|---|---|---|
| 545 | 1-benzyl-3-(trans-4-((5-cyano-4-(2-oxa-6-azaspiro[3.4]octa-6-yl)pyrimidin-2-yl)amino)cyclohexyl)-1-methyl-3-(5-(1-methyl-1H-pyrazol-4-yl)pyridin-2-yl)urea | | | 633.4 |
| 546 | 3-benzyl-1-(trans-4-((5-cyano-4-(5-(methylsulfonyl)pyridin-3-yl)pyrimidin-2-yl)amino)cyclohexyl)-1-(4-(1-methyl-6-oxo-1,6-dihydropyridin-3-yl)phenyl)urea | | | 689.3 |
| 547 | 3-benzyl-1-(trans-4-((5-cyano-4-(4-methyl-5-oxo-1,4-diazepan-1-yl)pyrimidin-2-yl)amino)cyclohexyl)-1-(5-(1-methyl-1H-pyrazol-4-yl)pyridin-2-yl)urea | | | 634.4 |
| 548 | 3-benzyl-1-(trans-4-((5-cyano-4-(5-(methylsulfonyl)pyridin-3-yl)pyrimidin-2-yl)amino)cyclohexyl)-1-(1'-methyl-2'-oxo-1',2'-dihydro-2,4'-bipyridin-5-yl)urea | | | 690.3 |

TABLE 1-109-continued

| Ex. No. | IUPAC name | structural formula | salt | MS |
|---|---|---|---|---|
| 549 | 3-benzyl-1-(trans-4-((5-cyano-4-(3-methyl-1H-pyrazol-5-yl)pyrimidin-2-yl)amino)cyclohexyl)-1-(4-(1-methyl-6-oxo-1,6-dihydropyridin-3-yl)phenyl)urea | | | 614.4 |

TABLE 1-110

| Ex. No. | IUPAC name | structural formula | salt | MS |
|---|---|---|---|---|
| 550 | 3-benzyl-1-(trans-4-((5-cyano-4-(1H-pyrazol-5-yl)pyrimidin-2-yl)amino)cyclohexyl)-1-(4-(1-methyl-6-oxo-1,6-dihydropyridin-3-yl)phenyl)urea | | | 600.3 |
| 551 | 3-benzyl-1-(trans-4-((5-cyano-4-(1H-pyrazol-5-yl)pyrimidin-2-yl)amino)cyclohexyl)-1-(5-(1-methyl-1H-pyrazol-4-yl)pyrazin-2-yl)urea | | | 575.3 |

TABLE 1-110-continued

| Ex. No. | IUPAC name | structural formula | salt | MS |
|---|---|---|---|---|
| 552 | 3-benzyl-1-(trans-4-((5-cyano-4-(3-methyl-1H-pyrazol-5-yl)pyrimidin-2-yl)amino)cyclohexyl)-1-(5-(1-methyl-1H-pyrazol-4-yl)pyrazin-2-yl)urea | | | 589.4 |
| 553 | 3-benzyl-1-(trans-4-((5-cyano-4-(oxetan-3-ylamino)pyrimidin-2-yl)amino)cyclohexyl)-1-(5-(2-methoxypyrimidin-5-yl)pyridin-2-yl)urea | | | 607.3 |
| 554 | 3-benzyl-1-(trans-4-((5-cyano-4-(2-oxa-6-azaspiro[3.4]octa-6-yl)pyrimidin-2-yl)amino)cyclohexyl)-1-(5-(2-methoxypyrimidin-5-yl)pyridin-2-yl)urea | | | 647.3 |

TABLE 1-111

| Ex. No. | IUPAC name | structural formula | salt | MS |
|---|---|---|---|---|
| 555 | 3-benzyl-1-(trans-4-((5-chloro-4-(2-oxa-6-azaspiro[3.4]octa-6-yl)pyrimidin-2-yl)amino)-cyclohexyl)-1-(5-(1-methyl-1H-pyrazol-4-yl)pyridin-2-yl)urea | | | 628.3 |
| 556 | 3-benzyl-1-(trans-4-((5-cyano-4-(3-methyl-1-oxa-2,8-diazaspiro[4.5]deca-2-en-8-yl)pyrimidin-2-yl)amino)-cyclohexyl)-1-(5-(1-methyl-1H-pyrazol-4-yl)pyridin-2-yl)urea | | | 660.4 |
| 557 | 3-benzyl-1-(trans-4-((5-cyano-4-(3-methyl-1-oxa-2,8-diazaspiro[4.6]undeca-2-en-8-yl)pyrimidin-2-yl)amino)-cyclohexyl)-1-(5-(1-methyl-1H-pyrazol-4-yl)pyridin-2-yl)urea | | | 674.4 |
| 558 | 3-benzyl-1-(trans-4-((5-cyano-4-(7-methyl-5-oxa-2,6-diazaspiro[3.4]octa-6-en-2-yl)pyrimidin-2-yl)amino)-cyclohexyl)-1-(5-(1-methyl-1H-pyrazol-4-yl)pyridin-2-yl)urea | | | 632.3 |

TABLE 1-111-continued

| Ex. No. | IUPAC name | structural formula | salt | MS |
|---|---|---|---|---|
| 559 | 3-benzyl-1-(trans-4-((5-cyano-4-(1H-pyrazol-5-yl)pyrimidin-yl)amino)cyclohexyl)-1-(1'-methyl-2'-oxo-1',2'-dihydro-2,4'-bipyridin-5-yl)urea | | | 601.3 |

TABLE 1-112

| Ex. No. | IUPAC name | structural formula | salt | MS |
|---|---|---|---|---|
| 560 | 3-benzyl-1-(trans-4-((5-cyano-4-(3-methyl-1H-pyrazol-5-yl)pyrimidin-2-yl)amino)-cyclohexyl)-1-(1'-methyl-2'-oxo-1',2'-dihydro-2,4'-bipyridin-5-yl)urea | | | 615.3 |
| 561 | 3-benzyl-1-(trans-4-((5-cyano-4-(5-(methylsulfonyl)pyridin-3-yl)pyrimidin-2-yl)amino)-cyclohexyl)-1-(4-(1-methyl-2-oxo-1,2-dihydropyridin-4-yl)phenyl)urea | | | 689.3 |

TABLE 1-112-continued

| Ex. No. | IUPAC name | structural formula | salt | MS |
|---|---|---|---|---|
| 562 | 3-benzyl-1-(trans-4-((5-cyano-4-(3-methyl-1-oxa-2,7-diazaspiro[4.4]nona-2-en-7-yl)pyrimidin-2-yl)amino)-cyclohexyl)-1-(5-(1-methyl-1H-pyrazol-4-yl)pyridin-2-yl)urea | | | 646.4 |
| 563 | 3-benzyl-1-(5-bromopyrimidin-2-yl)-1-(trans-4-((5-cyano-4-(oxetan-3-ylamino)pyrimidin-2-yl)amino)cyclohexyl)urea | | | 578.2 |
| 564 | 3-benzyl-1-(trans-4-((4-(5,6-dihydro[1,2,4]triazolo-[1,5-a]pyrazine-7(8H)-yl)-5-(trifluoromethyl)pyrimidin-2-yl)amino)cyclohexyl)-1-(5-(1-methyl-1H-pyrazol-4-yl)pyridin-2-yl)urea hydrochloride | | HCl | 673.3 |

TABLE 1-113

| Ex. No. | IUPAC name | structural formula | salt | MS |
|---|---|---|---|---|
| 565 | 3-benzyl-1-(trans-4-((5-cyano-4-(oxetan-3-ylamino)pyrimidin-2-yl)amino)cyclohexyl)-1-(2'-methoxy-5,5'-bipyrimidin-2-yl)urea | | | 608.3 |

TABLE 1-113-continued

| Ex. No. | IUPAC name | structural formula | salt | MS |
|---|---|---|---|---|
| 566 | 3-benzyl-1-(5-(1-methyl-1H-pyrazol-4-yl)pyridin-2-yl)-1-(trans-4-((4-(2-oxa-6-azaspiro[3.4]octa-6-yl)-5-(trifluoromethyl)pyrimidin-2-yl)amino)cyclohexyl)urea | | | 662.4 |
| 567 | 3-benzyl-1-(trans-4-((4-(3,4-dihydro-2,6-naphthyridine-2(1H)-yl)-5-(trifluoromethyl)-pyrimidin-2-yl)amino)-cyclohexyl)-1-(5-(1-methyl-1H-pyrazol-4-yl)pyridin-2-yl)urea | | | 683.3 |
| 568 | 1-benzyl-3-(trans-4-((5-cyano-4-(oxetan-3-ylamino)pyrimidin-2-yl)amino)cyclohexyl)-3-(5-(2-methoxypyrimidin-5-yl)pyridin-2-yl)-1-methylurea | | | 621.4 |
| 569 | 3-benzyl-1-(trans-4-((5-cyano-4-(3-methyl-1-oxa-2,8-diazaspiro[4.6]undeca-2-en-8-yl)pyrimidin-2-yl)amino)-cyclohexyl)-1-(5-(1-methyl-1H-pyrazol-4-yl)pyridin-2-yl)urea | | | 674.4 |

TABLE 1-113-continued

| Ex. No. | IUPAC name | structural formula | salt | MS |
|---|---|---|---|---|

TABLE 1-114

| Ex. No. | IUPAC name | structural formula | salt | MS |
|---|---|---|---|---|
| 570 | 3-benzyl-1-(trans-4-((5-cyano-4-(3-methyl-1-oxa-2,8-diazaspiro[4.6]undeca-2-en-8-yl)pyrimidin-2-yl)amino)-cyclohexyl)-1-(5-(1-methyl-1H-pyrazol-4-yl)pyridin-2-yl)urea | | | 674.4 |
| 571 | N-(trans-4-((5-cyano-4-(oxetan-3-ylamino)pyrimidin-2-yl)amino)cyclohexyl)-N-(5-(2-methoxypyrimidin-5-yl)pyridin-2-yl)-2-phenylazetidine-1-carboxamide | | | 633.4 |
| 572 | 1-benzyl-3-(trans-4-((5-cyano-4-(oxetan-3-ylamino)pyrimidin-2-yl)amino)cyclohexyl)-1-ethyl-3-(5-(2-methoxypyrimidin-5-yl)pyridin-2-yl)urea | | | 635.4 |

TABLE 1-114-continued

| Ex. No. | IUPAC name | structural formula | salt | MS |
|---|---|---|---|---|
| 573 | 3-benzyl-1-(trans-4-((5-cyano-4-(oxetan-3-ylamino)pyrimidin-2-yl)amino)cyclohexyl)-1-(1-methyl-1H-indazol-6-yl)urea | | | 550.2 |
| 574 | 3-benzyl-1-(5-(1-methyl-1H-pyrazol-4-yl)pyridin-2-yl)-1-(trans-4-((4-(oxetan-3-ylamino)-5-(trifluoromethyl)-pyrimidin-2-yl)amino)-cyclohexyl)urea | | | 622.3 |

TABLE 1-115

| Ex. No. | IUPAC name | structural formula | salt | MS |
|---|---|---|---|---|
| 575 | 3-benzyl-1-(trans-4-((5-cyano-4-(oxetan-3-ylamino)pyrimidin-2-yl)amino)cyclohexyl)-1-(5-(1-methyl-1H-pyrazol-4-yl)pyrimidin-2-yl)urea | | | 580.3 |

TABLE 1-115-continued

| Ex. No. | IUPAC name | structural formula | salt | MS |
|---|---|---|---|---|
| 576 | 1-(trans-4-((5-cyano-4-(oxetan-3-ylamino)pyrimidin-2-yl)amino)cyclohexyl)-1-(5-(2-methoxypyrimidin-5-yl)pyridin-2-yl)-3-(pyridin-2-ylmethyl)urea | | | 608.3 |
| 577 | 3-benzyl-1-(trans-4-((5-cyano-4-(5-methyl-1H-pyrazol-4-yl)pyrimidin-2-yl)amino)cyclohexyl)-1-(5-(2-methoxypyrimidin-5-yl)pyridin-2-yl)urea | | | 616.3 |
| 578 | 3-benzyl-1-(trans-4-((5-cyano-4-(3-methyl-1H-pyrazol-4-yl)pyrimidin-2-yl)amino)cyclohexyl)-1-(2'-methoxy-5,5'-bipyrimidin-2-yl)urea | | | 617.3 |

TABLE 1-115-continued

| Ex. No. | IUPAC name | structural formula | salt | MS |
|---|---|---|---|---|
| 579 | 1-(trans-4-((5-cyano-4-(oxetan-3-ylamino)pyrimidin-2-yl)amino)cyclohexyl)-1-(5-(2-methoxypyrimidin-5-yl)pyridin-2-yl)-3-(pyrimidin-2-ylmethyl)urea | | | 609.3 |

TABLE 1-116

| Ex. No. | IUPAC name | structural formula | salt | MS |
|---|---|---|---|---|
| 580 | 1-benzyl-3-(trans-4-((5-cyano-4-(5-methyl-1H-pyrazol-4-yl)pyrimidin-2-yl)amino)cyclohexyl)-3-(5-(2-methoxypyrimidin-5-yl)pyridin-2-yl)-1-methylurea | | | 630.4 |
| 581 | benzyl (trans-4-((5-cyano-4-(oxetan-3-ylamino)pyrimidin-2-yl)amino)cyclohexyl)(5-(2-methoxypyrimidin-5-yl)pyridin-2-yl)carbamate | | | 608.3 |

TABLE 1-116-continued

| Ex. No. | IUPAC name | structural formula | salt | MS |
|---|---|---|---|---|
| 582 | 1-(trans-4-((5-cyano-4-(oxetan-3-ylamino)pyrimidin-2-yl)amino)cyclohexyl)-3-(2-fluorobenzyl)-1-(5-(2-methoxypyrimidin-5-yl)pyridin-2-yl)urea | | | 625.3 |
| 583 | 3-benzyl-1-(3-chloro-2-methyl-2H-pyrazolo[3,4-b]pyridin-5-yl)-1-(trans-4-((5-cyano-4-(oxetan-3-ylamino)pyrimidin-2-yl)amino)cyclohexyl)urea | | | 585.2 |
| 584 | 3-benzyl-1-(trans-4-((5-cyano-4-(1,4-oxazepan-4-yl)pyrimidin-2-yl)amino)cyclohexyl)-1-(2'-methoxy-5,5'-bipyrimidin-2-yl)urea | | | 636.4 |

TABLE 1-117

| Ex. No. | IUPAC name | structural formula | salt | MS |
|---|---|---|---|---|
| 585 | 3-benzyl-1-(trans-4-((5-cyano-4-(oxetan-3-ylamino)pyrimidin-2-yl)amino)cyclohexyl)-1-(5-(1-(tetrahydro-2H-pyran-4-yl)-1H-pyrazol-4-yl)pyrimidin-2-yl)urea | | | 650.3 |
| 586 | 3-benzyl-1-(trans-4-((5-cyano-4-(oxetan-3-ylamino)pyrimidin-2-yl)amino)cyclohexyl)-1-(2-methyl-2H-pyrazolo[3,4-c]pyridin-5-yl)urea | | | 553.3 |
| 587 | N-(trans-4-((5-cyano-4-(oxetan-3-ylamino)pyrimidin-2-yl)amino)cyclohexyl)-N-(5-(2-methoxypyrimidin-5-yl)pyridin-2-yl)-2-phenoxyacetamide | | | 608.3 |

TABLE 1-117-continued

| Ex. No. | IUPAC name | structural formula | salt | MS |
|---|---|---|---|---|
| 588 | 3-benzyl-1-(5-(2-methoxypyrimidin-5-yl)pyridin-2-yl)-1-(trans-4-((4-(oxetan-3-yloxy)-5-(trifluoromethyl)pyrimidin-2-yl)amino)cyclohexyl)urea | | | 651.2 |
| 589 | 3-benzyl-1-(5-(2-methoxypyrimidin-5-yl)pyridin-2-yl)-1-(trans-4-((4-(oxetan-3-ylamino)-5-(trifluoromethyl)pyrimidin-2-yl)amino)cyclohexyl)urea | | | 650.3 |

TABLE 1-118

| Ex. No. | IUPAC name | structural formula | salt | MS |
|---|---|---|---|---|
| 590 | 3-benzyl-1-(2'-methoxy-5,5'-bipyrimidin-2-yl)-1-(trans-4-((4-(oxetan-3-ylamino)-5-(trifluoromethyl)pyrimidin-2-yl)amino)cyclohexyl)urea | | | 651.3 |

TABLE 1-118-continued

| Ex. No. | IUPAC name | structural formula | salt | MS |
|---|---|---|---|---|
| 591 | 3-benzyl-1-(trans-4-((4-(4-hydroxyazepan-1-yl)-5-(trifluoromethyl)pyrimidin-2-yl)amino)cyclohexyl)-1-(2'-methoxy-5,5'-bipyrimidin-2-yl)urea | | | 693.3 |
| 592 | 3-benzyl-1-(trans-4-((4-(4-hydroxyazepan-1-yl)-5-(trifluoromethyl)pyrimidin-2-yl)amino)cyclohexyl)-1-(5-(2-methoxypyrimidin-5-yl)pyridin-2-yl)urea | | | 692.3 |
| 593 | 3-benzyl-1-(trans-4-((5-cyano-4-(oxetan-3-ylamino)pyrimidin-2-yl)amino)cyclohexyl)-1-(1-methyl-1H-pyrazolo[4,3-b]pyridin-5-yl)urea | | | 551.2 |

TABLE 1-118-continued

| Ex. No. | IUPAC name | structural formula | salt | MS |
|---|---|---|---|---|
| 594 | 3-benzyl-1-(trans-4-((5-cyano-4-(oxetan-3-ylamino)pyrimidin-2-yl)amino)cyclohexyl)-1-(2-methyl-2H-pyrazolo[4,3-b]pyridin-5-yl)urea | | | 551.2 |

TABLE 1-119

| Ex. No. | IUPAC name | structural formula | salt | MS |
|---|---|---|---|---|
| 595 | 3-benzyl-1-(trans-4-((5-cyano-4-(4-hydroxyazepan-1-yl)pyrimidin-2-yl)amino)cyclohexyl)-1-(5-(2-methoxypyrimidin-5-yl)pyridin-2-yl)urea | | | 649.3 |
| 596 | 3-benzyl-1-(trans-4-((5-cyano-4-(4-hydroxyazepan-1-yl)pyrimidin-2-yl)amino)cyclohexyl)-1-(2'-methoxy-5,5'-bipyrimidin-2-yl)urea | | | 650.3 |

TABLE 1-119-continued

| Ex. No. | IUPAC name | structural formula | salt | MS |
|---|---|---|---|---|
| 597 | 3-benzyl-1-(trans-4-((5-cyano-4-(oxetan-3-ylamino)pyrimidin-2-yl)amino)cyclohexyl)-1-(5-(2-methoxypyrimidin-5-yl)-4-methylpyridin-2-yl)urea | | | 621.3 |
| 598 | 3-benzyl-1-(trans-4-((5-cyano-4-(oxetan-3-ylamino)pyrimidin-2-yl)amino)cyclohexyl)-1-(2'-methoxy-4,6-dimethyl-5,5'-bipyrimidin-2-yl)urea | | | 636.3 |
| 599 | benzyl (trans-4-((5-cyano-4-(4-hydroxyazepan-1-yl)pyrimidin-2-yl)amino)cyclohexyl)(5-(2-methoxypyrimidin-5-yl)pyridin-2-yl)carbamate | | | 650.3 |

TABLE 1-120

| Ex. No. | IUPAC name | structural formula | salt | MS |
|---|---|---|---|---|
| 600 | benzyl (trans-4-((4-(3-fluoro-3-(hydroxymethyl)azetidin-1-yl)-5-(trifluoromethyl)pyrimidin-2-yl)amino)cyclohexyl)(5-(2-methoxypyrimidin-5-yl)pyridin-2-yl)carbamate | | | 683.2 |
| 601 | 3-benzyl-1-(trans-4-((4-(3-fluoro-3-(hydroxymethyl)-azetidin-1-yl)-5-(trifluoromethyl)pyrimidin-2-yl)amino)cyclohexyl)-1-(2'-methoxy-5,5'-bipyrimidin-2-yl)urea | | | 683.2 |
| 602 | benzyl (trans-4-((4-(4-hydroxyazepan-1-yl)-5-(trifluoromethyl)pyrimidin-2-yl)amino)cyclohexyl)(5-(2-methoxypyrimidin-5-yl)pyridin-2-yl)carbamate | | | 693.4 |

TABLE 1-120-continued

| Ex. No. | IUPAC name | structural formula | salt | MS |
|---|---|---|---|---|
| 603 | benzyl (trans-4-((5-cyano-4-(3-fluoro-3-(hydroxymethyl)-azetidin-1-yl)pyrimidin-2-yl)amino)cyclohexyl)(5-(2-methoxypyrimidin-5-yl)pyridin-2-yl)carbamate | | | 640.3 |
| 604 | 3-benzyl-1-(trans-4-((5-cyano-4-(3-fluoro-3-(hydroxymethyl)-azetidin-1-yl)pyrimidin-2-yl)amino)cyclohexyl)-1-(2'-methoxy-5,5'-bipyrimidin-2-yl)urea | | | 640.3 |

TABLE 1-121

| Ex. No. | IUPAC name | structural formula | salt | MS |
|---|---|---|---|---|
| 605 | 3-benzyl-1-(trans-4-((5-cyano-4-((3-methyloxetan-3-yl)amino)pyrimidin-2-yl)amino)cyclohexyl)-1-(5-(1-methyl-1H-pyrazol-4-yl)pyridin-2-yl)urea | | | 593.2 |

TABLE 1-121-continued

| Ex. No. | IUPAC name | structural formula | salt | MS |
|---|---|---|---|---|
| 606 | 3-benzyl-1-(2'-methoxy-5,5'-bipyrimidin-2-yl)-1-(trans-4-((4-(oxetan-3-yloxy)-5-(trifluoromethyl)pyrimidin-2-yl)amino)cyclohexyl)urea | | | 652.2 |
| 607 | 3-benzyl-1-(trans-4-((5-cyano-4-((3-methyloxetan-3-yl)amino)pyrimidin-2-yl)amino)cyclohexyl)-1-(2'-methoxy-5,5'-bipyrimidin-2-yl)urea | | | 622.2 |
| 608 | benzyl (trans-4-((5-cyano-4-(oxetan-3-ylamino)pyrimidin-2-yl)amino)cyclohexyl)(2'-methoxy-5,5'-bipyrimidin-2-yl)carbamate | | | 609.2 |
| 609 | 3-benzyl-1-(trans-4-((5-cyano-4-(oxetan-3-yloxy)pyrimidin-2-yl)amino)cyclohexyl)-1-(5-(2-methoxypyrimidin-5-yl)pyridin-2-yl)urea | | | 608.2 |

TABLE 1-121-continued

| Ex. No. | IUPAC name | structural formula | salt | MS |
|---|---|---|---|---|

TABLE 1-122

| Ex. No. | IUPAC name | structural formula | salt | MS |
|---|---|---|---|---|
| 610 | 1-(5-(2-methoxypyrimidin-5-yl)pyridin-2-yl)-1-(trans-4-((4-(oxetan-3-yloxy)-5-(trifluoromethyl)pyrimidin-2-yl)amino)cyclohexyl)-3-(pyridin-2-ylmethyl)urea | | | 652.2 |
| 611 | benzyl(trans-4-((5-cyano-4-(4-hydroxyazepan-1-yl)pyrimidin-2-yl)amino)cyclohexyl)(2'-methoxy-5,5'-bipyrimidin-2-yl)carbamate | | | 651.2 |
| 612 | 3-benzyl-1-(5-(2-methoxypyrimidin-5-yl)pyrazin-2-yl)-1-(trans-4-((4-(oxetan-3-yloxy)-5-(trifluoromethyl)pyrimidin-2-yl)amino)cyclohexyl)urea | | | 652.2 |

TABLE 1-122-continued

| Ex. No. | IUPAC name | structural formula | salt | MS |
|---|---|---|---|---|
| 613 | 3-benzyl-1-(trans-4-((4-(3-hydroxy-3-methylazetidin-1-yl)-5-(trifluoromethyl)pyrimidin-2-yl)amino)cyclohexyl)-1-(2'-methoxy-5,5'-bipyrimidin-2-yl)urea | | | 665.2 |
| 614 | 3-benzyl-1-(trans-4-((5-cyano-4-(3-hydroxy-3-methylazetidin-1-yl)pyrimidin-2-yl)amino)cyclohexyl)-1-(2'-methoxy-5,5'-bipyrimidin-2-yl)urea | | | 622.2 |

TABLE 1-123

| Ex. No. | IUPAC name | structural formula | salt | MS |
|---|---|---|---|---|
| 615 | 3-benzyl-1-(trans-4-((5-cyano-4-(4-hydroxypiperidin-1-yl)pyrimidin-2-yl)amino)cyclohexyl)-1-(2'-methoxy-5,5'-bipyrimidin-2-yl)urea | | | 636.3 |

TABLE 1-123-continued

| Ex. No. | IUPAC name | structural formula | salt | MS |
|---|---|---|---|---|
| 616 | 3-benzyl-1-(trans-4-((4-(4-hydroxypiperidin-1-yl)-5-(trifluoromethyl)pyrimidin-2-yl)amino)cyclohexyl)-1-(2'-methoxy-5,5'-bipyrimidin-2-yl)urea | | | 679.2 |
| 617 | 3-benzyl-1-(trans-4-((4-(3-hydroxy-3-methylazetidin-1-yl)-5-(trifluoromethyl)pyrimidin-2-yl)amino)cyclohexyl)-1-(5-(2-methoxypyrimidin-5-yl)pyrazin-2-yl)urea | | | 665.2 |
| 618 | 3-benzyl-1-(5-(1-methyl-1H-pyrazol-4-yl)pyrazin-2-yl)-1-(trans-4-((4-(oxetan-3-yloxy)-5-(trifluoromethyl)pyrimidin-2-yl)amino)cyclohexyl)urea | | | 624.2 |
| 619 | benzyl(trans-4-((5-cyano-4-(3-hydroxy-3-methylazetidin-1-yl)pyrimidin-2-yl)amino)cyclohexyl)(2'-methoxy-5,5'-bipyrimidin-2-yl)carbamate | | | 623.1 |

TABLE 1-124

| Ex. No. | IUPAC name | structural formula | salt | MS |
|---|---|---|---|---|
| 620 | 3-benzyl-1-(trans-4-((5-cyano-4-(3-hydroxy-3-methylazetidin-1-yl)pyrimidin-2-yl)amino)-cyclohexyl)-1-(5-(2-methoxypyrimidin-5-yl)pyrazin-2-yl)urea | | | 622.3 |
| 621 | 3-benzyl-1-(trans-4-((5-cyano-4-(4-fluoro-4-(hydroxymethyl)-piperidin-1-yl)pyrimidin-2-yl)amino)cyclohexyl)-1-(2'-methoxy-5,5'-bipyrimidin-2-yl)urea | | | 668.3 |
| 622 | pyridin-2-ylmethyl(trans-4-((4-(3-hydroxy-3-methylazetidin-1-yl)-5-(trifluoromethyl)pyrimidin-2-yl)amino)cyclohexyl)(2'-methoxy-5,5'-bipyrimidin-2-yl)carbamate | | | 667.2 |
| 623 | N-(trans-4-((4-(3-hydroxy-3-methylazetidin-1-yl)-5-(trifluoromethyl)pyrimidin-2-yl)amino)cyclohexyl)-N-(5-(2-methoxypyrimidin-5-yl)pyridin-2-yl)-2-phenoxyacetamide | | | 665.2 |

TABLE 1-124-continued

| Ex. No. | IUPAC name | structural formula | salt | MS |
|---|---|---|---|---|
| 624 | pyridin-2-ylmethyl(trans-4-((4-(4-hydroxypiperidin-1-yl)-5-(trifluoromethyl)pyrimidin-2-yl)amino)cyclohexyl)(2'-methoxy-5,5'-bipyrimidin-2-yl)carbamate | | | 681.3 |

TABLE 1-125

| Ex. No. | IUPAC name | structural formula | salt | MS |
|---|---|---|---|---|
| 625 | 3-benzyl-1-(trans-4-((4-(3-hydroxy-3-methylazetidin-1-yl)-5-(trifluoromethyl)pyrimidin-2-yl)amino)cyclohexyl)-1-(5-(2-methoxypyrimidin-5-yl)pyridin-2-yl)urea | | | 664.3 |
| 626 | 3-benzyl-1-(trans-4-((5-cyano-4-(3-hydroxy-3-methylazetidin-1-yl)pyrimidin-2-yl)amino)-cyclohexyl)-1-(5-(2-methoxypyrimidin-5-yl)pyridin-2-yl)urea | | | 621.3 |

TABLE 1-125-continued

| Ex. No. | IUPAC name | structural formula | salt | MS |
|---|---|---|---|---|
| 627 | N-(5-(2-methoxypyrimidin-5-yl)pyridin-2-yl)-N-(trans-4-((4-(oxetan-3-yloxy)-5-(trifluoromethyl)pyrimidin-2-yl)amino)cyclohexyl)-2-phenoxyacetamide | | | 652.2 |
| 628 | pyridin-2-ylmethyl(trans-4-((4-(3-hydroxy-3-methylazetidin-1-yl)-5-(trifluoromethyl)-pyrimidin-2-yl)amino)-cyclohexyl)(5-(2-methoxypyrimidin-5-yl)pyridin-2-yl)carbamate | | | 666.2 |
| 629 | pyridin-2-ylmethyl(5-(2-methoxypyrimidin-5-yl)pyridin-2-yl)(trans-4-((4-(oxetan-3-yloxy)-5-(trifluoromethyl)-pyrimidin-2-yl)amino)-cyclohexyl)carbamate | | | 653.3 |

TABLE 1-126

| Ex. No. | IUPAC name | structural formula | salt | MS |
|---|---|---|---|---|
| 630 | 1-(trans-4-((4-(3-hydroxy-3-methylazetidin-1-yl)-5-(trifluoromethyl)pyrimidin-2-yl)amino)cyclohexyl)-1-(5-(2-methoxypyrimidin-5-yl)pyridin-2-yl)-3-(pyridin-2-ylmethyl)urea | | | 665.3 |
| 631 | 1-(trans-4-((4-(3-hydroxy-3-methylazetidin-1-yl)-5-(trifluoromethyl)pyrimidin-2-yl)amino)cyclohexyl)-1-(5-(2-methoxypyrimidin-5-yl)pyridin-2-yl)-3-((1R)-1-phenylethyl)urea | | | 678.3 |
| 632 | 3-benzyl-1-(trans-4-((4-(4-fluoro-4-(hydroxymethyl)piperidin-1-yl)-5-(trifluoromethyl)pyrimidin-2-yl)amino)cyclohexyl)-1-(2'-methoxy-5,5'-bipyrimidin-2-yl)urea | | | 711.3 |

TABLE 1-126-continued

| Ex. No. | IUPAC name | structural formula | salt | MS |
|---|---|---|---|---|
| 633 | 1-(trans-4-((4-(3-hydroxy-3-methylazetidin-1-yl)-5-(trifluoromethyl)pyrimidin-2-yl)amino)cyclohexyl)-1-(5-(2-methoxypyrimidin-5-yl)pyridin-2-yl)-3-((1S)-1-phenylethyl)urea | | | 678.2 |

TABLE 1-127

| Ex. No. | IUPAC name | structural formula | salt | MS |
|---|---|---|---|---|
| 634 | 3-benzyl-1-(5-(2-methoxypyrimidin-5-yl)pyrazin-2-yl)-1-(trans-4-((4-((oxetan-3-yl)methoxy)-5-(trifluoromethyl)pyrimidin-2-yl)amino)cyclohexyl)urea | | | 666.3 |
| 635 | 3-benzyl-1-(5-(1-methyl-1H-pyrazol-3-yl)pyrazin-2-yl)-1-(trans-4-((4-((oxetan-3-yl)oxy)-5-(trifluoromethyl)-pyrimidin-2-yl)amino)cyclohexyl)urea | | | 624.3 |

TABLE 1-127-continued

| Ex. No. | IUPAC name | structural formula | salt | MS |
|---|---|---|---|---|
| 636 | 3-benzyl-1-(5-(2-methoxypyrimidin-5-yl)-6-methylpyridin-2-yl)-1-(trans-4-((4-((oxetan-3-yl)oxy)-5-(trifluoromethyl)pyrimidin-2-yl)amino)cyclohexyl)urea | | | 665.3 |
| 637 | (pyridin-2-yl)methyl(5-(2-methoxypyrimidin-5-yl)pyrazin-2-yl)(trans-4-((4-((oxetan-3-yl)oxy)-5-(trifluoromethyl)pyrimidin-2-yl)amino)cyclohexyl)carbamate | | | 654.3 |
| 638 | 3-benzyl-1-(5-(2-methoxypyrimidin-5-yl)pyrazin-2-yl)-1-(trans-4-((4-((oxetan-2-yl)methoxy)-5-(trifluoromethyl)pyrimidin-2-yl)amino)cyclohexyl)urea | | | 666.3 |

TABLE 1-127-continued

| Ex. No. | IUPAC name | structural formula | salt | MS |
|---|---|---|---|---|
| 639 | 3-benzyl-1-(5-(2-methoxypyrimidin-5-yl)pyrazin-2-yl)-1-(trans-4-((4-((oxetan-3-yl)oxy)-5-(trifluoromethyl)pyridin-2-yl)amino)cyclohexyl)urea | | | 651.3 |

TABLE 1-128

| Ex. No. | IUPAC name | structural formula | salt | MS |
|---|---|---|---|---|
| 640 | 3-benzyl-1-(5-(2-methoxypyrimidin-5-yl)pyrazin-2-yl)-1-(trans-4-((4-((3-methyloxetan-3-yl)oxy)-5-(trifluoromethyl)pyrimidin-2-yl)amino)cyclohexyl)urea | | | 666.3 |
| 641 | 3-((1S)-2-methoxy-1-phenylethyl)-1-(5-(2-methoxypyrimidin-5-yl)pyrazin-2-yl)-1-(trans-4-((4-((oxetan-3-yl)oxy)-5-(trifluoromethyl)pyrimidin-2-yl)amino)cyclohexyl)urea | | | 696.3 |

TABLE 1-128-continued

| Ex. No. | IUPAC name | structural formula | salt | MS |
|---|---|---|---|---|
| 642 | 3-((1R)-2-methoxy-1-phenylethyl)-1-(5-(2-methoxypyrimidin-5-yl)pyrazin-2-yl)-1-(trans-4-((4-((oxetan-3-yl)oxy)-5-(trifluoromethyl)pyrimidin-2-yl)amino)cyclohexyl)urea | | | 696.3 |
| 643 | 3-benzyl-1-(trans-4-((4-(4-chloro-1H-pyrazol-5-yl)-5-(trifluoromethyl)pyrimidin-2-yl)amino)cyclohexyl)-1-(5-(2-methoxypyrimidin-5-yl)pyrazin-2-yl)urea | | | 680.2 |
| 644 | 3-benzyl-1-(5-(2-methoxyethoxy)pyrazin-2-yl)-1-(trans-4-((4-((oxetan-3-yl)oxy)-5-(trifluoromethyl)pyrimidin-2-yl)amino)cyclohexyl)urea | | | 618.3 |
| 645 | 3-benzyl-1-(5-(2,2-difluoroethoxy)pyrazin-2-yl)-1-(trans-4-((4-((oxetan-3-yl)oxy)-5-(trifluoromethyl)pyrimidin-2-yl)amino)cyclohexyl)urea | | | 624.2 |

TABLE 1-129

| Ex. No. | IUPAC name | structural formula | salt | MS |
|---|---|---|---|---|
| 646 | N-(5-(2-methoxypyrimidin-5-yl)pyrazin-2-yl)-N-(trans-4-((4-((oxetan-3-yl)oxy)-5-(trifluoromethyl)pyrimidin-2-yl)amino)cyclohexyl)-2-phenoxyacetamide | | | 653.2 |
| 647 | N-(trans-4-((4-(4-chloro-1H-pyrazol-5-yl)-5-(trifluoromethyl)pyrimidin-2-yl)amino)cyclohexyl)-N-(5-(2-methoxypyrimidin-5-yl)pyrazin-2-yl)-2-phenoxyacetamide | | | 681.2 |
| 648 | 3-benzyl-1-(trans-4-((4-(4-chloro-1H-pyrazol-3-yl)-5-cyanopyrimidin-2-yl)amino)cyclohexyl)-1-(5-(2-methoxypyrimidin-5-yl)pyrazin-2-yl)urea | | | 637.3 |

TABLE 1-129-continued

| Ex. No. | IUPAC name | structural formula | salt | MS |
|---|---|---|---|---|
| 649 | 3-benzyl-1-(trans-4-((4-(4-chloro-1H-pyrazol-3-yl)-5-cyanopyrimidin-2-yl)amino)cyclohexyl)-1-(4-(2-methoxypyrimidin-5-yl)pyridin-2-yl)urea | | | 636.3 |
| 650 | 3-benzyl-1-(trans-4-((4-(4-chloro-1H-pyrazol-3-yl)-5-cyanopyrimidin-2-yl)amino)cyclohexyl)-1-(6-(2-methoxypyrimidin-5-yl)pyridin-2-yl)urea | | | 636.3 |
| 651 | 3-benzyl-1-(5-(2-methoxy-pyrimidin-5-yl)pyrazin-2-yl)-1-(trans-4-((4-(2-oxo-1,8-diazaspiro[4.5]decan-8-yl)-5-(trifluoromethyl)pyrimidin-2-yl)amino)cyclohexyl)urea | | | 732.4 |

TABLE 1-130

| Ex. No. | IUPAC name | structural formula | salt | MS |
|---|---|---|---|---|
| 652 | 3-benzyl-1-(1-(2-methoxypyrimidin-5-yl)-1H-pyrazol-4-yl)-1-(trans-4-((4-((oxetan-3-yl)oxy)-5-(trifluoromethyl)pyrimidin-2-yl)amino)cyclohexyl)urea | | | 640.3 |
| 653 | 5-((benzylcarbamoyl)(trans-4-((4-((oxetan-3-yl)oxy)-5-(trifluoromethyl)pyrimidin-2-yl)amino)cyclohexyl)-amino)-N-(2-methoxyethyl)-pyrazine-2-carboxamide | | | 645.3 |

TABLE 1-130-continued

| Ex. No. | IUPAC name | structural formula | salt | MS |
|---|---|---|---|---|
| 654 | 3-benzyl-1-(trans-4-((4-(cyclobutylamino)-5-(trifluoromethyl)pyrimidin-2-yl)amino)cyclohexyl)-1-(5-(2-methoxypyrimidin-5-yl)pyrazin-2-yl)urea | | | 649.3 |
| 655 | 3-benzyl-1-(trans-4-((4-(3,6-dihydro-2H-pyran-4-yl)-5-(trifluoromethyl)pyrimidin-2-yl)amino)cyclohexyl)-1-(5-(2-methoxypyrimidin-5-yl)pyrazin-2-yl)urea | | | 662.3 |
| 656 | 3-benzyl-1-(trans-4-((4-((cyclobutylmethyl)amino)-5-(trifluoromethyl)pyrimidin-2-yl)amino)cyclohexyl)-1-(5-(2-methoxypyrimidin-5-yl)pyrazin-2-yl)urea | | | 663.3 |
| 657 | 1-(trans-4-((4-(4-chloro-1H-pyrazol-3-yl)-5-cyanopyrimidin-2-yl)amino)cyclohexyl)-3-ethyl-1-(5-(2-methoxypyrimidin-5-yl)pyrazin-2-yl)urea | | | 575.3 |

TABLE 1-131

| Ex. No. | IUPAC name | structural formula | salt | MS |
|---|---|---|---|---|
| 658 | 1-(trans-4-((4-(4-chloro-1H-pyrazol-3-yl)-5-cyanopyrimidin-2-yl)amino)cyclohexyl)-1-(5-(2-methoxypyrimidin-5-yl)pyrazin-2-yl)-3,3-dimethylurea | | | 575.2 |
| 659 | N-(trans-4-((4-(4-chloro-1H-pyrazol-3-yl)-5-cyanopyrimidin-2-yl)amino)cyclohexyl)-N-(5-(2-methoxypyrimidin-5-yl)pyrazin-2-yl)butanamide | | | 574.2 |
| 660 | 3-((5-((benzylcarbamoyl)(trans-4-((4-((oxetan-3-yl)oxy)-5-(trifluoromethyl)pyrimidin-2-yl)amino)cyclohexyl)amino)pyrazin-2-yl)oxy)-N-methylpropanamide | | | 645.3 |
| 661 | 3-benzyl-1-(5-bromopyrazin-2-yl)-1-(trans-4-((4-(4-chloro-1H-pyrazol-3-yl)-5-cyanopyrimidin-2-yl)amino)cyclohexyl)urea | | | 607.1 |

TABLE 1-131-continued

| Ex. No. | IUPAC name | structural formula | salt | MS |
|---|---|---|---|---|
| 662 | 3-benzyl-1-(5-(2-methoxypyrimidin-5-yl)pyrazin-2-yl)-1-(trans-4-((4-(4-methyl-1H-pyrazol-5-yl)-5-(trifluoromethyl)pyrimidin-2-yl)amino)cyclohexyl)urea | | | 660.3 |
| 663 | 3-benzyl-1-(trans-4-((4-(4-chloro-1H-pyrazol-3-yl)-5-cyanopyrimidin-2-yl)amino)cyclohexyl)-1-(1-methyl-1H-pyrazol-4-yl)urea | | | 531.2 |

TABLE 1-132

| Ex. No. | IUPAC name | structural formula | salt | MS |
|---|---|---|---|---|
| 664 | 1-(trans-4-((4-(4-chloro-1H-pyrazol-3-yl)-5-cyanopyrimidin-2-yl)amino)cyclohexyl)-3-(2-methoxyethyl)-1-(5-(2-methoxypyrimidin-5-yl)pyrazin-2-yl)urea | | | 605.3 |

TABLE 1-132-continued

| Ex. No. | IUPAC name | structural formula | salt | MS |
|---|---|---|---|---|
| 665 | 1-(trans-4-((4-(4-chloro-1H-pyrazol-3-yl)-5-cyanopyrimidin-2-yl)amino)cyclohexyl)-3-(3-methoxypropyl)-1-(5-(2-methoxypyrimidin-5-yl)pyrazin-2-yl)urea | | | 619.4 |
| 666 | ethyl(trans-4-((4-(4-chloro-1H-pyrazol-3-yl)-5-cyanopyrimidin-2-yl)amino)cyclohexyl)(5-(2-methoxypyrimidin-5-yl)pyrazin-2-yl)carbamate | | | 576.2 |
| 667 | N-(trans-4-((4-(4-chloro-1H-pyrazol-3-yl)-5-cyanopyrimidin-2-yl)amino)cyclohexyl)-N-(5-(2-methoxypyrimidin-5-yl)pyrazin-2-yl)-2-phenoxyacetamide | | | 638.3 |

TABLE 1-132-continued

| Ex. No. | IUPAC name | structural formula | salt | MS |
|---|---|---|---|---|
| 668 | 3-benzyl-1-(trans-4-((4-(4-chloro-1-methyl-1H-pyrazol-3-yl)-5-(trifluoromethyl)pyrimidin-2-yl)amino)cyclohexyl)-1-(5-(2-methoxypyrimidin-5-yl)pyrazin-2-yl)urea | | | 694.3 |
| 669 | 3-benzyl-1-(trans-4-((4-(4-chloro-5-methyl-1H-pyrazol-3-yl)-5-(trifluoromethyl)pyrimidin-2-yl)amino)cyclohexyl)-1-(5-(2-methoxypyrimidin-5-yl)pyrazin-2-yl)urea | | | 694.2 |

TABLE 1-133

| Ex. No. | IUPAC name | structural formula | salt | MS |
|---|---|---|---|---|
| 670 | 3-benzyl-1-(5-(2-methoxypyrimidin-5-yl)pyrazin-2-yl)-1-(trans-4-((4-(2H-1,2,3-triazol-2-yl)-5-(trifluoromethyl)pyrimidin-2-yl)amino)cyclohexyl)urea | | | 647.3 |

TABLE 1-133-continued

| Ex. No. | IUPAC name | structural formula | salt | MS |
|---|---|---|---|---|
| 671 | 3-benzyl-1-(5-(1-ethyl-2-oxo-1,2-dihydropyridin-4-yl)pyrazin-2-yl)-1-(trans-4-((4-((oxetan-3-yl)oxy)-5-(trifluoromethyl)pyrimidin-2-yl)amino)cyclohexyl)urea | 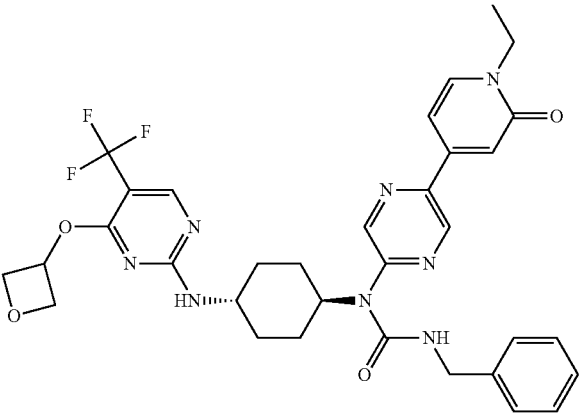 [SMILES: CCn1ccc(-c2cnc(N(C(=O)NCc3ccccc3)[C@H]3CC[C@H](Nc4ncc(C(F)(F)F)c(OC5COC5)n4)CC3)cn2)cc1=O] | | 665.3 |
| 672 | 3-benzyl-1-(trans-4-((4-(4-chloro-1H-pyrazol-3-yl)-5-cyanopyrimidin-2-yl)amino)cyclohexyl)-1-pyridin-2-ylurea | 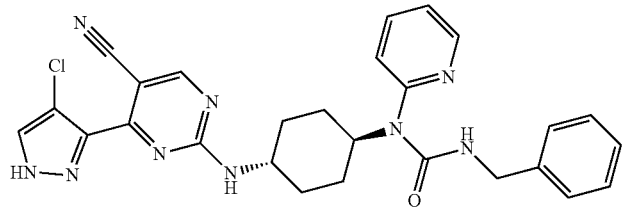 [SMILES: N#Cc1cnc(N[C@H]2CC[C@H](N(C(=O)NCc3ccccc3)c3ccccn3)CC2)nc1-c1n[nH]cc1Cl] | | 528.2 |
| 673 | 3-benzyl-1-(trans-4-((4-(4-chloro-1H-pyrazol-3-yl)-5-cyanopyrimidin-2-yl)amino)cyclohexyl)-1-(2'-methoxy(5,5'-bipyrimidin)-2-yl)urea | 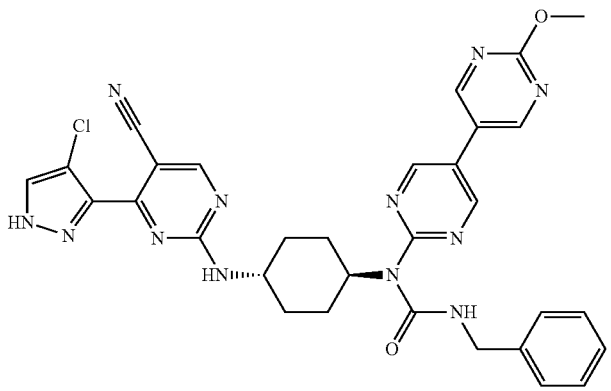 [SMILES: COc1ncc(-c2cnc(N(C(=O)NCc3ccccc3)[C@H]3CC[C@H](Nc4ncc(C#N)c(-c5n[nH]cc5Cl)n4)CC3)nc2)cn1] | | 637.3 |
| 674 | 3-benzyl-1-(trans-4-((4-(4-chloro-1H-pyrazol-3-yl)-5-cyanopyrimidin-2-yl)amino)cyclohexyl)-1-(5-(1-methyl-1H-pyrazol-4-yl)pyrimidin-2-yl)urea | 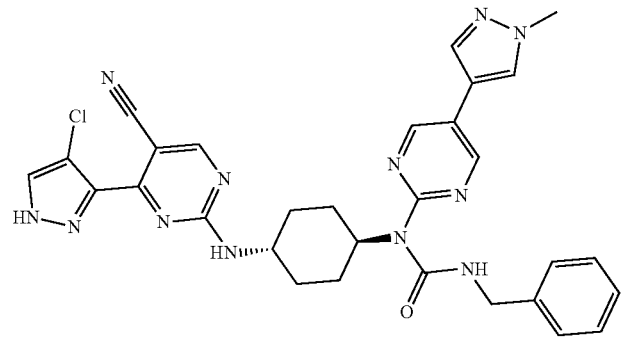 [SMILES: Cn1cc(-c2cnc(N(C(=O)NCc3ccccc3)[C@H]3CC[C@H](Nc4ncc(C#N)c(-c5n[nH]cc5Cl)n4)CC3)nc2)cn1] | | 609.3 |

TABLE 1-133-continued

| Ex. No. | IUPAC name | structural formula | salt | MS |
|---|---|---|---|---|
| 675 | 3-benzyl-1-(trans-4-((4-(4-chloro-1H-pyrazol-3-yl)-5-(trifluoromethyl)pyrimidin-2-yl)amino)cyclohexyl)-1-(2-(2-methoxypyrimidin-5-yl)pyridin-4-yl)urea | | | 679.2 |

TABLE 1-134

| Ex. No. | IUPAC name | structural formula | salt | MS |
|---|---|---|---|---|
| 676 | 3-benzyl-1-(trans-4-((4-(4-bromo-1H-pyrazol-3-yl)-5-(trifluoromethyl)pyrimidin-2-yl)amino)cyclohexyl)-1-(5-(2-methoxypyrimidin-5-yl)pyrazin-2-yl)urea | | | 724.2 |
| 677 | 3-benzyl-1-(trans-4-((4-(4-chloro-1H-pyrazol-3-yl)-5-(trifluoromethyl)pyrimidin-2-yl)amino)cyclohexyl)-1-(1-methyl-1H-pyrazol-3-yl)urea | | | 574.2 |
| 678 | 3-benzyl-1-(trans-4-((4-(4-chloro-1H-pyrazol-3-yl)-5-cyanopyrimidin-2-yl)amino)cyclohexyl)-1-(5-(2-methoxypyrimidin-5-yl)pyridin-2-yl)urea | | | 636.3 |

TABLE 1-134-continued

| Ex. No. | IUPAC name | structural formula | salt | MS |
|---|---|---|---|---|
| 679 | (pyridin-2-yl)methyl(trans-4-((4-(4-chloro-1H-pyrazol-3-yl)-5-cyanopyrimidin-2-yl)amino)cyclohexyl)(5-(2-methoxypyrimidin-5-yl)pyridin-2-yl)carbamate | | | 638.3 |
| 680 | 3-benzyl-1-(trans-4-((4-(4-chloro-1H-pyrazol-3-yl)-5-(trifluoromethyl)pyrimidin-2-yl)amino)cyclohexyl)-1-(2'-methoxy(2,5'-bipyrimidin)-4-yl)urea | | | 680.2 |
| 681 | 3-benzyl-1-(trans-4-((4-(4-chloro-1H-pyrazol-3-yl)-5-(trifluoromethyl)pyrimidin-2-yl)amino)cyclohexyl)-1-(2'-methoxy(4,5'-bipyrimidin)-2-yl)urea | | | 680.2 |

TABLE 1-135

| Ex. No. | IUPAC name | structural formula | salt | MS |
|---|---|---|---|---|
| 682 | 3-benzyl-1-(trans-4-((4-(4-cyclopropyl-1H-pyrazol-3-yl)-5-(trifluoromethyl)pyrimidin-2-yl)amino)cyclohexyl)-1-(5-(2-methoxypyrimidin-5-yl)pyrazin-2-yl)urea | | | 686.3 |

TABLE 1-135-continued

| Ex. No. | IUPAC name | structural formula | salt | MS |
|---|---|---|---|---|
| 683 | 3-benzyl-1-(trans-4-((4-(4-chloro-1-(difluoromethyl)-1H-pyrazol-3-yl)-5-(trifluoromethyl)pyrimidin-2-yl)amino)cyclohexyl)-1-(5-(2-methoxypyrimidin-5-yl)pyrazin-2-yl)urea | | | 730.3 |
| 684 | 1-benzyl-3-(trans-4-((4-(4-chloro-1H-pyrazol-3-yl)-5-cyanopyrimidin-2-yl)amino)cyclohexyl)-3-(5-(2-methoxypyrimidin-5-yl)pyrazin-2-yl)-1-methylurea | | | 651.3 |
| 685 | 1-(trans-4-((4-(4-chloro-1H-pyrazol-3-yl)-5-cyano-pyrimidin-2-yl)amino)-cyclohexyl)-1-(5-(2-methoxy-pyrimidin-5-yl)pyrazin-2-yl)-3-propan-2-ylurea | | | 589.3 |

TABLE 1-135-continued

| Ex. No. | IUPAC name | structural formula | salt | MS |
|---|---|---|---|---|
| 686 | 1-(trans-4-((4-(4-chloro-1H-pyrazol-3-yl)-5-cyanopyrimidin-2-yl)amino)cyclohexyl)-3-cyclopropyl-1-(5-(2-methoxypyrimidin-5-yl)pyrazin-2-yl)urea | | | 587.2 |
| 687 | propan-2-yl(trans-4-((4-(4-chloro-1H-pyrazol-3-yl)-5-cyanopyrimidin-2-yl)amino)cyclohexyl)(5-(2-methoxypyrimidin-5-yl)pyrazin-2-yl)carbamate | | | 590.2 |

TABLE 1-136

| Ex. No. | IUPAC name | structural formula | salt | MS |
|---|---|---|---|---|
| 688 | cyclopropylmethyl(trans-4-((4-(4-chloro-1H-pyrazol-3-yl)-5-cyanopyrimidin-2-yl)amino)cyclohexyl)(5-(2-methoxypyrimidin-5-yl)pyrazin-2-yl)carbamate | | | 602.3 |

TABLE 1-136-continued

| Ex. No. | IUPAC name | structural formula | salt | MS |
|---|---|---|---|---|
| 689 | 2,2-difluoroethyl(trans-4-((4-(4-chloro-1H-pyrazol-3-yl)-5-cyanopyrimidin-2-yl)amino)cyclohexyl)(5-(2-methoxypyrimidin-5-yl)pyrazin-2-yl)carbamate | | | 612.2 |
| 690 | 2,2-difluoroethyl(trans-4-((4-(4-chloro-1H-pyrazol-3-yl)-5-cyanopyrimidin-2-yl)amino)cyclohexyl)(5-(2-methoxypyrimidin-5-yl)-6-methylpyridin-2-yl)carbamate | | | 625.2 |
| 691 | 2-hydroxy-2-methylpropyl (trans-4-((4-(4-chloro-1H-pyrazol-3-yl)-5-cyanopyrimidin-2-yl)amino)cyclohexyl)(5-(2-methoxypyrimidin-5-yl)pyridin-2-yl)carbamate | | | 619.3 |

TABLE 1-136-continued

| Ex. No. | IUPAC name | structural formula | salt | MS |
|---|---|---|---|---|
| 692 | 1-(trans-4-((4-(4-chloro-1H-pyrazol-3-yl)-5-cyanopyrimidin-2-yl)amino)cyclohexyl)-3-(2,2-difluoroethyl)-1-(5-(2-methoxypyrimidin-5-yl)pyridin-2-yl)urea | | | 610.2 |
| 693 | 1-(trans-4-((4-(4-chloro-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyridin-2-yl)urea | | | 653.3 |

TABLE 1-137

| Ex. No. | IUPAC name | structural formula | salt | MS |
|---|---|---|---|---|
| 694 | 2,2-difluoroethyl(trans-4-((4-(4-chloro-1H-pyrazol-3-yl)-5-cyanopyrimidin-2-yl)amino)cyclohexyl)(5-(2-methoxypyrimidin-5-yl)pyridin-2-yl)carbamate | | | 611.2 |

TABLE 1-137-continued

| Ex. No. | IUPAC name | structural formula | salt | MS |
|---|---|---|---|---|
| 695 | 2,2-difluoroethyl(trans-4-((4-(4-chloro-1H-pyrazol-3-yl)-5-(trifluoromethyl)pyrimidin-2-yl)amino)cyclohexyl)(5-(2-methoxypyrimidin-5-yl)pyridin-2-yl)carbamate | | | 654.2 |
| 696 | 2,2-difluoroethyl(trans-4-((4-(4-chloro-1H-pyrazol-3-yl)-5-cyanopyrimidin-2-yl)amino)cyclohexyl)(1-(2-methoxypyrimidin-5-yl)-1H-pyrazol-4-yl)carbamate | | | 600.2 |
| 697 | 2,2-difluoroethyl(trans-4-((4-(4-chloro-1H-pyrazol-3-yl)-5-cyanopyrimidin-2-yl)amino)cyclohexyl)(4-(2-methoxypyrimidin-5-yl)pyridin-2-yl)carbamate | | | 611.2 |
| 698 | 2,2-difluoroethyl(trans-4-((4-(4-chloro-1H-pyrazol-3-yl)-5-(trifluoromethyl)pyrimidin-2-yl)amino)cyclohexyl)(4-(2-methoxypyrimidin-5-yl)pyridin-2-yl)carbamate | | | 654.2 |

TABLE 1-137-continued

| Ex. No. | IUPAC name | structural formula | salt | MS |
|---|---|---|---|---|
| 699 | ethyl(trans-4-((4-(4-chloro-1-methyl-1H-pyrazol-3-yl)-5-cyanopyrimidin-2-yl)amino)cyclohexyl)(5-(2-methoxypyrimidin-5-yl)pyridin-2-yl)carbamate | | | 589.2 |

TABLE 1-138

| Ex. No. | IUPAC name | structural formula | salt | MS |
|---|---|---|---|---|
| 700 | 2,2-difluoroethyl(trans-4-((4-(4-chloro-1-methyl-1H-pyrazol-3-yl)-5-cyanopyrimidin-2-yl)amino)cyclohexyl)(5-(2-methoxypyrimidin-5-yl)pyridin-2-yl)carbamate | | | 625.2 |
| 701 | (1-fluorocyclopropyl)methyl (trans-4-((4-(4-chloro-1H-pyrazol-3-yl)-5-(trifluoromethyl)pyrimidin-2-yl)amino)cyclohexyl)(5-(2-methoxypyrimidin-5-yl)pyridin-2-yl)carbamate | | | 662.2 |

TABLE 1-138-continued

| Ex. No. | IUPAC name | structural formula | salt | MS |
|---|---|---|---|---|
| 702 | 2,2-difluoroethyl(trans-4-((4-(4-chloro-1-methyl-1H-pyrazol-3-yl)-5-(trifluoromethyl)pyrimidin-2-yl)amino)cyclohexyl)(5-(2-methoxypyrimidin-5-yl)pyridin-2-yl)carbamate | | | 668.2 |
| 703 | ethyl(trans-4-((4-(4-chloro-1-methyl-1H-pyrazol-5-yl)-5-cyanopyrimidin-2-yl)amino)cyclohexyl)(5-(2-methoxypyrimidin-5-yl)pyridin-2-yl)carbamate | | | 589.2 |
| 704 | 2,2-difluoroethyl(trans-4-((4-(4-chloro-1-methyl-1H-pyrazol-5-yl)-5-cyanopyrimidin-2-yl)amino)cyclohexyl)(5-(2-methoxypyrimidin-5-yl)pyridin-2-yl)carbamate | | | 625.2 |

TABLE 1-138-continued

| Ex. No. | IUPAC name | structural formula | salt | MS |
|---|---|---|---|---|
| 705 | 3-benzyl-1-(trans-4-((4-(4-chloro-1H-pyrazol-3-yl)-5-(difluoromethyl)pyrimidin-2-yl)amino)cyclohexyl)-1-(5-(2-methoxypyrimidin-5-yl)pyrazin-2-yl)urea | | | 662.2 |

TABLE 1-139

| Ex. No. | IUPAC name | structural formula | salt | MS |
|---|---|---|---|---|
| 706 | 1-(trans-4-((4-(4-chloro-1-methyl-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyridin-2-yl)urea | | | 667.2 |
| 707 | 1-(trans-4-((4-(4-chloro-1-methyl-1H-pyrazol-3-yl)-5-cyanopyrimidin-2-yl)amino)cyclohexyl)-3-(2,2-difluoroethyl)-1-(5-(2-methoxypyrimidin-5-yl)pyridin-2-yl)urea | | | 624.2 |

TABLE 1-139-continued

| Ex. No. | IUPAC name | structural formula | salt | MS |
|---|---|---|---|---|
| 708 | 3-benzyl-1-(trans-4-((5-chloro-4-(4-chloro-1H-pyrazol-3-yl)pyrimidin-2-yl)amino)cyclohexyl)-1-(5-(2-methoxypyrimidin-5-yl)pyrazin-2-yl)urea | | | 646.2 |
| 709 | 2,2-difluoroethyl(trans-4-((4-(4-chloro-1H-pyrazol-3-yl)-5-(trifluoromethyl)pyrimidin-2-yl)amino)cyclohexyl)(1-(cyclopropylmethyl)-1H-pyrazol-4-yl)carbamate | | | 589.2 |
| 710 | 1-(trans-4-((4-(4-chloro-1-(difluoromethyl)-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyridin-2-yl)urea | | | 703.3 |
| 711 | 2,2-difluoroethyl(trans-4-((4-(4-chloro-1-methyl-1H-pyrazol-3-yl)-5-cyanopyrimidin-2-yl)amino)cyclohexyl)(4-(2-methoxypyrimidin-5-yl)pyridin-2-yl)carbamate | | | 625.3 |

TABLE 1-140

| Ex. No. | IUPAC name | structural formula | salt | MS |
|---|---|---|---|---|
| 712 | 2,2-difluoroethyl(trans-4-((4-(4-chloro-1-methyl-1H-pyrazol-3-yl)-5-(trifluoromethyl)pyrimidin-2-yl)amino)cyclohexyl)(4-(2-methoxypyrimidin-5-yl)pyridin-2-yl)carbamate | | | 668.3 |
| 713 | 3-(2,2-difluoroethyl)-1-(5-(2-methoxypyrimidin-5-yl)pyridin-2-yl)-1-(trans-4-((4-(6-oxa-2-azaspiro[3.4]octan-2-yl)-5-(trifluoromethyl)pyrimidin-2-yl)amino)cyclohexyl)urea | | | 664.3 |
| 714 | 1-(trans-4-((4-(4-chloro-1H-pyrazol-3-yl)-5-(difluoromethyl)pyrimidin-2-yl)amino)cyclohexyl)-3-(2,2-difluoroethyl)-1-(5-(2-methoxypyrimidin-5-yl)pyridin-2-yl)urea | | | 635.3 |
| 715 | 1-(trans-4-((4-(cyclopropylamino)-5-(trifluoromethyl)pyrimidin-2-yl)amino)cyclohexyl)-3-(2,2-difluoroethyl)-1-(5-(2-methoxypyrimidin-5-yl)pyridin-2-yl)urea | | | 608.3 |

TABLE 1-140-continued

| Ex. No. | IUPAC name | structural formula | salt | MS |
|---|---|---|---|---|
| 716 | 3-(2,2-difluoroethyl)-1-(trans-4-((4-(4-hydroxypiperidin-1-yl)-5-(trifluoromethyl)pyrimidin-2-yl)amino)cyclohexyl)-1-(5-(2-methoxypyrimidin-5-yl)pyridin-2-yl)urea | | | 652.3 |
| 717 | 3-(2,2-difluoroethyl)-1-(5-(2-methoxypyrimidin-5-yl)pyridin-2-yl)-1-(trans-4-((4-(2-oxa-7-azaspiro[3.5]nonan-7-yl)-5-(trifluoromethyl)pyrimidin-2-yl)amino)cyclohexyl)urea | | | 678.3 |

TABLE 1-141

| Ex. No. | IUPAC name | structural formula | salt | MS |
|---|---|---|---|---|
| 718 | 3-(2,2-difluoroethyl)-1-(5-(2-methoxypyrimidin-5-yl)pyridin-2-yl)-1-(trans-4-((4-(2-oxa-6-azaspiro[3.4]octan-6-yl)-5-(trifluoromethyl)pyrimidin-2-yl)amino)cyclohexyl)urea | | | 664.3 |

TABLE 1-141-continued

| Ex. No. | IUPAC name | structural formula | salt | MS |
|---|---|---|---|---|
| 719 | 3-(2,2-difluoroethyl)-1-(trans-4-((4-(3,4-dihydro-2,6-naphthyridin-2(1H)-yl)-5-(trifluoromethyl)-pyrimidin-2-yl)amino)cyclohexyl)-1-(5-(2-methoxypyrimidin-5-yl)pyridin-2-yl)urea | | | 685.4 |
| 720 | 3-(2,2-difluoroethyl)-1-(5-(2-methoxypyrimidin-5-yl)pyridin-2-yl)-1-(trans-4-((4-(2-oxa-7-azaspiro[4.4]nonan-7-yl)-5-(trifluoromethyl)pyrimidin-2-yl)amino)cyclohexyl)urea | | | 678.3 |
| 721 | 3-(2,2-difluoroethyl)-1-(5-(2-methoxypyrimidin-5-yl)pyridin-2-yl)-1-(trans-4-((4-(propylamino)-5-(trifluoromethyl)pyrimidin-2-yl)amino)cyclohexyl)urea | | | 610.3 |
| 722 | 3-(2,2-difluoroethyl)-1-(5-(2-methoxypyrimidin-5-yl)pyridin-2-yl)-1-(trans-4-((4-((propan-2-yl)amino)-5-(trifluoromethyl)pyrimidin-2-yl)amino)cyclohexyl)urea | | | 610.3 |

TABLE 1-141-continued

| Ex. No. | IUPAC name | structural formula | salt | MS |
|---|---|---|---|---|
| 723 | 1-(trans-4-((4-((3,3-difluorocyclobutyl)amino)-5-(trifluoromethyl)pyrimidin-2-yl)amino)cyclohexyl)-3-(2,2-difluoroethyl)-1-(5-(2-methoxypyrimidin-5-yl)pyridin-2-yl)urea | | | 658.3 |

TABLE 1-142

| Ex. No. | IUPAC name | structural formula | salt | MS |
|---|---|---|---|---|
| 724 | 3-(2,2-difluoroethyl)-1-(5-(2-methoxypyrimidin-5-yl)pyridin-2-yl)-1-(trans-4-((4-(((1-methyl-1H-imidazol-2-yl)methyl)amino)-5-(trifluoromethyl)pyrimidin-2-yl)amino)cyclohexyl)urea | | | 662.3 |
| 725 | 3-(2,2-difluoroethyl)-1-(5-(2-methoxypyrimidin-5-yl)pyridin-2-yl)-1-(trans-4-((4-(1,4-oxazepan-4-yl)-5-(trifluoromethyl)pyrimidin-2-yl)amino)cyclohexyl)urea | | | 652.3 |

TABLE 1-142-continued

| Ex. No. | IUPAC name | structural formula | salt | MS |
|---|---|---|---|---|
| 726 | 3-(2,2-difluoroethyl)-1-(trans-4-((4-(4-hydroxyazepan-1-yl)-5-(trifluoromethyl)pyrimidin-2-yl)amino)cyclohexyl)-1-(5-(2-methoxypyrimidin-5-yl)pyridin-2-yl)urea | | | 666.3 |
| 727 | 3-(2,2-difluoroethyl)-1-(trans-4-((4-(5,6-dihydroimidazo[1,5-a]pyrazin-7(8H)-yl)-5-(trifluoromethyl)pyrimidin-2-yl)amino)cyclohexyl)-1-(5-(2-methoxypyrimidin-5-yl)pyridin-2-yl)urea | | | 674.3 |
| 728 | 3-(2,2-difluoroethyl)-1-(5-(2-methoxypyrimidin-5-yl)pyridin-2-yl)-1-(trans-4-((4-(5-oxa-2-azaspiro[3.4]octan-2-yl)-5-(trifluoromethyl)pyrimidin-2-yl)amino)cyclohexyl)urea | | | 664.3 |

TABLE 1-142-continued

| Ex. No. | IUPAC name | structural formula | salt | MS |
|---|---|---|---|---|
| 729 | 1-(trans-4-((4-(4-chloro-1H-pyrazol-3-yl)-5-(trifluoromethyl)pyrimidin-2-yl)amino)cyclohexyl)-1-(5-(2-methoxypyrimidin-5-yl)pyridin-2-yl)-3-(2,2,2-trifluoroethyl)urea | | | 671.3 |

TABLE 1-143

| Ex. No. | IUPAC name | structural formula | salt | MS |
|---|---|---|---|---|
| 730 | 1-(trans-4-((4-(4-chloro-1-methyl-1H-pyrazol-3-yl)-5-(trifluoromethyl)pyrimidin-2-yl)amino)cyclohexyl)-1-(5-(2-methoxypyrimidin-5-yl)pyridin-2-yl)-3-(2,2,2-trifluoroethyl)urea | | | 685.3 |
| 731 | 1-(trans-4-((4-(4-chloro-1H-pyrazol-3-yl)-5-(trifluoromethyl)pyrimidin-2-yl)amino)cyclohexyl)-3-(cyclopropylmethyl)-1-(5-(2-methoxypyrimidin-5-yl)pyridin-2-yl)urea | | | 643.3 |

TABLE 1-143-continued

| Ex. No. | IUPAC name | structural formula | salt | MS |
|---|---|---|---|---|
| 732 | 1-(trans-4-((4-(4-chloro-1-methyl-1H-pyrazol-3-yl)-5-(trifluoromethyl)pyrimidin-2-yl)amino)cyclohexyl)-3-(cyclopropylmethyl)-1-(5-(2-methoxypyrimidin-5-yl)pyridin-2-yl)urea | | | 657.3 |
| 733 | 3-(2,2-difluoroethyl)-1-(trans-4-((4-(4-fluoro-1H-pyrazol-3-yl)-5-(trifluoromethyl)pyrimidin-2-yl)amino)cyclohexyl)-1-(5-(2-methoxypyrimidin-5-yl)pyridin-2-yl)urea | | | 637.3 |
| 734 | 1-(trans-4-((4-(4-chloro-1-methyl-1H-pyrazol-3-yl)-5-(difluoromethyl)pyrimidin-2-yl)amino)cyclohexyl)-3-(2,2-difluoroethyl)-1-(5-(2-methoxypyrimidin-5-yl)pyridin-2-yl)urea | | | 649.3 |

TABLE 1-143-continued

| Ex. No. | IUPAC name | structural formula | salt | MS |
|---|---|---|---|---|
| 735 | 2,2-difluoropropyl(trans-4-((4-(4-chloro-1H-pyrazol-3-yl)-5-(trifluoromethyl)-pyrimidin-2-yl)amino)cyclohexyl)(5-(2-methoxypyrimidin-5-yl)pyridin-2-yl)carbamate | | | 668.2 |

TABLE 1-144

| Ex. No. | IUPAC name | structural formula | salt | MS |
|---|---|---|---|---|
| 736 | 2,2-difluoropropyl(trans-4-((4-(4-chloro-1-methyl-1H-pyrazol-3-yl)-5-(trifluoromethyl)pyrimidin-2-yl)amino)cyclohexyl)(5-(2-methoxypyrimidin-5-yl)pyridin-2-yl)carbamate | | | 682.3 |
| 737 | 3-(2,2-difluoroethyl)-1-(trans-4-((4-(1-(difluoromethyl)-1H-pyrazol-3-yl)-5-(trifluoromethyl)pyrimidin-2-yl)amino)cyclohexyl)-1-(5-(2-methoxypyrimidin-5-yl)pyridin-2-yl)urea | | | 669.3 |

TABLE 1-144-continued

| Ex. No. | IUPAC name | structural formula | salt | MS |
|---|---|---|---|---|
| 738 | 3-(2,2-difluoroethyl)-1-(5-(2-methoxypyrimidin-5-yl)pyridin-2-yl)-1-(trans-4-((4-(1H-1,2,3-triazol-1-yl)-5-(trifluoromethyl)pyrimidin-2-yl)amino)cyclohexyl)urea | | | 620.3 |
| 739 | 3-(2,2-difluoroethyl)-1-(5-(2-methoxypyrimidin-5-yl)pyridin-2-yl)-1-(trans-4-((4-(3-methyl-1H-pyrazol-1-yl)-5-(trifluoromethyl)pyrimidin-2-yl)amino)cyclohexyl)urea | | | 633.3 |
| 740 | 1-(trans-4-((4-(4-chloro-1H-pyrazol-3-yl)-5-(trifluoromethyl)pyrimidin-2-yl)amino)cyclohexyl)-3-(2,2-difluoropropyl)-1-(5-(2-methoxypyrimidin-5-yl)pyrazin-2-yl)urea | | | 668.3 |

TABLE 1-144-continued

| Ex. No. | IUPAC name | structural formula | salt | MS |
|---|---|---|---|---|
| 741 | 3-(2,2-difluoroethyl)-1-(trans-4-((4-(5-(methane-sulfonyl)pyridin-3-yl)-5-(trifluoromethyl)pyrimidin-2-yl)amino)cyclohexyl)-1-(5-(2-methoxypyrimidin-5-yl)pyridin-2-yl)urea | | | 708.3 |

TABLE 1-145

| Ex. No. | IUPAC name | structural formula | salt | MS |
|---|---|---|---|---|
| 742 | 1-(trans-4-((4-(4-chloro-1H-pyrazol-3-yl)-5-(trifluoromethyl)pyrimidin-2-yl)amino)cyclohexyl)-3-((1-fluorocyclopropyl)methyl)-1-(5-(2-methoxypyrimidin-5-yl)pyrazin-2-yl)urea | | | 662.3 |
| 743 | 1-(trans-4-((4-(4-chloro-1H-pyrazol-3-yl)-5-(trifluoromethyl)pyrimidin-2-yl)amino)cyclohexyl)-1-(5-(2-methoxypyrimidin-5-yl)pyrazin-2-yl)-3-(2,2,2-trifluoroethyl)urea | | | 672.2 |

| Ex. No. | IUPAC name | structural formula | salt | MS |
|---|---|---|---|---|
| 744 | 1-(trans-4-((4-(4-chloro-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyrazin-2-yl)urea | | | 654.3 |
| 745 | 1-(trans-4-((4-(4-chloro-5-methyl-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyrazin-2-yl)urea | | | 668.3 |
| 746 | N-(trans-4-((4-(4-chloro-1H-pyrazol-3-yl)-5-(trifluoromethyl)pyrimidin-2-yl)amino)cyclohexyl)-3-hydroxy-N-(5-(2-methoxypyrimidin-5-yl)pyrazin-2-yl)-3-methylazetidine-1-carboxamide | | | 660.3 |

TABLE 1-145-continued

| Ex. No. | IUPAC name | structural formula | salt | MS |
|---|---|---|---|---|
| 747 | N-(trans-4-((4-(4-chloro-1H-pyrazol-3-yl)-5-(trifluoromethyl)pyrimidin-2-yl)amino)cyclohexyl)-3,3-difluoro-N-(5-(2-methoxypyrimidin-5-yl)pyrazin-2-yl)pyrrolidine-1-carboxamide | | | 680.3 |

TABLE 1-146

| Ex. No. | IUPAC name | structural formula | salt | MS |
|---|---|---|---|---|
| 748 | 2,2,2-trifluoroethyl(trans-4-((4-(4-chloro-1H-pyrazol-3-yl)-5-(trifluoromethyl)pyrimidin-2-yl)amino)cyclohexyl)(5-(2-methoxypyrimidin-5-yl)pyrazin-2-yl)carbamate | | | 673.2 |
| 749 | 2,2-difluoroethyl(trans-4-((4-(5-(methanesulfonyl)-pyridin-3-yl)-5-(trifluoromethyl)pyrimidin-2-yl)amino)cyclohexyl)(5-(2-methoxypyrimidin-5-yl)pyridin-2-yl)carbamate | | | 709.3 |

TABLE 1-146-continued

| Ex. No. | IUPAC name | structural formula | salt | MS |
|---|---|---|---|---|
| 750 | 2-(dimethylamino)ethyl (trans-4-((4-(4-chloro-1H-pyrazol-3-yl)-5-(trifluoromethyl)pyrimidin-2-yl)amino)cyclohexyl)(5-(2-methoxypyrimidin-5-yl)pyrazin-2-yl)carbamate | | | 662.3 |
| 751 | N-(trans-4-((4-(4-chloro-1H-pyrazol-3-yl)-5-(trifluoro-methyl)pyrimidin-2-yl)amino)-cyclohexyl)-3,3-difluoro-N-(5-(2-methoxypyrimidin-5-yl)pyrazin-2-yl)azetidine-1-carboxamide | | | 666.2 |
| 752 | 1-(trans-4-((4-(4-chloro-1-(difluoromethyl)-1H-pyrazol-3-yl)-5-(trifluoromethyl)-pyrimidin-2-yl)amino)cyclohexyl)-3-(2-methoxyethyl)-1-(5-(2-methoxypyrimidin-5-yl)pyrazin-2-yl)urea | | | 698.3 |

TABLE 1-146-continued

| Ex. No. | IUPAC name | structural formula | salt | MS |
|---|---|---|---|---|
| 753 | 1-(trans-4-((4-(1-(difluoromethyl)-1H-pyrazol-3-yl)-5-(trifluoromethyl)pyrimidin-2-yl)amino)cyclohexyl)-3-(2-methoxyethyl)-1-(5-(2-methoxypyrimidin-5-yl)pyrazin-2-yl)urea | | | 664.3 |

TABLE 1-147

| Ex. No. | IUPAC name | structural formula | salt | MS |
|---|---|---|---|---|
| 754 | 1-(trans-4-((4-(4-chloro-1-(difluoromethyl)-1H-pyrazol-3-yl)-5-(trifluoromethyl)-pyrimidin-2-yl)amino)cyclohexyl)-3-ethyl-1-(5-(2-methoxypyrimidin-5-yl)pyrazin-2-yl)urea | | | 668.3 |
| 755 | 1-(trans-4-((4-(1-(difluoromethyl)-1H-pyrazol-3-yl)-5-(trifluoromethyl)pyrimidin-2-yl)amino)cyclohexyl)-3-ethyl-1-(5-(2-methoxypyrimidin-5-yl)pyrazin-2-yl)urea | | | 634.3 |

TABLE 1-147-continued

| Ex. No. | IUPAC name | structural formula | salt | MS |
|---|---|---|---|---|
| 756 | 1-(trans-4-((4-(4-chloro-1-(difluoromethyl)-1H-pyrazol-3-yl)-5-(trifluoromethyl)-pyrimidin-2-yl)amino)cyclohexyl)-3-(2-methoxyethyl)-1-(5-(1-methyl-1H-pyrazol-4-yl)pyrazin-2-yl)urea | | | 670.3 |
| 757 | 1-(trans-4-((4-(4-chloro-1-(difluoromethyl)-1H-pyrazol-3-yl)-5-(trifluoromethyl)-pyrimidin-2-yl)amino)cyclohexyl)-3-ethyl-1-(5-(1-methyl-1H-pyrazol-4-yl)pyrazin-2-yl)urea | | | 640.3 |
| 758 | 1-(trans-4-((4-(4-chloro-1-(difluoromethyl)-1H-pyrazol-3-yl)-5-(trifluoromethyl)-pyrimidin-2-yl)amino)cyclohexyl)-3-(2,2-difluoroethyl)-1-(5-(1-methyl-1H-pyrazol-4-yl)pyrazin-2-yl)urea | | | 676.2 |
| 759 | 2-methoxyethyl(trans-4-((4-(4-chloro-1H-pyrazol-3-yl)-5-(trifluoromethyl)pyrimidin-2-yl)amino)cyclohexyl)(5-(2-methoxypyrimidin-5-yl)pyrazin-2-yl)carbamate | | | 649.3 |

TABLE 1-148

| Ex. No. | IUPAC name | structural formula | salt | MS |
|---|---|---|---|---|
| 760 | (1-fluorocyclopropyl)methyl (trans-4-((4-(4-chloro-1H-pyrazol-3-yl)-5-(trifluoromethyl)pyrimidin-2-yl)amino)cyclohexyl)(5-(1-methyl-1H-pyrazol-4-yl)pyrazin-2-yl)carbamate | | | 635.3 |
| 761 | (1-fluorocyclopropyl)methyl (trans-4-((4-(5-(methane-sulfonyl)pyridin-3-yl)-5-(trifluoromethyl)pyrimidin-2-yl)amino)cyclohexyl)(5-(2-methoxypyrimidin-5-yl)pyrazin-2-yl)carbamate | | | 718.3 |
| 762 | 1-(trans-4-((4-(4-chloro-1-(difluoromethyl)-1H-pyrazol-3-yl)-5-(trifluoromethyl)-pyrimidin-2-yl)amino)-cyclohexyl)-1-(5-(1-methyl-2-oxo-1,2-dihydropyridin-4-yl)pyrazin-2-yl)-3-(2,2,2-trifluoroethyl)urea | | | 721.2 |
| 763 | 1-(trans-4-((4-(1-(difluoro-methyl)-1H-pyrazol-3-yl)-5-(trifluoromethyl)pyrimidin-2-yl)amino)cyclohexyl)-3-(2-methoxyethyl)-1-(5-(1-methyl-1H-pyrazol-4-yl)pyrazin-2-yl)urea | | | 636.3 |

TABLE 1-148-continued

| Ex. No. | IUPAC name | structural formula | salt | MS |
|---|---|---|---|---|
| 764 | 1-(trans-4-((4-(1-(difluoro-methyl)-1H-pyrazol-3-yl)-5-(trifluoromethyl)pyrimidin-2-yl)amino)cyclohexyl)-3-ethyl-1-(5-(1-methyl-1H-pyrazol-4-yl)pyrazin-2-yl)urea | | | 606.3 |
| 765 | 3-(2,2-difluoroethyl)-1-(trans-4-((4-(1-(difluoro-methyl)-1H-pyrazol-3-yl)-5-(trifluoromethyl)pyrimidin-2-yl)amino)cyclohexyl)-1-(5-(1-methyl-1H-pyrazol-4-yl)pyrazin-2-yl)urea | | | 642.3 |

TABLE 1-149

| Ex. No. | IUPAC name | structural formula | salt | MS |
|---|---|---|---|---|
| 766 | 2,2-difluoroethyl(trans-4-((4-(5-(methanesulfonyl)-pyridin-3-yl)-5-(trifluoromethyl)pyrimidin-2-yl)amino)cyclohexyl)(5-(2-methoxypyrimidin-5-yl)pyrazin-2-yl)carbamate | | | 710.3 |

TABLE 1-149-continued

| Ex. No. | IUPAC name | structural formula | salt | MS |
|---|---|---|---|---|
| 767 | 2-(dimethylamino)ethyl(trans-4-((4-(5-(methanesulfonyl)-pyridin-3-yl)-5-(trifluoromethyl)pyrimidin-2-yl)amino)cyclohexyl)(5-(2-methoxypyrimidin-5-yl)pyrazin-2-yl)carbamate | | | 717.3 |
| 768 | 1-(trans-4-((4-(1-(difluoromethyl)-1H-pyrazol-3-yl)-5-(trifluoromethyl)-pyrimidin-2-yl)amino)-cyclohexyl)-1-(5-(1-methyl-2-oxo-1,2-dihydropyridin-4-yl)-pyrazin-2-yl)-3-(2,2,2-trifluoroethyl)urea | | | 687.3 |
| 769 | (1-fluorocyclopropyl)methyl (trans-4-((4-(4-chloro-1H-pyrazol-3-yl)-5-(trifluoromethyl)pyrimidin-2-yl)amino)-cyclohexyl)(5-(1-methyl-2-oxo-1,2-dihydropyridin-4-yl)-pyrazin-2-yl)carbamate | | | 662.2 |
| 770 | (1-fluorocyclopropyl)methyl (trans-4-((4-(4-chloro-5-methyl-1H-pyrazol-3-yl)-5-(trifluoromethyl)pyrimidin-2-yl)amino)cyclohexyl)(5-(1-methyl-2-oxo-1,2-dihydropyridin-4-yl)-pyrazin-2-yl)carbamate | | | 676.3 |

TABLE 1-149-continued

| Ex. No. | IUPAC name | structural formula | salt | MS |
|---|---|---|---|---|
| 771 | N-(trans-4-((4-(4-chloro-1H-pyrazol-3-yl)-5-(trifluoromethyl)pyrimidin-2-yl)amino)cyclohexyl)-3-fluoro-N-(5-(2-methoxypyrimidin-5-yl)pyrazin-2-yl)azetidine-1-carboxamide | | | 648.3 |

TABLE 1-150

| Ex. No. | IUPAC name | structural formula | salt | MS |
|---|---|---|---|---|
| 772 | N-(trans-4-((4-(4-chloro-1H-pyrazol-3-yl)-5-(trifluoromethyl)pyrimidin-2-yl)amino)cyclohexyl)-N-(5-(2-methoxypyrimidin-5-yl)pyrazin-2-yl)azetidine-1-carboxamide | | | 630.3 |
| 773 | N-(trans-4-((4-(4-chloro-1H-pyrazol-3-yl)-5-(trifluoromethyl)pyrimidin-2-yl)amino)-cyclohexyl)-3-methoxy-N-(5-(2-methoxypyrimidin-5-yl)pyrazin-2-yl)azetidine-1-carboxamide | | | 660.3 |

TABLE 1-150-continued

| Ex. No. | IUPAC name | structural formula | salt | MS |
|---|---|---|---|---|
| 774 | 1-(trans-4-((4-(4-chloro-1H-pyrazol-3-yl)-5-(trifluoromethyl)pyrimidin-2-yl)amino)cyclohexyl)-1-(5-(1,3-dimethyl-1H-pyrazol-4-yl)pyrazin-2-yl)-3-(2,2,2-trifluoroethyl)urea | | | 658.3 |
| 775 | 3-(2-methoxyethyl)-1-(5-(2-methoxypyrimidin-5-yl)pyrazin-2-yl)-1-(trans-4-((4-((3-methyloxetan-3-yl)oxy)-5-(trifluoromethyl)pyrimidin-2-yl)amino)cyclohexyl)urea | | | 634.3 |
| 776 | 3-ethyl-1-(5-(2-methoxypyrimidin-5-yl)pyrazin-2-yl)-1-(trans-4-((4-((3-methyloxetan-3-yl)oxy)-5-(trifluoromethyl)pyrimidin-2-yl)amino)cyclohexyl)urea | | | 604.3 |
| 777 | 3-(2,2-difluoroethyl)-1-(5-(2-methoxypyrimidin-5-yl)pyrazin-2-yl)-1-(trans-4-((4-((3-methyloxetan-3-yl)oxy)-5-(trifluoromethyl)pyrimidin-2-yl)amino)cyclohexyl)urea | | | 640.3 |

TABLE 1-151

| Ex. No. | IUPAC name | structural formula | salt | MS |
|---|---|---|---|---|
| 778 | 1-(trans-4-((4-(4-chloro-1H-pyrazol-3-yl)-5-(trifluoro-methyl)pyrimidin-2-yl)amino)-cyclohexyl)-1-(5-(2-ethoxy-pyrimidin-5-yl)pyrazin-2-yl)-3-(2,2,2-trifluoroethyl)urea | | | 686.3 |
| 779 | 1-(trans-4-((4-(4-chloro-1H-pyrazol-3-yl)-5-(trifluoro-methyl)pyrimidin-2-yl)amino)-cyclohexyl)-1-(5-(6-methoxy-pyridin-3-yl)-pyrazin-2-yl)-3-(2,2,2-trifluoroethyl)urea | | | 671.2 |
| 780 | 1-(trans-4-((4-(4-chloro-1H-pyrazol-3-yl)-5-(trifluoro-methyl)pyrimidin-2-yl)amino)-cyclohexyl)-1-(5-(pyrimidin-5-yl)pyrazin-2-yl)-3-(2,2,2-trifluoroethyl)urea | | | 642.2 |

TABLE 1-151-continued

| Ex. No. | IUPAC name | structural formula | salt | MS |
|---|---|---|---|---|
| 781 | 1-(trans-4-((4-(4-chloro-1H-pyrazol-3-yl)-5-(trifluoromethyl)pyrimidin-2-yl)amino)cyclohexyl)-1-(5-(1-cyclopropyl-1H-pyrazol-4-yl)pyrazin-2-yl)-3-(2,2,2-trifluoroethyl)urea | | | 670.3 |
| 782 | 1-(trans-4-((4-(4-chloro-1H-pyrazol-3-yl)-5-(trifluoromethyl)pyrimidin-2-yl)amino)cyclohexyl)-1-(5-(1,5-dimethyl-1H-pyrazol-4-yl)pyrazin-2-yl)-3-(2,2,2-trifluoroethyl)urea | | | 658.2 |
| 783 | 1-(trans-4-((4-(4-chloro-1H-pyrazol-3-yl)-5-(trifluoromethyl)pyrimidin-2-yl)amino)cyclohexyl)-1-(5-(1-(propan-2-yl)-1H-pyrazol-4-yl)pyrazin-2-yl)-3-(2,2,2-trifluoroethyl)urea | | | 672.3 |

TABLE 1-152

| Ex. No. | IUPAC name | structural formula | salt | MS |
|---|---|---|---|---|
| 784 | 1-(trans-4-((4-(4-chloro-1H-pyrazol-3-yl)-5-(trifluoromethyl)pyrimidin-2-yl)amino)cyclohexyl)-1-(5-(1-(cyclopropylmethyl)-1H-pyrazol-4-yl)pyrazin-2-yl)-3-(2,2,2-trifluoroethyl)urea | | | 684.3 |
| 785 | 1-(trans-4-((4-(4-chloro-1H-pyrazol-3-yl)-5-(trifluoromethyl)pyrimidin-2-yl)amino)cyclohexyl)-1-(5-(1-ethyl-1H-pyrazol-4-yl)pyrazin-2-yl)-3-(2,2,2-trifluoroethyl)urea | | | 658.2 |
| 786 | 1-(trans-4-((4-(4-chloro-1H-pyrazol-3-yl)-5-(trifluoromethyl)pyrimidin-2-yl)amino)cyclohexyl)-1-(5-(1-(oxan-4-yl)-1H-pyrazol-4-yl)pyrazin-2-yl)-3-(2,2,2-trifluoroethyl)urea | | | 714.3 |

TABLE 1-152-continued

| Ex. No. | IUPAC name | structural formula | salt | MS |
|---|---|---|---|---|
| 787 | 1-(trans-4-((4-(4-chloro-1H-pyrazol-3-yl)-5-(trifluoromethyl)pyrimidin-2-yl)amino)cyclohexyl)-1-(5-(1-(2-methylpropyl)-1H-pyrazol-4-yl)pyrazin-2-yl)-3-(2,2,2-trifluoroethyl)urea | | | 708.3 |
| 788 | 1-(trans-4-((4-(4-chloro-1H-pyrazol-3-yl)-5-(trifluoromethyl)pyrimidin-2-yl)amino)cyclohexyl)-1-(5-(1-methyl-1H-pyrazol-3-yl)pyrazin-2-yl)-3-(2,2,2-trifluoroethyl)urea | | | 666.2 |
| 789 | 1-(5-(2-aminopyrimidin-5-yl)pyrazin-2-yl)-1-(trans-4-((4-(4-chloro-1H-pyrazol-3-yl)-5-(trifluoromethyl)pyrimidin-2-yl)amino)cyclohexyl)-3-(2,2,2-trifluoroethyl)urea | | | 657.2 |

TABLE 1-153

| Ex. No. | IUPAC name | structural formula | salt | MS |
|---|---|---|---|---|
| 790 | 1-(trans-4-((4-(4-chloro-1H-pyrazol-3-yl)-5-(trifluoromethyl)pyrimidin-2-yl)amino)cyclohexyl)-1-(5-(1-(difluoromethyl)-1H-pyrazol-3-yl)pyrazin-2-yl)-3-(2,2,2-trifluoroethyl)urea | | | 702.2 |
| 791 | 1-(trans-4-((4-(4-chloro-1H-pyrazol-3-yl)-5-(trifluoromethyl)pyrimidin-2-yl)amino)cyclohexyl)-1-(5-(1-(difluoromethyl)-1H-pyrazol-4-yl)pyrazin-2-yl)-3-(2,2,2-trifluoroethyl)urea | | | 680.2 |
| 792 | 1-(trans-4-((4-(4-chloro-1-(difluoromethyl)-1H-pyrazol-3-yl)-5-(trifluoromethyl)-pyrimidin-2-yl)amino)-cyclohexyl)-1-(5-(1-methyl-1H-pyrazol-4-yl)pyrazin-2-yl)-3-(2,2,2-trifluoroethyl)urea | | | 694.3 |
| 793 | 1-(trans-4-((4-(1-(difluoromethyl)-1H-pyrazol-3-yl)-5-(trifluoromethyl)-pyrimidin-2-yl)amino)-cyclohexyl)-1-(5-(1-methyl-1H-pyrazol-4-yl)pyrazin-2-yl)-3-(2,2,2-trifluoroethyl)urea | | | 660.3 |

TABLE 1-153-continued

| Ex. No. | IUPAC name | structural formula | salt | MS |
|---|---|---|---|---|
| 794 | 3-(2,2-difluoroethyl)-1-(5-(2-methoxypyrimidin-5-yl)pyrazin-2-yl)-1-(trans-4-((4-((oxetan-3-yl)oxy)-5-(trifluoromethyl)pyrimidin-2-yl)amino)cyclohexyl)urea | | | 626.3 |
| 795 | 3-(2,2-difluoroethyl)-1-(5-(2-methoxypyrimidin-5-yl)pyridin-2-yl)-1-(trans-4-((4-((oxetan-3-yl)oxy)-5-(trifluoromethyl)pyrimidin-2-yl)amino)cyclohexyl)urea | | | 625.3 |

TABLE 1-154

| Ex. No. | IUPAC name | structural formula | salt | MS |
|---|---|---|---|---|
| 796 | N-(trans-4-((4-(4-chloro-1H-pyrazol-3-yl)-5-(trifluoromethyl)pyrimidin-2-yl)amino)cyclohexyl)-2-methoxy-N-(5-(2-methoxypyrimidin-5-yl)pyrazin-2-yl)acetamide | | | 619.3 |

TABLE 1-154-continued

| Ex. No. | IUPAC name | structural formula | salt | MS |
|---|---|---|---|---|
| 797 | N-(trans-4-((4-(1-(difluoro-methyl)-1H-pyrazol-3-yl)-5-(trifluoromethyl)pyrimidin-2-yl)amino)cyclohexyl)-2-methoxy-N-(5-(2-methoxypyrimidin-5-yl)pyrazin-2-yl)acetamide | | | 635.3 |
| 798 | N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)butanamide | | | 672.3 |
| 799 | 3-ethyl-1-(trans-4-((4-(5-(methanesulfonyl)pyridin-3-yl)-5-(trifluoromethyl)pyrimidin-2-yl)amino)cyclohexyl)-1-(5-(2-methoxypyrimidin-5-yl)pyrazin-2-yl)urea | | | 673.3 |

TABLE 1-154-continued

| Ex. No. | IUPAC name | structural formula | salt | MS |
|---|---|---|---|---|
| 800 | 2-methoxyethyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate | | | 704.2 |
| 801 | ethyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate | | | 674.3 |

TABLE 1-155

| Ex. No. | IUPAC name | structural formula | salt | MS |
|---|---|---|---|---|
| 802 | 3-((1-aminocyclopropyl)methyl)-1-(trans-4-((4-(1-(difluoromethyl)-1H-pyrazol-3-yl)-5-(trifluoromethyl)pyrimidin-2-yl)amino)cyclohexyl)-1-(5-(2-methoxypyrimidin-5-yl)pyrazin-2-yl)urea | | | 675.4 |

TABLE 1-155-continued

| Ex. No. | IUPAC name | structural formula | salt | MS |
|---|---|---|---|---|
| 803 | (1-aminocyclopropyl)methyl (trans-4-((4-(1-(difluoromethyl)-1H-pyrazol-3-yl)-5-(trifluoromethyl)pyrimidin-2-yl)amino)cyclohexyl) (5-(2-methoxypyrimidin-5-yl)pyrazin-2-yl)carbamate | | | 676.3 |
| 804 | 1-(trans-4-((4-(1-(difluoromethyl)-1H-pyrazol-3-yl)-5-(trifluoromethyl)-pyrimidin-2-yl)amino)cyclohexyl)-3-(2-hydroxy-2-methylpropyl)-1-(5-(2-methoxypyrimidin-5-yl)pyrazin-2-yl)urea | | | 678.3 |
| 805 | 1-(trans-4-((4-(1-(difluoromethyl)-1H-pyrazol-3-yl)-5-(trifluoromethyl)pyrimidin-2-yl)amino)cyclohexyl)-1-(5-(2-methoxypyrimidin-5-yl)pyrazin-2-yl)-3-((oxetan-3-yl)methyl)urea | | | 676.3 |

TABLE 1-155-continued

| Ex. No. | IUPAC name | structural formula | salt | MS |
|---|---|---|---|---|
| 806 | 3-(2,2-difluoroethyl)-1-(5-(1-methyl-1H-pyrazol-4-yl)pyrazin-2-yl)-1-(trans-4-((4-((oxetan-3-yl)oxy)-5-(trifluoromethyl)pyrimidin-2-yl)amino)cyclohexyl)urea | | | 598.3 |
| 807 | 3-(3,3-difluorocyclobutyl)-1-(trans-4-((4-(5-(methane-sulfonyl)pyridin-3-yl)-5-(trifluoromethyl)pyrimidin-2-yl)amino)cyclohexyl)-1-(5-(2-methoxypyrimidin-5-yl)pyrazin-2-yl)urea | | | 735.3 |

TABLE 1-156

| Ex. No. | IUPAC name | structural formula | salt | MS |
|---|---|---|---|---|
| 808 | 2-(morpholin-4-yl)ethyl (trans-4-((4-(5-(methanesulfonyl)-pyridin-3-yl)-5-(trifluoro-methyl)pyrimidin-2-yl)amino)cyclohexyl) (5-(2-methoxypyrimidin-5-yl)pyrazin-2-yl)carbamate | | | 759.4 |

TABLE 1-156-continued

| Ex. No. | IUPAC name | structural formula | salt | MS |
|---|---|---|---|---|
| 809 | 2,2-difluoroethyl (5-(1-methyl-1H-pyrazol-3-yl)-pyrazin-2-yl) (trans-4-((4-((oxetan-3-yl)oxy)-5-(trifluoromethyl)pyrimidin-2-yl)amino)cyclohexyl)carbamate | | | 599.3 |
| 810 | 2,2-difluoroethyl (5-(1-(oxan-4-yl)-1H-pyrazol-4-yl)pyrazin-2-yl)(trans-4-((4-((oxetan-3-yl)oxy)-5-(trifluoromethyl)pyrimidin-2-yl)amino)cyclohexyl)carbamate | | | 669.3 |
| 811 | N-(trans-4-((4-(1-(difluoromethyl)-1H-pyrazol-3-yl)-5-(trifluoromethyl)pyrimidin-2-yl)amino)cyclohexyl)-2-methoxy-N-(5-(1-methyl-1H-pyrazol-4-yl)pyrazin-2-yl)acetamide | | | 607.3 |

TABLE 1-156-continued

| Ex. No. | IUPAC name | structural formula | salt | MS |
|---|---|---|---|---|
| 812 | N-(trans-4-((4-(5-(methanesulfonyl)pyridin-3-yl)-5-(trifluoromethyl)pyrimidin-2-yl)amino)cyclohexyl)-2-methoxy-N-(5-(1-methyl-1H-pyrazol-4-yl)pyrazin-2-yl)acetamide | | | 646.3 |
| 813 | N-(trans-4-((4-(4-chloro-1H-pyrazol-3-yl)-5-(trifluoromethyl)pyrimidin-2-yl)amino)cyclohexyl)-N-(5-(1-methyl-1H-pyrazol-4-yl)pyrazin-2-yl)butanamide | | | 589.2 |

TABLE 1-157

| Ex. No. | IUPAC name | structural formula | salt | MS |
|---|---|---|---|---|
| 814 | N-(trans-4-((4-(5-(methanesulfonyl)pyridin-3-yl)-5-(trifluoromethyl)pyrimidin-2-yl)amino)cyclohexyl)-N-(5-(1-methyl-1H-pyrazol-4-yl)pyrazin-2-yl)butanamide | | | 644.3 |

TABLE 1-157-continued

| Ex. No. | IUPAC name | structural formula | salt | MS |
|---|---|---|---|---|
| 815 | 2-methoxy-N-(5-(1-methyl-1H-pyrazol-4-yl)pyrazin-2-yl)-N-(trans-4-((4-((oxetan-3-yl)oxy)-5-(trifluoromethyl)pyrimidin-2-yl)amino)cyclohexyl)acetamide | | | 563.3 |
| 816 | N-(5-(1-methyl-1H-pyrazol-4-yl)pyrazin-2-yl)-N-(trans-4-((4-((oxetan-3-yl)oxy)-5-(trifluoromethyl)pyrimidin-2-yl)amino)cyclohexyl)butanamide | | | 561.3 |
| 817 | N-(trans-4-((4-(5-(methanesulfonyl)pyridin-3-yl)-5-(trifluoromethyl)pyrimidin-2-yl)amino)cyclohexyl)-2-methoxy-N-(5-(2-methoxypyrimidin-5-yl)pyrazin-2-yl)acetamide | | | 674.3 |
| 818 | N-(trans-4-((4-(4-chloro-1H-pyrazol-3-yl)-5-(trifluoromethyl)pyrimidin-2-yl)amino)cyclohexyl)-N-(5-(2-methoxypyrimidin-5-yl)pyrazin-2-yl)butanamide | | | 617.3 |

TABLE 1-157-continued

| Ex. No. | IUPAC name | structural formula | salt | MS |
|---|---|---|---|---|
| 819 | 2,2-difluoroethyl (5-(1-methyl-1H-pyrazol-4-yl)pyrazin-2-yl)(trans-4-((4-((oxetan-3-yl)oxy)-5-(trifluoromethyl)pyrimidin-2-yl)amino)cyclohexyl)carbamate | | | 599.3 |

TABLE 1-158

| Ex. No. | IUPAC name | structural formula | salt | MS |
|---|---|---|---|---|
| 820 | 2,2-difluoroethyl (trans-4-((4-(5-(methanesulfonyl)-pyridin-3-yl)-5-(trifluoromethyl)pyrimidin-2-yl)amino)cyclohexyl) (5-(1-methyl-1H-pyrazol-4-yl)pyrazin-2-yl)carbamate | | | 682.2 |
| 821 | 2,2-difluoroethyl (trans-4-((4-(5-(methanesulfonyl)-pyridin-3-yl)-5-(trifluoromethyl)pyrimidin-2-yl)amino)cyclohexyl)(5-(1-(oxan-4-yl)-1H-pyrazol-4-yl)pyrazin-2-yl)carbamate | | | 752.3 |

TABLE 1-158-continued

| Ex. No. | IUPAC name | structural formula | salt | MS |
|---|---|---|---|---|
| 822 | 2,2-difluoroethyl (trans-4-((4-(5-(methanesulfonyl)-pyridin-3-yl)-5-(trifluoromethyl)pyrimidin-2-yl)amino)cyclohexyl) (5-(1-methyl-1H-pyrazol-3-yl)-pyrazin-2-yl)carbamate | | | 682.2 |
| 823 | 1-(trans-4-((4-(1-(difluoromethyl)-1H-pyrazol-3-yl)-5-(trifluoromethyl)pyrimidin-2-yl)amino)cyclohexyl)-3-(2,2-difluoropropyl)-1-(5-(1-methyl-1H-pyrazol-4-yl)pyrazin-2-yl)urea | | | 656.3 |
| 824 | 3-cyclopropyl-1-(trans-4-((4-(1-(difluoromethyl)-1H-pyrazol-3-yl)-5-(trifluoromethyl)pyrimidin-2-yl)amino)cyclohexyl)-1-(5-(1-methyl-1H-pyrazol-4-yl)pyrazin-2-yl)urea | | | 618.3 |
| 825 | 1-(trans-4-((4-(1-(difluoromethyl)-1H-pyrazol-3-yl)-5-(trifluoromethyl)-pyrimidin-2-yl)amino)-cyclohexyl)-1-(5-(1-methyl-1H-pyrazol-4-yl)pyrazin-2-yl)-3-propylurea | | | 620.3 |

TABLE 1-159

| Ex. No. | IUPAC name | structural formula | salt | MS |
|---|---|---|---|---|
| 826 | 4,4-difluoro-N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)butanamide | | | 708.3 |
| 827 | 2-ethoxy-N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)acetamide | | | 688.3 |
| 828 | N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)propanamide | | | 658.4 |

TABLE 1-159-continued

| Ex. No. | IUPAC name | structural formula | salt | MS |
|---|---|---|---|---|
| 829 | 4,4-difluoro-N-(trans-4-((4-(5-(methanesulfonyl)pyridin-3-yl)-5-(trifluoromethyl)pyrimidin-2-yl)amino)cyclohexyl)-N-(5-(1-methyl-1H-pyrazol-4-yl)pyrazin-2-yl)butanamide | | | 680.3 |
| 830 | N-(trans-4-((4-(5-(methane-sulfonyl)pyridin-3-yl)-5-(trifluoromethyl)pyrimidin-2-yl)amino)cyclohexyl)-3-methyl-N-(5-(1-methyl-1H-pyrazol-4-yl)pyrazin-2-yl)butanamide | | | 658.3 |
| 831 | 2-ethoxy-N-(trans-4-((4-(5-(methanesulfonyl)pyridin-3-yl)-5-(trifluoromethyl)pyrimidin-2-yl)amino)cyclohexyl)-N-(5-(1-methyl-1H-pyrazol-4-yl)pyrazin-2-yl)acetamide | | | 660.3 |

TABLE 1-160

| Ex. No. | IUPAC name | structural formula | salt | MS |
|---|---|---|---|---|
| 832 | N-(trans-4-((4-(5-(methanesulfonyl)pyridin-3-yl)-5-(trifluoromethyl)pyrimidin-2-yl)amino)cyclohexyl)-N-(5-(1-methyl-1H-pyrazol-4-yl)pyrazin-2-yl)pentanamide | | | 658.3 |
| 833 | 2-cyclopropyl-N-(trans-4-((4-(5-(methanesulfonyl)pyridin-3-yl)-5-(trifluoromethyl)-2-yl)amino)cyclohexyl)-N-(5-(1-methyl-1H-pyrazol-4-yl)pyrazin-2-yl)acetamide | | | 656 3 |
| 834 | 2-(dimethylamino)-2-methylpropyl (trans-4-((4-(5-(methanesulfonyl)pyridin-3-yl)-5-(trifluoromethyl)pyrimidin-2-yl)amino)cyclohexyl)(5-(2-methoxypyrimidin-5-yl)pyrazin-2-yl)carbamate | | | 745.4 |

TABLE 1-160-continued

| Ex. No. | IUPAC name | structural formula | salt | MS |
|---|---|---|---|---|
| 835 | 3-(2,2-difluoropropyl)-1-(trans-4-((4-(5-(methanesulfonyl)pyridin-3-yl)-5-(trifluoromethyl)pyrimidin-2-yl)amino)cyclohexyl)-1-(5-(2-methoxypyrimidin-5-yl)pyrazin-2-yl)urea | | | 723.3 |
| 836 | 2-hydroxy-2-methylpropyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate | | | 718.3 |
| 837 | 2-(azetidin-1-yl)ethyl (trans-4-((4-(5-(methanesulfonyl)pyridin-3-yl)-5-(trifluoromethyl)pyrimidin-2-yl)amino)cyclohexyl)(5-(2-methoxypyrimidin-5-yl)pyrazin-2-yl)carbamate | | | 729.3 |

TABLE 1-161

| Ex. No. | IUPAC name | structural formula | salt | MS |
|---|---|---|---|---|
| 838 | 2-hydroxy-2-methylpropyl (trans-4-((4-(5-(methanesulfonyl)pyridin-3-yl)-5-(trifluoromethyl)pyrimidin-2-yl)amino)cyclohexyl) (5-(1-methyl-1H-pyrazol-4-yl)pyrazin-2-yl)carbamate | | | 690.3 |
| 839 | 2-hydroxy-2-methylpropyl (trans-4-((4-(1-(difluoromethyl)-1H-pyrazol-3-yl)-5-(trifluoromethyl)pyrimidin-2-yl)amino)cyclohexyl) (5-(1-methyl-1H-pyrazol-4-yl)pyrazin-2-yl)carbamate | | | 651.3 |
| 840 | 2-hydroxy-2-methylpropyl (trans-4-((4-(1-(difluoromethyl)-1H-pyrazol-3-yl)-5-(trifluoromethyl)pyrimidin-2-yl)amino)cyclohexyl) (5-(2-methoxypyrimidin-5-yl)pyrazin-2-yl)carbamate | | | 679.3 |
| 841 | 2-hydroxy-2-methylpropyl (trans-4-((4-(4-chloro-1H-pyrazol-3-yl)-5-(trifluoromethyl)pyrimidin-2-yl)amino)cyclohexyl) (5-(2-methoxypyrimidin-5-yl)pyrazin-2-yl)carbamate | | | 663.3 |

TABLE 1-161-continued

| Ex. No. | IUPAC name | structural formula | salt | MS |
|---|---|---|---|---|
| 842 | 2-(3,3-difluoroazetidin-1-yl)ethyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate | | | 765.3 |
| 843 | 2-cyclopropyl-N-(trans-4-((4-(5-(methanesulfonyl)pyridin-3-yl)-5-(trifluoromethyl)-pyrimidin-2-yl)amino)cyclohexyl)-N-(5-(2-methoxypyrimidin-5-yl)pyrazin-2-yl)acetamide | | | 684.3 |

TABLE 1-162

| Ex. No. | IUPAC name | structural formula | salt | MS |
|---|---|---|---|---|
| 844 | (1-aminocyclopropyl)methyl (trans-4-((4-(5-(methanesulfonyl)pyridin-3-yl)-5-(trifluoromethyl)pyrimidin-2-yl)amino)cyclohexyl)(5-(2-methoxypyrimidin-5-yl)pyrazin-2-yl)carbamate | | | 715.3 |

TABLE 1-162-continued

| Ex. No. | IUPAC name | structural formula | salt | MS |
|---|---|---|---|---|
| 845 | propan-2-yl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate | | | 688.3 |
| 846 | 1-(trans-4-((4-(5-(methanesulfonyl)pyridin-3-yl)-5-(trifluoromethyl)pyrimidin-2-yl)amino)cyclohexyl)-1-(5-(2-methoxypyrimidin-5-yl)pyrazin-2-yl)-3-(2,2,2-trifluoroethyl)urea | | | 727.3 |
| 847 | ethyl (trans-4-((4-(5-(methane-sulfonyl)pyridin-3-yl)-5-(trifluoromethyl)pyrimidin-2-yl)amino)cyclohexyl) (5-(2-methoxypyrimidin-5-yl)pyridin-2-yl)carbamate | | | 673.3 |

TABLE 1-162-continued

| Ex. No. | IUPAC name | structural formula | salt | MS |
|---|---|---|---|---|
| 848 | 2-(dimethylamino) ethyl (trans-4-((4-(5-(methanesulfonyl)pyridin-3-yl)-5-(trifluoromethyl)-pyrimidin-2-yl)amino) cyclohexyl) (5-(2-methoxypyrimidin-5-yl)pyridin-2-yl)carbamate | | | 716.3 |
| 849 | 1-(trans-4-((4-(1-(difluoromethyl)-1H-pyrazol-3-yl)-5-(trifluoromethyl)pyrimidin-2-yl)amino)cyclohexyl)-3-(2-hydroxy-2-methylpropyl)-1-(5-(2-methoxypyrimidin-5-yl)pyridin-2-yl)urea | | | 677.3 |

TABLE 1-163

| Ex. No. | IUPAC name | structural formula | salt | MS |
|---|---|---|---|---|
| 850 | 1-(trans-4-((4-(1-(difluoro-methyl)-1H-pyrazol-3-yl)-5-(trifluoromethyl)pyrimidin-2-yl)amino)cyclohexyl)-1-(5-(2-methoxypyrimidin-5-yl)pyridin-2-yl)-3-propylurea | | | 647.3 |

TABLE 1-163-continued

| Ex. No. | IUPAC name | structural formula | salt | MS |
|---|---|---|---|---|
| 851 | 3-cyclopropyl-1-(trans-4-((4-(1-(difluoromethyl)-1H-pyrazol-3-yl)-5-(trifluoromethyl)-pyrimidin-2-yl)amino)cyclohexyl)-1-(5-(2-methoxy-pyrimidin-5-yl)pyridin-2-yl)urea | | | 645.3 |
| 852 | 1-(trans-4-((4-(1-(difluoromethyl)-1H-pyrazol-3-(trifluoromethyl)pyrimidin-2-yl)amino)cyclohexyl)-1-(5-(2-methoxypyrimidin-5-yl)pyridin-2-yl)-3-propan-2-ylurea | | | 647.3 |
| 853 | propan-2-yl (trans-4-((4-(5-(methanesulfonyl)pyridin-3-yl)-5-(trifluoromethyl)pyrimidin-2-yl)amino)cyclohexyl)(5-(2-methoxypyrimidin-5-yl)pyridin-2-yl)carbamate | | | 687.3 |

TABLE 1-163-continued

| Ex. No. | IUPAC name | structural formula | salt | MS |
|---|---|---|---|---|
| 854 | (1-fluorocyclopropyl)methyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyridin-2-yl)carbamate | | | 717.3 |
| 855 | 2-methoxyethyl (trans-4-((4-(5-(methanesulfonyl)pyridin-3-yl)-5-(trifluoromethyl)pyrimidin-2-yl)amino)cyclohexyl)(5-(2-methoxypyrimidin-5-yl)pyridin-2-yl)carbamate | | | 703.3 |

TABLE 1-164

| Ex. No. | IUPAC name | structural formula | salt | MS |
|---|---|---|---|---|
| 856 | N-(5-(2-methoxypyrimidin-5-yl)pyrazin-2-yl)-N-(trans-4-((4-(1H-pyrazol-3-yl)-5-(trifluoromethyl)pyrimidin-2-yl)amino)cyclohexyl)butanamide | | | 583.3 |

TABLE 1-164-continued

| Ex. No. | IUPAC name | structural formula | salt | MS |
|---|---|---|---|---|
| 857 | N-(5-(2-methoxypyrimidin-5-yl)pyridin-2-yl)-N-(trans-4-((4-(1H-pyrazol-3-yl)-5-(trifluoromethyl)pyrimidin-2-yl)amino)cyclohexyl)butanamide | | | 582.4 |
| 858 | N-(trans-4-((4-(5-(methane-sulfonyl)pyridin-3-yl)-5-(trifluoromethyl)pyrimidin-2-yl)amino)cyclohexyl)-N-(5-(2-methoxypyrimidin-5-yl)pyridin-2-yl)butanamide | | | 671.3 |

TABLE 2-1

| Ref. Ex. No. | IUPAC name | structural formula | salt | MS |
|---|---|---|---|---|
| 1 | cyclopropyl (trans-4-((4-(4-chloro-1H-pyrazol-3-yl)-5-cyanopyrimidin-2-yl)amino)cyclohexyl) (5-(2-methoxypyrimidin-5-yl)pyrazin-2-yl)carbamate | | | 588.2 |

TABLE 2-1-continued

| Ref. Ex. No. | IUPAC name | structural formula | salt | MS |
|---|---|---|---|---|
| 2 | N-(trans-4-((4-(5-(methanesulfonyl)pyridin-3-yl)-5-(trifluoromethyl)-pyrimidin-2-yl)amino)cyclohexyl)-N-(5-(2-methoxypyrimidin-5-yl)pyrazin-2-yl)cyclo-propanecarboxamide | | | 670.3 |
| 3 | cyclopropyl (trans-4-((4-(5-(methanesulfonyl)-pyridin-3-yl)-5-(trifluoromethyl)-pyrimidin-2-yl)amino)cyclohexyl) (5-(1-methyl-1H-pyrazol-4-yl)pyrazin-2-yl)carbamate | | | 658.3 |
| 4 | cyclopropyl (trans-4-((4-(5-(methanesulfonyl)pyridin-3-yl)-5-(trifluoromethyl)-pyrimidin-2-yl)amino)cyclohexyl) (5-(2-methoxypyrimidin-5-yl)pyridin-2-yl)carbamate | | | 685.3 |
| 5 | 1-(5-(2-methoxypyrimidin-5-yl)pyrazin-2-yl)-1-(trans-4-((4-((oxetan-3-yl)oxy)-5-(trifluoromethyl)pyrimidin-2-yl)amino)cyclohexyl)urea | | | 562.2 |

TABLE 2-1-continued

| Ref. Ex. No. | IUPAC name | structural formula | salt | MS |
|---|---|---|---|---|
| 6 | 3,3-difluorocyclobutyl (trans-4-((4-(4-chloro-1H-pyrazol-3-yl)-5-cyanopyrimidin-2-yl)amino)cyclohexyl) (5-(2-methoxypyrimidin-5-yl)pyridin-2-yl)carbamate | | | 637.2 |

TABLE 2-2

| Ref. Ex. No. | IUPAC name | structural formula | salt | MS |
|---|---|---|---|---|
| 7 | 3,3-difluorocyclobutyl (trans-4-((4-(5-(methanesulfonyl)pyridin-3-yl)-5-(trifluoromethyl)-pyrimidin-2-yl)amino)cyclohexyl) (5-(2-methoxypyrimidin-5-yl)pyrazin-2-yl)carbamate | | | 736.3 |
| 8 | cyclopropyl (trans-4-((4-(5-(methanesulfonyl)pyridin-3-yl)-5-(trifluoromethyl)pyrimidin-2-yl)amino)cyclohexyl) (5-(2-methoxypyrimidin-5-yl)pyrazin-2-yl)carbamate | | | 686.3 |

TABLE 2-2-continued

| Ref. Ex. No. | IUPAC name | structural formula | salt | MS |
|---|---|---|---|---|
| 9 | 3,3-difluorocyclobutyl (trans-4-((4-(5-(methanesulfonyl)pyridin-3-yl)-5-(trifluoromethyl)-pyrimidin-2-yl)amino)-cyclohexyl) (5-(2-methoxypyrimidin-5-yl)pyridin-2-yl)carbamate | | | 735.3 |
| 10 | 3-benzyl-1-(trans-4-((5-cyano-2-(oxetan-3-yloxy)pyrimidin-4-yl)amino)cyclohexyl)-1-(5-(1-methyl-1H-pyrazol-4-yl)pyridin-2-yl)urea | | | 580.4 |

Experimental Example 1: CDK12 Binding Assay (1) Synthesis of BODIPY-FL-Labeled AT-7519

To a mixture of 4-((2,6-dichlorobenzoyl)amino)-N-(piperidin-4-yl)-1H-pyrazole-3-carboxamide (AT-7519) (14.92 mg), (3-(2-((3,5-dimethyl-1H-pyrrol-2-yl-kappa-N)methylene)-2H-pyrrol-5-yl-kappa-N)propanoate) (difluoro)boron (9.5 mg), HATU (16.08 mg) and DMF (0.5 mL) was added DIPEA (0.017 mL) at room temperature, and the mixture was stirred at room temperature overnight. The mixture was purified by HPLC (water/acetonitrile, 0.1% TFA addition-based). The obtained fraction was neutralized with saturated aqueous sodium hydrogen carbonate solution, and extracted with ethyl acetate. The organic layer was separated, dried over magnesium sulfate and concentrated under reduced pressure. The obtained residue was passed through a silica gel short column (methanol/ethyl acetate), and the filtrate was concentrated under reduced pressure. The obtained solid was washed with ethyl acetate/heptane (1/1) to give (4-((2,6-dichlorobenzoyl)amino)-N-(1-(3-(2-((3,5-dimethyl-1H-pyrrol-2-yl-kappa-N)methylene)-2H-pyrrol-5-yl-kappa-N)propanoyl)piperidin-4-yl)-1H-pyrazole-3-carboxamidate) (difluoro)boron (BODIPY-FL-labeled AT-7519) (14 mg).

(2) Confirmation of Binding of CDK12 and BODIPY-FL-Labeled AT-by TR-FRET

Various concentrations of BODIPY-FL-labeled AT-7519 was added to an assay buffer (50 mM Hepes (pH 7.2-7.5), 10 mM MgCl$_2$, 1 mM EGTA, 0.01% Brij-35, 0.1 mM DTT) supplemented with His-tagged CDK12/CycK complex, terbium-labeled streptavidin (Cisbio) and biotin-labeled anti-histidine antibody (Thermo Fisher Scientific). The final concentration of CDK12/CycK complex, terbium-labeled streptavidin and biotin-labeled anti-histidine antibody was set to 2.5 nM, 0.2 nM, and 0.4 nM, respectively. After standing same for 120 min at room temperature, the fluorescence intensity derived from terbium and BODIPY-FL was measured using Envision (PerkinElmer). The signal value of each well was determined using the TR-FRET ratio calculated by the following formula.

TR-FRET ratio=(fluorescence value of BODIPY-FL)-(fluorescence value of terbium)

A similar test was performed in the presence of 2 μM AT-7519 and taken as a non-specific TR-FRET signal. It was confirmed that the BODIPY-FL-labeled AT-7519 specifically binds to CDK12 because the TR-FRET signal under conditions in the absence of AT-7519 was significantly high as compared to that in the presence of 2 μM AT-7519 (FIG. 1).

(3) Measurement of CDK12 Inhibitory Activity by Binding Assay

His-tagged CDK12/CycK complex was added to a binding assay buffer supplemented with BODIPY-FL labeled AT-7519, terbium-labeled streptavidin and biotin-labeled anti-histidine antibody, and the mixture was stood for not less than 60 min at room temperature. This solution was added to an assay plate containing a test compound dispensed therein, and the mixture was left standing for 120 min at room temperature. The final concentration of CDK12/CycK complex, BODIPY-FL-labeled AT-7519, terbium-labeled streptavidin and biotin-labeled anti-histidine antibody was set to 2 nM, 66 nM, 0.2 nM, and 0.4 nM, respectively. The fluorescence intensity derived from terbium and BODIPY-FL was measured using Envision. The signal value of each well was determined using the TR-FRET ratio calculated by the following formula.

TR-FRET ratio=(fluorescence value of BODIPY-FL)÷(fluorescence value of terbium)

The inhibitory rate (%) of the test compound against CDK12 was calculated by the following formula.

Inhibitory rate (%)=(1−(TR-FRET ratio of test compound−blank)÷(control−blank))×100

The TR-FRET ratio of the CDK12 enzyme reaction mixture under compound non-addition conditions is indicated as control, and the TR-FRET ratio under 3 µM AT-7519 addition conditions is indicated as blank.

The inhibitory rate of the test compound against CDK12 at µM is shown below.

TABLE 3-1

| Example No. | 1 µM inhibitory rate (%) |
|---|---|
| 199 | 101 |
| 319 | 94 |
| 440 | 99 |
| 469 | 94 |
| 482 | 104 |
| 483 | 103 |
| 485 | 102 |
| 492 | 92 |
| 495 | 81 |
| 527 | 102 |
| 530 | 100 |
| 532 | 106 |
| 536 | 96 |
| 538 | 86 |
| 539 | 99 |
| 542 | 100 |
| 552 | 98 |
| 553 | 100 |
| 566 | 102 |
| 574 | 103 |
| 575 | 101 |
| 577 | 88 |
| 581 | 88 |
| 582 | 91 |
| 587 | 102 |
| 588 | 99 |
| 589 | 100 |
| 592 | 101 |
| 595 | 104 |
| 596 | 103 |
| 599 | 102 |
| 600 | 83 |
| 603 | 76 |
| 605 | 90 |
| 606 | 96 |
| 608 | 98 |
| 609 | 99 |
| 610 | 103 |

TABLE 3-2

| Example No. | 1 µM inhibitory rate (%) |
|---|---|
| 611 | 101 |
| 614 | 95 |
| 619 | 98 |
| 620 | 97 |
| 623 | 100 |
| 625 | 103 |
| 626 | 105 |
| 627 | 98 |
| 628 | 100 |
| 629 | 100 |
| 630 | 104 |
| 631 | 103 |
| 633 | 102 |

(4) Measurement of CDK12 Inhibitory Activity by Binding Assay (BODIPY-FL Labeled AT-7519 High Concentration Conditions)

His-tagged CDK12/CycK complex was blended with a binding assay buffer supplemented with BODIPY-FL labeled AT-7519, terbium-labeled streptavidin and biotin-labeled anti-histidine antibody. This solution was added to an assay plate containing a test compound dispensed therein, and the mixture was left standing for 120 min at room temperature. The final concentration of CDK12/CycK complex, BODIPY-FL-labeled AT-7519, terbium-labeled streptavidin and biotin-labeled anti-histidine antibody was set to 8 nM, 1320 nM, 0.2 nM, and 0.4 nM, respectively. The fluorescence intensity derived from terbium and BODIPY-FL was measured using Envision. The signal value of each well was determined using the TR-FRET ratio calculated by the following formula.

TR-FRET ratio=(fluorescence value of BODIPY-FL)÷(fluorescence value of terbium)

The inhibitory rate (%) of the test compound against CDK12 was calculated by the following formula.

Inhibitory rate (%)=(1−(TR-FRET ratio of test compound−blank)÷(control−blank))×100

The TR-FRET ratio of the CDK12 enzyme reaction mixture under compound non-addition conditions is indicated as control, and the TR-FRET ratio under 30 µM AT-7519 addition conditions is indicated as blank.

The inhibitory rate of the test compound against CDK12 at 1 µM is shown below.

TABLE 3-3

| Example No. | 1 µM inhibitory rate (%) |
|---|---|
| 612 | 100 |
| 640 | 105 |
| 693 | 100 |
| 729 | 92 |
| 740 | 86 |
| 741 | 87 |
| 742 | 87 |
| 743 | 81 |
| 744 | 92 |
| 745 | 94 |
| 746 | 91 |
| 752 | 90 |
| 756 | 90 |
| 764 | 91 |
| 766 | 96 |
| 767 | 102 |
| 768 | 92 |
| 777 | 92 |
| 796 | 95 |
| 797 | 92 |
| 798 | 92 |
| 799 | 96 |

TABLE 3-3-continued

| Example No. | 1 μM inhibitory rate (%) |
|---|---|
| 800 | 91 |
| 804 | 94 |
| 808 | 99 |
| 811 | 94 |
| 812 | 95 |
| 814 | 99 |
| 820 | 99 |
| 826 | 106 |
| 827 | 109 |
| 831 | 107 |
| 836 | 106 |
| 838 | 103 |
| 841 | 79 |
| 848 | 108 |
| 849 | 110 |
| 858 | 109 |

Experimental Example 2: Measurement of CDK12/CycK Inhibitory Activity

A test compound dissolved in DMSO was added to a reaction solution (50 mM HEPES (pH 7.5), 10 mM MgCl$_2$, 1 mM DTT, 0.01% Tween 20, 0.01% BSA) containing CDK12/CycK enzyme and ULight-labeled eIF4E-binding protein 1 (4E-BP1) (Thr37/Thr46) peptide (PerkinElmer), and the mixture was reacted at room temperature for 60 min. The test compound was added to give an ATP solution with a final concentration of 10 μM or 500 μM to start the enzyme reaction, and the mixture was reacted at room temperature for 60 min. A LANCE Detection buffer (PerkinElmer) containing europium-labeled anti-phosphorylation 4E-BP1 (Thr37/Thr46) antibody (PerkinElmer) and EDTA (final concentration 10 mM) was added to discontinue the reaction. After standing for 60 min, time decomposition fluorescence value (excitation 320 nm, emission 615 nm, 665 nm) was measured by Envision (PerkinElmer). The inhibitory rate (%) of the test compound against CDK12/CyclinK was calculated by the following formula.

Inhibitory rate (%)=(1−(count of test compound−blank)÷(control−blank))×100

The count of the CDK12 enzyme reaction mixture under compound non-addition conditions is indicated as control, and the count under compound non-addition and CDK12/CycK enzyme non-addition conditions is indicated as blank.

The results measured by the above-mentioned method (inhibitory rate (%) of the signal value at 1 μM test compound relative to control is shown below.

TABLE 4

| Example No. | 1 μM inhibitory rate (%) |
|---|---|
| 319 | 98 |
| 440 | 101 |
| 469 | 103 |
| 485 | 103 |
| 527 | 99 |
| 530 | 104 |
| 536 | 95 |
| 539 | 109 |
| 553 | 106 |
| 566 | 100 |
| 574 | 99 |
| 575 | 97 |
| 577 | 98 |
| 581 | 102 |
| 582 | 110 |

TABLE 4-continued

| Example No. | 1 μM inhibitory rate (%) |
|---|---|
| 588 | 100 |
| 589 | 115 |
| 596 | 100 |
| 600 | 108 |
| 603 | 103 |
| 605 | 100 |
| 608 | 102 |
| 609 | 107 |
| 610 | 99 |
| 611 | 101 |
| 614 | 105 |

Experimental Example 3: CTD pSer2 Measurement Using Human Ovarian Cancer Cell A2780 and In-Cell Western Method A2780 cells (ATCC) were seeded in a 96 well plate at $1.8 \times 10^4$ cells/well, and the cells were cultured overnight in a cell culture medium RPMI1640 (FUJIFILM Wako Pure Chemical Corporation) containing 10% FBS (fetal bovine serum) and 1% penicillin/streptomycin. A test compound dissolved in a cell medium was added, and the mixture was stood for 4 hr in a CO$_2$ incubator (37° C.). The cells were fixed with ALTFiX (Falma) for 30 min, and washed 3 times with a washing buffer (20 mM Tris-HCl (pH 7.5), 500 mM NaCl, 0.1% Tween20). 0.1% Triton-X-100 diluted with PBS(−) was added and the mixture was incubated at room temperature for 15 min. Thereafter, a blocking buffer (LI-COR) was added, and the mixture was incubated at room temperature for 1 hr. An anti-CTD pS2 antibody (Abcam) suspended in an antibody diluent (blocking buffer: PBS(−)-diluted 0.1% Tween20=1:1) was added, and the mixture was incubated at room temperature for 1 hr. The mixture was washed times with a washing buffer, IRDye800CW-labeled anti-goat antibody (LI-COR) was added, and the mixture was incubated at room temperature for 1 hr. The mixture was washed 3 times with a washing buffer, and the fluorescence wavelength at 800 nm was measured by Aerius (LI-COR).

The inhibitory rate (%) of the test compound against A2780 intracellular CTD pSer2 was calculated by the following formula.

Inhibitory rate (%)=(1−(count of test compound−blank)÷(control−blank))×100

The count of the A2780 cell under compound non-addition conditions is indicated as control, and the count under compound non-addition and primary antibody non-addition conditions is indicated as blank.

The results measured by the above-mentioned method (inhibitory rate of the signal value at 1 μM test compound relative to control) are shown below.

TABLE 5

| Example No. | 1 μM inhibitory rate (%) |
|---|---|
| 319 | 69 |
| 440 | 54 |
| 469 | 62 |
| 485 | 63 |
| 527 | 70 |
| 530 | 64 |
| 536 | 82 |
| 539 | 71 |
| 553 | 74 |
| 566 | 72 |

TABLE 5-continued

| Example No. | 1 μM inhibitory rate (%) |
|---|---|
| 574 | 83 |
| 575 | 63 |
| 577 | 87 |
| 581 | 70 |
| 582 | 72 |
| 588 | 75 |
| 589 | 78 |
| 596 | 71 |
| 600 | 81 |
| 603 | 81 |
| 605 | 73 |
| 608 | 44 |
| 609 | 41 |
| 610 | 49 |
| 611 | 48 |
| 614 | 54 |

Experimental Example 4: In Vitro Proliferation Suppression Test

The proliferation suppressive activity of compound in A2780 cells was evaluated by the following method.

A2780 cells were seeded in a 384-well white plate at a cell density of 1,000 cells/40 μL/well or a 96-well white plate at a cell density of 1,000 cells/90 μL/well using an assay medium (RPMI1640 medium containing 10% fetal bovine serum (FUJIFILM Wako Pure Chemical Corporation)) and incubated at 37° C. in 5% $CO_2$.

The next day, a test compound dissolved in dimethyl sulfoxide (DMSO) was diluted with an assay medium, the obtained compound solution was added by 40 μL/well or 10 μL/well to each well of the plate containing A2780 cells and the mixture was incubated (test compound addition group). In addition, a similar reaction was performed without adding the test compound (test compound non-addition group).

Three days later, 80 μL or 100 μL of CellTiter-Glo reagent (Promega) was added, and the mixture was stirred for 10 min. Thereafter, the luminescence of each well was measured by ARVO-MX multilabel counter (Perkin Elmer Inc.).

The proliferation inhibitory rate (%) of each test compound against A2780 cells was calculated by the following calculation formula.

Proliferation inhibitory rate (%)=(1−luminescence of test compound addition group÷luminescence of test compound non-addition group)×100

The A2780 cell proliferation inhibitory rate (%) of 1 μM test compound is shown below.

TABLE 6-1

| Example No. | 1 μM inhibitory rate (%) |
|---|---|
| 319 | 97 |
| 440 | 98 |
| 469 | 97 |
| 485 | 97 |
| 527 | 97 |
| 530 | 97 |
| 536 | 91 |
| 539 | 96 |
| 553 | 98 |
| 566 | 98 |
| 574 | 97 |
| 575 | 99 |
| 577 | 94 |
| 581 | 99 |
| 582 | 97 |

TABLE 6-1-continued

| Example No. | 1 μM inhibitory rate (%) |
|---|---|
| 588 | 98 |
| 589 | 97 |
| 596 | 99 |
| 600 | 93 |
| 603 | 93 |
| 605 | 98 |
| 608 | 99 |
| 609 | 99 |
| 610 | 98 |
| 611 | 97 |
| 612 | 97 |
| 614 | 94 |
| 693 | 98 |
| 729 | 98 |
| 740 | 96 |
| 742 | 96 |
| 743 | 95 |
| 744 | 97 |
| 764 | 95 |
| 766 | 99 |
| 767 | 99 |

TABLE 6-2

| Example No. | 1 μM inhibitory rate (%) |
|---|---|
| 798 | 99 |
| 799 | 99 |
| 804 | 96 |
| 820 | 99 |
| 826 | 98 |
| 827 | 99 |
| 831 | 99 |
| 836 | 99 |
| 838 | 98 |
| 841 | 99 |
| 848 | 99 |
| 849 | 97 |
| 858 | 99 |

Experimental Example 6: Antitumor Action on SUM149PT CELLS Tumor-Bearing Model

Human breast cancer cells SUM149PT were suspended in a solution of Matrigel (BD BIOSCIENCES):HBSS (Thermo Fisher Scientific)=1:1, and subcutaneously transplanted at $3\times10^6$ cells to the abdomen of BALB/cAJcl-nu/nu (CLEA Japan, Inc.). The tumor diameter of the engrafted tumor was measured and the tumor volume was calculated by the following formula.

Tumor volume=major axis×minor axis×minor axis×(1/2)

Individuals having a tumor grown to a volume of about 120 $mm^3$ were selected, and 5 mice per group were used for the experiment. A suspension of the test compound in 0.5% methylcellulose solution (FUJIFILM Wako Pure Chemical Corporation) was orally administered at a dose of 60 mg/kg (10 mL/kg) two times per day for 2 weeks. The tumor volume was measured over time one day before the start of the administration, and every 4 days from day 3. The next day of the completion of medication for 14 days, the tumor diameter was finally measured and the tumor volume was calculated. The tumor proliferation rate of the test compound administration group in comparison with the control administration group was taken as an average tumor volume increase ratio T/C and calculated by the following formula.

T/C=(tumor volume of test compound administration group after completion of administration−tumor volume of test compound administration group one day before start of administration)/(tumor volume of control administration group after completion of administration−tumor volume of control administration group before start of administration)× 100

The T/C of the test compound is shown below.

TABLE 7

| test compound (Example No.) | dose (mg/kg) | T/C (%) |
|---|---|---|
| 612 | 60 | −22 |

| Formulation Example 1 (production of capsule) | |
|---|---|
| 1) compound of Example 1 | 30 mg |
| 2) finely-powdered cellulose | 10 mg |
| 3) lactose | 19 mg |
| 4) magnesium stearate | 1 mg |
| total | 60 mg |

1), 2), 3) and 4) are mixed and filled in a gelatin capsule.

| Formulation Example 2 (production of tablets) | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Example 1 per tablet are obtained.

INDUSTRIAL APPLICABILITY

The compound of the present invention may have a superior CDK12 inhibitory action and is expected to be useful as a prophylactic or therapeutic drug for cancer and the like.

This application is based on patent application No. 2018-063740 filed in Japan, the contents of which are encompassed in full herein.

The invention claimed is:

1. A compound represented by the formula (I):

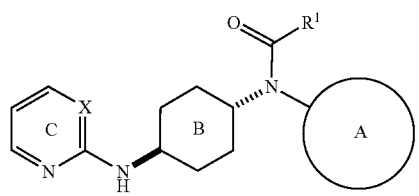

(I)

wherein
X is N;

$R^1$ is an optionally substituted $C_{1-6}$ alkyl group, an optionally substituted $C_{1-6}$ alkoxy group, an optionally substituted $C_{6-14}$ aryl group, an optionally substituted heterocyclic group, or —$NR^2R^3$;
$R^2$ is a hydrogen atom or a substituent;
$R^3$ is a substituent;
ring A is an optionally further substituted aromatic ring;
ring B is an optionally further substituted cyclohexane ring;
ring C is an optionally further substituted 6-membered nitrogen-containing aromatic heterocycle,
or a salt thereof.

2. The compound according to claim 1, wherein
$R^1$ is (1) a $C_{1-6}$ alkyl group optionally substituted by 1 to 3 substituents selected from the group consisting of an optionally substituted $C_{6-14}$ aryl group, an optionally substituted $C_{6-14}$ aryloxy group and an optionally substituted 5- to 14-membered aromatic heterocyclic group, (2) a $C_{1-6}$ alkoxy group optionally substituted by 1 to 3 substituents selected from the group consisting of an optionally substituted $C_{6-14}$ aryl group and an optionally substituted 5- to 14-membered aromatic heterocyclic group, (3) an optionally substituted $C_{6-14}$ aryl group, (4) a 3- to 14-membered non-aromatic heterocyclic group optionally substituted by 1 to 3 substituents selected from an optionally substituted $C_{6-14}$ aryl group or (5) —$NR^2R^3$ (wherein $R^2$ is a hydrogen atom or a $C_{1-6}$ alkyl group optionally substituted by 1 to 3 substituents selected from an optionally substituted $C_{6-14}$ aryl group, and $R^3$ is (i) a $C_{1-6}$ alkyl group optionally substituted by 1 to 3 substituents selected from the group consisting of an optionally substituted $C_{3-10}$ cycloalkyl group, an optionally substituted $C_{6-14}$ aryl group, an optionally substituted 3- to 14-membered non-aromatic heterocyclic group and an optionally substituted 5- to 14-membered aromatic heterocyclic group or (ii) an optionally substituted $C_{6-14}$ aryl group);
ring A is a $C_{6-14}$ aromatic hydrocarbon ring or a 5- to 14-membered aromatic heterocycle each of which is optionally further substituted by 1 to 5 substituents selected from the group consisting of (1) a halogen atom, (2) a cyano group, (3) a hydroxy group, (4) an optionally substituted $C_{1-6}$ alkyl group, (5) an optionally substituted $C_{2-6}$ alkenyl group, (6) an optionally substituted $C_{6-14}$ aryl group, (7) an optionally substituted $C_{1-6}$ alkoxy group, (8) an optionally substituted amino group, (9) a carboxy group, (10) an optionally substituted carbamoyl group, (11) an optionally substituted 3- to 14-membered non-aromatic heterocyclic group (wherein the 3- to 14-membered non-aromatic heterocyclic group includes one having a spiro ring structure) and (12) an optionally substituted 5- to 14-membered aromatic heterocyclic group;
ring B is a cyclohexane ring not further substituted; and
ring C is a pyrimidine ring which is optionally further substituted by 1 to 3 substituents selected from the group consisting of (1) a halogen atom, (2) a cyano group, (3) an optionally substituted $C_{1-6}$ alkyl group, (4) an optionally substituted $C_{6-14}$ aryl group, (5) an optionally substituted $C_{1-6}$ alkoxy group, (6) an optionally substituted $C_{6-14}$ aryloxy group, (7) an optionally substituted 3- to 14-membered non-aromatic heterocyclic-oxy group, (8) an optionally substituted amino group, (9) an optionally substituted carbamoyl group, (10) an optionally substituted 3- to 14-membered non-aromatic heterocyclic group (wherein the 3- to 14-membered non-aromatic heterocyclic group includes one having a bicyclo ring structure, a bridged ring structure, or a spiro ring structure) and (11) an optionally substituted 5- to 14-membered aromatic heterocyclic group.

3. The compound according to claim 1, wherein
$R^1$ is (1) a $C_{1-6}$ alkyl group optionally substituted by 1 to 3 substituents selected from the group consisting of a $C_{6-14}$ aryl group optionally substituted by 1 to 3 halogen atoms, a $C_{6-14}$ aryloxy group and a 5- to 14-membered aromatic heterocyclic group, (2) a $C_{1-6}$ alkoxy group optionally substituted by 1 to 3 substituents selected from the group consisting of a $C_{6-14}$ aryl group and a 5- to 14-membered aromatic heterocyclic group, (3) a $C_{6-14}$ aryl group, (4) a 3- to 14-membered non-aromatic heterocyclic group optionally substituted by 1 to 3 $C_{6-14}$ aryl groups, or (5) —$NR^2R^3$ (wherein $R^2$ is a hydrogen atom or a $C_{1-6}$ alkyl group optionally substituted by 1 to 3 $C_{6-14}$ aryl groups, and $R^3$ is (i) a $C_{1-6}$ alkyl group optionally substituted by 1 to 3 substituents selected from the group consisting of (a) a $C_{3-10}$ cycloalkyl group, (b) a $C_{6-14}$ aryl group optionally substituted by 1 to 3 substituents selected from the group consisting of a halogen atom, a cyano group, a $C_{1-6}$ alkoxy group, a $C_{1-6}$ alkylsulfonyl group and a $C_{1-6}$ alkylsulfonylamino group, (c) a 3- to 14-membered non-aromatic heterocyclic group, and (d) a 5- to 14-membered aromatic heterocyclic group optionally substituted by 1 to 3 substituents selected from the group consisting of a $C_{1-6}$ alkyl group and a $C_{1-6}$ alkoxy group, or (ii) a $C_{6-14}$ aryl group);
ring A is a $C_{6-14}$ aromatic hydrocarbon ring or a 5- to 14-membered aromatic heterocycle each of which is optionally further substituted by 1 to 5 substituents selected from the group consisting of (1) a halogen atom, (2) a cyano group, (3) a hydroxy group, (4) a $C_{1-6}$ alkyl group optionally substituted by 1 to 3 substituents selected from the group consisting of (a) a halogen atom, (b) a $C_{1-6}$ alkoxy group and (c) a 3- to 14-membered non-aromatic heterocyclic group optionally substituted by 1 to 3 $C_{1-6}$ alkyl groups, (5) a $C_{2-6}$ alkenyl group, (6) a $C_{6-14}$ aryl group optionally substituted by 1 to 3 substituents selected from the group consisting of (a) a halogen atom, (b) a cyano group, (c) a $C_{1-6}$ alkoxy group and (d) a carbamoyl group, (7) a $C_{1-6}$ alkoxy group, (8) an amino group optionally mono- or di-substituted by substituent(s) selected from the group consisting of (a) a $C_{1-6}$ alkyl group optionally substituted by 1 to 3 $C_{1-6}$ alkoxy groups, (b) a $C_{6-14}$ aryl group optionally substituted by 1 to 3 substituents selected from the group consisting of a cyano group and a $C_{1-6}$ alkoxy group, and (c) a 5- to 14-membered aromatic heterocyclic group optionally substituted by 1 to 3 $C_{1-6}$ alkyl groups, (9) a carboxy group, (10) a carbamoyl group optionally mono- or di-substituted by a $C_{1-6}$ alkyl group, (11) a 3- to 14-membered non-aromatic heterocyclic group optionally substituted by 1 to 3 substituents selected from the group consisting of (a) an oxo group, (b) a cyano group, (c) a $C_{1-6}$ alkyl group, (d) a $C_{1-6}$ alkoxy group, (e) a $C_{1-6}$ alkyl-carbonyl group, (f) a carbamoyl group, (g) a mono- or di-$C_{1-6}$ alkylamino group and (h) a $C_{1-6}$ alkylsulfonyl group (wherein the 3- to 14-membered non-aromatic heterocyclic group al-se-includes one having a spiro ring structure) and (12) a 5- to 14-membered aromatic heterocyclic group optionally substituted by 1 to 3 substituents selected from the group consisting of (a) an oxo group, (b) a $C_{1-6}$ alkyl group optionally substituted by 1 to 3 substituents selected from the group consisting of a hydroxy group, a $C_{1-6}$ alkoxy group, a carbamoyl group, a 3- to 14-membered non-aromatic heterocyclic group and a 5- to 14-membered aromatic heterocyclic group, (c) a $C_{1-6}$ alkoxy group, (d) an amino group, (e) a carboxy group, (f) a $C_{1-6}$ alkoxy-carbonyl group, (g) a carbamoyl group and (h) a 3- to 14-membered non-aromatic heterocyclic group;
ring B is a cyclohexane ring not further substituted;
ring C is a pyrimidine ring which is optionally further substituted by 1 to 3 substituents selected from the group consisting of (1) a halogen atom, (2) a cyano group, (3) $C_{1-6}$ alkyl group optionally substituted by 1 to 3 halogen atoms, (4) a $C_{6-14}$ aryl group optionally substituted by 1 to 3 substituents selected from the group consisting of (a) a halogen atom, (b) a cyano group, (c) a $C_{1-6}$ alkyl group optionally substituted by 1 to 3 halogen atoms, (d) a $C_{1-6}$ alkoxy group optionally substituted by 1 to 3 halogen atoms, (e) a mono- or di-$C_{1-6}$ alkylamino group, (f) a $C_{1-6}$ alkyl-carbonylamino group, (g) a $C_{1-6}$ alkyl-carbonyl group, (h) a carbamoyl group, (i) a sulfamoyl group and (j) a 3- to 14-membered non-aromatic heterocyclic-sulfonyl group, (5) a $C_{1-6}$ alkoxy group optionally substituted by 1 to 3 substituents selected from the group consisting of (a) a halogen atom and (b) a 5- to 14-membered aromatic heterocyclic group optionally substituted by 1 to 3 $C_{1-6}$ alkyl groups, (6) a $C_{6-14}$ aryloxy group optionally substituted by 1 to 3 $C_{1-6}$ alkylsulfonyl groups, (7) a 3- to 14-membered non-aromatic heterocyclic-oxy group, (8) an amino group optionally mono- or di-substituted by substituent(s) selected from the group consisting of (a) a $C_{1-6}$ alkyl group optionally substituted by 1 to 3 substituents selected from the group consisting of (i) a halogen atom, (ii) a hydroxy group, (iii) a cyano group, (iv) a $C_{3-10}$ cycloalkyl group optionally substituted by 1 to 3 hydroxy groups, (v) a $C_{6-14}$ aryl group optionally substituted by 1 to 3 substituents selected from the group consisting of a $C_{1-6}$ alkylsulfonyl group and a sulfamoyl group, (vi) a $C_{1-6}$ alkoxy group optionally substituted by 1 to halogen atoms, (vii) a mono- or di-$C_{1-6}$ alkylamino group, (viii) a $C_{1-6}$ alkyl-carbonylamino group, (ix) a carbamoyl group, (x) a $C_{1-6}$ alkylsulfonyl group, (xi) a 3- to 14-membered non-aromatic heterocyclic group optionally substituted by 1 to 3 substituents selected from the group consisting of an oxo group and a $C_{1-6}$ alkyl group and (xii) a $C_{1-6}$ alkyl group optionally substituted by 1 to 3 substituents selected from a 5- to 14-membered aromatic heterocyclic group optionally substituted by 1 to 3 substituents selected from the group consisting of a $C_{1-6}$ alkyl group, a $C_{3-10}$ cycloalkyl group and a ($C_{1-6}$ alkyl)($C_{1-6}$ alkyl-sulfonyl)amino group, (b) a $C_{3-10}$ cycloalkyl group optionally substituted by 1 to 3 substituents selected from the group consisting of a halogen atom, a hydroxy group, a $C_{1-6}$ alkyl group optionally substituted by 1 to 3 hydroxy groups and a $C_{1-6}$ alkoxy group optionally substituted by 1 to 3 halogen atoms (wherein the $C_{3-10}$ cycloalkyl group includes one having a spiro ring structure), (c) a $C_{6-14}$ aryl group optionally substituted by 1 to 3 $C_{1-6}$ alkylsulfonyl groups, (d) a $C_{3-10}$ cycloalkyl-carbonyl group, (e) a 3- to 14-membered non-aromatic heterocyclic group optionally substituted by 1 to 3 substituents selected from the group consisting of an oxo group, a hydroxy group and a $C_{1-6}$ alkyl group (wherein the 3- to 14-membered non-aromatic heterocyclic group al-se-includes one having a bicyclo ring structure, a bridged ring structure, or a spiro ring structure) and (f) a 5- to 14-membered aromatic heterocyclic group, (9) a carbamoyl group, (10) a 3- to 14-membered non-aromatic heterocyclic group optionally substituted by 1 to 3 substituents selected from the group consisting of (a) an oxo group, (b) a halogen atom, (c) a hydroxy group, (d) a cyano group, (e) a $C_{1-6}$ alkyl group optionally substituted by 1 to 3 substituents selected from the group consisting of a halogen atom, a hydroxy group and a $C_{1-6}$ alkoxy group, (f) a $C_{3-10}$ cycloalkyl group, (g) a $C_{1-6}$ alkoxy group optionally substituted by 1 to 3 halogen atoms, (h) a $C_{1-6}$ alkyl-carbonyl group, (i) a carbamoyl group, (j) a $C_{1-6}$ alkylsulfonyl group, (k) a ($C_{1-6}$ alkyl)($C_{1-6}$ alkyl-carbonyl)amino group, (l) a dimethyl(oxide)-$\lambda^6$-sulfanylideneamino group and (m) a methylimino group (wherein the 3- to 14-membered non-aromatic heterocyclic group includes one having a bicyclo ring structure, a bridged ring structure, or a spiro ring structure) and (11) a 5- to 14-membered aromatic heterocyclic group optionally substituted by 1 to 3 substituents selected from the group consisting of (a) an oxo group, (b) a hydroxy group, (c) a cyano group, (d) a halogen atom, (e) a $C_{1-6}$ alkyl group optionally substituted by 1 to 3 substituents selected from the group consisting of a hydroxy group, a halogen atom, a $C_{3-10}$ cycloalkyl group, a $C_{6-14}$ aryl group, a $C_{1-6}$ alkoxy-carbonyl group and a carbamoyl group, (f) a $C_{1-6}$ alkoxy group, (g) a $C_{1-6}$ alkoxy-carbonyl group, (h) a $C_{1-6}$ alkylsulfonyl group and (i) a 3- to 14-membered non-aromatic heterocyclic group.

4. The compound according to claim 1, wherein
$R^1$ is (1) a $C_{1-6}$ alkyl group optionally substituted by 1 to 3 substituents selected from the group consisting of a $C_{6-14}$ aryl group, a $C_{6-14}$ aryloxy group and a 5- to 14-membered aromatic heterocyclic group, (2) a $C_{1-6}$ alkoxy group optionally substituted by 1 to 3 substituents selected from the group consisting of a $C_{6-14}$ aryl group and a 5- to 14-membered aromatic heterocyclic group, or (3) —$NR^2R^3$ (wherein $R^2$ is a hydrogen atom, and $R^3$ is a $C_{1-6}$ alkyl group optionally substituted by 1 to 3 substituents selected from the group consisting of (a) a $C_{6-14}$ aryl group optionally substituted by 1 to 3 halogen atoms and (b) a 5- to 14-membered aromatic heterocyclic group);
ring A is a $C_{6-14}$ aromatic hydrocarbon ring or a 5- to 14-membered aromatic heterocycle each of which is optionally further substituted by 1 to 5 substituents selected from the group consisting of (a) an oxo group, (b) a $C_{1-6}$ alkyl group and (c) a 5- to 14-membered aromatic heterocyclic group optionally substituted by 1 to 3 substituents selected from a $C_{1-6}$ alkoxy group;
ring B is a cyclohexane ring not further substituted; and
ring C is a pyrimidine ring optionally further substituted by 1 to 3 substituents selected from the group consisting of (1) a cyano group, (2) a $C_{1-6}$ alkyl group optionally substituted by 1 to 3 halogen atoms, (3) a 3- to 14-membered non-aromatic heterocyclic-oxy group, (4) an amino group optionally mono- or di-substituted by substituent(s) selected from the group consisting of (a) a $C_{1-6}$ alkyl group optionally substituted by 1 to 3 hydroxy groups and (b) a 3- to 14-membered non-aromatic heterocyclic group optionally substituted by 1 to 3 $C_{1-6}$ alkyl groups (wherein the 3- to 14-membered non-aromatic heterocyclic group includes one having a bicyclo ring structure, a bridged ring structure, or a spiro ring structure), (5) a 3- to 14-membered non-aromatic heterocyclic group optionally substituted by 1 to 3 substituents selected from the group consisting of (a) a halogen atom, (b) a hydroxy group and (c) a $C_{1-6}$ alkyl group optionally substituted by 1 to 3 hydroxy groups (wherein the 3- to 14-membered non-aromatic heterocyclic group includes one having a bicyclo ring structure, a bridged ring structure, or a spiro ring structure) and (6) a 5- to 14-membered aromatic heterocyclic group optionally substituted by 1 to 3 substituents selected from the group consisting of (a) a cyano group, (b) a halogen atom, (c) a $C_{1-6}$ alkyl group and (d) a $C_{1-6}$ alkylsulfonyl group.

5. The compound according to claim 1, wherein
$R^1$ is (1) a $C_{1-6}$ alkyl group optionally substituted by 1 to 3 substituents selected from the group consisting of a halogen atom, an optionally substituted $C_{3-10}$ cycloalkyl group, an optionally substituted $C_{1-6}$ alkoxy group, an optionally substituted $C_{6-14}$ aryl group and an optionally substituted $C_{6-14}$ aryloxy group, (2) a $C_{1-6}$ alkoxy group optionally substituted by 1 to substituents selected from the group consisting of a halogen atom, a hydroxy group, an optionally substituted $C_{3-10}$ cycloalkyl group, an optionally substituted $C_{1-6}$ alkoxy group, an optionally substituted $C_{6-14}$ aryl group, an optionally substituted amino group, an optionally substituted 3- to 14-membered non-aromatic heterocyclic group and an optionally substituted 5-to 14-membered aromatic heterocyclic group, (3) an optionally substituted $C_{6-14}$ aryl group, (4) a 3- to 14-membered non-aromatic heterocyclic group optionally substituted by 1 to 3 substituents selected from the group consisting of a halogen atom, a hydroxy group, an optionally substituted $C_{1-6}$ alkyl group, an optionally substituted $C_{1-6}$ alkoxy group and an optionally substituted $C_{6-14}$ aryl group or (5) —$NR^2R^3$ (wherein $R^2$ is a hydrogen atom or a $C_{1-6}$ alkyl group optionally substituted by 1 to 3 substituents selected from the group consisting of an optionally substituted $C_{6-14}$ aryl group, and $R^3$ is (i) a $C_{1-6}$ alkyl group optionally substituted by 1 to 3 substituents selected from the group consisting of a halogen atom, a hydroxy group, an optionally substituted $C_{3-10}$ cycloalkyl group, an optionally substituted $C_{1-6}$ alkoxy group, an optionally substituted $C_{6-14}$ aryl group, an optionally substituted amino group, an optionally substituted 3- to 14-membered non-aromatic heterocyclic group and an optionally substituted 5- to 14-membered aromatic heterocyclic group, (ii) an optionally substituted $C_{3-10}$ cycloalkyl group or (iii) an optionally substituted $C_{6-14}$ aryl group);
ring A is a $C_{6-14}$ aromatic hydrocarbon ring or a 5- to 14-membered aromatic heterocycle each of which is optionally further substituted by 1 to 5 substituents selected from the group consisting of (1) a halogen atom, (2) a cyano group, (3) a hydroxy group, (4) an optionally substituted $C_{1-6}$ alkyl group, (5) an optionally substituted $C_{2-6}$ alkenyl group, (6) an optionally substituted $C_{6-14}$ aryl group, (7) an optionally substituted $C_{1-6}$ alkoxy group, (8) an optionally substituted amino group, (9) a carboxy group, (10) an optionally substituted carbamoyl group, (11) an optionally substituted 3- to 14-membered non-aromatic heterocyclic group (wherein the 3- to 14-membered non-aromatic heterocyclic group includes one having a spiro ring structure) and (12) an optionally substituted 5- to 14-membered aromatic heterocyclic group;

ring B is a cyclohexane ring not further substituted; and ring C is a pyrimidine ring which is optionally further substituted by 1 to 3 substituents selected from the group consisting of (1) a halogen atom, (2) a cyano group, (3) an optionally substituted $C_{1-6}$ alkyl group, (4) an optionally substituted $C_{6-14}$ aryl group, (5) an optionally substituted $C_{1-6}$ alkoxy group, (6) an optionally substituted $C_{6-14}$ aryloxy group, (7) an optionally substituted 3- to 14-membered non-aromatic heterocyclic-oxy group, (8) an optionally substituted amino group, (9) an optionally substituted carbamoyl group, (10) an optionally substituted 3- to 14-membered non-aromatic heterocyclic group (wherein the 3- to 14-membered non-aromatic heterocyclic group al-se-includes one having a bicyclo ring structure, a bridged ring structure, or a spiro ring structure) and (11) an optionally substituted 5- to 14-membered aromatic heterocyclic group.

6. The compound according to claim 1, wherein $R^1$ is (1) a $C_{1-6}$ alkyl group optionally substituted by 1 to 3 substituents selected from the group consisting of a halogen atom, a $C_{3-10}$ cycloalkyl group, a $C_{1-6}$ alkoxy group, and a $C_{6-14}$ aryloxy group, (2) a $C_{1-6}$ alkoxy group optionally substituted by 1 to 3 substituents selected from the group consisting of (a) a halogen atom, (b) a hydroxy group, (c) a $C_{3-10}$ cycloalkyl group optionally substituted by 1 to 3 substituents selected from the group consisting of a halogen atom and an amino group, (d) a $C_{6-14}$ aryl group, (e) a $C_{1-6}$ alkoxy group, (f) an amino group optionally mono- or di-substituted by a $C_{1-6}$ alkyl group, (g) a 3- to 14-membered non-aromatic heterocyclic group optionally substituted by 1 to 3 halogen atoms and (h) a 5- to 14-membered aromatic heterocyclic group, (3) a 3- to 14-membered non-aromatic heterocyclic group optionally substituted by 1 to 3 substituents selected from the group consisting of a halogen atom, a hydroxy group, a $C_{1-6}$ alkyl group, a $C_{1-6}$ alkoxy group and a $C_{6-14}$ aryl group or (4) —$NR^2R^3$ (wherein $R^2$ is a hydrogen atom or a $C_{1-6}$ alkyl group, and $R^3$ is (i) a $C_{1-6}$ alkyl group optionally substituted by 1 to 3 substituents selected from the group consisting of (a) a halogen atom, (b) a hydroxy group, (c) a $C_{3-10}$ cycloalkyl group optionally substituted by 1 to 3 substituents selected from the group consisting of a halogen atom and an amino group, (d) a $C_{1-6}$ alkoxy group, (e) a $C_{6-14}$ aryl group optionally substituted by 1 to 3 halogen atoms, (f) an amino group optionally mono- or di-substituted by a $C_{1-6}$ alkyl group, (g) a 3- to 14-membered non-aromatic heterocyclic group and (h) a 5- to 14-membered aromatic heterocyclic group, or (ii) a $C_{3-10}$ cycloalkyl group optionally substituted by 1 to 3 halogen atoms);

ring A is a $C_{6-14}$ aromatic hydrocarbon ring or a 5- to 14-membered aromatic heterocycle each of which is optionally further substituted by 1 to 5 substituents selected from the group consisting of (1) a halogen atom, (2) a $C_{1-6}$ alkyl group optionally substituted by 1 to 3 substituents selected from the group consisting of (a) a halogen atom and (b) a $C_{3-10}$ cycloalkyl group, (3) a $C_{1-6}$ alkoxy group optionally substituted by 1 to 3 substituents selected from the group consisting of (a) a halogen atom, (b) a $C_{1-6}$ alkoxy group and (c) a carbamoyl group optionally mono- or di-substituted by a $C_{1-6}$ alkyl group, (4) a carbamoyl group optionally mono- or di-substituted by a $C_{1-6}$ alkyl group optionally substituted by a $C_{1-6}$ alkoxy group, (5) a 3- to 14-membered non-aromatic heterocyclic group (wherein the 3- to 14-membered non-aromatic heterocyclic group includes one having a spiro ring structure) and (6) a 5- to 14-membered aromatic heterocyclic group optionally substituted by 1 to 3 substituents selected from the group consisting of (a) an oxo group, (b) a $C_{1-6}$ alkyl group optionally substituted by 1 to 3 substituents selected from the group consisting of a halogen atom, a $C_{3-10}$ cycloalkyl group and a 3- to 14-membered non-aromatic heterocyclic group, (c) a $C_{3-10}$ cycloalkyl group, (d) a $C_{1-6}$ alkoxy group, (e) an amino group, (f) a carboxy group, (g) a $C_{1-6}$ alkoxy-carbonyl group and (h) a 3- to 14-membered non-aromatic heterocyclic group;

ring B is a cyclohexane ring not further substituted;

ring C is a pyrimidine ring optionally further substituted by 1 to 3 substituents selected from the group consisting of (1) a halogen atom, (2) a cyano group, (3) $C_{1-6}$ alkyl group optionally substituted by 1 to 3 halogen atoms, (4) a $C_{6-14}$ aryl group optionally substituted by 1 to 3 substituents selected from the group consisting of (a) a halogen atom, (b) a cyano group, (c) a $C_{1-6}$ alkyl group optionally substituted by 1 to 3 halogen atoms, (d) a $C_{1-6}$ alkoxy group optionally substituted by 1 to 3 halogen atoms, (e) a mono- or di-$C_{1-6}$ alkylamino group, (f) a $C_{1-6}$ alkyl-carbonylamino group, (g) a $C_{1-6}$ alkyl-carbonyl group, (h) a carbamoyl group, (i) a sulfamoyl group and (j) a 3- to 14-membered non-aromatic heterocyclic-sulfonyl group, (5) a $C_{1-6}$ alkoxy group optionally substituted by 1 to 3 substituents selected from the group consisting of (a) a halogen atom, (b) a 3- to 14-membered non-aromatic heterocyclic group and (c) a 5- to 14-membered aromatic heterocyclic group optionally substituted by 1 to 3 $C_{1-6}$ alkyl groups, (6) a $C_{6-14}$ aryloxy group optionally substituted by 1 to 3 $C_{1-6}$ alkylsulfonyl groups, (7) a 3- to 14-membered non-aromatic heterocyclic-oxy group optionally substituted by to 3 $C_{1-6}$ alkyl groups, (8) an amino group optionally mono- or di-substituted by substituent(s) selected from the group consisting of (a) a $C_{1-6}$ alkyl group optionally substituted by 1 to 3 substituents selected from the group consisting of (i) a halogen atom, (ii) a hydroxy group, (iii) a cyano group, (iv) a $C_{3-10}$ cycloalkyl group optionally substituted by 1 to 3 hydroxy groups, (v) a $C_{6-14}$ aryl group optionally substituted by 1 to 3 substituents selected from the group consisting of a $C_{1-6}$ alkylsulfonyl group and a sulfamoyl group, (vi) a $C_{1-6}$ alkoxy group optionally substituted by 1 to 3 halogen atoms, (vii) a mono- or di-$C_{1-6}$ alkylamino group, (viii) a $C_{1-6}$ alkyl-carbonylamino group, (ix) a carbamoyl group, (x) a $C_{1-6}$ alkylsulfonyl group, (xi) a 3- to 14-membered non-aromatic heterocyclic group optionally substituted by 1 to 3 substituents selected from the group consisting of an oxo group and a $C_{1-6}$ alkyl group and (xii) a 5- to 14-membered aromatic heterocyclic group optionally substituted by 1 to 3 substituents selected from the group consisting of a $C_{1-6}$ alkyl group, a $C_{3-10}$ cycloalkyl group and a ($C_{1-6}$ alkyl)($C_{1-6}$ alkyl-sulfonyl)amino group, (b) a $C_{3-10}$ cycloalkyl group optionally substituted by 1 to 3 substituents selected from the group consisting of a halogen atom, a hydroxy group, a $C_{1-6}$ alkyl group optionally substituted by 1 to 3 hydroxy groups and a $C_{1-6}$ alkoxy group optionally substituted by 1 to 3 halogen atoms (wherein the $C_{3-10}$ cycloalkyl group includes one having a spiro ring structure), (c) a $C_{6-14}$ aryl group optionally substituted by 1 to 3 $C_{1-6}$ alkylsulfonyl groups, (d) a $C_{3-10}$ cycloalkyl-carbonyl group, (e) a 3- to 14-membered non-aromatic heterocyclic group optionally substituted by 1 to 3 substituents selected from the group consisting of an oxo group, a hydroxy group and a $C_{1-6}$ alkyl group (wherein the 3- to 14-membered non-aromatic heterocyclic group includes one having a bicyclo ring structure, a bridged ring structure, or a spiro ring structure) and (f) a 5- to 14-membered aromatic heterocyclic group, (9) a carbamoyl group, (10) a 3- to 14-membered non-aromatic heterocyclic group optionally substituted by 1 to 3 substituents selected from the group consisting of (a) an oxo group, (b) a halogen atom, (c) a hydroxy group, (d) a cyano group, (e) a $C_{1-6}$ alkyl group optionally substituted by 1 to 3 substituents selected from the group consisting of a halogen atom, a hydroxy group and a $C_{1-6}$ alkoxy group, (f) a $C_{3-10}$ cycloalkyl group, (g) a $C_{1-6}$ alkoxy group optionally substituted by 1 to halogen atoms, (h) a $C_{1-6}$ alkyl-carbonyl group, (i) a carbamoyl group, (j) a $C_{1-6}$ alkylsulfonyl group, (k) a ($C_{1-6}$ alkyl)($C_{1-6}$ alkyl-carbonyl)amino group, (l) a dimethyl(oxide)-$\lambda^6$-sulfanylideneamino group and (m) a methylimino group (wherein the 3- to 14-membered non-aromatic heterocyclic group includes one having a bicyclo ring structure, a bridged ring structure, or a spiro ring structure) and (11) a 5- to 14-membered aromatic heterocyclic group optionally substituted by 1 to 3 substituents selected from the group consisting of (a) an oxo group, (b) a hydroxy group, (c) a cyano group, (d) a halogen atom, (e) a $C_{1-6}$ alkyl group optionally substituted by 1 to 3 substituents selected from the group consisting of a hydroxy group, a halogen atom, a $C_{3-10}$ cycloalkyl group, a $C_{6-14}$ aryl group, a $C_{1-6}$ alkoxy-carbonyl group and a carbamoyl group, (f) a $C_{3-10}$ cycloalkyl group, (g) a $C_{1-6}$ alkoxy group, (h) a $C_{1-6}$ alkoxy-carbonyl group, (i) a $C_{1-6}$ alkylsulfonyl group and (j) a 3- to 14-membered non-aromatic heterocyclic group.

7. The compound according to claim 1, wherein
$R^1$ is (1) a $C_{1-6}$ alkyl group optionally substituted by 1 to 3 substituents selected from the group consisting of a halogen atom, a $C_{1-6}$ alkoxy group and a $C_{6-14}$ aryloxy group, (2) a $C_{1-6}$ alkoxy group optionally substituted by 1 to 3 substituents selected from the group consisting of (a) a halogen atom, (b) a hydroxy group, (c) a $C_{6-14}$ aryl group, (d) an amino group optionally mono- or di-substituted by a $C_{1-6}$ alkyl group and (e) a 5- to 14-membered aromatic heterocyclic group or (3) —$NR^2R^3$ (wherein $R^2$ is a hydrogen atom, and $R^3$ is a $C_{1-6}$ alkyl group optionally substituted by 1 to 3 substituents selected from the group consisting of (a) a halogen atom, (b) a hydroxy group, (c) a $C_{3-10}$ cycloalkyl group optionally substituted by 1 to 3 halogen atoms, (d) a $C_{6-14}$ aryl group optionally substituted by 1 to 3 halogen atoms and (e) a 5- to 14-membered aromatic heterocyclic group);
ring A is a $C_{6-14}$ aromatic hydrocarbon ring or a 5- to 14-membered aromatic heterocycle each of which is optionally further substituted by 1 to 5 substituents selected from a 5- to 14-membered aromatic heterocyclic group optionally substituted by 1 to 3 substituents selected from the group consisting of (a) an oxo group, (b) a $C_{1-6}$ alkyl group and (c) a $C_{1-6}$ alkoxy group;
ring B is a cyclohexane ring not further substituted; and
ring C is a pyrimidine ring optionally further substituted by 1 to 3 substituents selected from the group consisting of (1) a cyano group, (2) a $C_{1-6}$ alkyl group optionally substituted by 1 to 3 halogen atoms, (3) a 3- to 14-membered non-aromatic heterocyclic-oxy group, (4) an amino group optionally mono- or di-substituted by substituent(s) selected from the group consisting of (a) a $C_{1-6}$ alkyl group optionally substituted by 1 to 3 hydroxy groups and (b) a 3- to 14-membered non-aromatic heterocyclic group optionally substituted by 1 to 3 $C_{1-6}$ alkyl groups (wherein the 3- to 14-membered non-aromatic heterocyclic group includes one having a bicyclo ring structure, a bridged ring structure, or a spiro ring structure), (5) a 3- to 14-membered non-aromatic heterocyclic group optionally substituted by 1 to 3 substituents selected from the group consisting of (a) a halogen atom, (b) a hydroxy group and (c) a $C_{1-6}$ alkyl group optionally substituted by 1 to 3 hydroxy groups (wherein the 3- to 14-membered non-aromatic heterocyclic group includes one having a bicyclo ring structure, a bridged ring structure, or a spiro ring structure) and (6) a 5- to 14-membered aromatic heterocyclic group optionally substituted by 1 to 3 substituents selected from the group consisting of (a) a cyano group, (b) a halogen atom, (c) a $C_{1-6}$ alkyl group optionally substituted by 1 to 3 halogen atoms and (d) a $C_{1-6}$ alkylsulfonyl group.

8. A medicament comprising the compound according to claim 1 or a salt thereof.

9. The medicament according to claim 8, wherein the medicament is a CDK12 inhibitor.

10. The compound according to claim 1, which is 1-(trans-4-((4-(4-chloro-1H-pyrazol-3-yl)-5-(trifluoromethyl)pyrimidin-2-yl)amino)cyclohexyl)-3-(2,2-difluoroethyl)-1-(5-(2-methoxypyrimidin-5-yl)pyridin-2-yl)urea or a salt thereof.

11. The compound according to claim 1, which is 1-(trans-4-((4-(1-(difluoromethyl)-1H-pyrazol-3-yl)-5-(trifluoromethyl)pyrimidin-2-yl)amino)cyclohexyl)-3-ethyl-1-(5-(1-methyl-1H-pyrazol-4-yl)pyrazin-2-yl)urea or a salt thereof.

12. The compound according to claim 1, which is N-(trans-4-((4-(5-(methanesulfonyl)pyridin-3-yl)-5-(trifluoromethyl)pyrimidin-2-yl)amino)cyclohexyl)-N-(5-(2-methoxypyrimidin-5-yl)pyrazin-2-yl)butanamide or a salt thereof.

13. The compound according to claim 1, which is 1-(trans-4-((4-(1-(difluoromethyl)-1H-pyrazol-3-yl)-5-(trifluoromethyl)pyrimidin-2-yl)amino)cyclohexyl)-3-(2-hydroxy-2-methylpropyl)-1-(5-(2-methoxypyrimidin-5-yl)pyrazin-2-yl)urea or a salt thereof.

14. The compound according to claim 1, which is 2-hydroxy-2-methylpropyl (trans-4-((4-(5-(methanesulfonyl)pyridin-3-yl)-5-(trifluoromethyl)pyrimidin-2-yl)amino)cyclohexyl)(5-(2-methoxypyrimidin-5-yl)pyrazin-2-yl)carbamate or a salt thereof.

15. A method of treating cancer, comprising administering an effective amount of a compound of formula (I) of claim 1, or a salt thereof, to a patient in need thereof, wherein the cancer is at least one cancer selected from the group consisting of lung cancer, pancreatic cancer, breast cancer, ovarian cancer, testicular cancer, and prostate cancer.

* * * * *